(12) United States Patent
Tobinaga et al.

(10) Patent No.: US 11,345,716 B2
(45) Date of Patent: May 31, 2022

(54) NITROGEN-CONTAINING CONDENSED RING COMPOUNDS HAVING DOPAMINE D3 ANTAGONISTIC EFFECT

(71) Applicant: Shionogi & Co., Ltd., Osaka (JP)

(72) Inventors: Hiroyuki Tobinaga, Osaka (JP); Koji Masuda, Osaka (JP); Satoshi Kasuya, Osaka (JP); Masanao Inagaki, Osaka (JP); Manami Masuda, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 17/022,558

(22) Filed: Sep. 16, 2020

(65) Prior Publication Data

US 2021/0009607 A1   Jan. 14, 2021

Related U.S. Application Data

(62) Division of application No. 16/320,693, filed as application No. PCT/JP2017/027141 on Jul. 27, 2017, now Pat. No. 10,870,660.

(30) Foreign Application Priority Data

Jul. 28, 2016 (JP) .............................. JP2016-148076
Apr. 12, 2017 (JP) .............................. JP2017-078842

(51) Int. Cl.

| | |
|---|---|
| *A61K 31/4709* | (2006.01) |
| *A61K 31/4985* | (2006.01) |
| *A61K 31/519* | (2006.01) |
| *A61K 31/55* | (2006.01) |
| *A61P 25/18* | (2006.01) |
| *A61P 25/22* | (2006.01) |
| *A61P 25/24* | (2006.01) |
| *A61P 25/28* | (2006.01) |
| *A61P 25/30* | (2006.01) |
| *C07D 471/04* | (2006.01) |
| *C07D 519/00* | (2006.01) |
| *C07D 513/04* | (2006.01) |
| *C07D 487/04* | (2006.01) |
| *C07D 498/04* | (2006.01) |
| *A61K 31/437* | (2006.01) |
| *C07D 513/08* | (2006.01) |
| *A61K 31/5377* | (2006.01) |
| *A61P 39/02* | (2006.01) |
| *A61P 43/00* | (2006.01) |

(52) U.S. Cl.
CPC .......... *C07D 513/04* (2013.01); *A61K 31/437* (2013.01); *A61K 31/4709* (2013.01); *A61K 31/4985* (2013.01); *A61K 31/519* (2013.01); *A61K 31/5377* (2013.01); *A61P 25/18* (2018.01); *A61P 25/22* (2018.01); *A61P 25/24* (2018.01); *A61P 25/28* (2018.01); *A61P 25/30* (2018.01); *A61P 39/02* (2018.01); *A61P 43/00* (2018.01); *C07D 471/04* (2013.01); *C07D 487/04* (2013.01); *C07D 498/04* (2013.01); *C07D 513/08* (2013.01); *C07D 519/00* (2013.01); *Y02P 20/55* (2015.11)

(58) Field of Classification Search
CPC ............ A61K 31/4709; A61K 31/4985; A61K 31/519; A61K 31/55; A61P 25/18; A61P 25/22; A61P 25/24; A61P 25/28; A61P 25/30; C07D 471/04; C07D 519/00
See application file for complete search history.

(56) References Cited

U.S. PATENT DOCUMENTS

| | | | |
|---|---|---|---|
| 4,988,699 | A | 1/1991 | Caprathe et al. |
| 5,294,621 | A | 3/1994 | Russell |
| 5,703,091 | A | 12/1997 | Steiner et al. |
| 6,143,762 | A | 11/2000 | Nash et al. |
| 2003/0195216 | A1 | 10/2003 | Goldstein et al. |
| 2006/0079504 | A1 | 4/2006 | Rudlof et al. |
| 2006/0241137 | A1 | 10/2006 | Starck et al. |
| 2007/0299091 | A1 | 12/2007 | Gmeiner et al. |

(Continued)

FOREIGN PATENT DOCUMENTS

| | | |
|---|---|---|
| CA | 2 342 432 | 9/2002 |
| CN | 1948315 | 4/2007 |

(Continued)

OTHER PUBLICATIONS

Jeffrey N. Joyce and Mark J. Millan, "Dopamine $D_3$ receptor antagonists as therapeutic agents", Drug Discovery Today, 2005, vol. 10, No. 13, pp. 917-925.

(Continued)

*Primary Examiner* — Brenda L Coleman
(74) *Attorney, Agent, or Firm* — Wenderoth, Lind & Ponack, L.L.P.

(57) ABSTRACT

Novel compounds having D3 receptor antagonistic activity are provided.
A compound represented by formula (I):

(I)

wherein
ring A is a heterocycle, $X^1$ is each independently $CR^{4a}R^{4b}$, $X^2$ is each independently $CR^{4c}R^{4d}$, $Y^1$ and $Y^2$ are each independently a carbon atom or a nitrogen atom,
L is $-N(R^6)-C(=O)-$ or the like, W is cyclyl or the like, $R^2$ and $R^3$ are each independently substituted or unsubstituted alkyl or the like, $R^{1a}$, $R^{1b}$, $R^{4a}$ to $R^{4d}$, and $R^6$ are each independently hydrogen atoms or the like,
p is 1 or 2, q is an integer of 1 to 3, n is an integer of 1 to 4, s is an integer of 0 to 4, or a pharmaceutically acceptable salt thereof.

18 Claims, 1 Drawing Sheet

(56) References Cited

U.S. PATENT DOCUMENTS

| | | | |
|---|---|---|---|
| 2009/0143398 | A1 | 6/2009 | Szalai et al. |
| 2011/0021490 | A1 | 1/2011 | De Nanteuil et al. |
| 2011/0319423 | A1 | 12/2011 | Li et al. |
| 2016/0096811 | A1 | 4/2016 | Li et al. |
| 2018/0297975 | A1 | 10/2018 | Huang et al. |

FOREIGN PATENT DOCUMENTS

| | | |
|---|---|---|
| CN | 107793408 | 3/2018 |
| EP | 0 431 580 | 6/1991 |
| EP | 0 465 254 | 1/1992 |
| EP | 0 981 516 | 3/2000 |
| EP | 1 275 647 | 1/2003 |
| EP | 1 870 405 | 12/2007 |
| EP | 2 995 617 | 3/2016 |
| WO | 95/15327 | 6/1995 |
| WO | 96/02249 | 2/1996 |
| WO | 97/38998 | 10/1997 |
| WO | 97/43262 | 11/1997 |
| WO | 98/06699 | 2/1998 |
| WO | 98/49145 | 11/1998 |
| WO | 98/50363 | 11/1998 |
| WO | 98/50364 | 11/1998 |
| WO | 98/51671 | 11/1998 |
| WO | 99/59974 | 11/1999 |
| WO | 99/64412 | 12/1999 |
| WO | 00/21950 | 4/2000 |
| WO | 00/21951 | 4/2000 |
| WO | 00/24717 | 5/2000 |
| WO | 02/40471 | 5/2002 |
| WO | 02/066446 | 8/2002 |
| WO | 02/066468 | 8/2002 |
| WO | 02/066469 | 8/2002 |
| WO | 02/079151 | 10/2002 |
| WO | 03/029233 | 4/2003 |
| WO | 2004/037810 | 5/2004 |
| WO | 2004/069830 | 8/2004 |
| WO | 2004/091490 | 10/2004 |
| WO | 2005/012266 | 2/2005 |
| WO | 2005/094834 | 10/2005 |
| WO | 2006/050239 | 5/2006 |
| WO | 2006/050976 | 5/2006 |
| WO | 2006/082456 | 8/2006 |
| WO | 2006/102610 | 9/2006 |
| WO | 2007/056155 | 5/2007 |
| WO | 2007/148208 | 12/2007 |
| WO | 2008/125891 | 10/2008 |
| WO | 2009/011904 | 1/2009 |
| WO | 2009/013212 | 1/2009 |
| WO | 2009/015067 | 1/2009 |
| WO | 2009/056805 | 5/2009 |
| WO | 2009/095438 | 8/2009 |
| WO | 2009/112568 | 9/2009 |
| WO | 2010/025235 | 3/2010 |
| WO | 2010/031735 | 3/2010 |
| WO | 2010/034646 | 4/2010 |
| WO | 2010/034648 | 4/2010 |
| WO | 2010/034656 | 4/2010 |
| WO | 2010/060854 | 6/2010 |
| WO | 2011/109441 | 9/2011 |
| WO | 2011/161009 | 12/2011 |
| WO | 2012/004206 | 1/2012 |
| WO | 2012/080149 | 6/2012 |
| WO | 2012/110470 | 8/2012 |
| WO | 2012/117001 | 9/2012 |
| WO | 2012/121919 | 9/2012 |
| WO | 2012/150231 | 11/2012 |
| WO | 2014/059265 | 4/2014 |
| WO | 2014/064038 | 5/2014 |
| WO | 2014/086098 | 6/2014 |
| WO | 2014/140246 | 9/2014 |
| WO | 2017/021920 | 2/2017 |
| WO | 2017/122116 | 7/2017 |

OTHER PUBLICATIONS

Jeffrey N. Joyce, "Dopamine D3 receptor as a therapeutic target for antipsychotic and antiparkinsonian drugs", Pharmacology & Therapeutics, 2001, vol. 90, pp. 231-259.

V. Barth et al., In Vivo Occupancy of Dopamine $D_3$ Receptors by Antagonists Produces Neurochemical and Behavioral Effects of Potential Relevance to Attention-Deficit-Hyperactivity Disorder, Journal of Pharmacology and Experimental Therapeutics, 2013, vol. 344, pp. 501-510.

Mach, U.R. et al., "Development of Novel 1,2,3,4-Tetrahydroisoquinoline Derivatives and Closely Related Compounds as Potent and Selective Dopamine $D_3$ Receptor Ligands", ChemBioChem, 2004, vol. 5, pp. 508-518.

Jeremy Shonberg et al., "Structure—Activity Study of N-((trans)-4-(2-(7-Cyano-3,4-dihydroisoquinolin-2(1H)-yl)ethyl)cyclohexyl)-1H-indole-2-carboxamide (SB269652), a Bitopic Ligand That Acts as a Negative Allosteric Modulator of the Dopamine$_2$ Receptor", Journal of Medicinal Chemisby, 2015, vol. 58, pp. 5287-5307.

Guanghua Fang et al., "CCLab—a multi-objective genetic algorithm based combinatorial library design software and an application for histone deacetylase inhibitor design", Bioorganic & Medicinal Chemistry Letters, 2012, vol. 22, No. 14, pp. 4540-4545.

Nigel E. Austin et al., "Novel 2,3,4,5-Tetrahydro-1H-3-benzazepines with High Affinity and Selectivity for the Dopamine $D_3$ Receptor", Bioorganic & Medicinal Chemistry Letters, 2000, vol. 10, pp. 2553-2555.

Gregor J. Macdonald et al., "Design and Synthesis of trans-3-(2-(4-((3-(3-(5-Methyl-1,2,4-oxadiazolyl))-phenyl)carboxamido)cyclohexyl)ethyl)-7-methylsulfonyl-2,3,4,5-tetrahydro-1H-3-benzazepine (SB-414796): A Potent and Selective Dopamine $D_3$ Receptor Antagonist", Journal of Medicinal Chemishy, 2003, vol. 46, pp. 4952-4964.

Pawel Zajdel et al., "Arene- and quinoline-sulfonamides as novel 5-HT$_7$ receptor ligands", Bioorganic & Medicinal Chemistry, 2011, vol. 19, No. 22, pp. 6750-6759.

Xiao-Wen Chen et al., Synthesis and pharmacological characterization of novel N-(trans-4-(2-(4-(benzo[d]isothiazol-3-yl)piperazin-1-yl)ethyl)cyclohexyl) amides as potential multireceptor atypical antipsychotics, European Journal of Medicinal Chemistry, 2016, vol. 123, pp. 332-353.

Thomas R. Belliotti et al., "Novel Cyclohexyl Amides as Potent and Selective $D_3$ Dopamine Receptor Ligands", Bioorganic & Medicinal Chemistry Letters, 1997, vol. 7, No. 18, pp. 2403-2408.

Jianyong Chen et al., "Tranylcypromine Substituted cis-Hydroxycyclobuty lnaphthamides as Potent and Selective Dopamine $D_3$ Receptor Antagonists", Journal of Medicinal Chemistry, 2014, vol. 57, pp. 4962-4968.

Jianyong Chen et al., "High-affinity and selective dopamine $D_3$ receptor full agonists", Bioorganic & Medicinal Chemistry Letters, 2012, vol. 22, No. 17, pp. 5612-5617.

Gabriella Ortore et al., "Different Binding Modes of Structurally Diverse Ligands for Human D3DAR", Journal of Chemical Information and Modeling, 2010, vol. 50, No. 12, pp. 2162-2175.

Fabrizio Micheli et al., "Exploration of the Amine Terminus in a Novel Series of 1,2,4-Triazolo-3-yl-azabicyclo[3.1.0]hexanes as Selective Dopamine D3 Receptor Antagonists", Journal of Medicinal Chemistry, 2010, vol. 53, No. 19, pp. 7129-7139.

Fabrizio Micheli et al., "1,2,4-Triazol-3-yl-thiopropyl-tetrahydrobenzazepines: A Series of Potent and Selective Dopamine $D_3$ Receptor Antagonists", Journal of Medicinal Chemistry, 2007, vol. 50, No. 21, pp. 5076-5089.

Laurent P. Lacroix et al., "Selective dopamine D3 receptor antagonists enhance cortical acetylcholine levels measured with high-performance liquid chromatography/tandem mass spectrometry without anti-cholinesterases", Journal of Neuroscience Methods, 2006, vol. 157, No. 1, pp. 25-31.

Hye-Jung Kim et al., "Classification of dopamine antagonists using functional feature hypothesis and topological descriptors", Bioorganic & Medicinal Chemistry, 2006, vol. 14, No. 5, 1454-1461.

(56) References Cited

OTHER PUBLICATIONS

Christian A. Heidbreder et al., "The role of central dopamine $D_3$ receptors in drug addiction: a review of pharmacological evidence", Brain Research Reviews, 2005, vol. 49, No. 1, pp. 77-105.
Éva Ágai-Csongor et al., "Novel sulfonamides having dual dopamine D2 and D3 receptor affinity show in vivo antipsychotic efficacy with beneficial cognitive and EPS profile", Bioorganic & Medicinal Chemistry Letters, 2007, vol. 17, No. 19, pp. 5340-5344.
David Wustrow et al., "Aminopyrimidines with High Affinity for Both Serotonin and Dopamine Receptors", Journal of Medicinal Chemistry, 1998, vol. 41, No. 5, pp. 760-771.
Shailesh N. Mistry et al., "Discovery of a Novel Class of Negative Allosteric Modulator of the Dopamine $D_2$ Receptor Through Fragmentation of a Bitopic Ligand", Journal of Medicinal Chemistry, 2015, vol. 58, pp. 6819-6843.
Geoffrey Stemp et al., "Design and Synthesis of trans-N-[4-[2-(6-Cyano-1,2,3,4-tetrahydroisoquinolin-2-yl)ethyl]cyclohexyl]-4-quinolinecarboxamide (SB-277011): A Potent and Selective Dopamine $D_3$ Receptor Antagonist with High Oral Bioavailability and CNS Penetration in the Rat", Journal of Medicinal Chemistry, 2000, vol. 43, No. 9, pp. 1878-1885.
Vivek Kumar et al., "Synthesis and Pharmacological Characterization of Novel trans-Cyclopropylmethyl-Linked Bivalent Ligands That Exhibit Selectivity and Allosteric Pharmacology at the Dopamine $D_3$ Receptor ($D_3R$)", Journal of Medicinal Chemistry, 2017, vol. 60, pp. 1478-1494.
Satishkumar Gadhiya et al, "New Dopamine D3-Selective Receptor Ligands Containing a 6-Methoxy-1,2,3,4-tetrahydroisoquinolin-7-ol Motif", ACS Medicinal Chemistry Letters, 2018, vol. 9, pp. 990-995.
Jianyong Chen et al., "Design of novel hexahydropyrazinoquinolines as potent and selective dopamine $D_3$ receptor ligands with improved solubility", Bioorganic & Medicinal Chemistry Letters, 2006, vol. 16, pp. 443-446.
Fabrizio Micheli et al., "New fused benzazepine as selective Ds receptor antagonists. Synthesis and biological evaluation. Part 2: [g]-Fused and hetero-fused systems", Bioorganic & Medicinal Chemistry Letters, 2008, vol. 18, pp. 908-912.
Jianyong Chen et al., "Pramipexole Derivatives as Potent and Selective Dopamine $D_3$ Receptor Agonists with Improved Human Microsomal Stability", ChemMedChem 2014, vol. 9, pp. 2653-2660.
Márton Vass et al., "Multiple Fragment Docking and Linking in Primary and Secondary Pockets of Dopamine Receptors", ACS Medicinal Chemistry Letters, 2014, vol. 5, pp. 1010-1014.
Jianyong Chen et al., "CJ-1639: A Potent and Highly Selective Dopamine D3 Receptor Full Agonist", ACS Medicinal Chemistry Letters, 2011, vol. 2, pp. 620-625.
Margherita Brindisi et al., "Targeting Dopamine $D_3$ and Serotonin 5-$HT_{1A}$ and 5-$HT_{2A}$ Receptors for Developing Effective Antipsychotics: Synthesis, Biological Characterization, and Behavioral Studies", Journal of Medicinal Chemisuy, 2014, vol. 57, pp. 9578-9597.
Thomas M. Keck et al., "Identifying Medication Targets for Psychostimulant Addiction: Umaveling the Dopamine D3 Receptor Hypothesis", Journal of Medicinal Chemistry, 2015, vol. 58, pp. 5361-5380.
Nuska Tschammer et al., "Highly Potent 5-Aminotetrahydropyrazolopyridines: Enantioselective Dopamine $D_3$ Receptor Binding, Functional Selectivity, and Analysis of Receptor-Ligand Interactions", Journal of Medicinal Chemishy, 2011, vol. 54, pp. 2477-2491.
International Search Report dated Oct. 3, 2017 in International Application No. PCT/JP2017/027141.
International Preliminary Report on Patentability dated Feb. 7, 2019 in International Application No. PCT/JP2017/027141.
Ryosuke Arakawa et al., "Positron Emission Tomography Measurement of Dopamine $D_2$ Receptor Occupancy in the Pituitary and Cerebral Cortex: Relation to Antipsychotic-Induced Hyperprolactinemia" Journal of Clinical Psychiatry, 2010, vol. 71, 9, 1131-1137.
David JG Watson et al., "Selective Blockade of Dopamine $D_3$ Receptors Enhances while $D_2$ Receptor Antagonism Impairs Social Novelty Discrimination and Novel Object Recognition in Rats: A Key Role for the Prefrontal Cortex", Neuropsychopharmacology, 2012, 37, 770-786.
Mitul A. Mehta et al., "Dopamine D2 receptor occupancy levels of acute sulpiride challenges that produce working memory and learning impairments in healthy volunteers", Psychopharmacology, 2008, vo. 196, 1, 157-165.
Hiroyuki Uchida et al., "$D_2$ Receptor Blockade by Risperidone Correlates with Attention Deficits in Late-Life Schizophrenia", Journal of Clinical Psychopharmacology, 2009, vol. 29, 6, 571-575.
Katalin Deak et al., "Physico-chemical characterization of a novel group of dopamine $D_3/D_2$ receptor ligands, potential atypical antipsychotic agents", Journal of Pharmaceutical and Biomedical Analysis, 2008, vo.48, 3, 678-684.
Extended European Search Report dated Feb. 6, 2020 in corresponding European Patent Application No. 17834449.5.

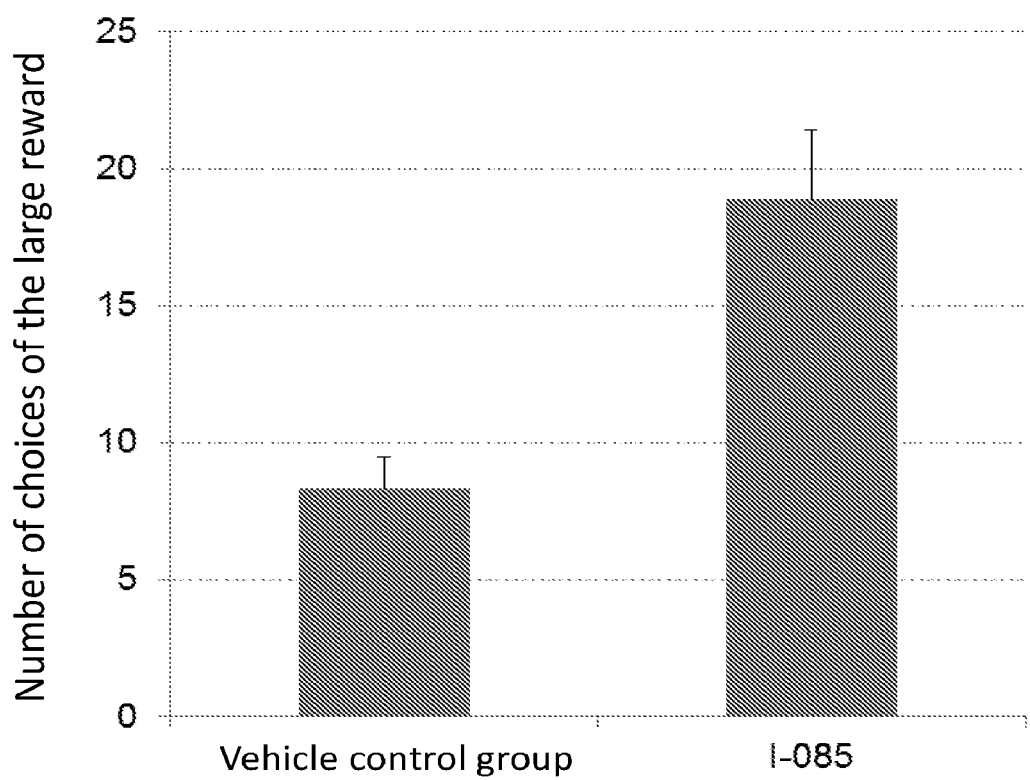

NITROGEN-CONTAINING CONDENSED RING COMPOUNDS HAVING DOPAMINE D3 ANTAGONISTIC EFFECT

TECHNICAL FIELD

The present invention relates to a compound which has antagonistic activity for dopamine D3 receptor (hereinafter, referred to as D3 receptor) and is useful as an agent for treating or preventing diseases induced by D3 receptor, a pharmaceutically acceptable salt thereof, and a pharmaceutical composition containing thereof.

BACKGROUND ART

Dopamine is an important neuromediator in central nervous system. The biological activities of dopamine are mediated through G protein-coupled receptors (GPCRs) and involved in the regulation of a variety of functions which include emotion, cognition, and motor functions. In human, five different dopamine receptors D1 to D5 have been identified. These receptors can be divided into two subtypes: D2-like receptors consisting of D2, D3 and D4 receptors, and D1-like receptors consisting of D1 and D5 receptors.

D3 receptor is selectively distributed in marginal brain area, such as nucleus accumbens, Callejia island, olfactory tubercle. Some research reports suggest that D3 receptor antagonists are useful for treating and/or preventing a number of neurosises, such as schizophrenia, Parkinson's disease, drug dependence, any forms of stress, anxiety, and somnipathy. Further, it is considered that selective D3 receptor antagonists would have less D2 receptor-mediated side-effects (extrapyramidal symptom and the like) compared to existing antipsychotics which are D2 receptor antagonists (Non-patent Document 1, 2).

It is also suggested that D3 receptor antagonists are useful for the treatment and/or preventing Attention-deficit/hyperactivity disorder (AD/IID) (Non-patent Document 3).

Therefore, it is highly likely that compounds having antagonistic activity for D3 receptor, especially preferably compounds having high D3/D2 selectivity, are useful as an agent for treating and/or preventing diseases associated with D3 receptor.

The compounds having similar structures to those of the compounds of the present invention and having affinity for D3 receptor are described in Patent Document 1 to 15, Non-patent Document 4, 7 and 8. However, substantially disclosed compounds have different structure from the compounds of the present invention. The compounds having similar structures to those of the compounds of the present invention are described in Patent Document 16 to 18, Non-patent Document 5 and 6. However, substantially disclosed compounds have different structure from the compounds of the present invention, and there is neither disclosure nor suggestion about an antagonistic activity for D3 receptor.

PRIOR ART REFERENCES

Patent Document

[Patent Document 1] WO 9602249
[Patent Document 2] WO 9738998
[Patent Document 3] WO 9806699
[Patent Document 4] WO 9849145
[Patent Document 5] WO 9850363
[Patent Document 6] WO 9850364
[Patent Document 7] WO 9851671
[Patent Document 8] WO 9959974
[Patent Document 9] WO 9964412
[Patent Document 10] WO 2000/021950
[Patent Document 11] WO 2000/021961
[Patent Document 12] WO 2000/024717
[Patent Document 13] WO 2002/040471
[Patent Document 14] WO 2004/069830
[Patent Document 15] WO 2006/050976
[Patent Document 16] U.S. Pat. No. 5,294,621
[Patent Document 17] WO 2011/109441
[Patent Document 18] WO 2009/011904

Non-Patent Document

[Non-patent Document 1] Drug Discovery Today, 2005, 10 (13), 917-925
[Non-patent Document 2] Pharmacology & Therapeutics, 2001, 9, 231-259
[Non-patent Document 3] Journal of Pharmacology and Experimental Therapeutics, 2013, 344, 501-510
[Non-patent Document 4] ChemBioChem, 2004, 5, 508-518
[Non-patent Document 5] Journal of Medicinal Chemistry, 2015, 58, 5287-5307
[Non-patent Document 6] Bioorganic & Medicinal Chemistry Letters, 2012, 22 (14), 4540-4545
[Non-patent Document 7] Bioorganic & Medicinal Chemistry Letters, 2000, 10, 2553-2555
[Non-patent Document 8] Journal of Medicinal Chemistry, 2003, 46, 4952-4964

SUMMARY OF THE INVENTION

Problems to be Solved by the Invention

The objective of the present invention is to provide a compound which has antagonistic activity for D3 receptor, and preferably high D3/D2 selectivity, and is useful as an agent for treating or precenting diseases associated with D3 receptor, or a pharmaceutically acceptable salt thereof, and a pharmaceutical composition containing thereof.

Means for Solving the Problem

The present invention relates to, for example, the following inventions.

(1) A compound represented by Formula (I):

[Chemical Formula 1]

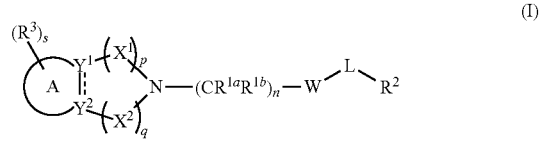

(I)

wherein
a ring represented by:

[Chemical Formula 2]

is a 5-membered aromatic heterocycle, a 6-membered aromatic heterocycle, a 5-membered non-aromatic heterocycle, or a 6-membered non-aromatic heterocycle;

$Y^1$ and $Y^2$ are each independently a carbon atom or a nitrogen atom;

when $Y^1$ and $Y^2$ are both carbon atoms, then a broken line represents the presence or absence of a bond;

when at least one of $Y^1$ and $Y^2$ is a nitrogen atom, then a broken line represents the absence of a bond;

$X^1$ is each independently $CR^{4a}R^{4b}$, $X^2$ is each independently $CR^{4c}R^{4d}$, p is 1 or 2;

q is an integer of 1 to 3;

$R^{4a}$ is each independently a hydrogen atom, halogen, hydroxy, substituted or unsubstituted alkyl, or substituted or unsubstituted alkyloxy;

$R^{4b}$ is each independently a hydrogen atom, halogen, hydroxy, substituted or unsubstituted alkyl, or substituted or unsubstituted alkyloxy;

$R^{4a}$ and $R^{4b}$ attached to a same carbon atom, together with the carbon atom to which they are attached, may form substituted or unsubstituted 3- to 5-membered non-aromatic carbocycle or substituted or unsubstituted 3- to 5-membered non-aromatic heterocycle;

two $R^{4a}$s attached to adjacent carbon atoms may be taken together with the carbon atoms to which they are attached to form a substituted or unsubstituted 3- to 5-membered non-aromatic carbocycle or a substituted or unsubstituted 3- to 5-membered non-aromatic heterocycle;

$R^{4c}$ is each independently a hydrogen atom, halogen, hydroxy, substituted or unsubstituted alkyl, or substituted or unsubstituted alkyloxy;

$R^{4d}$ is each independently a hydrogen atom, halogen, hydroxy, substituted or unsubstituted alkyl, or substituted or unsubstituted alkyloxy;

$R^{4c}$ and $R^{4d}$ attached to a same carbon atom may be taken together with the carbon atom to which they are attached to form a substituted or unsubstituted 3- to 5-membered non-aromatic carbocycle or a substituted or unsubstituted 3- to 5-membered non-aromatic heterocycle;

two $R^{4c}$s attached to adjacent carbon atoms may be taken together with the carbon atoms to which they are attached to form a substituted or unsubstituted 3- to 5-membered non-aromatic carbocycle or a substituted or unsubstituted 3- to 5-membered non-aromatic heterocycle;

any one of $R^{4a}$s and any one of $R^{4c}$s may be taken together to form a substituted or unsubstituted (C1-C3) bridge, wherein one of carbon atoms constituting the (C1-C3) bridge may be replaced with an oxygen atom or a nitrogen atom;

$R^{1a}$ is each independently a hydrogen atom, halogen, hydroxy, substituted or unsubstituted alkyl, or substituted or unsubstituted alkyloxy;

$R^1 b$ is each independently a hydrogen atom, halogen, hydroxy, substituted or unsubstituted alkyl, or substituted or unsubstituted alkyloxy;

n is an integer of 1 to 4;

—W— is a g p represented by:

[Chemical Formula 3]

wherein

Ring B is a non-aromatic carbocycle, a non-aromatic heterocycle, an aromatic carbocycle, or an aromatic heterocycle;

$R^5$ is each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alknylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, or substituted or unsubstituted alkynyloxycarbonylamino;

two $R^5$s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom; and r is an integer of 0 to 4, or —$(CR^{1c}R^{1d})_m$—;

$R^{1c}$ is each independently a hydrogen atom, halogen, hydroxy, substituted or unsubstituted alkyl (provided that the substituents are not aromatic heterocyclylcarbamoyloxy), or substituted or unsubstituted alkyloxy;

$R^{1d}$ is each independently a hydrogen atom, halogen, hydroxy, substituted or unsubstituted alkyl (provided that the substituents are not aromatic heterocyclylcarbamoyloxy), or substituted or unsubstituted alkyloxy;

m is an integer of 1 to 3;

-L- is —N($R^6$)—C(=O)—, —C(=O)—N($R^6$)—, —N($R^6$)—$SO_2$—, or $SO_2$N($R^6$)—;

$R^6$ is a hydrogen atom, or substituted or unsubstituted alkyl;

$R^2$ is substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or substituted or unsubstituted non-aromatic heterocyclylamino;

$R^5$ is each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

s is an integer of 0 to 4, provided that the following compounds (i) to (iv) are excluded:

(i) a compound wherein the ring represented by:

[Chemical Formula 4]

is a 5-membered non-aromatic heterocycle or a 6-membered non-aromatic heterocycle and —W— is —$(CR^{1e}R^{1d})_m$—, (ii) a compound wherein the ring represented by:

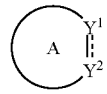

[Chemical Formula 5]

is a 5-membered non-aromatic heterocycle or a 6-membered non-aromatic heterocycle and Ring B is an aromatic carbocycle, (iii) a compound wherein the ring represented by:

[Chemical Formula 6]

is a thiophene ring, p is 1, and s is 0, and, (iv) following compounds:

[Chemical Formula 7]

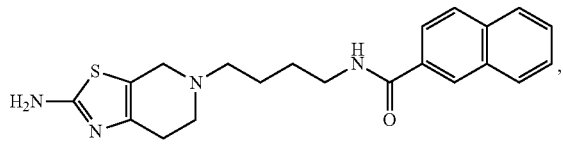

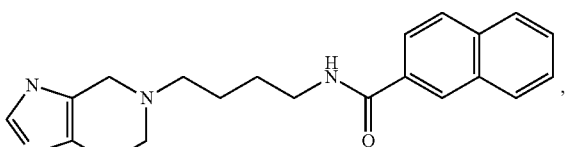

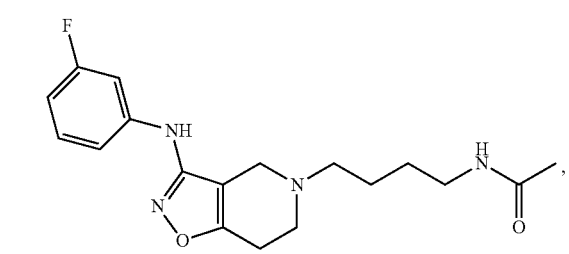

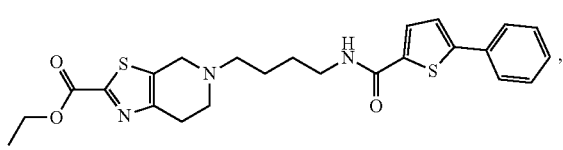

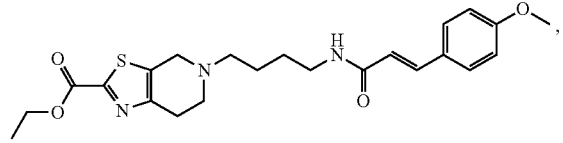

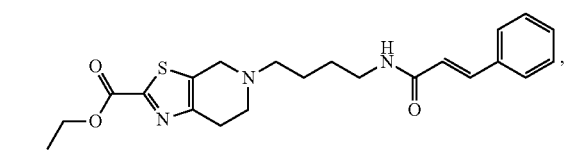

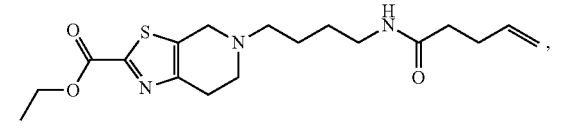

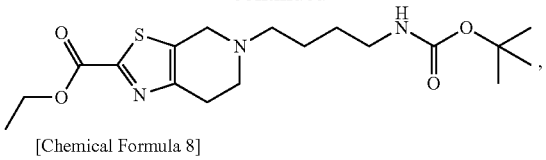

[Chemical Formula 8]

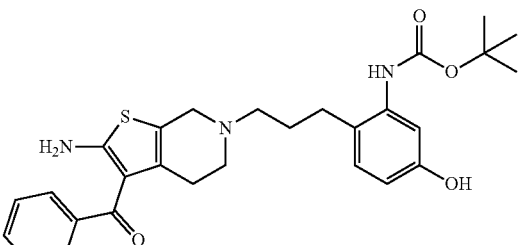

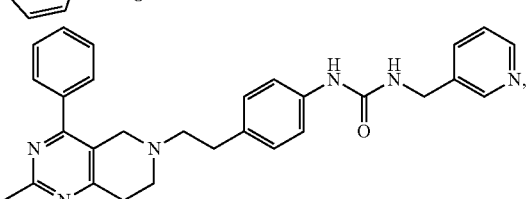

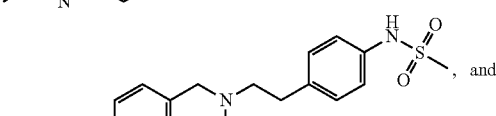

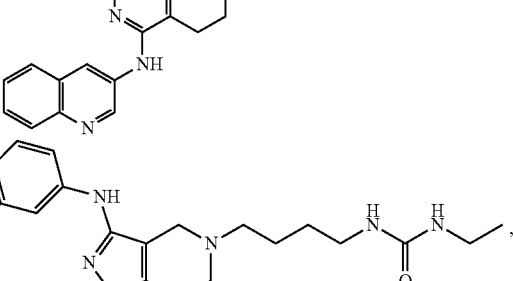

or a pharmaceutically acceptable salt thereof.

Provided that when a ring represented by:

[Chemical Formula 9]

is a 5-membered non-aromatic heterocycle or a 6-membered non-aromatic heterocycle and $Y^1$ is a carbon atom, then a hydrogen atom or $R^5$ may be attached to the carbon atom; when a ring represented by:

[Chemical Formula 10]

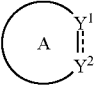

is a 5-membered non-aromatic heterocycle or a 6-membered non-aromatic heterocycle and $Y^2$ is a carbon atom, then a hydrogen atom or $R^5$ may be attached to the carbon atom.

(2) The compound according to above (1), wherein
-L- is —N(R$^6$)—C(=O)— or —N(R$^6$)—SO$_2$—;
Ring B is a non-aromatic carbocycle, a non-aromatic heterocycle, or an aromatic heterocycle;
n is an integer of 2 to 4; and
m is 2,
or a pharmaceutically acceptable salt thereof.

(3) The compound according to above (1), wherein
-L- is —N(R$^6$)—C(=O)—;
Ring B is a non-aromatic carbocycle or a non-aromatic heterocycle;
n is 2;
m is 2; and
q is 2,
or a pharmaceutically acceptable salt thereof.

(4) The compound according to any one of above (1) to (3), wherein the ring represented by:

[Chemical Formula 11]

is a thiazole ring, a pyridine ring, a pyrimidine ring, an imidazole ring, a pyrazole ring, an oxazole ring, a thiophene ring, a pyrrole ring, a furan ring, a pyrazine ring, a pyridazine ring, or a pyrrolidine ring,
or a pharmaceutically acceptable salt thereof.

(5) The compound according to any one of above (1) to (4), wherein

[Chemical Formula 12]

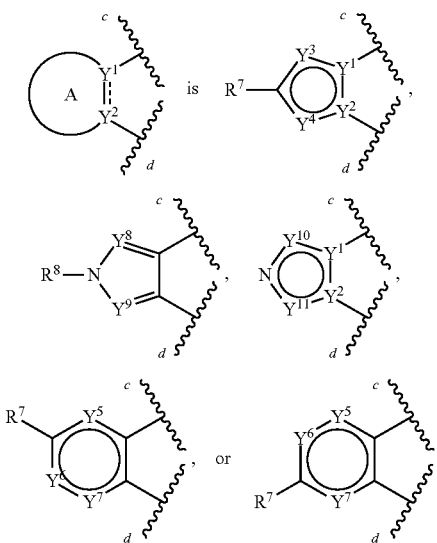

wherein
a bonding hand "c" is bonded to CR$^{4a}$R$^{4b}$; a bonding hand "d" is bonded to CR$^{4c}$R$^{4d}$;
Y$^3$ and Y$^4$ are each independently CR$^{9a}$, N, NR$^8$, S, or O;
the ring constituted of Y$^1$ to Y$^4$ and a carbon atom is a 5-membered aromatic heterocycle, and 1 or 2 atom(s) constituting the 5-membered aromatic heterocycle are heteroatoms;

Y$^8$ and Y$^9$ are each independently CR$^{9a}$ or N; provided that Y$^8$ and Y$^9$ are not simultaneously both N
Y$^5$ is CR$^{9b}$ or N; Y$^6$ is CR$^{9c}$ or N; Y$^7$ is CR$^{9d}$ or N; the ring constituted of Y$^5$ to Y$^7$ and carbon atoms is a 6-membered aromatic heterocycle; 1 or 2 atoms constituting the 6-membered aromatic heterocycle are heteroatoms;
Y$^{10}$ and Y$^{11}$ are each independently CR$^{9a}$ or NR$^8$; the ring constituted of Y$^1$, Y$^2$, Y$^{10}$, Y$^{11}$ and a nitrogen atom is a 5-membered aromatic heterocycle, and 1 or 2 atoms constituting the 5-membered aromatic heterocycle are heteroatoms;
R$^7$ is each independently a hydrogen atom, halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbonyl, substituted or unsubstituted alkylcarbonylamino, substituted or unsubstituted alkenylcarbonylamino, substituted or unsubstituted alkenylcarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonyl amino, substituted or unsubstituted non-aromatic carbocyclylcarbonylamino, or substituted or unsubstituted aromatic heterocyclylcarbonylamino;

$R^8$ is each independently a hydrogen atom, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkylcarbonyl, substituted or unsubstituted alkenylcarbonyl, substituted or unsubstituted alkynylcarbonyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl;

$R^{9a}$ to $R^{9d}$ are each independently a hydrogen atom, halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonylamino, substituted or unsubstituted alkenylcarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, or substituted or unsubstituted aromatic heterocyclylcarbonylamino; the other symbols are the same as defined in above (1); provided that when the ring constituted of $Y^1$ to $Y^4$ and a carbon atom is thiophene Ring And p is 1, then $R^7$ is not a hydrogen atom, or a pharmaceutically acceptable salt thereof.

(6) The compound according to any one of above (1) to (5), wherein

[Chemical Formula 13]

wherein each symbol is the same as defined in above (5), or a pharmaceutically acceptable salt thereof.

(7) The compound according to above (5) or (6), wherein

[Chemical Formula 14]

wherein each symbol is the same as defined in above (5). or a pharmaceutically acceptable salt thereof.

(8) The compound according to any one of above (5) to (7), wherein

[Chemical Formula 15]

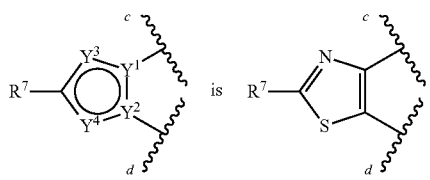 is 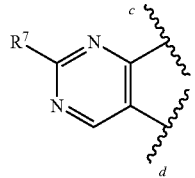

wherein each symbol is the same as defined in above (5), or a pharmaceutically acceptable salt thereof.

(9) The compound according to any one of above (1) to (5), wherein

[Chemical Formula 16]

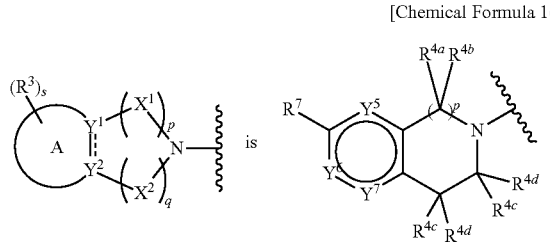

wherein each symbol is the same as defined in above (6). or a pharmaceutically acceptable salt thereof.

(10) The compound according to any one of above (5) to (9), wherein

[Chemical Formula 17]

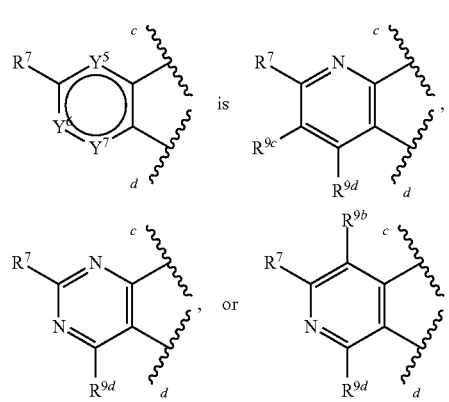

wherein each symbol is the same as defined in above (5), or a pharmaceutically acceptable salt thereof.

(11) The compound according to any one of (5) to (10), wherein

[Chemical Formula 18]

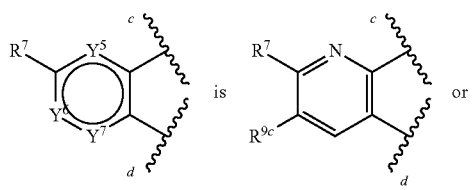

wherein each symbol is the same as defined in above or a pharmaceutically acceptable salt thereof.

(12) The compound according to any one of above (5) to (11), wherein
$R^7$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclyl amino, or substituted or unsubstituted non-aromatic heterocyclylamino,
or a pharmaceutically acceptable salt thereof.

(13) The compound according to any one of above (5) to (12), wherein
$R^8$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.

(14) The compound according to any one of above (5) to (13), wherein
$R^{9a}$ to $R^{9d}$ are each independently a hydrogen atom, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy,
or a pharmaceutically acceptable salt thereof.

(15) The compound according to any one of above (1) to (14), wherein
$R^2$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.

(16) The compound according to any one of above (1) to (15), wherein
—W— is a group represented by:

[Chemical Formula 19]

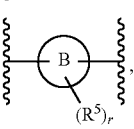

or a pharmaceutically acceptable salt thereof.

(17) The compound according to any one of above (1) to (15), wherein —W— is —(CR$^{1c}$R$^{1d}$)$_m$—, or a pharmaceutically acceptable salt thereof.
(18) The compound according to any one of above (1) to (17), wherein R$^{1a}$ and R$^{1b}$ are hydrogen atoms, or a pharmaceutically acceptable salt thereof.
(19) The compound according to any one of above (1) to (18), wherein R$^{4a}$ to R$^{4d}$ are hydrogen atoms, or a pharmaceutically acceptable salt thereof.
(20) The compound according to any one of above (1) to (19), wherein R$^6$ is a hydrogen atom, or a pharmaceutically acceptable salt thereof.
(21) The compound according to above (1), wherein the compound is selected from a group consisting of examples II-026, II-046, II-072, II-077, III-001, III-019, III-037, III-102, III-104, III-128, III-165, III-68, III-69, III-71, III-75, III-80, III-441, III-452, III-464, III-578, III-581, III-624, and III-642, or a pharmaceutically acceptable salt thereof.
(21A) The compound according to above (1), wherein the compound is selected from a group consisting of examples III-441, III-452, III-464, III-578, III-581, III-624, and III-642, or a pharmaceutically acceptable salt thereof.
(21B) The compound according to above (1), wherein the compound is selected from a group consisting of examples II-026, II-046, II-072, II-077, III-001, III-019, III-037, III-102, III-104, III-128, III-165, III-68, III-69, III-71, III-75, and III-80, or a pharmaceutically acceptable salt thereof.
(22) A pharmaceutical composition comprising the compound according to any one of above (1) to (21), (21A), and (21B) or a pharmaceutically acceptable salt thereof.
(23) The pharmaceutical composition according to above (22), wherein the composition is a dopamine D3 receptor antagonist.
(23A) The pharmaceutical composition according to above (22), wherein the composition has an antagonistic activity for dopamine D3 receptor.
(24) A method for treating and/or preventing a disease associated with dopamine D3 receptor comprising administering the compound according to any one of above (1) to (21), (21A), and (21B) or a pharmaceutically acceptable salt thereof.
(25) The compound according to any one of above (1) to (21), (21A), and (21B) or a pharmaceutically acceptable salt thereof for use in treating and/or preventing a disease associated with dopamine D3 receptor.
(1)' A compound represented by Formula (I):

[Chemical Formula 20]

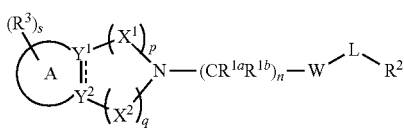

(I)

wherein

[Chemical Formula 21]

is a 5-membered aromatic heterocycle, a 6-membered aromatic heterocycle, a 5-membered non-aromatic heterocycle, or a 6-membered non-aromatic heterocycle;
Y$^1$ and Y$^2$ are each independently a carbon atom or a nitrogen atom;

when Y$^1$ and Y$^2$ are both carbon atoms, then a broken line represents the presence or absence of a bond;
when at least one of Y$^1$ and Y$^2$ is a nitrogen atom, then a broken line represents the absence of a bond;
X$^1$ is each independently CR$^{4a}$R$^{4b}$,
X$^2$ is each independently CR$^{4c}$R$^{4d}$,
p is 1 or 2;
q is an integer of 1 to 3;
R$^{4a}$ is each independently a hydrogen atom, halogen, hydroxy, substituted or unsubstituted alkyl, or substituted or unsubstituted alkyloxy;
R$^{4b}$ is each independently a hydrogen atom, halogen, hydroxy, substituted or unsubstituted alkyl, or substituted or unsubstituted alkyloxy;
R$^{4c}$ is each independently a hydrogen atom, halogen, hydroxy, substituted or unsubstituted alkyl, or substituted or unsubstituted alkyloxy;
R$^{4d}$ is each independently a hydrogen atom, halogen, hydroxy, substituted or unsubstituted alkyl, or substituted or unsubstituted alkyloxy;
any one of R$^{4a}$s and any one of R$^{4c}$s may be taken together to form a substituted or unsubstituted (C1-C3) bridge, wherein one of carbon atoms constituting the (C1-C3) bridge may be replaced with an oxygen atom or a nitrogen atom;
R$^{1a}$ is each independently a hydrogen atom, halogen, hydroxy, substituted or unsubstituted alkyl, or substituted or unsubstituted alkyloxy;
R$^{1b}$ is each independently a hydrogen atom, halogen, hydroxy, substituted or unsubstituted alkyl, or substituted or unsubstituted alkyloxy;
n is an integer of 1 to 4;
—W— is;

[Chemical Formula 22]

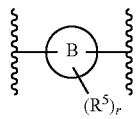

wherein
Ring B is a non-aromatic carbocycle, a non-aromatic heterocycle, an aromatic carbocycle, or an aromatic heterocycle;
R$^5$ is the same as defined in above (1);
r is an integer of 0 to 4, or
—(CR$^{1c}$R$^{1d}$)$_m$—;
R$^{1c}$ is each independently a hydrogen atom, halogen, hydroxy, substituted or unsubstituted alkyl (provided that the substituents are not aromatic heterocyclylcarbamoyloxy), or substituted or unsubstituted alkyloxy;
R$^{1d}$ is each independently a hydrogen atom, halogen, hydroxy, substituted or unsubstituted alkyl (provided that the substituents are not aromatic heterocyclylcarbamoyloxy), or substituted or unsubstituted alkyloxy;
m is an integer of 1 to 3;
-L- is —N(R$^6$)—C(=O)—, —C(=O)—N(R$^6$)—, —N(R$^6$)—SO$_2$—, or SO$_2$N(R$^6$)—;
R$^6$ is a hydrogen atom, or substituted or unsubstituted alkyl;
R$^2$ and R$^3$ are the same as defined in above (1);
s is an integer of 0 to 4
provided that:
when

[Chemical Formula 23]

is a 5-membered non-aromatic heterocycle or a 6-membered non-aromatic heterocycle, then —W— is not —(CR$^{1c}$R$^{1d}$)$_m$—;

when

[Chemical Formula 24]

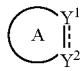

is a thiophene ring, then s is not 0,
provided that following compounds are excluded:

[Chemical Formula 25]

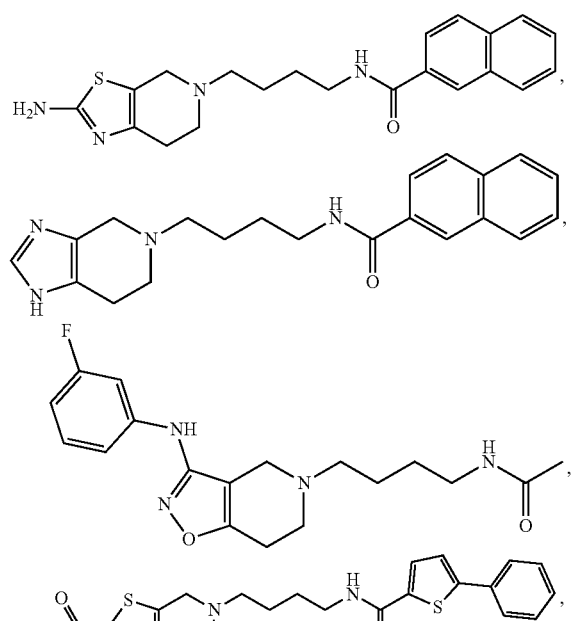

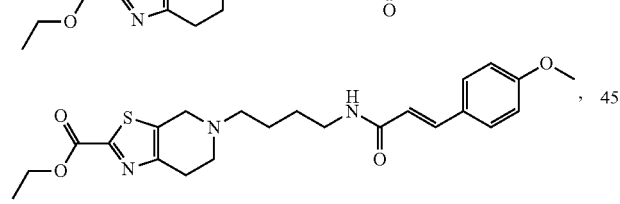

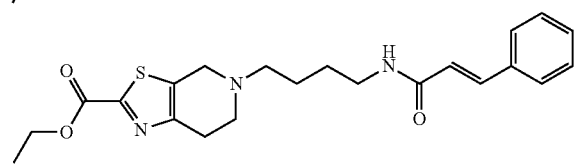

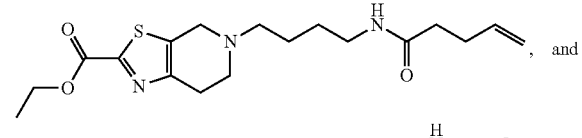

, and

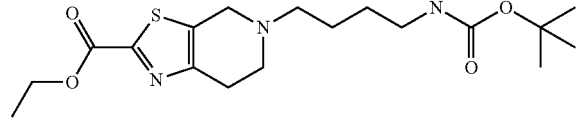

or a pharmaceutically acceptable salt thereof.

Provided that when

[Chemical Formula 26]

is a 5-membered non-aromatic heterocycle or a 6-membered non-aromatic heterocycle and Y$^1$ is a carbon atom, then a hydrogen atom or R$^5$ may be attached to the carbon atom;
when

[Chemical Formula 27]

is a 5-membered non-aromatic heterocycle or a 6-membered non-aromatic heterocycle and Y$^2$ is a carbon atom, then a hydrogen atom or R$^5$ may be attached to the carbon atom.

(2)' The compound according to above (1)', wherein
 -L- is —N(R$^6$)—C(=O)—;
 Ring B is a non-aromatic carbocycle, a non-aromatic a heterocycle, or a aromatic heterocycle;
 n is an integer of 2 to 4; and
 m is 2,
or a pharmaceutically acceptable salt thereof.

(2A)' The compound according to above (1)', wherein
 -L- is —N(R$^6$)—C(=O)—, or —N(R$^6$)—SO$_2$—;
 Ring B is a non-aromatic carbocycle, a non-aromatic heterocycle, or an aromatic heterocycle;
 n is an integer of 2 to 4; and
 m is 2,
or a pharmaceutically acceptable salt thereof.

(3)' The compound according to any one of above (1)', (2)', and (2A)', wherein

[Chemical Formula 28]

is a 5-membered aromatic heterocycle, a 6-membered aromatic heterocycle, or a 5-membered non-aromatic heterocycle,
or a pharmaceutically acceptable salt thereof.

(4)' The compound according to any one of above (1)' to (3)' and (2A)', wherein

[Chemical Formula 29]

is a thiazole ring, an imidazole ring, a pyrazole ring, an oxazole ring, a thiophene ring, a pyrrole ring, a furan ring, a pyridine ring, a pyrazine ring, a pyrimidine ring, a pyridazine ring, or a pyrrolidine ring
or a pharmaceutically acceptable salt thereof.

(5)' The compound according to any one of above (1') to (4)', and (2A)', wherein
—W— is a group represented by:

[Chemical Formula 30]

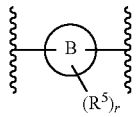

or a pharmaceutically acceptable salt thereof.
(6)' The compound according to any one of above (1)' to (5)', and (2A)', wherein Ring B is a 6-membered non-aromatic carbocycle or a 6-membered non-aromatic heterocycle.
or a pharmaceutically acceptable salt thereof.
(7)' The compound according to any one of above (1)' to (6)' and (2A)', wherein
—W— is a group represented by:

[Chemical Formula 31]

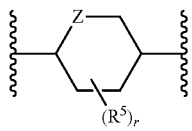

wherein Z is a carbon atom, an oxygen atom, or a nitrogen atom, and the other symbols are the same as defined above, or a pharmaceutically acceptable salt thereof.
(8)' The compound according to above (7)', wherein Z is a carbon atom or an oxygen atom,
or a pharmaceutically acceptable salt thereof.
(9)' The compound according to any one of above (1)' to (8)' and (2A)', wherein
$R^2$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.
(10)' The compound according to any one of above (1)' to (9)' and (2A)', wherein
$R^3$ is each independently halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonyl amino, substituted or unsubstituted alkynylcarbonyl amino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocycly-loxy, substituted or unsubstituted non-aromatic carbocycly-loxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocycly-lamino, substituted or unsubstituted aromatic heterocycly-lamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocycly-loxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbo-nylamino, substituted or unsubstituted non-aromatic carbo-cyclylcarbonylamino, or substituted or unsubstituted aromatic heterocyclylcarbonylamino,
or a pharmaceutically acceptable salt thereof.
(11)' The compound according to any one of above (1)' to (10)' and (2A)', wherein s is an integer of 1 to 3,
or a pharmaceutically acceptable salt thereof.
(12)' The compound according to any one of above (1) to (11) and (2A), wherein

[Chemical Formula 32]

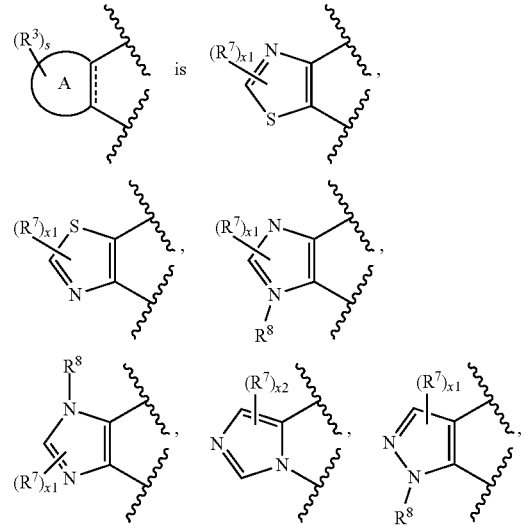

-continued

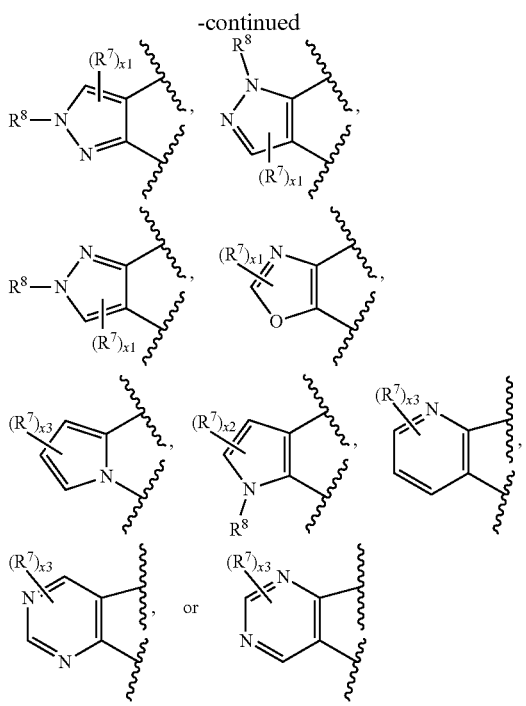

wherein
R[7] is each independently halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonylamino, substituted or unsubstituted alkynylcarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocycyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, or substituted or unsubstituted aromatic heterocyclylcarbonylamino;

R[8] is a hydrogen atom, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkylcarbonyl, substituted or unsubstituted alkenylcarbonyl, substituted or unsubstituted alkynylcarbonyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl;

x1 is 0 or 1; x2 is on integer of 0 to 2; x3 is an integer of 0 to 3, or a pharmaceutically acceptable salt thereof.

(12A)' The compound according to any one of above (1)' to (11)' and (2A)', wherein

[Chemical Formula 33]

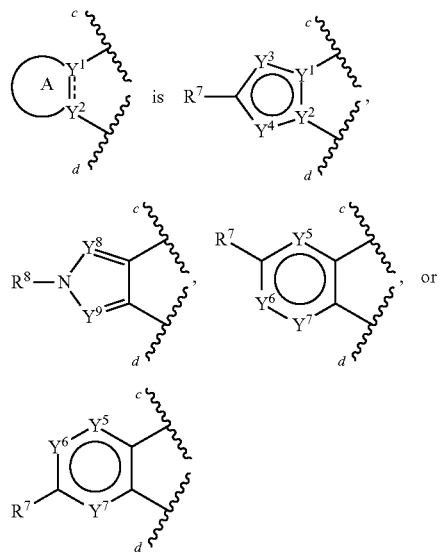

wherein
Y[3] and Y[4] are each independently, CR[9], N, NR[8], S, or O;
the ring constituted of Y[1] to Y[4] and a carbon atom is a 5-membered aromatic heterocycle, and 1 or 2 atoms constituting the 5-membered aromatic heterocycle are heteroatoms;

Y⁸ and Y⁹ are each independently CR⁹ or N; provided that Y⁸ and Y⁹ are not simultaneously both N;
Y⁵ to Y⁷ are each independently CR⁹ or N;
the ring constituted of Y⁵ to Y⁷ and carbon atoms is a 6-membered aromatic heterocycle, and 1 or 2 atoms constituting the 6-membered aromatic heterocycle are heteroatoms;
R⁹ is each independently a hydrogen atom, halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonyl amino, substituted or unsubstituted alkynylcarbonyl amino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, or substituted or unsubstituted aromatic heterocyclylcarbonylamino; the other symbols are the same as defined above,
or a pharmaceutically acceptable salt thereof.
(13)' The compound according to above (12)', wherein
x1 is 1; x2 is 1 or 2; x3 is an integer of 1 to 3
or a pharmaceutically acceptable salt thereof.

(14)' The compound according to any one of above (1)' to (13)', (2A)', and (13A)',
wherein

[Chemical Formula 34]

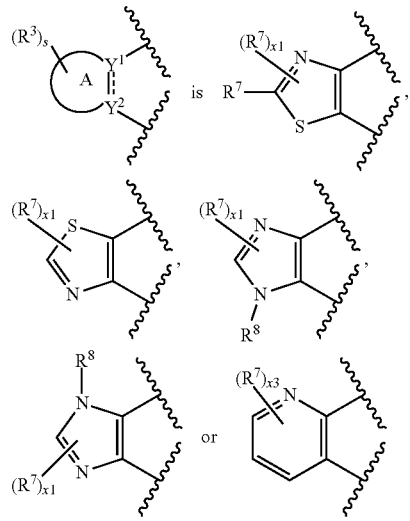

wherein each symbol is the same as defined in (12)',
or a pharmaceutically acceptable salt thereof.
(15)' The compound according to any one of above (12)' to (14)', and (12A)', wherein
R⁷ is each independently halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl, or a pharmaceutically acceptable salt thereof.

(16)' The compound according to any one of above (12)' to (15)', and (12A)', wherein $R^8$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

(17)' The compound according to any one of above (1)' to (16)', (2A)', and (12A)', wherein $R^{1a}$ and $R^{1b}$ are hydrogen atoms, or a pharmaceutically acceptable salt thereof.

(18)' The compound according to any one of above (1)' to (17)', (2A)', and (12A)', wherein $R^6$ is a hydrogen atom, or a pharmaceutically acceptable salt thereof.

(19)' The compound according to any one of above (1)' to (18)', (2A)', and (12A)', wherein p is 1, or a pharmaceutically acceptable salt thereof.

(20)' The compound according to any one of above (1)' to (19)', (2A)', and (12A)', wherein q is 2, or a pharmaceutically acceptable salt thereof.

(21)' The compound according to any one of above (1)' to (20)', (2A)', and (12A)', wherein n is 2, or a pharmaceutically acceptable salt thereof.

(22)' A pharmaceutical composition comprising the compound according to any one of above (1)' to (21)', (2A)', and (12A)' or a pharmaceutically acceptable salt thereof.

(23)' The pharmaceutical composition according to above (22)', wherein the composition is a dopamine D3 receptor antagonist.

(23A)' The pharmaceutical composition according to above (22)', wherein the composition has an antagonistic activity for dopamine D3 receptor.

(1)'' A compound represented by Formula (Ie):

[Chemical Formula 35]

(Ie)

wherein
a ring represented by:

[Chemical Formula 36]

is a 5-membered aromatic heterocycle, a 6-membered aromatic heterocycle, a 5-membered non-aromatic heterocycle, or a 6-membered non-aromatic heterocycle;

$Y^1$ and $Y^2$ are each independently a carbon atom or a nitrogen atom;

when $Y^1$ and $Y^2$ are both carbon atoms, then a broken line represents the presence or absence of a bond;

when at least one of $Y^1$ and $Y^2$ is a nitrogen atom, then a broken line represents the absence of a bond;

$R^{4a}$ is each independently a hydrogen atom, halogen, hydroxy, substituted or unsubstituted alkyl, or substituted or unsubstituted alkyloxy;

$R^{4b}$ is each independently a hydrogen atom, halogen, hydroxy, substituted or unsubstituted alkyl, or substituted or unsubstituted alkyloxy;

$R^{4r}$ is each independently a hydrogen atom, halogen, hydroxy, substituted or unsubstituted alkyl, or substituted or unsubstituted alkyloxy;

$R^{4d}$ is each independently a hydrogen atom, halogen, hydroxy, substituted or unsubstituted alkyl, or substituted or unsubstituted alkyloxy;

any one of $R^{4a}$s and any one of $R^{4c}$s may be taken together to form a substituted or unsubstituted (C1-C3) bridge, wherein one of carbon atoms constituting the (C1-C3) bridge may be replaced with an oxygen atom or a nitrogen atom;

$R^{1a}$ is each independently a hydrogen atom, halogen, hydroxy, substituted or unsubstituted alkyl, or substituted or unsubstituted alkyloxy;

$R^{1b}$ is each independently a hydrogen atom, halogen, hydroxy, substituted or unsubstituted alkyl, or substituted or unsubstituted alkyloxy;

n is an integer of 1 to 4;

—W— is a group represented by:

[Chemical Formula 37]

wherein
Ring B is a non-aromatic carbocycle, a non-aromatic heterocycle, an aromatic carbocycle, or an aromatic heterocycle;

$R^5$ is each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, or substituted or unsubstituted alkynyloxycarbonylamino;

two $R^5$s attached to different ring-constituting atoms may be taken together to form a bond or a substituted or unsubstituted (C1-C3) bridge wherein one of the carbon atoms constituting the (C1-C3) bridge may be replaced with an oxygen atom or a nitrogen atom; and r is an integer of 0 to 4, or —$(CR^{1c}R^{1d})_m$—;

$R^{1c}$ is each independently a hydrogen atom, halogen, hydroxy, substituted or unsubstituted alkyl (provided that the substituents are not aromatic heterocyclylcarbamoyloxy), or substituted or unsubstituted alkyloxy;

$R^{1d}$ is each independently a hydrogen atom, halogen, hydroxy, substituted or unsubstituted alkyl (provided that the substituents are not aromatic heterocyclylcarbamoyloxy), or substituted or unsubstituted alkyloxy;

m is an integer of 1 to 3;

-L- is —$N(R^6)$—$C(=O)$—, —$C(=O)$—$N(R^6)$—, —$N(R^6)$—$SO_2$—, or $SO_2N(R^6)$—;

$R^6$ is a hydrogen atom, or substituted or unsubstituted alkyl;

$R^2$ is substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or substituted or unsubstituted non-aromatic heterocyclylamino;

$R^3$ is each independently a halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

s is an integer of 0 to 4 provided that when a ring represented by:

[Chemical Formula 38]

is a 5-membered non-aromatic heterocycle or a 6-membered non-aromatic heterocycle, then —W— is not —(CR$^{1c}$R$^{1d}$)$_m$—, or a pharmaceutically acceptable salt thereof.
Provided that when a ring represented by:

[Chemical Formula 39]

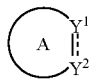

is a 5-membered non-aromatic heterocycle or a 6-membered non-aromatic heterocycle and Y$^1$ is a carbon atom, then a hydrogen atom or R$^5$ may be attached to the carbon atom; when a ring represented by:

[Chemical Formula 40]

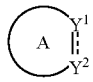

is a 5-membered non-aromatic heterocycle or a 6-membered non-aromatic heterocycle and Y$^2$ is a carbon atom, then then a hydrogen atom or R$^5$ may be attached to the carbon atom.

(2)" The compound according to above (1), wherein

-L- is —N(R$^6$)—C(=O)—;

Ring B is a non-aromatic carbocycle, a non-aromatic heterocycle, or an aromatic heterocycle;

n is an integer of 2 to 4; and m is 2, or a pharmaceutically acceptable salt thereof.

(2A) The compound according to above (1)", wherein

-L- is —N(R$^6$)—C(=O)—, or N(R$^6$)—SO$_2$—;

Ring B is a non-aromatic carbocycle, a non-aromatic heterocycle, or an aromatic heterocycle;

n is an integer of 2 to 4; and m is 2, or a pharmaceutically acceptable salt thereof.

(3)" The compound according to any one of above (1)", (2)", and (2A)' wherein a ring represented by:

[Chemical Formula 41]

is a 5-membered aromatic heterocyclo, a 6-membered aromatic heterocycle, or a 5-membered non-aromatic heterocycle, or a pharmaceutically acceptable salt thereof.

(4)" The compound according to any one of above (1)" to (3)" and (2A)", wherein a ring represented by:

[Chemical Formula 42]

is a thiazole ring, an imidazole ring, a pyrazole ring, an oxazole ring, a thiophene ring, a pyrrole ring, a furan ring, a pyridine ring, a pyrazine ring, a pyrimidine ring, a pyridazine ring, or a pyrrolidine ring, or a pharmaceutically acceptable salt thereof.

(5)" The compound according to any one of above (1)" to (4)", and (2A)", wherein —W— is a group represented by:

[Chemical Formula 43]

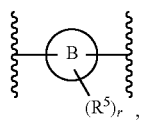

or a pharmaceutically acceptable salt thereof.

(6)" The compound according to any one of above (1)" to (5)", and (2A)", wherein Ring B is a 6-membered non-aromatic carbocycle or a 6-membered non-aromatic heterocycle, or a pharmaceutically acceptable salt thereof.

(7)" The compound according to any one of above (1)" to (6)" and (2A)", wherein
—W— is a group represented by:

[Chemical Formula 44]

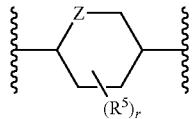

wherein Z is a carbon atom, an oxygen atom, or a nitrogen atom, and the other symbols are the same as defined above, or a pharmaceutically acceptable salt thereof.
(8)" The compound according to above (7)", wherein Z is a carbon atom or an oxygen atom,
or a pharmaceutically acceptable salt thereof.
(9)" The compound according to any one of above (1)" to (8)" and (2A)", wherein
$R^2$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.
(10)" The compound according to any one of above (1)" to (9)" and (2A)", wherein
$R^3$ is each independently halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonylamino, substituted or unsubstituted alkynylcarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocycly-loxy, substituted or unsubstituted non-aromatic carbocycly-loxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocycly-lamino, substituted or unsubstituted aromatic heterocycly-lamino, substituted or unsubstituted non-aromatic heterocy-clylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocycly-loxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbo-nylamino, substituted or unsubstituted non-aromatic carbo-cyclylcarbonylamino, or substituted or unsubstituted aromatic heterocyclylcarbonylamino,
or a pharmaceutically acceptable salt thereof.
(11)" The compound according to any one of above (1)" to (10)" and (2A)", wherein s is an integer of 1 to 3,
or a pharmaceutically acceptable salt thereof.
(12)" The compound according to any one of above (1)" to (11)" and (2A)", wherein

[Chemical Formula 45]

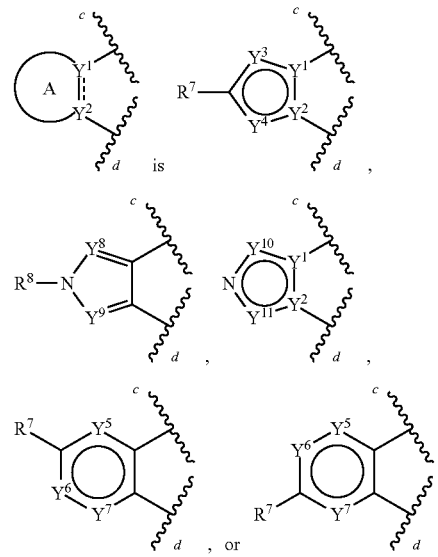

wherein,
a bonding hand "c" is bonded to $CR^{4a}R^{4b}$; a bonding hand "d" is bonded to $CR^{4c}R^{4d}$;
$Y^3$ and $Y^4$ are each independently $CR^{9a}$, N, $NR^8$, S, or O;
$Y^3$ and $Y^4$ are each independently $CR^{9a}$, N, $NR^8$, S, or O;
the ring constituted of $Y^1$ to $Y^4$ and a carbon atom is a 5-membered aromatic heterocycle, and 1 or 2 atoms constituting the 5-membered aromatic heterocycle are heteroatoms;
$Y^8$ and $Y^9$ are each independently $CR^{9a}$ or N; provided that $Y^8$ and $Y^9$ are not simultaneously both N;
$Y^{10}$ and $Y^{11}$ are each independently $CR^{9a}$ or $NR^8$; the ring constituted of $Y^1$, $Y^2$, $Y^{10}$, $Y^{11}$ and a nitrogen atom is a 5-membered aromatic heterocycle, and 1 or 2 atoms constituting the 5-membered aromatic heterocycle are heteroatoms;
$Y^5$ is $CR^{9b}$ or N; $Y^6$ is $CR^{9c}$ or N; $Y^7$ is $CR^{9d}$ or N; the ring constituted of $Y^5$ to $Y^7$ and carbon atoms is a 6-membered aromatic heterocycle; 1 or 2 atoms constituting the 6-membered aromatic heterocycle are heteroatoms;

$R^7$ is each independently a hydrogen atom, halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonyl amino, substituted or unsubstituted alkenylcarbonyl amino, substituted or unsubstituted alkynylcarbonyl amino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclyl amino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyl carbonyl oxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, or substituted or unsubstituted aromatic heterocyclylcarbonylamino;

$R^8$ is a hydrogen atom, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkylcarbonyl, substituted or unsubstituted alkenylcarbonyl, substituted or unsubstituted alkynylcarbonyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl;

$R^{9a}$ to $R^{9d}$ ore each independently a hydrogen atom, halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonylamino, substituted or unsubstituted alkynylcarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, or substituted or unsubstituted aromatic heterocyclylcarbonylamino, or a pharmaceutically acceptable salt thereof.

(12A)" The compound according to any one of above (1)" to (12)" and (2A)", wherein

[Chemical Formula 46]

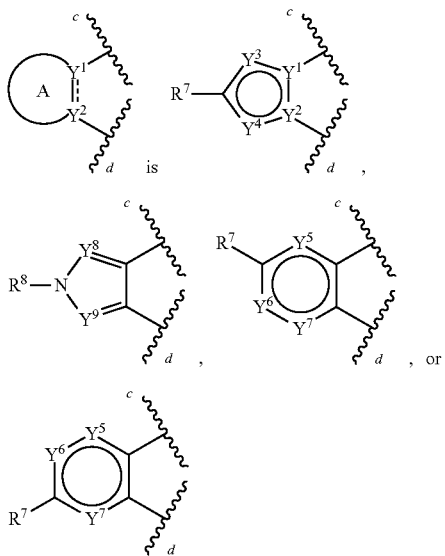

wherein each symbol is the same as defined in (12)", or a pharmaceutically acceptable salt thereof.

(13)" The compound according to any one of above (1)" to (12)", (2A)", and (12A)", wherein

[Chemical Formula 47]

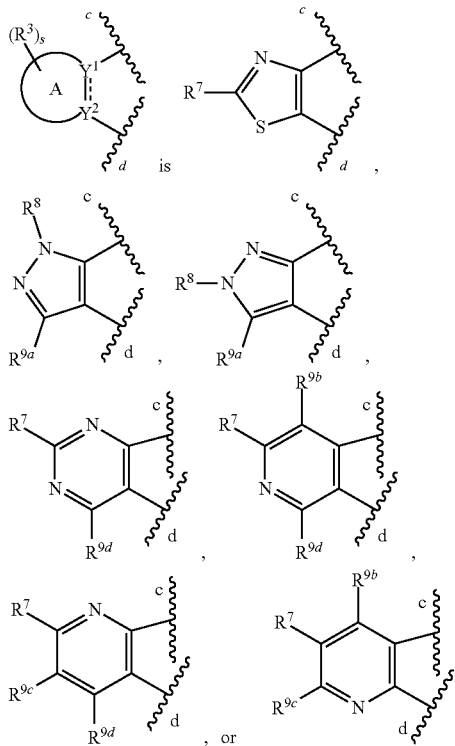

wherein each symbol is the same as defined in (12)", or a pharmaceutically acceptable salt thereof.

(14)" The compound according to any one of above (12)", (12A)", and (13)", wherein $R^7$ is each independently halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl, or a pharmaceutically acceptable salt thereof.

(15)" The compound according to any one of above (12)" to (14)" and (12A)", wherein $R^7$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, or a pharmaceutically acceptable salt thereof.

(16)" The compound according to any one of above (12)" to (15)", and (12A)", wherein $R^8$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

(17)" The compound according to any one of above (12)" to (16)", and (12A)" wherein $R^{9a}$ to $R^{9d}$ are each independently a hydrogen atom, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy, or a pharmaceutically acceptable salt thereof.

(18)" The compound according to any one of above (1)" to (17)", (2A)", and (12A)", wherein $R^{1a}$ and $R^{1b}$ are hydrogen atoms, or a pharmaceutically acceptable salt thereof.

(19)" The compound according to any one of above (1)" to (18)", (2A)", and (12A)", wherein $R^6$ is a hydrogen atom, or a pharmaceutically acceptable salt thereof.

(20)" The compound according to any one of above (1)" to (19)", (2A)", and (12A)", wherein n is 2, or a pharmaceutically acceptable salt thereof.

(21)" A pharmaceutical composition comprising the compound according to any one of above (1)" to (20)", (2A)", and (12A)" or a pharmaceutically acceptable salt thereof.

(22)" The pharmaceutical composition according to above (21)", wherein the composition is a dopamine D3 receptor antagonist.

(23)" The pharmaceutical composition according to above (21)" having an antagonistic activity for dopamine D3 receptor.

(26) The pharmaceutical composition according to any one of above (22), (23), (23A), (22)', (23)', (23A)', and (21)" to (23)" having effect for treating or preventing diseases associated with dopamine D3 receptor.

(27) The pharmaceutical composition according to any one of above (22), (23), (23A), (22)', (23)', (23A)', and (21)" to (23)" having effect for treating or preventing cognitive disorders, drug addiction, depression, anxiety, drug dependence, gambling addiction, dementias, memory impairment, schizophrenia, schizoaffective disorders, bipolar disorder, mania, psychotic disorders including psychotic depression, psychoses including paranoia and delusions, attention-deficit/hyperactivity disorder, addiction, and/or obsessive compulsive disorder.

(28) The pharmaceutical composition according to any one of above (22), (23), (23A), (22)', (23)', (23A)', and (21)" to (23)" having effect for treating or preventing attention-deficit/hyperactivity disorder.

(29) A method for treating or preventing diseases associated with D3 receptor comprising administering the compound according to any one of above (1) to (21), (21A), (21B), (1)' to (21)'. (2A)', (12A)', (1)" to (20)", (2A)", and (12A)", or a pharmaceutically acceptable salt thereof.

(30) A method for treating or preventing cognitive disorders, drug addiction, depression, anxiety, drug dependence, gambling addiction, dementias, memory impairment, schizophrenia, schizoaffective disorders, bipolar disorder, mania, psychotic disorders including psychotic depression, psychoses including paranoia and delusions, attention-deficit/hyperactivity disorder, addiction, and/or obsessive compulsive disorder comprising administering the compound according to any one of above (1) to (21), (21A), (21B), (1)' to (21)', (2A)', (12A)', (1)" to (20)", (2A)", and (12A)", or a pharmaceutically acceptable salt thereof.

(31) A method for treating or preventing attention-deficit/hyperactivity disorder comprising administering the compound according to any one of above (1) to (21), (21A), (21B), (1)' to (21)', (2A)', (12A)', (1)" to (20)", (2A)", and (12A)", or a pharmaceutically acceptable salt thereof.

(32) Use of the compound according to any one of above (1) to (21), (21A), (21B), (1)' to (21)', (2A)', (12A)', (1)" to (20)", (2A)", and (12A)", or a pharmaceutically acceptable salt thereof for manufacturing a medicament for treating and/or preventing diseases associated with D3 receptor.

(33) Use of the compound according to any one of above (1) to (21), (21A), (21B), (1)' to (21)', (2A)', (12A)', (1)" to (20)", (2A)", and (12A)", or a pharmaceutically acceptable salt thereof for manufacturing a medicament for treating and/or preventing cognitive disorders, drug addiction, depression, anxiety, drug dependence, gambling addiction, dementias, memory impairment, schizophrenia, schizoaffective disorders, bipolar disorder, mania, psychotic disorders including psychotic depression, psychoses including paranoia and delusions, attention-deficit/hyperactivity disorder, addiction, and/or obsessive compulsive disorder.

(34) Use of the compound according to any one of above (1) to (21), (21A), (21R), (1)' to (21)', (2A)', (12A)', (1)" to (20)", (2A)", and (12A)", or a pharmaceutically acceptable salt thereof for manufacturing a medicament for treating and/or preventing attention-deficit/hyperactivity disorder.

(35) The compound according to any one of above (1) to (21), (21A), (21B), (1)' to (21)', (2A)', (12A)', (1)" to (20)", (2A)", and (12A)", or a pharmaceutically acceptable salt thereof for treating and/or preventing diseases associated with D3 receptor.

(36) The compound according to any one of above (1) to (21), (21A), (21B), (1)' to (21)', (2A)', (12A)', (1)" to (20)", (2A)", and (12A)", or a pharmaceutically acceptable salt thereof for treating and/or preventing cognitive disorders, drug addiction, depression, anxiety, drug dependence, gambling addiction, dementias, memory impairment, schizophrenia, schizoaffective disorders, bipolar disorder, mania, psychotic disorders including psychotic depression, psychoses including paranoia and delusions, attention-deficit/hyperactivity disorder, addiction, and/or obsessive compulsive disorder.

(37) The compound according to any one of above (1) to (21), (21A), (21B), (1)' to (21)', (2A)', (12A)', (1)" to (20)", (2A)", and (12A)", or a pharmaceutically acceptable salt thereof for treating and/or preventing attention-deficit/hyperactivity disorder.

(101) A pharmaceutical composition comprising the compound according to any one of the above (1) to (21), (21A), (21B), (1)' to (21)', (2A)', (12A)', (1)" to (20)", (2A)", and (12A)", or a pharmaceutically acceptable salt thereof, for oral administration.

(102) The pharmaceutical composition according to (101), which is a tablet, powder, granule, capsule, pill, film, suspension, emulsion, elixir, syrup, lemonade, spirit, aromatic water, extract, decoction or tincture.

(103) The pharmaceutical composition according to (102), which is a sugar-coated tablet, film-coated tablet, enteric-coated tablet, sustained-release tablet, troche tablet, sublingual tablet, buccal tablet, chewable tablet, orally dispersing tablet, dry syrup, soft capsule, micro capsule or sustained-release capsule.

(104) A pharmaceutical composition comprising the compound according to any one of the above (1) to (21), (21A), (21B), (1)' to (21)', (2A)', (12A)', (1)" to (20)", (2A)", (12A)", or a pharmaceutically acceptable salt thereof, for parenteral administration.
(105) The pharmaceutical composition according to (104), for dermal, subcutaneous, intravenous, intraarterial, intramuscular, intraperitoneal, transmucosal, inhalation, transnasal, ophthalmic, inner ear or vaginal administration.
(106) The pharmaceutical composition according to (104) or (105), which is injection, infusion, eye drop, nose drop, ear drop, aerosol, inhalation, lotion, impregnation, liniment, mouthwash, enema, ointment, plaster, jelly, cream, patch, cataplasm, external powder or suppository.
(107) A pharmaceutical composition comprising the compound according to any one of the above (1) to (21), (21A), (21B), (1)' to (21)', (2A)', (12A)', (1)" to (20)", (2A)", and (12A)", or a pharmaceutically acceptable salt thereof, for a pediatric or geriatric patient.

Effect of the Invention

The compounds of the present invention have antagonistic activity for D3 receptor, and and preferably have high D3/D2 selectivity, and are useful as an agent for treating or precenting diseases associated with D3 receptor.

BRIEF DESCRIPTION OF DRAWINGS

The FIGURE shows the test results of effect of suppressing impulsivity in rat of a compound I-085 (3 mg/kg, i.p.) and vehicle control group. The vertical axis shows the number of choices of the large reward during total 50-trials of 5 days.

MODE FOR CARRYING OUT THE INVENTION

Terms used in this description are explained below. Each term, unless otherwise indicated, has the same meaning when it is used alone or together with other terms.

The term "consist of" means having only components.
The term "comprise" means not restricting with components and not excluding undescribed factors.
"Halogen" includes a fluorine atom, a chlorine atom, a bromine atom and an iodine atom. A fluorine atom and a chlorine atom are preferable. A fluorine atom is more preferable.
"Alkyl" includes a C1 to C15, preferably C1 to C10, more preferably C1 to C6 and further preferably C1 to C4 linear or branched hydrocarbon group. For example, it includes methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.
A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.
"Alkenyl" includes a C2 to C15, preferably C2 to C10, more preferably C2 to C6 and further preferably C2 to C4 linear or branched hydrocarbon group having one or more double bond(s) at any position(s). For example, it includes vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl or butenyl.
"Alkynyl" includes a C2 to C10, preferably C2 to C8, more preferably C2 to C6 and further preferably C2 to C4 linear or branched hydrocarbon group having one or more triple bond(s) at any position(s). Furthermore, it may have double bond(s) at any position(s). For example, it includes ethynyl, propynyl, butynyl, pentynyl, hexynyl, heptynyl, octynyl, nonynyl, decynyl and the like.
A preferred embodiment of "alkynyl" is ethynyl, propynyl, butynyl or pentynyl.
"Aromatic carbocycle" means a cyclic aromatic hydrocarbon ring which is monocyclic or polycyclic having two or more rings. For example, it includes benzene ring, naphthalene ring, anthracene ring, phenanthrene Ring And the like.
A preferred embodiment of "aromatic carbocycle" is benzene ring.
"Aromatic carbocyclyl" means a cyclic aromatic hydrocarbon group which is monocyclic or polycyclic having two or more rings. For example, it includes phenyl, naphthyl, anthryl, phenanthryl and the like.
A preferred embodiment of "aromatic carbocyclyl" is phenyl.
"Non-aromatic carbocycle" means a cyclic saturated hydrocarbon ring or a cyclic unsaturated non-aromatic hydrocarbon ring, which is monocyclic or polycyclic having two or more rings. "Non-aromatic carbocycle", which is polycyclic having two or more rings, includes a fused ring wherein a non-aromatic carbocycle, which is monocyclic or polycyclic having two or more rings, is fused with a ring of the above "aromatic carbocycle".
In addition, the "non-aromatic carbocycle" also includes a ring having a bridge or a ring to form a spiro Ring As follows.

[Chemical Formula 48]

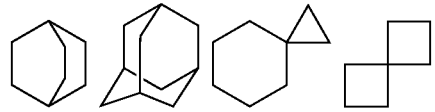

A non-aromatic carbocycle which is monocyclic is preferably C3 to C16, more preferably C3 to C12 and further preferably 03 to 06 carbocycle. For example, it includes cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclohexadiene and the like.
A non-aromatic carbocycle which is polycyclic having two or more rings includes, for example, indane, indene, acenaphthalene, tetrahydronaphthalene, fluorene and the like.
"Non-aromatic carbocyclyl" means a cyclic saturated hydrocarbon group or a cyclic unsaturated non-aromatic hydrocarbon group, which is monocyclic or polycyclic having two or more rings. "Non-aromatic carbocyclyl", which is polycyclic having two or more rings, includes a fused ring group wherein a non-aromatic carbocyclyl, which is monocyclic or polycyclic having two or more rings, is fused with a ring of the above "aromatic carbocyclyl".
In addition, the "non-aromatic carbocyclyl" also includes a group having a bridge or a group forming a spiro Ring As follows:

[Chemical Formula 49]

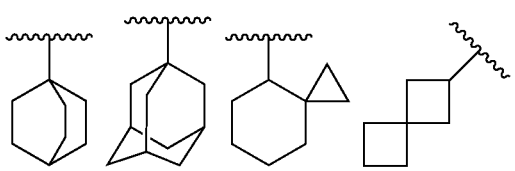

A non-aromatic carbocyclyl which is monocyclic is preferably C3 to C16, more preferably C3 to C12 and further preferably C3 to C6 carbocyclyl. For example, it includes cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

A non-aromatic carbocyclyl which is polycyclic having two or more rings includes, for example, indanyl, indenyl, acenapltlhyl, tetrahydronaphthyl, fluorenyl and the like.

"Aromatic heterocycle" means an aromatic ring, which is monocyclic or polycyclic having two or more rings, containing one or more, same or different, heteroatom(s) selected independently from O, S and N.

"Aromatic heterocycle", which is polycyclic having two or more rings, includes a fused ring wherein an aromatic heterocycle, which is monocyclic or polycyclic having two or more rings, is fused with a ring of the above "aromatic carbocycle".

An aromatic heterocycle which is monocyclic is preferably a 5- to 8-membered and more preferably 5- to 6-membered ring. For example, it includes "5-membered aromatic heterocycle" such as pyrrole, imidazole, pyrazole, triazole, tetrazole, furan, thiophene, isoxazole, oxazole, oxadiazole, isothiazole, thiazole, thiadiazole and the like, and "6-membered aromatic heterocycle" such as pyridine, pyridazine, pyrimidine, pyrazine, triazine, and the like.

An aromatic heterocycle which is bicyclic includes, for example, indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, pyrazolopyridin, imidazopyridine, triazolopyridine, imidazothiazole, pyrazinopyridazine, oxazolopyridine, thiazolopyridine and the like.

An aromatic heterocycle which is polycyclic having three or more rings includes, for example, carbazole, acridine, xanthene, phenothiazine, phenoxathiine, phenoxazine, dibenzofuran and the like.

"Aromatic heterocyclyl" means an aromatic cyclyl, which is monocyclic or polycyclic having two or more rings, containing one or more, same or different heteroatom(s) selected independently from O, S and N.

"Aromatic heterocyclyl", which is polycyclic having two or more rings, includes a fused ring group wherein an aromatic heterocyclyl, which is monocyclic or polycyclic having two or more rings, is fused with a ring of the above "aromatic carbocyclyl".

An aromatic heterocyclyl which is monocyclic is preferably a 5- to 8-membered and more preferably 5- to 6-membered ring. For example, it includes pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like.

An aromatic heterocyclyl which is bicyclic includes, for example, indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, pyrazolopyridyl, imidazopyridyl, triazolopyridyl, imidazothiazolyl, pyrazinopyridazinyl, oxazolopyridyl, thiazolopyridyl and the like.

An aromatic heterocyclyl which is polycyclic having three or more rings includes, for example, carbazolyl, acridinyl, xanthenyl, phenothiazinyl, phenoxathiinyl, phenoxazinyl, dibenzofuryl and the like.

"Non-aromatic heterocycle" means a non-aromatic ring, which is monocyclic or polycyclic having two or more rings, containing one or more, same or different, heteroatom(s) selected independently from O, S and N.

"Non-aromatic heterocycle", which is polycyclic having two or more rings, includes a fused ring wherein a non-aromatic heterocycle, which is monocyclic or polycyclic having two or more ring(s), is fused with a ring of the above "aromatic carbocycle", "non-aromatic carbocycle" and/or "aromatic heterocycle". The non-aromatic heterocycle, which is polycyclic having two or more rings, further includes a fused ring wherein an aromatic heterocycle, which is monocyclic or polycyclic having two or more rings, is fused with a ring of the above "non-aromatic carbocycle".

In addition, the "non-aromatic heterocycle" also includes a ring having a bridge or a ring forming a spiro Ring As follows.

[Chemical Formula 50]

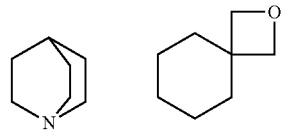

A non-aromatic heterocycle which is monocyclic is preferably a 3- to 8-membered, more preferably 3 to a 6-membered, and more preferably 5- to 6-membered ring. For example, it includes
"5-membered non-aromatic heterocycle" such as thiazolidine, pyrrolidine, pyrroline, imidazolidine, imidazoline, pyrazolidine, pyrazoline, tetrahydrofuran, dihydrothiazole, tetrahydrothiazole, tetrahydroisothiazole, dioxolane, dioxoline and the like,
"6-membered non-aromatic heterocycle" such as dioxane, thiane, piperidine, piperazine, morpholine, thiomorpholine, dihydropyridine, tetrahydropyridine, tetrahydropyran, dihydrooxazine, tetrahydropyridazine, hexahydropyrimidine, thiazine and the like, and,
thiirane, oxirane, oxetane, oxathiolane, azetidine, hexahydroazepine, tetrahydrodiazepine, dioxazine, aziridine, oxepane, thiolane, thiine and the like.

A non-aromatic heterocycle which is polycyclic having two or more rings includes, for example, indoline, isoindoline, chromane, isochromane, dihydrobenzofuran, dihydroisobenzofuran, dihydroquinoline, dihydroisoquinoline, tetrahydroquinoline, tetrahydroisoquinoline and the like.

"Non-aromatic heterocyclyl" means a non-aromatic cyclyl, which is monocyclic or polycyclic having two or more rings, containing one or more, same or different, heteroatom(s) selected independently from O, S and N.

"Non-aromatic heterocyclyl", which is polycyclic having two or more rings, includes a fused ring group wherein a non-aromatic heterocycle, which is monocyclic or polycyclic having two or more ring(s), is fused with a ring of the above "aromatic carbocyclyl", "non-aromatic carbocyclyl" and/or "aromatic heterocyclyl". In addition, the "non-aromatic heterocyclyl" also includes a group having a bridge or a group forming a spiro Ring As follows:

[Chemical Formula 51]

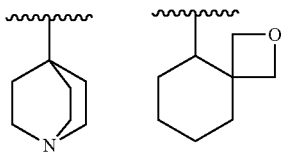

A non-aromatic heterocyclyl which is monocyclic is preferably a 3- to 8-membered and more preferably 5- to 6-membered ring. For example, it includes dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidinyl, piperazinyl, morpholinyl, morpholine, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, thiazinyl and the like.

A non-aromatic heterocyclyl which is polycyclic having two or more rings includes, for example, indolinyl, isoindolinyl, chromanyl, isochromanyl dihydrobenzofuryl, dihydroisobenzofuryl, dihydroquinolyl, dihydroisoquinolyl, tetrahydroquinolyl, tetrahydroisoquinolyl and the like.

"Hydroxy alkyl" means a group wherein hydrogen atom(s) bonded to carbon atom(s) of above "alkyl" is replaced with one or more hydroxy groups. For example, it includes hydroxymethyl, 1-hydroxyethyl, 2-hydroxyethyl, 1-hydroxypropyl, 2-hydroxypropyl, 1,2-hydroxyethyl and the like.

A preferred embodiment of "hydroxy alkyl" is hydroxymethyl.

"Alkyloxy" means a group wherein the above "alkyl" is bonded to an oxygen atom. For example, it includes methyloxy, ethyloxy, n-propyloxy, isopropyloxy, n-butyloxy, tert-butyloxy, isobutyloxy, sec-butyloxy, pentyloxy, isopentyloxy, hexyloxy and the like.

A preferred embodiment of "alkyloxy" is methyloxy, ethyloxy, n-propyloxy, isopropyloxy or tert-butyloxy.

"Alkenyloxy" means a group wherein the above "alkenyl" is bonded to an oxygen atom. For example, it includes vinyloxy, allyloxy, 1-propenyloxy, 2-butenyloxy, 2-pentenyloxy, 2-hexenyloxy, 2-heptenyloxy, 2-octenyloxy and the like.

"Alkynyloxy" means a group wherein the above "alkynyl" is bonded to an oxygen atom. For example, it includes ethynyloxy, 1-propynyloxy, 2-propynyloxy, 2-butynyloxy, 2-pentynyloxy, 2-hexynyloxy, 2-heptynyloxy, 2-octynyloxy and the like.

"Haloalkyl" means a group wherein one or more "halogen" described above is bonded to the above "alkyl". For example, it includes monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropan-2-yl and the like.

A preferred embodiment of "haloalkyl" is trifluoromethyl or trichloromethyl.

"Haloalkyloxy" means a group wherein the above "haloalkyl" is bonded to an oxygen atom. For example, it includes monofluoromethoxy, monofluoroethoxy, trifluoromethoxy, trichloromethoxy, trifluoroethoxy, trichloroethoxy and the like.

A preferred embodiment of "haloalkyloxy" is trifluoromethoxy or trichloromethoxy.

"Alkylcarbonyl" means a group wherein the above "alkyl" is bonded to a carbonyl group. For example, it includes methylcarbonyl, ethylcarbonyl, propylcarbonyl, isopropylcarbonyl, tert-butylcarbonyl, isobutylcarbonyl, sec-butylcarbonyl, pentylcarbonyl, isopenthylcarbonyl, hexylcarbonyl and the like.

A preferred embodiment of "alkylcarbonyl" is methylcarbonyl, ethylcarbonyl or n-propylcarbonyl.

"Alkenylcarbonyl" means a group wherein the above "alkenyl" is bonded to a carbonyl group. For example, it includes ethylenylcarbonyl, propenylcarbonyl and the like.

"Alkynylcarbonyl" means a group wherein the above "alkynyl" is bonded to a carbonyl group. For example, it includes ethynylcarbonyl, propynylcarbonyl and the like.

"Alkylamino" includes "monoalkylamino" and "dialkylamino".

"Monoalkylamino" means a group wherein a hydrogen atom bonded to a nitrogen atom of an amino group is replaced with the above "alkyl". For example, it includes methylamino, ethylamino, isopropylamino and the like.

A preferred embodiment of "monoalkylamino" is methylamino or ethylamino.

"Dialkylamino" means a group wherein two hydrogen atoms bonded to a nitrogen atom of an amino group are replaced with two above "alkyl". These two alkyl groups may be the same or different. For example, it includes dimethylamino, diethylamino, N,N-diisopropylamino, N-methyl-N-ethylamino, N-isopropyl-N-ethylamino, and the like.

A preferred embodiment of "dialkylamino" is dimethylamino or diethylamino.

"Alkylsulfonyl" means a group wherein the above "alkyl" is bonded to a sulfonyl group. For example, it includes methylsulfonyl, ethylsulfonyl, propylsulfonyl, isopropylsulfonyl, tert-butylsulfonyl, isobutylsulfonyl, sec-butylsulfonyl and the like.

A preferred embodiment of "alkylsulfonyl" is methylsulfonyl or ethylsulfonyl.

"Alkenylsulfonyl" means a group wherein the above "alkenyl" is bonded to a sulfonyl group. For example, it includes ethylenylsulfonyl, propenylsulfonyl and the like.

"Alkynylsulfonyl" means a group wherein the above "alkynyl" is bonded to a sulfonyl group. For example, it includes ethynylsulfonyl, propynylsulfonyl and the like.

"Alkylcarbonylamino" includes "monoalkylcarbonylamino" and "dialkylcarbonylamino".

"Monoalkylcarbonylamino" means a group wherein a hydrogen atom bonded to a nitrogen atom of an amino group is replaced with the above "alkylcarbonyl". For example, it includes methylcarbonylamino, ethylcarbonylamino, propylcarbonylamino, isopropylcarbonylamino, tert-butylcarbonylamino, isobutylcarbonylamino, sec-butylcarbonylamino and the like.

A preferred embodiment of "monoalkylcarbonylamino" is methylcarbonylamino or ethylcarbonylamino.

"Dialkylcarbonylamino" includes a group wherein two hydrogen atoms bonded to a nitrogen atom of an amino group are replaced with two above "alkylcarbonyl". These two alkylcarbonyl groups may be the same or different. For example, it includes dimethylcarbonylamino, diethylcarbonylamino, N,N-diisopropylcarbonylamino, and the like.

A preferred embodiment of "dialkylcarbonylamino" is dimethylcarbonylamino or diethylcarbonylamino.

"Alkylimino" means a group wherein a hydrogen atom bonded to a nitrogen atom of an imino group is replaced with the above "alkyl". For example, it includes methylimino, ethylimino, n-propylimino, isopropylimino and the like.

"Alkyloxyimino" means a group wherein a hydrogen atom bonded to a nitrogen atom of an imino group is replaced with the above"alkyloxy". For example, it includes methyloxyimino, ethyloxyimino, n-propyloxyimino, isopropyloxyimino and the like.

"Alkylsulfonylamino" includes "monoalkylsulfonylamino" and "dialkylsulfonylamino".

"Monoalkylsulfonylamino" means a group wherein a hydrogen atom bonded to a nitrogen atom of an amino group is replaced with the above "alkylsulfonyl".

For example, it includes methylsulfonylamino, ethylsulfonylamino, propylsulfonylamino, isopropylsulfonylamino, tert-butylsulfonylamino, isobutylsulfonylamino and sec-butylsulfonylamino.

A preferred embodiment of "monoalkylsulfonylamino" is methylsulfonylamino or ethylsulfonylamino.

"Dialkylsulfonylamino" means a group wherein two hydrogen atoms attached to a nitrogen atom of an amino group are replaced with two above "alkylsulfonyl". These two alkylsulfonyl groups may be the same or different. For examples, it includes dimethylsulfonylamino, diethylsulfonylamino, N,N-diisopropylsulfonylamino and the like.

A preferred embodiment of "dialkylsulfonylamino" is dimethylsulfonylamino or diethylsulfonylamino.

"Alkylcarbonyloxy" means a group wherein the above "alkylcarbonyl" is bonded to an oxygen atom. For example, it includes methylcarbonyloxy, ethylcarbonyloxy, propylcarbonyloxy, isopropylcarbonyloxy, tert-butylcarbonyloxy, isobutylcarbonyloxy, sec-butylcarbonyloxy and the like.

A preferred embodiment of "alkylcarbonyloxy" is methylcarbonyloxy or ethylcarbonyloxy.

"Alkenylcarbonyloxy" means a group wherein the above "alkenylcarbonyl" is bonded to an oxygen atom. For example, it includes ethylenylcarbonyloxy, propenylcarbonyloxy and the like.

"Alkynylcarbonyloxy" moans a group wherein the above "alkynylcarbonyl" is bonded to an oxygen atom. For example, it includes ethynylcarbonyloxy, propynylcarbonyloxy and the like.

"Alkyloxycarbonyl" means a group wherein the above "alkyloxy" is bonded to a carbonyl group. For example, it includes methyloxycarbonyl, ethyloxycarbonyl, propyloxycarbonyl, isopropyloxycarbonyl, tert-butyloxycarbonyl, isobutyloxycarbonyl, sec-butyloxycarbonyl, penthyloxycarbonyl, isopenthyloxycarbonyl, hexyloxycarbonyl and the like.

A preferred embodiment of "alkyloxycarbonyl" is methyloxycarbonyl, ethyloxycarbonyl or propyloxycarbonyl.

"Alkenyloxycarbonyl" means a group wherein the above "alkenyloxy" is bonded to a carbonyl group. For example, it includes ethylenyloxycarbonyl, propenyloxycarbonyl and the like.

"Alkynyloxycarbonyl" means a group wherein the above "alkynyloxy" is bonded to a carbonyl group. For example, it includes ethynyloxycarbonyl, propynyloxycarbonyl and the like.

"Alkylsulfanyl" means a group wherein a hydrogen atom bonded to a sulfur atom of a sulfanyl group is replaced with the above "alkyl". For example, it includes methylsulfanyl, ethylsulfanyl, n-propylsulfanyl, isopropylsulfanyl and the like.

"Alkenylsulfanyl" means a group wherein a hydrogen atom bonded to a sulfur atom of a sulfanyl group is replaced with the above "alkenyl". For example, it includes ethylenylsulfanyl, propenylsulfanyl and the like.

"Alkynylsulfanyl" means a group wherein a hydrogen atom bonded to a sulfur atom of a sulfanyl group is replaced with the above "alkynyl". For example, it includes ethynylsulfanyl, propynylsulfanyl and the like.

"Alkylsulfinyl" means a group wherein the above "alkyl" is bonded to a sulfinyl group. For example, it includes methylsulfinyl, ethylsulfinyl, n-propylsulfinyl, isopropylsulfinyl, and the like.

"Alkenylsulfinyl" means a group wherein the above "alkenyl" is bonded to a sulfinyl group. For example, it includes ethylenylsulfinyl, propenylsulfinyl and the like.

"Aalkynylsulfinyl" means a group wherein the above "alkynyl" is bonded to a sulfinyl group. For example, it includes ethynylsulfinyl, propynylsulfinyl and the like.

"Alkylcarbamoyl" includes "monoalkylcarbamoyl" and "dialkylcarbamoyl".

"Monoalkylcarbamoyl" means a group wherein a hydrogen atom bonded to a nitrogen atom of a carbamoyl group is replaced with the above "alkyl". For example, it includes methylcarbamoyl, ethylcarbamoyl and the like.

"Dialkylcarbamoyl" means a group wherein two hydrogen atoms bonded to a nitrogen atom of a carbamoyl group are replaced with two above "alkyl". These two alkyl groups may be the same or different. For example, it includes dimethylcarbamoyl, diethylcarbamoyland the like.

"Alkylsulfamoyl" includes "monoalkylsulfamoyl" and "dialkylsulfamoyl".

"Monoalkylsulfamoyl" means a group wherein a hydrogen atom bonded to a nitrogen atom of a sulfamoyl group is replaced with the above "alkyl". For examples, it includes methylsulfamoyl, dimethylsulfamoyl and the like.

"Dialkylsulfamoyl" means a group wherein two hydrogen atoms bonded to a nitrogen atom of a sulfamoyl group are replaced with two above "alkyl". These two alkyl groups may be the same or different. For example, it includes dimethylsulfamoyl, diethylsulfamoyl and the like.

The alkyl portion of "aromatic carbocyclylalkyl", "non-aromatic carbocyclylalkyl", "aromatic heterocyclylalkyl", and "non-aromatic heterocyclylalkyl" means the same as above "alkyl".

"Aromatic carbocyclylalkyl" means alkyl substituted with one or more above "aromatic carbocyclyl". For example, it includes benzyl, phenethyl, phenylpropyl, benzhydryl, trityl, naphthylmethyl, a group of the formula of

[Chemical Formula 52]

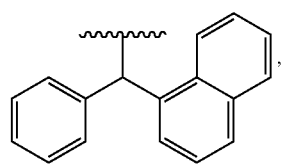

and the like.

A preferred embodiment of "aromatic carbocyclylalkyl" is benzyl, phenethyl or benzhydryl.

"Non-aromatic carbocyclylalkyl" means alkyl substituted with one or more above "non-aromatic carbocyclyl". Also, "non-aromatic carbocyclylalkyl" includes a "non-aromatic carbocyclyl alkyl" wherein the alkyl portion thereof is substituted with one or more above "aromatic carbocyclyl". For example, it includes cyclopropylmethyl, cyclobutyl methyl, cyclopentylmethyl, cyclohexylmethyl, a group of

[Chemical Formula 53]

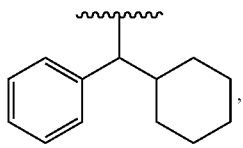

and the like.

"Aromatic heterocyclylalkyl" means alkyl substituted with one or more above "aromatic heterocyclyl". Also, "aromatic heterocyclylalkyl" includes "aromatic heterocyclyl alkyl" wherein the alkyl portion thereof is substituted with one or more above "aromatic carbocyclyl", and/or "non-aromatic carbocyclyl". For example, it includes pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, groups of the formula of

[Chemical Formula 54]

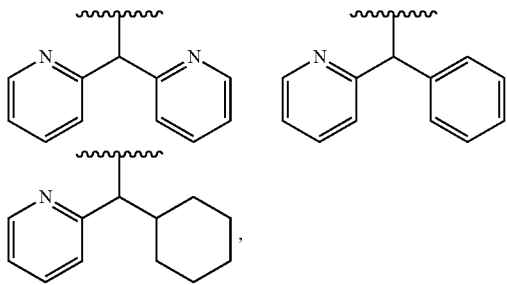

and the like.

"Non-aromatic heterocyclylalkyl" means alkyl substituted with one or more above "non-aromatic heterocyclyl". Also, "non-aromatic heterocyclylalkyl" includes a "non-aromatic heterocyclylalkyl" wherein the alkyl portion thereof is substituted with one or more above "aromatic carbocyclyl", "non-aromatic carbocyclyl" and/or "aromatic heterocyclyl". For example, it includes tetrahydropyranylmethyl, morpholinylmethyl, morpholinylethyl, piperidinylmethyl, piperazinylmethyl, groups of the formula of

[Chemical Formula 55]

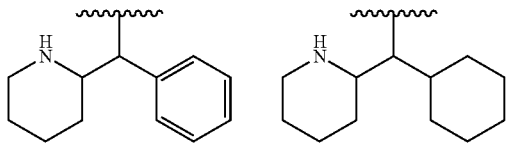

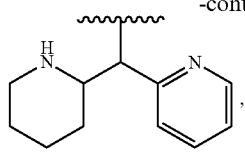

and the like.

The "aromatic carbocycle" portion of "aromatic carbocyclyloxy", "aromatic carbocyclylamino", "aromatic carbocyclylsulfanyl", "aromatic carbocyclylcarbonyl", "aromatic carbocyclylsulfonyl", "aromatic carbocyclylcarbonyloxy", "aromatic carbocyclylsulfonyloxy", "aromatic carbocycly-loxycarbonyl", "aromatic carbocyclyloxysulfonyl", "aromatic carbocyclylcarbamoyl", "aromatic carbocyclylsulfamoyl", "aromatic carbocyclylcarbonylamino", "aromatic carbocyclylsulfonylamino", and "aromatic carbocyclyloxycarbonylamino" is the same as above "aromatic carbocyclyl".

"Aromatic carbocyclyloxy" means a group wherein "aromatic carbocycle" is bonded to an oxygen atom. For example, it includes phenyloxy, naphthyloxy and the like.

"Aromatic carbocyclylamino" means a group wherein a hydrogen atom attached to a nitrogen atom of an amino group is replaced with the "aromatic carbocycle". For example, it includes phenylamino, naphthylamino and the like. Another hydrogen atom bonded to the nitrogen atom of the amino group may be replaced with the above "alkyl".

"Aromatic carbocyclylsulfanyl" means a group wherein a hydrogen atom bonded to a sulfur atom of a sulfanyl group is replaced with "aromatic carbocycle". For example, it includes phenylsulfanyl, naphthylsulfanyl and the like.

"Aromatic carbocyclylcarbonyl" means a group wherein "aromatic carbocycle" is bonded to a carbonyl group. For example, it includes phenylcarbonyl, naphthylcarbonyl and the like.

"Aromatic carbocyclylsulfonyl" means a group wherein "aromatic carbocycle" is bonded to a sulfonyl group. For example, it includes phenylsulfonyl, naphthylsulfonyl and the like.

"Aromatic carbocyclylcarbonyloxy" means a group wherein the above "aromatic carbocyclylcarbonyl" is bonded to an oxygen atom. For example, it includes phenylcarbonyloxy, naphthylcarbonyloxy and the like.

"Aromatic carbocyclylsulfonyloxy" means a group wherein the above "aromatic carbocyclylsulfonyl" is bonded to an oxygen atom. For example, it includes phenylsulfonyloxy, naphthylsulfonyloxy and the like.

"Aromatic carbocyclyloxycarbonyl" means a group wherein the above "aromatic carbocyclyloxy" is bonded to a carbonyl group. For example, it includes phenyloxycarbonyl, naphthyloxycarbonyl and the like.

"Aromatic carbocyclyloxysulfonyl" means a group wherein the above "aromatic carbocyclyloxy" is bonded to a sulfonyl group. For example, it includes phenyloxysulfonyl, naphthyloxysulfonyl and the like.

"Aromatic carbocyclylcarbamoyl" means a group wherein a hydrogen atom bonded to a nitrogen atom of a carbamoyl group is replaced with the "aromatic carbocycle". For example, it includes phenylcarbamoyl, naphthylcarbamoyl and the like. Another hydrogen atom bonded to the nitrogen atom of the carbamoyl group may be replaced with the above "alkyl".

"Aromatic carbocyclylsulfamoyl" means a group wherein a hydrogen atom bonded to a nitrogen atom of a sulfamoyl group is replaced with the "aromatic carbocycle". For example, it includes phenylsulfamoyl, naphthylsulfamoyl and the like. Another hydrogen atom bonded to the nitrogen atom of the sulfamoyl group may be replaced with the above "alkyl".

"Aromatic carbocyclylcarbonylamino" means a group wherein a hydrogen atom attached to a nitrogen atom of an amino group is replaced with the above "aromatic carbocyclylcarbonyl". For example, it includes phenylcarbonylamino, naphthylcarbonyl amino and the like. Another hydrogen atom bonded to the nitrogen atom of the amino group may be replaced with the above "alkyl".

"Aromatic carbocyclylsulfonylamino" means a group wherein a hydrogen atom bonded to a nitrogen atom of an amino group is replaced with the above "aromatic carbocyclylsulfonyl". For example, it includes phenylsulfonylamino, naphthylsulfonylamino and the like. Another hydrogen atom bonded to the nitrogen atom of the amino group may be replaced with the above "alkyl".

"Aromatic carbocyclyloxycarbonylamino" means a group wherein a hydrogen atom attached to a nitrogen atom of an amino group is replaced with the above "aromatic carbocyclyloxycarbonyl". For example, it includes phenyloxycarbonylamino, naphthyloxycarbonylamino and the like. Another hydrogen atom bonded to the nitrogen atom of the amino group may be replaced with the above "alkyl".

The "non-aromatic carbocycle" portion of "non-aromatic carbocyclyloxy", "non-aromatic carbocyclylamino", "non-aromatic carbocyclylsulfanyl", "non-aromatic carbocyclylcarbonyl", "non-aromatic carbocyclylsulfonyl", "non-aromatic carbocyclylcarbonyloxy", "non-aromatic carbocyclylsulfonyloxy", "non-aromatic carbocyclyloxycarbonyl", "non-aromatic carbocyclyloxysulfonyl", "non-aromatic carbocyclylcarbamoyl", "non-aromatic carbocyclylsulfamoyl", "non-aromatic carbocyclylcarbonyl amino", "non-aromatic carbocyclylsulfonylamino", and "non-aromatic carbocyclyl oxycarbonylamino" is the same as the above "non-aromatic carbocyclyl".

"Non-aromatic carbocyclyloxy" means a group wherein "non-aromatic carbocycle" is bonded to an oxygen atom. For example, it includes cyclopropyloxy, cyclohexyloxy, cyclohexenyloxy and the like.

"Non-aromatic carbocyclylamino" means a group wherein a hydrogen atom attached to a nitrogen atom of an amino group is replaced with the "non-aromatic carbocycle". For example, it includes cyclopropylamino, cyclohexylamino, cyclohexenylamino and the like. Another hydrogen atom bonded to the nitrogen atom of the amino group may be replaced with the above "alkyl".

"Non-aromatic carbocyclylsulfanyl" means a group wherein a hydrogen atom bonded to a sulfur atom of a sulfanyl group is replaced with "non-aromatic carbocycle". For example, it includes cyclopropylsulfanyl, cyclohexylsulfanyl, cyclohexenylsulfanyl and the like.

"Non-aromatic carbocyclylcarbonyl" means a group wherein "non-aromatic carbocycle" is bonded to a carbonyl group. For example, it includes cyclopropylcarbonyl, cyclohexylcarbonyl, cyclohexenylcarbonyl and the like.

"Non-aromatic carbocyclylsulfonyl" means a group wherein "non-aromatic carbocycle" is bonded to a sulfonyl group. For example, it includes cyclopropylsulfonyl, cyclohexylsulfonyl, cyclohexenylsulfonyl and the like.

"Non-aromatic carbocyclylcarbonyloxy" means a group wherein the above "non-aromatic carbocyclylcarbonyl" is bonded to an oxygen atom. For example, it includes cyclopropylcarbonyloxy, cyclohexylcarbonyloxy, cyclohexenylcarbonyloxy and the like.

"Non-aromatic carbocyclylsulfonyloxy" means a group wherein the above "non-aromatic carbocyclylsulfonyl" is bonded to an oxygen atom. For example, it includes cyclopropylsulfonyloxy, cyclohexylsulfonyloxy, cyclohexcnylsulfonyloxy and the like.

"Non-aromatic carbocyclyloxycarbonyl" means a group wherein the above "non-aromatic carbocyclyloxy" is bonded to a carbonyl group. For example, it includes cyclopropyloxycarbonyl, cyclohexyloxycarbonyl, cyclohexenyloxycarbonyl and the like.

"Non-aromatic carbocyclyloxysulfonyl" means a group wherein the above "non-aromatic carbocyclyloxy" is bonded to a sulfonyl group. For example, it includes cyclopropyloxysulfonyl, cyclohexyloxysulfonyl, cyclohexenyloxysulfonyl and the like.

"Non-aromatic carbocyclylcarbamoyl" means a group wherein a hydrogen atom bonded to a nitrogen atom of a carbamoyl group is replaced with the "non-aromatic carbocycle". For example, it includes cyclopropyl carbamoyl, cyclohexyl carbamoyl, cyclohexenylcarbamoyl and the like. Another hydrogen atom bonded to the nitrogen atom of the carbamoyl group may be replaced with the above "alkyl".

"Non-aromatic carbocyclylsulfamoyl" means a group wherein a hydrogen atom bonded to a nitrogen atom of a sulfamoyl group is replaced with the "non-aromatic carbocycle". For example, it includes cyclopropylsulfamoyl, cyclohexylsulfamoyl, cyclohexenylsulfamoyl and the like. Another hydrogen atom bonded to the nitrogen atom of the sulfamoyl group may be replaced with the above "alkyl".

"Non-aromatic carbocyclylcarbonylamino" means a group wherein a hydrogen atom attached to a nitrogen atom of an amino group is replaced with the above "non-aromatic carbocyclylcarbonyl". For example, it includes cyclopropylcarbonylamino, cyclohexylcarbonylamino, cyclohexenylcarbonylamino and the like. Another hydrogen atom bonded to the nitrogen atom of the amino group may be replaced with the above "alkyl".

"Non-aromatic carbocyclylsulfonylamino" means a group wherein a hydrogen atom bonded to a nitrogen atom of an amino group is replaced with the above "non-aromatic carbocyclyl sulfonyl". For example, it includes cyclopropyl sulfonyl amino, cyclohexylsulfonylamino, cyclohexenylsulfonylamino and the like. Another hydrogen atom bonded to the nitrogen atom of the amino group may be replaced with the above "alkyl".

"Non-aromatic carbocyclyloxycarbonylamino" means a group wherein a hydrogen atom attached to a nitrogen atom of an amino group is replaced with the above "non-aromatic carbocyclyloxycarbonyl". For example, it includes cyclopropyloxycarbonylamino, cyclohexyloxycarbonylamino, cyclohexenyloxycarbonylamino and the like. Another hydrogen atom bonded to the nitrogen atom of the amino group may be replaced with the above "alkyl".

The "aromatic heterocycle" portion of "aromatic heterocyclyloxy", "aromatic heterocyclylamino", "aromatic heterocyclylsulfanyl", "aromatic heterocyclylcarbonyl", "aromatic heterocyclylsulfonyl", "aromatic heterocyclylcarbonyloxy", "aromatic heterocyclylsulfonyloxy", "aromatic heterocyclyloxycarbonyl", "aromatic heterocyclyloxysulfonyl", "aromatic heterocyclylcarbamoyl", "aromatic heterocyclylsulfamoyl", "aromatic heterocyclylcarbonylamino", "aromatic heterocyclylsulfonylamino", and "aromatic heterocyclyloxycarbonylamino" is the same as above "aromatic heterocyclyl".

"Aromatic heterocyclyloxy" means a group wherein "aromatic heterocycle" is bonded to an oxygen atom. For example, it includes pyridyloxy, oxazolyloxy and the like.

"Aromatic heterocyclylamino" means a group wherein a hydrogen atom attached to a nitrogen atom of an amino group is replaced with the "aromatic heterocycle". For example, it includes pyridylamino, oxazolylamino and the like. Another hydrogen atom bonded to the nitrogen atom of the amino group may be replaced with the above "alkyl".

"Aromatic heterocyclylsulfanyl" means a group wherein a hydrogen atom bonded to a sulfur atom of a sulfanyl group is replaced with "aromatic heterocycle". For example, it includes pyridylsulfanyl, oxazolylsulfanyl and the like.

"Aromatic heterocyclylcarbonyl" means a group wherein "aromatic heterocycle" is bonded to a carbonyl group. For example, it includes pyridylcarbonyl, oxazolylcarbonyl and the like.

"Aromatic heterocyclylsulfonyl" means a group wherein "aromatic heterocycle" is bonded to a sulfonyl group. For example, it includes pyridylsulfonyl, oxazolylsulfonyl and the like.

"Aromatic heterocyclylcarbonyloxy" means a group wherein the above "aromatic heterocyclylcarbonyl" is bonded to an oxygen atom. For example, it includes pyridylcarbonyloxy, oxazolylcarbonyloxy and the like.

"Aromatic heterocyclylsulfonyloxy" means a group wherein the above "aromatic heterocyclylsulfonyl" is bonded to an oxygen atom. For example, it includes pyridylsulfonyloxy, oxazolylsulfonyloxy and the like.

"Aromatic heterocyclyloxycarbonyl" means a group wherein the above "aromatic heterocyclyloxy" is bonded to a carbonyl group. For example, it includes pyridyloxycarbonyl, oxazolyloxycarbonyl and the like.

"Aromatic heterocyclyloxysulfonyl" means a group wherein the above "aromatic heterocyclyloxy" is bonded to a sulfonyl group. For example, it includes pyridyloxysulfonyl, oxazolyloxysulfonyl and the like.

"Aromatic heterocyclylcarbamoyl" means a group wherein a hydrogen atom bonded to a nitrogen atom of a carbamoyl group is replaced with the "aromatic heterocycle". For example, it includes pyridylcarbamoyl, oxazolylcarbamoyl and the like. Another hydrogen atom bonded to the nitrogen atom of the carbamoyl group may be replaced with the above "alkyl".

"Aromatic heterocyclylsulfamoyl" means a group wherein a hydrogen atom bonded to a nitrogen atom of a sulfamoyl group is replaced with the "aromatic heterocycle". For example, it includes pyridylsulfamoyl, oxazolylsulfamoyl and the like. Another hydrogen atom bonded to the nitrogen atom of the sulfamoyl group may be replaced with the above "alkyl".

"Aromatic heterocyclylcarbonylamino" means a group wherein a hydrogen atom attached to a nitrogen atom of an amino group is replaced with the above "aromatic heterocyclylcarbonyl". For example, it includes pyridylcarbonylamino, oxazolylcarbonylamino and the like. Another hydrogen atom bonded to the nitrogen atom of the amino group may be replaced with the above "alkyl".

"Aromatic heterocyclylsulfonylamino" means a group wherein a hydrogen atom bonded to a nitrogen atom of an amino group is replaced with the above "aromatic heterocyclylsulfonyl". For example, it includes pyridylsulfonylamino, oxazolylsulfonylamino and the like. Another hydrogen atom bonded to the nitrogen atom of the amino group may be replaced with the above "alkyl".

"Aromatic heterocyclyloxycarbonylamino" means a group wherein a hydrogen atom attached to a nitrogen atom of an amino group is replaced with the above "aromatic heterocyclyloxycarbonyl". For example, it includes pyridyloxycarbonyl amino, oxazolyloxycarbonylamino and the like. Another hydrogen atom bonded to the nitrogen atom of the amino group may be replaced with the above "alkyl".

The "non-aromatic heterocyclyl" portion of "non-aromatic heterocyclyloxy", "non-aromatic heterocyclylamino", "non-aromatic heterocyclylsulfanyl", "non-aromatic heterocyclylcarbonyl", "non-aromatic heterocyclylsulfonyl", "non-aromatic heterocyclylcarbonyloxy", "non-aromatic heterocyclylsulfonyloxy", "non-aromatic heterocyclyloxycarbonyl", "non-aromatic heterocyclyloxysulfonyl", "non-aromatic heterocyclylcarbamoyl", "non-aromatic heterocyclylsulfamoyl", "non-aromatic heterocyclylcarbonylamino", "non-aromatic heterocyclylsulfonylamino", and "non-aromatic heterocyclyloxycarbonylamino" is the same as above "non-aromatic heterocyclyl".

"Non-aromatic heterocyclyloxy" means a group wherein "non-aromatic heterocycle" is bonded to an oxygen atom. For example, it includes piperidinyloxy, tetrahydrofuryloxy and the like.

"Non-aromatic heterocyclylamino" means a group wherein a hydrogen atom attached to a nitrogen atom of an amino group is replaced with the "non-aromatic heterocycle". For example, it includes piperidinylamino, tetrahydrofurylamino and the like. Another hydrogen atom bonded to the nitrogen atom of the amino group may be replaced with the above "alkyl".

"Non-aromatic heterocyclylsulfanyl" means a group wherein a hydrogen atom bonded to a sulfur atom of a sulfanyl group is replaced with "non-aromatic heterocycle". For example, it includes piperidinylsulfanyl, tetrahydrofurylsulfanyl and the like.

"Non-aromatic heterocyclylcarbonyl" means a group wherein "non-aromatic heterocycle" is bonded to a carbonyl group. For example, it includes piperidinylcarbonyl, tetrahydrofurylcarbonyl and the like.

"Non-aromatic heterocyclylsulfonyl" means a group wherein "non-aromatic heterocycle" is bonded to a sulfonyl group. For example, it includes piperidinylsulfonyl, tetrahydrofurylsulfonyl and the like.

"Non-aromatic heterocyclylcarbonyloxy" means a group wherein the above "non-aromatic heterocyclylcarbonyl" is bonded to an oxygen atom. For example, it includes piperidinylcarbonyloxy, tetrahydrofurylcarbonyloxy and the like.

"Non-aromatic heterocyclylsulfonyloxy" means a group wherein the above "non-aromatic heterocyclylsulfonyl" is bonded to an oxygen atom. For example, it includes piperidinylsulfonyloxy, tetrahydrofurylsulfonyloxy and the like.

"Non-aromatic heterocyclyloxycarbonyl" means a group wherein the above "non-aromatic heterocyclyloxy" is bonded to a carbonyl group. For example, it includes piperidinyloxycarbonyl, tetrahydrofuryloxycarbonyl and the like.

"Non-aromatic heterocyclyloxysulfonyl" means a group wherein the above "non-aromatic heterocyclyloxy" is bonded to a sulfonyl group. For example, it includes piperidinyloxysulfonyl, tetrahydrofuryloxysulfonyl and the like.

"Non-aromatic heterocyclylcarbamoyl" means a group wherein a hydrogen atom bonded to a nitrogen atom of a carbamoyl group is replaced with the "non-aromatic heterocycle". For example, it includes piperidinylcarbamoyl, tetrahydrofurylcarbamoyl and the like. Another hydrogen atom bonded to the nitrogen atom of the carbamoyl group may be replaced with the above "alkyl".

"Non-aromatic heterocyclylsulfamoyl" means a group wherein a hydrogen atom bonded to a nitrogen atom of a sulfamoyl group is replaced with the "non-aromatic heterocycle". For example, it includes piperidinylsulfamoyl, tetrahydrofurylsulfamoyl and the like. Another hydrogen atom bonded to the nitrogen atom of the sulfamoyl group may be replaced with the above "alkyl".

"Non-aromatic heterocyclylcarbonylamino" means a group wherein a hydrogen atom attached to a nitrogen atom of an amino group is replaced with the above "non-aromatic heterocyclylcarbonyl". For example, it includes piperidinylcarbonylamino, tetrahydrofurylcarbonylamino and the like. Another hydrogen atom bonded to the nitrogen atom of the amino group may be replaced with the above "alkyl".

"Non-aromatic heterocyclylsulfonylamino" means a group wherein a hydrogen atom bonded to a nitrogen atom of an amino group is replaced with the above "non-aromatic heterocyclylsulfonyl". For example, it includes piperidinylsulfonylamino, tetrahydrofurylsulfonylamino and the like. Another hydrogen atom bonded to the nitrogen atom of the amino group may be replaced with the above "alkyl".

"Non-aromatic heterocyclyloxycarbonylamino" means a group wherein a hydrogen atom attached to a nitrogen atom of an amino group is replaced with the above "non-aromatic heterocyclyloxycarbonyl". For example, it includes piperidinyloxycarbonylamino, tetrahydrofuryloxycarbonylamino and the like. Another hydrogen atom bonded to the nitrogen atom of the amino group may be replaced with the above "alkyl".

"Substituted or unsubstituted non-aromatic carbocyclyl" and "substituted or unsubstituted non-aromatic heterocyclyl" can be substituted with "oxo". When substituted with "oxo", it means a group wherein two hydrogen atoms attached to a carbon atom are replaced with oxo as follows:

[Chemical Formula 56]

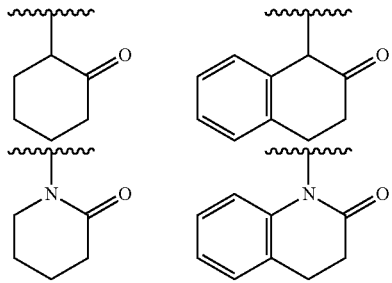

Non-aromatic carbocycle and non-aromatic heterocycle portion of above "non-aromatic carbocyclyloxy", "non-aromatic carbocyclylamino", "non-aromatic carbocyclylsulfanyl", "non-aromatic carbocyclylcarbonyl", "non-aromatic carbocyclylsulfonyl", "non-aromatic carbocyclylcarbonyloxy", "non-aromatic carbocyclylsulfonyloxy", "non-aromatic carbocyclyloxycarbonyl", "non-aromatic carbocyclyloxysulfonyl", "non-aromatic carbocyclylcarbamoyl", "non-aromatic carbocyclylsulfamoyl", "non-aromatic carbocyclylcarbonylamino", "non-aromatic carbocyclylsulfonylamino", "non-aromatic carbocyclyloxycarbonylamino", "non-aromatic heterocyclyloxy", "non-aromatic heterocyclylamino", "non-aromatic heterocyclylsulfanyl", "non-aromatic heterocyclylcarbonyl", "non-aromatic heterocyclylsulfonyl", "non-aromatic heterocyclylcarbonyloxy", "non-aromatic heterocyclylsulfonyloxy", "non-aromatic heterocyclyloxycarbonyl", "non-aromatic heterocyclyloxysulfonyl", "non-aromatic heterocyclylcarbamoyl", "non-aromatic heterocyclylsulfamoyl", "non-aromatic heterocyclylcarbonylamino", "non-aromatic heterocyclylsulfonylamino", and "non-aromatic heterocyclyloxycarbonylamino" can be substituted with "oxo" as the same as described above.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted alkyloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkynyloxycarbonylamino" include the following substituent group C1. They can be substituted with one or more substitutents selected from the group.

The substituent group C1: halogen, hydroxy, carboxy, amino, carbamoyl, sulfamoyl, cyano, nitro, ureido, amidino, guanidino, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, alkylamino optionally substituted with one or more group(s) selected from the substituent group A, alkenylamino optionally substituted with one or more group(s) selected from the substituent group A, alkynylamino optionally substituted with one or more group(s) selected from the substituent group A, alkylsulfanyl optionally substituted with one or more group(s) selected from the substituent group A, alkenylsulfanyl optionally substituted with one or more group(s) selected from the substituent group A, alkynylsulfanyl optionally substituted with one or more group(s) selected from the substituent group A, alkyl imino optionally substituted with one or more group(s) selected from the substituent group A, alkyloxy imino optionally substituted with one or more group(s) selected from the substituent group A, alkylcarbonyl optionally substituted with one or more group(s) selected from the substituent group A, alkylsulfonyl optionally substituted with one or more group(s) selected from the substituent group A, alkylcarbonylamino optionally substituted with one or more group(s) selected from the substituent group A, alkylsulfonylamino optionally substituted with one or more group(s) selected from the substituent group A, alkylcarbamoyl optionally substituted with one or more group(s) selected from the substituent group A, alkylsulfamoyl optionally substituted with one or more group(s) selected from the substituent group A, aromatic carbocyclyl optionally substituted with one or more group(s) selected from the substituent group B1, non-aromatic carbocyclyl optionally substituted with one or more group(s) selected from the substituent group B1', aromatic heterocyclyl optionally substituted with one or more group(s) selected from the substituent group B1, non-aromatic heterocyclyl optionally substituted with one or more group(s) selected from the substituent group B1', aromatic carbocyclyloxy optionally substituted with one or more group(s) selected from the substituent group B1, non-aromatic carbocyclyloxy optionally substituted with one or more group(s) selected from the substituent group B1', aromatic heterocyclyloxy optionally substituted with one or more group(s) selected from the substituent group B1, non-aromatic heterocyclyloxy optionally substituted with one or more group(s) selected from the substituent group B1', aromatic carbocyclylsulfanyl optionally substituted with one or more group(s) selected from the substituent group B1, non-aromatic carbocyclylsulfanyl optionally substituted with one or more group(s) selected from the substituent group B1', aromatic heterocyclylsulfanyl optionally substituted with one or more group(s) selected from the substituent group B1, non-aromatic heterocyclylsulfanyl optionally substituted with one or more group(s) selected from the substituent group B1', aromatic carbocyclylamino optionally substituted with one or more group(s) selected from the substituent group B1, non-aromatic carbocyclylamino optionally substituted with one or more group(s) selected from the substituent group B1', aromatic heterocyclylamino optionally substituted with one or more group(s) selected from the substituent group B1, and non-aromatic heterocyclylamino optionally substituted with one or more group(s) selected from the substituent group B1'.

The substituent group A: halogen, hydroxy, carboxy, amino, carbamoyl, sulfamoyl, cyano, and nitro.

One embodiment of the substituent group A is halogen and hydroxy.

One embodiment of the substituent group A is halogen.

The substituent group B1: halogen, hydroxy, carboxy, amino, carbamoyl, sulfamoyl, cyano, nitro, ureido, amidino, guanidino, alkyl optionally substituted with one or more group(s) selected from the substituent group A, alkenyl optionally substituted with one or more group(s) selected from the substituent group A, alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, alkylamino optionally substituted with one or more group(s) selected from the substituent group A, alkenylamino optionally substituted with one or more group(s) selected from the substituent group A, alkynylamino optionally substituted with one or more group(s) selected from the substituent group A, alkylsulfanyl optionally substituted with one or more group(s) selected from the substituent group A, alkenylsulfanyl optionally substituted with one or more group(s) selected from the substituent group A, alkynylsulfanyl optionally substituted with one or more group(s) selected from the substituent group A, alkylcarbonyl optionally substituted with one or more group(s) selected from the substituent group A, alkylsulfonyl optionally substituted with one or more group(s) selected from the substituent group A, alkylcarbonylamino optionally substituted with one or more group(s) selected from the substituent group A, alkylsulfonylamino optionally substituted with one or more group(s) selected from the substituent group A, alkylcarbamoyl optionally substituted with one or more group(s) selected from the substituent group A, alkylsulfamoyl optionally substituted with one or more group(s) selected from the substituent group A, alkylcarbonyloxy optionally substituted with one or more group(s) selected from the substituent group A, alkyloxycarbonyl optionally substituted with one or more group(s) selected from the substituent group A, alkylsulfonyloxy optionally substituted with one or more group(s) selected from the substituent group A, alkyloxysulfonyl optionally substituted with one or more group(s) selected from the substituent group A; and aromatic carbocyclyl, non-aromatic carbocyclyl, aromatic heterocyclyl, non-aromatic heterocyclyl, aromatic carbocyclylalkyl, non-aromatic carbocyclylalkyl, aromatic heterocyclylalkyl, non-aromatic heterocyclylalkyl, aromatic carbocyclyloxy, non-aromatic carbocyclyloxy, aromatic heterocyclyloxy, non-aromatic heterocyclyloxy, aromatic carbocyclylamino, non-aromatic carbocyclylamino, aromatic heterocyclylamino and non-aromatic heterocyclylamino (each aromatic carbocycle, non-aromatic carbocycle, aromatic heterocycle and non-aromatic heterocycle can be substituted with one or more group(s) selected from halogen, alkyl, hydroxy and alkyloxy).

The substituent group B1': oxo, halogen, hydroxy, carboxy, amino, carbamoyl, sulfamoyl, cyano, nitro, ureido, amidino, guanidino, alkyl optionally substituted with one or more group(s) selected from the substituent group A, alkenyl optionally substituted with one or more group(s) selected from the substituent group A, alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, alkylamino optionally substituted with one or more group(s) selected from the substituent group A, alkenylamino optionally substituted with one or more group(s) selected from the substituent group A, alkynylamino optionally substituted with one or more group(s) selected from the substituent group A, alkylsulfanyl optionally substituted with one or more group(s) selected from the substituent group A, alkenylsulfanyl optionally substituted with one or more group(s) selected from the substituent group A, alkynylsulfanyl optionally substituted with one or more group(s) selected from the substituent group A, alkylcarbonyl optionally substituted with one or more group(s) selected from the substituent group A, alkylsulfonyl optionally substituted with one or more group(s) selected from the substituent group A, alkylcarbonylamino optionally substituted with one or more group(s) selected from the substituent group A, alkylsulfonyl amino optionally substituted with one or more group (s) selected from the substituent group A, alkylcarbamoyl optionally substituted with one or more group(s) selected from the substituent group A, alkylsulfamoyl optionally substituted with one or more group(s) selected from the substituent group A, alkylcarbonyloxy optionally substituted with one or more group(s) selected from the substituent group A, alkyloxycarbonyl optionally substituted with one or more group(s) selected from the substituent group A, alkylsulfonyloxy optionally substituted with one or more group(s) selected from the substituent group A, alkyloxysulfonyl optionally substituted with one or more group(s) selected from the substituent group A; and aromatic carbocyclyl, non-aromatic carbocyclyl, aromatic heterocyclyl, non-aromatic heterocyclyl, aromatic carbocyclylalkyl, non-aromatic carbocyclylalkyl, aromatic heterocyclylalkyl, non-aromatic heterocyclylalkyl, aromatic carbocyclyloxy, non-aromatic carbocyclyloxy, aromatic heterocyclyloxy, non-aromatic heterocyclyloxy, aromatic carbocyclylamino, non-aromatic carbocyclylamino, aromatic heterocyclylamino and non-aromatic heterocyclylamino (each aromatic carbocycle, non-aromatic carbocycle, aromatic heterocycle and non-aromatic heterocycle can be substituted with one or more group(s) selected from halogen, alkyl, hydroxy and alkyloxy).

The preferred substituents of "substituted or unsubstituted alkyl" and "substituted or unsubstituted alkyloxy" in $R^{1a}$ to $R^{1d}$ and $R^{4a}$ to $R^{4d}$; "substituted or unsubstituted alkyl" in $R^6$; and, "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted alkyloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkynyloxycarbonyl amino" in $R^5$ include, for example, the substituent group A. They can be substituted with one or more substitutents selected from the group.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylamino", "substituted or unsubstituted alkenylamino", "substituted or unsubstituted alkynylamino" in $R^2$;

"substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted alkyloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkynyloxycarbonylamino" in $R^3$; "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylcarbamoyl", "substituted or unsubstituted alkenylcarbamoyl", "substituted or unsubstituted alkynylcarbamoyl", "substituted or unsubstituted alkylcarbonylamino", "substituted or unsubstituted alkenylcarbonylamino", "substituted or unsubstituted alkynylcarbonylamino" in $R^7$ and $R^{9a}$ to $R^{9d}$; and, "substituted or unsubstituted alkyl", "substituted or unsubstituted alkenyl", "substituted or unsubstituted alkynyl", "substituted or unsubstituted alkylcarbonyl", "substituted or unsubstituted alkenylcarbonyl", "substituted or unsubstituted alkynylcarbonyl" in $R^8$ include, for example, the substituent group C1, and preferably the substituent group C2. They can be substituted with one or more substitutents selected from the group.

The substituent group C2: halogen, hydroxy, cyano, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, aromatic carbocyclyl optionally substituted with one or more group(s) selected from the substituent group B2, non-aromatic carbocyclyl optionally substituted with one or more group(s) selected from the substituent group B2 aromatic heterocyclyl optionally substituted with one or more group(s) selected from the substituent group B2, non-aromatic heterocyclyl optionally substituted with one or more group(s) selected from the substituent group B2', aromatic carbocyclyloxy optionally substituted with one or more group(s) selected from the substituent group B2, non-aromatic carbocyclyloxy optionally substituted with one or more group(s) selected from the substituent group B2 aromatic heterocyclyloxy optionally substituted with one or more group(s) selected from the substituent group B2, non-aromatic heterocyclyloxy optionally substituted with one or more group(s) selected from the substituent group B2'.

One embodiment of the substituent group C2 is halogen, hydroxy, cyano, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, aromatic carbocyclyl optionally substituted with one or more group(s) selected from the substituent group B2, non-aromatic carbocyclyl optionally substituted with one or more group(s) selected from the substituent group B2 aromatic heterocyclyl optionally substituted with one or more group(s) selected from the substituent group B2, and non-aromatic heterocyclyl optionally substituted with one or more group(s) selected from the substituent group B2'.

One embodiment of the substituent group C2 is halogen.

One embodiment of the substituent group C2 is aromatic heterocyclyl optionally substituted with one or more group(s) selected from (alkyl; haloalkyl; hydroxy alkyl; alkyloxy and haloalkyloxy).

The substituent group B2: halogen, hydroxy, cyano, alkyl optionally substituted with one or more group(s) selected from the substituent group A, alkenyl optionally substituted with one or more group(s) selected from the substituent group A, alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, alkylsulfonyl optionally substituted with one or more group(s) selected from the substituent group A.

One embodiment of the substituent group B2 is halogen.

One embodiment of the substituent group B2 is alkyl, haloalkyl, and hydroxy alkyl.

The substituent group B2': oxo, halogen, hydroxy, cyano, alkyl optionally substituted with one or more group(s) selected from the substituent group A, alkenyl optionally substituted with one or more group(s) selected from the substituent group A, alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, alkylsulfonyl optionally substituted with one or more group(s) selected from the substituent group A.

One embodiment of the substituent group B2' is halogen.

One embodiment of the substituent group B2' is oxo, alkyl, haloalkyl, and hydroxy alkyl.

The substituents on the rings of "aromatic carbocycle" and "aromatic heterocycle" of "substituted or unsubstituted aromatic carbocyclyl", "substituted or unsubstituted aromatic heterocyclyl", "substituted or unsubstituted aromatic carbocyclyloxy", "substituted or unsubstituted aromatic heterocyclyloxy", "substituted or unsubstituted aromatic carbocyclylamino", "substituted or unsubstituted aromatic heterocyclylamino", "substituted or unsubstituted aromatic carbocyclylsulfanyl", "substituted or unsubstituted aromatic heterocyclylsulfanyl", "substituted or unsubstituted aromatic carbocyclylcarbonyl", "substituted or unsubstituted aromatic heterocyclylcarbonyl", "substituted or unsubstituted aromatic carbocyclylsulfonyl", "substituted or unsubstituted aromatic heterocyclylsulfonyl", "substituted or unsubstituted aromatic carbocyclylcarbonyloxy", "substituted or unsubstituted aromatic heterocyclylcarbonyloxy", "substituted or unsubstituted aromatic carbocyclyloxycarbonyl", "substituted or unsubstituted aromatic heterocyclyloxycarbonyl", "substituted or unsubstituted aromatic carbocyclylsulfonyloxy", "substituted or unsubstituted aromatic heterocyclylsulfonyloxy", "substituted or unsubstituted aromatic carbocyclyloxysulfonyl", "substituted or unsubstituted aromatic heterocyclyloxysulfonyl", "substituted or unsubstituted aromatic carbocyclylcarbamoyl", "substituted or unsubstituted aromatic heterocyclylcarbamoyl", "substituted or unsubstituted aromatic carbocyclylsulfamoyl", "substituted or unsubstituted aromatic heterocyclylsulfamoyl", "substituted or unsubstituted aromatic carbocyclylcarbonylamino", "substituted or unsubstituted aromatic heterocyclylcarbonylamino", "substituted or unsubstituted aromatic carbocyclylsulfonylamino", "substituted or unsubstituted aromatic heterocyclylsulfonylamino", "substituted or unsubstituted aromatic carbocyclyloxycarbonylamino", and "substituted or unsubstituted aromatic heterocyclyloxycarbonylamino" include, for example, the substituent group B1, and preferably the substituent group B2. They can be substituted with one or more substitutents selected from the group.

The substituents on the rings of "non-aromatic carbocycle" and "non-aromatic heterocycle" of "substituted or unsubstituted non-aromatic carbocyclyl", "substituted or unsubstituted non-aromatic heterocyclyl", "substituted or unsubstituted non-aromatic carbocyclyloxy", "substituted or unsubstituted non-aromatic heterocyclyloxy", "substituted or unsubstituted non-aromatic carbocyclylamino", "substituted or unsubstituted non-aromatic heterocyclylamino", "substituted or unsubstituted non-aromatic carbocyclylsulfanyl", "substituted or unsubstituted non-aromatic heterocyclylsulfanyl", "substituted or unsubstituted non-aromatic carbocyclylcarbonyl", "substituted or unsubstituted non-aromatic heterocyclylcarbonyl", "substituted or unsubstituted non-aromatic carbocyclylsulfonyl", "substituted or unsubstituted non-aromatic heterocyclylsulfonyl", "substituted or unsubstituted non-aromatic carbocyclylcarbonyloxy", "substituted or unsubstituted non-aromatic heterocyclylcarbonyloxy", "substituted or unsubstituted non-aromatic carbocyclyloxycarbonyl", "substituted or unsubstituted non-aromatic heterocyclyloxycarbonyl", "substituted or unsubstituted non-aromatic carbocyclylsulfonyloxy", "substituted or unsubstituted non-aromatic heterocyclylsulfonyloxy", "substituted or unsubstituted non-aromatic carbocyclyloxysulfonyl", "substituted or unsubstituted non-aromatic heterocyclyloxy sulfonyl", "substituted or unsubstituted non-aromatic carbocyclylcarbamoyl", "substituted or unsubstituted non-aromatic heterocyclylcarbamoyl", "substituted or unsubstituted non-aromatic carbocyclylsulfamoyl", "substituted or unsubstituted non-aromatic heterocyclylsulfamoyl", "substituted or unsubstituted non-aromatic carbocyclylcarbonylamino", "substituted or unsubstituted non-aromatic heterocyclylcarbonylamino", "substituted or unsubstituted non-aromatic carbocyclylsulfonylamino", "substituted or unsubstituted non-aromatic heterocyclylsulfonylamino", "substituted or unsubstituted non-aromatic carbocyclyloxycarbonylamino", and "substituted or unsubstituted non-aromatic heterocyclyloxycarbonylamino" include, for example, the substituent group B1', and preferably the substituent group B2'. They can be substituted with one or more substitutents selected from the group.

The preferred substituents of "substituted or unsubstituted alkyl", "substituted or unsubstituted alkenyl", and "substituted or unsubstituted alkynyl" in $R^2$ include aromatic heterocyclyl optionally substituted with one or more group(s) selected from (halogen; cyano; alkyl; haloalkyl; alkyloxy; haloalkyloxy), aromatic carbocyclyl optionally substituted with one or more group(s) selected from (halogen; cyano; alkyl; haloalkyl), non-aromatic heterocyclyl optionally substituted with one or more group(s) selected from (oxo; halogen; alkyl; haloalkyl), non-aromatic carbocyclyl optionally substituted with halogen, aromatic heterocyclyloxy optionally substituted with one or more group(s) selected from (halogen; alkyl; haloalkyl), aromatic carbocyclyloxy optionally substituted with one or more group(s) selected from (halogen; alkyl; haloalkyl), halogen, alkyloxy, or, haloalkyloxy.

The preferred substituents of "substituted or unsubstituted aromatic heterocyclyl" and "substituted or unsubstituted aromatic carbocyclyl" in $R^2$ include halogen, alkyl optionally substituted with one or more group(s) selected from (aromatic carbocyclyl optionally substituted with halogen; halogen; alkyloxy; haloalkyloxy).

The preferred substituents of "substituted or unsubstituted non-aromatic heterocyclyl" and "substituted or unsubstituted non-aromatic carbocyclyl" in $R^2$ include oxo, halogen, or alkyl optionally substituted with one or more group(s) selected from (halogen; alkyloxy; haloalkyloxy; non-aromatic carbocyclyl).

The preferred substituents of "substituted or unsubstituted alkyl", "substituted or unsubstituted alkenyl", and "substituted or unsubstituted alkynyl" in $R^3$ and $R^7$ include halogen, hydroxy, non-aromatic carbocyclyl, alkyloxy, or haloalkyloxy.

The preferred substituents of "substituted or unsubstituted alkyloxy", "substituted or unsubstituted alkenyloxy", and "substituted or unsubstituted alkynyloxy" in $R^3$ and $R^7$ include, non-aromatic carbocyclyl optionally substituted with halogen, non-aromatic heterocyclyl, aromatic carbocyclyl, halogen, hydroxy, cyano, alkyloxy, or haloalkyloxy.

The preferred substituents of "substituted or unsubstituted aromatic carbocyclyl" and "substituted or unsubstituted aromatic heterocyclyl" in $R^3$ and $R^7$ include halogen, alkyl, or haloalkyl.

The preferred substituents of "substituted or unsubstituted non-aromatic heterocyclyl" in $R^3$ and $R^7$ include oxo, halogen, hydroxy, cyano, alkyl, haloalkyl, alkyloxy, or haloalkyloxy.

The preferred substituents of "substituted or unsubstituted non-aromatic carbocyclyl" in $R^3$ and $R^7$ include halogen, alkyl, haloalkyl, alkyloxy, or haloalkyloxy.

The preferred substituents of "substituted or unsubstituted alkylamino", "substituted or unsubstituted alkenylamino", and "substituted or unsubstituted alkynylamino" in $R^3$ and $R^7$ include halogen, cyano, alkyloxy, or haloalkyloxy.

The preferred substituents of "substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy" in $R^3$ and $R^7$ include halogen, cyano, alkyl, haloalkyl, alkyloxy, or haloalkyloxy.

The preferred substituents of "substituted or unsubstituted alkyl", "substituted or unsubstituted alkenyl", and "substituted or unsubstituted alkynyl" in $R^8$ and $R^{9a}$ to $R^{9d}$ include halogen.

When "any one of $R^{4a}$s and any one of $R^{4c}$s may be taken together to form a substituted or unsubstituted (C1-C3) bridge, wherein one of carbon atoms constituting the (C1-C3) bridge may be replaced with a nitrogen atom", then a hydrogen atom or alkyl may be bonded to the nitrogen atom, and the carbon atoms constituting the (C1-C3) bridge can be substituted with alkyl or halogen. For example, it includes the following:

[Chemical Formula 57]

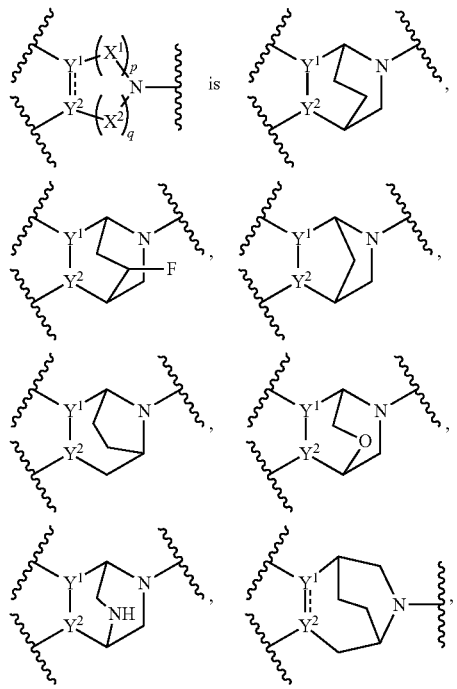

-continued

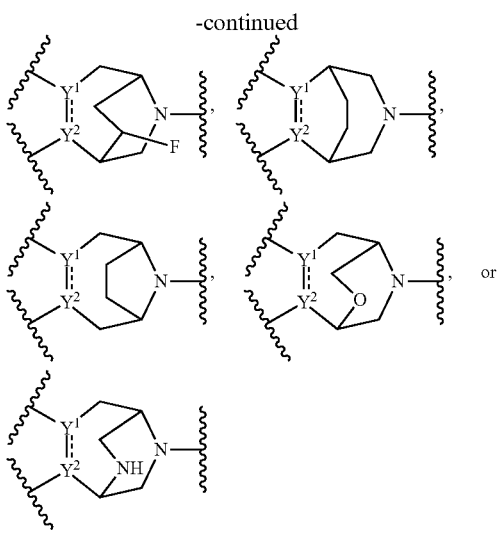

The phrase "$R^{4a}$ and $R^{4b}$ attached to a same carbon atom, together with the carbon atom to which they are attached, may form a substituted or unsubstituted 3- to 5-membered non-aromatic carbocycle or a substituted or unsubstituted 3- to 5-membered non-aromatic heterocycle", "two $R^{4a}$s attached to adjacent carbon atoms, may be taken together with the carbon atoms to which they are attached to form a substituted or unsubstituted 3- to 5-membered non-aromatic carbocycle or a substituted or unsubstituted 3- to 5-membered non-aromatic heterocycle", "$R^{4c}$ and $R^{4d}$ attached to a same carbon atom may be taken together with the carbon atom to which they are attached to form a substituted or unsubstituted 3- to 5-membered non-aromatic carbocycle or a substituted or unsubstituted 3- to 5-membered non-aromatic heterocycle", and "two $R^{4c}$s attached to adjacent carbon atoms may be taken together with the carbon atoms to which they are attached to form a substituted or unsubstituted 3- to 5-membered non-aromatic carbocycle or a substituted or unsubstituted 3- to 5-membered non-aromatic heterocycle" include, for example, the following:

[Chemical Formula 58]

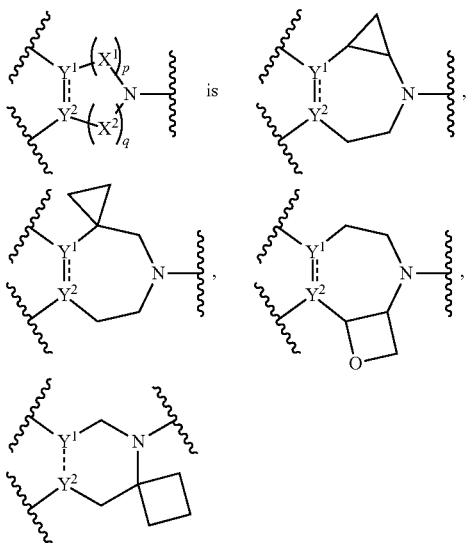

The substituents of the 3- to 5-membered non-aromatic carbocycle or the 3- to 5-membered non-aromatic heterocycle include the substituent group B2
When —W— is

[Chemical Formula 59]

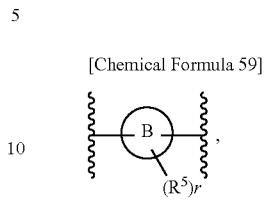

then any ring constituting atom, to which a substituent can attach, may be substituted with substituent $R^5$. For example, when

[Chemical Formula 60]

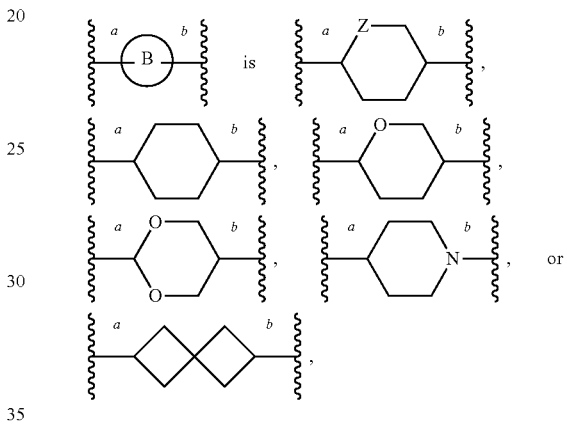

then any ring constituting atom, to which a substituent can attach, may be substituted with substituent $R^5$.
The phrase "Z is a carbon atom" means

[Chemical Formula 61]

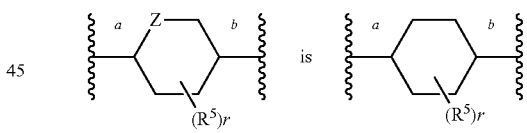

wherein each symbol is the same as defined above, and any ring constituting atom can be substituted with $R^G$.
The phrase "Z is a nitrogen atom" means

[Chemical Formula 62]

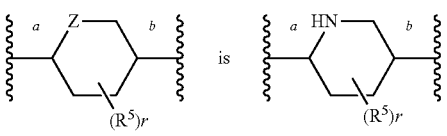

wherein each symbol is the same as defined above, and a hydrogen atom or alkyl may be attached to the nitrogen atom, any ring constituting atom can be substituted with $R^5$.
When "two $R^5$s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom", then a hydrogen atom or alkyl may be attached to a nitrogen atom, and the carbon atoms constituting the (C1-C3) bridge can be substituted with alkyl or halogen. It includes, for example, the following:

[Chemical Formula 63]

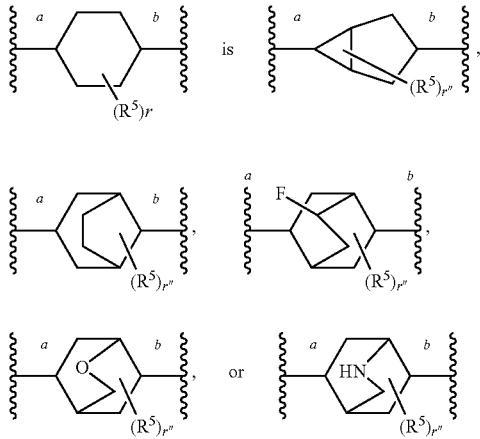

wherein r" is an integer of 0 to 2, $R^5$ is the same as defined above.

Examples of specific embodiments of a compound represented by Formula (I) or a pharmaceutically acceptable salt thereof are illustrated below. A compound represented by Formula (IA) and (IB):

[Chemical Formula 64]

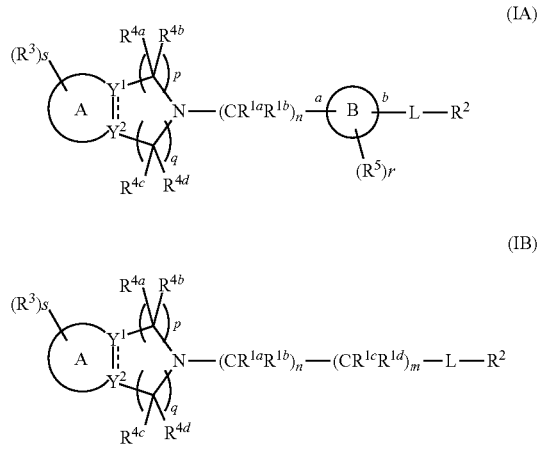

wherein a bonding hand "a" is bonded to —(CR$^{1a}$R$^{1b}$)$_n$—; a bonding hand "b" is bonded to -L-, the other symbols are the same as defined above,
or a pharmaceutically acceptable salt thereof.

Specific examples of each substituent in the compound represented by Formula (I), Formula (Ie), (IA) or (IB), or a pharmaceutically acceptable salt thereof are illustrated bellow. All combination of these embodiments are examples of the compound represented by Formula (I), (IA) or (IB).

In Formula (I), Formula (Ie), Formula (IA) or (IB),

[Chemical Formula 65]

(Hereinafter above ring is referred to as Ring A)
is a 5-membered aromatic heterocycle, a 6-membered aromatic heterocycle, a 5-membered non-aromatic heterocycle, or a 6-membered non-aromatic heterocycle (Hereinafter referred to as "Ring A is A1").

Ring A is a 5-membered aromatic heterocycle, a 6-membered aromatic heterocycle, or a 6-membered non-aromatic heterocycle (Hereinafter referred to as "Ring A is A2").

Ring A is a 5-membered aromatic heterocycle or a 6-membered aromatic heterocycle (Hereinafter referred to as "Ring A is A3").

Ring A is a thiazole ring, an imidazole ring, a pyrazole ring, an oxazole ring, a thiophene ring, a pyrrole ring, a furan ring, a pyridine ring, a pyrazine ring, a pyrimidine ring, a pyridazine ring, or a pyrrolidine ring (Hereinafter referred to as "Ring A is A4").

Ring A is a thiazole ring, an imidazole ring, a pyrazole ring, an oxazole ring, a pyrrole ring, a pyridine ring, a pyrazine ring, a pyrimidine ring, or a pyridazine ring (Hereinafter referred to as "Ring A is A5").

Ring A is a thiazole ring (Hereinafter referred to as "Ring A is A6").

Ring A is an imidazole ring (Hereinafter referred to as "Ring A is A7").

Ring A is a pyridine ring (Hereinafter referred to as "Ring A is A8").

Ring A is a pyrimidine ring (Hereinafter referred to as "Ring A is A9").

[Chemical Formula 66]

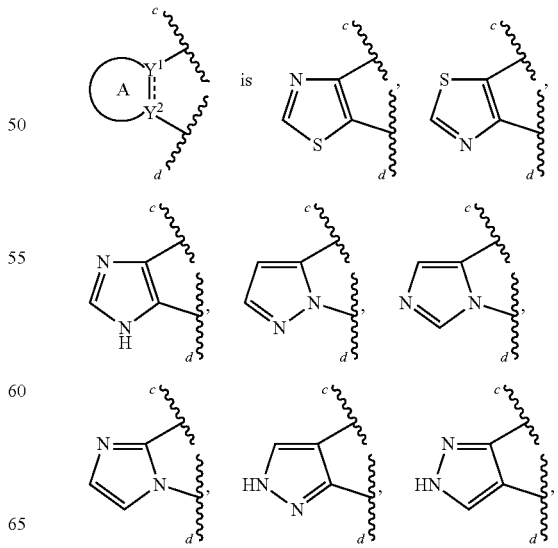

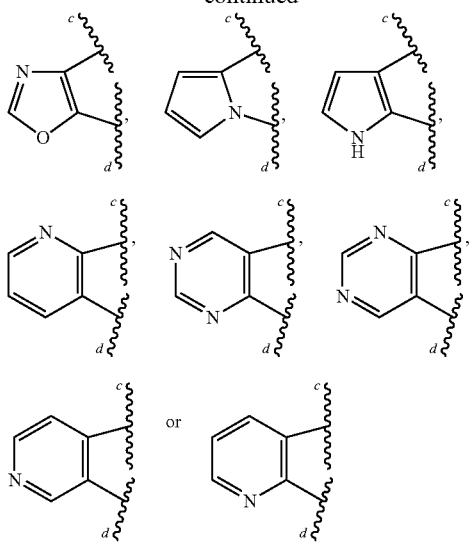
wherein a bonding hand "c" is bonded to $CR^{4a}R^{4b}$; a bonding hand "d" is bonded to $CR^{4c}R^{4d}$ (Hereinafter referred to as "Ring A is A10").
[Chemical Formula 67]
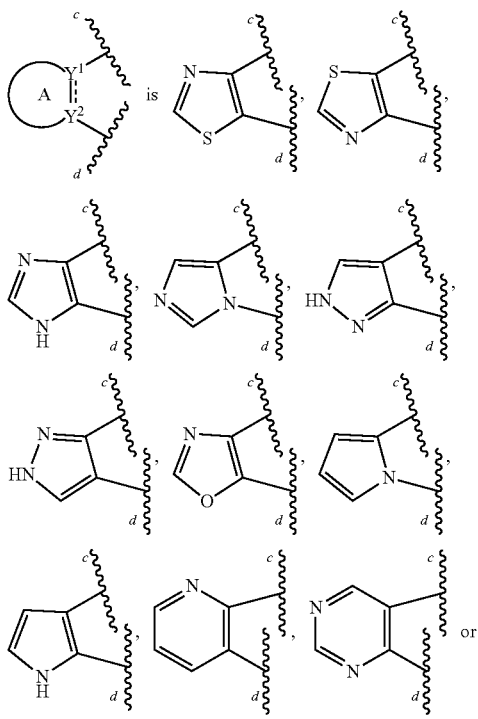
(Hereinafter referred to as "Ring A is A11").
[Chemical Formula 68]
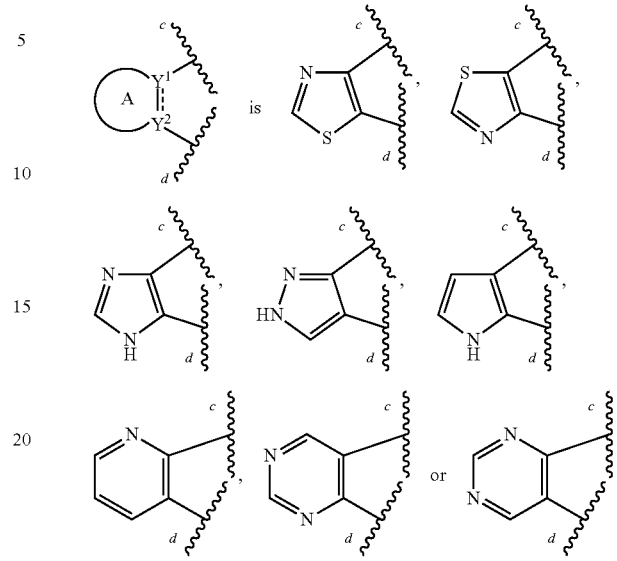
(Hereinafter referred to as "Ring A is A12").
[Chemical Formula 69]
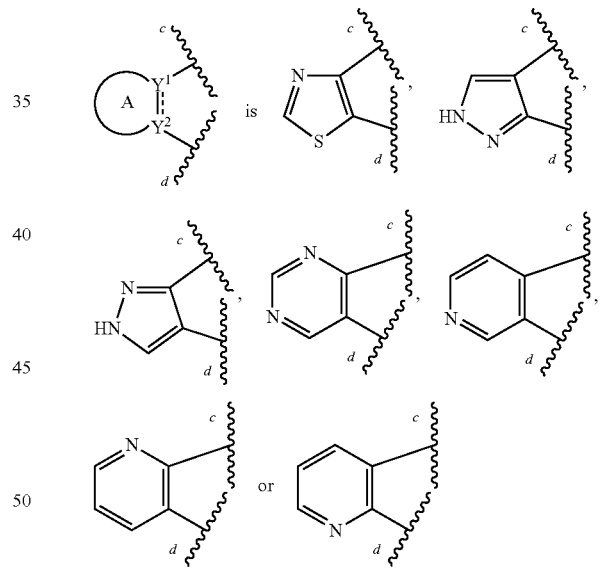
(Hereinafter referred to as "Ring A is A13").
[Chemical Formula 70]
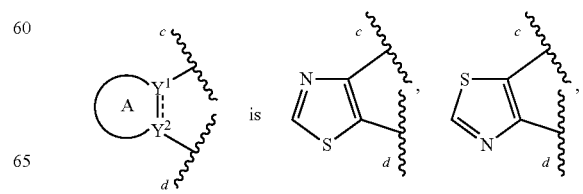

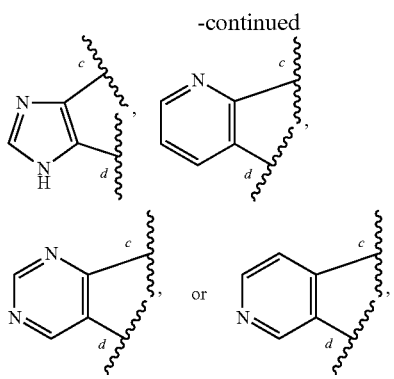

(Hereinafter referred to as "Ring A is A14").

[Chemical Formula 71]

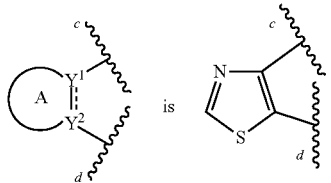

(Hereinafter referred to as "Ring A is A15").

[Chemical Formula 72]

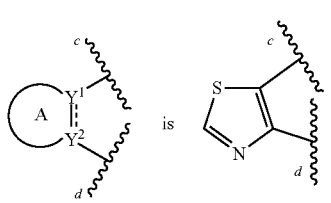

(Hereinafter referred to as "Ring A is A16").

[Chemical Formula 73]

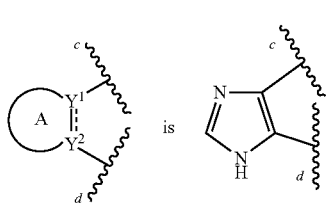

(Hereinafter referred to as "Ring A is A17").

[Chemical Formula 74]

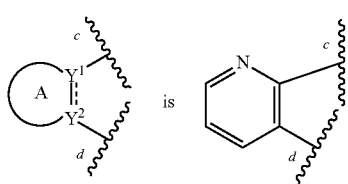

(Hereinafter referred to as "Ring A is A18").

[Chemical Formula 75]

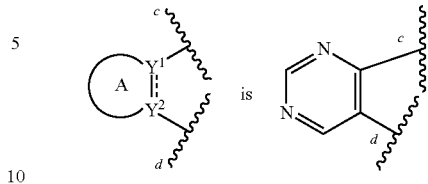

(Hereinafter referred to as "Ring A is A19").

p is 1 or 2 (Hereinafter referred to as "p is p1"),
p is 1 (Hereinafter referred to as "p is p2").
p is 2 (Hereinafter referred to as "p is p3").
q is an integer of 1 to 3 (Hereinafter referred to as "q is q1").
q is 1 or 2 (Hereinafter referred to as "q is q2").
q is 2 (Hereinafter referred to as "q is q3").

$R^{4a}$ is each independently a hydrogen atom, halogen, hydroxy, substituted or unsubstituted alkyl, or substituted or unsubstituted alkyloxy; $R^{4b}$ is each independently a hydrogen atom, halogen, hydroxy, substituted or unsubstituted alkyl, or substituted or unsubstituted alkyloxy; $R^{4c}$ is each independently a hydrogen atom, halogen, hydroxy, substituted or unsubstituted alkyl, or substituted or unsubstituted alkyloxy; $R^{4d}$ is each independently a hydrogen atom, halogen, hydroxy, substituted or unsubstituted alkyl, or substituted or unsubstituted alkyloxy;

any one of $R^{4a}$s and any one of $R^{4c}$s may be taken together to form a substituted or unsubstituted (C1-C3) bridge, wherein one of carbon atoms constituting the (C1-C3) bridge may be replaced with an oxygen atom or a nitrogen atom;

$R^{4a}$ and $R^{4b}$ attached to a same carbon atom may be taken together with the carbon atom to which they are attached to form a substituted or unsubstituted 3- to 5-membered non-aromatic carbocycle or a substituted or unsubstituted 3- to 5-membered non-aromatic heterocycle;

two $R^{4a}$s attached to adjacent carbon atoms may be taken together with the carbon atoms to which they are attached to form a substituted or unsubstituted 3- to 5-membered non-aromatic carbocycle or a substituted or unsubstituted 3- to 5-membered non-aromatic heterocycle;

$R^{4c}$ and $R^{4d}$ attached to a same carbon atom may be taken together with the carbon atom to which they are attached to form a substituted or unsubstituted 3- to 5-membered non-aromatic carbocycle or a substituted or unsubstituted 3- to 5-membered non-aromatic heterocycle;

two $R^{4c}$s attached to adjacent carbon atoms may be taken together with the carbon atoms to which they are attached to form a substituted or unsubstituted 3- to 5-membered non-aromatic carbocycle or a substituted or unsubstituted 3- to 5-membered non-aromatic heterocycle (Hereinafter referred to as "$R^{4a}$ to $R^{4d}$ are $R^{41}$").

$R^{4a}$ is each independently a hydrogen atom, halogen, hydroxy, substituted or unsubstituted alkyl, or substituted or unsubstituted alkyloxy; $R^{4b}$ is each independently a hydrogen atom, halogen, hydroxy, substituted or unsubstituted alkyl, or substituted or unsubstituted alkyloxy; $R^{4c}$ is each independently a hydrogen atom, halogen, hydroxy, substituted or unsubstituted alkyl, or substituted or unsubstituted alkyloxy; $R^{4d}$ is each independently a hydrogen atom, halogen, hydroxy, substituted or unsubstituted alkyl, or substituted or unsubstituted alkyloxy; any one of $R^{4a}$s and any one of $R^{4c}$s may be taken together to form a substituted or unsubstituted (C1-C3) bridge, wherein one of carbon atoms constituting the (C1-C3) bridge may be replaced with an oxygen atom or a nitrogen atom (Hereinafter referred to as "$R^{4a}$ to $R^{4d}$ are $R^{42}$").

$R^{4a}$ is each independently a hydrogen atom, halogen, or alkyl optionally substituted with the substituent group A; $R^{4b}$ is each independently hydrogen atom, halogen, or alkyl optionally substituted with the substituent group A; $R^{4r}$ is each independently a hydrogen atom, halogen, or alkyl optionally substituted with the substituent group A; $R^{4d}$ is each independently a hydrogen atom, halogen, or alkyl optionally substituted with the substituent group A; any one of $R^{4a}$s and any one of $R^{4c}$s may be taken together to form a C2 bridge (Hereinafter referred to as "$R^{4a}$ to $R^{4d}$ is $R^{43}$").

$R^{4a}$ is each independently a hydrogen atom, halogen, or alkyl optionally substituted with the substituent group A; $R^{4b}$ is each independently a hydrogen atom, halogen, or alkyl optionally substituted with the substituent group A; $R^{4c}$ is each independently a hydrogen atom, halogen, or alkyl optionally substituted with the substituent group A; $R^{4d}$ is each independently a hydrogen atom, halogen, or alkyl optionally substituted with the substituent group A (Hereinafter referred to as "$R^{4a}$ to $R^{4d}$ is $R^{44}$").

$R^{4a}$ to $R^{4d}$ are hydrogen atoms (Hereinafter referred to as "$R^{4a}$ to $R^{4d}$ are $R^{45}$").

$R^{1a}$ is each independently a hydrogen atom, halogen, hydroxy, alkyl optionally substituted with the substituent group A, or alkyloxy optionally substituted with the substituent group A; $R^{1b}$ is each independently a hydrogen atom, halogen, hydroxy, alkyl optionally substituted with the substituent group A, or alkyloxy optionally substituted with the substituent group A (Hereinafter referred to as "$R^{1a}$ and $R^{1b}$ is R11").

$R^{1a}$ and $R^{1b}$ are hydrogen atoms (Hereinafter referred to as "$R^{1a}$ and $R^{1b}$ are $R^{12}$").

n is an integer of 1 to 4 (Hereinafter referred to as "n is n1").

n is an integer of 2 to 4 (Hereinafter referred to as "n is n2").

n is 2 or 3 (Hereinafter referred to as "n is n3").

n is 2 (Hereinafter referred to as "n is n4").

-L- is —N($R^6$)—C(=O)—, —C(=O)—N($R^6$)—, —N($R^6$)—SO$_2$—, or SO$_2$N($R^6$)—, wherein $R^6$ is alkyl optionally substituted with the substituent group A or a hydrogen atom (Hereinafter referred to as "L is L1").

-L- is —N($R^6$)—C(=O)— or —N($R^6$)—SO$_2$—, wherein $R^6$ is alkyl optionally substituted with the substituent group A or a hydrogen atom (Hereinafter referred to as "L is L2").

-L- is —NH—C(=O)— or —NH—SO$_2$— (Hereinafter referred to as "L is L3").

-L- is —N($R^6$)—C(=O)—, wherein $R^6$ is a hydrogen atom or substituted or unsubstituted alkyl (the substituent includes, for example, the substituent group A) (Hereinafter referred to as "L is L4").

-L- is —NH—C(=O)— (Hereinafter referred to as "L is L5").

$R^2$ is substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclyl amino, substituted or unsubstituted non-aromatic carbocyclylamino, substituted or unsubstituted aromatic heterocyclylamino, or substituted or unsubstituted non-aromatic heterocyclylamino (Hereinafter referred to as "$R^2$ is R21").

$R^2$ is substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy (Hereinafter referred to as "$R^2$ is R22").

$R^2$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl (Hereinafter referred to as "$R^2$ is R23").

$R^2$ is alkyl optionally substituted with the substituent group C2, alkenyl optionally substituted with the substituent group C2, alkynyl optionally substituted with the substituent group C2, aromatic carbocyclyl optionally substituted with the substituent group B2, non-aromatic carbocyclyl optionally substituted with the substituent group B2, aromatic heterocyclyl optionally substituted with the substituent group B2, or non-aromatic heterocyclyl optionally substituted with the substituent group B2 (Hereinafter referred to as "$R^2$ is R24").

$R^2$ is substituted or unsubstituted alkyl, substituted or unsubstituted alkenyl, substituted or unsubstituted non-aromatic heterocyclyl, or substituted or unsubstituted aromatic heterocyclyl (Hereinafter referred to as "$R^2$ is R25").

$R^2$ is alkyl optionally substituted with the substituent group C2, monocyclic or bicyclic aromatic carbocyclyl optionally substituted with the substituent group B2, monocyclic or bicyclic non-aromatic heterocyclyl optionally substituted with the substituent group B2, or monocyclic or bicyclic aromatic heterocyclyl optionally substituted with the substituent group B2 (Hereinafter referred to as "$R^2$ is R26").

$R^2$ is substituted or unsubstituted alkyl (the alkyl includes, for example, methyl and the substituents include, for example, aromatic heterocyclyl optionally substituted with the substituent group B2, aromatic carbocyclyl optionally substituted with the substituent group B2, non-aromatic carbocyclyl optionally substituted with the substituent group B2', non-aromatic heterocyclyl optionally substituted with the substituent group B2', aromatic heterocyclyloxy optionally substituted with the substituent group B2, aromatic carbocyclyloxy optionally substituted with the substituent group B2, non-aromatic carbocyclyloxy optionally substituted with the substituent group B2', and non-aromatic heterocyclyloxy optionally substituted with the substituent group B2') (Hereinafter referred to as "$R^2$ is R27").

R² is substituted or unsubstituted C1 to C3 alkyl (the substituents include monocyclic aromatic heterocyclyl optionally substituted with the substituent group B2, phenyl optionally substituted with the substituent group B2, monocyclic aromatic heterocyclyloxy optionally substituted with the substituent group B2, and halogen) (Hereinafter referred to as "R² is R28").

R² is bicyclic aromatic heterocyclyl optionally substituted with the substituent group B2 or bicyclic non-aromatic heterocyclyl optionally substituted with the substituent group B2' (Hereinafter referred to as "R² is R29").

R³ is each independently halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkynylsulfamoyl, substituted or unsubstituted alkylcarbonylamino, substituted or unsubstituted alkenylcarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, or substituted or unsubstituted non-aromatic heterocyclylcarbonylamino (Hereinafter referred to as "R³ is R31").

R³ is each independently halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl (Hereinafter referred to as "R³ is R32")

R³ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or substituted or unsubstituted non-aromatic heterocyclylamino (Hereinafter referred to as "R³ is R33").

R³ is each independently alkyl optionally substituted with the substituent group C2, alkenyl optionally substituted with the substituent group C2, alkynyl optionally substituted with the substituent group C2, alkyloxy optionally substituted with the substituent group C2, alkenyloxy optionally substituted with the substituent group C2, alkynyloxy optionally substituted with the substituent group C2, alkylamino optionally substituted with the substituent group C2, alkenylamino optionally substituted with the substituent group C2, alkynylamino optionally substituted with the substituent group C2, aromatic carbocyclyl optionally substituted with the substituent group B2, non-aromatic carbocyclyl optionally substituted with the substituent group B2', aromatic heterocyclyl optionally substituted with the substituent group B2, non-aromatic heterocyclyl optionally substituted with the substituent group B2', aromatic carbocyclyloxy optionally substituted with the substituent group B2, non-aromatic carbocyclyloxy optionally substituted with the substituent group B2', aromatic heterocyclyloxy optionally substituted with the substituent group B2, non-aromatic heterocyclyloxy optionally substituted with the substituent group B2', aromatic carbocyclylamino optionally substituted with the substituent group B2, non-aromatic carbocyclylamino optionally substituted with the substituent group B2', aromatic heterocyclylamino optionally substituted with the substituent group B2, or non-aromatic heterocyclylamino optionally substituted with the substituent group B2'(Hereinafter referred to as "$R^3$ is R34").

$R^3$ is each independently substituted or unsubstituted alkyl, substituted or unsubstituted alkyloxy, substituted or unsubstituted alkylamino, substituted or unsubstituted aromatic carbocyclyl, substituted or unsubstituted non-aromatic carbocyclyl, substituted or unsubstituted non-aromatic heterocyclyl, or substituted or unsubstituted non-aromatic carbocyclyloxy (Hereinafter referred to as "$R^3$ is R35").

$R^3$ is each independently alkyloxy optionally substituted with the substituent group C2, alkyl optionally substituted with the substituent group C2, or, $-NR^{10}R^{11}$; $R^{10}$ and $R^{11}$ are each independently a hydrogen atom or alkyl optionally substituted with the substituent group C2; or, $R^{10}$ and $R^{11}$, together with the adjacent nitrogen atom, may form non-aromatic heterocycle optionally substituted with the substituent group B2' (provided that $R^{10}$ and $R^{11}$ are not simultaneously both hydrogen atoms) (Hereinafter referred to as "$R^3$ is R36").

s is an integer of 0 to 4 (provided that when Ring A is a thiophene ring and q is 2, then s is not 0) (Hereinafter referred to as "s is s1").

s is an integer of 1 to 3 (Hereinafter referred to as "s is s2").

s is 1 or 2 (Hereinafter referred to as "s is s3").

s is 1 (Hereinafter referred to as "s is s4").

In Formula (IA),

Ring B is a non-aromatic carbocycle, a non-aromatic heterocycle, an aromatic carbocycle, or an aromatic heterocycle (Hereinafter referred to as "Ring B is B1").

Ring B is a non-aromatic carbocycle, a non-aromatic heterocycle, or an aromatic heterocycle (Hereinafter referred to as "Ring B is B2").

Ring B is a non-aromatic carbocycle or a non-aromatic heterocycle (Hereinafter referred to as "Ring B is B3").

Ring B is a 6-membered non-aromatic carbocycle or a 6-membered non-aromatic heterocycle (Hereinafter referred to as "Ring B is B4").

Ring B is a cyclohexane ring or a tetrahydropyran ring (Hereinafter referred to as "Ring B is B5").

[Chemical Formula 76]

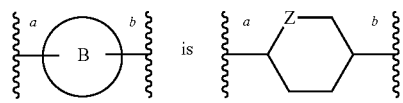

wherein Z is a carbon atom, an oxygen atom, or a nitrogen atom (Hereinafter referred to as "Ring B is B6").

[Chemical Formula 77]

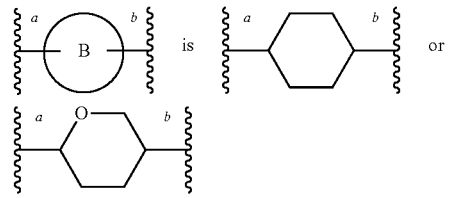

(Hereinafter referred to as "Ring B is B7").

[Chemical Formula 78]

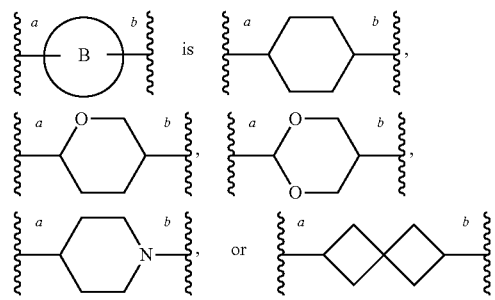

(Hereinafter referred to as "King B is B8").

[Chemical Formula 79]

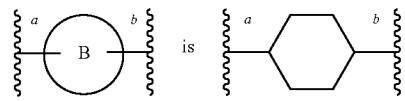

(Hereinafter referred to as "Ring B is B9").

[Chemical Formula 80]

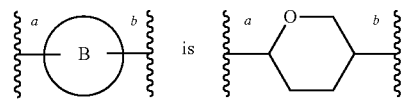

(Hereinafter referred to as "King B is B10").

[Chemical Formula 81]

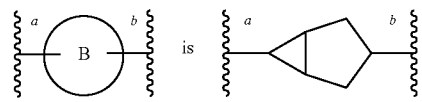

(Hereinafter referred to as "Ring B is B11").

$R^5$ is each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenyl carbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonyl amino, substituted or unsubstituted alkynylcarbonyl amino, substituted or unsubstituted alkylsulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, or substituted or unsubstituted alkynyloxycarbonylamino; two $R^5$s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom (Hereinafter referred to as "$R^8$ is R51").

$R^5$ is each independently halogen, hydroxy, alkyl optionally substituted with the substituent group A, or alkyloxy optionally substituted with the substituent group A; two $R^5$s attached to different ring-constituting atoms may be taken together to form a bond (Hereinafter referred to as "$R^8$ is R52").

$R^8$ is each independently halogen, hydroxy, or substituted or unsubstituted alkyl (Hereinafter referred to as "$R^5$ is R53").

$R^8$ is each independently halogen (Hereinafter referred to as "$R^8$ is R54").

r is an integer of 0 to 4 (Hereinafter referred to as "r is r1").

r is an integer of 0 to 2 (Hereinafter referred to as "r is r2").

r is 0 (Hereinafter referred to as "r is r3").

In Formula (IB), $R^{1c}$ is each independently a hydrogen atom, halogen, hydroxy, alkyl optionally substituted with the substituent group A, or alkyloxy optionally substituted with the substituent group A; $R^{1d}$ is each independently a hydrogen atom, halogen, hydroxy, alkyl optionally substituted with the substituent group A, or alkyloxy optionally substituted with the substituent group A (Hereinafter referred to as "$R^{1c}$ and $R^{1d}$ are r11").

$R^{1e}$ and $R^{1d}$ are hydrogen atoms (Hereinafter referred to as "$R^{1c}$ and $R^{1d}$ are r12").

m is an integer of 1 to 3 (Hereinafter referred to as "m is m1"), m is 2 (Hereinafter referred to as "m is m2").

Examples of the compound represented by Formula (IA) include compounds wherein '("Ring A", "Ring B", "$R^{1a}$ and $R^{1b}$", $R^2$, $R^3$, $R^{4a}$ to $R^{4d}$, $R^5$, L, n, p, q, r, and s)', which stands for combinations of Ring A, Ring B, $R^{1a}$ and $R^{1b}$, $R^2$, $R^3$, $R^{4a}$ to $R^{4d}$, R6, L, n, p, q, r, and s, is represented by: '((A1 to A19), (B1 to B11), (R11 to R12), (R21 to R29), (R31 to R36), (R41 to R45), (R51 to R54), (L1 to L5), (n1 to n4), (p1 to p3), (q1 to q3), (r1 to r3), and (s1 to s4))'.

'((A1 to A19), (R1 to R11), (R11 to R12), (R21 to R29), (R31 to R36), (R41 to R45), (R51 to R54), (L1 to L5), (n1 to n4), (p1 to p3), (q1 to q3), (r1 to r3), and (s1 to s4))' means all the embodiments which are the combinations of:

Ring A is one embodiment selected from A1 to A19;
Ring B is one embodiment selected from B1 to B11;
$R^{1a}$ and $R^{1b}$ is one embodiment selected from R11 to R12;
R2 is one embodiment selected from R21 to R29;
R3 is one embodiment selected from R31 to R36;
$R^{4a}$ to $R^{4d}$ is one embodiment selected from R41 to R45;
R6 is one embodiment selected from R51 to R54;
L is one embodiment selected from L1 to L5;
n is one embodiment selected from n1 to n4;
p is one embodiment selected from p1 to p3;
q is one embodiment selected from q1 to q3;
r is one embodiment selected from r1 to r3; and,
s is one embodiment selected from s1 to s4.

Examples of the compound represented by Formula (IB) include compounds wherein '("Ring A", "$R^{1a}$ and $R^{1b}$", "$R^{1c}$ and $R^{1d}$", $R^2$, $R^3$, $R^{4a}$ to $R^{4d}$, L, m, n, p, q, and s)', which stands for combinations of Ring A, Ring B, $R^{1a}$ and $R^{1b}$, $R^2$, $R^3$, $R^{4a}$ to $R^{4d}$, $R^5$, L, n, p, q, r, and s, is represented by: '((A1 to A19), (R11 to R12), (r11 to r12), (R21 to R29), (R31 to R36), (R41 to R45), (L1 to L5), (m1 to m2), (n1 to n4), (p1 to p3), (q1 to q3), and (s1 to s4))'.

'((A1 to A19), (R11 to R12), (r11 to r12), (R21 to R29), (R31 to R36), (R41 to R45), (L1 to L5), (m1 to m2), (n1 to n4), and (s1 to s4))' means all the embodiments which are the combinations of:

Ring A is one embodiment selected from A1 to A19;
$R^{1a}$ and $R^{1b}$ is one embodiment selected from R11 to R12;
$R^{1c}$ and $R^{1d}$ is one embodiment selected from r11 to r12;
$R^2$ is one embodiment selected from R21 to R29;
$R^3$ is one embodiment selected from R31 to R36;
$R^{4a}$ to $R^{4d}$ is one embodiment selected from R41 to R45;
L is one embodiment selected from L1 to L5;
m is one embodiment selected from m1 to m2;
n is one embodiment selected from n1 to n4;
p is one embodiment selected from p1 to p3;
q is one embodiment selected from q1 to q31 and,
s is one embodiment selected from s1 to s4.

Examples of proffered embodiments of the compound of Formula (I) or a pharmaceutically acceptable salt thereof are illustrated bellow. A compound represented by the following Formula (IC-1), (ID-1), (IE-1), (IF-1), (IG-1), (IH-1), (II-1), (IJ-1), (IK-1), (IL-1), (IM-1), or (IN-1) (Hereinafter referred to as Formula (IC-1) to (IN-1)):

[Chemical Formula 82]

(IC-1)

-continued (ID-1)
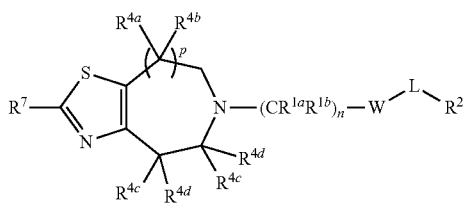

(IE-1)
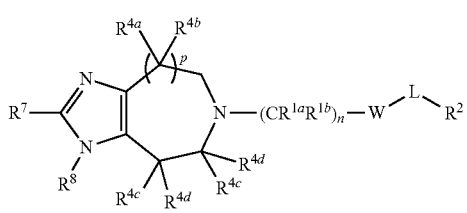

(IF-1)
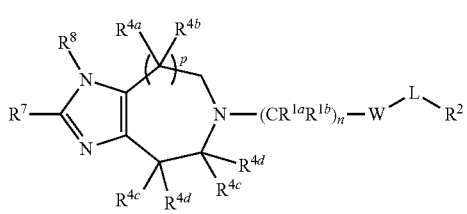

(IG-1)
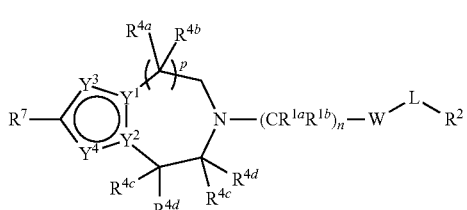

(IH-1)
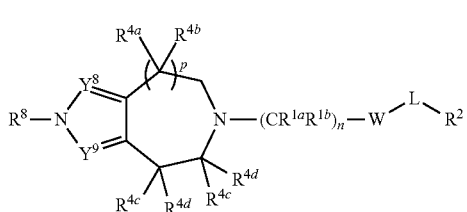

(II-1)
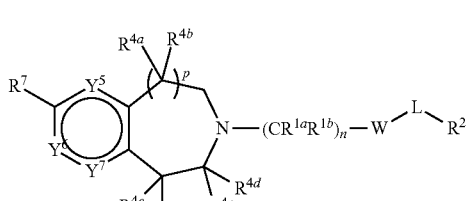

(IJ-1)
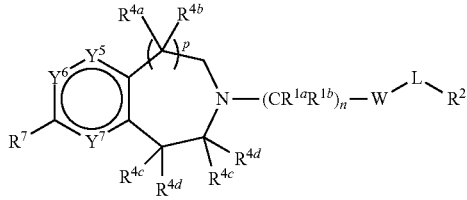

-continued (IK-1)
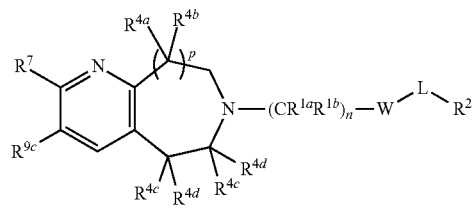

(IL-1)
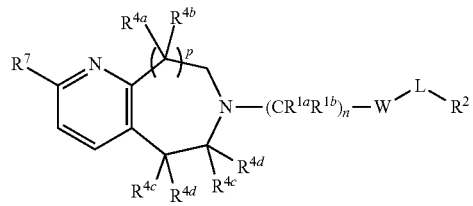

(IM-1)
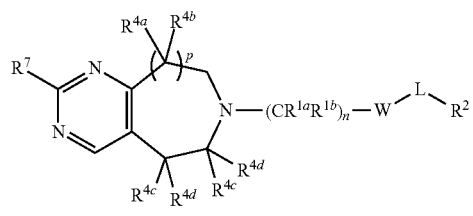

(IN-1)
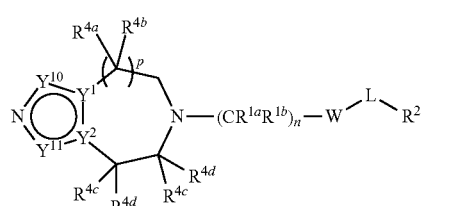

wherein,
$R^{1a}$ and $R^{1b}$ are any one of "R11 to R12", $R^2$ is any one of "R21 to R29", $R^{4a}$ to $R^{4d}$ are any one of "R41 to R45", L is any one of "L1 to L5", n is any one of "n1 to n4"; p is any one of "p1 to p3";
—W— is a group represented by:

[Chemical Formula 83]

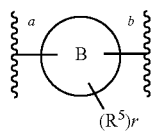

wherein Ring R is any one of "R1 to B11", $R^5$ is any one of "R51 to R54", r is any one of r1 to r3), or,
—$(CR^{1c}R^{1d})_m$—;
$R^{1c}$ and $R^{1d}$ are any one of "r11 to r12", m is any one of "m1 to m2"; and the other symbols are the same as defined above,
or a pharmaceutically acceptable salt thereof.

Other examples of preferred embodiments of the compound of Formula (I) or a pharmaceutically acceptable salt thereof are illustrated bellow. A compound represented by the following Formula (IC-2), (ID-2), (IE-2), (IF-2), (IG-2), (IH-2), (II-2), (IJ-2), (IK-2), (IL-2), (IM-2) or (IN-2) (Hereinafter referred to as Formula (IC-2) to (IN-2)):

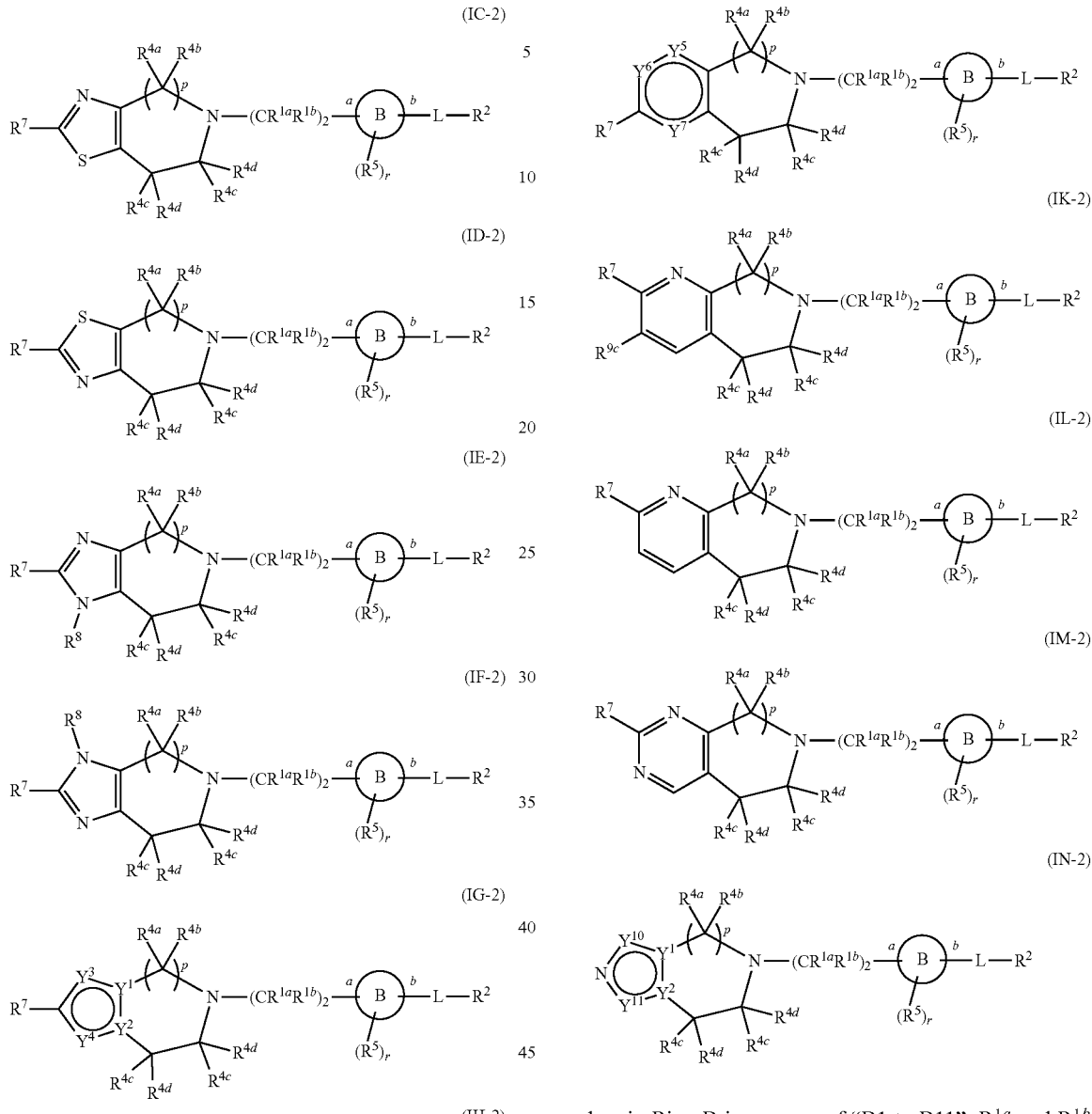

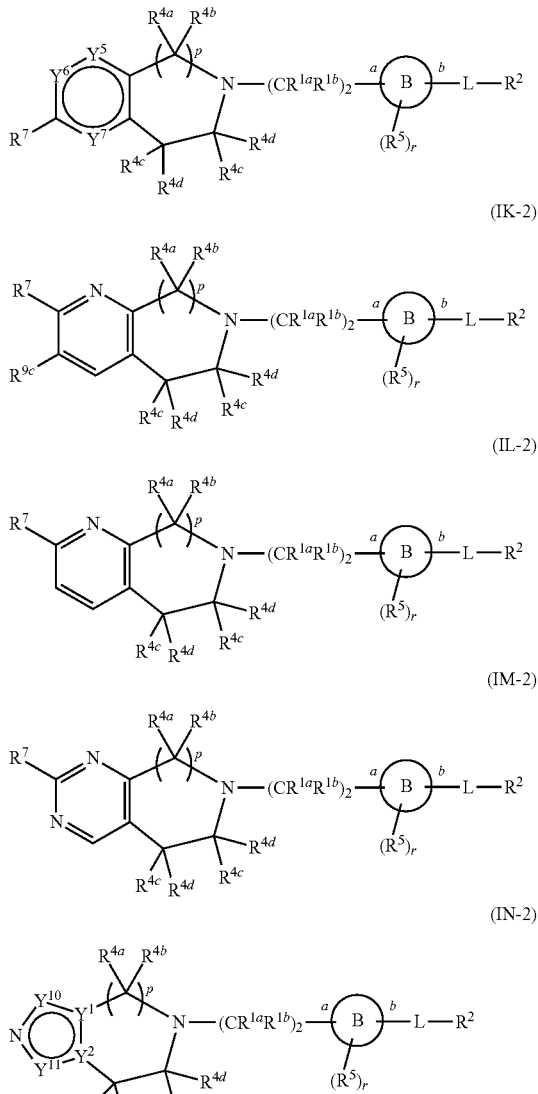

wherein Ring B is any one of "B1 to B11", $R^{1a}$ and $R^{1b}$ are any one of "R11 to R12", $R^2$ is any one of "R21 to R29", $R^{4a}$ to $R^{4d}$ are any one of "R41 to R45", $R^8$ is any one of "R51 to R54", L is any one of "L1 to L5", p is any one of "p1 to p3", r is any one of r1 to r3, and the other symbols are the same as defined above, or a pharmaceutically acceptable salt thereof.

Specific examples of each substituent in the compound represented by Formula (I), Formula (Ie), Formula (IC-1) to (IN-1), Formula (IC-2) to (IN-2), or a pharmaceutically acceptable salt thereof are illustrated bellow. All considerable combinations of specific examples of each substituent are examples of the compound represented by Formula (I), Formula (Ie), Formula (IC-1) to (IN-1), or Formula (IC-2) to (IN-2), or a pharmaceutically acceptable salt thereof.

In Formula (I), Formula (Ie), Formula (IC-1) to (IM-1), or Formula (IC-2) to (IM-2), $R^7$ is each independently a hydrogen atom, halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkynylsulfamoyl, substituted or unsubstituted alkylcarbonylamino, substituted or unsubstituted alkenylcarbonyl amino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclyl carbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonyl amino, substituted or unsubstituted non-aromatic carbocyclylcarbonyl amino, substituted or unsubstituted aromatic heterocyclylcarbonyl amino, or substituted or unsubstituted non-aromatic heterocyclylcarbonylamino (Hereinafter referred to as "R701").

R7 is each independently halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl (Hereinafter referred to as "$R^7$ is R702").

$R^7$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or substituted or unsubstituted non-aromatic heterocyclylamino (Hereinafter referred to as "$R^7$ is R703").

$R^7$ is each independently optionally substituted with the substituent group C2 alkyl, alkenyl optionally substituted with the substituent group C2, alkynyl optionally substituted with the substituent group C2, alkyloxy optionally substituted with the substituent group C2, alkenyloxy, optionally substituted with the substituent group C2 alkynyloxy optionally substituted with the substituent group C2, alkylamino optionally substituted with the substituent group C2, alkenylamino optionally substituted with the substituent group C2, alkynylamino optionally substituted with the substituent group C2, aromatic carbocyclyl optionally substituted with the substituent group B2, non-aromatic carbocyclyl optionally substituted with the substituent group B2', aromatic heterocyclyl optionally substituted with the substituent group B2, non-aromatic heterocyclyl optionally substituted with the substituent group B2', aromatic carbocyclyloxy optionally substituted with the substituent group B2, non-aromatic carbocyclyloxy optionally substituted with the substituent group B2', aromatic heterocyclyloxy optionally substituted with the substituent group B2, non-aromatic heterocyclyloxy optionally substituted with the substituent group B2', aromatic carbocyclylamino optionally substituted with the substituent group B2, non-aromatic carbocyclylamino optionally substituted with the substituent group B2', aromatic heterocyclylamino optionally substituted with the substituent group B2, or non-aromatic heterocyclylamino optionally substituted with the substituent group B2' (Hereinafter referred to as "$R^7$ is R704").

$R^7$ is each independently substituted or unsubstituted alkyl, substituted or unsubstituted alkyloxy, substituted or unsubstituted alkylamino, substituted or unsubstituted aromatic carbocyclyl, substituted or unsubstituted non-aromatic carbocyclyl, substituted or unsubstituted non-aromatic heterocyclyl, or substituted or unsubstituted non-aromatic carbocyclyloxy (Hereinafter referred to as "$R^7$ is R705").

$R^7$ is each independently alkyl optionally substituted with the substituent group C2, alkyloxy optionally substituted with the substituent group C2, alkylamino optionally substituted with the substituent group C2, aromatic carbocyclyl optionally substituted with the substituent group B2, non-aromatic carbocyclyl optionally substituted with the substituent group B2', non-aromatic heterocyclyl optionally substituted with the substituent group B2', or non-aromatic carbocyclyloxy optionally substituted with the substituent group B2' (Hereinafter referred to as "$R^7$ is R706").

$R^7$ is substituted or unsubstituted alkyl (the alkyl includes, for example, C1-C6alkyl, for example, C2-C6 alkyl) (Hereinafter referred to as "$R^7$ is R707").

$R^7$ is C1-C6 alkyl optionally substituted with the substituent group C2 (for example, halogen) (Hereinafter referred to as "$R^7$ is R708").

$R^7$ is substituted or unsubstituted alkyloxy (the alkyl includes, for example, C1-C6 alkyloxy, for example, C2-CG alkyloxy) (Hereinafter referred to as "$R^7$ is R709").

$R^7$ is C1-C6 alkyloxy optionally substituted with the substituent group C2 (for example, halogen, cyano, alkyloxy optionally substituted with one or more group(s) selected from the substituent group A, non-aromatic carbocyclyl optionally substituted with one or more group(s) selected from the substituent group B2', and non-aromatic heterocyclyl optionally substituted with one or more group(s) selected from the substituent group B2') (Hereinafter referred to as "$R^7$ is R710").

$R^7$ is substituted or unsubstituted phenyl (the substituents include, for example, the substituent group B2) (Hereinafter referred to as "$R^7$ is R711").

$R^7$ is —$NR^{10}R^{11}$;
$R^{10}$ and $R^{11}$ are each independently substituted or unsubstituted alkyl (the substituents include, for example, the substituent group C2); or,
$R^{10}$ and $R^{11}$ may be taken together with the adjacent nitrogen atom to form a substituted or unsubstituted non-aromatic heterocycle (the substituents include, for example, the substituent group B2') (provided that $R^{10}$ and $R^{11}$ are not simultaneously both hydrogen atoms) (Hereinafter referred to as "$R^7$ is R712").

$R^7$ is —$NR^{10}R^{11}$; $R^{10}$ and $R^{11}$ are each independently, C1-C6 alkyl optionally substituted with the substituent group C2; or, $R^{10}$ and $R^{11}$ may be taken together with the adjacent nitrogen atom to form a pyrrolidine ring, a piperidine ring or an azetidine ring optionally substituted with the substituent group B2' (Hereinafter referred to as "$R^7$ is R713").

$R^7$ is C2-C6 alkyl substituted with halogen, or, C2-C6 alkyloxy substituted with halogen (Hereinafter referred to as "$R^7$ is R714").

In Formula (I), Formula (Ie), (IE-1) to (IH-1), (IN-1), (IE-2) to (IH-2), or (IN-2),
$R^8$ is a hydrogen atom, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkylcarbonyl, substituted or unsubstituted alkenylcarbonyl, substituted or unsubstituted alkynylcarbonyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl (Hereinafter referred to as "$R^8$ is R81").

$R^8$ is a hydrogen atom, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl (Hereinafter referred to as "$R^8$ is R82").

$R^8$ is a substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl (Hereinafter referred to as "$R^8$ is R83").

$R^8$ is a hydrogen atom, alkyl optionally substituted with the substituent group C2, alkenyl optionally substituted with the substituent group C2, alkynyl optionally substituted with the substituent group C2, aromatic carbocyclyl optionally substituted with the substituent group B2, non-aromatic carbocyclyl optionally substituted with the substituent group B2', aromatic heterocyclyl optionally substituted with the substituent group B2, or non-aromatic heterocyclyl optionally substituted with the substituent group B2' (Hereinafter referred to as "$R^8$ is R84").

$R^8$ is alkyl optionally substituted with the substituent group C2, alkenyl optionally substituted with the substituent group C2, alkynyl optionally substituted with the substituent group C2, aromatic carbocyclyl optionally substituted with the substituent group B2, non-aromatic carbocyclyl optionally substituted with the substituent group B2', aromatic heterocyclyl optionally substituted with the substituent group B2, or non-aromatic heterocyclyl optionally substituted with the substituent group B2' (Hereinafter referred to as "$R^8$ is R85").

$R^8$ is alkyl optionally substituted with the substituent group C2, alkenyl optionally substituted with the substituent group C2, or alkynyl optionally substituted with the substituent group C2 (Hereinafter referred to as "$R^8$ is R86").

$R^8$ is substituted or unsubstituted alkyl (the substituents include, for example, the substituent group 02) (Hereinafter referred to as "$R^8$ is R87").

$R^8$ is substituted or unsubstituted phenyl ((the substituents include, for example, the substituent group B2) (Hereinafter referred to as "$R^8$ is R88").

$R^8$ is a hydrogen atom (Hereinafter referred to as "$R^8$ is R89").

In Formula (I), Formula (Ie), (IG-1) to (IK-1), (IN-1), (IG-2) to (IK-2), or (IN-2),
$R^{9a}$ to $R^{9d}$ are each independently a hydrogen atom, halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonyl amino, substituted or unsubstituted alkenylcarbonyl amino, substituted or unsubstituted alkynylcarbonyl amino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, or substituted or unsubstituted aromatic heterocyclylcarbonyl amino (Hereinafter referred to as "$R^{9a}$ to $R^{9d}$ are R91").

$R^{9a}$ to $R^{9d}$ are each independently a hydrogen atom, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl (Hereinafter referred to as "$R^{9a}$ to $R^{9d}$ are R92").

$R^{9a}$ to $R^{9d}$ are each independently hydrogen atom, cyano, halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, or substituted or unsubstituted alkynylamino (Hereinafter referred to as "$R^{9a}$ to $R^{9d}$ are R93").

$R^{9a}$ to $R^{9d}$ are each independently hydrogen atom, cyano, halogen, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy (Hereinafter referred to as "$R^{9a}$ to $R^{9d}$ are R94").

$R^{9a}$ to $R^{9d}$ are each independently a hydrogen atom, halogen, C1-C6 alkyl optionally substituted with the substituent group C2, or C1-C6 alkyloxy optionally substituted with the substituent group C2 (Hereinafter referred to as "$R^{9a}$ to $R^{9d}$ are R95").

$R^{9a}$ to $R^{9d}$ are hydrogen atoms (Hereinafter referred to as "$R^{9a}$ to $R^{9d}$ are R9G").

In Formula (I), Formula (Ie), (IG-1), or (IG-2), $Y^1$ and $Y^2$ are each independently a carbon atom or a nitrogen atom; $Y^3$ and $Y^4$ are each independently $CR^{9a}$, N, $NR^8$, S, or O; the ring constituted of $Y^1$ to $Y^4$ and a carbon atom is a 5-membered aromatic heterocycle; 1 or 2 atoms constituting the 5-membered aromatic heterocycle are heteroatoms (Hereinafter referred to as "$Y^1$ to $Y^4$ are Y11").

$Y^1$ and $Y^2$ ore each independently a carbon atom or a nitrogen atom; $Y^3$ and $Y^4$ are each independently $CR^{9a}$, N, $NR^8$, S, or O; the ring constituted of $Y^1$ to $Y^4$ and a carbon atom is a 5-membered aromatic heterocycle (provided that thiophene ring is excluded); 1 or 2 atoms constituting the 5-membered aromatic heterocycle are heteroatoms (Hereinafter referred to as "$Y^1$ to $Y^4$ are Y12").

$Y^1$ and $Y^2$ are carbon atoms; $Y^3$ and $Y^4$ are each independently $CR^{9a}$, N, $NR^8$, S, or O; the ring constituted of $Y^1$ to $Y^4$ and a carbon atom is a 5-membered aromatic heterocycle; 2 atoms constituting the 5-membered aromatic heterocycle are heteroatoms (Hereinafter referred to as "$Y^1$ to $Y^4$ are Y13").

$Y^1$ and $Y^2$ are carbon atoms; $Y^3$ and $Y^4$ are each independently $CR^{9a}$, N, $NR^8$, S, or O; the ring constituted of $Y^1$ to $Y^4$ and a carbon atom is a 5-membered aromatic heterocycle (provided that thiophene ring is excluded); 1 or 2 atoms constituting the 5-membered aromatic heterocycle are heteroatoms (Hereinafter referred to as "$Y^1$ to $Y^4$ are Y14").

[Chemical Formula 86]

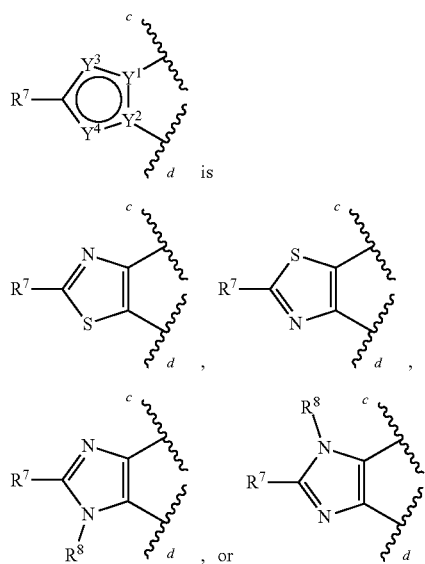

(Hereinafter referred to as "$Y^1$ to $Y^4$ are Y15").

[Chemical Formula 87]

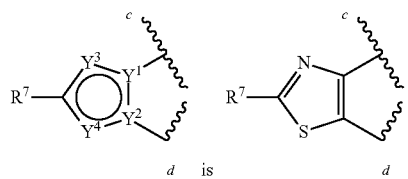

(Hereinafter referred to as "$Y^1$ to $Y^4$ are Y16").

In Formula (I), Formula (Ie), (IH-1), or (IH-2), $Y^8$ and $Y^9$ are each independently $CR^{9a}$ or N; provided that $Y^3$ and $Y^4$ are not simultaneously both N (Hereinafter referred to as "$Y^8$ and $Y^9$ are Y81").

$Y^8$ is N; $Y^9$ is $CR^{9a}$ (Hereinafter referred to as "$Y^8$ and $Y^9$ are Y82").

$Y^8$ is $CR^{9a}$; $Y^9$ is N (Hereinafter referred to as "$Y^8$ and $Y^9$ are Y83").

In Formula (I), Formula (Ie), (II-1), (IJ-1), (II-2), or (IJ-2), $Y^5$ is $CR^{9b}$ or N; $Y^6$ is $CR^{9c}$ or N; $Y^7$ is $CR^{9d}$ or N; the ring constituted of $Y^5$ to $Y^7$ and carbon atoms is a 6-membered aromatic heterocycle; 1 or 2 atoms constituting the G-membered aromatic heterocycle are heteroatoms (Hereinafter referred to as "$Y^5$ to $Y^7$ are Y51").

$Y^5$ is $CR^{9b}$ or N; $Y^6$ is $CR^{9c}$ or N; $Y^7$ is $CR^{9d}$ or N; the ring constituted of $Y^5$ to $Y^7$ and carbon atoms is pyridine (Hereinafter referred to as "$Y^5$ to $Y^7$ are Y52").

$Y^5$ is N; $Y^6$ is $CR^{9c}$ or N; $Y^7$ is $CR^{9d}$; the ring constituted of $Y^6$ to $Y^7$ and carbon atoms is a 6-membered aromatic heterocyclic; 1 or 2 atoms constituting the 6-membered aromatic heterocycle are heteroatoms (Hereinafter referred to as "$Y^5$ to $Y^7$ are Y53").

$Y^5$ is N; $Y^6$ is $CR^{9c}$; $Y^7$ is $CR^{9d}$; the ring constituted of $Y^5$ to $Y^7$ and carbon atoms is pyridine, for example,

[Chemical Formula 88]

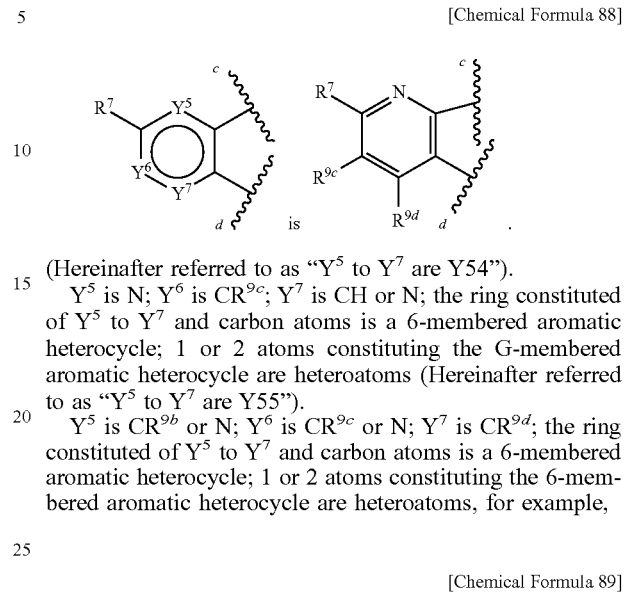

(Hereinafter referred to as "$Y^5$ to $Y^7$ are Y54").

$Y^5$ is N; $Y^6$ is $CR^{9c}$; $Y^7$ is CH or N; the ring constituted of $Y^5$ to $Y^7$ and carbon atoms is a 6-membered aromatic heterocycle; 1 or 2 atoms constituting the G-membered aromatic heterocycle are heteroatoms (Hereinafter referred to as "$Y^5$ to $Y^7$ are Y55").

$Y^5$ is $CR^{9b}$ or N; $Y^6$ is $CR^{9c}$ or N; $Y^7$ is $CR^{9d}$; the ring constituted of $Y^5$ to $Y^7$ and carbon atoms is a 6-membered aromatic heterocycle; 1 or 2 atoms constituting the 6-membered aromatic heterocycle are heteroatoms, for example,

[Chemical Formula 89]

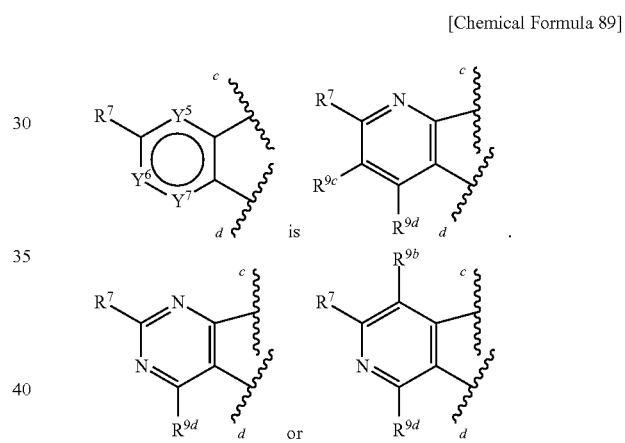

(Hereinafter referred to as "$Y^5$ to $Y^7$ are Y56").

$Y^5$ is N; $Y^6$ is $CR^{9c}$ or N; $Y^7$ is $CR^{9d}$; the ring constituted of $Y^5$ to $Y^7$ and carbon atoms is a 6-membered aromatic heterocycle; 1 or 2 atoms constituting the 6-membered aromatic heterocycle are heteroatoms, for example,

[Chemical Formula 89]

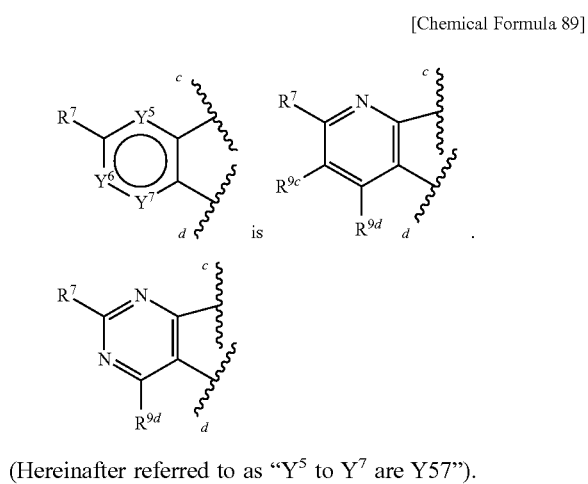

(Hereinafter referred to as "$Y^5$ to $Y^7$ are Y57").

$Y^5$ is N; $Y^6$ is $CR^{9c}$ or N; $Y^7$ is CH; the ring constituted of $Y^5$ to $Y^7$ and carbon atoms is a 6-membered aromatic heterocycle; 1 or 2 atoms constituting the 6-membered aromatic heterocycle are heteroatoms, for example,

[Chemical Formula 91]

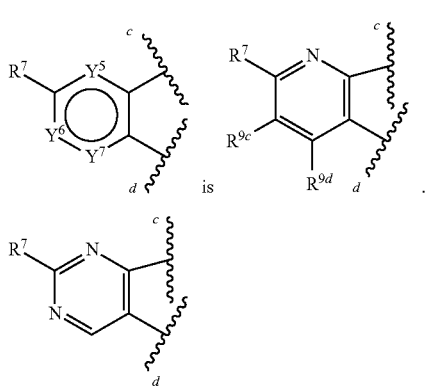

(Hereinafter referred to as "$Y^5$ to $Y^7$ are Y58").

$Y^5$ is N; $Y^6$ is CH; $Y^7$ is $CR^{9d}$; the ring constituted of $Y^5$ to $Y^7$ and carbon atoms is pyridine, for example,

[Chemical Formula 92]

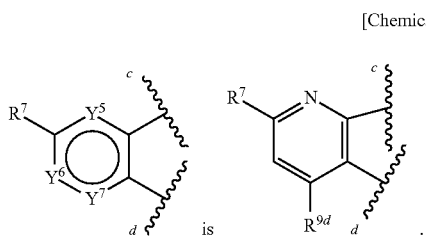

(Hereinafter referred to as "$Y^5$ to $Y^7$ are Y59").

In Formula (I), Formula (Ie), (IN-1), or (IN-2), $Y^1$ and $Y^2$ are each independently a carbon atom or a nitrogen atom; $Y^{10}$ and $Y^{11}$ are each independently $CR^{9a}$ or $NR^8$; the ring constituted of $Y^1$, $Y^2$, $Y^{10}$, $Y^{11}$ and a nitrogen atom is a 5-membered aromatic heterocycle, 1 or 2 atoms constituting the 5-membered aromatic heterocycle are heteroatoms (Hereinafter referred to as "$Y^1$, $Y^2$, $Y^{10}$ and $Y^{11}$ are Y101").

$Y^1$ and $Y^2$ are carbon atoms; $Y^{10}$ is $NR^8$; the ring constituted of $Y^1$, $Y^2$, $Y^{10}$, $Y^{11}$ and a nitrogen atom is pyrazole ring (Hereinafter referred to as "$Y^1$, $Y^2$, $Y^{10}$ and $Y^{11}$ are Y102").

All considerable combinations of specific examples of each substituent are examples of the compound represented by Formula (I), Formula (Ie), Formula (IC-1) to (IN-1), or Formula (IC-2) to (IN-2), or a pharmaceutically acceptable salt thereof.

Examples of the compound represented by Formula (IC-1), (ID-1), (IL-1), or (IM-1), respectively, include
1) compounds wherein
—W— is a group represented by:

[Chemical Formula 93]

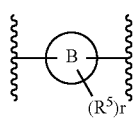

(Hereinafter referred to as "W is W1") and
'("Ring B", "$R^{1a}$ and $R^{1b}$", $R^2$, $R^{4a}$ to $R^{4d}$, $R^5$, $R^7$, L, n, p, and r)', which stands for combinations of Ring B, $R^{1a}$ and $R^{1b}$, $R^2$, $R^{4a}$ to $R^{4d}$, $R^5$, $R^7$, L, n, p, and r, is represented by: '((B1 to B11), (R11 to R12), (R21 to R29), (R41 to R45), (R51 to R54), (R701 to R714), (L1 to L5), (n1 to n4), (p1 to p3), and (r1 to r3))'; and, 2) compounds wherein
—W— is —$(CR^{1c}R^{1d})_m$— (Hereinafter referred to as "W is W2"), and
'("$R^{1a}$ and $R^{1b}$", "$R^{1c}$ and $R^{1d}$", $R^2$, $R^{4a}$ to $R^{4d}$, $R^7$, L, m, n, p, and r)', which stands for combinations of $R^{1a}$ and $R^{1b}$, $R^{1c}$ and $R^{1d}$, $R^2$, $R^{4a}$ to $R^{4d}$, $R^7$, L, m, n, p, and r, is represented by: '((R11 to R12), (r11 to r12), (R21 to R29), (R41 to R45), (R701 to R714), (L1 to L5), (m1 to m2), (n1 to n4), (p1 to p3), and (r1 to r3))'.

Examples of the compound represented by Formula (IC-2), (ID-2), (IL-2), or (IM-2), respectively, include compounds wherein '("Ring B", "$R^{1a}$ and $R^{1b}$", $R^2$, $R^{4a}$ to $R^{4d}$, $R^5$, $R^7$, L, p, and r)', which stands for combinations of Ring B, $R^{1a}$ and $R^{1b}$, $R^2$, $R^{4a}$ to $R^{4d}$, $R^5$, $R^7$, L, p, and r, is represented by: '((B1 to B11), (R11 to R12), (R21 to R29), (R41 to R45), (R51 to R54), (R701 to R714), (L1 to L5), (p1 to p3), and (r1 to r3))'.

'((B1 to B11), (R11 to R12), (R21 to R29), (R41 to R45), (R51 to R54), (R701 to R714), (L1 to L5), (p1 to p3), and (r1 to r3))' means all the embodiments which are the combinations of:
Ring B is one embodiment selected from B1 to B11;
$R^{1a}$ and $R^{1b}$ is one embodiment selected from R11 to R12;
$R^2$ is one embodiment selected from R21 to R29;
$R^{4a}$ to $R^{4d}$ is one embodiment selected from R41 to R455
$R^5$ is one embodiment selected from R51 to R54;
$R^7$ is one embodiment selected from R701 to R714;
L is one embodiment selected from L1 to L5;
p is one embodiment selected from p1 to p3l and,
r is one embodiment selected from r1 to r3.

'((B1 to B11), (R11 to R12), (R21 to R29), (R41 to R45), (R51 to R54), (R701 to R714), (L1 to L5), (n1 to n4), (p1 to p3), and (r1 to r3))' and '((R11 to R12), (r11 to r12), (R21 to R29), (R41 to R45), (R701 to R714), (L1 to L5), (m1 to m2), (n1 to n4), (p1 to p3), and (r1 to r3))' also means all combinations of each embodiments of the substituents as above.

Examples of the compound represented by Formula (IE-1) or (IF-1), respectively, include
1) compounds wherein
—W— is W1, and
'("Ring B", "$R^{1a}$ and $R^{1b}$", $R^2$, $R^{4a}$ to $R^{4d}$, $R^6$, $R^7$, $R^8$, L, n, p, and r)', which stands for combinations of Ring B, $R^{1a}$ and $R^{1b}$, $R^2$, $R^{4a}$ to $R^{4d}$, $R^5$, $R^7$, $R^8$, L, n, p, and r, is represented by: '((B1 to B11), (R11 to R12), (R21 to R29), (R41 to R45), (R51 to R54), (R701 to R714), (R81 to R89), (L1 to L5), (n1 to n4), (p1 to p3), and (r1 to r3))'; and, 2) compounds wherein
—W— is W2, and
'("$R^{1a}$ and $R^{1b}$", "$R^{1c}$ and $R^{1d}$", $R^2$, $R^{4a}$ to $R^{4d}$, $R^7$, $R^8$, L, m, n, p, and r)', which stands for combinations of $R^{1a}$ and $R^{1b}$, $R^{1c}$ and $R^{1d}$, R2, $R^{4a}$ to $R^{4d}$, R7, R8, L, m, n, p, and r, is represented by: '((R11 to R12), (r11 to r12), (R21 to R29), (R41 to R45), (R701 to R714), (R81 to R89), (L1 to L5), (m1 to m2), (n1 to n4), (p1 to p3), and (r1 to r3)).

Examples of the compound represented by Formula (IE-2) or (IF-2), respectively, include compounds wherein
'("Ring B", "$R^{1a}$ and $R^{1b}$", $R^2$, $R^{4a}$ to $R^{4d}$, $R^6$, $R^7$, $R^8$, L, p, and r)', which stands for combinations of Ring B, $R^{1a}$ and $R^{1b}$, $R^2$, $R^{4a}$ to $R^{4d}$, $R^5$, $R^7$, $R^8$, L, p, and r, is represented by: '((B1 to B11), (R11 to R12), (R21 to R29), (R41 to R45), (R51 to R54), (R701 to R714), (R81 to R89), (L1 to L5), (p1 to p3), and (r1 to r3))'.

'((B1 to B11), (R11 to R12), (R21 to R29), (R41 to R45), (R51 to R54), (R701 to R714), (R81 to R89), (L1 to L5), (p1 to p3), and (r1 to r3))' means all the embodiments which are the combinations of:
Ring B is one embodiment selected from B1 to B11;
$R^{1a}$ and $R^{1b}$ is one embodiment selected from R11 to R12;
$R^2$ is one embodiment selected from R21 to R29;
$R^{4a}$ to $R^{4d}$ is one embodiment selected from R41 to R45;
$R^5$ is one embodiment selected from R51 to R54;
$R^7$ is one embodiment selected from R701 to R714;
$R^8$ is one embodiment selected from R81 to R89;
L is one embodiment selected from L1 to L5;
p is one embodiment selected from p1 to p3; and,
r is one embodiment selected from r1 to r3.

'((B1 to B11), (R11 to R12), (R21 to R29), (R41 to R45), (R51 to R54), (R701 to R714), (R81 to R89), (L1 to L5), (n1 to n4), (p1 to p3), (r1 to r3))' and '((R11 to R12), (r11 to r12), (R21 to R29), (R41 to R45), (R701 to R714), (R81 to R89), (L1 to L5), (m1 to m2), (n1 to n4), (p1 to p3), and (r1 to r3))' also means all combinations of each embodiments of the substituents as above.

Examples of the compound represented by Formula (IG-1) include
1) compounds wherein
—W— is W1, and
'("$Y^1$ to $Y^4$", "Ring B", "$R^{1a}$ and $R^{1b}$", $R^2$, $R^{4a}$ to $R^{4d}$, $R^5$, $R^7$, $R^8$, $R^{9a}$, L, n, p, and r)', which stands for combinations of $Y^1$ to $Y^4$, Ring B, $R^{1a}$ and $R^{1b}$, $R^2$, $R^{4a}$ to $R^{4d}$, R5, R7, R8, $R^{9a}$, L, n, p, and r, is represented by: '((Y11 to Y16), (B1 to B11), (R11 to R12), (R21 to R29), (R41 to R45), (R51 to R54), (R701 to R714), (R81 to R89), (R91 to R96), (L1 to L5), (n1 to n4), (p1 to p3), and (r1 to r3))'; and,
2) compounds wherein
—W— is W2, and
'("$Y^1$ to $Y^4$", "$R^{1a}$ and $R^{1b}$", "$R^{1c}$ and $R^{1d}$", $R^2$, $R^{4a}$ to $R^{4d}$, $R^7$, $R^8$, $R^{9a}$, L, m, n, p, and r)', which stands for combinations of $Y^1$ to $Y^4$, $R^{1a}$ and $R^{1b}$, $R^{1c}$ and $R^{1d}$, $R^2$, $R^{4a}$ to $R^{4d}$, $R^7$, $R^8$, $R^{9a}$, L, m, n, p, and r, is represented by: '((Y11 to Y16), (R11 to R12), (r11 to r12), (R21 to R29), (R41 to R45), (R701 to R714), (R81 to R89), (R91 to R96), (L1 to L5), (m1 to m2), (n1 to n4), (p1 to p3), and (r1 to r3))'.

Examples of the compound represented by Formula (IG-2) include compounds wherein '("$Y^1$ to $Y^4$", "Ring B", "$R^{1a}$ and $R^{1b}$", $R^2$, $R^{4a}$ to $R^{4d}$, $R^5$, $R^7$, $R^8$, $R^{9a}$, L, p, and r)', which stands for combinations of $Y^1$ to $Y^4$, Ring B, $R^{1a}$ and $R^{1b}$, $R^2$, $R^{4a}$ to $R^{4d}$, $R^5$, $R^7$, $R^8$, $R^{9a}$, L, p, and r, is represented by: '((Y11 to Y16), (B1 to B11), (R11 to R12), (R21 to R29), (R41 to R45), (R51 to R54), (R701 to R714), (R81 to R89), (R91 to R96), (L1 to L5), (p1 to p3), and (r1 to r3))'.

'((Y11 to Y16), (B1 to B11), (R11 to R12), (R21 to R29), (R41 to R45), (R51 to R54), (R701 to R714), (R81 to R89), (R91 to R96), (L1 to L5), (p1 to p3), and (r1 to r3))' means all the embodiments which are the combinations of:
$Y^1$ to $Y^4$ is one embodiment selected from Y11 to Y16;
Ring B is one embodiment selected from B1 to B11;
$R^{1a}$ and $R^{1b}$ is one embodiment selected from R11 to R12;
$R^2$ is one embodiment selected from R21 to R29;
$R^{4a}$ to $R^{4d}$ is one embodiment selected from R41 to R45;
$R^5$ is one embodiment selected from R51 to R54;
$R^7$ is one embodiment selected from R701 to R714;
R8 is one embodiment selected from R81 to R89;
$R^{9a}$ is one embodiment selected from R91 to R96;
L is one embodiment selected from L1 to L5;
p is one embodiment selected from p1 to p3; and,
r is one embodiment selected from r1 to r3.

'((Y11 to Y16), (B1 to B11), (R11 to R12), (R21 to R29), (R41 to R45), (R51 to R54), (R701 to R714), (R81 to R89), (R91 to R96), (L1 to L5), (n1 to n4), (p1 to p3), and (r1 to r3))' and '((Y11 to Y16), (R11 to R12), (r11 to r12), (R21 to R29), (R41 to R45), (R701 to R714), (R81 to R89), (R91 to R96), (L1 to L5), (m1 to m2), (n1 to n4), (p1 to p3), and (r1 to r3))' also mean all combinations of each embodiments of the substituents as above.

Examples of the compound represented by Formula (IH-1) include
1) compounds wherein
—W— is W1, and
'("$Y^8$ and $Y^9$", "Ring R", "$R^{1a}$ and $R^{1b}$", $R^2$, $R^{4a}$ to $R^{4d}$, $R^5$, $R^8$, $R^{9a}$, L, n, p, and r)', which stands for combinations of $Y^8$ and $Y^9$, Ring R, $R^{1a}$ and $R^{1b}$, $R^2$, $R^{4a}$ to $R^{4d}$, $R^5$, $R^8$, $R^{9a}$, L, n, p, and r, is represented by: '((Y81 to Y83), (R1 to R11), (R11 to R12), (R21 to R29), (R41 to R45), (R51 to R54), (R81 to R89), (R91 to R96), (L1 to L5), (n1 to n4), (p1 to p3), and (r1 to r3))'; and,
2) compounds wherein
—W— is W2, and
'("$Y^8$ and $Y^9$", "$R^{1a}$ and $R^{1b}$", "$R^{1a}$ and $R^{1d}$", $R^2$, $R^{4a}$ to $R^{4d}$, $R^7$, $R^{9a}$, L, m, n, p, and r)', which stands for combinations of $Y^8$ and $Y^9$, $R^{1a}$ and $R^{1b}$, $R^{1c}$ and $R^{1d}$, $R^2$, $R^{4a}$ to $R^{4d}$, $R^5$, $R^{9a}$, L, m, n, p, and r, is represented by: '((Y81 to Y83), (R11 to R12), (r11 to r12), (R21 to R29), (R41 to R45), (R81 to R89), (R91 to R96), (L1 to L5), (m1 to m2), (n1 to n4), (p1 to p3), and (r1 to r3))'.

Examples of the compound represented by Formula (IH*2) include compounds wherein
'("$Y^8$ and $Y^9$", "Ring R", "$R^{1a}$ and $R^{1b}$", $R^2$, $R^{4a}$ to $R^{4d}$, $R^5$, $R^7$, $R^{9a}$, L, p, r)', which stands for combinations of $Y^8$ and $Y^9$, Ring R, $R^{1a}$ and $R^{1b}$, $R^2$, $R^{4a}$ to $R^{4d}$, $R^5$, $R^7$, $R^{9a}$, L, p, and r, is represented by: '((Y81 to Y83), (R1 to R11), (R11 to R12), (R21 to R29), (R41 to R45), (R51 to R54), (R81 to R89), (R91 to R96), (L1 to L5), (p1 to p3), and (r1 to r3))'.

'((Y81 to Y83), (R1 to R11), (R11 to R12), (R21 to R29), (R41 to R45), (R51 to R54), (R81 to R89), (R91 to R96), (L1 to L5), (p1 to p3), and (r1 to r3))' means all the embodiments which are the combinations of:
$Y^8$ and $Y^9$ is one embodiment selected from Y81 to Y83;
Ring B is one embodiment selected from B1 to B11;
$R^{1a}$ and $R^{1b}$ is one embodiment selected from R11 to R12;
$R^2$ is one embodiment selected from R21 to R29;
$R^{4a}$ to $R^{4d}$ is one embodiment selected from R41 to R45;
$R^5$ is one embodiment selected from R51 to R54;
$R^8$ is one embodiment selected from R81 to R89;
$R^{9a}$ is one embodiment selected from R91 to R9G;
L is one embodiment selected from L1 to L5;
p is one embodiment selected from p1 to p3; and,
r is one embodiment selected from r1 to r3.

'((Y81 to Y83), (B1 to B11), (R11 to R12), (R21 to R29), (R41 to R45), (R51 to R54), (R81 to R89), (R91 to R96), (L1 to L5), (n1 to n4), (p1 to p3), and (r1 to r3))' and '((Y81 to Y83), (R11 to R12), (r11 to r12), (R21 to R29), (R41 to R45), (R81 to R89), (R91 to R96), (L1 to L5), (m1 to m2), (n1 to n4), (p1 to p3), and (r1 to r3))' also mean all combinations of each embodiments of the substituents as above.

Examples of the compound represented by Formula (II-1) or (IJ-1), respectively, include
1) compounds wherein
—W— is W1, and
'("$Y^5$ to $Y^7$", "Ring B", "$R^{1a}$ and $R^{1b}$", $R^2$, $R^{4a}$ to $R^{4d}$, $R^5$, $R^7$, $R^{9b}$ to $R^{9d}$, L, n, p, and r)', which stands for combinations of $Y^5$ to $Y^7$, Ring B, $R^{1a}$ and $R^{1b}$, $R^2$, $R^{4a}$ to $R^{4d}$, $R^5$, $R^7$, $R^{9b}$ to $R^{9d}$, L, n, p, and r, is represented by: '((Y51 to Y59), (B1 to B11), (R11 to R12), (R21 to R29), (R41 to R45), (R51 to R54), (R701 to R714), (R91 to R96), (L1 to L5), (n1 to n4), (p1 to p3), and (r1 to r3))'; and,
2) compounds wherein
—W— is W2, and
'("$Y^5$ to $Y^7$", "$R^{1a}$ and $R^{1b}$", "$R^{1c}$ and $R^{1d}$", $R^2$, $R^{4a}$ to $R^{4d}$, $R^7$, $R^{9b}$ to $R^{9d}$, L, m, n, p, r)', which stands for combinations of $Y^5$ to $Y^7$, $R^{1a}$ and $R^{1b}$, $R^{1c}$ and $R^{1d}$, R2, $R^{4a}$ to $R^{4d}$, R7, $R^{9b}$ to $R^{9d}$, L, m, n, p, and r, is represented by: '((Y51 to Y59), (R11 to R12), (r11 to r12), (R21 to R29), (R41 to R45), (R701 to R714), (R91 to R96), (L1 to L5), (m1 to m2), (n1 to n4), (p1 to p3), and (r1 to r3))'.

Examples of the compound represented by Formula (II-2) or (IJ-2), respectively, include compounds wherein
'("$Y^5$ to $Y^7$", "Ring B", "$R^{1a}$ and $R^{1b}$", $R^2$, $R^{4a}$ to $R^{4d}$, $R^5$, $R^7$, L, p, and r)', which stands for combinations of $Y^5$ to $Y^7$, Ring B, $R^{1a}$ and $R^{1b}$, $R^2$, $R^{4a}$ to $R^{4d}$, $R^5$, $R^7$, $R^{9b}$ to $R^{9d}$, L, p, and r, is represented by: '((Y51 to Y59), (B1 to B11), (R11 to R12), (R21 to R29), (R41 to R45), (R51 to R54), (R701 to R714), (R91 to R96), (L1 to L5), (p1 to p3), and (r1 to r3))'.

'((Y51 to Y59), (B1 to B11), (R11 to R12), (R21 to R29), (R41 to R45), (R51 to R54), (R701 to R714), (R91 to R96), (L1 to L5), (p1 to p3), and (r1 to r3))' means all the embodiments which are the combinations of:
$Y^5$ to $Y^7$ is one embodiment selected from Y51 to Y59;
Ring B is one embodiment selected from B1 to B11;
$R^{1a}$ and $R^{1b}$ is one embodiment selected from R11 to R12;
$R^2$ is one embodiment selected from R21 to R29;
$R^{4a}$ to $R^{4d}$ is one embodiment selected from R41 to R45;
$R^5$ is one embodiment selected from R51 to R54;
$R^7$ is one embodiment selected from R701 to R714;
$R^{9b}$ to $R^{9d}$ is one embodiment selected from R91 to R96;
L is one embodiment selected from L1 to L5;
p is one embodiment selected from p1 to p3l and,
r is one embodiment selected from r1 to r3.

'((Y51 to Y59), (B1 to B11), (R11 to R12), (R21 to R29), (R41 to R45), (R51 to R54), (R701 to R714), (R91 to R96), (L1 to L5), (n1 to n4), (p1 to p3), and (r1 to r3))', and '((Y51 to Y59), (R11 to R12), (r11 to r12), (R21 to R29), (R41 to R45), (R701 to R714), (R91 to R96), (L1 to L5), (m1 to m2), (n1 to n4), (p1 to p3), and (r1 to r3))' also mean all combinations of each embodiments of the substituents as above.

Examples of the compound represented by Formula (IK-1), respectively, include
1) compounds wherein
—W— is W1, and
'("Ring B", "$R^{1a}$ and $R^{1b}$", $R^2$, $R^{4a}$ to $R^{4d}$, $R^6$, $R^7$, $R^{9c}$, L, n, p, and r)', which stands for combinations of Ring R, $R^{1a}$ and $R^{1b}$, $R^2$, $R^{4a}$ to $R^{4d}$, $R^5$, $R^7$, $R^{9c}$, L, n, p, and r, is represented by: '((B1 to B11), (R11 to R12), (R21 to R29), (R41 to R45), (R51 to R54), (R701 to R714), (R91 to R96), (L1 to L5), (n1 to n4), (p1 to p3), and (r1 to r3))'; and,
2) compounds wherein
—W— is W2, and
'("$R^{1a}$ and $R^{1b}$", "$R^{1c}$ and $R^{1d}$", $R^2$, $R^{4a}$ to $R^{4d}$, $R^7$, $R^{9c}$, L, m, n, p, and r)', which stands for combinations of $R^{1a}$ and $R^{1b}$, $R^{1c}$ and $R^{1d}$, $R^2$, $R^{4a}$ to $R^{4d}$, $R^7$, $R^{9c}$, L, m, n, p, and r, is represented by: '((R11 to R12), (r11 to r12), (R21 to R29), (R41 to R45), (R701 to R714), (R91 to R96), (L1 to L5), (m1 to m2), (n1 to n4), (p1 to p3), and (r1 to r3))'.

Examples of the compound represented by Formula (IK-2), respectively, include
1) compounds wherein
'("Ring B". "$R^{1a}$ and $R^{1b}$", $R^2$, $R^{4a}$ to $R^{4d}$, $R^5$, $R^7$, $R^{9c}$, L, p, and r)', which stands for combinations of Ring B, $R^{1a}$ and $R^{1b}$, $R^2$, $R^{4a}$ to $R^{4d}$, $R^5$, $R^7$, $R^{9c}$, L, p, and r, is represented by: '((B1 to B11), (R11 to R12), (R21 to R29), (R41 to R45), (R51 to R45), (R701 to R714), (R91 to R96), (L1 to L5), (p1 to p3), and (r1 to r3))'.

'((B1 to B11), (R11 to R12), (R21 to R29), (R41 to R45), (R51 to R54), (R701 to R714), (R91 to R96), (L1 to L5), (p1 to p3), and (r1 to r3))' means all the embodiments which are the combinations of:
Ring B is one embodiment selected from B1 to B11;
$R^{1a}$ and $R^{1b}$ is one embodiment selected from R11 to R12;
$R^2$ is one embodiment selected from R21 to R29;
$R^{4a}$ to $R^{4d}$ is one embodiment selected from R41 to R45;
$R^6$ is one embodiment selected from R51 to R54;
$R^7$ is one embodiment selected from R701 to R714;
$R^{9c}$ is one embodiment selected from R91 to R96;
L is one embodiment selected from L1 to L5;
p is one embodiment selected from p1 to p3; and,
r is one embodiment selected from r1 to r3.

'((B1 to B11), (R11 to R12), (R21 to R29), (R41 to R45), (R51 to R54), (R701 to R714), (R91 to R96), (L1 to L5), (n1 to n4), (p1 to p3), and (r1 to r3))', and '((R11 to R12), (r11 to r12), (R21 to R29), (R41 to R45), (R701 to R714), (R91 to R96), (L1 to L5), (m1 to m2), (n1 to n4), (p1 to p3), and (r1 to r3))' also mean all combinations of each embodiments of the substituents as above.

Examples of the compound represented by Formula (IN-1) include
1) compounds wherein
—W— is W1, and
'("$Y^1$, $Y^2$, $Y^{10}$ and $Y^{11}$", "Ring B", "$R^{1a}$ and $R^{1b}$", $R^2$, $R^{4a}$ to $R^{4d}$, $R^5$, $R^8$, $R^{9a}$, L, n, p, and r)', which stands for combinations of $Y^1$, $Y^2$, $Y^{10}$ and $Y^{11}$, Ring B, $R^{1a}$ and $R^{1b}$, $R^2$, $R^{4a}$ to $R^{4d}$, $R^5$, $R^8$, $R^{9a}$, L, n, p, and r, is represented by: '((Y101 to Y102), (B1 to B11), (R11 to R12), (R21 to R29), (R41 to R45), (R51 to R54), (R81 to R89), (R91 to R96), (L1 to L5), (n1 to n4), (p1 to p3), and (r1 to r3))'; and,
2) compounds wherein
—W— is W2, and
'("$Y^1$, $Y^2$, $Y^{10}$ and $Y^{11}$", "$R^{1a}$ and $R^{1b}$", "$R^{1c}$ and $R^{1d}$", $R^2$, $R^{4a}$ to $R^{4d}$, $R^{9a}$, L, m, n, p, and r)', which stands for combinations of $Y^1$, $Y^2$, $Y^{10}$ and $Y^{11}$, $R^{1a}$ and $R^{1b}$, $R^{1c}$ and $R^{1d}$, $R^2$, $R^{4a}$ to $R^{4d}$, $R^5$, $R^{9a}$, L, m, n, p, and r, is represented by: '((Y101 to Y102), (R11 to R12), (r11 to r12), (R21 to R29), (R41 to R45), (R81 to R89), (R91 to R96), (L1 to L5), (m1 to m2), (n1 to n4), (p1 to p3), and (r1 to r3))'.

Examples of the compound represented by Formula (IN-2) include compounds wherein
'("$Y^1$, $Y^2$, $Y^{10}$ and $Y^{11}$", "Ring B", "$R^{1a}$ and $R^{1b}$", $R^2$, $R^{4a}$ to $R^{4d}$, $R^6$, $R^{9a}$, L, p, and r)', which stands for combinations of $Y^1$, $Y^2$, $Y^{10}$ and $Y^{11}$, Ring B, $R^{1a}$ and $R^{1b}$, $R^2$, $R^{4a}$ to $R^{4d}$, $R^5$, $R^{9a}$, L, p, and r, is represented by: '((Y101 to Y102), (B1 to B11), (R11 to R12), (R21 to R29), (R41 to R45), (R51 to R54), (R81 to R89), (R91 to R96), (L1 to L5), (p1 to p3), and (r1 to r3))'.

'((Y101 to Y102), (B1 to B11), (R11 to R12), (R21 to R29), (R41 to R45), (R51 to R54), (R81 to R89), (R91 to R96), (L1 to L5), (p1 to p3), and (r1 to r3))' means all the embodiments which are the combinations of:
$Y^1$, $Y^2$, $Y^{10}$ and $Y^{11}$ is one embodiment selected from Y101 to Y102;
Ring B is one embodiment selected from B1 to B11;
$R^{1a}$ and $R^{1b}$ is one embodiment selected from R11 to R12;
$R^2$ is one embodiment selected from R21 to R29;
$R^{4a}$ to $R^{4d}$ is one embodiment selected from R41 to R45;
R5 is one embodiment selected from R51 to R54;
$R^8$ is one embodiment selected from R81 to R89;
$R^{9a}$ is one embodiment selected from R91 to R96;
L is one embodiment selected from L1 to L5;
p is one embodiment selected from p1 to p3; and,
r is one embodiment selected from r1 to r3.

'((Y101 to Y102), (B1 to B11), (R11 to R12), (R21 to R29), (R41 to R45), (R51 to R54), (R81 to R89), (R91 to R96), (L1 to 1.5), (n1 to n4), (p1 to p3), and (r1 to r3))' and '((Y101 to Y102), (R11 to R12), (r11 to r12), (R21 to R29), (R41 to R45), (R81 to R89), (R91 to R96), (L1 to L5), (m1 to m2), (n1 to n4), (p1 to p3), and (r1 to r3))' also mean all combinations of each embodiments of the substituents as above.

Other examples of proffered embodiments of the compound of Formula (I) or a pharmaceutically acceptable salt thereof are illustrated bellow.

A compound represented by Formula (IQ:

[Chemical Formula 94]

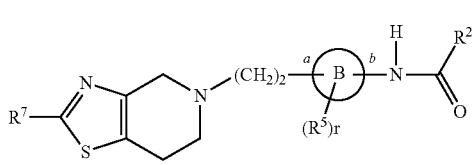
(If)

wherein each symbol is the same as defined above, or a pharmaceutically acceptable salt thereof.

Examples of specific embodiments of Formula (If) include all the embodiments which are the combinations of:
Ring B is one embodiment selected from B1 to B11;
$R^2$ is one embodiment selected from R21 to R29;
R8 is one embodiment selected from R51 to R54;
$R^7$ is one embodiment selected from R701 to R714;
r is one embodiment selected from r1 to r3.

Other specific embodiments of Formula (If) are illustrated bellow.

$R^2$ is non-aromatic heterocyclyl optionally substituted with one or more group(s) selected from alkyl and oxy, aromatic heterocyclyl optionally substituted with alkyl, aromatic heterocyclylalkyl (aromatic heterocycle of the aromatic heterocyclylalkyl can be further substituted with one or more group(s) selected from alkyl and alkyloxy), alkyl substituted with aromatic heterocyclyloxy optionally substituted with alkyl, or, alkenyl substituted with aromatic heterocyclyloxy optionally substituted with alkyl;

[Chemical Formula 95]

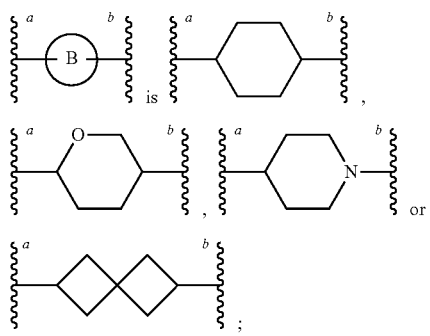

r is 0 or 1; R5 is halogen;
$R^7$ is alkyl substituted with halogen, alkyloxy substituted with halogen, or non-aromatic heterocyclyl substituted with halogen (the non-aromatic heterocyclyl includes, preferably monocyclic non-aromatic heterocyclyl, more preferably azetidinyl, pyrrolidinyl, and piperidyl).

A compound represented by Formula (Ig):

[Chemical Formula 96]

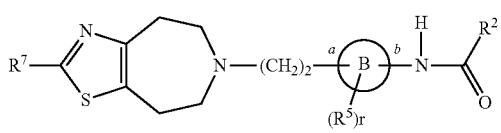
(Ig)

wherein each symbol is the same as defined above, or a pharmaceutically acceptable salt thereof.

Examples of specific embodiments of Formula (Ig) include all the embodiments which are the combinations of:
Ring B is one embodiment selected from B1 to B11;
$R^2$ is one embodiment selected from R21 to R29;
$R^8$ is one embodiment selected from R51 to R54;
$R^7$ is one embodiment selected from R701 to R714;
r is one embodiment selected from r1 to r3.

Other specific embodiments of Formula (Ig) are illustrated bellow.

$R^2$ is non-aromatic heterocyclyl optionally substituted with one or more group(s) selected from alkyl and oxy, aromatic heterocyclyl optionally substituted with alkyl, aromatic heterocyclylalkyl (aromatic heterocycle of the aromatic heterocyclylalkyl can be further substituted with one or more group(s) selected from alkyl and alkyloxy), alkyl substituted with aromatic heterocyclyloxy optionally substituted with alkyl, or, alkenyl substituted with aromatic heterocyclyloxy optionally substituted with alkyl;

$R^7$ is alkyl substituted with halogen, or alkyloxy substituted with halogen;

[Chemical Formula 97]

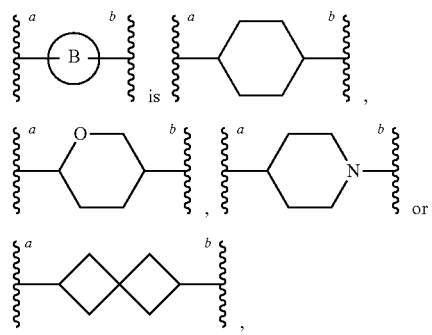

preferably,

[Chemical Formula 98]

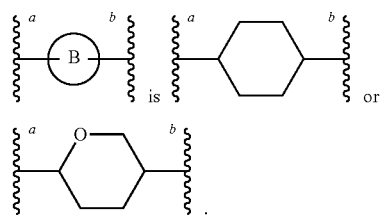

A compound represented by Formula (Ih):

[Chemical Formula 99]

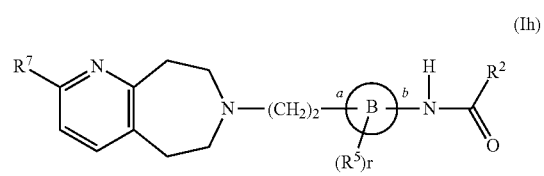
(Ih)

wherein each symbol is the same as defined above, or a pharmaceutically acceptable salt thereof.

Examples of specific embodiments of Formula (Ih) include all the embodiments which are the combinations of:
Ring B is one embodiment selected from B1 to B11;
$R^2$ is one embodiment selected from R21 to R29;
$R^8$ is one embodiment selected from R51 to R54;
$R^7$ is one embodiment selected from R701 to R714;
r is one embodiment selected from r1 to r3.

Other specific embodiments of Formula (Ih) are illustrated bellow.

$R^2$ is non-aromatic heterocyclyl optionally substituted with one or more group(s) selected from alkyl and oxy, aromatic heterocyclyl optionally substituted with alkyl, aromatic heterocyclylalkyl (aromatic heterocyclic of the aromatic heterocyclylalkyl can be further substituted with one or more group(s) selected from alkyl and alkyloxy), alkyl substituted with aromatic heterocyclyloxy optionally substituted with alkyl, or, alkenyl substituted with aromatic heterocyclyloxy optionally substituted with alkyl;

$R^7$ is alkyl substituted with halogen, or alkyloxy substituted with halogen;

[Chemical Formula 100]

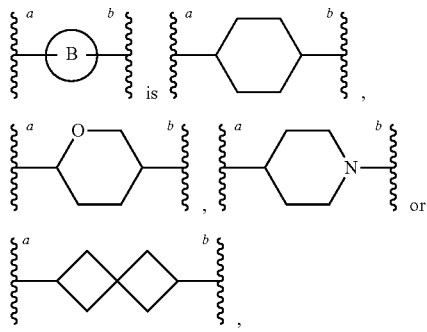

preferably,

[Chemical Formula 101]

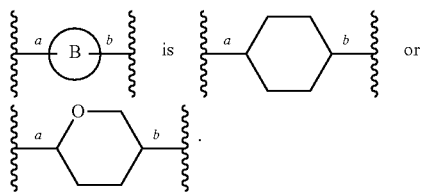

A compound represented by Formula (Ii):

[Chemical Formula 102]

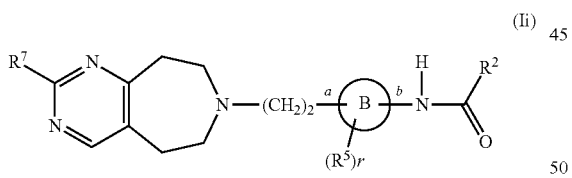

wherein each symbol is the same as defined above, or a pharmaceutically acceptable salt thereof.

Examples of specific embodiments of Formula (Ii) include all the embodiments which are the combinations of:
Ring B is one embodiment selected from B1 to B11;
$R^2$ is one embodiment selected from R21 to R29;
$R^8$ is one embodiment selected from R51 to R54;
$R^7$ is one embodiment selected from R701 to R714;
r is one embodiment selected from r1 to r3.

Other specific embodiments of Formula (Ii) are illustrated bellow.

$R^2$ is aromatic heterocyclyl optionally substituted with alkyl, or, aromatic heterocyclylalkyl (aromatic heterocycle of the aromatic heterocyclylalkyl can be further substituted with one or more group(s) selected from alkyl and alkyloxy);

$R^7$ is alkyl substituted with halogen, or alkyloxy substituted with halogen;

[Chemical Formula 103]

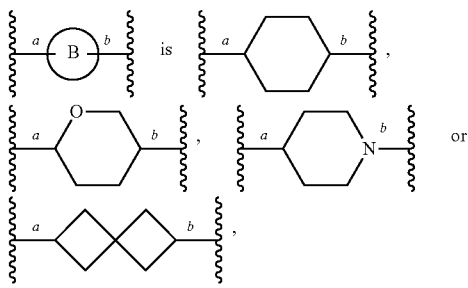

preferably,

[Chemical Formula 104]

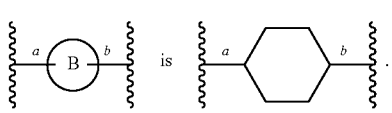

The compound represented by Formula (I) is not limited to a specific isomer, and includes all possible isomers such as keto-enol isomers, imine-enamine isomers, diastereoisomers, optical isomers and rotation isomers, racemate and the mixture thereof.

For example, a compound of Formula (I) wherein —W— is

[Chemical Formula 105]

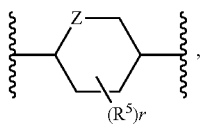

n is 2, and $R^{1a}$ and $R^{1b}$ are hydrogen atoms, includes both enantiomers and diastereoisomers shown bellow.

[Chemical Formula 106]

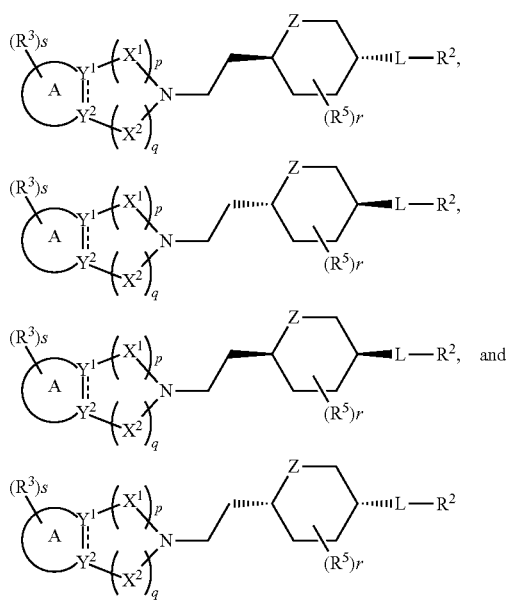

For example, a compound of Formula (I) wherein

[Chemical Formula 107]

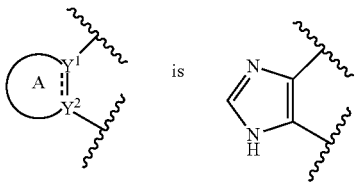

includes a compound of Formula (I) wherein

[Chemical Formula 108]

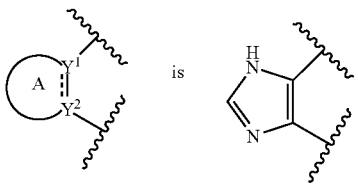

For example, a compound of Formula (I) wherein

[Chemical Formula 109]

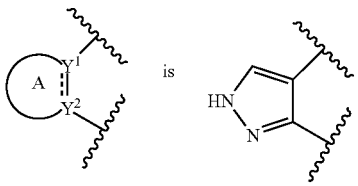

includes a compound of Formula (I) wherein

[Chemical Formula 110]

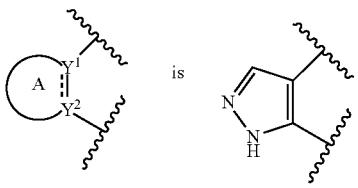

For example, a compound of Formula (I) wherein

[Chemical Formula 111]

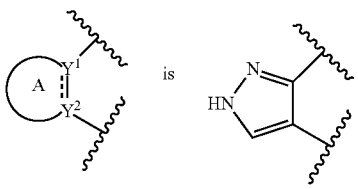

includes a compound of Formula (I) wherein

[Chemical Formula 112]

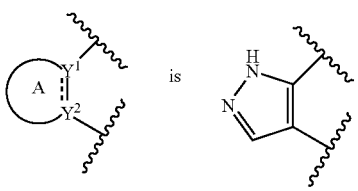

One or more hydrogen, carbon and/or other atoms in the compounds represented by Formula (I) may be replaced with isotopes of hydrogen, carbon and/or other atoms respectively. Example s of isotopes include hydrogen, carbon, nitrogen, oxygen, phosphorus, sulfur, fluorine, iodine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds represented by Formula (I) include the compounds replaced with these isotopes. The compounds replaced with the above isotopes are useful as medicines and include all of radiolabeled compounds of the compound of Formula (I). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds represented by Formula (I) con be prepared using well-known methods in the art. For example, a tritium-labeled compound represented by Formula (I) can be prepared by introducing a tritium to a certain compound represented by Formula (I), through a catalytic dehalogenation reaction using a tritium. This method comprises reacting with an appropriately-halogenated precursor of the compound represented by Formula (I) with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds represented by Formula (I) include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds represented by Formula (I) of the present invention or pharmaceutically acceptable salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds represented by Formula (I). When the compounds represented by Formula (I) or pharmaceutically acceptable salts thereof are allowed to stand in the atmosphere, the compounds may absorb water, resulting in attachment of adsorbed water or formation of hydrates. Recrystallization of the compounds represented by Formula (I) or pharmaceutically acceptable salts thereof may produce crystal polymorphs.

The compounds represented by Formula (I) of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds represented by Formula (I) through enzymatic oxidation, reduction, hydrolysis or the like under physiological conditions in vivo, compounds that are converted to the compounds represented by Formula (I) through hydrolysis by gastric acid etc., and the like. Methods for selecting and preparing suitable prodrug derivatives are described in, for example, "Design of Prodrugs, Elsevier, Amsterdam, 1985". Prodrugs themselves may have some activity.

When the compounds represented by Formula (I) or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride and mixed anhydride, or with a condensing agent. For example, they include $CH_3COO$, $C_2H_5COO$, tert-BuCOO—, $C_{15}H_{31}COO$—, PhCOO—, (m-NaOOCPh)COO—, $NaOOCCH_2CH_2COO$—, $CH_3CH(NH_2)COO$—, $CH_2N(CH_3)_2COO$—, $CH_3SO_3$—, $CH_3CH_2SO_3$—, $CF_3SO_3$—, $CH_2FSO_3$—, $CF_3CH_2SO_3$—, $p\text{-}CH_3O\text{-}PhSO_3$—, $PhSO_3$— and $p\text{-}CH_3PhSO_3$.

(Synthetic Procedures for the Compound of the Present Invention)

The compounds represented by Formula (I) of the present invention can be, for example, prepared by the general procedures described below. The starting materials and reagents used for synthesizing these compounds are commercially available or can be manufactured in accordance with a widely known method in this field using commercially available compounds. The methods for extraction, purification, and the like may be carried out by using the usual method for the experiments of organic chemistry.

The compounds of the present invention can be synthesized by referring to the known methods in the art.

In all the following steps, when a substituent which interferes with the reaction, e.g. hydroxy, mercapto, amino, formyl, carbonyl, carboxyl, is possessed, the substituent may be protected by the method such as those described in Protective Groups in Organic Synthesis, Theodora W Greene (John Wiley & Sons) in advance, and the protective group may be removed at a desirable step.

During all the following steps, the order of the steps to be performed may be appropriately changed. In each step, an intermediate may be isolated and then used in the next step. All of reaction time, reaction temperature, solvents, reagents, protecting groups, etc. are mere exemplification and not limited as long as they do not cause an adverse effect on a reaction.

The compounds represented by Formula (I) of the present invention can be, for example, prepared by the synthetic routes described below.

(Method A)

[Chemical Formula 113]

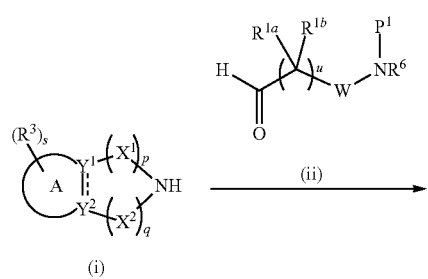

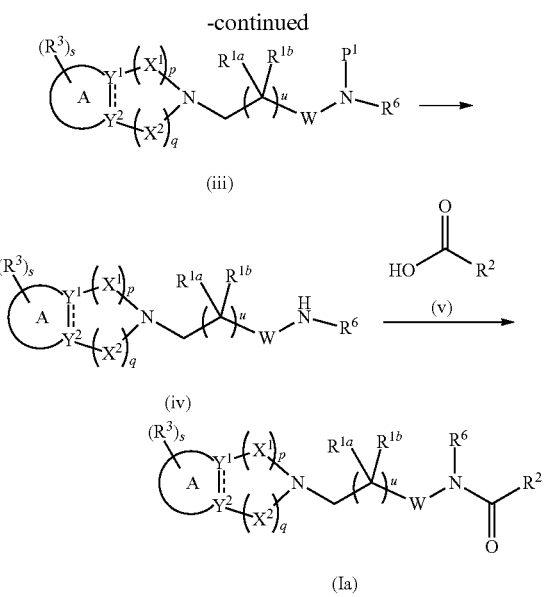

wherein u is an integer of 0 to 3, $P^1$ is a protective group for amino group, and the other symbols are the same as defined above.

(Step 1)

A compound (iii) can be prepared by condensation of a compound (ii) and an amine (i) or the salt thereof in the presence or absence of a condensing agent, and reduction of the resulted compound using a reducing agent.

As the condensing agent, 4-toluenesulfonic acid, methanesulfonic acid, acetic acid, magnesium sulfate anhydrous, tetraisopropyl orthotitanate, titanium tetrachloride, molecular sieve and the like are exemplified. 1 to 10 mole equivalent(s) of the condensing agent can be used per an equivalent of the compound (ii).

1 to 10 mole equivalent(s) of the amine (i) or the salt thereof can be used per an equivalent of the compound (ii).

As the reducing agent, sodium borohydride, sodium cyanoborohydride, sodium triacetoxyborohydride, borane and a complex thereof, lithium borohydride, potassium borohydride, diisobutylaluminum hydride and the like are exemplified. 1 to 10 mole equivalent(s) of the reducing agent can be used per an equivalent of the compound (ii).

The reaction temperature is −78° C. to reflux temperature of the solvent, preferably 0 to 25° C.

The reaction time is 0.5 to 48 hours, preferably 1 hour to 6 hours.

As the reaction solvent, tetrahydrofuran, toluene, dichloromethane, 1,2-dichloroethane, chloroform, methanol, ethanol and the like are exemplified. The reaction solvent can be used alone or in combination.

(Step 2)

A compound (iv) can be synthesized by removing a protective group $P^1$ of a compound (iii) according to the methods described in Protective Group in Organic Synthesis, Greene (4th edition).

(Step 3)

A compound (Ia) can be prepared by reacting a compound (iv) with a compound (v) in the presence of a condensing agent.

As the condensing agent, dicyclohexylcarbodiimide, carbonyldiimidazole, dicyclohexylcarbodiimide-N-hydroxybenzotriazole, EDC, 4-(4,6-dimethoxy-1,3,5,-triazin-2-yl)-4-methylmorpholinium chloride, HATU and the like are exemplified. 1 to 5 mole equivalent(s) of the condensing agent can be used per an equivalent of the compound (iv).

The reaction temperature is −20° C. to 60° C., preferably 0° C. to 30° C.

The reaction time is 0.1 hour to 24 hours, preferably 1 hour to 12 hours.

As the reaction solvent, DMF, DMA, N-methyl-2-pyrrolidone, tetrahydrofuran, dioxane, dichloromethane, acetonitrile and the like are exemplified. The reaction solvent can be used alone or in combination.

(Method B)

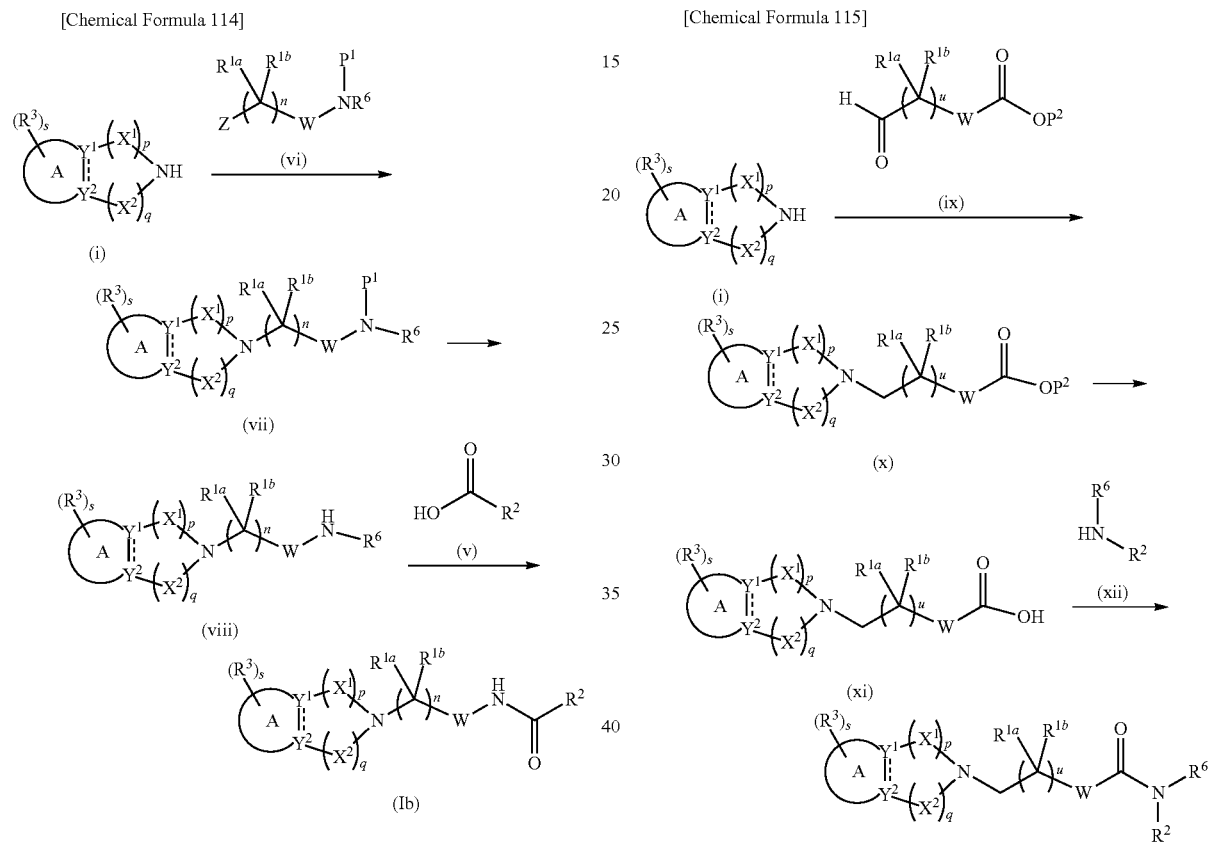

wherein Z is halogen or sulfonate ester, and the other symbols are the same as defined above.

(Step 1)

A compound (vii) can be prepared by reacting a compound (vi) with an amine (i) in the presence of a base such as potassium carbonate and the like.

The reaction temperature is 0° C. to reflux temperature of the solvent, preferably room temperature to reflux temperature of the solvent.

The reaction time is 0.1 hour to 24 hours, preferably 1 hour to 12 hours.

As the reaction solvent, DMF, DMA, N-methyl-2-pyrrolidone, tetrahydrofuran, dioxane, dichloromethane, acetonitrile and the like are exemplified. The reaction solvent can be used alone or in combination.

(Step 2)

A compound (viii) can be synthesized according to the similar synthetic procedures described in the Step 2 of Method A.

(Step 3)

A compound (Ib) can be synthesized according to the similar synthetic procedures described in the Step 3 of Method A.

A compound of Formula (I) wherein -L- is —N($R^6$)—$SO_2$— can be synthesized according to the similar methods described in Method A or Method B by using a sulfonic acid corresponding to a compound (v).

A compound of Formula (I) wherein -L- is —C(=O)—N($R^6$)— can be, for example, synthesized by the synthetic routes described below.

(Method C)

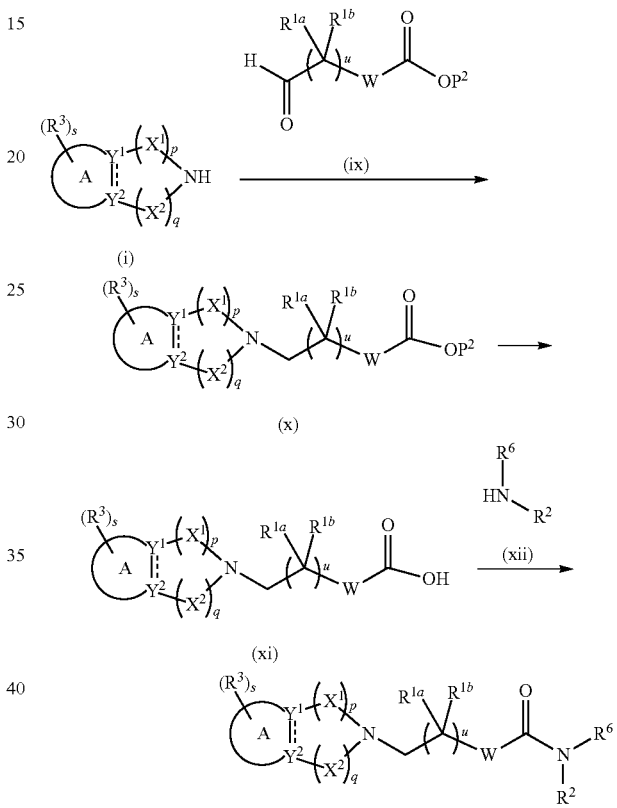

wherein $P^2$ is a protective group for carboxyl group, and the other symbols are the same as defined above.

(Step 1)

A compound (x) can be synthesized according to the similar synthetic procedures described in the Step 1 of Method A.

(Step 2)

A compound (xi) can be synthesized by removing a protective group $P^2$ of a compound (x) according to the methods described in Protective Group in Organic Synthesis, Greene (4th edition).

(Step 3)

A compound (Ic) can be synthesized according to the similar synthetic procedures described in the Step 3 of Method A.

(Method D)

A compound of Formula (I) wherein -L- is —SO$_2$—N(R$^6$)— can be, for example, synthesized by the synthetic routes described below.

[Chemical Formula 116]

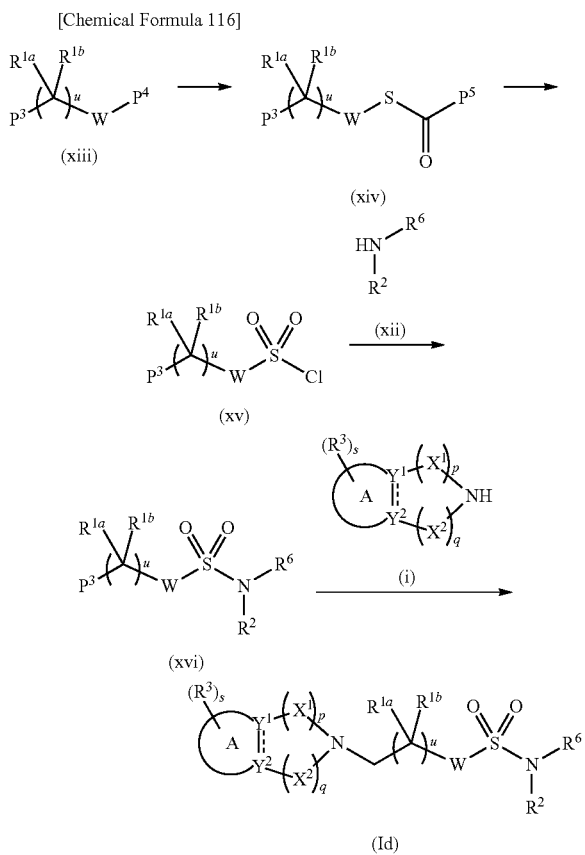

wherein P$^3$ is a group which can be converted to aldehyde or halogen by a known method (protected hydroxy or ester and the like), P$^4$ is halogen or hydroxy, P$^5$ is substituted or unsubstituted benzene or substituted or unsubstituted alkyl, and the other symbols are the same as defined above.

(Step 1)

When P$^4$ is hydroxy, a compound (xiv) can be prepared by condensing a compound (xiii) and thiocarbonic acid in the presence of a condensing agent and phosphine.

As the thiocarboxylic acid, thioacetic acid, thiobenzoic acid and the like are exemplified. 1 to 10 mole equivalent(s) of the thiocarboxylic acid can be used per an equivalent of the compound (xiii).

As the condensing agent, DEAD, DIAD and the like are exemplified. 1 to 10 mole equivalent(s) of the condensing agent can be used per an equivalent of the compound (xiii).

As the phosphine, triphenylphosphine, tri (n-butyl) phosphine and the like are exemplified. 1 to 10 mole equivalent(s) of the phosphine can be used per an equivalent of the compound (xiii).

The reaction temperature is 0° C. to 60° C., preferably 10° C. to 40° C.

The reaction time is 0.1 hour to 12 hours, preferably 0.2 hours to 6 hours.

As the reaction solvent, tetrahydrofuran, dioxane, ethyl acetate, toluene, acetonitrile and the like are exemplified. The reaction solvent can be used alone or in combination.

When P$^4$ is halogen, in the presence of a base, a compound (xiv) can be prepared by condensing a compound (xiii) and thiocarboxylic acid.

As the thiocarboxylic acid, thioacetic acid, thiobenzoic acid and the like are exemplified. 1 to 10 mole equivalent(s) of the thiocarboxylic acid can be used per an equivalent of the compound (xiii).

As the base, potassium carbonate, cesium carbonate and the like are exemplified. 1 to 10 mole equivalent(s) of the base can be used per an equivalent of the compound (xiii).

The reaction temperature is 0° C. to 60° C., preferably 10° C. to 40° C.

The reaction time is 0.1 hour to 12 hours, preferably 0.2 hours to 6 hours.

As the reaction solvent, tetrahydrofuran, dioxane, DMF, DMSO, ethyl acetate, toluene, acetonitrile and the like are exemplified. The reaction solvent can be used alone or in combination.

When —W— is aromatic cyclyl, a compound (xiv) can be prepared, using iodine for P$^4$, in accordance with Tetrahedron Letters 52 (2011) 820-823.

(Step 2)

A compound (xv) can be prepared, using a compound (xiv), in accordance with Synthesis 2006, No. 24, 4131*4134, Tetrahedron Letters 53 (2012) 3203*3205.

(Step 3)

A compound (xvi) can be prepared by condensing a compound (xv) and an amine (xii) or the salt thereof in the presence of a base.

1 to 5 mole equivalent(s) of the amine (xii) or the salt thereof can be used per an equivalent of the compound (xv).

As the base, triethylamine, DIEA, pyridine and the like are exemplified. 1 to 10 mole equivalent(s) of the base can be used per an equivalent of the compound (xv).

The reaction temperature is 0° C. to 150° C., preferably 20° C. to 100° C.

The reaction time is 0.5 hours to 120 hours, preferably 1 hour to 72 hours.

As the reaction solvent, acetonitrile, tetrahydrofuran, toluene, dichloromethane and the like are exemplified. The reaction solvent can be used alone or in combination.

(Step 4)

A compound (Id) can be prepared by converting P$^3$ to aldehyde or halogen by a known method followed by the similar synthetic procedures described in the Step 1 of Method A or Method B.

The compounds of the present invention have an antagonistic activity for the D3 receptor and preferably high D3/D2 selectivity, and therefore, are useful as agents for treating and/or preventing diseases associated with the D3 receptor. In the present invention, "agents for treating and/or preventing" includes agents for symptom improving.

As diseases associated with the D3 receptor, central nervous system diseases are exemplified.

As central nervous system diseases, cognitive disorders (e.g., mild cognitive impairment, Alzheimer's disease and the like), drug addiction, depression, anxiety, drug dependence, gambling addiction, dementias, memory impairment, schizophrenia, schizoaffective disorders, bipolar disorder, mania, acute mania, psychotic disorders including psychotic depression, psychoses including paranoia and delusions, attention-deficit/hyperactivity disorder (AD/HD), attention deficit disorder (ADD), obsessive-compulsive disorder (OCD), dyskinesia disorder, Parkinson's disease, neuroleptic-induced Parkinson's syndrome and tardive dyskinesia, eating disorders (e.g., anorexia or bulimia), sexual dysfunction, intellectual disabilities, learning disabilities, developmental disorders, sleep disorders, emesis, movement disorders, obsessive-compulsive disorder, amnesia, aggression, autism, vertigo, circadian rhythm disorders and gastric motility disorders, drug abuse (e.g., opioid drugs, alcohol, cocaine and nicotine addiction and the like), and psychological dependence due to drug abuse and the like are exemplified.

As central nervous system diseases, more preferably, attention-deficit/hyperactivity disorder (AD/HD) is exemplified.

The compound of the present invention has not only an antagonistic activity for D3 receptor but also is useful as a medicine and has any or all of the following superior characteristics:

a) The inhibitory activity for CYP enzymes (e.g., CYP1A2, CYP2C9, CYP2C19, CYP2D6, CYP3A4 and the like) is weak.
b) The compound demonstrates good pharmacokinetics, such as a high bioavailability, moderate clearance and the like.
c) The compound has a high metabolic stability.
d) The compound has no irreversible inhibitory effect against CYP enzymes (e.g., CYP3A4) when the concentration is within the range described in the present description as the measurement conditions.
e) The compound has no mutagenicity.
f) The compound is associated with a low cardiovascular risk.
g) The compound has a high solubility.
h) The compound has a high selectivity for D3 receptor.
i) The compound has a high D3 receptor selectivity over D2 receptor.
j) The compound has a high safety (e.g., mydriasis can be avoided).

Since the compound of the present invention has high antagonistic activity for D3 receptor and/or high selectivity on other receptors, for example, D2 receptor, it can be a medicament with reduced side effect. As D3 receptor antagonists, for example, compounds which show Ki value of less than or equal to 10 µM in the test of binding inhibition for dopamine D3 receptor, which is described later, are desirable.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration and the like.

In case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may prepared according to the usual method and administered. The tablets can be sugar-coated tablets, film-coated tablets, enteric-coating tablets, sustained-release tablets, troche tablets, sublingual tablets, buccal tablets, chewable tablets or orally dispersing tablets. Powders and granules can be dry syrups. Capsules can be soft capsules, micro capsules or sustained-release capsules.

In case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, disintegrants, lubricants and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

The compound of the present invention can be used in combination with other drugs such as central nervous system stimulants (Methylphenidate, Lisdexamfetamine and the like), noradrenaline reuptake inhibitor, dopamine-noradrenaline reuptake inhibitor, serotonin-noradrenaline reuptake inhibitor (Atomoxetine and the like), α2A adrenergic receptor agonist (Guanfacine and the like) and the like (hereinafter referred to as a concomitant medicament) for the purpose of enforcement of the activity of the compound of the present invention or the concomitant medicament, or reduction of the amount of medication of the compound of the present of the present invention or the concomitant medicament or the like.

In this case, timing of administration of the compound of the present invention and the concomitant medicament is not limited and these may be administered to the subject simultaneously or at regular intervals. Furthermore, the compound of the present invention and concomitant medicament may be administered as two different compositions containing each active ingredient or as a single composition containing both active ingredients.

The dose of the concomitant medicament can be suitably selected on the basis of the dose used on clinical. Moreover, the mix ratio of the compound of the present invention and a concomitant medicament can be suitably selected in consideration of the subject of administration, administration route, target diseases, symptoms, combinations, etc. For example, when the subject of administration is human, the concomitant medicament can be used in the range of 0.01 to 100 parts by weight relative to 1 part by weight of the compounds of the present invention.

Example

The present invention will be described in more detail with reference to, but not limited to, the following Examples and Test Examples.

In this description, the meaning of each abbreviation is as follows:

Me methyl
Et ethyl
Boc tert-butoxycarbonyl
Bn benzyl
Tf trifluoromethanesulfonyl
TFA trifluoroacetic acid
THF tetrahydrofuran
EDC 1-ethyl3-(3-dimethylaminopropyl)carbodiimide
TBAF tetrabutylammonium fluoride
DMSO dimethyl sulfoxide
DMF dimethylformamide
DMA dimethylacetamide
DME 1,2-dimethoxyethane
dba dibenzylideneacetone
dppf 1,1'-Bis(diphenylphosphino)ferrocene
DIAD diisopropyl azodicarboxylate
DEAD diethyl azodicarboxylate
DIEA N,N-diisopropylethylamine
DIBAL diisobutylaluminum hydride
LHMDS lithium hexamethyldisilazide
NaHMDS sodium hexamethyldisilazide
NBS N-bromosuccinimide
TBS tert-butyldimethylsilyl
HATU 1-[Bis(dimethylamino)methylene]-1H-1,2,3-triazolo[4,5-b]pyridinium 3-oxid hexafluorophosphate
HOBt 1-hydroxybenzotriazole
Ruphos Pd G3 (2-Dicyclohexylphosphino-2',6'-diisopropoxy-1,1'-biphenyl)[2-(2'-amino-1,1'-biphenyl)]palladium(II) methanesulfonate
Pd2(dba)3 tris(dibenzylideneacetone)dipalladium(0)
xantphos 4,5-Bis(diphenylphosphino)-9,9-dimethyxanthene
CDCl$_3$ deuterochloroform
CD$_3$OD tetradeuteromethanol
MS mass spectrometry
SFC supercritical fluid chromatography NMR analysis of each example was performed by 400 MHz using DMSO-d$_6$, CDCl$_3$, or CD$_3$OD. Sometimes not all the peaks detected are shown in NMR data.

LC/MS data of the compounds of the present invention were measured under the conditions as below. Retention time (min) and m/z are described.

(Method 1)
Column: ACQUITY UPLC(R) BEH C18 (1.7 μm, i.d.2.1×50 mm)(Waters)
Flow rate: 0.8 mL/min
UV detection wavelength: 254 nm
Mobile phases: [A] is 10 mM aqueous Ammonium Carbonate solution, and [B] is acetonitrile.
Gradient: linear gradient of 5% to 100% solvent [B] for 3.5 minutes was performed, and 100% solvent [B] was maintained for 0.5 minute.

(Method 2)
Column: ACQUITY UPLC(R) BEH C18 (1.7 μm, i.d.2.1×50 mm)(Waters)
Flow rate: 0.8 mL/min
UV detection wavelength: 254 nm
Mobile phases: [A] is 0.1% aqueous formic acid solution, and [B] is 0.1% formic acid in acetonitrile solvent.
Gradient: linear gradient of 5% to 100% solvent [B] for 3.5 minutes was performed, and 100% solvent [B] was maintained for 0.5 minute.

(Method 3)
Column: Shim-pack XR-ODS (2.2 μm, i.d.3.0×50 mm) (Shimadzu)
Flow rate: 1.6 mL/min
UV detection wavelength: 254 nm
Mobile phases: [A] is 0.1% aqueous formic acid solution, and [B] is 0.1% formic acid in acetonitrile solvent.
Gradient: linear gradient of 10% to 100% solvent [B] for 3 minutes was performed, and 100% solvent [B] was maintained for 0.5 minute.

(Method 4)
Column: ACQUITY UPLC(R) BEH C18 (1.7 μm, i.d.2.1×50 mm)(Waters)
Flow rate: 0.55 mL/min
UV detection wavelength: 254 nm
Mobile phases: [A] is 0.1% aqueous formic acid solution, and [B] is 0.1% formic acid in acetonitrile solvent.
Gradient: linear gradient of 5% to 100% solvent [B] for 3 minutes was performed, and 100% solvent [B] was maintained for 0.5 minute.

Example 1 Synthesis of Compound I-073

[Chemical Formula 117]

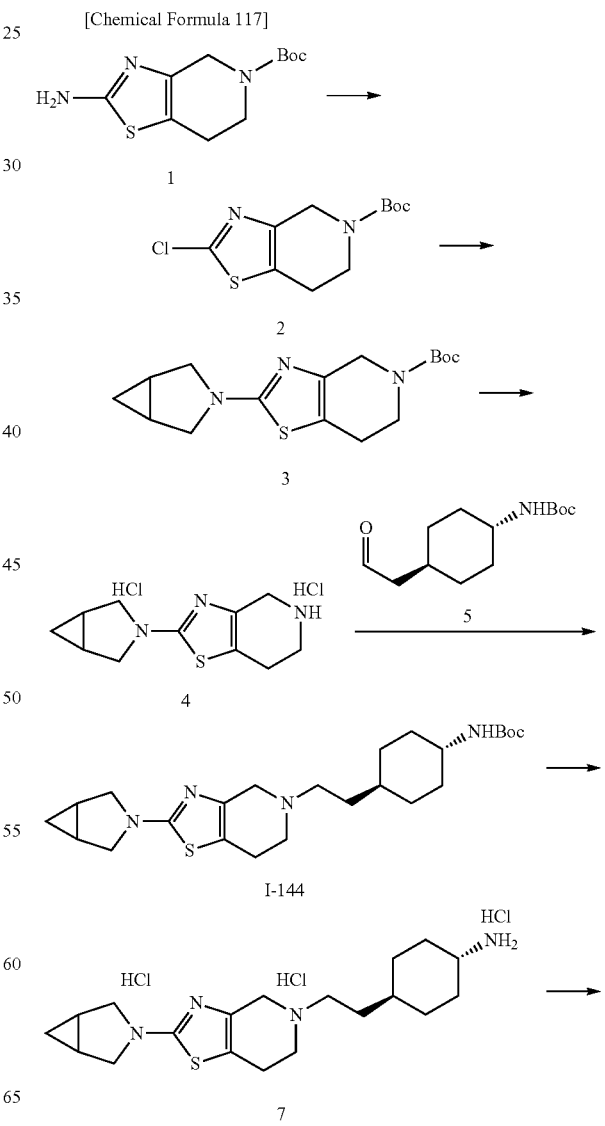

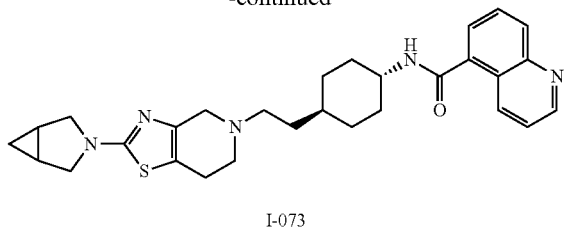

I-073

Step 1 Synthesis of Compound 2

Under nitrogen atmosphere, to copper(II) chloride (1.118 g, 8.32 mmol) was added acetonitrile (26.6 mL), then under ice cooling was added tert-butyl nitrite (1.25 mL, 10.4 mmol). The mixture was stirred at 0° C. for 5 minutes. The compound 1 (1.77 g, 6.93 mmol) dissolved in acetonitrile (14.16 mL) was added dropwise to the mixture at 0° C. The mixture was stirred at room temperature for 2 hours. The solvent was evaporated under reduced pressure. To the obtained residue was added saturated aqueous solution of ammonium chloride and saturated aqueous solution of sodium hydrogen carbonate. The mixture was extracted with ethyl acetate. The organic layer was washed by water and brine, and dried over anhydrous sodium sulfate. The solvent was evaporated under reduced pressure. The obtained residue was purified by silica-gel column chromatography (hexane-ethyl acetate) to give a compound 2 (1.11 g, yield 58%).

1H-NMR (CDCl$_3$) δ: 1.48 (s, 9H), 2.79 (br, 2H), 3.74 (br, 2H), 4.55 (s, 2H).

Step 2 Synthesis of Compound 3

Under nitrogen atmosphere, the compound 2 (2.0 g, 7.28 mmol) was dissolved in dioxane (40 mL). To the mixture were added 3-azabicyclo[3,1,0]hexane hydrochloride (1.30 g, 10.9 mmol), Pd$_2$(dba)$_3$ (333 mg, 0.364 mmol), 2-dicyclohexylphosphino-2',6'-diisopropoxy-1,1'-biphenyl (679 mg, 1.456 mmol), sodium-tert-butoxide (2.1 g, 21.84 mmol). The mixture was stirred at 100° C. for 3 hours.

Water was added to the reaction mixture. The mixture was extracted with ethyl acetate. The organic layer was washed by water and brine, and then dried over anhydrous sodium sulfate. The solvent was evaporated under reduced pressure. The obtained residue was purified by silica-gel column chromatography (hexane-ethyl acetate) to give a compound 3 (664 mg, yield 28%).

1H-NMR (CDCl$_3$) δ: 0.27-0.31 (m, 1H), 0.75-0.80 (m, 1H), 1.46 (s, 9H), 1.62-1.66 (m, 2H), 2.65 (br, 2H), 3.47-3.50 (m, 2H), 3.55-3.58 (m, 2H), 3.69 (br, 2H), 4.41 (s, 2H).

Step 3 Synthesis of Compound 4

The compound 3 (664 mg, 2.06 mmol) was dissolved in dioxane (10 mL). To the mixture was added 4 mol/L hydrochloric acid (dioxane solution, 10 mL, 40 mmol). The mixture was stirred at room temperature for 3 hours. The solvent was evaporated under reduced pressure to give a compound 4 (610 mg, 100%) as a crude product.

Step 4 Synthesis of I-144

To the compound 4 (610 mg) obtained as a crude product in Step 3 were added dioxane (30 mL), triethylamine (1.44 mL, 10.4 mmol), a compound 5 (600 mg, 2.49 mmol, synthetic method for the compound 5 is described in J. Med. Chem. 2015, 58, 6819-6843). The mixture was stirred at room temperature for 30 minutes. To the mixture was added sodium triacetoxyborohydride (879 mg, 4.15 mmol). The mixture was stirred at room temperature for 3 hours. To the reaction mixture was added saturated aqueous solution of sodium hydrogen carbonate. The mixture was extracted with chloroform. The organic layer was separated and the solvent was evaporated under reduced pressure. The obtained residue was purified by silica-gel column chromatography (hexane-ethyl acetate) to give a compound I-144 (851 mg, yield 92%).

1H-NMR (CDCl$_3$) δ: 0.27-0.31 (m, 1H), 0.72-0.78 (m, 1H), 0.97-1.11 (m, 4H), 1.22-1.30 (m, 1H), 1.44-1.48 (m, 11H), 1.60-1.63 (m, 2H), 1.75-1.78 (m, 2H), 1.96-2.00 (m, 2H), 2.50-2.54 (m, 2H), 2.66-2.74 (m, 4H), 3.36 (br, 1H), 3.45-3.47 (m, 4H), 3.54-3.57 (m, 2H), 4.35 (br, 1H).

Step 5 Synthesis of Compound 7

The compound I-144 (288 mg, 0.645 mmol) was dissolved in dioxane (6 mL). To the mixture was added 4 mol/L hydrochloric acid (dioxane solution, 6 mL, 24 mmol). The mixture was stirred at room temperature for 1 hour. The solvent was evaporated under reduced pressure to give a compound 7 as a crude product.

Step 6 Synthesis of Compound I-073

The compound 7 obtained as a crude product in Step 5 was dissolved in DMF (6 mL). To the mixture were added quinoline-5-carboxylic acid (134 mg, 0.774 mmol), EDC hydrochloride (148 mg, 0.774 mmol), HOBt (105 mg, 0.774 mmol), triethylamine (0.536 mL, 3.87 mmol). The mixture was stirred at room temperature for 3 hours. To the reaction mixture was added saturated aqueous solution of sodium hydrogen carbonate. The mixture was extracted with a mixed solvent of ethyl acetate and tetrahydrofuran. The organic layer was washed by water and brine, and then dried over anhydrous sodium sulfate. The solvent was evaporated under reduced pressure. The obtained residue was purified by amino silica-gel column chromatography (hexane-ethyl acetate) to give a compound I-073 (205 mg, 0.409 mmmol).

$^1$H-NMR (CDCl$_3$) δ: 0.28-0.31 (m, 1H), 0.73-0.78 (m, 1H), 1.13-1.29 (m, 4H), 1.37 (br, 1H), 1.50-1.55 (m, 2H), 1.60-1.65 (m, 2H), 1.85-1.88 (m, 2H), 2.16-2.20 (m, 2H), 2.54-2.59 (m, 2H), 2.68-2.76 (m, 4H), 3.46-3.48 (m, 4H), 3.56 (d, J=9.7 Hz, 2H), 3.98-4.08 (m, 1H), 5.83 (d, J=8.2 Hz, 1H), 7.47 (dd, J=4.2, 8.7 Hz, 1H), 7.66-7.71 (m, 2H), 8.18 (d, J=8.0 Hz, 1H), 8.74 (d, J=8.3 Hz, 1H), 8.95 (dd, J=1.6, 4.0 Hz, 1H)

Example 2 Synthesis of Compound I-053

[Chemical Formula 118]

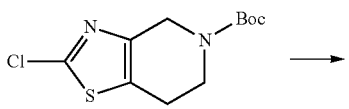

2

→

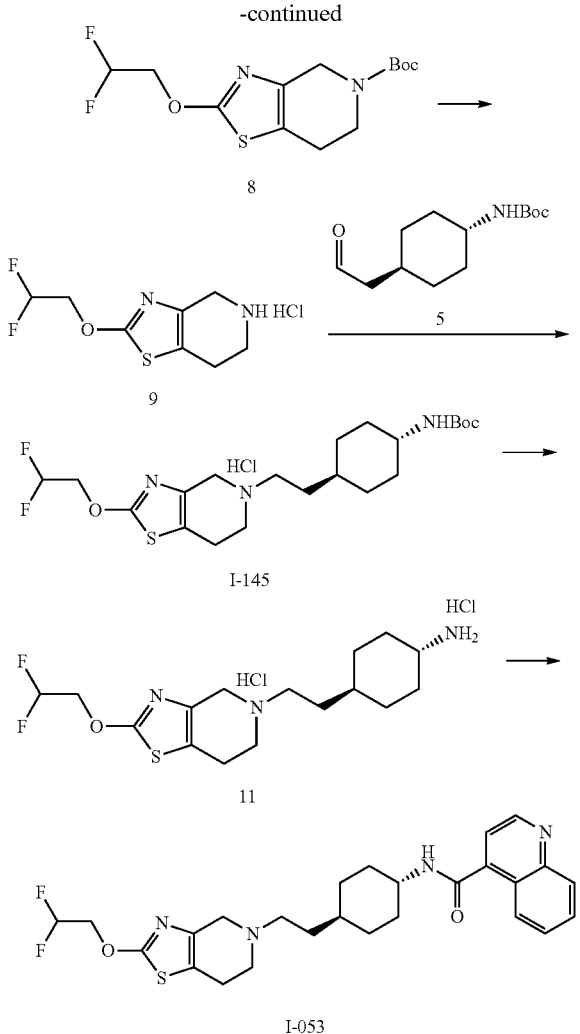

Step 1 Synthesis of Compound 8

Under nitrogen atmosphere, 2,2-difluoroethanol (1.52 mL, 24.02 mmol) dissolved in DMF (36 mL) was cooled with ice. To the solution was added sodium hydride (60 wt %, 873 mg, 21.84 mmol) portion wise. The mixture was stirred at 0° C. for 1 hour. To the mixture was added a compound 2 (1.2 g, 4.37 mmol) portion wise. Then, the mixture was stirred at 65° C. for 2 hours. Ice water was added to the reaction mixture. The mixture was extracted with ethyl acetate. The organic layer was washed by water and brine, and then dried over anhydrous sodium sulfate. The solvent was evaporated under reduced pressure. The obtained residue was purified by silica-gel column chromatography (hexane-ethyl acetate) to give a compound 8 (1.33 g, yield 95%).

$^1$H-NMR (CDCl$_3$) δ: 1.49 (s, 9H), 2.69 (br, 2H), 3.71 (br, 2H), 4.39 (s, 2H), 4.56 (dt, J=4.1, 13.2 Hz, 2H), 6.12 (tt, J=4.1, 55.1 Hz, 1H).

Step 2 Synthesis of Compound 9

The compound 8 (1.33 g, 4.15 mmol) was dissolved in dichloromethane (6 mL). To the mixture was added 4 mol/L Hydrochloric acid (dioxane solution, 10 mL, 40 mmol). The mixture was stirred at room temperature for 3 hours. The solvent was evaporated under reduced pressure to give a compound 9 (1.07 g, 100%) as a crude product.

Step 3 Synthesis of Compound I-145

To the compound 9 (950 mg, 3.70 mmol) obtained as a crude product in Step 2 were added dichloromethane (20 mL), triethylamine (1.54 mL, 11.1 mmol), a compound 6 (938 mg, 3.89 mmol). The mixture was stirred at room temperature for 10 minutes. To the mixture was added sodium triacctoxyborohydrido (1.57 g, 7.40 mmol). The mixture was stirred at room temperature for 2 hours. To the reaction mixture was added saturated aqueous solution of sodium hydrogen carbonate. The mixture was extracted with ethyl acetate. The organic layer was washed by saturated aqueous solution of sodium hydrogen carbonate, brine, and then dried over anhydrous sodium sulfate. The solvent was evaporated under reduced pressure. The obtained residue was purified by amino silica-gel column chromatography (hexane-ethyl acetate) to give a compound I-145 (1.59 g, yield 96%).

$^1$H-NMR (CDCl$_3$) δ: 0.99-1.12 (m, 4H), 1.26 (br, 1H), 1.42-1.49 (m, 11H), 1.75-1.80 (m, 2H), 1.97-2.02 (m, 2H), 2.52-2.56 (m, 2H), 2.71-2.75 (m, 2H), 3.37 (br, 1H), 3.44 (s, 2H), 4.35 (br, 1H), 4.53 (t, J=13.0 Hz, 2H), 6.11 (t, J=55.3 Hz, 1H).

Step 4 Synthesis of Compound 11

A compound I-146 (1.90 g, 4.17 mmol) was dissolved in dichloromethane (19 mL). To the solution was added TFA (9.9 mL, 129 mmol). The mixture was stirred at room temperature for 6 hours. The solvent was evaporated under reduced pressure. To the mixture, excess amount of 4 mol/L hydrochloric acid dioxane solution was added. The solvent was evaporated under reduced pressure. To the residue was added ethyl acetate. The solvent was evaporated under reduced pressure to give a compound 11 (1.90 g) as a crude product.

[M+H] 346.20, method 4, retention time 0.64 min

Step 5 Synthesis of Compound I-053

To the crude compound 11 (30 mg, 0.072 mmol) were added dichloromethane (1.5 mL), quinoline-4-carboxylic acid (14.9 mg, 0.086 mmol), HATU (32.7 mg, 0.086 mmol), triethylamine (0.060 mL, 0.430 mmol). The mixture was stirred at room temperature for 20 minutes. To the reaction mixture was added saturated aqueous solution of sodium hydrogen carbonate. The mixture was extracted with ethyl acetate. The organic layer was washed by saturated aqueous solution of sodium hydrogen carbonate, water, brine, and then dried over anhydrous sodium sulfate. The solvent was evaporated under reduced pressure. The obtained residue was purified by silica gel column chromatography (chloroform-methanol) to give a compound I-053 (27 mg, yield 75%).

$^1$H-NMR (CDCl$_3$) δ: 1.14-1.41 (m, 5H), 1.51-1.56 (m, 2H), 1.87-1.91 (m, 2H), 2.18-2.22 (m, 2H), 2.56-2.60 (m, 2H), 2.71-2.80 (m, 4H), 3.47 (s, 2H), 4.01-4.13 (m, 1H), 4.54 (td, J=13.1, 4.1 Hz, 2H), 5.83 (d, J=8.2 Hz, 1H), 6.12 (tt, J=55.1, 4.1 Hz, 1H), 7.43 (d, J=4.3 Hz, 1H), 7.62 (t, J=7.7 Hz, 1H), 7.77 (t, J=7.7 Hz, 1H), 8.14 (d, J=8.5 Hz, 1H), 8.21 (d, J=8.5 Hz, 1H), 8.94 (d, J=4.3 Hz, 1H).

Example 3 Synthesis of Compound I-005

[Chemical Formula 119]

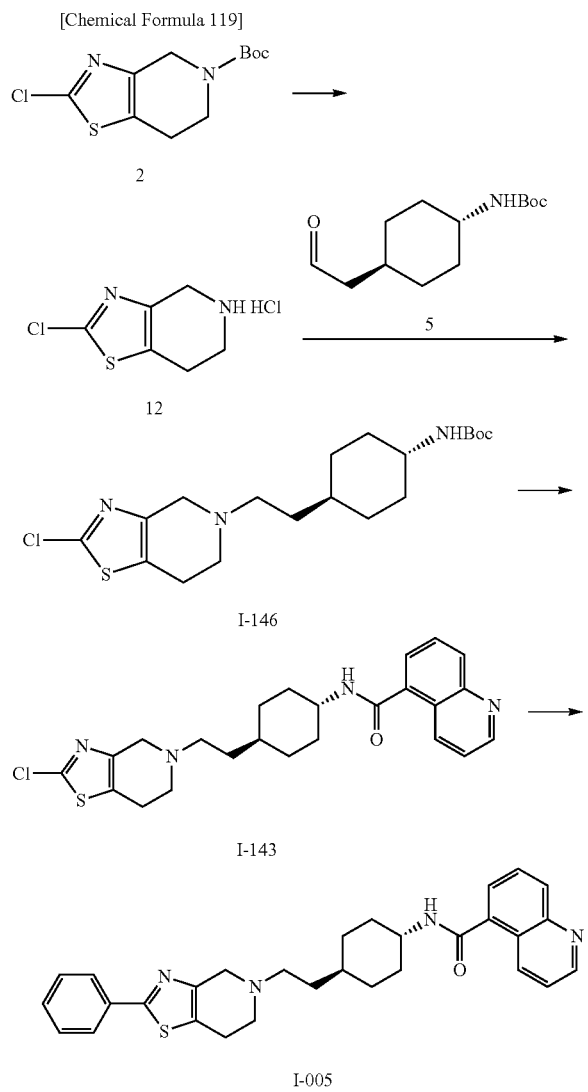

Step 1 Synthesis of Compound 12

A compound 12 was obtained as a crude product by using the compound 2 instead of the compound 8 in Step 2 of Example 2.

Step 2 Synthesis of Compound I-146

A compound I-146 was obtained by the similar method of Step 3 of Example 2, by using the crude compound 12 obtained in Step 1.

1H-NMR (CDCl$_3$) δ: 0.99-1.12 (m, 4H), 1.28 (br, 1H), 1.44-1.49 (m, 11H), 1.76-1.79 (m, 2H), 1.97-2.01 (m, 2H), 2.54-2.58 (m, 2H), 2.76-2.82 (m, 4H), 3.37 (br, 1H), 3.58 (s, 2H), 4.36 (br, 1H).

Step 3 Synthesis of Compound 14

A compound 14 was obtained as a crude product by the similar method of Step 4 of Example 2.

Step 4 Synthesis of Compound I-143

A compound I-143 was obtained by the similar method of Step 5 of Example 2, using the crude compound 14 obtained in Step 3.

$^1$H-NMR (CDCl$_3$) δ: 1.15-1.40 (m, 5H), 1.50-1.56 (m, 2H), 1.87-1.90 (m, 2H), 2.18-2.22 (m, 2H), 2.58-2.62 (m, 2H), 2.78-2.84 (m, 4H), 3.60 (s, 2H), 3.99-4.08 (m, 1H), 6.84 (d, J=8.3 Hz, 1H), 7.47 (dd, J=8.6, 4.2 Hz, 1H), 7.64-7.71 (m, 2H), 8.18 (d, J=8.0 Hz, 1H), 8.74 (d, J=8.3 Hz, 1H), 8.96 (dd, J=4.1, 1.5 Hz, 1H).

Step 5 Synthesis of Compound I-005

To a mixture of compound I-143 (30 mg, 0.060 mmol), phenylboronic acid (11 mg, 0.090 mmol), PdCl$_3$ (dppf)(4.4 mg, 6.0 μmol) and potassium phosphate (38.2 mg, 0.180 mmol) were added DME (0.5 mL), ethanol (0.5 mL) and water (0.25 mL). The mixture was stirred under microwave irradiation at 140° C. for 30 minutes. To the reaction mixture, water was added. The mixture was extracted with chloroform. The organic layer was evaporated under reduced pressure. The obtained residue was purified by amino silica-gel column chromatography (hexane-ethyl acetate), and further purified by preparative TLC (chloroform-methanol) to give compound I-005 (18.6 mg, yield 62%).

$^1$H-NMR (CDCl$_3$) δ: 1.15-1.43 (m, 5H), 1.54-1.59 (m, 2H), 1.86-1.92 (m, 2H), 2.16-2.21 (m, 2H), 2.62-2.66 (m, 2H), 2.82-2.85 (m, 2H), 2.92-2.95 (m, 2H), 3.74 (s, 2H), 3.98-4.07 (m, 1H), 5.97 (d, J=8.2 Hz, 1H), 7.36-7.47 (m, 4H), 7.61-7.68 (m, 2H), 7.86-7.89 (m, 2H), 8.15 (dd, J=8.0, 0.9 Hz, 1H), 8.72 (t, J=4.3 Hz, 1H), 8.94 (dd, J=4.2, 1.7 Hz, 1H).

Example 4 Synthesis of Compound I-116

[Chemical Formula 120]

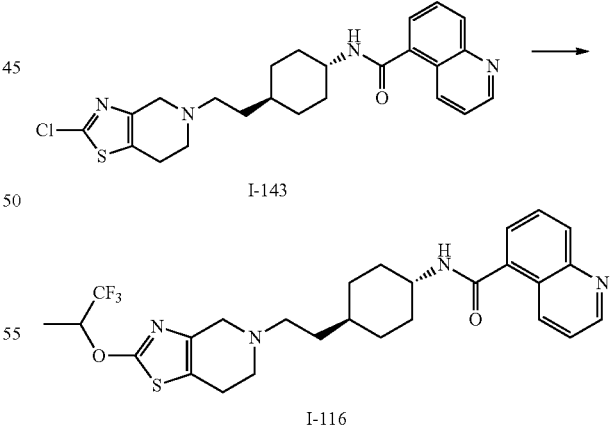

A compound I-116 was obtained by using a compound I-143 instead of a compound 2, and 1,1,1-trifluoropropan-2-ol instead of 2,2-difluoroethanol in Step 1 of Example 2.

1H-NMR (CDCl$_3$) δ: 1.14-1.39 (m, 5H), 1.50-1.56 (m, 5H), 1.85-1.90 (m, 2H), 2.17-2.22 (m, 2H), 2.56-2.60 (m, 2H), 2.72-2.81 (m, 4H), 3.42-3.51 (m, 2H), 3.99-4.08 (m, 1H), 5.45-5.55 (m, 1H), 5.85 (d, J=8.2 Hz, 1H), 7.47 (dd,

J=8.6, 4.2 Hz, 1H), 7.64-7.71 (m, 2H), 8.18 (d, J=7.9 Hz, 1H), 8.74 (d, J=8.5 Hz, 1H), 8.95 (dd, J=4.1, 1.5 Hz, 1H).

Example 5 Synthesis of Compound I-012

[Chemical Formula 121]

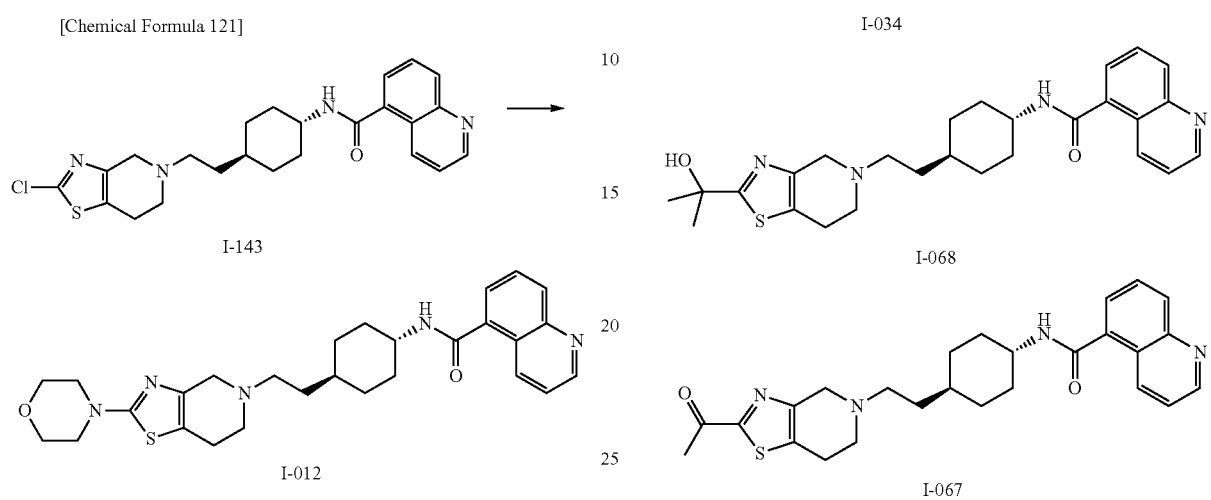

Under nitrogen atmosphere, to a mixture of compound I-143 (30 mg, 0.066 mmol), sodium-tert-butoxide (15.8 mg, 0.165 mmol), Pd$_2$(dba)$_3$ (3.0 mg, 3.3 μmol) and 2-dicyclohexylphosphino-2',6'-diisopropoxy-1,1'-biphenyl (6.2 mg, 0.013 mmol) were added dioxane (1 mL) and morpholine (6.9 μL, 0.079 mmol). Then, the mixture was stirred under microwave irradiation at 140° C. for 1 hour.

The reaction mixture was filtered, and washed by chloroform. The organic layer was combined and then the solvent was evaporated under reduced pressure. The obtained residue was purified by silica gel column chromatography (hexane-ethyl acetate), preparative TLC (chloroform-methanol), reverse-phase HPLC (water-acetonitrile) to give a compound I-012 (13 mg, yield 39%).

1H-NMR (CDCl$_3$) δ: 1.13-1.41 (m, 5H), 1.50-1.55 (m, 2H), 1.85-1.89 (m, 2H), 2.16-2.20 (m, 2H), 2.55-2.59 (m, 2H), 2.71-2.78 (m, 4H), 3.38-3.41 (m, 4H), 3.48 (s, 2H), 3.78-3.81 (m, 4H), 3.97-4.07 (m, 1H), 5.89 (d, J=8.2 Hz, 1H), 7.47 (dd, J=8.7, 4.1 Hz, 1H), 7.63-7.70 (m, 2H), 8.17 (d, J=7.9 Hz, 1H), 8.73 (d, J=8.5 Hz, 1H), 8.95 (dd, J=4.0, 1.4 Hz, 1H).

Example 6 Synthesis of Compound I-067 and I-068

[Chemical Formula 122]

Step 1 Synthesis of Compound I-034

The compound I-143 (120 mg, 0.264 mmol) was dissolved in DMF (3 mL) and methanol (1 mL). To the mixture were added PdCl$_2$(dppf)(19.3 mg, 0.026 mmol) and triethylamine (0.183 mL, 1.319 mmol). The mixture was stirred at 80° C. for 6 hours under carbon monoxide (0.5 Mpa). To the reaction mixture, ethyl acetate and water were added. The mixture was filtered to remove insoluble matters. The filtrate was extracted with ethyl acetate. The organic layer was washed by water, brine, and dried over anhydrous magnesium sulfate. The solvent was evaporated under reduced pressure. The obtained residue was purified by amino silica-gel column chromatography (hexane-ethyl acetate) to give a compound I-034 (92 mg, yield 73%).

[M+H] 479.2, method 1, retention time 1.70 min

Step 2 Synthesis of Compound I-067 and I-068

The compound I-034 (15 mg, 0.031 mmol) was dissolved in tetrahydrofuran (1 mL). Under ice cooling, to the mixture was added 3 mol/L methylmagnesium bromide (diethyl ether solution, 0.104 mL, 0.313 mmol). The mixture was stirred at 0° C. for 4 hours and then, stirred at room temperature overnight. To the reaction mixture, saturated aqueous solution of ammonium chloride was added. The mixture was extracted with ethyl acetate. The organic layer was washed by brine, and dried over anhydrous magnesium sulfate. The solvent was evaporated under reduced pressure. The obtained residue was purified by preparative TLC (chloroform-methanol) to give a compound I-067 (1.6 mg, yield 11%) and I-068 (3.4 mg, yield 23%).

I-067; [M+H] 463.2, method 1, retention time 1.78 min

I-068; [M+H] 479.2, method 1, retention time 1.53 min

Example 7 Synthesis of Compound I-141

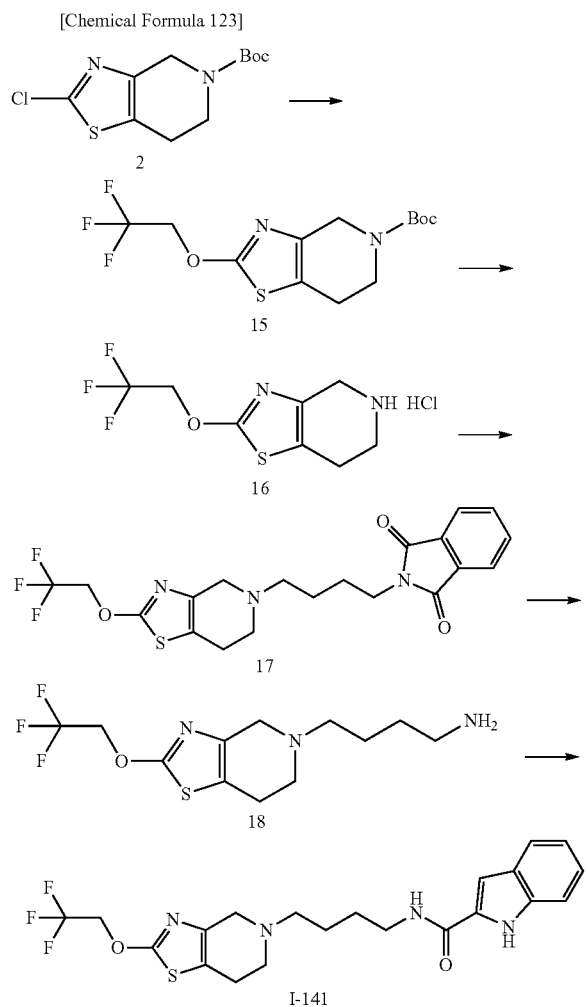

Step 1 Synthesis of Compound 15

A compound 15 was synthesized by using 2,2,2-trifluoroethanol instead of 2,2-difluoroethanol in Step 1 of Example 2.

1H-NMR (CDCl$_3$) δ: 1.49 (s, 9H), 2.70 (br, 2H), 3.72 (br, 2H), 4.39 (s, 2H), 4.76 (q, J=8.2 Hz, 2H).

Step 2 Synthesis of Compound 16

A compound 16 was synthesized by the similar method of Step 2 of Example 2.

1H-NMR (DMSO-d$_6$) δ: 2.93-2.96 (m, 2H), 3.40-3.42 (m, 2H), 4.10 (s, 2H), 5.13 (q, J=8.8 Hz, 2H), 9.58 (br, 2H).

Step 3 Synthesis of Compound 17

Under nitrogen atmosphere, to a compound 16 (75 mg, 0.273 mmol) was added acetonitrile (2.5 mL), and then were added N-(4-bromobutyl)phthalimide (154 mg, 0.546 mmol) and potassium carbonate (113 mg, 0.819 mmol). Then, the mixture was stirred at 90° C. for 5 hours. To the reaction mixture, water was added. The mixture was extracted with ethyl acetate. The organic layer was washed by water and brine, and dried over anhydrous sodium sulfate. The solvent was evaporated under reduced pressure. The obtained residue was purified by silica-gel column chromatography (hexane-ethyl acetate) to give a compound 17 (112 mg, yield 93%).

[M+H] 440.05, method 4, retention time 1.50 min

Step 4 Synthesis of Compound 18

The compound 17 (110 mg, 0.250 mmol) was dissolved in ethanol (2 mL). To the solution, hydrazine monohydrate (0.061 mL, 1.25 mmol) was added. The mixture was stirred at room temperature for 2 days. To the reaction mixture, saturated aqueous solution of sodium hydrogen carbonate was added. The mixture was extracted with ethyl acetate. The organic layer was washed by saturated aqueous solution of sodium hydrogen carbonate and brine, and then dried over anhydrous sodium sulfate. The solvent was evaporated under reduced pressure to give a compound 18 (63 mg, yield 81%).

$^1$H-NMR (CDCl$_3$) δ: 1.50-1.66 (m, 4H), 2.54-2.58 (m, 2H), 2.73-2.81 (m, 6H), 3.47 (s, 2H), 4.74 (q, J=8.3 Hz, 2H).

Step 5 Synthesis of Compound I-141

The compound 18 (21 mg, 0.068 mmol) was dissolved in DMF (1 mL). To the solution were added indole-2-carboxylic acid (13.1 mg, 0.081 mmol), EDC hydrochloride (15.6 mg, 0.081 mmol), HOBt (9.2 mg, 0.068 mmol). The mixture was stirred at room temperature overnight. To the reaction mixture, saturated aqueous solution of sodium hydrogen carbonate was added. The mixture was extracted with ethyl acetate. The organic layer was washed by saturated aqueous solution of sodium hydrogen carbonate, water and brine, and then dried over anhydrous sodium sulfate. The solvent was evaporated under reduced pressure. The obtained residue was purified by amino silica-gel column chromatography (hexane-ethyl acetate) to give a compound I-141 (15 mg, yield 49%).

1H-NMR (CDCl$_3$) δ: 1.72-1.78 (m, 4H), 2.61-2.64 (m, 2H), 2.77-2.82 (m, 4H), 3.47-3.54 (m, 4H), 4.69 (q, J=8.3 Hz, 2H), 6.57 (s, 1H), 7.08-7.14 (m, 2H), 7.27-7.29 (m, 2H), 7.41 (d, J=8.3 Hz, 1H), 7.52 (d, J=8.0 Hz, 1H), 9.13 (s, 1H).

Reference Example 1 Synthesis of Compound 23

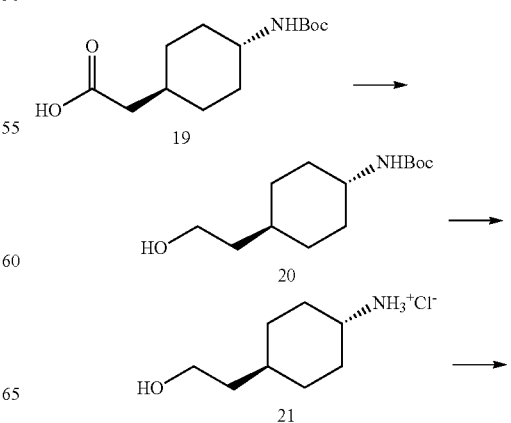

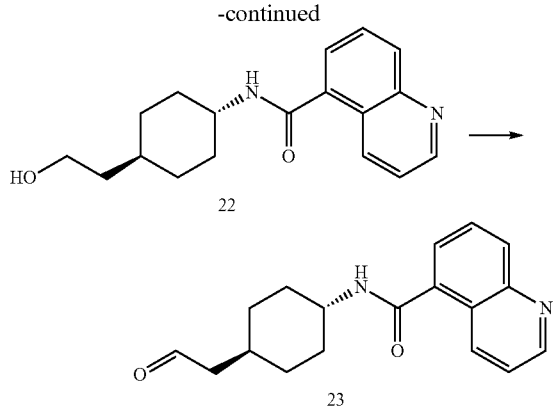

Step 1 Synthesis of Compound 20

Under nitrogen atmosphere, a compound 19 (4.0 g, 15.54 mmol) and triethylamine (3.23 mL, 23.32 mmol) were dissolved in tetrahydrofuran (40 mL). Under cooling at −15° C., isobutyl chloroformate (2.45 mL, 18.65 mmol) was added dropwise to the resulting solution. The mixture was stirred for 30 minutes. To the mixture, a suspension of sodium borohydride (1.18 g, 31.1 mmol) in methanol (5 mL) was added slowly. Then, the mixture was stirred for 30 minutes. Sodium borohydride (0.588 g, 15.54 mmol) was further added and then the mixture was stirred for 30 minutes. To the reaction mixture, saturated aqueous solution of ammonium chloride was added. The mixture was extracted with ethyl acetate. The organic layer was washed by water and brine, and dried over anhydrous sodium sulfate. The solvent was evaporated under reduced pressure. The obtained residue was purified by silica-gel column chromatography (hexane-ethyl acetate) to give a compound 20 (3.40 g, yield 90%).

1H-NMR (CDCl$_3$) δ: 0.98-1.13 (m, 4H), 1.20 (t, J=5.0 Hz, 1H), 1.32-1.50 (m, 12H), 1.76-1.80 (m, 2H), 1.98-2.02 (m, 2H), 3.37 (br, 1H), 3.68 (dd, J=11.4, 6.5 Hz, 2H), 4.37 (br, 1H).

Step 2 Synthesis of Compound 21

The compound 20 (3.40 g, 13.97 mmol) was dissolved in dichloromethane (34 mL). To the solution was added 4 mol/L hydrochloric acid (dioxane solution, 34.9 mL, 140 mmol). The mixture was stirred at room temperature for 3 hours. To the mixture, methanol (5 mL) was added and the mixture was stirred at room temperature for 1 hour. The solvent was evaporated under reduced pressure to give a compound 21 as a crude product.

Step 3 Synthesis of Compound 22

To the compound 21 obtained as a crude product in Step 2 was added dichloromethane (58.2 mL), and then were added quinoline-5-carboxylic acid (2.65 g, 15.32 mmol), triethylamine (11.58 mL, 84 mmol), HOBt (0.188 g, 1.39 mmol) and EDC hydrochloride (3.34 g, 17.41 mmol). The mixture was stirred at room temperature overnight. To the reaction mixture, saturated aqueous solution of sodium hydrogen carbonate was added. The mixture was extracted with a mixture of ethyl acetate and tetrahydrofuran. The organic layer was washed by saturated aqueous solution of sodium hydrogen carbonate and brine, and dried over anhydrous sodium sulfate. The solvent was evaporated under reduced pressure to give a compound 22 as a crude product.

Step 4 Synthesis of Compound 23

The compound 22 (3.00 g) obtained as a crude product in Step 3 was dissolved in DMSO (30 mL). To the resulting solution, 2-iodoxybenzoic acid (7.04 g, 25.4 mmol) was added. The mixture was stirred at room temperature for 2 hours. To the reaction mixture, saturated aqueous solution of sodium hydrogen carbonate was added. The mixture was extracted with a mixture of ethyl acetate, tetrahydrofuran and methanol. The organic layer was washed by saturated aqueous solution of sodium hydrogen carbonate, water and brine, and dried over anhydrous sodium sulfate. The solvent was evaporated under reduced pressure. The obtained residue was purified by silica gel column chromatography (chloroform-ethyl acetate) to give a compound 23 (1.93 g, yield 65%).

1H-NMR (CDCl$_3$) δ: 1.19-1.38 (m, 4H), 1.86-1.98 (m, 3H), 2.19-2.24 (m, 2H), 2.40 (dd, J=6.5, 1.8 Hz, 2H), 3.99-4.09 (m, 1H), 5.89 (d, J=8.0 Hz, 1H), 7.47 (dd, J=8.7, 4.1 Hz, 1H), 7.64-7.71 (m, 2H), 8.18 (d, J=8.0 Hz, 1H), 8.73 (d, J=8.5 Hz, 1H), 8.95 (dd, J=4.1, 1.6 Hz, 1H), 9.80 (t, J=1.8 Hz, 1H).

Example 8 Synthesis of Compound I-137

[Chemical Formula 125]

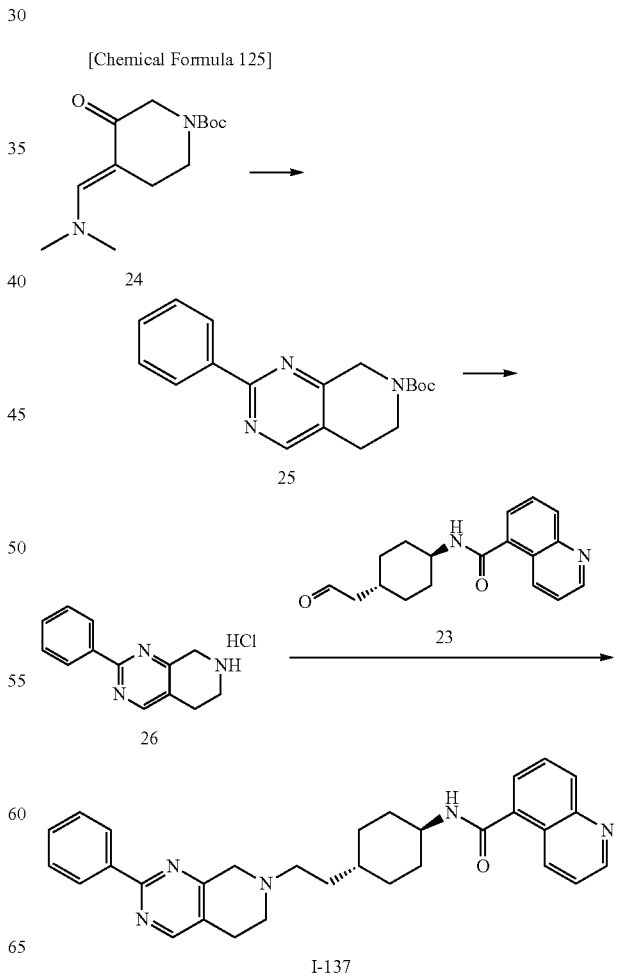

Step 1 Synthesis of Compound 25

Under nitrogen atmosphere, known compound 24 (50 mg, 0.20 mmol) and benzamidine (26 mg, 0.22 mmol) were dissolved in pyridine (2 mL). The mixture was stirred under microwave irradiation at 150° C. for 30 minutes. To the reaction solution, water was added. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a compound 25 (15.6 mg, yield 26%).

$^1$H-NMR (CDCl$_3$) δ: 1.52 (s, 9H), 2.86 (t, J=5.6 Hz, 2H), 3.74 (t, J=5.6 Hz, 2H), 4.70 (s, 2H), 7.46-7.50 (m, 3H), 8.40 (m, 2H), 8.57 (s, 1H).

Step 2 Synthesis of Compound 26

To a compound 25 (15.6 mg, 0.05 mmol) was added 4 mol/L hydrochloric acid (dioxane solution, 1 mL, 4 mmol). The mixture was stirred at room temperature for 4 hours. The solvent was evaporated under reduced pressure to give a compound 26 (13.9 mg) as a crude product.

Step 3 Synthesis of Compound I-137

To the crude compound 26 (13.9 mg) obtained in Step 2 were added dichloromethane (2 mL), triethylamine (0.035 mL, 0.25 mmol) and the compound 23 (14.8 mg, 0.05 mmol). The mixture was stirred at room temperature for 1 hour. To the mixture, sodium triacetoxyborohydride (31.8 mg, 0.15 mmol) was added. The mixture was stirred at room temperature for 5 hours. To the reaction mixture, saturated aqueous solution of sodium hydrogen carbonate was added. The mixture was extracted with ethyl acetate. The organic layer was washed by brine, and dried over anhydrous sodium sulfate. The solvent was evaporated under reduced pressure. The obtained residue was purified by amino silica-gel column chromatography (hexane-ethyl acetate) to give a compound I-137 (16.3 mg, yield 66%).

1H-NMR (CDCl$_3$) δ: 1.20-1.29 (m, 4H), 1.40 (m, 1H), 1.56-1.61 (m, 2H), 1.91 (d, J=10.3 Hz, 2H), 2.21 (d, J=9.8 Hz, 2H), 2.63 (t, J=7.5 Hz, 2H), 2.80 (t, J=5.6 Hz, 2H), 2.91 (t, J=5.5 Hz, 2H), 3.75 (s, 2H), 3.98-4.10 (m, 1H), 5.84 (d, J=8.3 Hz, 1H), 7.45-7.49 (m, 4H), 7.64-7.71 (m, 2H), 8.18 (d, J=8.0 Hz, 1H), 8.37-8.40 (m, 2H), 8.54 (s, 1H), 8.74 (d, J=8.6 Hz, 1H), 8.95 (dd, J=4.3, 1.6 Hz, 1H)

Example 9 Synthesis of Compound I-136

[Chemical Formula 126]

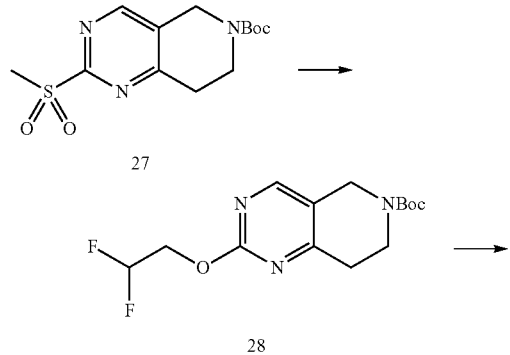

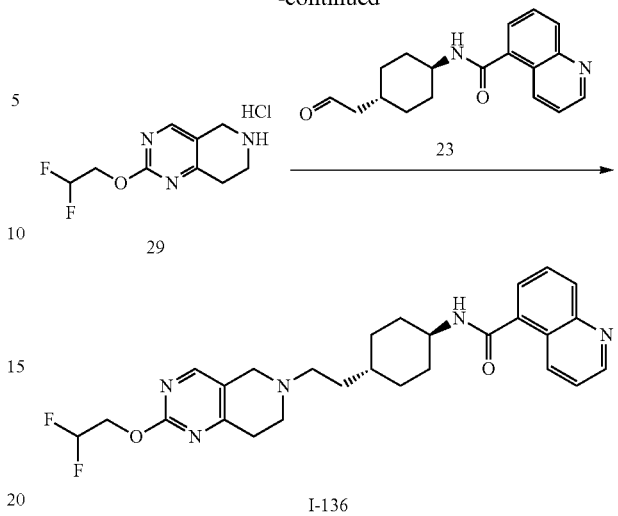

Step 1 Synthesis of Compound 28

Under nitrogen atmosphere, 2,2-difluoroethanol (65.5 mg, 0.50 mmol) dissolved in DMF (2 mL) was cooled with ice. To the solution was added sodium hydride (60 wt %, 31.9 mg, 0.80 mmol) portionwise. The mixture was stirred at 0° C. for 1 hour. To the mixture was added a compound 27 (50 mg, 0.16 mmol) portionwise. Then, the mixture was stirred at 0° C. for 2 hours. Ice water was added to the reaction mixture. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a compound 28 (28.8 mg, yield 57%).

1H-NMR (CDCl$_3$) δ: 1.50 (s, 9H), 2.89 (s, 2H), 3.73 (s, 2H), 4.53-4.61 (m, 4H), 6.14 (t, J=55.4 Hz, 1H), 8.27 (s, 1H).

Step 2 Synthesis of Compound 29

A compound 29 was obtained as a crude product by the similar method of Step 2 of Example 8.

Step 3 Synthesis of Compound I-136

A compound I-136 was obtained by the similar method of Step 3 of Example 8.

1H-NMR (CDCl$_3$) δ: 1.19-1.56 (m, 7H), 1.89 (d, J=10.4 Hz, 2H), 2.20 (d, J=10.4 Hz, 2H), 2.56-2.61 (m, 2H), 2.77-2.82 (m, 2H), 2.92-2.96 (m, 2H), 3.56 (s, 2H), 4.00-4.07 (m, 1H), 4.51-4.59 (m, 2H), 5.82-5.85 (m, 1H), 6.13 (t, J=56.0 Hz, 1H), 7.46-7.49 (m, 1H), 7.64-7.71 (m, 2H), 8.17-8.20 (m, 2H), 8.74 (d, J=7.9 Hz, 1H), 8.95 (s, 1H).

Example 10 Synthesis of Compound I-139

[Chemical Formula 127]

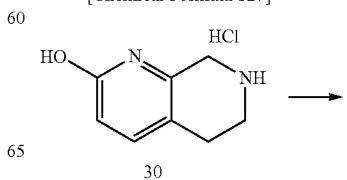

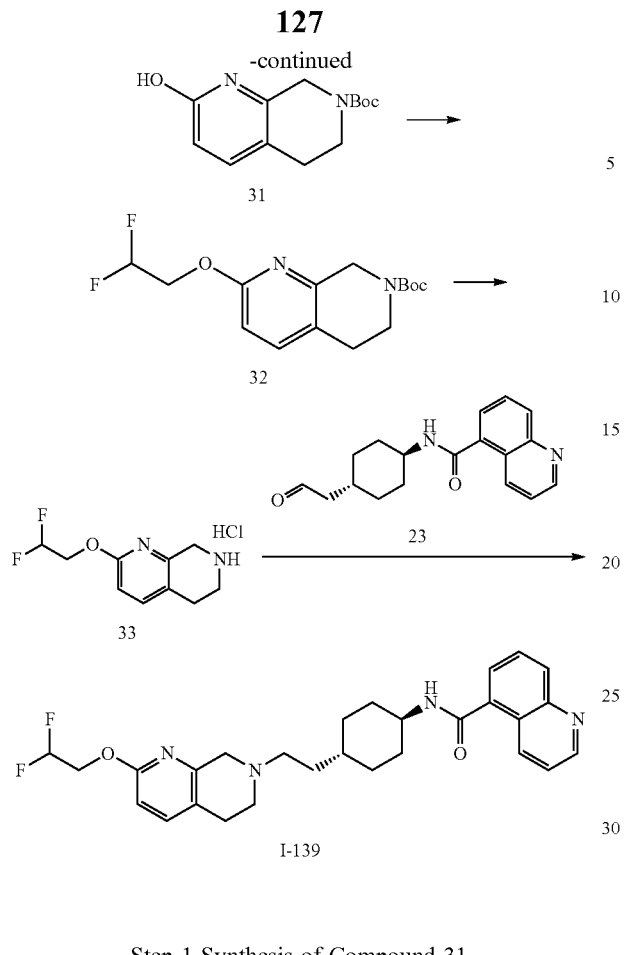

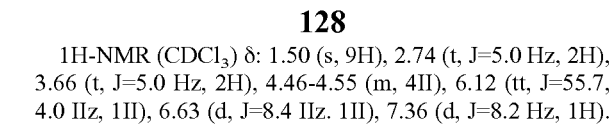

1H-NMR (CDCl₃) δ: 1.50 (s, 9H), 2.74 (t, J=5.0 Hz, 2H), 3.66 (t, J=5.0 Hz, 2H), 4.46-4.55 (m, 4H), 6.12 (tt, J=55.7, 4.0 Hz, 1H), 6.63 (d, J=8.4 Hz, 1H), 7.36 (d, J=8.2 Hz, 1H).

Step 3 Synthesis of Compound 33

A compound 33 as a crude product was obtained by the similar method of Step 2 of Example 8.

Step 4 Synthesis of Compound I-139

A compound I-139 was obtained by the similar method of Step 3 of Example 8.
1H-NMR (CDCl₃) δ: 1.16-1.42 (m, 5H), 1.54-1.60 (m, 2H), 1.90 (d, J=11.0 Hz, 2H), 2.20 (d, J=10.2 Hz, 2H), 2.58 (t, J=7.7 Hz, 2H), 2.72 (t, J=5.5 Hz, 2H), 2.80 (t, J=5.2 Hz, 2H), 3.58 (s, 2H), 3.99-4.09 (m, 1H), 4.49 (td, J=13.6, 4.3 Hz, 2H), 5.85 (d, J=8.2 Hz, 1H), 6.12 (tt, J=55.8, 4.2 Hz, 1H), 6.60 (d, J=8.3 Hz, 1H), 7.34 (d, J=8.4 Hz, 1H), 7.48 (dd, J=8.6, 4.2 Hz, 1H), 7.64-7.71 (m, 2H), 8.18 (d, J=7.9 Hz, 1H), 8.74 (d, J=8.5 Hz, 1H), 8.95 (dd, J=4.1, 1.6 Hz, 1H).

Example 11 Synthesis of Compound I-104

[Chemical Formula 128]

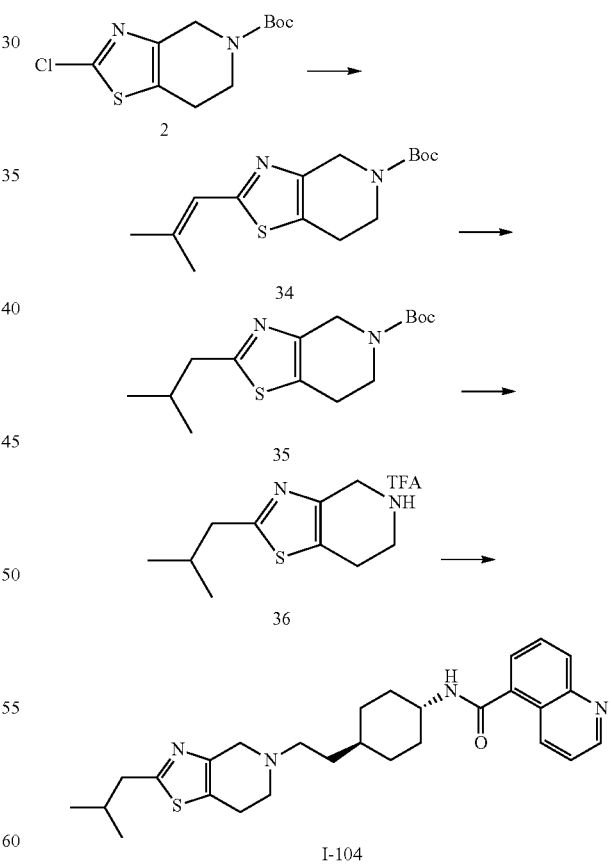

Step 1 Synthesis of Compound 31

To a solution of a compound 30 (90 mg, 0.48 mmol), triethylamine (0.17 mL, 1.21 mmol), water (a few drops), DMF (1 mL) and tetrahydrofuran (1.8 mL) was added Boc₂O (0.13 mL, 0.58 mmol). Then, the mixture was stirred at room temperature for 4.5 hours. To the reaction mixture, water was added. The mixture was extracted with ethyl acetate. The organic layer was washed by saturated aqueous solution of sodium hydrogen carbonate and brine, and then dried over anhydrous sodium sulfate. The solvent was evaporated under reduced pressure. The obtained residue was purified by silica-gel column chromatography (chloroform-methanol) to give compound 31 (45.4 mg, yield 38%).

1H-NMR (CDCl₃) δ: 1.49 (s, 9H), 2.55 (m, 2H), 3.63 (t, J=5.4 Hz, 2H), 4.44 (s, 2H), 6.42 (d, J=9.3 Hz, 1H), 7.22 (d, J=9.2 Hz, 1H).

Step 2 Synthesis of Compound 32

Under nitrogen atmosphere, to a solution of compound 31 (45.4 mg, 0.18 mmol) in DMF (2 mL) was added potassium carbonate (50.1 mg, 0.36 mmol) and 2,2-difluoroethyl trifluoromethanesulfonate (58.3 mg, 0.27 mmol). Then, the mixture was stirred at room temperature for 1.6 hours. To the reaction mixture, water was added. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a compound 32 (43.8 mg, yield 77%).

Step 1 Synthesis of Compound 34

Under nitrogen atmosphere, 2-methyl-1-propenylboronic acid pinacol ester (49.7 mg, 0.273 mmol) was dissolved in DME (1.6 mL). To the solution were added the compound 2 (50 mg, 0.182 mmol), PdCl₃ (dppf)(13.3 mg, 0.018 mmol), potassium phosphate (116 mg, 0.546 mmol) and water (0.4 mL). The mixture was stirred under microwave irradiation at 120° C. for 30 minutes. 2-methyl-1-propenylboronic acid pinacol ester (49.7 mg, 0.273 mmol) and PdCl₃ (dppf), (13.3 mg, 0.018 mmol) were added and the mixture was stirred under microwave irradiation at 130° C. for 1 hour. The reaction mixture was poured into water. The mixture was extracted with ethyl acetate. The organic layer was washed by brine, and dried over anhydrous magnesium sulfate. The solvent was evaporated under reduced pressure. The obtained residue was purified by silica-gel column chromatography (hexane-ethyl acetate) to give compound 34 (30 mg, yield 56%).

1H-NMR (CDCl₃) δ: 1.49 (s, 9H), 1.97 (s, 3H), 2.10 (s, 3H), 2.85 (br, 2H), 3.74 (br, 2H), 4.60 (s, 2H), 6.47 (s, 1H).

Step 2 Synthesis of Compound 35

The compound 34 (30 mg, 0.102 mmol) was dissolved in methanol (1.5 mL). To the solution was added 10% palladium on carbon (11 mg). The mixture was stirred under hydrogen atmosphere at room temperature for 2 hours. The reaction mixture was filtered. The filtrate was evaporated under reduced pressure. The obtained residue was purified by silica-gel column chromatography (hexane-ethyl acetate) to give a compound 35 (27 mg, yield 89%).

1H-NMR (CDCl₃) δ: 0.99 (d, J=6.5 Hz, fill). 1.48 (s, 9H), 2.03-2.10 (m, 1H), 2.79-2.83 (m, 4H), 3.73 (s, 2H), 4.59 (s, 2H).

Step 3 Synthesis of Compound 36

The compound 35 (27 mg, 0.091 mmol) was dissolved in dichloromethane (1.5 mL). To the solution was added TFA (0.5 mL). The mixture was stirred at room temperature for 2 hours. The reaction mixture was evaporated under reduced pressure to give a compound 36 as a crude product.

Step 4 Synthesis of Compound I-104

A compound I-104 was synthesized by the similar method of Step 3 of Example 8.
[M+H] 477.3, method 2, retention time 1.31 min Example 12 Synthesis of Compound I-097

[Chemical Formula 129]

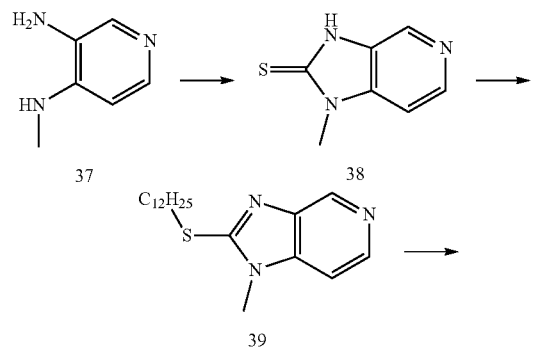

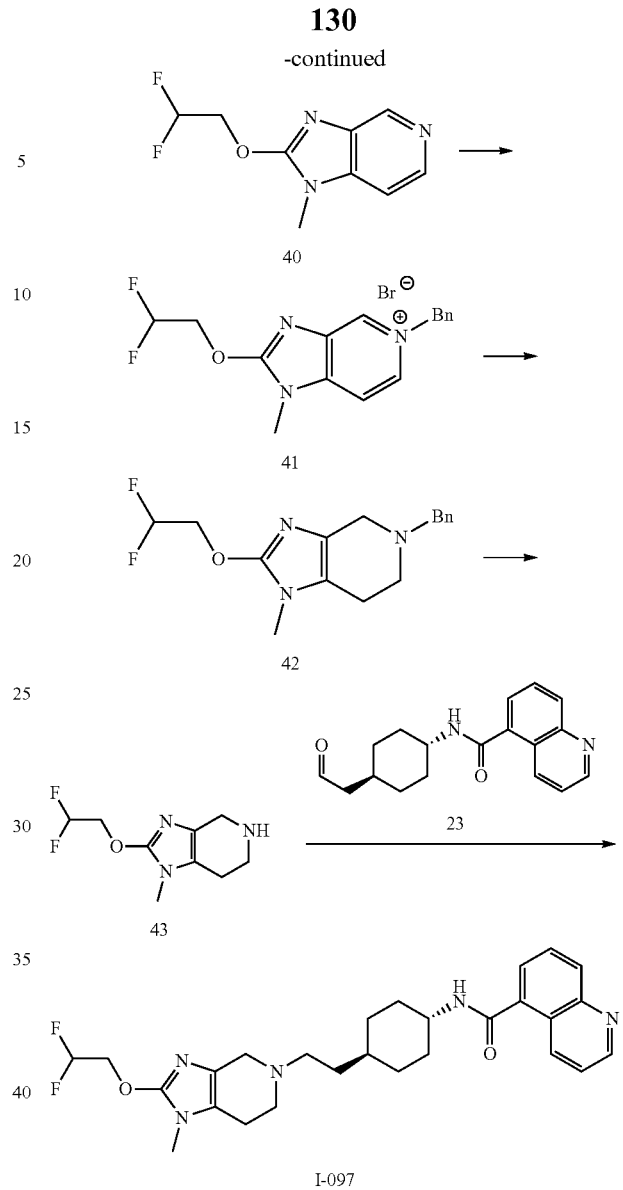

Step 1 Synthesis of Compound 38

A compound 37 (500 mg, 4.06 mmol) was suspended in acetonitrile (15 mL). To the suspension was added 1,1'-thiocarbonyldiimidazole (868 mg, 4.87 mmol). The mixture was stirred at room temperature for 2 hours. To the reaction mixture, water was added. A solid was obtained by filtration, washed by water and dried to give a compound 38 (619 mg) as a crude product.

Step 2 Synthesis of Compound 39

The crude compound 38 obtained in Step 1 was suspended in DMF (7 mL). To the suspension were added potassium carbonate (619 mg, 4.48 mmol) and 1-bromododecane (0.98 mL, 4.11 mmol). The mixture was stirred at room temperature for 3 hours. To the reaction mixture, saturated aqueous solution of ammonium chloride was added under ice cooling. The mixture was extracted with ethyl acetate. The organic layer was washed by water and brine, and dried over magnesium sulfate anhydrous. The solvent was evaporated under reduced pressure. The obtained residue was purified by silica-gel column chromatography (hexane-ethyl acetate) to give a compound 39 (378 mg, yield 30%, 2 steps) as a solid.

1H-NMR (CDCl$_3$) δ: 0.88 (t, J=6.7 Hz, 3H), 1.25-1.38 (m, 16H), 1.45-1.62 (m, 2H), 1.78-1.86 (m, 2H), 3.42 (t, J=7.3 Hz, 2H), 3.68 (s, 3H), 7.18 (d, J=5.5 Hz, 1H), 8.36 (d, J=5.5 Hz, 1H), 8.95 (s, 1H).

Step 3 Synthesis of Compound 40

2,2-difluoroethanol (123 mg, 1.50 mmol) was dissolved in DMF (1.5 mL). To the solution, under ice cooling, sodium hydride (60 wt %, 60 mg, 1.50 mmol) was added portionwise. The mixture was stirred at room temperature for 30 minutes. To the mixture, the compound 39 (100 mg, 0.30 mmol) was added portion wise. The mixture was stirred at 80° C. for 5 hours. Under ice cooling, to the reaction mixture was added saturated aqueous solution of ammonium chloride. The mixture was extracted with ethyl acetate. The organic layer was washed by water and brine, and then dried over anhydrous magnesium sulfate. The solvent was evaporated under reduced pressure. The obtained residue was purified by silica-gel column chromatography (hexane-ethyl acetate) to give a compound 40 (18 mg, yield 28%).

1H-NMR (CDCl$_3$) δ: 3.63 (s, 3H), 4.77 (td, J=13.2, 3.9 Hz, 2H), 6.24 (tt, J=54.8, 4.0 Hz, 1H), 7.15 (d, J=5.5 Hz, 1H), 8.38 (d, J=5.5 Hz, 1H), 8.81 (s, 1H).

Step 4 Synthesis of Compound 41

The compound 40 (18 mg, 0.084 mmol) was dissolved in acetonitrile (1 mL). To the solution was added benzyl bromide (10 µL, 0.084 mmol). The mixture was stirred at room temperature for 2 days. The solvent was evaporated under reduced pressure to give a compound 41 as a crude product.

Step 5 Synthesis of Compound 42

The crude compound 41 obtained in Step 4 was dissolved in ethanol (1 mL). To the solution, under ice cooling, was added sodium borohydride (9.6 mg, 0.253 mmol). The mixture was stirred at room temperature for 2 hours. To the reaction mixture, under ice cooling, was added saturated aqueous solution of ammonium chloride. The mixture was extracted with ethyl acetate. The organic layer was washed by brine, and dried over anhydrous magnesium sulfate. The solvent was evaporated under reduced pressure to give a compound 42 (25 mg) as a crude product.

[M+H] 308.1, method 1, retention time 1.66 min

Step 6 Synthesis of Compound 43

The crude compound 42 obtained in Step 5 was dissolved in ethanol (1.5 mL). To the solution was added palladium hydroxide (20 wt %, 11.4 mg, 0.016 mmol). The mixture was stirred under hydrogen atmosphere at room temperature for 5 hours. The reaction mixture was filtered through Celite, and washed by methanol. The solvent was evaporated under reduced pressure. The obtained residue was purified by amino silica gel column chromatography (chloroform-methanol) to give a crude compound 43 (10 mg) as an oil.

Step 7 Synthesis of I-097

The crude compound 43 obtained in Step 6 was dissolved in dichloromethane (1 mL). To the solution were added a compound 23 (13.6 mg. 0.046 mmol) and acetic acid (5.3 µL, 0.092 mmol). The mixture was stirred at room temperature for 15 minutes. To the mixture was added sodium triacetoxyborohydride (29.3 mg, 0.138 mmol). The mixture was stirred at room temperature for 2 hours. To the reaction mixture was added saturated aqueous solution of sodium hydrogen carbonate. The mixture was extracted with ethyl acetate. The organic layer was washed by brine, and then dried over anhydrous magnesium sulfate. The solvent was evaporated under reduced pressure. The obtained residue was purified by preparative TLC (chloroform-methanol) to give a compound I-097 (13.5 mg, yield 59%, 4 steps).

[M+H] 498.2, method 2, retention time 0.94 min

Example 13 Synthesis of Compound I-096

[Chemical Formula 130]

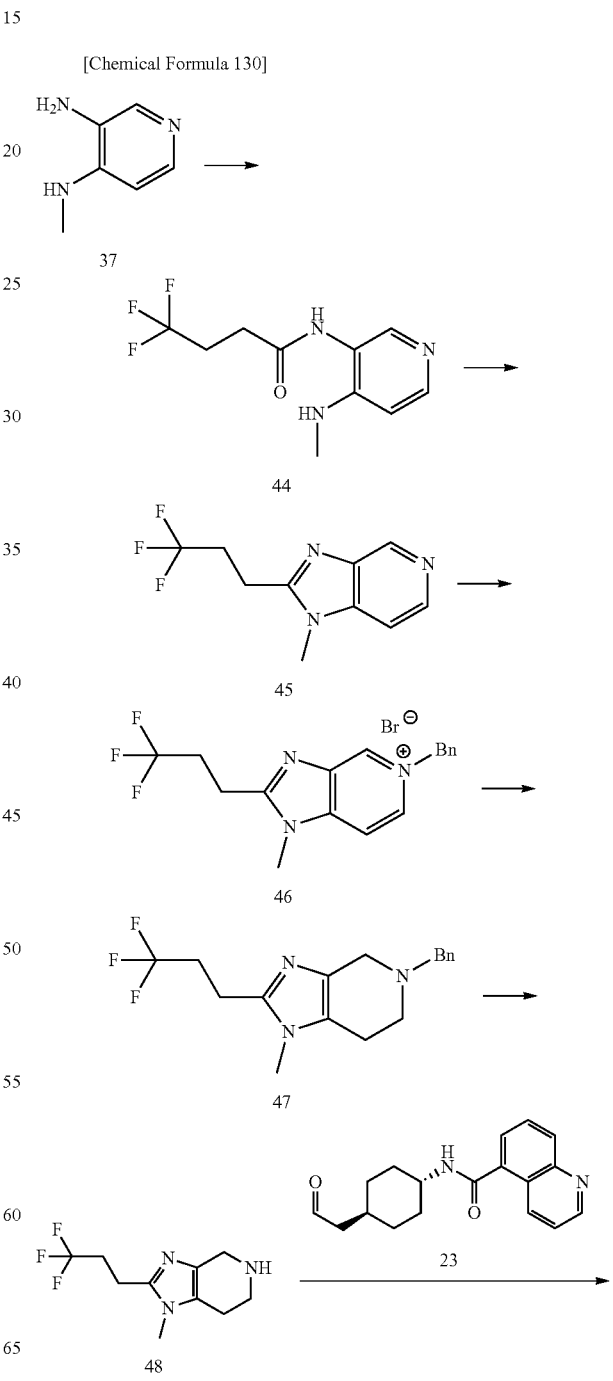

133

-continued

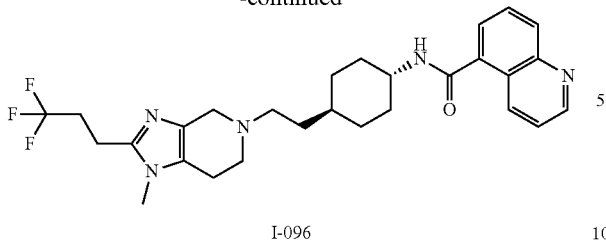
I-096

Step 1 Synthesis of Compound 44

4,4,4-trifluorobutyric acid (127 mg, 0.89 mmol) was dissolved in DMF (2 mL). To the solution were added a compound 37 (100 mg, 0.81 mmol) and HATU (340 mg, 0.89 mmol), then under ice cooling was added DIEA (170 μL, 0.97 mmol). The mixture was stirred at room temperature for 8 hours. The reaction mixture was poured into saturated aqueous solution of sodium hydrogen carbonate. The mixture was extracted with ethyl acetate. The organic layer was washed by brine, and then dried over anhydrous sodium sulfate. The solvent was evaporated under reduced pressure to give a compound 44 (159 mg) as a crude product.

[M+H] 248.0, method 1, retention time 0.96 min

Step 2 Synthesis of Compound 45

The crude compound 44 obtained in Step 1 was dissolved in acetic acid (1.5 mL). The solution was stirred under microwave irradiation at 160° C. for 30 minutes, and further stirred under microwave irradiation at 160° C. for 1 hour. The solvent was evaporated under reduced pressure. To the mixture was added 1 mol/L aqueous sodium hydroxide solution. The mixture was extracted with chloroform. The organic layer was washed by brine, and then and dried over anhydrous magnesium sulfate. The solvent was evaporated under reduced pressure. The obtained residue was purified by silica-gel column chromatography (chloroform-methanol) to give a compound 45 (104 mg, yield 56%, 2 steps).

1H-NMR (CDCl$_3$) δ: 2.82-2.94 (m, 2H), 3.12-3.18 (m, 2H), 3.78 (s, 3H), 7.28 (d, J=5.5 Hz, 1H), 8.45 (d, J=5.8 Hz, 1H), 9.03 (s, 1H).

Step 3 Synthesis of Compound 46

A compound 46 was obtained as a crude product by the similar method of Step 4 of Example 12 using the compound 45 (101 mg, 0.441 mmol) as a starting material.

Step 4 Synthesis of Compound 47

A compound 47 (123 mg) was obtained as a crude product by the similar method of Step 5 of Example 12 using the crude compound 46 obtained in Step 3 as a starting material.

[M+H] 324.2, method 1, retention time 1.66 min

Step 5 Synthesis of Compound 48

A compound 48 (39 mg, 3 steps yield 38%) was obtained as a solid by the similar method of Step 6 of Example 12 using the crude compound 47 (123 mg) obtained in Step 4 as a starting material.

134

1H-NMR (CDCl$_3$) δ: 2.50-2.56 (m, 2H), 2.59-2.71 (m, 2H), 2.85-2.92 (m, 2H), 3.12-3.18 (m, 2H), 3.42 (s, 3H), 3.83 (s, 2H).

Step 6 Synthesis of I-096

A compound I-096 (12.3 mg, yield 28%) was obtained by the similar method of Step 7 of Example 12 using the compound 48 (39 mg) as a starting material.

[M+H] 514.2, method 2, retention time 0.79 min

Example 14 Synthesis of Compound I-125

[Chemical Formula 131]

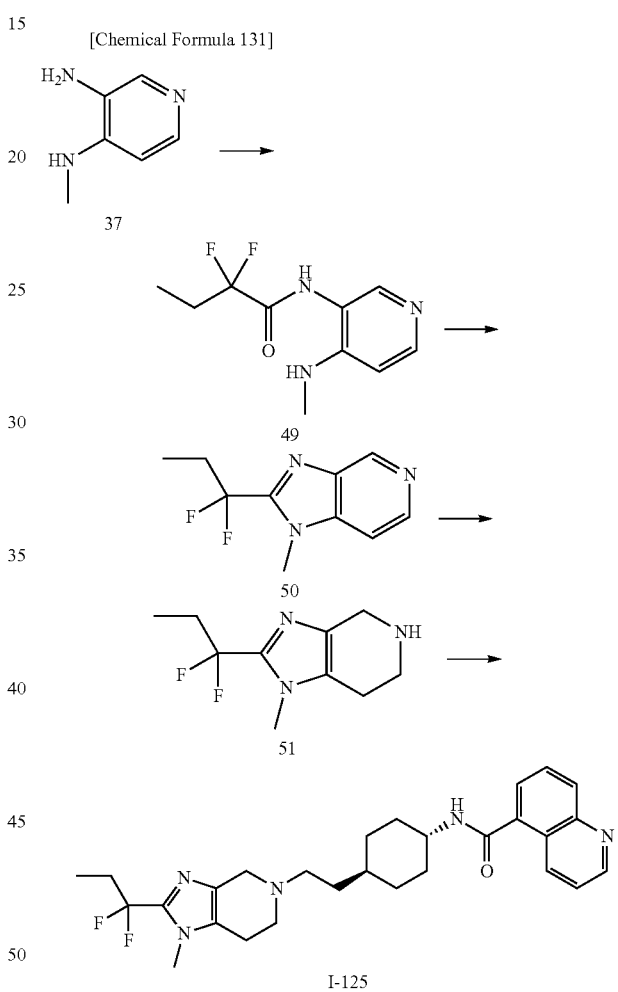

Step 1 Synthesis of Compound 49

A compound 49 (71 mg, yield 7G %) was obtained by the similar method of Step 1 of Example 13.

1H-NMR (CDCl$_3$) δ: 1.12 (t, J=7.5 Hz, 3H), 2.17-2.31 (m, 2H), 2.91 (d, J=4.6 Hz, 3H), 4.51 (br s, 1H), 6.60 (d, J=5.8 Hz, 1H), 7.88 (br s, 1H), 8.14 (s, 1H), 8.25 (d, J=5.8 Hz, 1H).

Step 2 Synthesis of Compound 50

The compound 49 (70 mg, 0.31 mmol) was dissolved in acetic acid (1 mL). The solution was stirred at 110° C. overnight. The solvent was evaporated under reduced pressure. To the residue was added 1 mol/L aqueous sodium hydroxide solution. The mixture was extracted with chloroform. The organic layer was washed by brine, and then dried over anhydrous magnesium sulfate. The solvent was evaporated under reduced pressure. The obtained residue was purified by amino silica gel column chromatography (chloroform-methanol) to give a compound 50 (58 mg, yield 90%).

1H-NMR (CDCl$_3$) δ: 1.26 (t, J=7.5 Hz, 3H), 2.57-2.71 (m, 2H), 3.99 (s, 3H), 7.38 (d, J=5.6 Hz, 1H), 8.53 (d, J=5.6 Hz, 1H), 9.14 (s, 1H).

Step 3 Synthesis of Compound 51

The compound 50 (56 mg, 0.27 mmol) was dissolved in ethanol (2.5 mL). To the solution was added platinum oxide (12 mg, 0.053 mmol). The mixture was stirred under 0.5 MPa hydrogen atmosphere overnight. The reaction mixture was filtered, and washed by ethanol. The solvent was evaporated under reduced pressure. The obtained residue was purified by amino silica gel column chromatography (chloroform-methanol) to give a compound 51 (47 mg, yield 82%).

1H-NMR (CDCl$_3$) δ: 1.16 (t, J=7.5 Hz, 3H,), 2.39-2.54 (m, 2H), 2.54-2.60 (m, 2H), 3.16 (t, J=5.7 Hz, 2H), 3.65 (s, 3H), 3.85 (s, 2H).

Step 4 Synthesis of I-125

A compound I-125 (58.5 mg, yield 54%) was obtained in a similar manner of Step 7 of Example 12 using the compound 51 (47 mg) as a starting material.

1H-NMR (DMSO-d$_6$) δ: 1.01-1.12 (m, 5H), 1.22-1.37 (m, 3H), 1.39-1.47 (m, 2H), 1.78-1.86 (m, 2H), 1.91-2.00 (m, 2H), 2.31-2.47 (m, 2H), 2.51-2.55 (m, 2H), 2.57-2.62 (m, 2H), 2.67-2.75 (m, 2H), 3.29-3.33 (m, 2H), 3.60 (s, 3H), 3.75-3.86 (m, 1H), 7.58 (dd, J=8.5, 4.1 Hz, 1H), 7.67 (d, J=7.0 Hz, 1H), 7.78 (t, J=7.8 Hz, 1H), 8.09 (d, J=8.4 Hz, 1H), 8.49 (d, J=7.9 Hz, 1H), 8.58 (d, J=8.5 Hz, 1H), 8.92-8.95 (m, 1H).

[M+H] 514.2, method 1, retention time 1.81 min

Example 15 Synthesis of Compound I-033

[Chemical Formula 132]

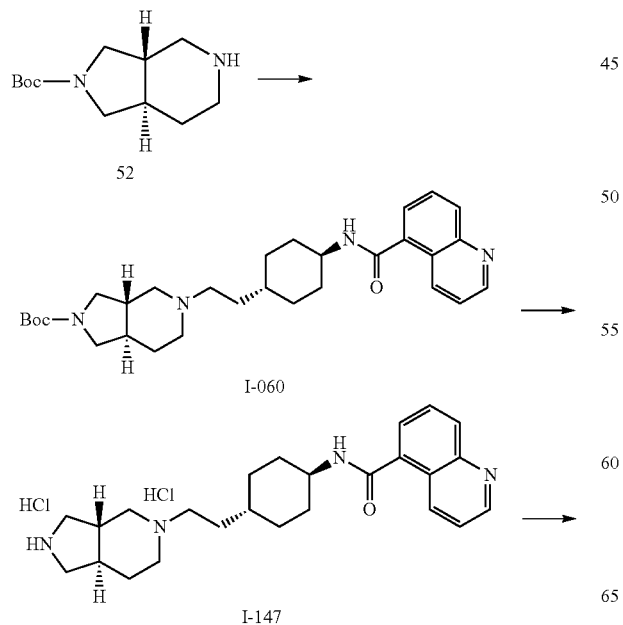

Step 1 Synthesis of I-060

A compound I-060 (60 mg, yield 89%) was obtained in a similar manner of Step 7 of Example 12 using a racemic compound 52 (30 mg) as a starting material.

1H-NMR (DMSO-d$_6$) δ: 0.99-1.10 (m, 2H), 1.20-1.41 (m, 16H), 1.71-1.82 (m, 5H), 1.86-1.98 (m, 3H), 2.32-2.38 (m, 2H), 2.66-2.80 (m, 2H), 2.89-2.94 (m, 1H), 2.99-3.07 (m, 1H), 3.36-3.47 (m, 2H), 3.73-3.85 (m, 1H), 7.58 (dd, J=8.6, 4.2 Hz, 1H), 7.67 (d, J=6.9 Hz, 1H), 7.78 (t, J=7.8 Hz, 1H), 8.09 (d, J=8.4 Hz, 1H), 8.48 (d, J=7.9 Hz, 1H). 8.58 (d, J=8.3 Hz, 1H), 8.94 (dd, J=4.1, 1.4 Hz, 1H).

[M+H] 507.3, method 1, retention time 1.52 min

Step 2 Synthesis of Compound I-147

A compound I-147 (70 mg) was obtained as a crude product in a similar manner of Step 3 of Example 1 using I-060 (55 mg) as a starting material.

[M+H] 407.3, method 1, retention time 1.01 min

Step 3 Synthesis of I-033

The crude compound I-147 (70 mg) was suspended in 1,4-dioxane (2 mL). To the suspension were added bromobenzene (14 μL, 0.13 mmol), Pd2 (dba)$_3$ (5.0 mg, 5.5 μmol), 2-dicyclohexylphosphino-2',6'-diisopropoxy-1,1'-biphenyl(10 mg, 0.022 mmol) and sodium-tert-butoxide (52 mg, 0.55 mmol). After nitrogen purge, the mixture was stirred at 100° C. for 6 hours. The reaction mixture was filtered, and washed by chloroform. The solvent was evaporated under reduced pressure. The obtained residue was purified by silica-gel column chromatography (chloroform-methanol), and further purified by amino silica gel column chromatography (hexane-ethyl acetate) to give a compound I-033 (35 mg, yield 67%, 2 steps).

[M+H] 483.2, method 1, retention time 2.42 min

Example 16 Synthesis of Compound I-020

[Chemical Formula 133]

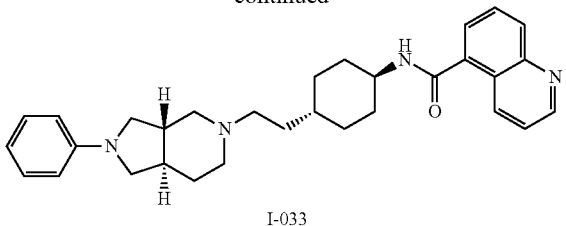

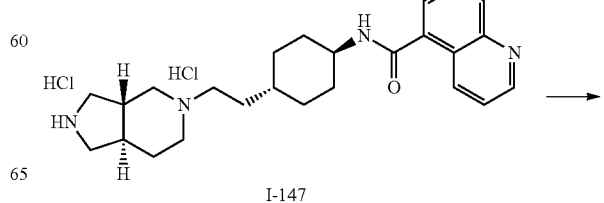

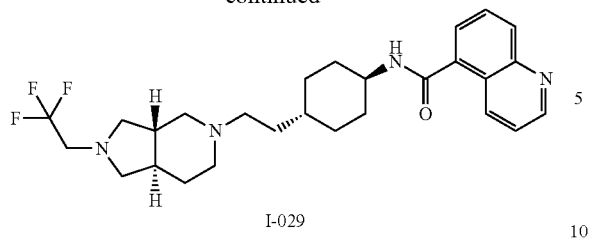

I-029

Step 1 Synthesis of I-029

The compound I-147 (40 mg, 0.083 mmol) was suspended in DMF (1.5 mL). To the suspension, under ice cooling, were added 2,2,2-trifluoroethyl triflate (23 mg, 0.10 mmol) and DIEA (52 µL, 0.30 mmol). The mixture was stirred at room temperature overnight. To the reaction mixture, water was added. The mixture was extracted with ethyl acetate. The organic layer was washed by water and brine, and dried over anhydrous magnesium sulfate. The solvent was evaporated under reduced pressure. The obtained residue was purified by silica-gel column chromatography (chloroform-methanol) to give a compound I-029 (9.1 mg, yield 22%).

[M+H] 489.3, method 1, retention time 1.79 min

Example 17 Synthesis of Compound I-050

[Chemical Formula 134]

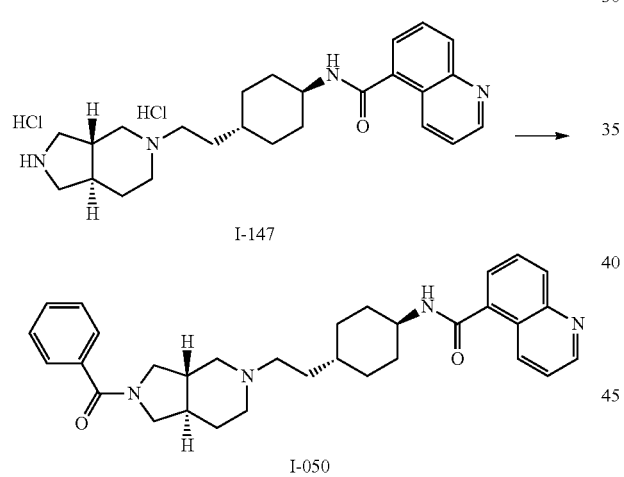

Step 1 Synthesis of I-050

A compound I-050 (15 mg, yield 27%) was obtained in a similar manner of Step 1 of Example 13 using the compound I-147 (50 mg, 010 mmol) as a starting material.

[M+H] 511.3, method 1, retention time 1.67 min

Reference Example 2 Synthesis of Compound 57

[Chemical Formula 135]

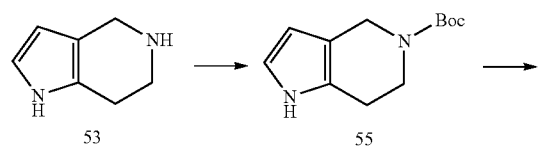

53    55

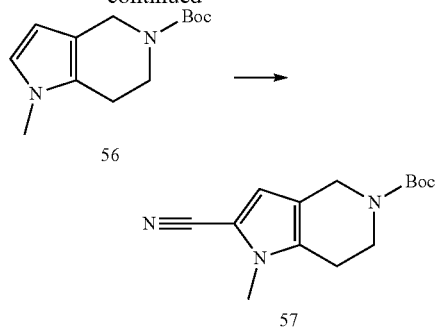

56

57

Step 1 Synthesis of Compound 55

A compound 53 (300 mg, 2.46 mmol) was dissolved in tetrahydrofuran (6 mL) and water (6 mL). To the solution were added sodium hydrogen carbonate (619 mg, 7.37 mmol) and Boc$_2$O (0.68 mL, 2.95 mmol). The mixture was stirred at room temperature for 2 days. To the reaction mixture, water was added. The mixture was extracted with ethyl acetate. The organic layer was washed by brine, and dried over anhydrous magnesium sulfate. The solvent was evaporated under reduced pressure. The obtained residue was purified by silica-gel column chromatography (hexane-ethyl acetate) to give a compound 55 (446 mg, yield 82%).

1H-NMR (CDCl$_3$) δ: 1.47 (s, 9H), 2.67 (s, 2H), 3.72 (s, 2H), 4.43 (s, 2H), 6.01 (t, J=2.6 Hz, 1H), 6.67 (s, 1H), 7.88 (br s, 1H).

Step 2 Synthesis of Compound 56

The compound 55 (442 mg, 1.99 mmol) was dissolved in DMF (5 mL). To the solution, under ice cooling, was added sodium hydride (60 wt. %, 87 mg, 2.19 mmol) portion wise. The mixture was stirred at 0° C. for 1 hour. To the mixture was added iodomethane (149 µL, 2.39 mmol) and then the mixture was stirred at room temperature overnight. To the reaction mixture, under ice cooling, was added saturated aqueous solution of ammonium chloride. The mixture was extracted with ethyl acetate. The organic layer was washed by water and brine, and then dried over anhydrous magnesium sulfate. The solvent was evaporated under reduced pressure. The obtained residue was purified by silica-gel column chromatography (hexane-ethyl acetate) to give a compound 56 (335 mg, yield 71%).

1H-NMR (CDCl$_3$) δ: 1.47 (s, 9H), 2.60 (br 2H), 3.49 (s, 3H), 3.73 (br, 2H), 4.41 (s, 2H), 5.93 (d, J=2.6 Hz, 1H), 6.52 (d, J=2.1 Hz, 1H).

Step 3 Synthesis of Compound 57

The compound 56 (30 mg, 0.13 mmol) was dissolved in acetonitrile (1 mL). To the solution, under ice cooling, was added chlorosulfonyl isocyanate (11 µL, 0.13 mmol). The mixture was stirred at 0° C. for 30 minutes. To the mixture were added DMF (20 µL, 0.25 mmol) and triethylamine (35 µL, 0.254 mmol). The mixture was stirred at 0° C. for 1 hour. To the reaction mixture was added saturated aqueous solution of sodium hydrogen carbonate. The mixture was extracted with ethyl acetate. The organic layer was washed by brine, and then dried over anhydrous magnesium sulfate. The solvent was evaporated under reduced pressure. The obtained residue was purified by silica-gel column chromatography (hexane-ethyl acetate) to give a compound 57 (16 mg, yield 48%).

1H-NMR (CDCl₃) δ: 1.47 (s, 9H), 2.63 (br, 2H), 3.61 (s, 3H), 3.73 (br, 2H), 4.36 (s, 2H), 6.57 (s, 1H).

Example 18 Synthesis of Compound I-148

[Chemical Formula 136]

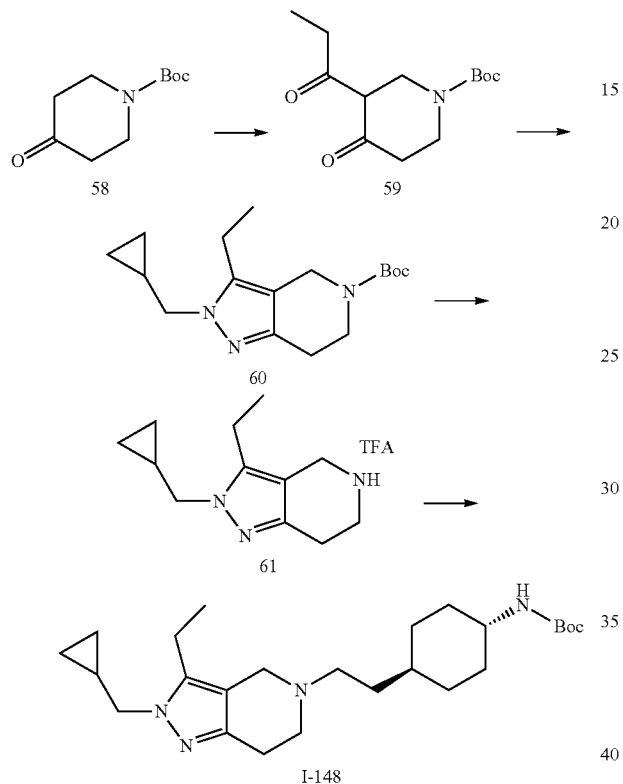

Step 1 Synthesis of Compound 59

Under argon atmosphere, a compound 58 (2 g, 10 mmol) was dissolved in toluene (30 mL). To the solution was added 1 mol/L LHMDS (12 mL, 12 mmol) dropwise over 30 minutes at −78° C. To the mixture was added propionyl-chloride (0.96 mL, 11 mol). The mixture was stirred at −78° C. for 30 minutes and then stirred at room temperature for 30 minutes. To the reaction mixture was added saturated aqueous solution of ammonium chloride. The mixture was extracted with ethyl acetate. The organic layer was separated and the solvent was evaporated under reduced pressure. The obtained residue was purified by silica gel column chromatography (petroleum ether-ethyl acetate) to give a compound 59 (690 mg, yield 35%).

Step 2 Synthesis of Compound 60

The compound 59 (690 mg, 2.7 mmol) was dissolved in tetrahydrofuran (10 mL). To the solution were added acetic acid (3 mL) and cyclopropylmethylhydrazine dihydrochloride (473 mg, 3 mmol). The mixture was refluxed for 3 hours. The reaction mixture was concentrated under reduced pressure. The obtained residue was purified by silica gel column chromatography (dichloromethane-methanol) to give a compound 60 (230 mg, yield 28%).

1H NMR (CDCl₃) δ0.25-0.33 (m, 2H), 0.53-0.58 (m, 2H), 1.19-1.26 (m, 4H), 1.48 (s, 9H), 2.55-2.61 (q, J=8.0 Hz, 2H), 2.65 (br, 2H), 3.82-3.83 (d, J=4.0 Hz, 2H), 4.36 (br, 2H).

Step 3 Synthesis of Compound 61

A compound 61 was synthesized by the similar method of Step 3 of Example 11.

Step 4 Synthesis of Compound I-148

A compound I-148 was synthesized by the similar method of Step 4 of Example 1.

1H NMR (CD₃OD): δ 0.32 0.34 (m, 2H), 0.50-0.54 (m, 2H), 0.84-0.89 (m, 1H), 1.08-1.32 (m, 8H), 1.42 (s, 9H), 1.51-1.60 (m, 2H), 1.79-1.82 (d, J=12.4 Hz, 2H), 1.87-1.91 (m, 2H), 2.51-2.57 (m, 2H), 2.81-2.87 (m, 4H), 3.05-3.08 (m, 2H), 3.21-3.27 (m, 1H), 3.71 (s, 2H), 3.93-3.94 (d, J=6.8 Hz, 2H).

Reference Example 3 Synthesis of Compound 65

[Chemical Formula 137]

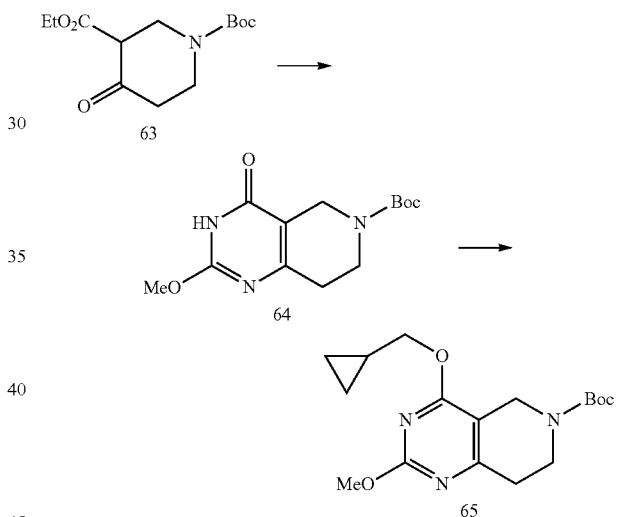

Step 1 Synthesis of Compound 64

A compound 63 (1.0 g, 3.69 mmol) and O-methylisourea hydrochloride (448 mg, 4.06 mmol) were dissolved in ethanol (10 mL). To the solution was added sodium methoxide (398 mg, 7.37 mmol). The mixture was refluxed for 7 hours. To the reaction mixture, water was added. The mixture was neutralized by 2 mol/L hydrochloric acid and then extracted with ethyl acetate. The organic layer was washed by water and brine, and dried over anhydrous sodium sulfate. The solvent was evaporated under reduced pressure. The obtained residue was purified by silica-gel column chromatography (hexane-ethyl acetate) to give a compound 64 (404.8 mg, yield 39%).

1H-NMR (CDCl₃) δ: 1.49 (s, 9H), 2.62-2.65 (m, 2H), 3.64-3.67 (m, 2H), 3.97 (s, 3H), 4.32 (s, 2H), 11.20 (br, 1H).

Step 2 Synthesis of Compound 65

The compound 64 (200 mg, 0.711 mmol) was dissolved in DMF (2 mL). To the solution were added cesium carbonate (463 mg, 1.422 mmol) and cyclopropylmethyl bromide (144 mg, 1.066 mmol). The mixture was stirred at room temperature for 3 hours. To the reaction mixture, water was added. The mixture was extracted with ethyl acetate. The organic layer was washed by water and brine, and dried over anhydrous sodium sulfate. The solvent was evaporated under reduced pressure. The obtained residue was purified by silica-gel column chromatography (hexane-ethyl acetate) to give a compound 65 (47 mg, yield 20%).

1H-NMR (CDCl$_3$) δ: 0.32-0.35 (m, 2H), 0.57-0.62 (m, 2H), 1.23-1.31 (m, 1H), 1.50 (s, 9H), 2.75-2.78 (m, 2H), 3.67-3.70 (m, 2H), 3.94 (s, 3H), 4.21 (d, J=6.1 Hz, 2H), 4.39 (br, 2H).

Reference Example 4 Synthesis of Compound 71 and Compound 72

[Chemical Formula 138]

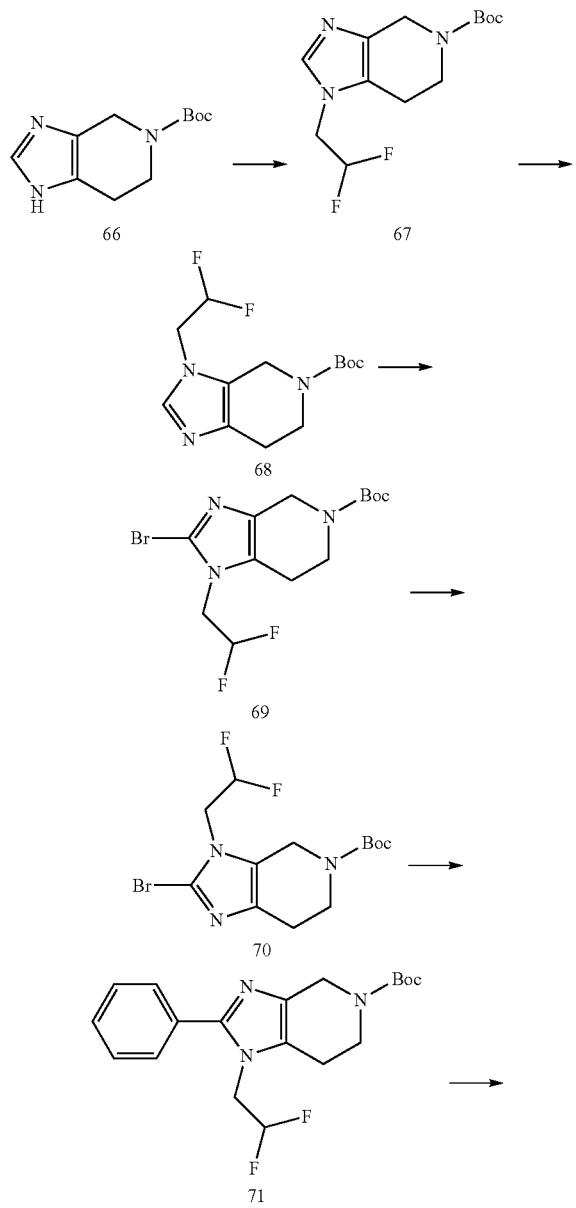
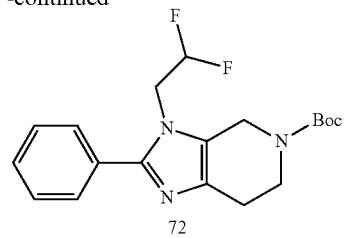

Step 1 Synthesis of Compound 67 and Compound 68

A compound 66 (100 mg, 0.45 mmol) was dissolved in DMF (2 mL). To the solution were added potassium carbonate (93 mg, 0.67 mmol), 2,2-difluoroethyl triflate (144 mg, 0.67 mmol). The mixture was stirred at room temperature for 2 hours. To the reaction mixture, water was added. The mixture was extracted with ethyl acetate. The organic layer was washed by water and brine, and then dried over anhydrous magnesium sulfate. The solvent was evaporated under reduced pressure. The obtained residue was purified by silica-gel column chromatography (chloroform-methanol) to give a compound 67 and a compound 68 as a mixture (50 mg).

Step 2 Synthesis of Compound 69 and Compound 70

The mixture (50 mg) of the compound 67 and the compound 68 obtained in Step 1 was dissolved in acetonitrile (1 mL). To the solution was added NBS (37 mg, 0.21 mmol). The mixture was stirred at room temperature for 3 hours. The reaction mixture was evaporated under reduced pressure. The obtained residue was purified by silica-gel column chromatography (chloroform-methanol) to give a compound 69 and a compound 70 as a mixture (23 mg).

Step 3 Synthesis of Compound 71 and Compound 72

To the mixture (23 mg) of the compound 69 and the compound 70 obtained in Step 2, phenylboronic acid (11 mg, 0.094 mmol), PdCl$_3$ (dppf) (4.6 mg, 6.3 µmol) and potassium phosphate (40 mg, 0.19 mmol) were added DME (0.8 mL), ethanol (0.8 mL) and water (0.4 mL). The mixture was stirred under microwave irradiation at 120° C. for 30 minutes. To the reaction mixture, water was added. The mixture was extracted with chloroform. The organic layer was washed by brine, and dried over anhydrous magnesium sulfate. The solvent was evaporated under reduced pressure. The obtained residue was purified by silica-gel column chromatography (hexane-ethyl acetate), and further purified by preparative TLC (hexane-ethyl acetate) to give a compound 71 (3 mg, yield 2%, 3 steps) and a compound 72 (2 mg, yield 1%, 3 steps), a compound 71

1H-NMR (CDCl$_3$) δ: 1.49 (s, 9H), 2.72 (br, 2H), 3.81 (br, 2H), 4.27 (td, J=13.7, 4.0 Hz, 2H), 4.52 (s, 2H), 5.82 (tt, J=55.1, 4.0 Hz, 1H), 7.44-7.55 (m, 5H).

a compound 72

1H-NMR (CDCl3) δ: 1.50 (s, 9H), 2.75 (br, 2H), 3.75 (br, 2H), 4.24 (td, J=13.9, 3.8 Hz, 2H), 4.64 (s, 2H), 5.70-6.02 (m, 1H), 7.44-7.54 (m, 5H).

Reference Example 5 Synthesis of Compound 75

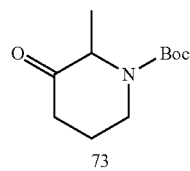

73

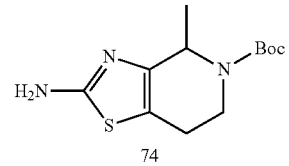

74

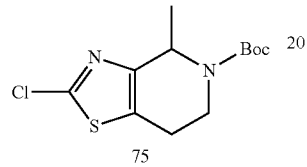

75

Step 1 Synthesis of Compound 74

A compound 73 (180 mg, 0.844 mmol) was dissolved in cyclohexane (1.5 mL). To the solution were added tosic acid monohydrate (0.8 mg, 4.2 µmol) and pyrrolidine (0.105 mL, 1.266 mmol). The mixture was refluxed for 3 hours. The solvent was evaporated under reduced pressure and the obtained residue was dissolved in methanol (1.5 mL). To the solution were added cyanamide (35.5 mg, 0.844 mmol) and sulfur (27.1 mg, 0.844m mmol). The mixture was stirred at room temperature for 2 days. The solvent was evaporated under reduced pressure and the obtained residue was purified by silica gel column chromatography (chloroform-methanol) to give a compound 74 (201 mg, yield 88%).

1H-NMR (CDCl$_3$) δ: 1.38 (d, J=6.8 Hz, 3H), 1.47 (s, 9H), 2.50 (dd, J=15.2, 2.6 Hz, 1H), 2.69-2.78 (m, 1H), 3.02-3.08 (m, 1H), 4.37 (br, 1H), 4.74 (s, 2H), 4.94 (br, 1H).

Step 2 Synthesis of Compound 75

A compound 75 was synthesized by using the compound 74 instead of the compound 1 in Step 1 of Example 1.

1H-NMR (CDCl$_3$) δ: 1.44 (d, J=6.7 Hz, 3H), 1.48 (s, 9H), 2.67 (dd, J=16.0, 2.9 Hz, 1H), 2.79-2.87 (m, 1H), 3.03-3.10 (m, 1H), 4.41 (br, 1H), 5.14 (br, 1H).

Example 19 Synthesis of Compound I-149

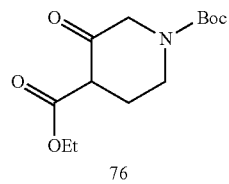

76

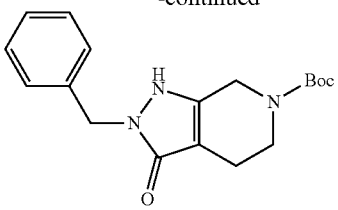

77

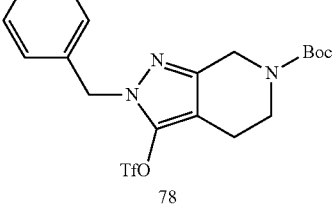

78

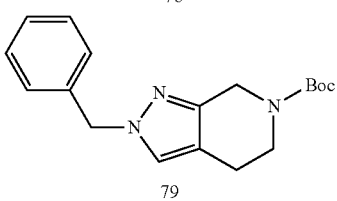

79

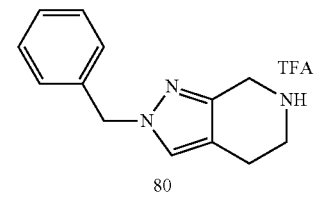

80

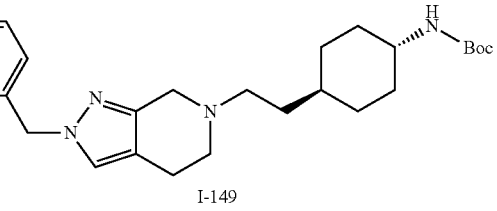

I-149

Step 1 Synthesis of Compound 77

Benzylhydrazine dihydrochloride (1.6 g, 7.38 mmol) was dissolved in ethanol (20 mL). To the solution was added triethylamine (1.64 g, 16.24 mmol). The mixture was stirred at 0° C. for 10 minutes. To the mixture was added the compound 76 (2.0 g, 7.38 mmol) and the mixture was stirred at 70° C. overnight. The solvent was evaporated under reduced pressure to give a compound 77 as a crude product.

Step 2 Synthesis of Compound 78

The crude compound 77 (2.0 g) obtained in Step 1 was dissolved in dichloromethane (50 mL). To the solution were added triethylamine (920 mg, 9.0 mmol) and N,N-bis(trifluoromethanesulfonyl)aniline (2.0 g, 6.0 mmol). The mixture was stirred at room temperature overnight. The reaction mixture was concentrated under reduced pressure. The obtained residue was purified by silica-gel column chromatography (petroleum ether-ethyl acetate) to give a compound 78 (2.3 g, yield 72%).

Step 3 Synthesis of Compound 79

The compound 78 (400 mg, 0.87 mmol) was dissolved in methanol (10 mL). To the solution was added palladium on carbon (100 mg). The mixture was stirred under hydrogen atmosphere at room temperature overnight. The reaction mixture was filtered, and the obtained filtrate was concentrated under reduced pressure. The obtained residue was purified by silica-gel column chromatography (petroleum ether-ethyl acetate) to give a compound 79 (110 mg, yield 40%).

Step 4 Synthesis of Compound 80

A compound 80 was synthesized by the similar method of Step 3 of Example 11.

Step 5 Synthesis of Compound I-149

A compound I-149 was synthesized by the similar method of Step 4 of Example 1.

1H NMR (CD$_3$OD): δ, 1.02-1.24 (m, 5H), 1.42 (s, 9H), 1.54-1.64 (m, 2H), 1.77-1.85 (m, 2H), 1.85-1.94 (m, 2H), 2.77-2.83 (m, 2H), 2.85-2.92 (m, 2H), 3.03-3.10 (m, 2H), 3.20-3.30 (m, 1H), 3.88 (s, 2H), 5.27 (s, 2H), 7.21 (d, J=6.8 Hz, 2H), 7.24-7.34 (m, 3H). 7.51 (s, 1H).

Example 20 Synthesis of Compound I-124

[Chemical Formula 141]

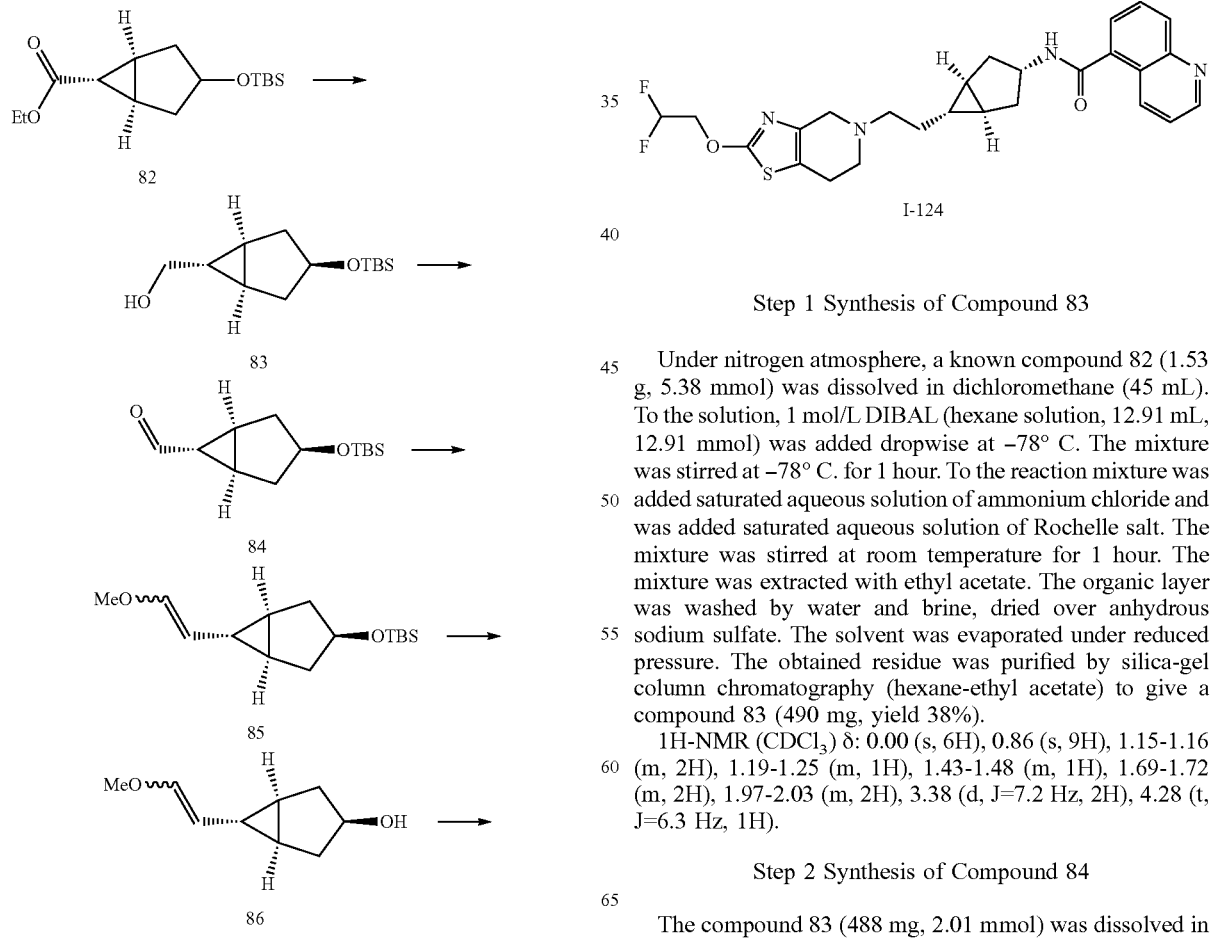

Step 1 Synthesis of Compound 83

Under nitrogen atmosphere, a known compound 82 (1.53 g, 5.38 mmol) was dissolved in dichloromethane (45 mL). To the solution, 1 mol/L DIBAL (hexane solution, 12.91 mL, 12.91 mmol) was added dropwise at −78° C. The mixture was stirred at −78° C. for 1 hour. To the reaction mixture was added saturated aqueous solution of ammonium chloride and was added saturated aqueous solution of Rochelle salt. The mixture was stirred at room temperature for 1 hour. The mixture was extracted with ethyl acetate. The organic layer was washed by water and brine, dried over anhydrous sodium sulfate. The solvent was evaporated under reduced pressure. The obtained residue was purified by silica-gel column chromatography (hexane-ethyl acetate) to give a compound 83 (490 mg, yield 38%).

1H-NMR (CDCl$_3$) δ: 0.00 (s, 6H), 0.86 (s, 9H), 1.15-1.16 (m, 2H), 1.19-1.25 (m, 1H), 1.43-1.48 (m, 1H), 1.69-1.72 (m, 2H), 1.97-2.03 (m, 2H), 3.38 (d, J=7.2 Hz, 2H), 4.28 (t, J=6.3 Hz, 1H).

Step 2 Synthesis of Compound 84

The compound 83 (488 mg, 2.01 mmol) was dissolved in dichloromethane (10 mL). To the solution were added sodium hydrogen carbonate (1.69 g, 20.1 mmol) and Dess-Martin periodinane (1.28 g, 3.02 mmol). The mixture was stirred at 0° C. for 2 hours, and then at room temperature for 1 hour. To the reaction mixture was added saturated aqueous solution of sodium hydrogen carbonate. The mixture was extracted with ethyl acetate. The organic layer was washed by saturated aqueous solution of sodium hydrogen carbonate and brine, and dried over anhydrous sodium sulfate. The solvent was evaporated under reduced pressure. The obtained residue was purified by silica-gel column chromatography (hexane-ethyl acetate) to give a compound 84 (367 mg, yield 76%).

Step 3 Synthesis of Compound 85

To (methoxymethyl)triphenylphosphonium chloride (1069 mg, 3.12 mmol) was added tetrahydrofuran (10 mL), and under ice cooling was added 1.1 mol/L NaHMDS (tetrahydrofuran solution, 3.40 mL, 3.74 mmol), and the mixture was stirred for 30 minutes. To the mixture was added a solution of the compound 84 (250 mg, 1.04 mmol) in tetrahydrofuran (2 mL). The mixture was stirred at 0° C. for 30 minutes. After the mixture was left standing overnight, water was added to the reaction mixture. The mixture was extracted with ethyl acetate. The organic layer was washed by water and brine, dried over anhydrous sodium sulfate. The solvent was evaporated under reduced pressure. The obtained residue was purified by silica-gel column chromatography (hexane-ethyl acetate) to give a compound 85 containing impurities.

Step 4 Synthesis of Compound 86

The compound 85 obtained in Step 3 was dissolved in tetrahydrofuran (3 mL). To the solution was added 1 mol/L TBAF (tetrahydrofuran solution, 2.6 mL, 2.60 mmol). The mixture was stirred at room temperature for 3 hours. To the reaction mixture, water was added. The mixture was extracted with chloroform. The organic layer was separated and the solvent was evaporated under reduced pressure. The obtained residue was purified by silica-gel column chromatography (hexane-ethyl acetate) to give a compound 86 (80 mg, yield 50%, 2 steps, mixture of cis-trans of vinyl ether).

Step 5 Synthesis of Compound 87

Under nitrogen atmosphere, the compound 86 (70 mg, 0.454 mmol), phthalimide (100 mg, 0.681 mmol) and triphenylphosphine (179 mg, 0.681 mmol) were dissolved in tetrahydrofuran (2 mL). To the solution was added DIAD (0.132 mL, 0.681 mmol) at 0° C. The mixture was stirred at room temperature for 1 hour. The solvent was evaporated under reduced pressure. The obtained residue was purified by silica-gel column chromatography (hexane-ethyl acetate) to give a compound 87 (88 mg, yield 68%, mixture of cis-trans of vinyl ether).

1H-NMR (CDCl$_3$) δ: 1.24-1.28 (m, 0.6H), 1.35-1.40 (m, 2H), 1.70-1.74 (m, 0.4H), 1.98-2.07 (m, 2H), 2.52-2.59 (m, 2H), 3.49 (s, 1.8H), 3.63 (s, 1.2H), 3.85 (dd, J=9.5, 6.1 Hz, 0.4H), 4.31-4.48 (m, 2H), 5.88 (d, J=6.1 Hz, 0.4H), 6.36 (d, J=12.7 Hz, 1.2H), 7.68-7.70 (m, 2H), 7.80-7.82 (m, 2H).

Step 6 Synthesis of Compound 88

The compound 87 88 mg, 0.311 mmol) was dissolved in ethanol (2 mL) and dichloromethane (2 mL). To the solution was added hydrazine monohydrate (0.150 mL, 3.11 mmol).

The mixture was stirred at 50° C. for 7 hours. To the reaction mixture was added saturated aqueous solution of sodium hydrogen carbonate. The mixture was extracted with chloroform. The organic layer was separated and the solvent was evaporated under reduced pressure to give a compound 88 as a crude product.

Step 7 Synthesis of Compound 89

The compound 88 obtained as a crude product in Step 6 was dissolved in DMF (1 mL). To the solution were added EDC hydrochloride (89 mg, 0.467 mmol), HOBt (21 mg, 0.156 mmol), quinoline-5-carboxylic acid (64.6 mg, 0.373 mmol) and triethylamine (0.065 mL, 0.467 mmol). The mixture was stirred at room temperature for 30 minutes and then left standing overnight. To the reaction mixture was added saturated aqueous solution of sodium hydrogen carbonate. The mixture was extracted with ethyl acetate. The organic layer was washed by saturated aqueous solution of sodium hydrogen carbonate and water, and dried over anhydrous sodium sulfate. The solvent was evaporated under reduced pressure. The obtained residue was purified by silica-gel column chromatography (hexane-ethyl acetate) to give a compound 89 (68.7 mg, yield 72%, mixture of cis-trans of vinyl ether).

1H-NMR (CDCl$_3$) δ: 1.24-1.33 (m, 2.8H), 1.63-1.76 (m, 1.2H), 2.44-2.52 (m, 2H), 3.49 (s, 1.8H), 3.63 (s, 1.2H), 3.83 (dd, J=9.5, 6.2 Hz, 0.4H), 4.23-4.43 (m, 1.6H), 5.86-5.90 (m, 1.4H), 6.35 (d, J=12.7 Hz, 0.6H), 7.47 (dd, J=8.6, 4.2 Hz, 1H), 7.61-7.69 (m, 2H). 8.17 (d, J=8.3 Hz, 1H), 8.70 (d, J=8.5 Hz, 1H), 8.95 (d, J=3.4 Hz, 1H).

Step 8 Synthesis of Compound 90

The compound 89 (60 mg, 0.195 mmol) was dissolved in acetonitrile (2 mL) and water (0.2 mL). To the solution was added TFA (0.150 mL, 1.946 mmol). The mixture was stirred at 50° C. for 2 hours. To the reaction mixture was added saturated aqueous solution of sodium hydrogen carbonate. The mixture was extracted with chloroform. The organic layer was separated and the solvent was evaporated under reduced pressure to give a compound 90 (44.7 mg, yield 78%).

1H-NMR (CDCl$_3$) δ: 1.00-1.05 (m, 1H), 1.23-1.25 (m, 2H), 1.65-1.72 (m, 2H), 2.29 (dd, J=7.0, 1.9 Hz, 2H), 2.49 (dd, J=12.5, 7.5 Hz, 2H), 4.24-4.35 (m, 1H), 5.89 (d, J=7.9 Hz, 1H), 7.47 (dd, J=8.6, 4.2 Hz, 1H), 7.62-7.69 (m, 2H), 8.17 (d, J=8.2 Hz, 1H), 8.71 (d, J=8.7 Hz, 1H), 8.95 (dd, J=4.1, 1.6 Hz, 1H), 9.77 (t, J=1.9 Hz, 1H).

Step 9 Synthesis of Compound I-124

A compound I-124 was obtained by using the compound 90 instead of the compound 5 in Step 3 of Example 2.
[M+H] 499.25, method 3, retention time 1.05 min Example 1' Synthesis of Compound II-013

[Chemical Formula 142]

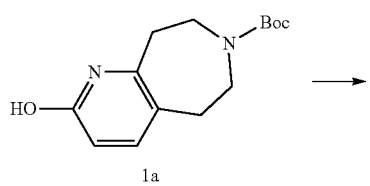

1a

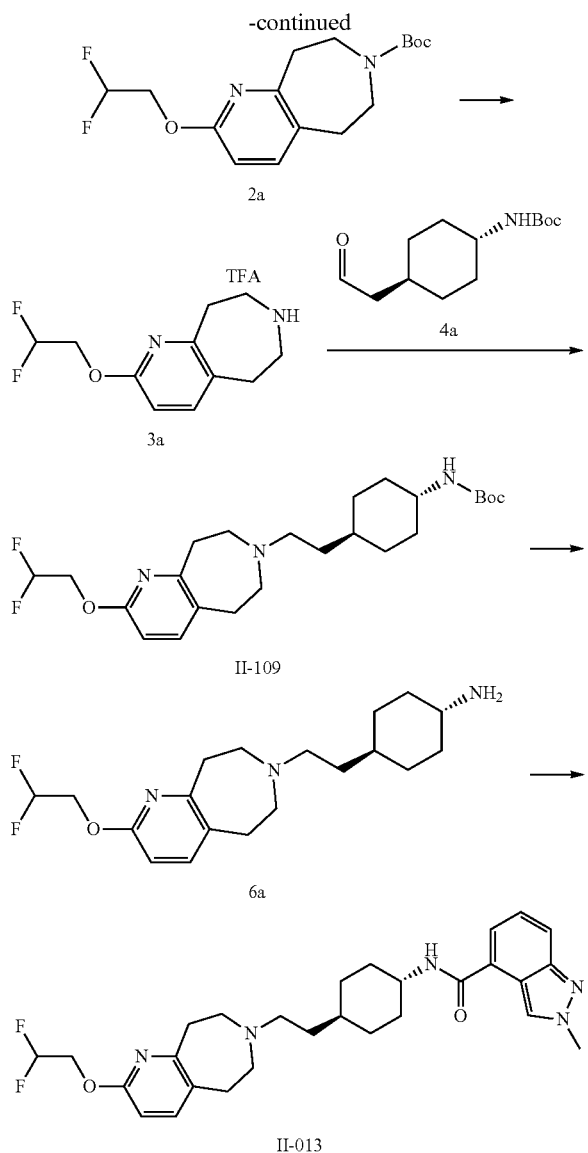

Step 3 Synthesis of Compound II-109

The crude compound 3a was dissolved in dichloromethane (5 mL). To the solution were added triethylamine (0.475 mL, 3.43 mmol) and, the compound 4a (182 mg, 0.754 mmol). The mixture was stirred at room temperature for 1 hour. To the mixture was added sodium triacetoxyborohydride (436 mg, 2.06 mmol). The mixture was stirred at room temperature for 40 minutes. To the reaction solution was added saturated aqueous solution of sodium hydrogen carbonate. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a compound II-109 (299 mg, 2 steps yield 96%).

1H-NMR (CDCl3) δ: 1.05 (m, 4H), 1.21 (m, 1H), 1.41 (m, 2H), 1.44 (s, 9H), 1.77 (m, 2H), 1.99 (m, 2H), 2.48 (m, 2H), 2.68-2.64 (m, 4H), 2.81 (m, 2H), 3.02 (m, 2H), 3.37 (m, 1H), 4.36 (m, 1H), 4.51 (td, J=13.7, 4.3 Hz, 2H), 6.13 (tt, J=56.0, 4.3 Hz, 1H), 6.54 (d, J=8.0 Hz, 1H), 7.30 (d, J=8.0 Hz, 1H).

Step 4 Synthesis of Compound 6a

The compound II-109 (23.2 mg, 0.051 mmol) was dissolved in dichloromethane (2 mL). To the solution was added TFA (115 μL, 1.50 mmol). The mixture was stirred at room temperature overnight. The solvent was evaporated under reduced pressure. Then, to the mixture was added 10% aqueous potassium carbonate. The mixture was extracted with chloroform. The organic layer was dried over anhydrous sodium sulfate and then the solvent was evaporated under reduced pressure to give a crude compound 6a.

[M+H] 354.3, method 3, retention time 0.83 min

Step 5 Synthesis of II-013

The crude compound 6a was dissolved in DMF (2 mL). To the solution were added 2-methyl-2H-indazole-4-carboxylic acid (6.85 mg, 0.039 mmol), HOBt (5.26 mg, 0.039 mmol), EDC hydrochloride (7.46 mg, 0.039 mmol). The mixture was stirred at room temperature for 1 day. To the reaction mixture, water was added. The mixture was extracted with ethyl acetate. The organic layer was washed by saturated aqueous solution of sodium hydrogen carbonate, water and brine, and then dried over anhydrous sodium sulfate. The solvent was evaporated under reduced pressure. The obtained residue was purified by silica-gel column chromatography (hexane-ethyl acetate) to give II-013 (13.6 mg, yield 69%, 2 steps).

1H-NMR (CDCl3) δ: 1.11-1.36 (m, 5H), 1.48 (m, 2H), 1.86 (d, J=12.2 Hz, 2H), 2.53 (t, J=7.7 Hz, 2H), 2.59-2.68 (m, 4H), 2.82 (m, 2H), 3.04 (m, 2H), 3.98 (m, 1H), 4.25 (s, 3H), 4.52 (td, J=13.6, 4.3 Hz, 2H), 5.98-6.29 (m, 2H), 6.55 (d, J=8.0 Hz, 1H), 7.26-7.34 (m, 3H), 7.83 (d, J=8.5 Hz, 1H), 8.47 (s, 1H).

[M+H] 512.3, method 3, retention time 1.21 min

Step 1 Synthesis of Compound 2a

The compound 1a (200 mg, 0.76 mmol) was dissolved in DMF (4 mL). To the solution were added 2,2-difluoroethyl trifluoromethanesulfonate (324 mg, 1.51 mmol) and potassium carbonate (282 mg, 2.04 mmol). The mixture was stirred at room temperature overnight. To the reaction solution, water was added. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a compound 2a (225 mg, yield 91%).

1H-NMR (CDCl3) δ: 1.49 (s, 9H), 2.81 (m, 2H), 3.02 (m, 2H), 3.56 (m, 4H), 4.51 (id, J=13.6, 4.3 Hz, 2H), 6.12 (tt, J=55.8, 4.3 Hz, 1H), 6.57 (d, J=8.3 Hz, 1H), 7.34 (d, J=8.3 Hz, 1H).

Step 2 Synthesis of Compound 3a

The compound 2a (225 mg, 0.69 mmol) was dissolved in dichloromethane (4.5 mL). To the solution was added TFA (1.1 mL). The mixture was stirred at room temperature overnight. The solvent was evaporated under reduced pressure to give a compound 3a as a crude product.

Reference Example 1' Synthesis of Compound 7a

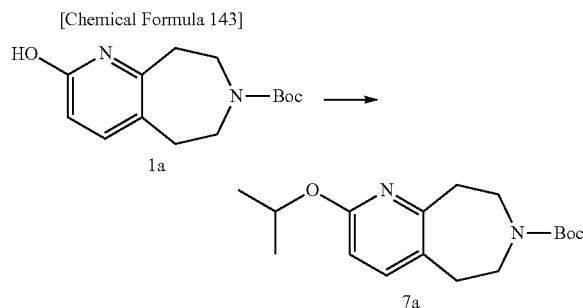

Step 1 Synthesis of Compound 7a

The compound 1a (150 mg, 0.667 mmol) was dissolved in THF (3 mL). To the solution were added 2-propanol (87 μL, 1.14 mmol), triphenylphosphine (298 mg, 1.14 mmol), DIAD (221 μL, 1.14 mmol). The mixture was stirred at room temperature overnight. The solvent was evaporated under reduced pressure. The obtained residue was purified by silica-gel column chromatography (hexane-ethyl acetate) to give a compound 7a (119 mg, yield 68%).

1H-NMR (CDCl3) δ: 1.33 (d, J=6.1 Hz, 6H), 1.49 (s, 9H), 2.78 (m, 2H), 3.02 (m, 2H), 3.55 (m, 4H), 5.22 (m, 1H), 6.44 (d, J=8.2 Hz, 1H), 7.28 (d, J=8.2 Hz, 1H).

Reference Example 2' Synthesis of Compound 9a

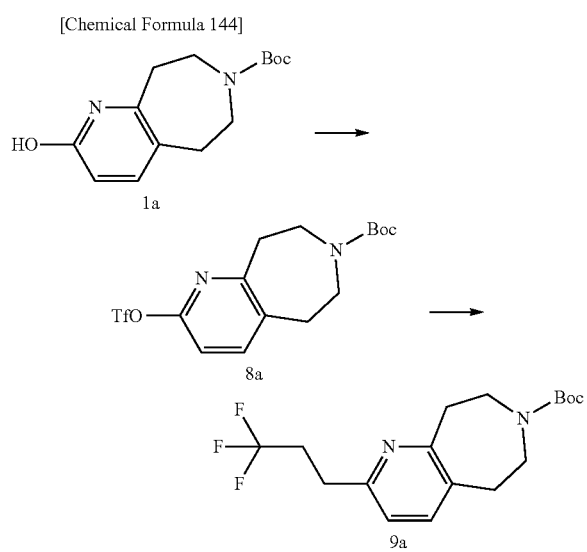

Step 1 Synthesis of Compound 8a

The compound 1a (200 mg, 0.757 mmol) was dissolved in dichloromethane (4 mL). To the solution was added triethylamine (0.21 mL, 1.51 mmol) and the mixture was cooled to 0° C. To the mixture was added trifluoromethanesulfonic anhydride (1 mol/L dichloromethane solution, 1.14 mL). The mixture was stirred at 0° C. for 2 hours. To the reaction solution was added saturated aqueous solution of sodium hydrogen carbonate. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a compound 8a (291 mg, yield 97%).

1H-NMR (CDCl3) δ: 1.49 (s, 9H), 2.93 (m, 2H), 3.12 (m, 2H), 3.61 (m, 4H), 6.94 (d, J=8.2 Hz, 1H), 7.59 (d, J=8.0 Hz, 1H).

Step 2 Synthesis of Compound 9a

The compound 8a (99 mg, 0.25 mmol) was dissolved in toluene (2 mL) and water (1 mL), and then nitrogen was purged. To the solution were added potassium trifluoro(3,3,3-trifluoropropyl)borate (102 mg, 0.50 mmol), Ruphos Pd G3 (10.4 mg, 0.012 mmol) and cesium carbonate (244 mg, 0.749 mmol). The mixture was stirred at 110° C. for 6 hours. The mixture was cooled to room temperature and then water was added to the mixture. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a compound 9a (75.5 mg, yield 88%).

1H-NMR (CDCl3) δ: 1.49 (s, 9H), 2.57 (m, 2H), 2.85 (m, 2H), 2.97 (m, 2H), 3.12 (m, 2H), 3.58 (m, 4H), 6.94 (d, J=7.7 Hz, 1H), 7.34 (d, J=7.5 Hz, 1H).

Reference Example 3' Synthesis of Compound 10a

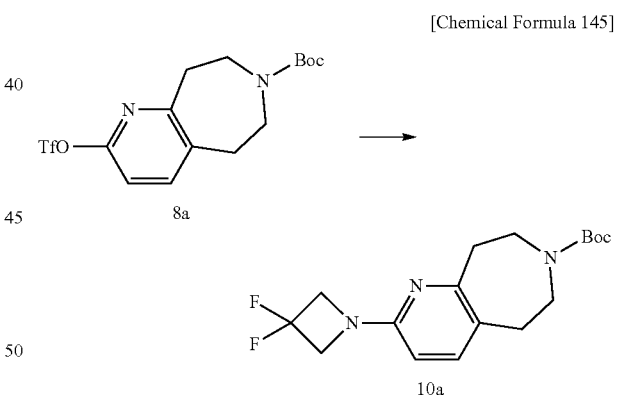

Step 1 Synthesis of Compound 10a

The compound 8a (99.5 mg, 0.251 mmol) was dissolved in 1,4-dioxane (3 mL) and then nitrogen was purged. To the mixture were added 3,3-difluoroazetidine hydrochloride (35.8 mg, 0.276 mmol), Pd2(dba)3 (11.5 mg, 0.013 mmol), xantphos (14.5 mg, 0.025 mmol) and sodium tert-butoxide (72.4 mg, 0.753 mmol). The mixture was stirred at 80° C. for 3.5 hours. The mixture was cooled to room temperature and filtered through Celite. The solvent was evaporated under reduced pressure. The obtained residue was purified by silica-gel column chromatography (hexane-ethyl acetate) to give a compound 10a (3.2 mg, yield 4%).

1H-NMR (CDCl3) δ: 1.49 (s, 9H), 2.77 (m, 2H), 3.01 (m, 2H), 3.57 (m, 4H), 4.31 (t, J=12.2 Hz, 4H), 6.18 (d, J=8.2 Hz, 1H), 7.26 (m, 1H).
Example 2' Synthesis of Compound II-110
Step 1 Synthesis of Compounds 12a, 13a
A solution of a compound 11a (100 mg, 0.469 mmol) in N,N-dimethylformamide dimethyl acetal (2 mL) was stirred at 130° C. for 14 hours. The mixture was cooled to room
[Chemical Formula 146]
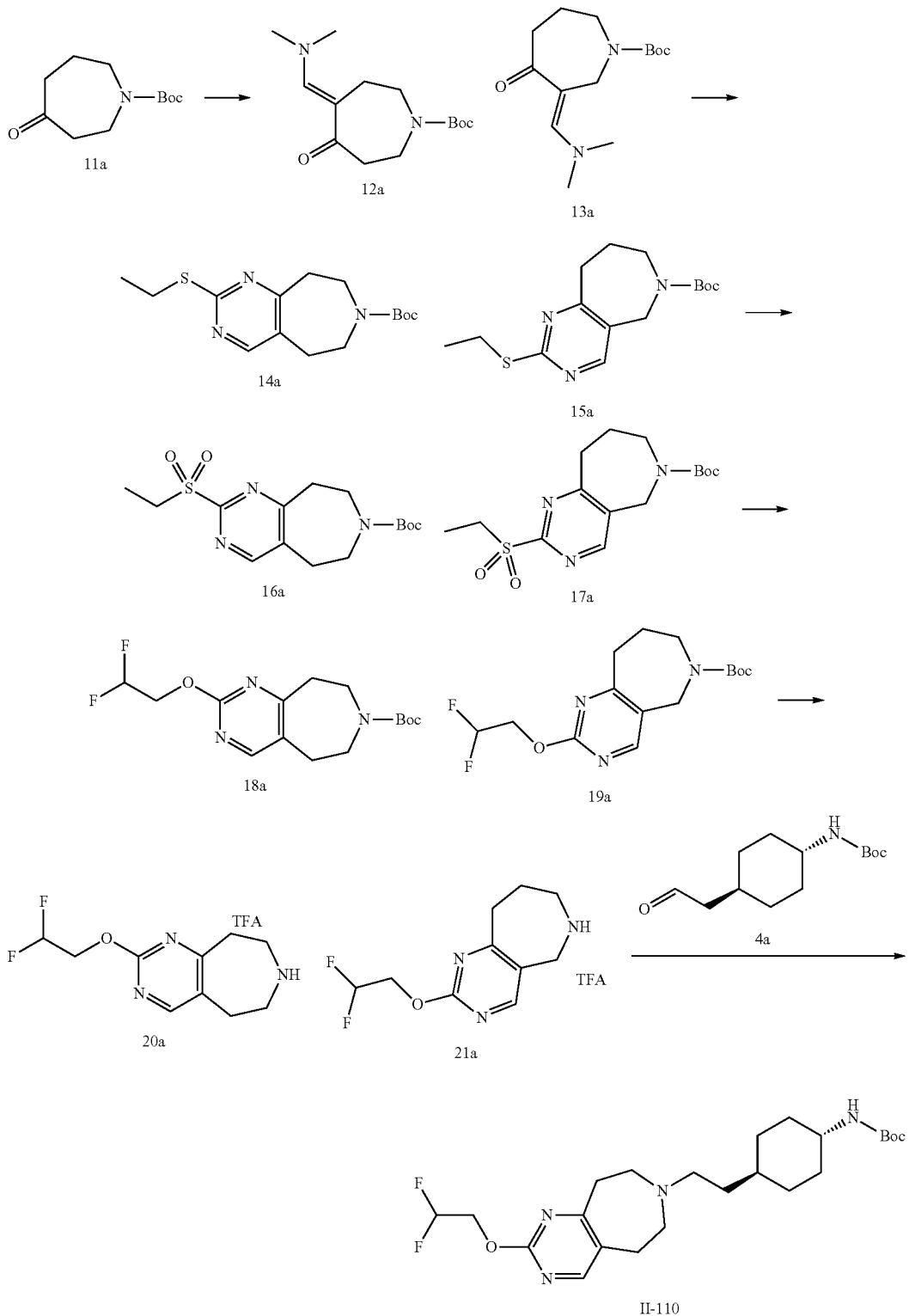

temperature and then the solvent was evaporated under reduced pressure to give a mixture of compounds 12a and 13a as a crude product.

Step 2 Synthesis of Compound 14a, 15a

The crude compounds 12a and 13a obtained in Step 1 were dissolved in ethanol (3 mL). To the solution were added S-ethylisothiourea hydrobromide (190 mg, 1.03 mmol) and potassium carbonate (143 mg, 1.03 mmol). The mixture was stirred at 80° C. for 8 hours. The mixture was cooled to room temperature and then water was added to the mixture. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a mixture of compounds 14a and 15a (22.9 mg, yield 16%, 2 steps).

[M+H] 310.2, method 3, retention time 2.14 min, 2.19 min

Step 3 Synthesis of Compound 16a, 17a

The mixture of compounds 14a and 15a (56.4 mg, 0.182 mmol) was dissolved in dichloromethane (2 mL). The solution was cooled at 0° C. To the mixture was added m-chloroperoxybenzoic acid (90 mg, 0.365 mmol). The mixture was stirred at 0° C. for 6 hours. To the reaction solution was added saturated aqueous solution of sodium hydrogen carbonate. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a mixture of compounds 16a and 17a (56.6 mg, yield 91%).

[M+H] 342.2, method 3, retention time 1.56 min

Step 4 Synthesis of Compound 18a, 19a

DMF (1.5 mL) solution of 2,2-difluoroethane-1-ol (40.8 mg, 0.497 mmol) was cooled to 0° C. To the solution was added sodium hydride (60 wt %, 19.9 mg, 0.497 mmol). The mixture was stirred at 0° C. for 1 hour and then a solution of the mixture of compounds 16a and 17a (56.6 mg, 0.166 mmol) in DMF (0.5 mL) was added to the mixture. The mixture was further stirred for 1 hour. To the reaction solution was added saturated aqueous solution of ammonium chloride. The mixture was extracted with ethyl acetate. The organic layer was washed by water and brine, and then dried over anhydrous sodium sulfate. The solvent was evaporated under reduced pressure. The obtained residue was purified by silica-gel column chromatography (hexane-ethyl acetate) to give a mixture of compounds 18a and 19a (42.2 mg, yield 77%).

[M+H] 330.1, method 3, retention time 1.95 min, 1.99 min

Step 5 Synthesis of Compound 20a, 21a

The mixture of compounds 18a and 19a (40 mg, 0.121 mmol) was dissolved in dichloromethane (2 mL). To the solution was added TFA (120 μL). The mixture was stirred at room temperature overnight. The solvent was evaporated under reduced pressure to give a mixture of compounds 20a and 21a as a crude product.

Step 6 Synthesis of Compound II-110

The crude compound 20a and 21a were dissolved in dichloromethane (2 mL). To the solution were added triethylamine (84 μL, 0.605 mmol) and the compound 4a (32.1 mg, 0.133 mmol). The mixture was stirred at room temperature for 1 hour. To the mixture was added sodium triacetoxyborohydride (77 mg, 0.363 mmol) and the mixture was stirred at room temperature for 3 hours. To the reaction solution was added saturated aqueous solution of sodium hydrogen carbonate. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a mixture of compound II-110 and the diastereomer. The mixture was separated using SFC to give a compound II-110 (7 mg).

1H-NMR (CDCl3) δ: 1.05 (m, 4H), 1.22 (m, 1H), 1.41 (m, 2H), 1.45 (s, 9H), 1.76 (m, 2H), 1.99 (m, 2H), 2.52 (m, 2H), 2.60-2.70 (m, 4H), 2.81 (m, 2H), 3.04 (m, 2H), 3.37 (m, 1H), 4.36 (m, 1H), 4.55 (td, J=13.2, 4.4 Hz, 2H), 6.14 (tt, J=55.5, 4.3 Hz, 1H), 8.15 (s, 1H).

Preparative Method
Preparative column (IE-IE, Daicel)
Flow rate: 30 mL/min
mobile phase: methanol+0.1% diethylamine 30%
Sample: 25.5 mg/m L (methanol/chloroform=1/1)
Loading amount: 51 mg
detection wavelength: 220 nm, Back pressure: 8 MPa Example 3' Synthesis of Compound II-111

[Chemical Formula 147]

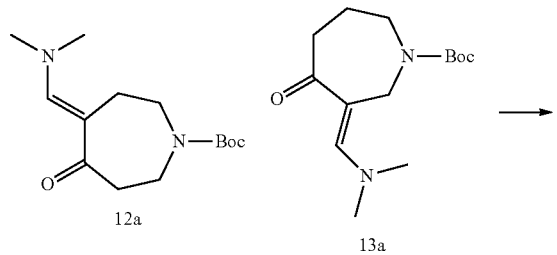

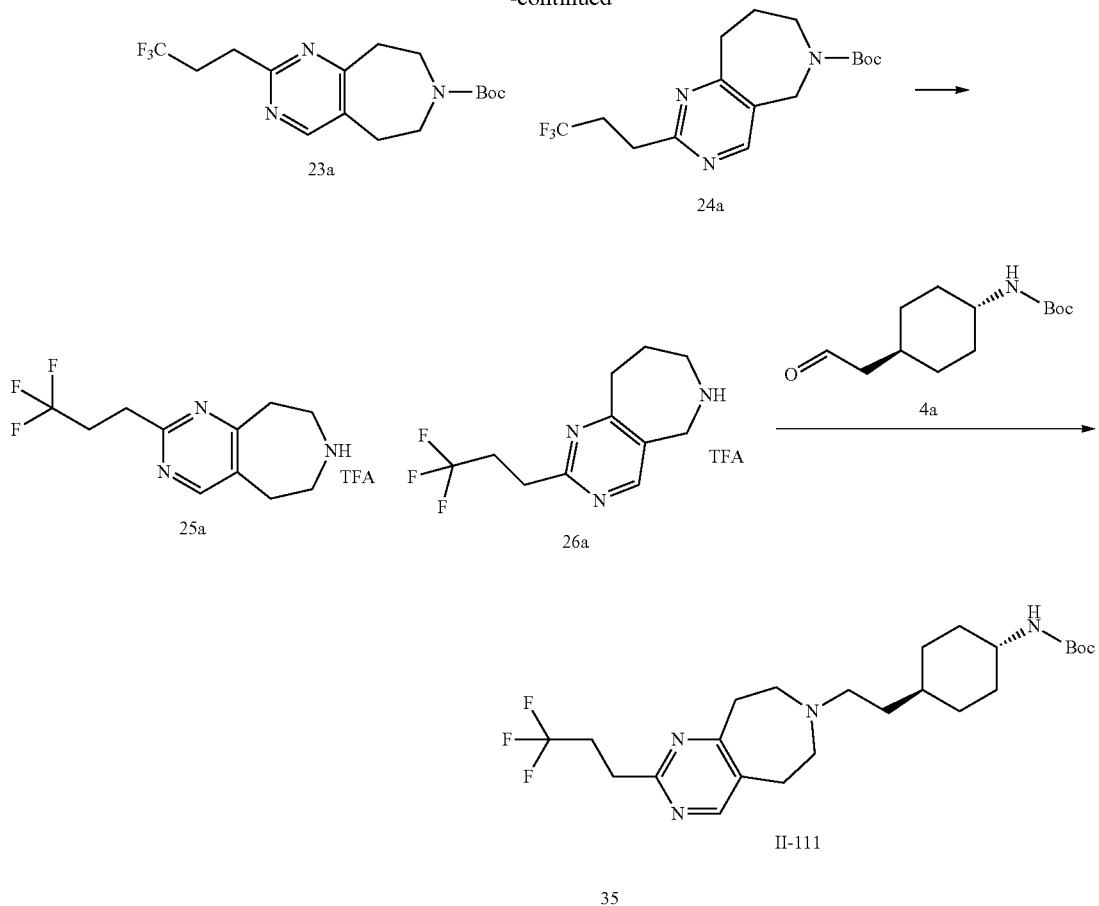

Step 1 Synthesis of Compounds 23a, 24a

A mixture of compounds 23a and 24a was obtained by using 4,4,4-trifluorobutanimidamide hydrochloride instead S-ethylisothiourea hydrobromide in Step 2 of Example 2'.

[M+H] 346.3, method 3, retention time 2.02 min, 2.07 min

Step 2 Synthesis of Compounds 25a, 26a

A mixture of compounds 25a and 26a was obtained as a crude product by using the compounds 23a and 24a instead of the compounds 18a and 19a in Step 5 of Example 2'.

Step 3 Synthesis of Compound II-111

A compound II-111 and the diastereomer were obtained by using the compounds 25a and 26a instead of the compounds 20a and 21a in Step 6 of Example 2'. The compound II-111 was obtained by separating this mixture using SFC.

1H-NMR (CDCl3) δ: 1.05 (m, 4H), 1.23 (m, 1H), 1.41 (m, 2H), 1.44 (s, 9H), 1.77 (m, 2H), 1.99 (m, 2H), 2.52 (m, 2H), 2.61-2.73 (m, 6H), 2.84 (m, 2H), 3.07 (m, 2H), 3.15 (m, 2H), 3.37 (m, 1H), 4.36 (m, 1H), 8.31 (s, 1H).

Preparative Method
Preparative column (IE-IE, Daicel)
Flow rate: 30 mL/min
Mobile phase: methanol+0.1% diethylamine 25%
Sample: 36 mg/mL (methanol/chloroform=1/1)
Loading amount: 54 mg
Detection wavelength: 220 nm, Back pressure: 8 MPa

Example 4' Synthesis of Compound II-112 and Compound II-113

[Chemical Formula 148]

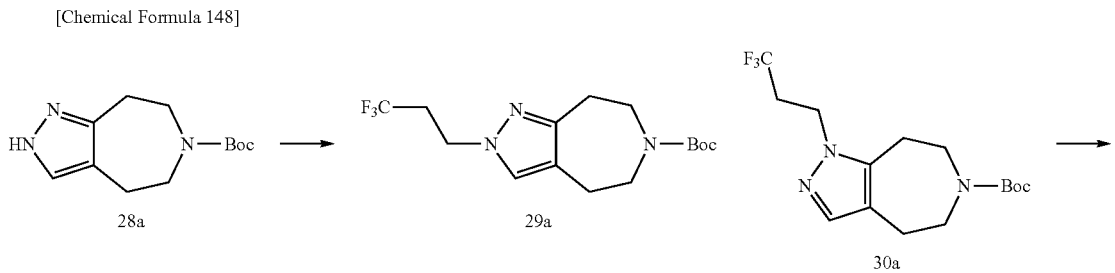

-continued

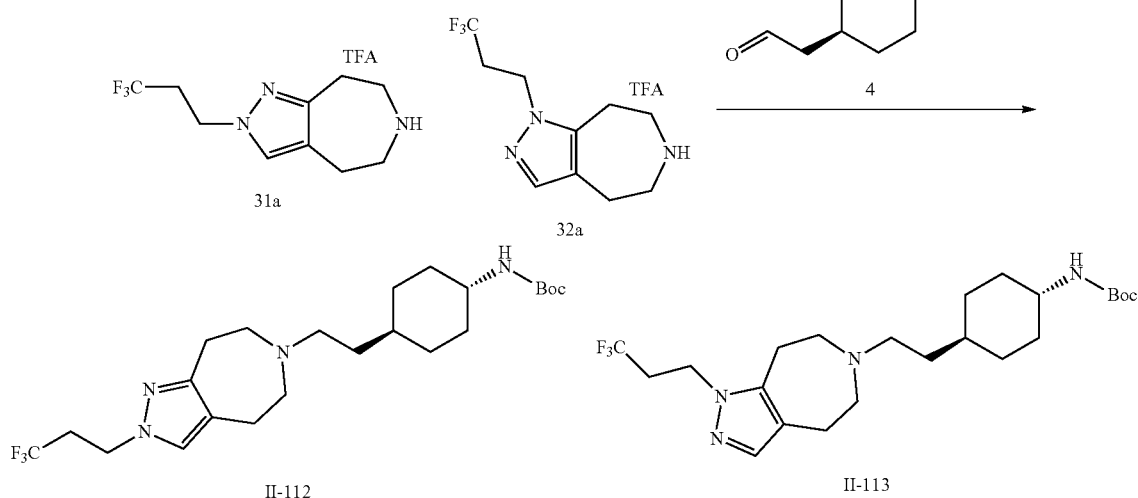

31a

32a

II-112

II-113

Step 1 Synthesis of Compounds 29a, 30a

A solution of a compound 28a (109 mg, 0.459 mmol), 1,1,1-trifluoro-3-iodopropane (512 mg, 1.84 mmol) and cesium carbonate (299 mg, 0.919 mmol) in DMF (2 mL) was stirred at 85° C. for 8 hours. The reaction solution was cooled to room temperature and then water was added to the mixture. The mixture was extracted with ethyl acetate. The organic layer was washed by water and brine, and then dried over anhydrous sodium sulfate. The solvent was evaporated under reduced pressure. The obtained residue was purified by silica-gel column chromatography (hexane-ethyl acetate) to give a mixture of compounds 29a and 30a.

[M+H] 334.2, method 3, retention time 1.99 min

Step 2 Synthesis of Compounds 31a, 32a

A mixture of a compound 31a and 32a was obtained as a crude product by using the compound 29a and 30a instead of the compound 18a and 19a in Step 5 of Example 2'.

Step 3 Synthesis of Compounds II-112, II-113

A mixture of compounds II-112 and 11-113 was obtained by using the compound 31a and 32a instead of the compound 20a and 21a in Step 6 of Example 2'. The compounds II-112 and II-113 were obtained by separating this mixture using SFC.

a compound II-112: 1H-NMR (CDCl3) δ: 1.06 (m, 4H), 1.24 (m, 1H), 1.39-1.44 (m, 11H), 1.77 (m, 2H), 1.99 (m, 2H), 2.59-2.85 (m, 12H), 3.37 (m, 1H), 4.21 (t, J=7.4 Hz, 2H), 4.36 (m, 1H), 7.06 (s, 1H).

a compound II-113: 1H-NMR (CDCl3) δ: 1.06 (m, 4H), 1.25 (m, 1H), 1.38-1.45 (m, 11H), 1.77 (m, 2H), 1.99 (m, 2H), 2.59-2.70 (m, 6H), 2.77 (m, 2H), 2.82 (m, 2H), 2.88 (m, 2H), 3.37 (m, 1H), 4.24 (t, J=7.4 Hz, 2H), 4.35 (m, 1H), 7.22 (s, 1H).

Preparative Method
Preparative column (IE-IE, Daicel)
Flow rate: 30 mL/min
Mobile phase: methanol+0.1% diethylamine 25%
Sample: 19 mg/mL (methanol/chloroform=1/1)
Loading amount: 19 mg
Detection wavelength: 220 nm, Back pressure: 8 MPa Reference Example 4' Synthesis of Compound 37a

[Chemical Formula 149]

35a

36a

37a

Step 1 Synthesis of Compound 36a

A compound 35a (1.3 g, 7.23 mmol) was dissolved in DMF (26 mL). To the solution were added triethylamine (6.02 mL, 43.4 mmol), 2-(2-methylthiazol-5-yl)acetic acid (1.25 g, 7.96 mmol), HOBt (98 mg, 0.723 mmol) and EDC hydrochloric (1.73 g, 9.04 mmol). The mixture was stirred at room temperature overnight. To the reaction mixture, water was added. The mixture was extracted with a mixed solvent of ethyl acetate and THF. The organic layer was washed by saturated aqueous solution of sodium hydrogen carbonate, water and brine, and then dried over anhydrous sodium sulfate. The solvent was evaporated under reduced pressure. The obtained residue was purified by silica-gel column chromatography (hexane-ethyl acetate) to give a compound 36a as a crude product.

[M+H] 283.2, method 3, retention time 0.87 min

Step 2 Synthesis of Compound 37a

The crude compound 36a was dissolved in DMSO (22 mL). To the solution was added 2-iodoxybenzoic acid (4.37 g, 15.6 mmol). The mixture was stirred at room temperature for 3 hours. To the reaction mixture, water was added. The mixture was extracted with a mixed solvent of ethyl acetate and THF. The organic layer was washed by saturated aqueous solution of sodium hydrogen carbonate, water and brine, and then dried over anhydrous sodium sulfate. The solvent was evaporated under reduced pressure. The obtained residue was purified by silica-gel column chromatography (hexane-ethyl acetate) to give a compound 37a (1.25 g, yield 59%, 2 steps).

1H-NMR (CDCl3) δ: 1.12 (m, 4H), 1.77-1.87 (m, 3H), 1.96 (m, 2H), 2.33 (dd, J=6.4, 1.4 Hz, 2H), 2.69 (s, 3H), 3.68 (s, 2H), 3.71 (m, 1H), 5.36 (m, 1H), 7.42 (s, 1H), 9.75 (s, 1H).

Example 5' Synthesis of Compound II-114

[Chemical Formula 150]

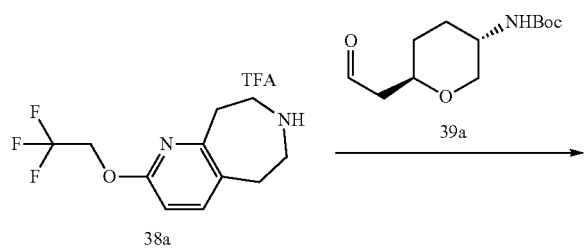

Step 1 A compound II-114 was obtained by using the compound 38a instead of the compound 3a and using a compound 39a, which was synthesized referring to the methods described in Journal of Medicinal Chemistry, 2013, volume 56, 18, 7396-7415, instead of the compound 4a in Example 1' of Step 3.

$^1$H-NMR (CDCl$_3$) δ: 1.22-1.76 (m, 14H), 2.08 (d, J=12.5 Hz, 1H), 2.49-2.67 (m, 6H), 2.80-2.83 (m, 2H), 2.95-3.03 (m, 3H), 3.22-3.28 (m, 1H), 3.58 (brs, 1H), 4.03-4.07 (m, 1H), 4.23 (brs, 1H), 4.74 (q, J=8.7 Hz, 2H), 6.59 (d, J=8.3 Hz, 1H), 7.32 (d, J=8.3 Hz, 1H).

Example 6' Synthesis of Compound II-067

[Chemical Formula 151]

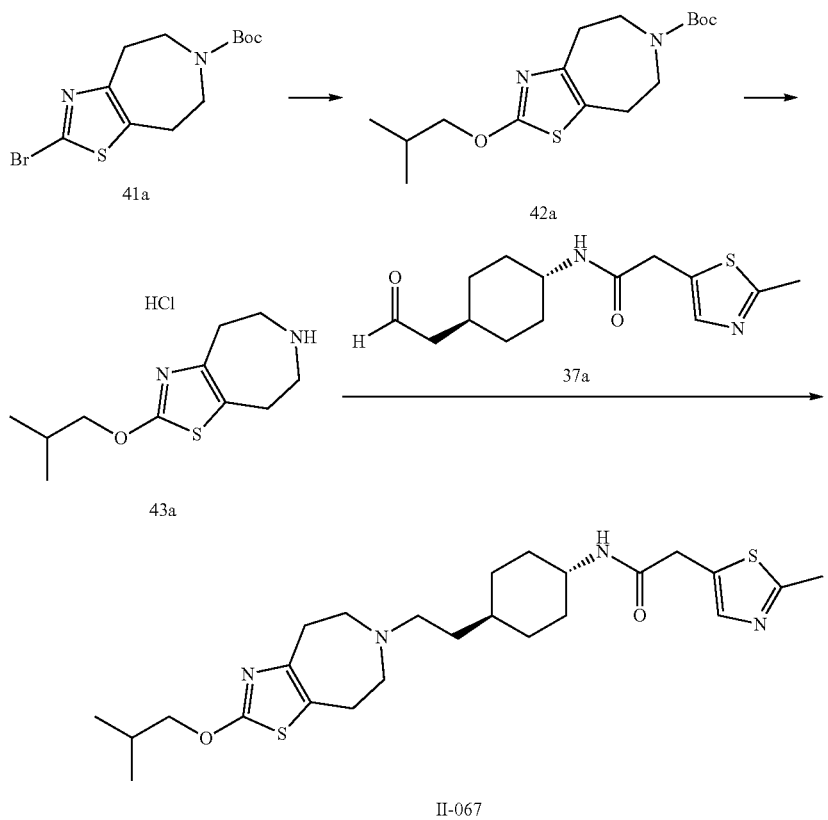

Step 1 Synthesis of Compound 42a 2-methylpropan-1-ol (234 mg, 3.15 mmol) was dissolved in DMF (1 mL). To the solution was added sodium hydride (60 wt %, 126 mg, 3.15 mmol) portion wise under ice cooling. The mixture was stirred at room temperature for 15 minutes. To the mixture was added the compound 41a (360 mg, 1.05 mmol) dissolved in DMF (3 mL). The mixture was stirred at 60° C. for 1 hour. To the reaction mixture, water was added under ice cooling, and the mixture was extracted with ethyl acetate. The organic layer was washed by water and dried over anhydrous sodium sulfate. The solvent was evaporated under reduced pressure. The obtained residue was purified by silica-gel column chromatography (hexane-ethyl acetate) to give a compound 42a (179.5 mg, yield 52%).

1H-NMR (CDCl3) δ: 0.99 (6H, d, J=6.8 Hz), 1.48 (9H, s), 2.03-2.13 (1H, m), 2.70-2.82 (2H, m), 2.83-2.96 (2H, m), 3.49-3.67 (4H, m), 4.05 (2H, d, J=6.5 Hz).

Step 2 Synthesis of Compound 43a

The compound 42a (179.5 mg, 0.55 mmol) was dissolved in methanol (1 mL). To the solution was added 4 mol/L hydrochloric acid/1,4-dioxane solution (1 mL, 4.00 mmol). The mixture was stirred at room temperature overnight. The reaction mixture was concentrated and dried to give a compound 43a (180 mg) as a crude product.

Step 3 Synthesis of II-067

The compound 43a (30 mg) and the compound 37a (28.2 mg, 0.101 mmol) was dissolved in 1,2-dichloroethane (1 mL). To the solution was added triethylamine (127 μL, 0.916 mmol). The mixture was stirred at room temperature for 30 minutes. To the mixture was added sodium triacetoxyborohydride (38.8 mg, 0.183 mmol). The mixture was stirred at room temperature for 2 hours. To the reaction mixture was added saturated aqueous solution of sodium hydrogen carbonate and the mixture was extracted with chloroform. The solvent was evaporated under reduced pressure. The obtained residue was purified by silica gel column chromatography (ethyl acetate) to give a compound II-067 (29.3 mg, yield 65%, 2 steps) as a white solid.

1H-NMR (CDCl3) δ: 0.99 (6H, d, J=6.8 Hz), 0.99-1.13 (4H, m), 1.17-1.27 (1H, m), 1.36-1.45 (2H, m), 1.71-1.81 (2H, m), 1.89-1.99 (2H, m), 2.01-2.14 (1H, m), 2.58 (2H, t, J=7.5 Hz), 2.69 (3H, s), 2.74-2.87 (6H, m), 3.67 (2H, s), 3.70 (1H, brs), 4.04 (2H, d, J=6.8 Hz), 5.32 (1H, d, J=8.3 Hz), 7.41 (1H, s).

[M+H] 491.35, method 3, retention time 1.36 min

Example 7' Synthesis of compound II-115

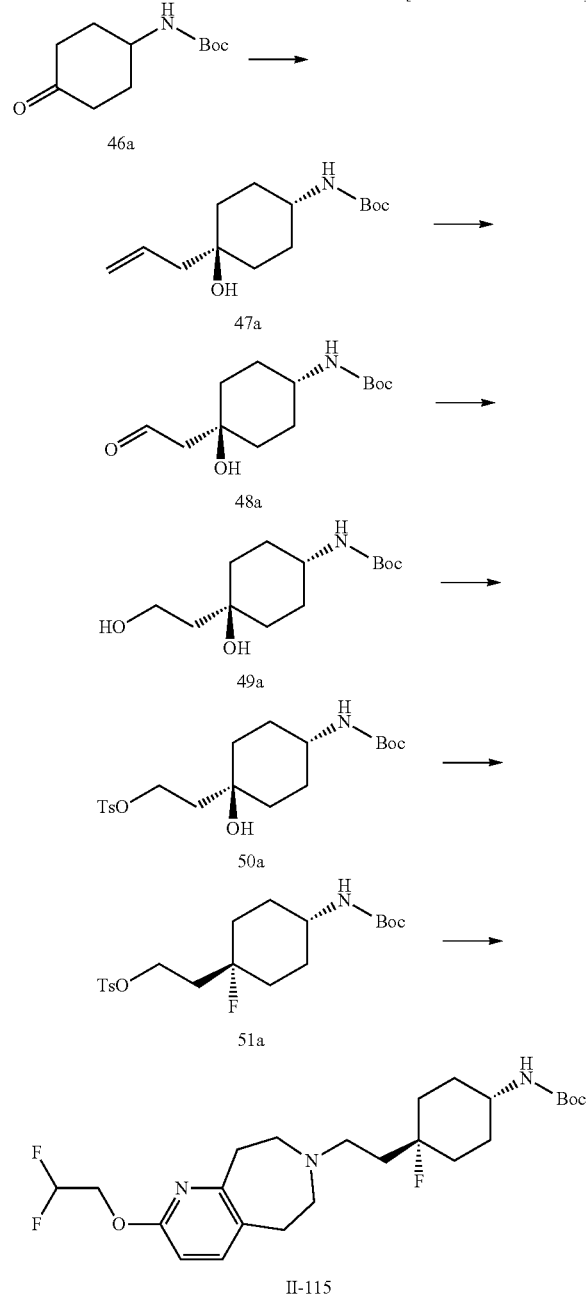

[Chemical Formula 152]

Step 1 Synthesis of Compound 47a

A compound 46a (90.0 g, 422.2 mmol) was dissolved in THF (1000 mL). To the solution was added allylmagnesium bromide (1.0 mol/L diethyl ether solution, 1266 mL, 1266 mmol) at −70° C. and the mixture was stirred for 1 hour. To the reaction solution, ice water was added. The mixture was extracted with ethyl acetate. The organic layer was washed by water and brine, and then dried over anhydrous sodium sulfate. The solvent was evaporated under reduced pressure. The obtained residue was purified by silica gel column chromatography (petroleum ether-ethyl acetate) to give a compound 47a (35.0 g, yield 32%).

¹H NMR (CDCl₃) δ 1.38-1.53 (m, 15H), 1.62-1.64 (m, 1H), 1.91-1.94 (m, 2H), 2.28 (d, J=7.5 Hz, 2H), 3.61 (brs, 1H), 4.51 (brs, 1H), 5.12-5.20 (m, 2H), 5.85-5.90 (m, 1H).

Step 2 Synthesis of Compound 48a

The compound 47a (35.0 g, 137.2 mmol) was dissolved in THF (500 mL) and water (500 mL). To the solution were added potassium osmate (VI) dihydrate (5.05 g, 13.72 mmol) and sodium periodate (117.34 g, 548.63 mmol) at 0° C. The mixture was stirred at room temperature for 8 hours. To the reaction solution were added water and aqueous solution of sodium thiosulfate. The mixture was extracted with ethyl acetate. The organic layer was washed by water and brine, and then dried over anhydrous sodium sulfate. The solvent was evaporated under reduced pressure to give a compound 48a (35.0 g) as a crude product.

Step 3 Synthesis of Compound 49a

The compound 48a (15.0 g, 58.33 mmol) was dissolved in THF (150 mL) and methanol (150 mL). To the solution was added sodium borohydride (4.41 g, 116.66 mmol) portion wise at 0° C. The mixture was stirred at 0° C. for 1 hour. To the reaction solution was added saturated aqueous solution of ammonium chloride. The mixture was extracted with ethyl acetate. The organic layer was washed by brine, and then dried over anhydrous sodium sulfate. The solvent was evaporated under reduced pressure to give a compound 49a (12.0 g) as a crude product.

Step 4 Synthesis of Compound 50a

The compound 49a (713 mg, 2.75 mmol) was dissolved in dichloromethane (7.4 mL). To the solution were added 4-dimethylaminopyridine (33.6 mg, 0.275 mmol), triethylamine (0.762 mL, 5.50 mmol) and p-toluenesulfonyl chloride (577 mg, 3.02 mmol) at 0° C. The mixture was stirred at 0° C. for 4 hours. To the reaction solution was added 0.1 mol/L hydrochloric acid. The mixture was extracted with ethyl acetate. The organic layer was washed by saturated aqueous solution of sodium bicarbonate, water and brine, and then dried over anhydrous sodium sulfate. The solvent was evaporated under reduced pressure. The obtained residue was purified by silica-gel column chromatography (hexane-ethyl acetate) to give a compound 50a (761 mg, yield 67%).

¹H-NMR (CDCl₃) δ: 1.29-1.38 (m, 3H), 1.43-1.50 (m, 11H), 1.57-1.66 (m, 2H), 1.86-1.93 (m, 4H), 2.46 (s, 3H), 3.57 (brs, 1H), 4.22 (t, J=6.7 Hz, 2H), 4.46 (brs, 1H), 7.36 (d, J=8.0 Hz, 2H), 7.79 (d, J=8.3 Hz, 2H).

Step 5 Synthesis of Compound 51a

The compound 50a (759 mg, 1.83 mmol) was dissolved in dichloromethane (30.4 mL). To the solution was added diethylaminosulfur trifluoride (1.45 mL, 11.0 mmol) at −78° C. The mixture was stirred at −78° C. for 40 minutes. To the reaction mixture, water was added. The mixture was extracted with ethyl acetate. The organic layer was washed by water and brine, and then dried over anhydrous sodium sulfate. The solvent was evaporated under reduced pressure. The obtained residue was purified by silica-gel column chromatography (hexane-ethyl acetate) to give a compound 51a (345 mg, yield 45%).

¹H-NMR (CDCl₃) δ: 1.36-1.48 (m, 13H), 1.80-1.99 (m, 6H), 2.46 (s, 3H), 3.40 (brs, 1H), 4.17 (t, J=6.7 Hz, 2H), 4.38 (brs, 1H), 7.35 (d, J=8.0 Hz, 2H), 7.79 (d, J=8.3 Hz, 2H).

Step 6 Synthesis of Compound II-115

The compound 3a (124 mg, 0.362 mmol) was dissolved in acetonitrile (3 mL). To the solution were added potassium carbonate (200 mg, 1.45 mmol) and the compound 51a (150 mg, 0.362 mmol). The mixture was heated to 70° C. and stirred for 9 hours, and cooled to room temperature. Then, water was added to the reaction mixture. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a compound II-115 (125 mg, yield 73%).

1H-NMR (CDCl3) δ: 1.41-1.52 (m, 13H), 1.76-1.98 (m, 6H), 2.58-2.66 (m, 6H), 2.81 (m, 2H), 3.02 (m, 2H), 3.44 (m, 1H), 4.42 (m, 1H), 4.51 (td, J=13.6, 4.3 Hz, 2H), 6.13 (tt, J=55.8, 4.3 Hz, 1H), 6.55 (d, J=8.0 Hz, 1H), 7.31 (d, J=8.3 Hz, 1H).

[M+H] 472.35, method 3, retention time 1.67 min

Example 1" Synthesis of Compound III-624, III-625

[Chemical Formula 153]

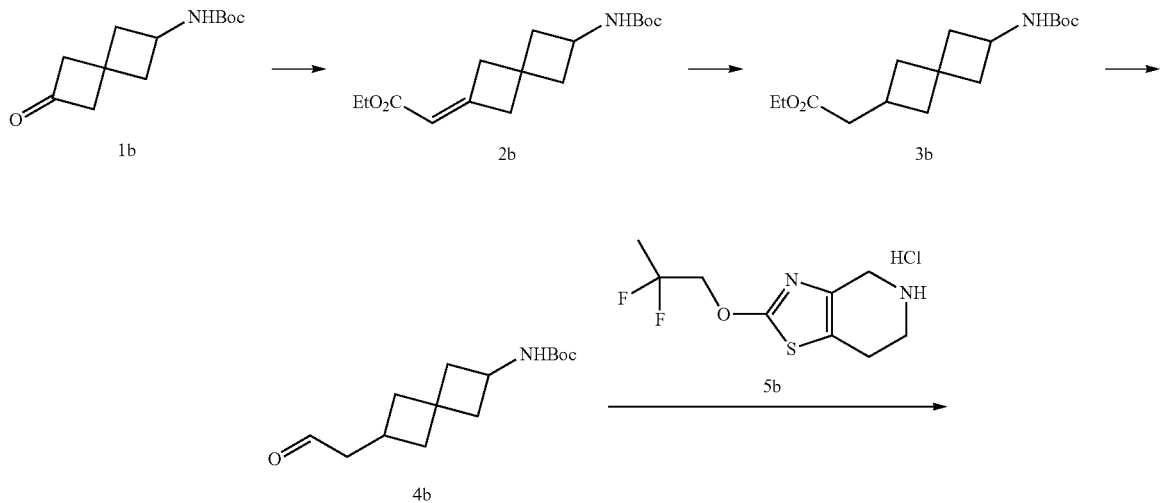

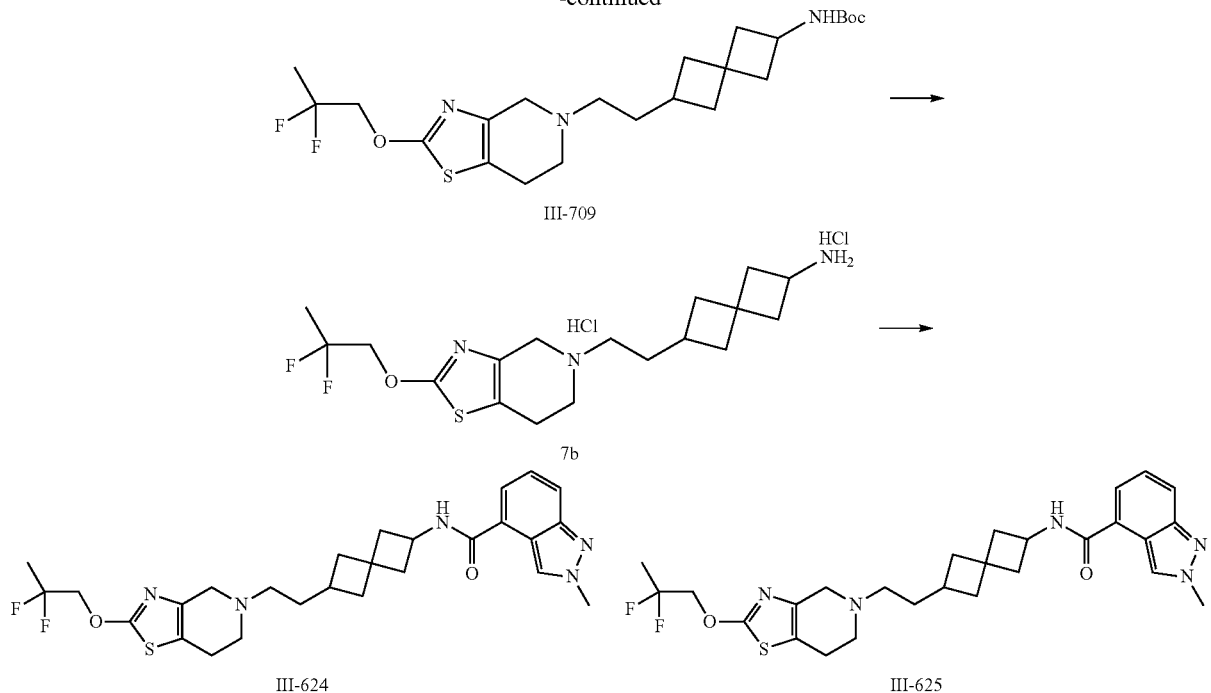

Step 1 Synthesis of Compound 2b

Triethyl phosphonoacetate (358 mg, 1.59 mmol) was dissolved in THF (9 mL). To the solution was added sodium hydride (60 wt %, 64 mg, 1, 59 mmol) at 0° C. The mixture was stirred at 0° C. for 30 minutes. THF (3 mL) solution of the compound 1b (300 mg, 1.33 mmol) was added to the reaction solution. The mixture was stirred at room temperature overnight. The reaction mixture was cooled to 0° C. To the reaction mixture was added saturated aqueous solution of ammonium chloride. The mixture was extracted with ethyl acetate. The organic layer was washed by water and brine, and then dried over anhydrous magnesium sulfate. The solvent was evaporated under reduced pressure a compound 2b (410 mg, yield 100%) as a crude product.

Step 2 Synthesis of Compound 3b

The compound 2b (393 mg) obtained in Step 1 was dissolved in ethanol (8 mL). To the solution was added 10% palladium on carbon (142 mg). The mixture was stirred under hydrogen atmosphere at room temperature for 3 hours. The reaction mixture was filtered through Celite, and the solvent was evaporated under reduced pressure. The obtained residue was purified by silica-gel column chromatography (hexane-ethyl acetate) to give a compound 3b (302 mg, yield 76%, 2 steps).

Step 3 Synthesis of Compound 4b

The compound 3b (300 mg, 1.00 mmol) was dissolved in dichloromethane (6 mL). To the solution was added DIBAL (1.0 mol/L hexane solution, 1.62 mL, 1.62 mmol) at −78° C. and the mixture was stirred for 1.5 hours. To the reaction mixture were added saturated aqueous solution of Rochelle salt and ethyl acetate. The mixture was stirred at room temperature for 3 hours. To the reaction mixture, water was added. The mixture was extracted with ethyl acetate. The organic layer was washed by brine, and then dried over anhydrous magnesium sulfate. The solvent was evaporated under reduced pressure. The obtained residue was purified by silica-gel column chromatography (hexane-ethyl acetate) to give a compound 4b (216 mg, yield 85%).

$^1$H-NMR (CDCl$_3$) δ: 1.43 (s, 9H), 1.67-1.84 (m, 4H), 2.10-2.16 (m, 1H), 2.26-2.32 (m, 2H), 2.46-2.52 (m, 3H), 2.56-2.65 (m, 1H), 3.98 (brs, 1H), 4.57 (brs, 1H), 9.68 (s, 1H).

Step 4 Synthesis of Compound III-709

The compound 4b (50 mg, 0.197 mmol) and the compound 5b (53.4 mg, 0.197 mmol, which can be synthesized by the similar methods of Step 1, 2 of Example 2) were dissolved in dichloromethane (2 mL). To the solution were added triethylamine (137 μL, 0.987 mmol) and sodium triacetoxyborohydride (125 mg, 0.592 mmol) at 0° C. The mixture was stirred at room temperature for 3 hours. To the reaction solution was added saturated aqueous solution of sodium hydrogen carbonate. The mixture was extracted with ethyl acetate. The organic layer was washed by water and brine, and then dried over anhydrous magnesium sulfate. The solvent was evaporated under reduced pressure to give a compound III-709 (88 mg, yield 95%).

$^1$H-NMR (CDCl$_3$) δ: 1.43 (s, 9H), 1.59-1.80 (m, 6H), 1.99-2.05 (m, 1H), 2.11-2.31 (m, 3H), 2.38-2.47 (m, 3H), 2.70-2.76 (m, 4H), 3.43 (s, 2H), 3.98 (brs, 1H), 4.50 (t, J=11.8 Hz, 2H), 4.57 (brs, 1H).

Step 5 Synthesis of Compound 7b

The compound III-709 (86 mg, 0.182 mmol) was dissolved in 1,4-dioxane (1 mL). To the solution was added 4 mol/L hydrochloric acid (1,4-dioxane solution, 0.912 mL, 3.65 mmol). The mixture was stirred at room temperature overnight. The solvent was evaporated under reduced pressure to give a compound 7b (82 mg, yield 100%).

Step 6 Synthesis of III-624, 111*625

The compound 7b (40 mg, 0.090 mmol) was dissolved in DMF (1.5 mL). To the solution were added 2-methyl-2H-indazole-4-carboxylic acid (19 mg, 0.108 mmol), HOBt (14.6 mg, 0.108 mmol), EDC hydrochloride (20.7 mg, 0.108 mmol) and triethylamine (62 μL, 0.45 mmol). The mixture was stirred at room temperature overnight. To the reaction solution was added saturated aqueous solution of sodium hydrogen carbonate. The mixture was extracted with ethyl acetate. The organic layer was washed by water and brine, and then dried over anhydrous magnesium sulfate. The solvent was evaporated under reduced pressure. The obtained residue was purified by silica-gel column chromatography (chloroform-methanol). Then optical resolution was conducted by SFC to give III-624 (11.9 mg, yield 25%), III-625 (9.3 mg, yield 20%) as optically active compounds.
Preparative Method
Preparative column (IF-IF, Daicel)
Flow rate: 24 mL/min
mobile phase: methanol+0.1% diethylamine 55%
Sample: 13 mg/mL (methanol/chloroform=1/1)
Loading amount: 2.6 mg
Detection wavelength: 220 nm, Back pressure: 8 MPa
III-624; [M+H] 530.3, method 2, retention time 1.57 min
III-625; [M+H] 530.3, method 2, retention time 1.59 min Reference Example 1" Synthesis of Compound 11b added DMF (1 drop) and oxalyl chloride (184 μL, 2.11 mmol) at 0° C. The mixture was stirred at room temperature for 30 minutes. To the mixture were added the compound 8b (400 mg, 1.41 mmol) and THF (2 mL), and then a solution of triethylamine (682 μL, 4.92 mmol) in THF (2 mL) was slowly added dropwise at 0° C. To the reaction solution was added saturated aqueous solution of sodium hydrogen carbonate. The mixture was extracted with ethyl acetate. The organic layer was washed by water and brine, and then dried over anhydrous magnesium sulfate. The solvent was evaporated under reduced pressure to give a compound 9b (550 mg) as a crude product.

Step 2 Synthesis of Compound 10b

The crude compound 9b (550 mg) obtained in Step 1 was dissolved in THF (10 mL). To the solution was added Lawesson's reagent (1137 mg, 2.81 mmol). The mixture was stirred at 60° C. for 3 hours. The solvent was evaporated under reduced pressure. The obtained residue was purified by silica-gel column chromatography (hexane-ethyl acetate) to give a compound 10b (120 mg, yield 23%).
$^1$H-NMR (CDCl$_3$) δ: 1.60-1.70 (m, 3H), 2.29-2.41 (m, 2H), 2.80-2.87 (br, 2H), 3.12-3.18 (m, 2H), 3.78-3.84 (br, 2H), 4.66 (s, 2H), 5.18 (s, 2H), 7.32-7.39 (m, 5H).

Step 3 Synthesis of Compound 11b

The compound 10b (119 mg, 0.325 mmol) was dissolved in TFA (2 mL). The solution was stirred at 70° C. for 4 hours. The solvent was evaporated under reduced pressure to give a compound 11b (120 mg) as a crude product.
[M+H] 233.1, method 2, retention time 0.88 min Reference Example 2" Synthesis of Compound 14b

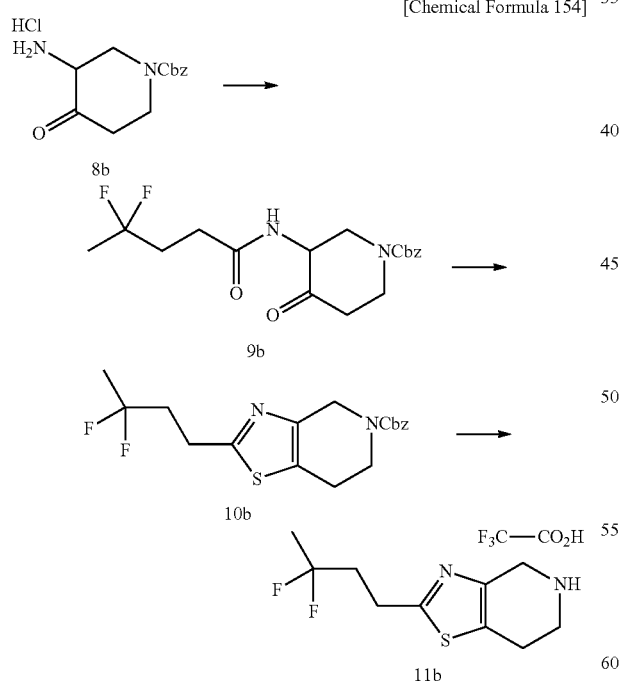

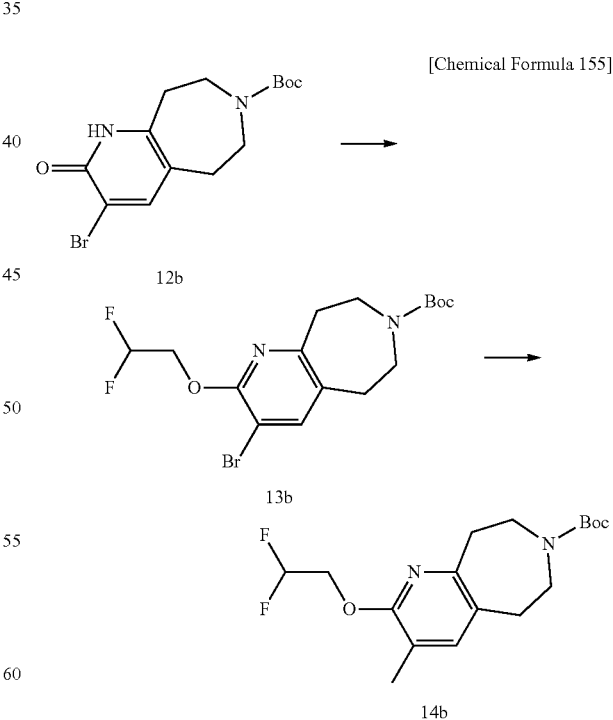

Step 1 Synthesis of Compound 9b 4,4-difluoropentanoic acid (233 mg, 1.68 mmol) was dissolved in dichloromethane (6 mL). To the solution were Step 1 Synthesis of Compound 13b A compound 12b (212 mg, 0.618 mmol) was dissolved in DMF (4.24 mL). To the solution were added potassium carbonate (256 mg, 1.85 mmol) and 2,2-difluoroethyl triflate (264 mg, 1.24 mmol). The mixture was stirred at room temperature for 4.5 hours. To the reaction mixture, water was added. The mixture was extracted with ethyl acetate. The organic layer was washed by water and brine, and then dried over anhydrous sodium sulfate. The solvent was evaporated under reduced pressure. The obtained residue was purified by silica-gel column chromatography (hexane-ethyl acetate) to give a compound 13b (189 mg, yield 75%).

$^1$H-NMR (CDCl$_3$) δ: 1.49 (s, 9H), 2.77-2.80 (br, 2H), 2.99-3.01 (brm, 2H), 3.54-3.59 (brm, 4H), 4.56 (td, J=13.3, 4.3 Hz, 2H), 6.15 (tt, J=55.6, 4.4 Hz, 1H), 7.57 (s, 1H).

Step 2 Synthesis of Compound 14b

The compound 13b (30 mg, 0.074 mmol) was dissolved in 1,4-dioxane (2 mL) and water (0.2 mL) and then nitrogen was purged. To the solution was added 2,4,6-trimethyl-boroxin (14 mg, 0.0.110 mmol), PdCl$_2$(dppf)(5.4 mg, 7.37 μmol), and potassium carbonate (30.5 mg, 0.221 mmol). The mixture was stirred at 95° C. for 4.5 hours. To the reaction mixture, water was added. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a compound 14b (20.4 mg, yield 81%).

$^1$H-NMR (CDCl$_3$) δ: 1.49 (s, 9H), 2.15 (s, 3H), 2.75-2.77 (br, 2H), 2.97-0.3.00 (brm, 2H), 3.52-3.57 (brm, 4H), 4.52 (td, J=13.6, 4.3 Hz, 2H), 6.14 (tt, J=56.0, 4.3 Hz, 1H), 7.15 (s, 1H).

Reference Example 3" Synthesis of Compound 20b

[Chemical Formula 156]

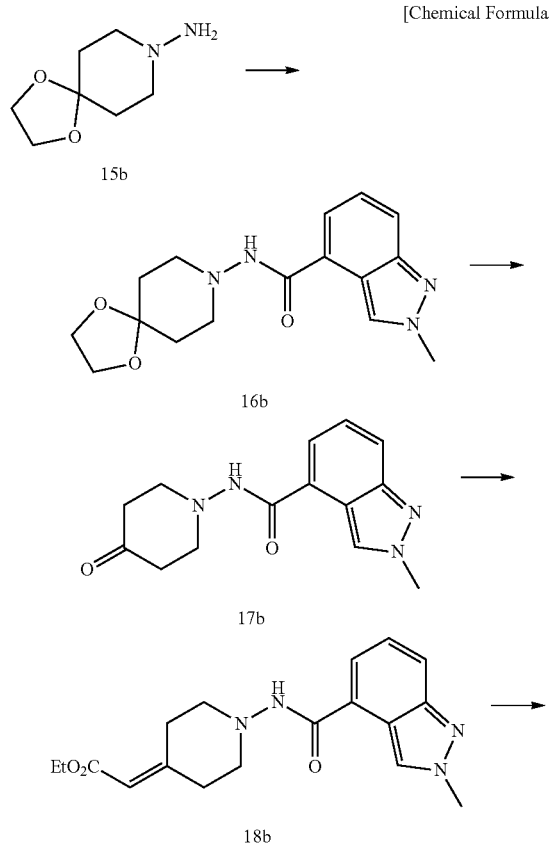

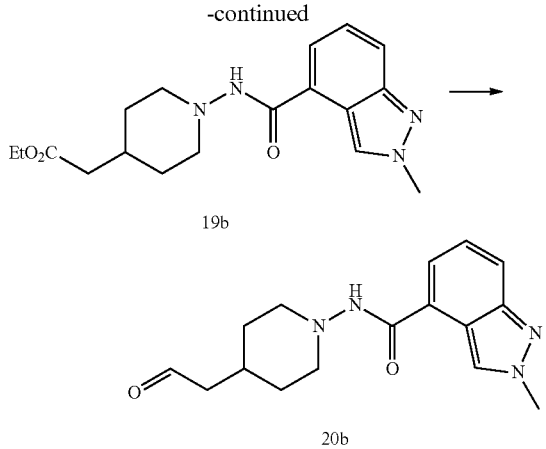

Step 1 Synthesis of Compound 16b 2-methylindazole-4-carboxylic acid (1164 mg, 6.61 mmol) was suspended in ethyl acetate (14.3 mL). To the suspension were added thionyl chloride (526 μL, 7.21 mmol) and DMF (23.4 μL, 0.30 mmol). The mixture was stirred at 80° C. for 1.5 hours. The solvent was evaporated under reduced pressure. To the obtained residue, THF (9.5 mL) was added. To the mixture were added a solution of the compound 15b (950 mg, 6.01 mmol) and triethylamine (2.5 mL, 18.0 mmol) in THF (1 mL) at 0° C. The mixture was stirred at 0° C. for 25 minutes and then stirred at room temperature for 50 minutes. To the reaction mixture was added saturated aqueous solution of sodium hydrogen carbonate. The mixture was extracted with ethyl acetate. The organic layer was dried over anhydrous sodium sulfate. The solvent was evaporated under reduced pressure. The obtained residue was purified by silica-gel column chromatography (chloroform-methanol) to give a compound 16b (663 mg, yield 35%).

$^1$H-NMR (DMSO-d$_6$) δ: 1.73-1.76 (m, 4H), 2.96-2.99 (m, 4H), 3.89 (s, 4H), 4.20 (s, 3H), 7.27 (dd, J=8.5, 7.0 Hz, 1H), 7.46 (d, J=6.8 Hz, 1H), 7.74 (d, J=8.8 Hz, 1H), 8.52 (s, 1H), 9.45 (s, 1H).

Step 2 Synthesis of Compound 17b

The compound 16b (660 mg, 2.09 mmol) was dissolved in THF (6.6 mL). To the solution was added 2 mol/L hydrochloric acid (3.13 mL, 6.26 mmol). The mixture was stirred at room temperature for 1 hour and then refluxed for 4.5 hours. To the reaction mixture was added saturated aqueous solution of sodium hydrogen carbonate. The mixture was extracted with chloroform. The organic layer was dried over anhydrous sodium sulfate. The solvent was evaporated under reduced pressure. The obtained residue was purified by silica-gel column chromatography (chloroform-methanol) to give a compound 17b (331 mg, yield 58%).

Step 3 Synthesis of Compound 18b

The compound 17b (325 mg, 1.19 mmol) and triethyl phosphonoacetate (301 mg, 1.79 mmol) were dissolved in THF (6.5 mL). To the solution was added sodium hydride (60 wt %, 119 mg, 2.98 mmol) at 0° C. The mixture was stirred at 0° C. for 1 hour. To the reaction mixture, water was added. The mixture was extracted with chloroform. The organic layer was dried over anhydrous sodium sulfate. The solvent was evaporated under reduced pressure. The obtained residue was purified by silica-gel column chromatography (hexane-ethyl acetate) to give a compound 18b (406 mg, yield 99%).

$^1$H-NMR (CDCl$_3$) δ: 1.29 (t, J=7.2 Hz, 3H), 2.54-2.57 (m, 2H), 3.02-3.08 (m, 4H), 3.20-3.23 (m, 2H), 4.17 (q, J=7.1 Hz, 2H), 4.25 (s, 3H), 5.72 (s, 1H), 6.97 (brs, 1H), 7.26-7.34 (m, 2H), 7.86 (d, J=8.5 Hz, 1H), 8.43 (s, 1H).

Step 4 Synthesis of Compound 19b

The compound 18b (342 mg, 1.00 mmol) was dissolved in a mixed solvent of THF (3.4 mL) and methanol (6.8 mL). To the solution were added nickel(II) chloride hexahydrate (178 mg, 0.749 mmol) and sodium borohydride (189 mg, 4.99 mmol) at 0° C. The mixture was stirred at 0° C. for 2 hours. To the reaction mixture, water was added. The mixture was extracted with ethyl acetate. The organic layer was washed by brine, dried over anhydrous sodium sulfate. The solvent was evaporated under reduced pressure. The obtained residue was purified by silica-gel column chromatography (chloroform-methanol) to give a compound 19b (286 mg, yield 83%).

Step 5 Synthesis of Compound 20b

The compound 19b (54.8 mg, 0.159 mmol) was dissolved in dichloromethane (2.2 mL). To the solution was added DIBAL (1.02 mol/L hexane solution, 468 μL, 0.477 mmol) at −78° C., and the mixture was stirred for 3 hours. To the reaction mixture were added water and methanol. The mixture was extracted with chloroform. The organic layer was dried over anhydrous sodium sulfate. The solvent was evaporated under reduced pressure to give a compound 20b (45 mg, 94%) as a crude product.

Reference Example 4" Synthesis of compound 26b

[Chemical Formula 157]

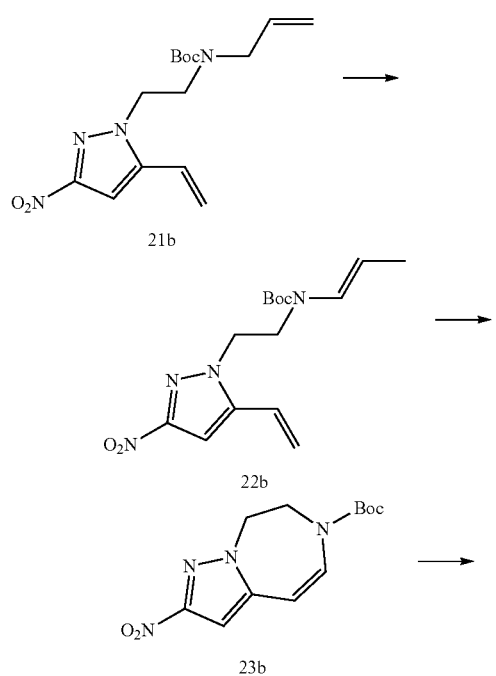

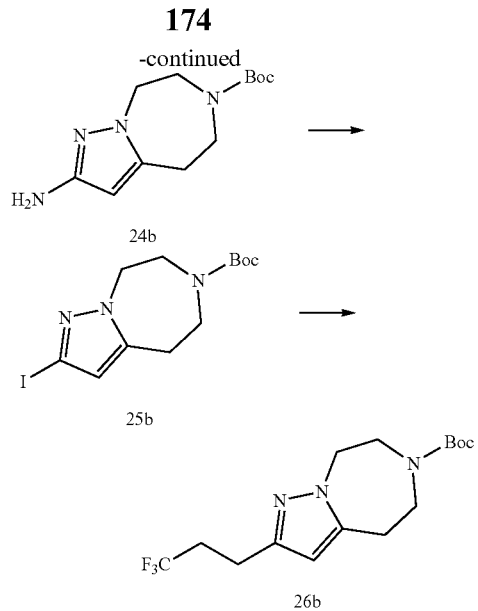

Step 1 Synthesis of Compound 22b

A compound 21b (560 mg, 1.74 mmol, which was synthesized by the methods described in Angewandte Chemie, International Edition (2016), 55(40), 12479-12483.) and vinyloxytrimethylsilane (0.262 mL, 1.74 mmol) was dissolved in dichloromethane (5.6 mL). To the solution were added benzylidene{1,3-bis(2,4,6-trimethylphenyl)-2-imidazolidinylidene}dichloro(tricyclohexylphosphine)ruthenium (148 mg, 0.174 mmol). The mixture was refluxed for 4 hours. After cooling to room temperature, the solvent was evaporated under reduced pressure. The obtained residue was purified by silica-gel column chromatography (hexane-ethyl acetate) to give a compound 22b (560 mg, yield 94%).

[M+H] 323.2, method 2, retention time 2.37 min

Step 2 Synthesis of Compound 23b

The compound 22b (89 mg, 0.276 mmol) was dissolved in toluene (1.78 mL). To the solution was added (1,3-bis-(2,4,6-trimethylphenyl)-2-imidazolidinylidene)dichloro (o-isopropoxyphenylmethylene)ruthenium (34.8 mg, 0.028 mmol). The mixture was refluxed for 3.5 hours. After cooling to room temperature, the solvent was evaporated under reduced pressure. The obtained residue was purified by silica-gel column chromatography (hexane-ethyl acetate) to give a compound 23b (33.9 mg, yield 44%).

$^1$H-NMR (DMSO-d$_6$) δ: 1.49 (s, 9H), 4.04-4.06 (m, 2H), 4.55-4.57 (m, 2H), 5.67 (d, J=10.0 Hz, 1H), 6.98 (s, 1H), 7.15 (d, J=10.3 Hz, 1H).

Step 3 Synthesis of Compound 24b

The compound 23b (33 mg, 0.118 mmol) was dissolved in ethanol (0.7 mL). To the solution was added palladium on carbon (21 mg). The mixture was stirred under hydrogen atmosphere at room temperature. The reaction mixture was filtered through Celite. The solvent was evaporated under reduced pressure to give a compound 24b (28.5 mg, yield 96%).

[M+H] 253.3, method 2, retention time 1.14 min

Step 4 Synthesis of Compound 25b

The compound 24b (28 mg, 0.111 mmol) was dissolved in acetonitrile (0.5 mL). To the solution were added aqueous solution (0.2 mL) of p-toluenesulfonic acid monohydrate (63.3 mg, 0.333 mmol) and aqueous solution (0.2 mL) of sodium nitrite (19.14 mg, 0.277 mmol) and sodium iodide (41.6 mg, 0.277 mmol) at 0° C. The mixture was stirred at 0° C. for 1 hour, and then stirred at room temperature. To the reaction mixture was added 10% aqueous solution of sodium hydrogen sulfite. The mixture was extracted with chloroform. The solvent was evaporated under reduced pressure. The obtained residue was purified by silica-gel column chromatography (hexane-ethyl acetate) to give a compound 25b (22.9 mg, yield 57%).

$^1$H-NMR (CDCl$_3$) δ: 1.49 (s, 9H), 2.85-2.90 (br, 2H), 3.55-3.61 (br, 2H), 3.65-3.69 (br, 2H), 4.35-4.39 (br, 2H), 6.21 (s, 1H).

Step 5 Synthesis of Compound 26b

The compound 25b (22 mg, 0.061 mmol) was dissolved in toluene (0.44 mL). To the solution were added water (0.22 mL), potassium trifluoro(3,3,3-trifluoropropyl)borate (49.4 mg, 0.242 mmol), RuPhos Pd G3 (10.1 mg, 12.1 μmol), and cesium carbonate (59.2 mg, 0.182 mmol). The mixture was stirred at 130° C. for 2.5 hours and then stirred at 150° C. for 1 hour. To the reaction mixture was added saturated aqueous solution of ammonium chloride. The mixture was extracted with chloroform. The solvent was evaporated under reduced pressure. The obtained residue was purified by silica-gel column chromatography (hexane-ethyl acetate) to give a compound 26b (6.1 mg, yield 30%).

1H-NMR (CDCl3) δ: 1.50 (s, 9H), 2.38-2.50 (m, 2H), 2.79-2.86 (m, 4H), 3.57-0.3.61 (br, 2H), 3.66-3.70 (br, 2H), 4.26-4.30 (br, 2H), 5.87 (s, 1H).

Example 2" Synthesis of Compound III-707

[Chemical Formula 158]

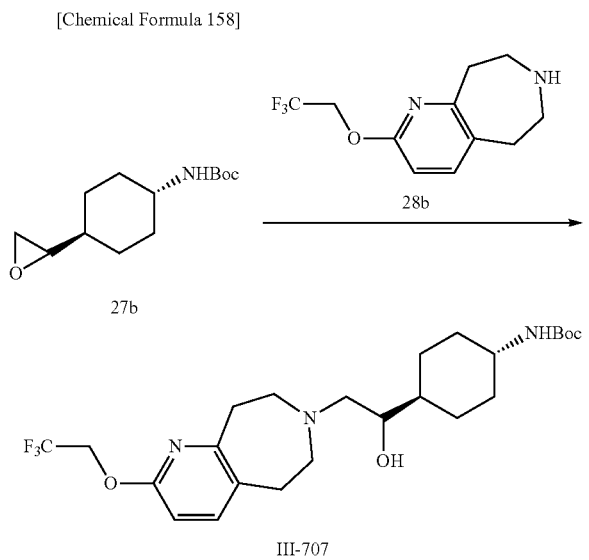

Step 1 Synthesis of Compound III-707

A compound 27b (180 mg, 0.746 mmol) and a compound 28b (177 mg, 0.72 mmol) were dissolved in 2-propanol (3.55 mL). To the solution was added DIEA (189 μL, 1.08 mmol). The mixture was stirred at 70° C. for 3 days. To the reaction mixture, water was added. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a compound III-707 (308 mg, yield 88%).

$^1$H-NMR (CDCl$_3$) δ: 1.01-1.31 (m, 5H), 1.44 (s, 9H), 1.68-1.71 (m, 1H), 2.02-2.07 (m, 3H), 2.28-2.34 (m, 1H), 2.52-2.61 (m, 3H), 2.76-2.89 (m, 4H), 2.97-3.09 (m, 2H), 3.36-3.45 (m, 2H), 4.37 (brs, 1H), 4.74 (q, J=8.7 Hz, 2H), 6.60 (d, J=8.0 Hz, 1H), 7.33 (d, J=8.2 Hz, 1H).

Reference Example 6" Synthesis of Compound 31b

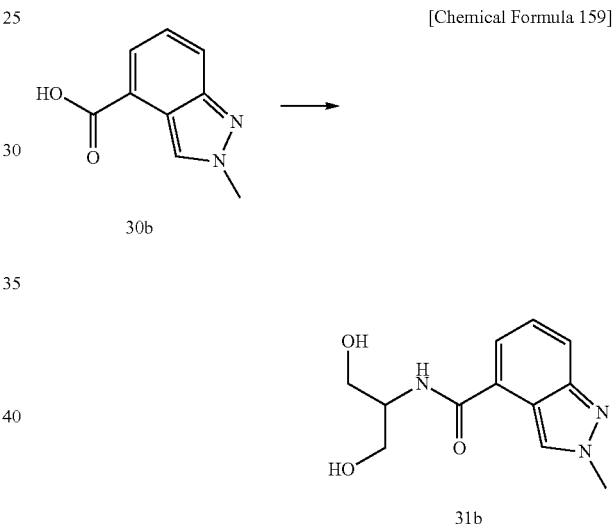

Step 1 Synthesis of Compound 31b

A compound 30b (300 mg, 1.70 mmol) was suspended in ethyl acetate (6 mL). To the suspension were added thionyl chloride (174 μL, 2.38 mmol) and DMF (13.2 μL, 0.170 mmol). The mixture was stirred at 90° C. for 1 hour. After cooling to 0° C., aqueous solution (1.5 mL) of 2-aminopropane-1,3-diol (465 mg, 5.11 mmol), and triethylamine (2.5 mL, 18.0 mmol) were added to the mixture. The mixture was stirred at 0° C. for 40 minutes and then stirred at room temperature for 80 minutes. To the reaction mixture, brine was added. The mixture was extracted with a mixed solvent of chloroform and methanol. The solvent was evaporated under reduced pressure. The obtained residue was purified by silica-gel column chromatography (chloroform-methanol) to give a compound 31b (327 mg, yield 77%).

Example 3" Synthesis of III-690, III-689

[Chemical Formula 160]

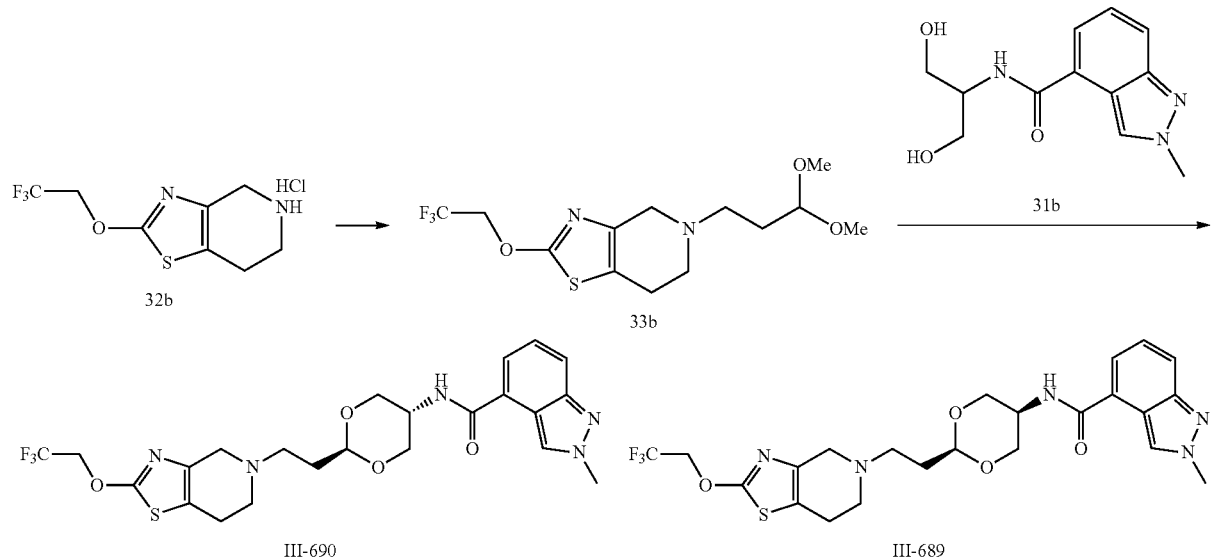

Step 1 Synthesis of Compound 33b

The compound 32b (200 mg, 0.728 mmol) and 3-bromo 1,1-dimethoxypropane (147 μL, 1.09 mmol) were suspended in acetonitrile (4 mL). To the suspension was added DIEA (382 μL, 2.18 mmol). The mixture was stirred at 70° C. for 3 hours. To the reaction mixture, water was added. The mixture was extracted with ethyl acetate. The organic layer was dried over anhydrous sodium sulfate. The solvent was evaporated under reduced pressure. The obtained residue was purified by silica-gel column chromatography (hexane-ethyl acetate) to give a compound 33b (192 mg, yield 78%).

$^1$H-NMR (CDCl$_3$) δ: 1.86-1.91 (m, 2H), 2.59-2.63 (m, 2H), 2.71-2.80 (m, 4H), 3.34 (s, 6H), 3.47-3.48 (m, 2H), 4.49 (t, J=5.6 Hz, 1H), 4.74 (q, J=8.3 Hz, 2H).

Step 2 Synthesis of III-690, III-689

The compound 33b (192 mg, 0.564 mmol) and the compound 31b (141 mg, 0.564 mmol) were dissolved in 1,2-dichloroethane (3.8 mL). To the solution was added p-toluenesulfonic acid monohydrate (129 mg, 0.677 mmol). The mixture was stirred at 90° C. for 2 hours. To the reaction mixture was added saturated aqueous solution of sodium hydrogen carbonate. The mixture was extracted with chloroform. The organic layer was dried over anhydrous sodium sulfate. The solvent was evaporated under reduced pressure. The obtained residue was purified by silica gel column chromatography (hexane-ethyl acetate) and reverse-phase HPLC (water-acetonitrile) to give III-690 (11.5 mg, yield 4%), and III-689 (44.2 mg, yield 15%).

III-689

$^1$H-NMR (DMSO-d$_6$) δ: 1.80-1.85 (m, 2H), 2.57-2.61 (m, 2H), 2.65-2.73 (m, 4H), 3.82 (d, J=5.9 Hz, 1H), 3.99 (d, J=11.2 Hz, 2H), 4.10 (d, J=11.4 Hz, 2H), 4.21 (s, 3H), 4.75 (t, J=5.1 Hz, 1H), 5.06 (q, J=8.9 Hz, 2H), 7.31 (dd, J=8.5, 7.0 Hz, 1H), 7.70 (d, J=6.9 Hz, 1H), 7.78 (d, J=8.5 Hz, 1H), 8.35 (d, J=6.1 Hz, 1H), 8.57 (s, 1H).

III-690

$^1$H-NMR (DMSO-d$_6$) δ: 1.77-1.82 (m, 2H), 2.56-2.60 (m, 2H), 2.67-2.74 (m, 4H), 3.55-3.60 (m, 2H), 4.08-4.20 (m, 6H), 4.59 (t, J=5.0 Hz, 1H), 5.07 (q, J=8.8 Hz, 2H), 7.30 (t, J=7.8 Hz, 1H), 7.55 (d, J=7.0 Hz, 1H), 7.78 (d, J=8.7 Hz, 1H), 8.26 (d, J=8.0 Hz, 1H), 8.60 (s, 1H).

Reference Example 7" Synthesis of Compounds 37b, 38b

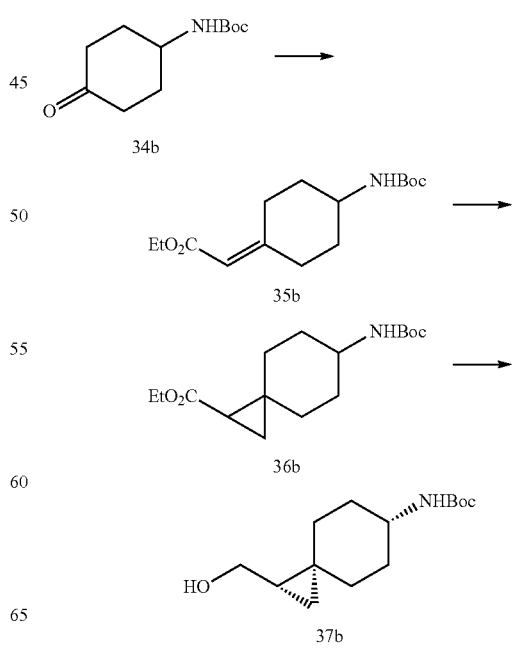

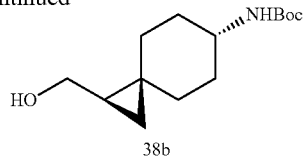

38b

Step 1 Synthesis of Compound 35b

A compound 35b synthesized by the similar method of Step 1 of Example 1".

$^1$H-NMR (CDCl$_3$) δ: 1.26-1.38 (m, 5H), 1.45 (s, 9H), 2.04-2.33 (m, 5H), 3.60-3.72 (m, 2H), 4.14 (q, J=7.1 Hz, 2H), 4.43 (br, 1H), 5.64 (s, 1H).

Step 2 Synthesis of Compound 36b

Sodium hydride (60 wt %, 176 mg, 4.41 mmol) was dissolved in DMSO (4 mL). To the solution, trimethylsulfonium Iodide (971 mg, 4.41 mmol) was added. The mixture was stirred at room temperature for 15 minutes. To the reaction solution was added DMSO (4 mL) solution of the compound 35b (500 mg, 1.76 mmol). The mixture was stirred at room temperature overnight. To the reaction mixture was added saturated aqueous solution of ammonium chloride. The mixture was extracted with diethyl ether. The organic layer was washed by water and brine, and then dried over anhydrous magnesium sulfate. The solvent was evaporated under reduced pressure. The obtained residue was purified by silica-gel column chromatography (hexane-ethyl acetate) to give a compound 36b (235 mg, yield 45%) as a diastereo mixture.

Step 3 Synthesis of Compound 37b, 38b

The compound 36b (233 mg, 0.783 mmol) was dissolved in dichloromethane (4 mL). To the solution was added DIBAL (1.03 mol/L hexane solution, 0.989 mL, 1.02 mmol) at −78° C. and the mixture was stirred for 1 hour. To the reaction mixture was added 10% aqueous solution of Rochelle salt. The mixture was stirred at room temperature for 3 hours. To the reaction mixture, water was added. The mixture was extracted with ethyl acetate. The organic layer was washed by water and brine, and then dried over anhydrous magnesium sulfate. The solvent was evaporated under reduced pressure. The obtained residue was purified by silica-gel column chromatography (hexane-ethyl acetate) to give a compound 37b (99 mg, yield 50%) and a compound 38b (14 mg, yield 7%), respectively, as a racemate (the relative configurations were as described in the structural formulas).

a compound 37b; $^1$H-NMR (CDCl$_3$) δ: 0.16-0.18 (m, 1H), 0.50-0.54 (m, 1H), 0.83-0.91 (m, 1H), 1.00-1.05 (m, 1H), 1.24-1.40 (m, 4H), 1.44 (s, 9H), 1.61-1.70 (m, 2H), 1.90-1.93 (m, 2H), 3.51-3.60 (m, 2H), 3.65-3.69 (m, 1H), 4.47 (brs, 1H).

a compound 38b; $^1$H-NMR (CDCl$_3$) δ: 0.12-0.15 (m, 1H), 0.45-0.49 (m, 1H), 0.92-1.02 (m, 2H), 1.23-1.32 (m, 4H), 1.45 (s, 9H), 1.66-1.81 (m, 2H), 1.89-2.00 (m, 2H), 3.48-3.57 (m, 2H), 3.66-3.70 (m, 1H), 4.45 (s, 1H).

Reference Example 8" Synthesis of Compound 39b

[Chemical Formula 161]

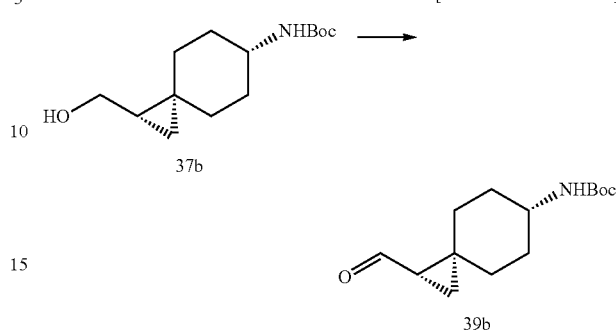

Step 1 Synthesis of Compound 39b

The racemic compound 37b (95 mg, 0.372 mmol) was dissolved in dichloromethane (2 mL). To the solution was added Dess-Martin periodinane (189 mg, 0.446 mmol). The mixture was stirred at room temperature for 2 hours. The obtained reaction solution was purified by silica gel column chromatography (hexane-ethyl acetate) to give a racemic compound 39b (76 mg, yield 81%).

$^1$H-NMR (CDCl$_3$) δ: 0.95-1.14 (m, 3H), 1.24-1.37 (m, 1H), 1.47 (s, 9H), 1.59-2.02 (m, 7H), 3.54 (brs, 1H), 4.44 (brs, 1H), 9.43 (d, J=4.6 Hz, 1H).

Reference Example 9" Synthesis of Compound 42b

[Chemical Formula 162]

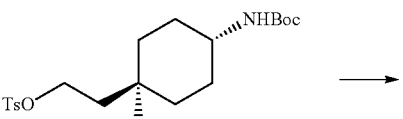

Step 1 Synthesis of Compound 41b

A compound 40b (759 mg, 1.83 mmol) was dissolved in dichloromethane (30.4 mL). To the solution was added diethylaminosulfur trifluoride (1.45 mL, 11.0 mmol) at −78° C. The mixture was stirred at −78° C. for 40 minutes. To the reaction mixture, water was added. The mixture was extracted with ethyl acetate. The organic layer was washed by water and brine, and then dried over anhydrous sodium sulfate. The solvent was evaporated under reduced pressure. The obtained residue was purified by silica-gel column chromatography (hexane-ethyl acetate) to give a compound 41b (179 mg, yield 25%) as a racemate.

Step 2 Synthesis of Compound 42b

The compound 41b (500 mg, 1.264 mmol) was dissolved in dichloromethane (10 mL). To the solution was added diethylzinc (1 mol/L toluene solution, 3.16 mL, 3.16 mmol) and diiodomethane (0.51 mL, 6.32 mmol) at 0° C. The mixture was stirred at room temperature for 6 hours. To the reaction mixture were added saturated aqueous solution of ammonium chloride and water. The mixture was extracted with chloroform. The organic layer was washed by brine, and then dried over anhydrous magnesium sulfate. The solvent was evaporated under reduced pressure. The obtained residue was purified by silica-gel column chromatography (hexane-ethyl acetate) to give a compound 42b (59 mg, yield 11%) as a racemate (the relative configuration was as described in the structural formula).

$^1$H-NMR (CDCl$_3$) δ: 0.19-0.21 (m, 1H), 0.45-0.48 (m, 1H), 0.66-0.72 (m, 1H), 0.77-0.87 (m, 1H), 1.05-1.11 (m, 1H), 1.43-1.50 (m, 11H), 1.60-1.74 (m, 2H), 1.81-1.87 (m, 1H), 2.27-2.36 (m, 1H), 2.46 (s, 3H), 3.21 (brs, 1H), 4.04-4.13 (m, 2H), 4.15-4.20 (m, 1H), 7.34-7.37 (m, 2H), 7.78-7.81 (m, 2H).

[M+H] 410.2, method 2, retention time 2.62 min

Reference Example 10" Synthesis of Compound 45b

[Chemical Formula 163]

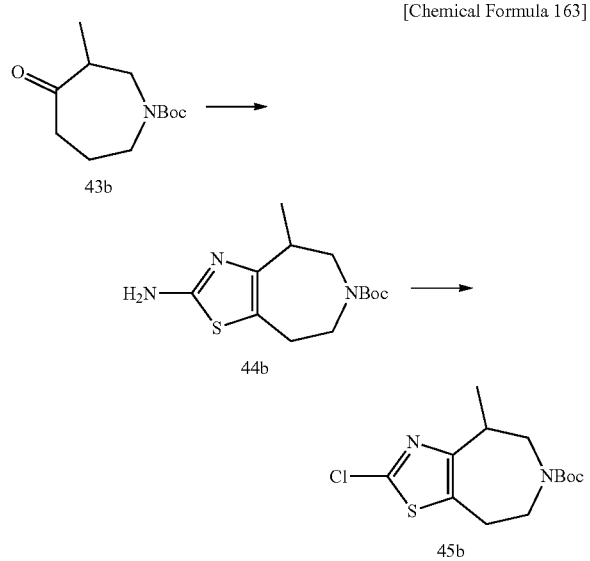

Step 1 Synthesis of Compound 44b

A compound 44b was synthesized by using the compound 43b instead of the compound 73 in Step 1 of Reference Example 5.

Step 2 Synthesis of Compound 45b

A compound 45b was synthesized by using the compound 44b instead of the compound 74 in Step 2 of Reference Example 5.

$^1$H-NMR (CDCl$_3$) δ: 1.25-1.28 (m, 3H), 1.48 (s, 9H), 2.80-2.99 (m, 2H), 3.22-4.01 (m, 6H).

Example 4" Synthesis of Compound III-708

[Chemical Formula 164]

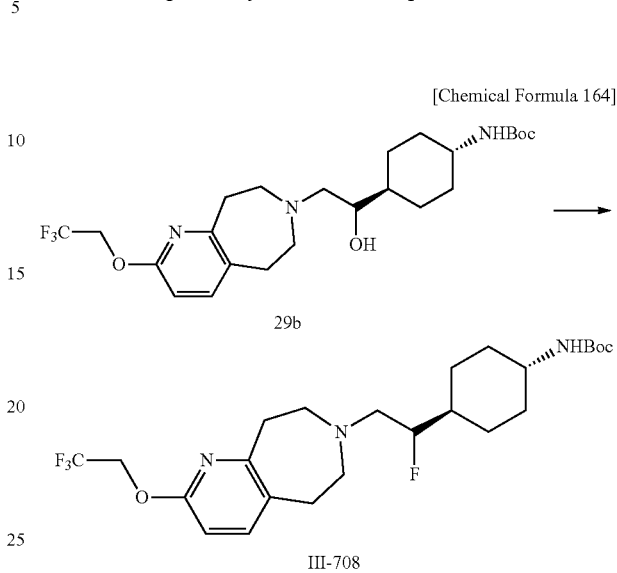

Step 1 Synthesis of Compound III-708

A compound 29b (50 mg, 0.103 mmol) was dissolved in dichloromethane (1 mL). To the solution was added (diethylamino)sulfur trifluoride (81 μL, 0.615 mmol) at −78° C. The mixture was stirred at −78° C. for 50 minutes and then stirred at room temperature overnight. To the mixture was added tetrabutylammonium fluoride (1 mol/L, THF solution, 206 μL, 0.206 mmol). The mixture was stirred at room temperature overnight. To the reaction mixture was added saturated aqueous solution of sodium hydrogen carbonate. The mixture was extracted with ethyl acetate. The organic layer was washed by brine, and then dried over anhydrous sodium sulfate. The solvent was evaporated under reduced pressure. The obtained residue was purified by silica-gel column chromatography (hexane-ethyl acetate) to give a compound III-708 (14.3 mg, yield 29%).

$^1$H-NMR (CDCl$_3$) δ: 1.03-1.32 (m, 5H), 1.44 (s, 9H), 1.69-1.74 (m, 1H), 1.88-1.93 (m, 1H), 2.05-2.08 (m, 2H), 2.62-2.84 (m, 8H), 3.03-3.05 (m, 2H), 3.38 (brs, 1H), 4.37-4.53 (m, 2H), 4.74 (q, J=8.7 Hz, 2H), 6.59 (d, J=8.0 Hz, 1H), 7.33 (d, J=8.3 Hz, 1H).

Example 5" Synthesis of Compound III-711

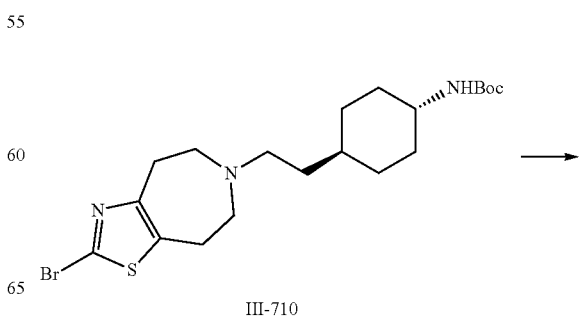

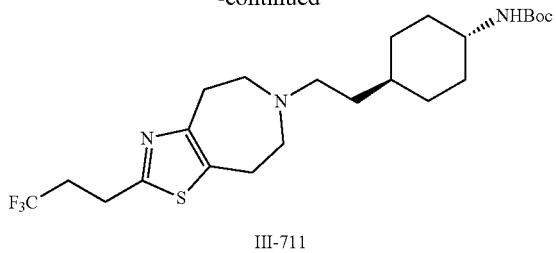

III-711

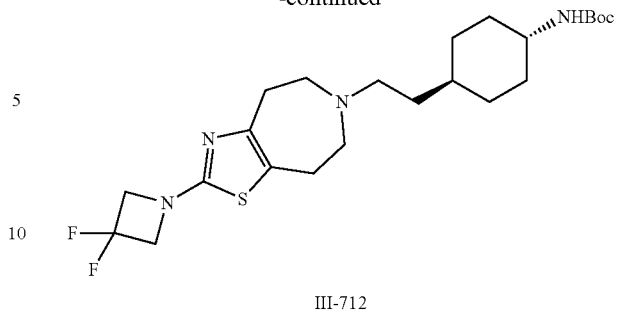

III-712

Step 1 Synthesis of Compound III-711

A compound III-710 (200 mg, 0.436 mmol, which can be synthesized by the similar methods of Step 3, 4 of Example 1 using 41a as a starting material), potassium trifluoro(3,3,3-trifluoropropyl)borate (356 mg, 1.745 mmol), RuPhos Pd G3 (36.5 mg, 0.044 mmol) were suspended in toluene (8 mL). To the suspension was added cesium carbonate (426 mg, 1.309 mmol) dissolved in water (4 mL). The mixture was stirred at 110° C. for 41 hours. To the reaction mixture, water was added. The mixture was extracted with ethyl acetate. The organic layer was washed by brine, and then dried over anhydrous sodium sulfate. The solvent was evaporated under reduced pressure. The obtained residue was purified by silica gel column chromatography (ethyl acetate) to give a compound III-711 (133.3 mg, 64%) as a yellow solid.

1H-NMR (CDCl3) δ: 0.96-1.14 (4H, m), 1.18-1.30 (1H, m), 1.37-1.44 (2H, m), 1.44 (9H, s), 1.73-1.80 (2H, m), 1.95-2.04 (2H, m), 2.54-2.64 (4H, m), 2.77-2.88 (6H, m), 2.97-3.02 (2H, m), 3.08-3.15 (2H, m), 3.37 (1H, brs), 4.37 (1H, brs).

[M+H] 476.30, method 3, retention time 1.56 min

Example 6″ Synthesis of Compound III-712

[Chemical Formula 165]

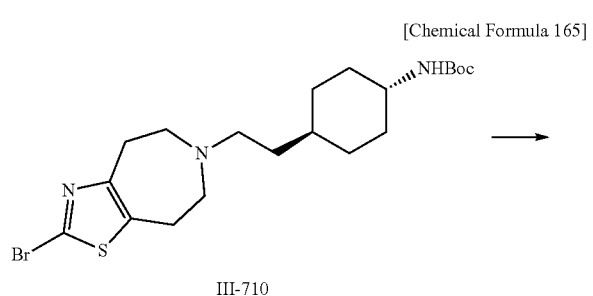

III-710

Step 1 Synthesis of Compound III-712

3,3-difluoroazetidine hydrochloride (62.2 mg, 0.480 mmol), sodium tert-butoxide (126 mg, 1.309 mmol), xantphos (25.2 mg, 0.044 mmol), Pd2(dba)3 (19.97 mg, 0.022 mmol) were suspended in 1,4-dioxane (5 mL). To the suspension was added the compound III-710 (200 mg, 0.436 mmol). The mixture was stirred at 80° C. for 2.5 hours. To the mixture was added Boc2O (0.101 mL, 0.436 mmol) and the mixture was stirred at room temperature for 30 minutes. Then, to the reaction solution were added water and sodium chloride. The mixture was extracted with chloroform. The solvent was evaporated under reduced pressure. The obtained residue was purified by silica-gel column chromatography (chloroform-methanol) to give a compound III-712 (106.6 mg, 52%) as an orange solid.

1H-NMR (CDCl3) δ: 0.96-1.14 (4H, m), 1.18-1.30 (1H, m), 1.37-1.44 (2H, m), 1.44 (9H, s), 1.73-1.80 (2H, m), 1.95-2.04 (2H, m), 2.54-2.64 (2H, m), 2.69-2.76 (2H, m), 2.77-2.88 (6H, m), 3.36 (1H, brs), 4.35 (3H, t, J=11.9 Hz), 4.37 (1H, brs).

[M+H] 471.30, method 3, retention time 1.48 min

The following compounds were synthesized in similar manners as described above. In the tables, RT represents LC/MS retention time (min). In the following tables, regarding stereo-information, the stereostructures of the compounds were determined as described in the structural formulas. If there are no specific descriptions of stereo-information, it indicates the compounds are racemates.

I-029, I-033, I-050, I-060, I-091, and I-147 are racemates, and the relative configurations of them are as described in the structural formulas.

III-624, III-625, III-628, and III-629 are respectively either R enantiomer or S enantiomer, though the stereo-information is unknown.

III-626, III-627, III-668, and III-669 are single optical isomers and the relative configurations of them were determined as described in the structural formulas, though the absolute configurations of them are unknown.

| Compound No | Structure | LC/MS method | RT (min) | MS (m/z) |
|---|---|---|---|---|
| I-001 | 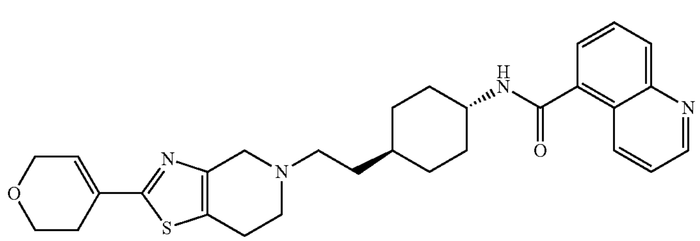 | 1 | 1.85 | 503.3 |

| | | | | |
|---|---|---|---|---|
| I-002 | 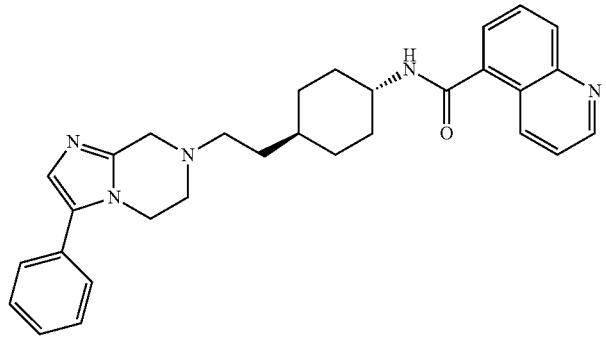 | 3 | 1.03 | 480.3 |
| I-003 | 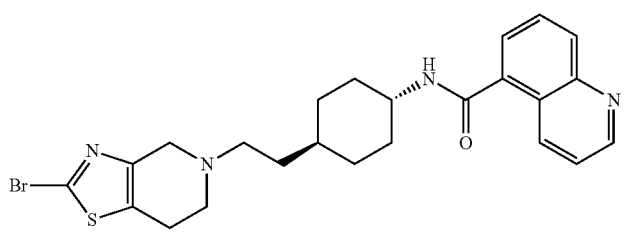 | 1 | 2.01 | 499, 501 |
| I-004 | 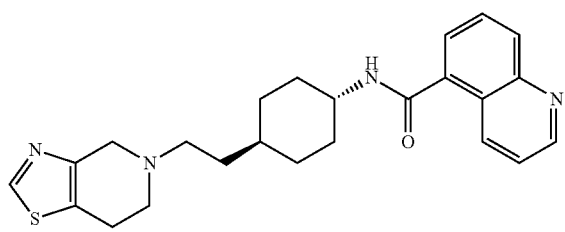 | 1 | 1.36 | 421.2 |
| I-005 | 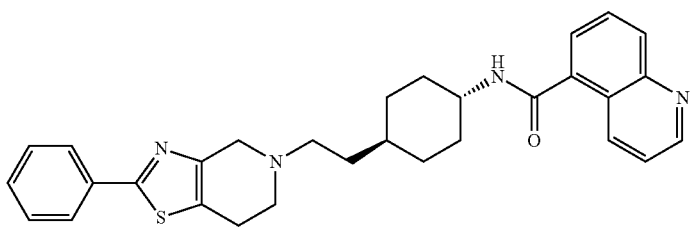 | 1 | 1.71 | 497.3 |
| I-006 | 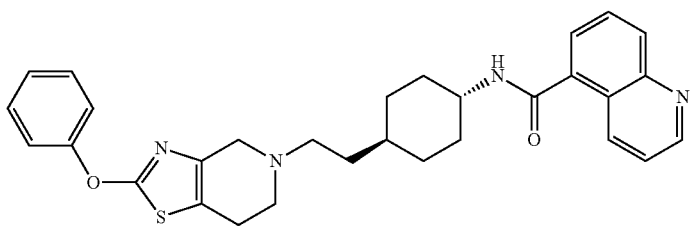 | 2 | 1.34 | 513.3 |
| I-007 | 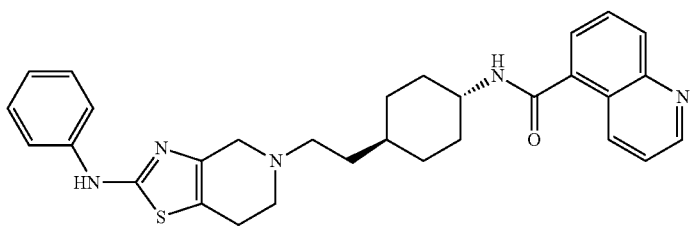 | 2 | 1.35 | 512.3 |

| | | | | |
|---|---|---|---|---|
| I-008 | 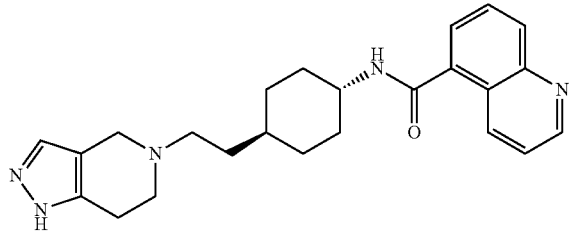 | 1 | 1.3 | 404.3 |
| I-009 | 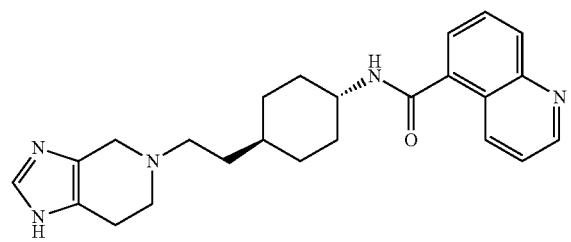 | 1 | 1.19 | 404.3 |
| I-010 | 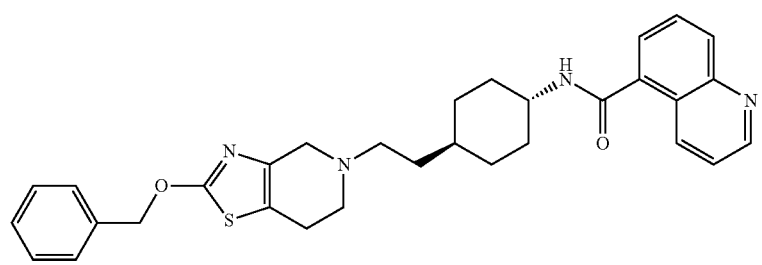 | 1 | 2.31 | 527 |
| I-011 | 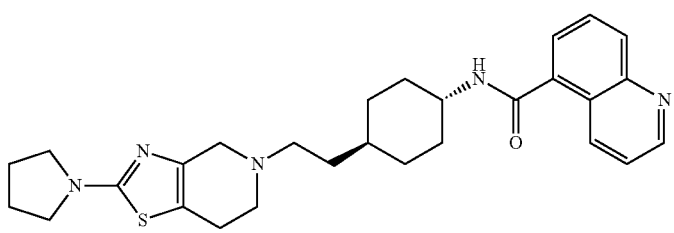 | 1 | 1.57 | 490.3 |
| I-012 | 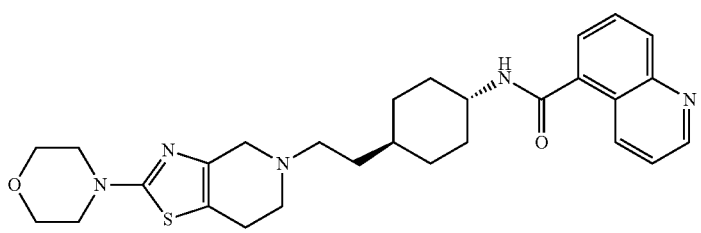 | 1 | 1.49 | 506.3 |
| I-013 | 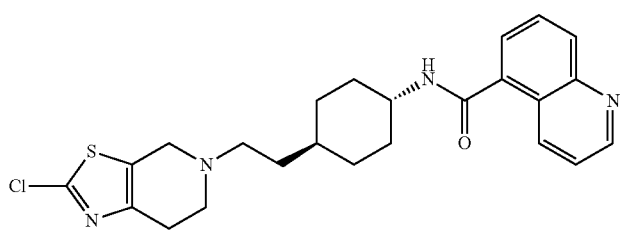 | 2 | 0.88 | 455, 457 |

| | | | | |
|---|---|---|---|---|
| I-014 | 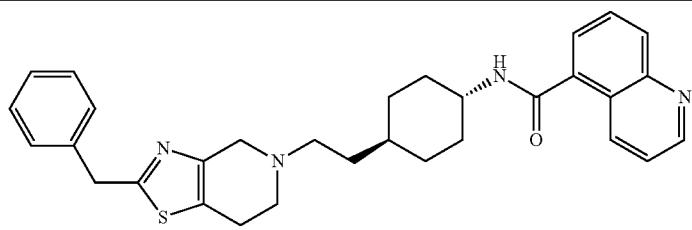 | 2 | 1.36 | 511.3 |
| I-015 | 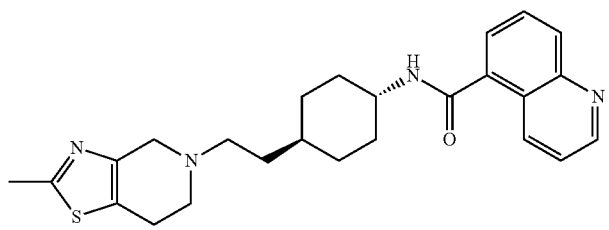 | 2 | 0.92 | 435.3 |
| I-016 | 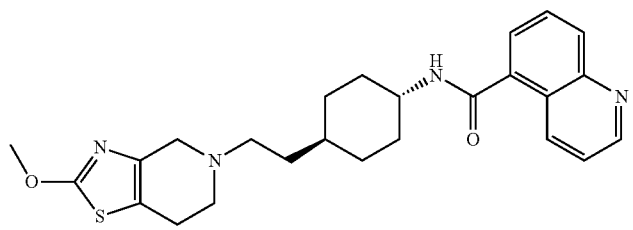 | 2 | 0.93 | 451.3 |
| I-017 | 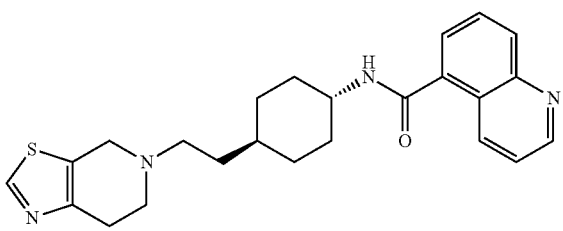 | 2 | 0.59 | 421.2 |
| I-018 | 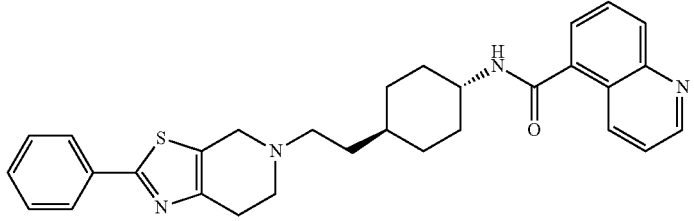 | 2 | 1.28 | 497.3 |
| I-019 | 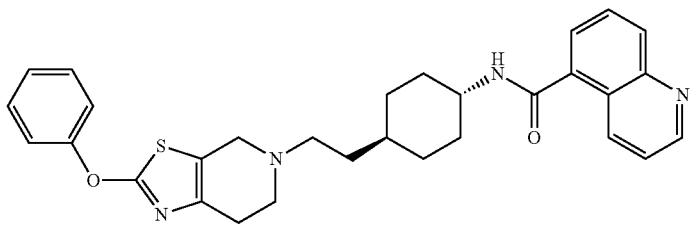 | 2 | 1.3 | 513.3 |
| I-020 | 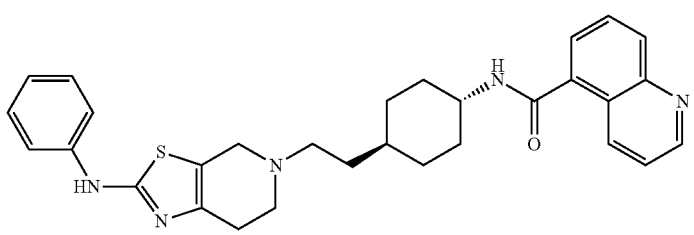 | 2 | 1.29 | 512.3 |

| | | | | |
|---|---|---|---|---|
| I-021 | 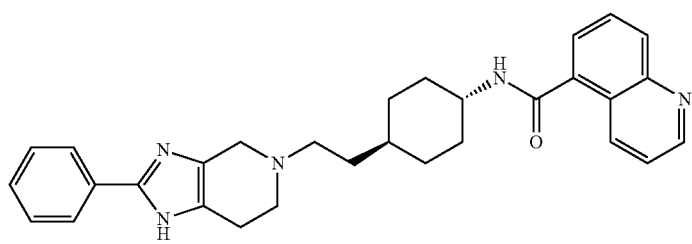 | 2 | 0.87 | 240.7 |
| I-022 | 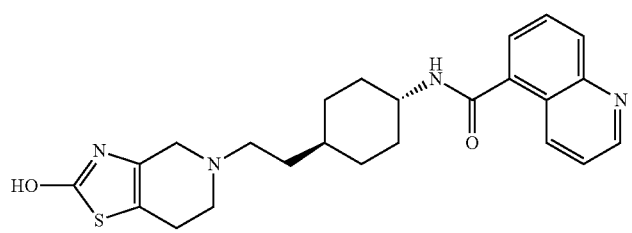 | 2 | 0.7 | 437.2 |
| I-023 | 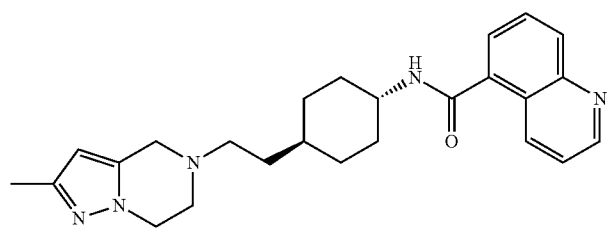 | 1 | 1.67 | 418.2 |
| I-024 | 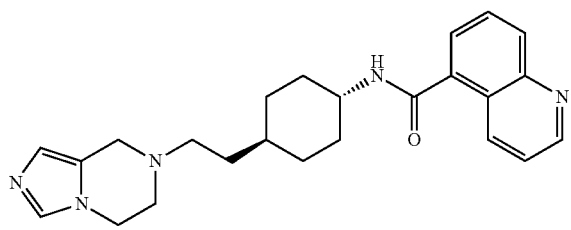 | 1 | 1.42 | 404.2 |
| I-025 | 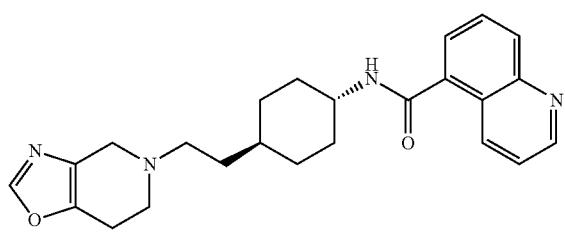 | 1 | 1.59 | 405.2 |
| I-026 | 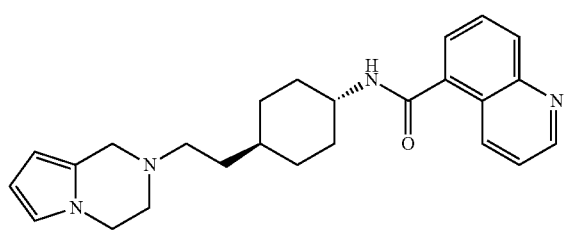 | 1 | 1.97 | 403.2 |

| | | | | |
|---|---|---|---|---|
| I-027 | 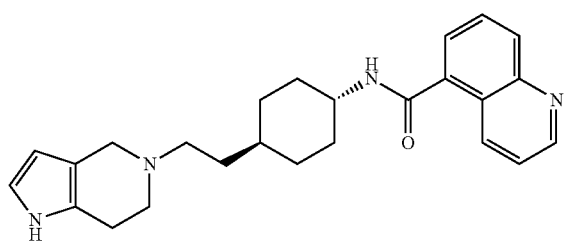 | 1 | 1.57 | 403.2 |
| I-028 | 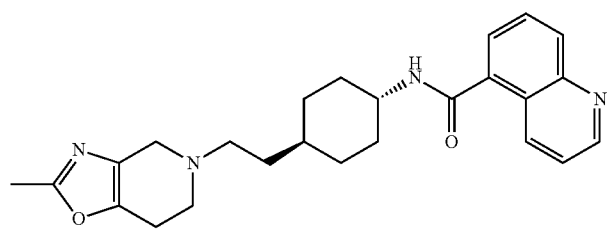 | 1 | 1.64 | 419.2 |
| I-029 | 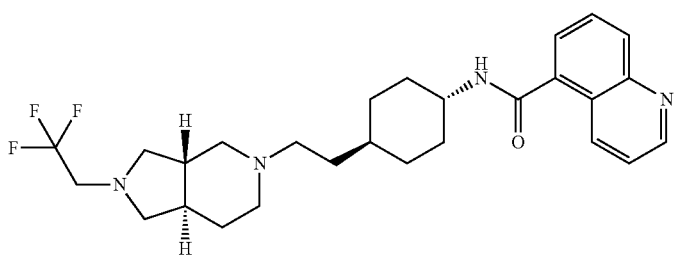 | 1 | 1.79 | 489.3 |
| I-030 | 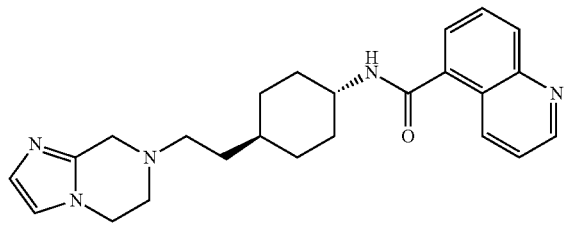 | 3 | 0.7 | 404.3 |
| I-031 | 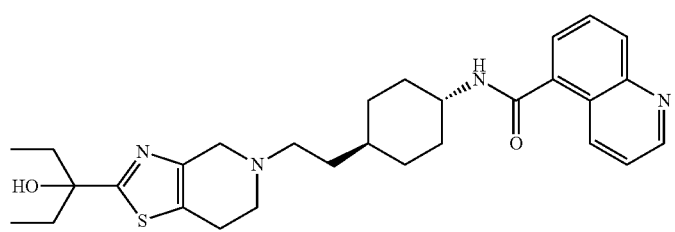 | 1 | 1.81 | 507.2 |
| I-032 | 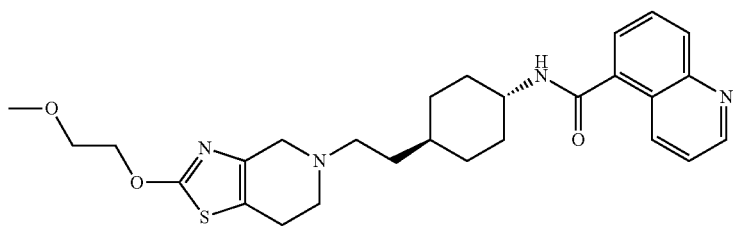 | 1 | 1.83 | 495.1 |

| | | | | |
|---|---|---|---|---|
| I-033 | 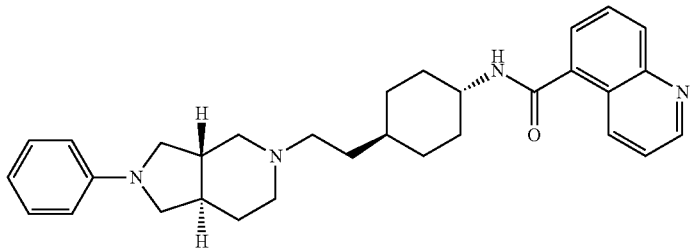 | 1 | 2.42 | 483.2 |
| I-034 | 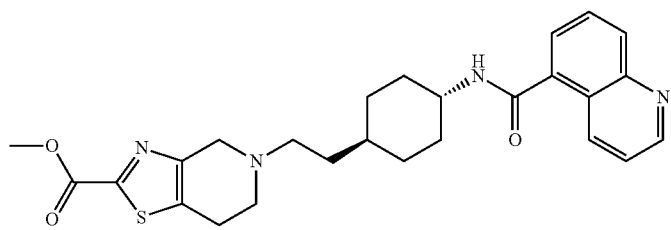 | 1 | 1.7 | 479.2 |
| I-035 | 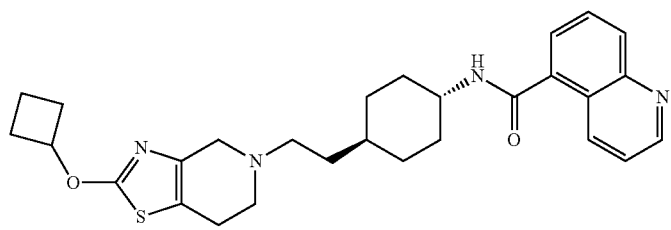 | 1 | 2.32 | 491 |
| I-036 | 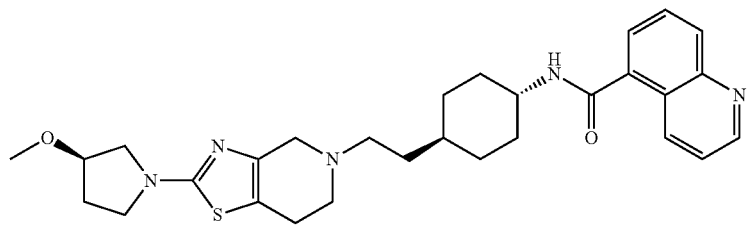 | 1 | 1.8 | 520.1 |
| I-037 | 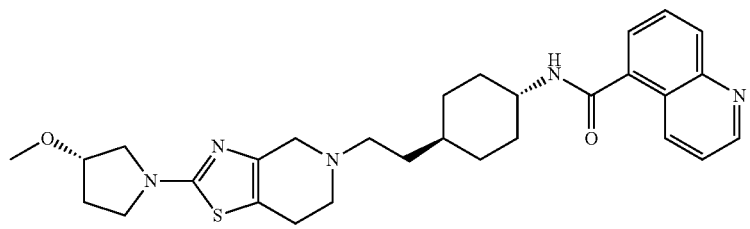 | 1 | 1.8 | 520.1 |
| I-038 | 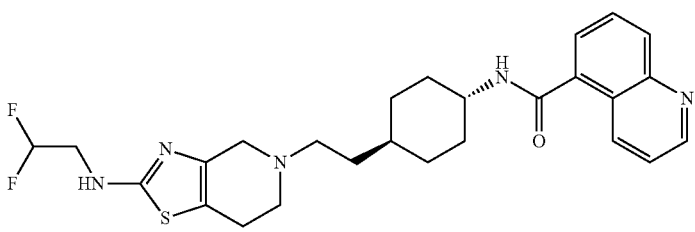 | 1 | 1.7 | 500.2 |
| I-039 | 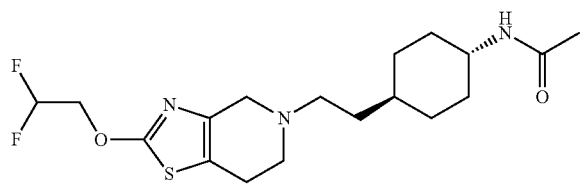 | 1 | 1.77 | 388 |

| | | | | |
|---|---|---|---|---|
| I-040 | 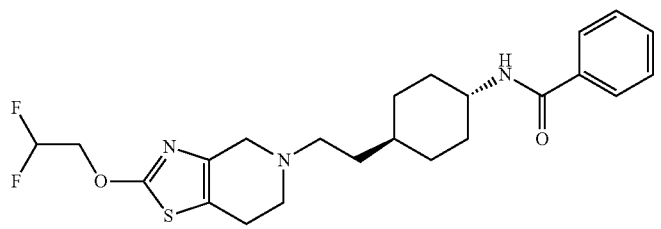 | 1 | 2.26 | 450 |
| I-041 | 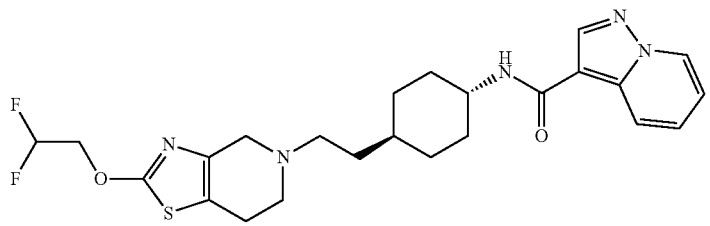 | 1 | 2.09 | 490 |
| I-042 | 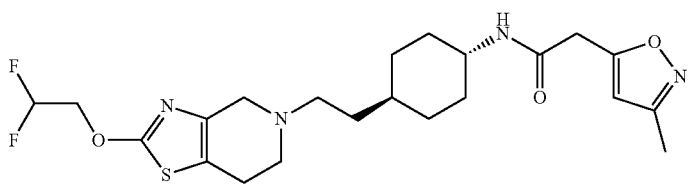 | 1 | 1.97 | 469.1 |
| I-043 | 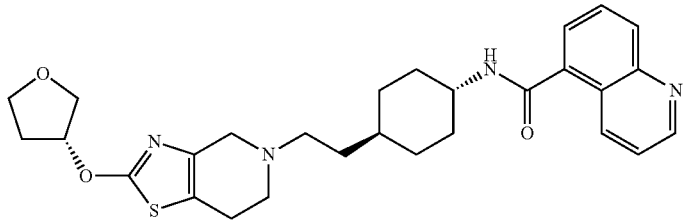 | 1 | 1.86 | 507.1 |
| I-044 | 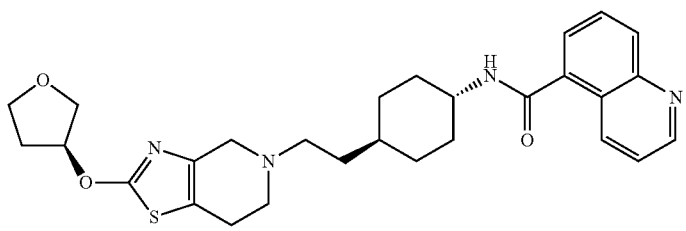 | 1 | 1.86 | 507.1 |
| I-045 | 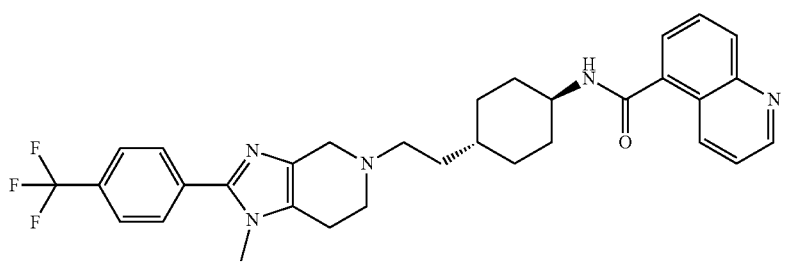 | 1 | 2 | 562.2 |
| I-046 | 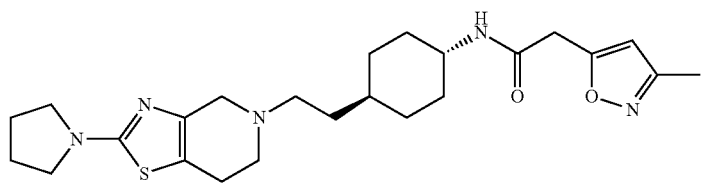 | 3 | 0.94 | 458.35 |

| | | | | |
|---|---|---|---|---|
| I-047 | 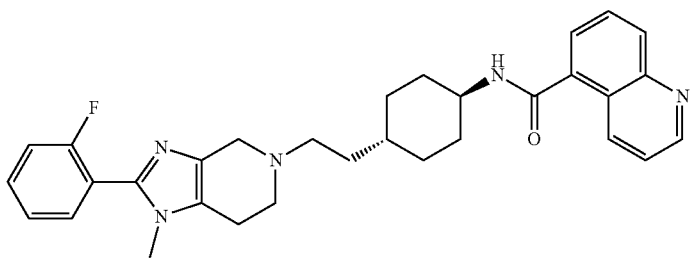 | 1 | 1.73 | 512.2 |
| I-048 | 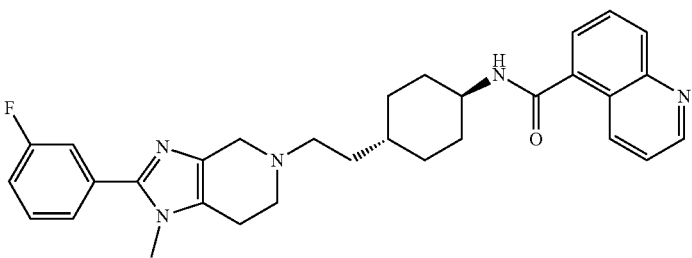 | 1 | 1.77 | 512.2 |
| I-049 | 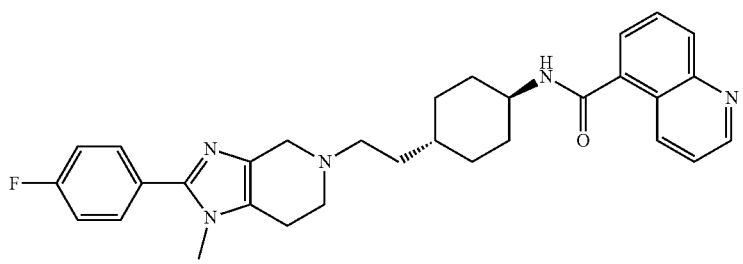 | 1 | 1.75 | 512.2 |
| I-050 | 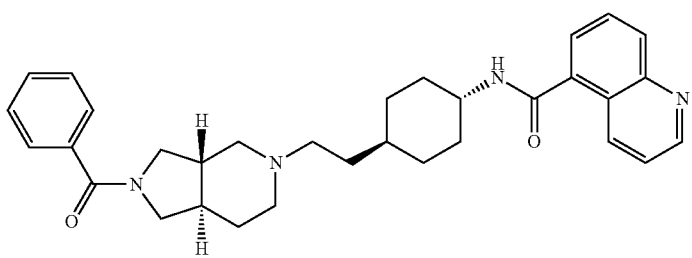 | 1 | 1.67 | 511.3 |
| I-051 | 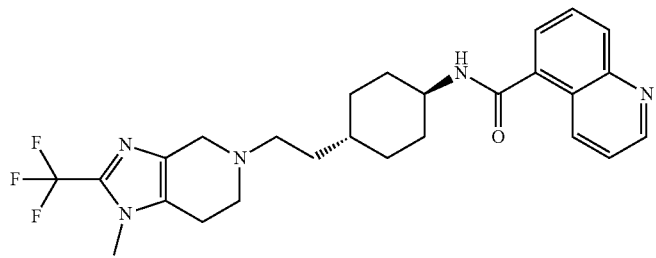 | 1 | 1.66 | 486.2 |
| I-052 | 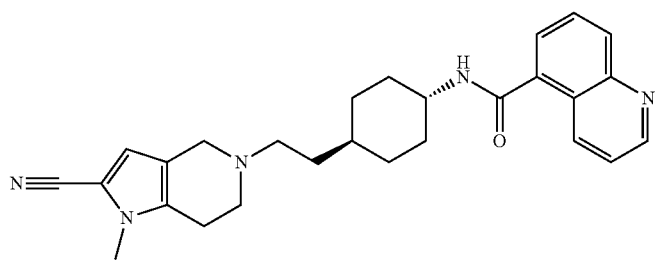 | 1 | 1.83 | 442.2 |

| | | | | |
|---|---|---|---|---|
| I-053 | 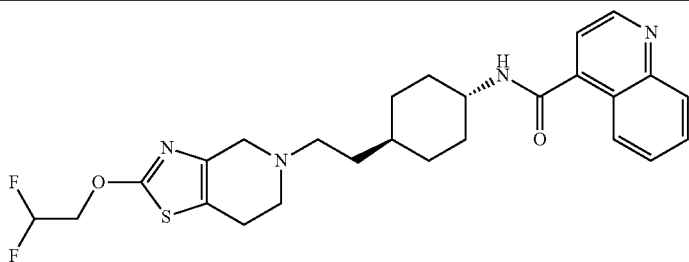 | 4 | 1.01 | 501.3 |
| I-054 | 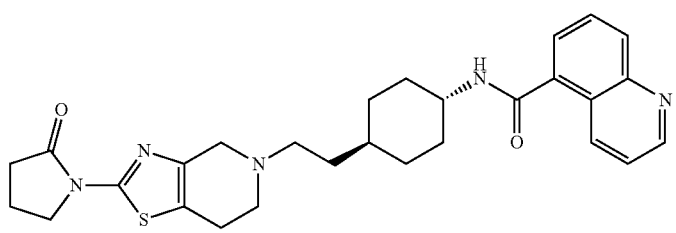 | 1 | 1.65 | 504.2 |
| I-055 | 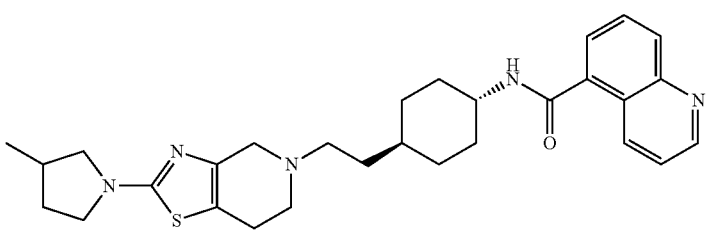 | 1 | 2.14 | 504.4 |
| I-056 | 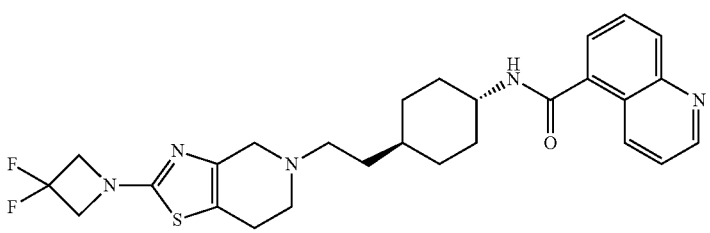 | 1 | 1.95 | 512.1 |
| I-057 | 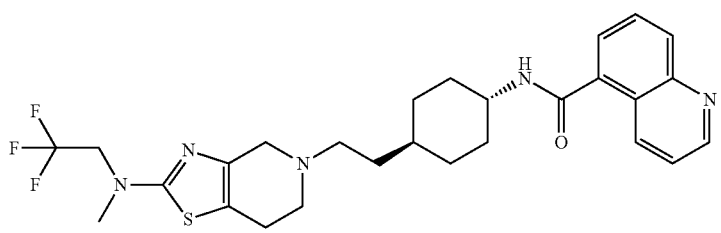 | 1 | 2.18 | 532.3 |
| I-058 | 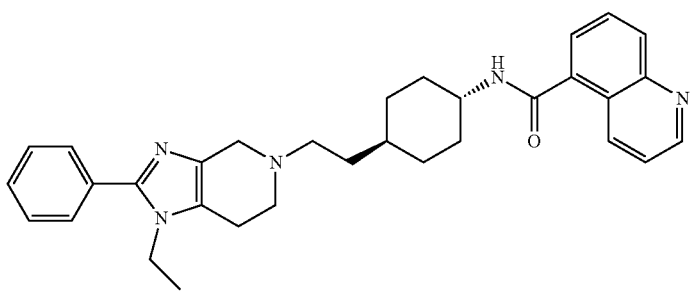 | 1 | 1.83 | 508.3 |

-continued
| | | | | | |
|---|---|---|---|---|---|
| I-059 | 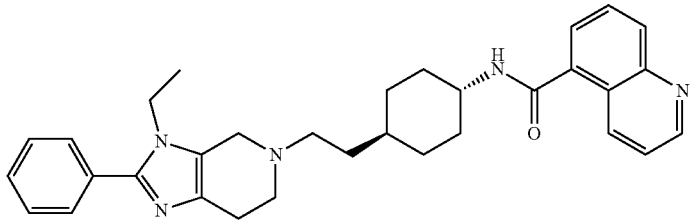 | | 1 | 1.81 | 508.3 |
| I-060 | 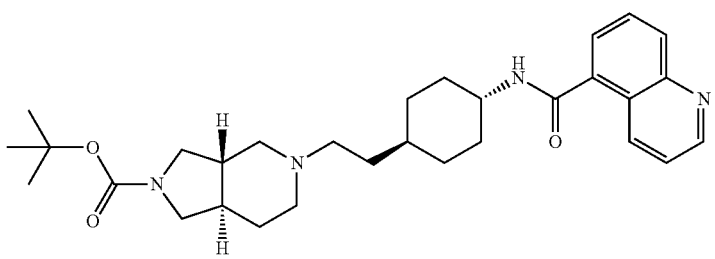 | | 1 | 1.52 | 507.3 |
| I-061 | 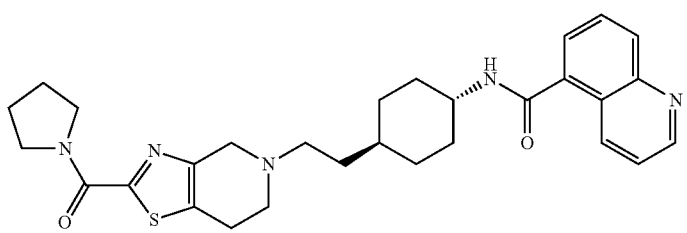 | | 1 | 1.84 | 518.3 |
| I-062 | 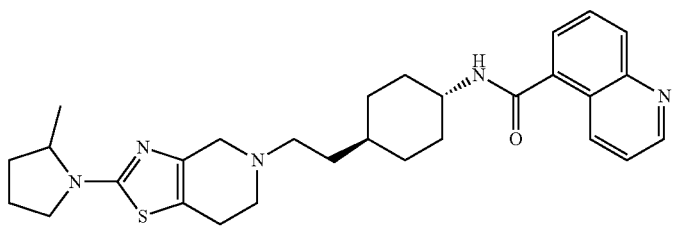 | | 1 | 2.1 | 504.2 |
| I-063 | 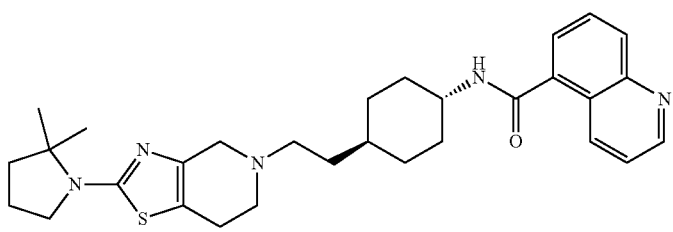 | | 1 | 2.38 | 518.2 |
| I-064 | 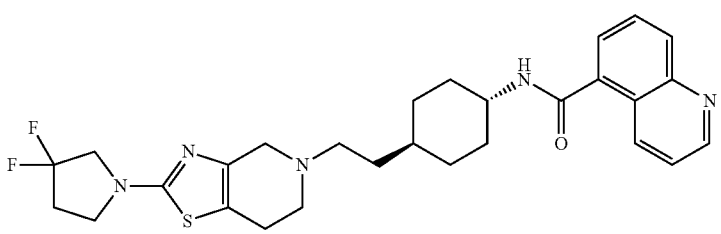 | | 1 | 1.98 | 526.1 |

-continued
| | | | | |
|---|---|---|---|---|
| I-065 | 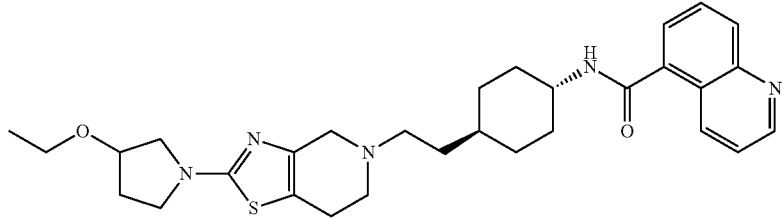 | 1 | 1.94 | 534.2 |
| I-066 | 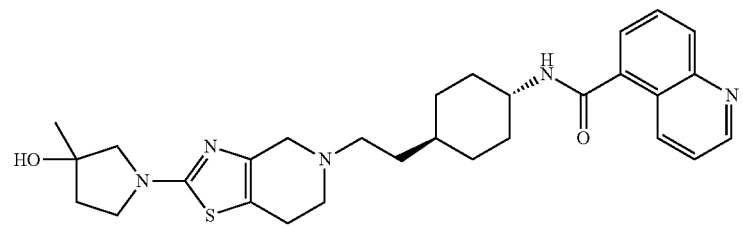 | 1 | 1.61 | 520.2 |
| I-067 | 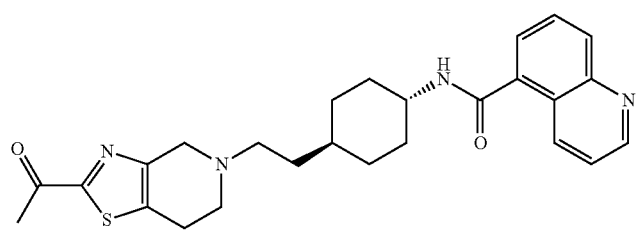 | 1 | 1.78 | 463.2 |
| I-068 | 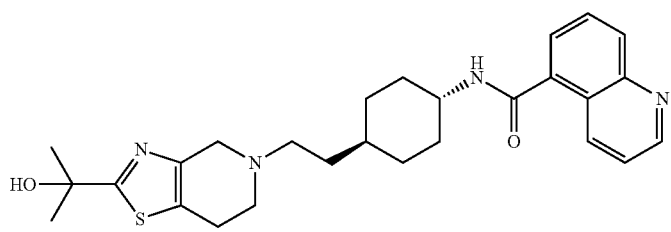 | 1 | 1.53 | 479.2 |
| I-069 | 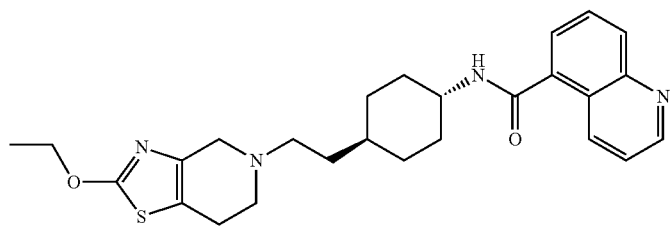 | 1 | 2.01 | 465.2 |
| I-070 | 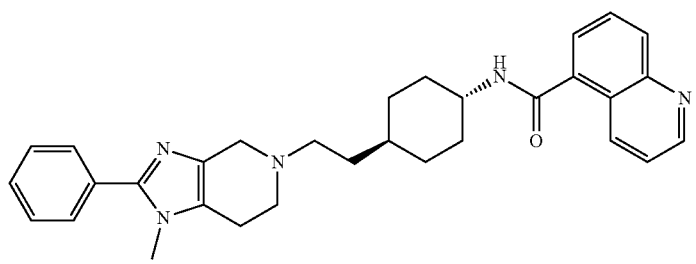 | 3 | 0.71 | 494.35 |

-continued
| | | | | |
|---|---|---|---|---|
| I-071 | 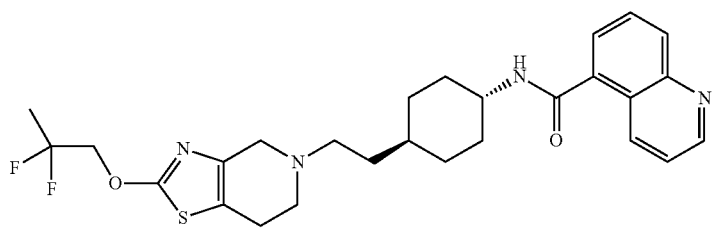 | 1 | 1.8 | 515.2 |
| I-072 | 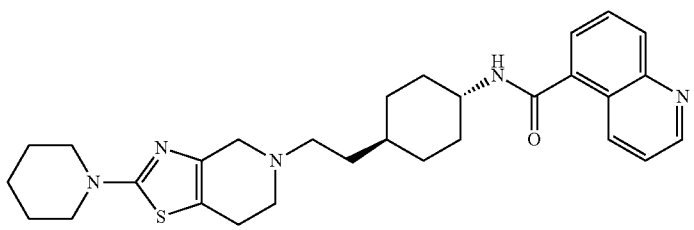 | 1 | 1.65 | 504 |
| I-073 | 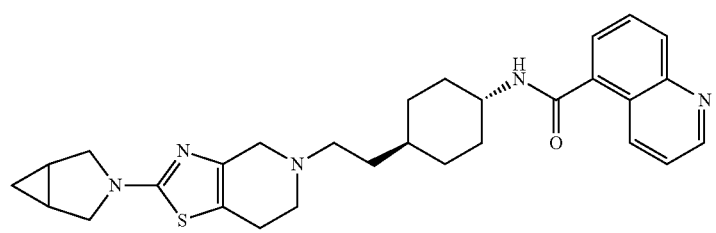 | 1 | 1.58 | 502 |
| I-074 | 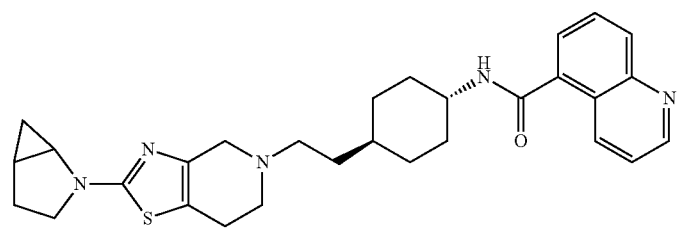 | 1 | 1.27 | 502 |
| I-075 | 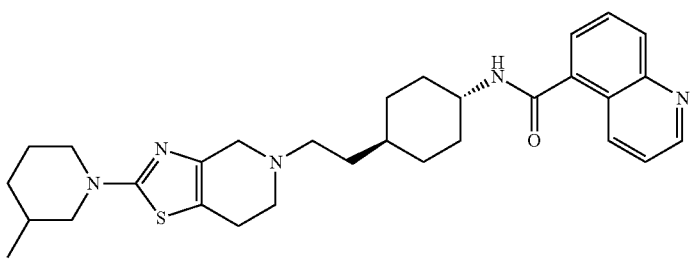 | 1 | 1.74 | 518 |
| I-076 | 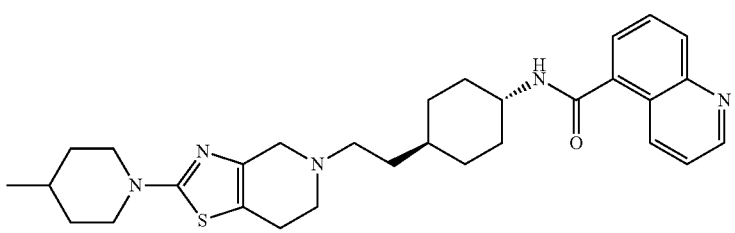 | 1 | 1.77 | 518 |

| | | | | |
|---|---|---|---|---|
| I-077 | 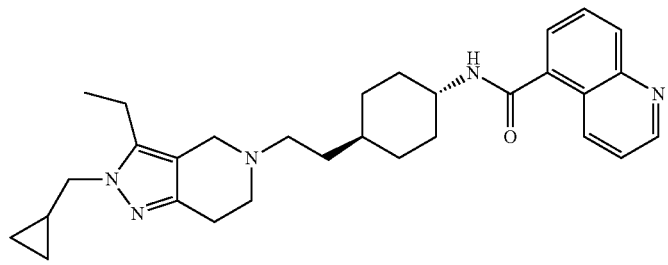 | 3 | 0.93 | 486 |
| I-078 | 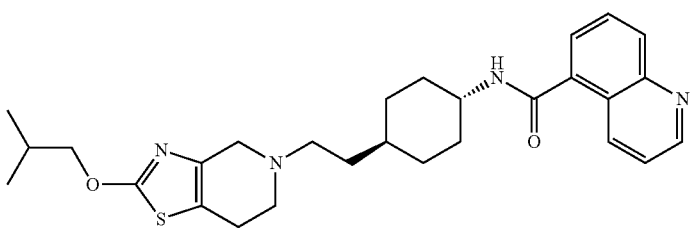 | 1 | 2.41 | 493.3 |
| I-079 | 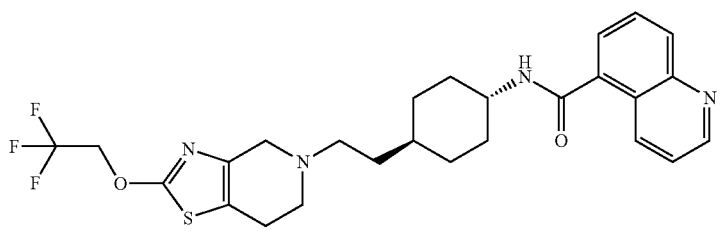 | 1 | 2.25 | 519.2 |
| I-080 | 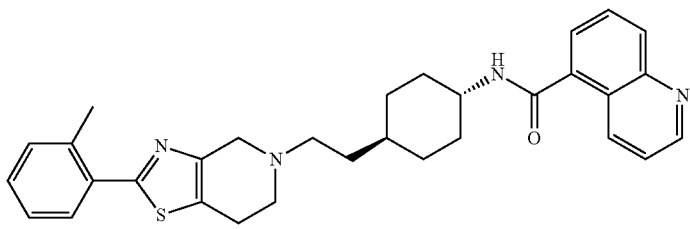 | 1 | 2.47 | 511.3 |
| I-081 | 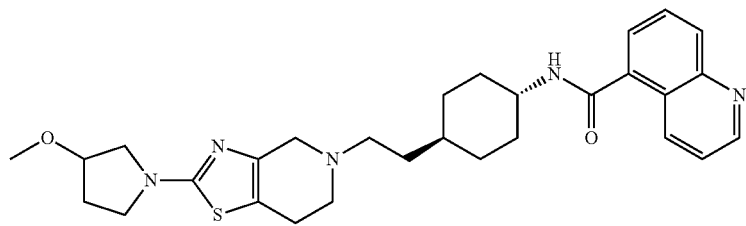 | 1 | 1.78 | 520.2 |
| I-082 | 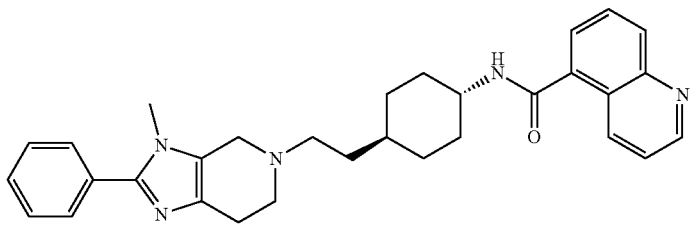 | 1 | 1.43 | 494 |

| | | | | |
|---|---|---|---|---|
| I-083 | 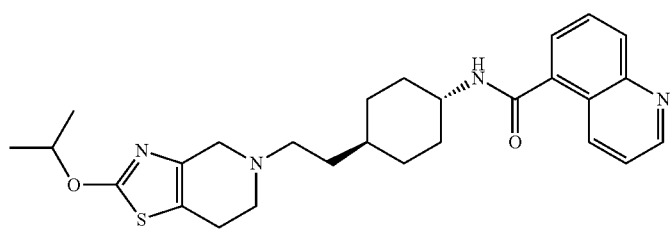 | 1 | 2.19 | 479.2 |
| I-084 | 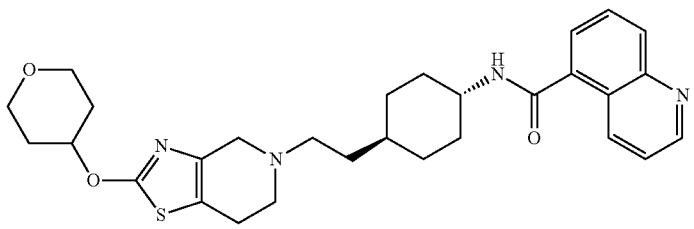 | 1 | 1.94 | 521.2 |
| I-085 | 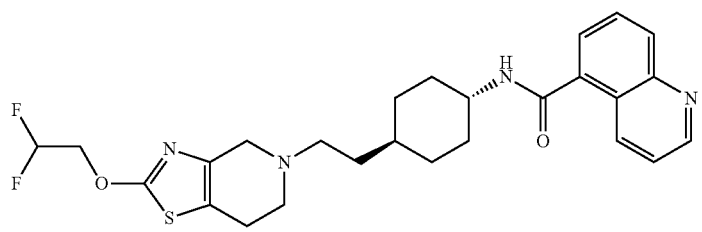 | 1 | 2.04 | 501.1 |
| I-086 | 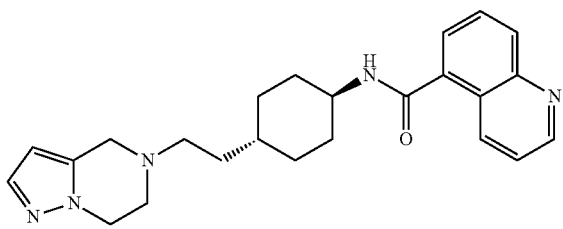 | 1 | 1.44 | 404.2 |
| I-087 | 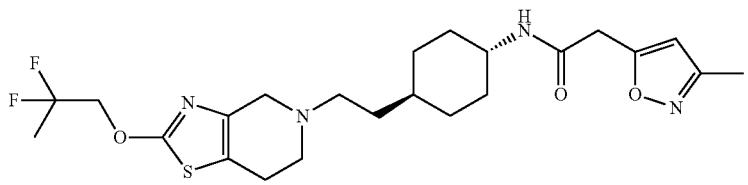 | 3 | 1.1 | 483 |
| I-088 | 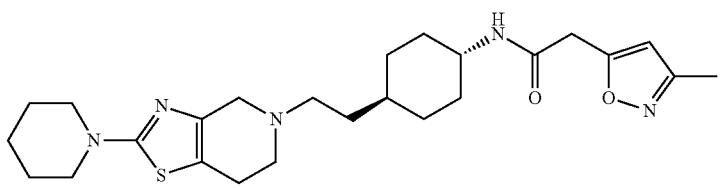 | 3 | 1.1 | 472.35 |
| I-089 | 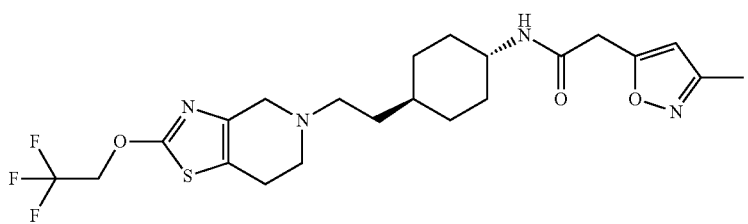 | 3 | 1.11 | 487.3 |

| | | | | |
|---|---|---|---|---|
| I-090 | 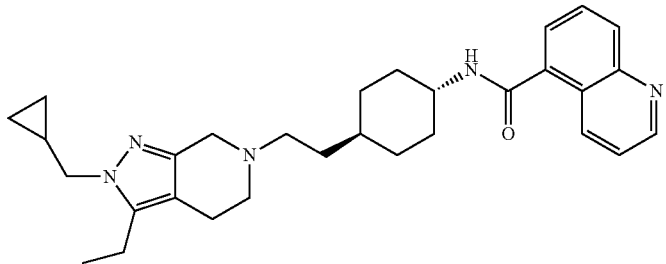 | 3 | 0.98 | 486 |
| I-091 | 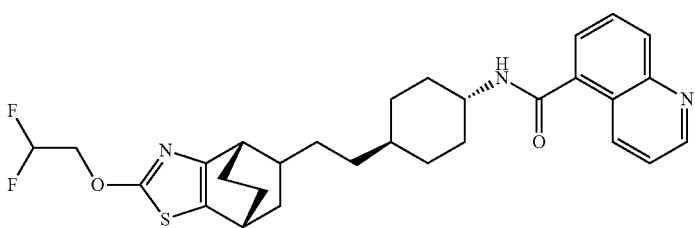 | 2 | 1.22 | 527.2 |
| I-092 | 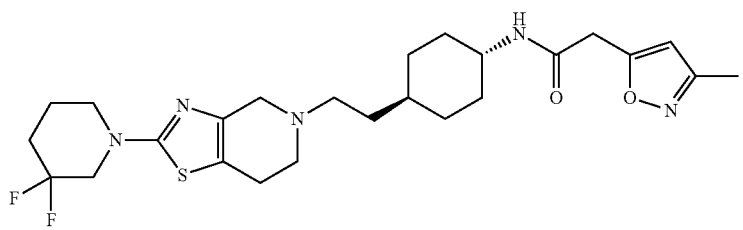 | 3 | 1.24 | 508 |
| I-093 | 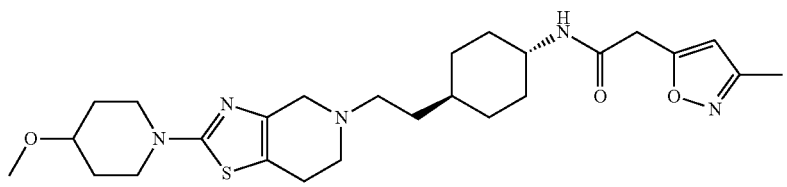 | 3 | 1.12 | 502 |
| I-094 | 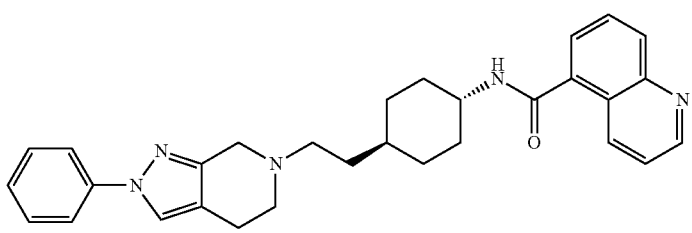 | 3 | 0.97 | 480 |
| I-095 | 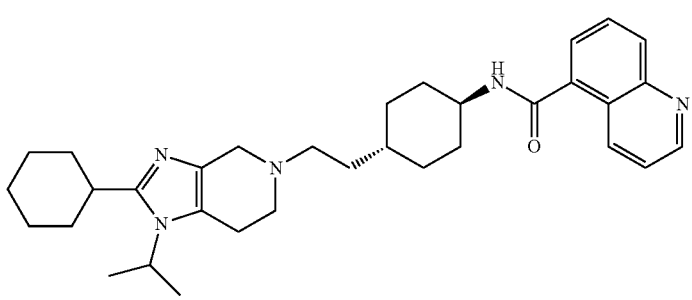 | 2 | 0.79 | 528.5 |

-continued
| | | | | |
|---|---|---|---|---|
| I-096 | 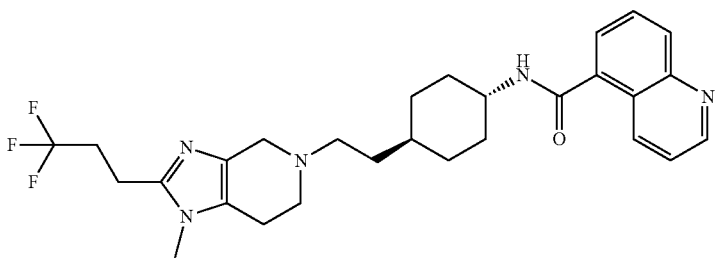 | 2 | 0.79 | 514.2 |
| I-097 | 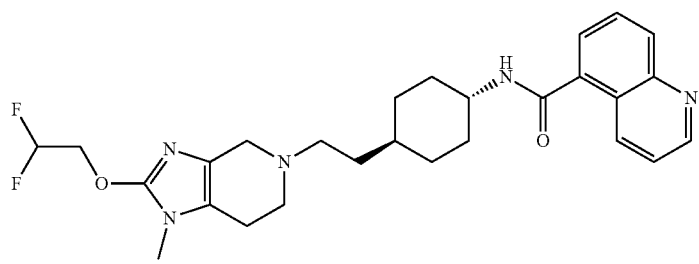 | 2 | 0.94 | 498.2 |
| I-098 | 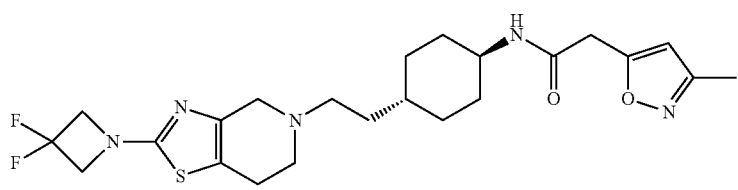 | 3 | 1.09 | 480 |
| I-099 | 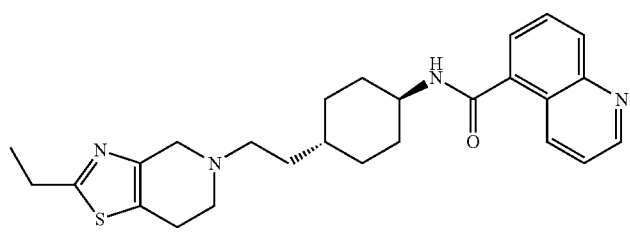 | 2 | 1.99 | 449.3 |
| I-100 | 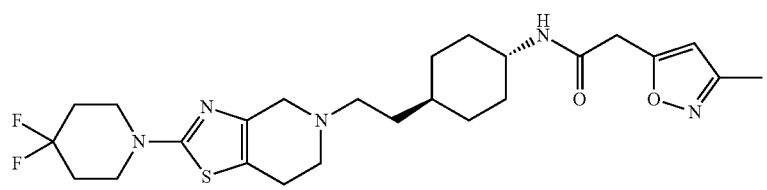 | 3 | 1.28 | 508 |
| I-101 | 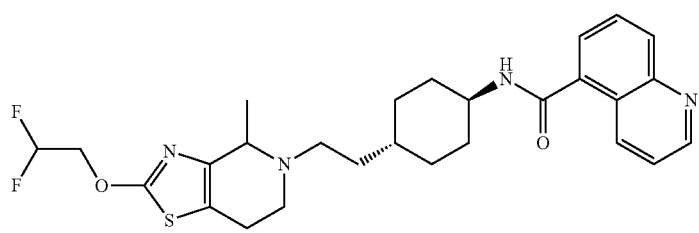 | 2 | 1.17 | 515.2 |

| | | | | |
|---|---|---|---|---|
| I-102 | 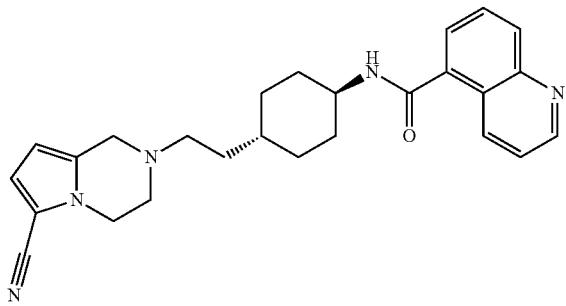 | 2 | 0.91 | 428.3 |
| I-103 | 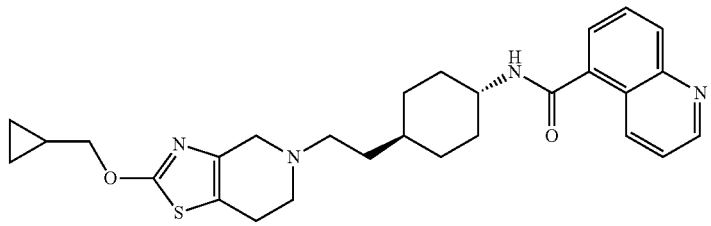 | 2 | 1.42 | 491.3 |
| I-104 | 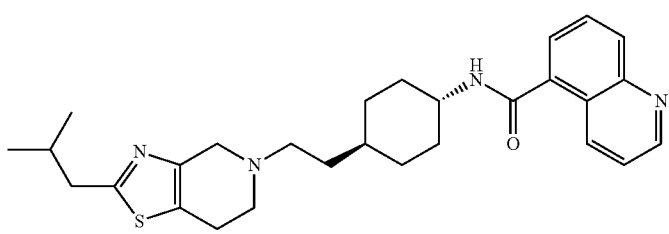 | 2 | 1.31 | 477.3 |
| I-105 | 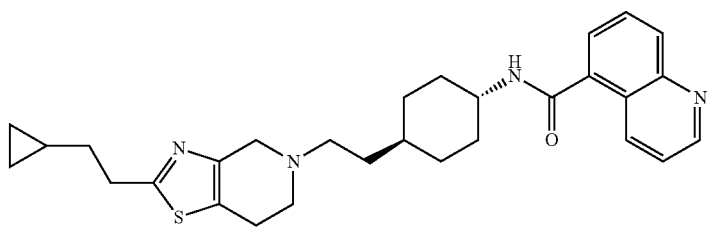 | 2 | 1.41 | 489.2 |
| I-106 | 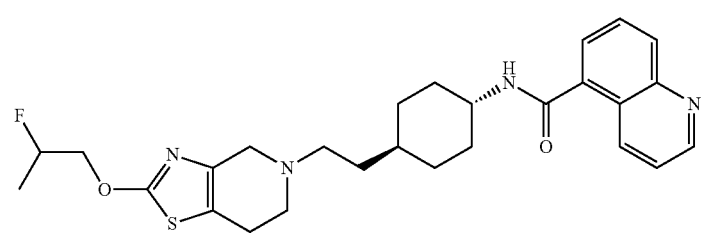 | 2 | 1.16 | 497.2 |
| I-107 | 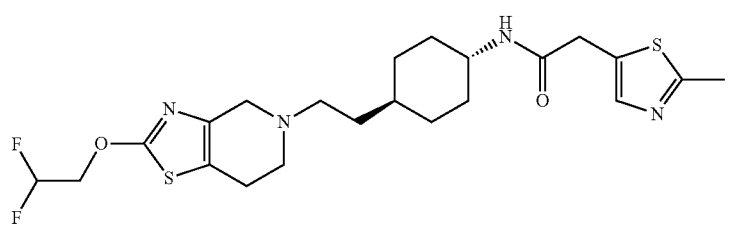 | 3 | 0.93 | 485.3 |

-continued
| | | | | |
|---|---|---|---|---|
| I-108 | 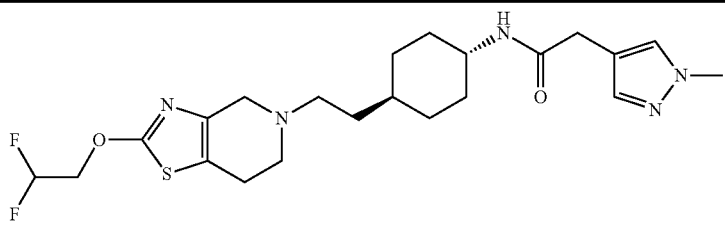 | 3 | 0.89 | 468.3 |
| I-109 | 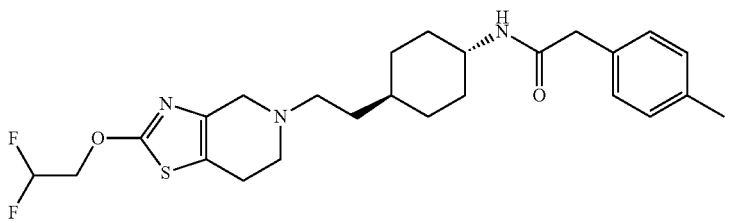 | 3 | 1.28 | 478.35 |
| I-110 | 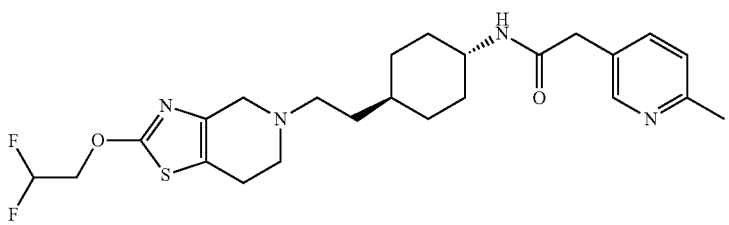 | 3 | 0.62 | 479.35 |
| I-111 | 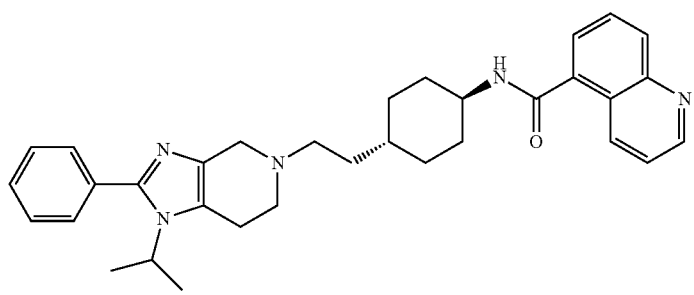 | 1 | 1.93 | 522.3 |
| I-112 | 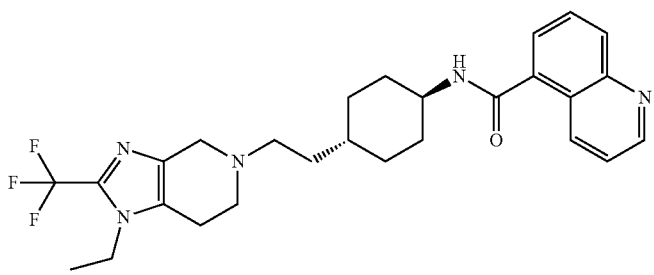 | 1 | 1.8 | 500.2 |
| I-113 | 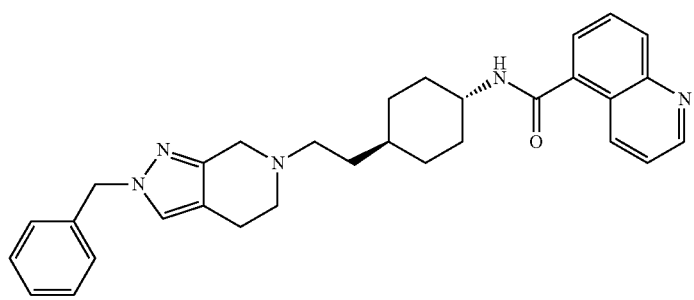 | 3 | 0.95 | 494 |

| | | | | |
|---|---|---|---|---|
| I-114 | 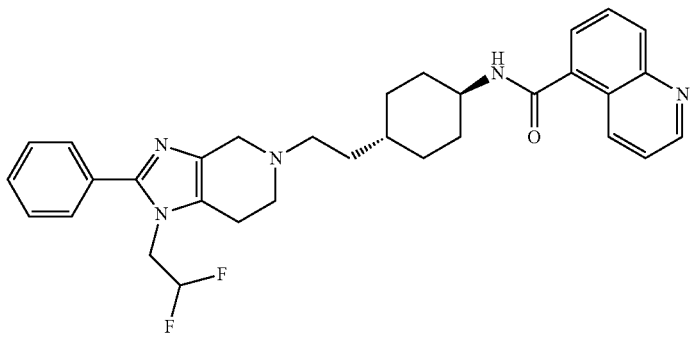 | 1 | 1.8 | 544 |
| I-115 | 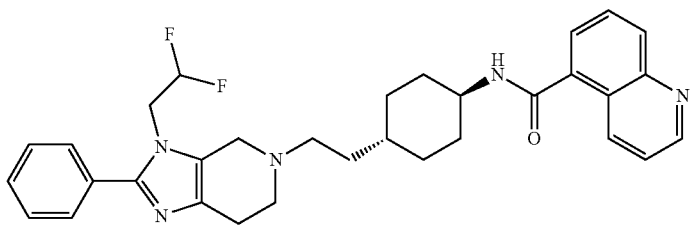 | 1 | 1.78 | 544 |
| I-116 | 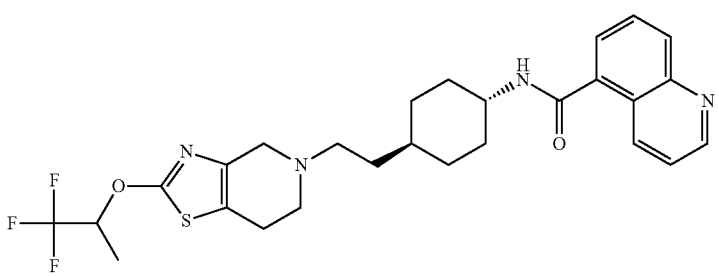 | 4 | 1.27 | 267.15 |
| I-117 | 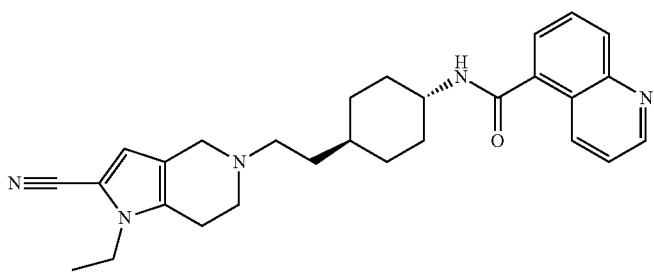 | 2 | 1.4 | 456.2 |
| I-118 | 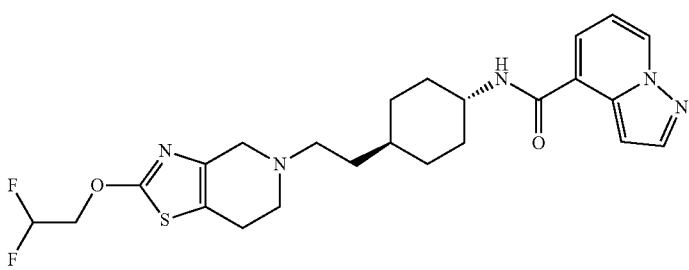 | 3 | 1.02 | 490.35 |
| I-119 | 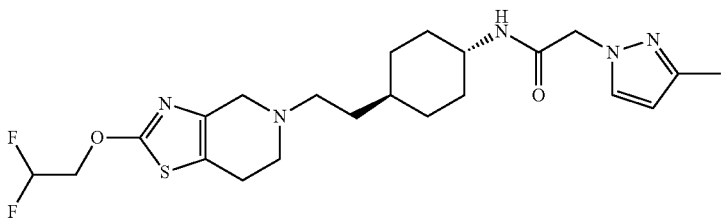 | 3 | 0.97 | 468.35 |

-continued
| | | | | |
|---|---|---|---|---|
| I-120 | 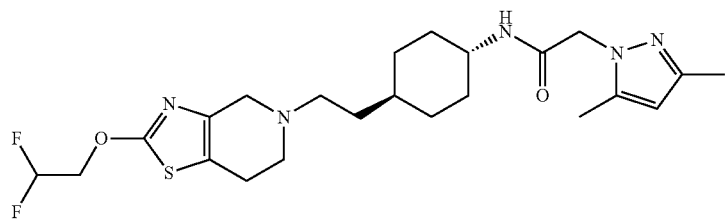 | 3 | 1.03 | 482.3 |
| I-121 | 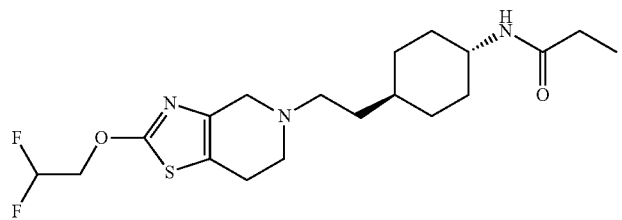 | 3 | 0.9 | 402.6 |
| I-122 | 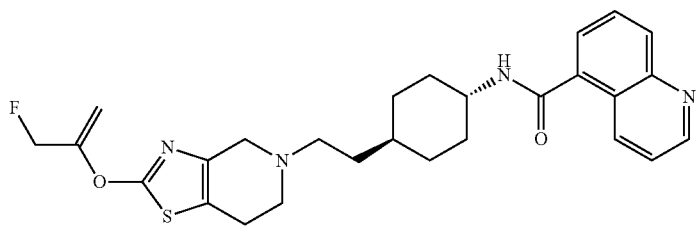 | 2 | 1.07 | 495.2 |
| I-123 | 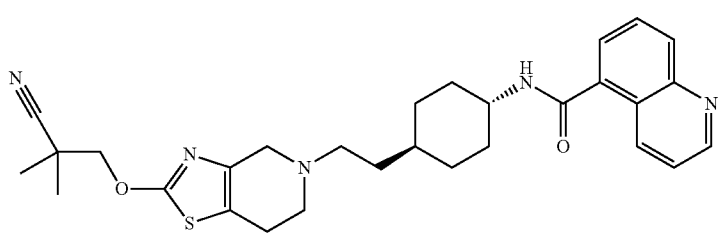 | 2 | 1.14 | 518.2 |
| I-124 | 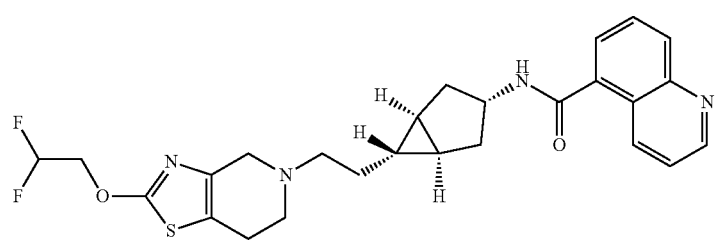 | 3 | 1.05 | 499.25 |
| I-125 | 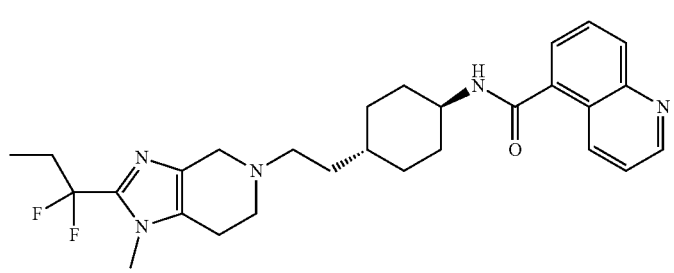 | 1 | 1.81 | 496.3 |

| | | | | |
|---|---|---|---|---|
| I-126 | 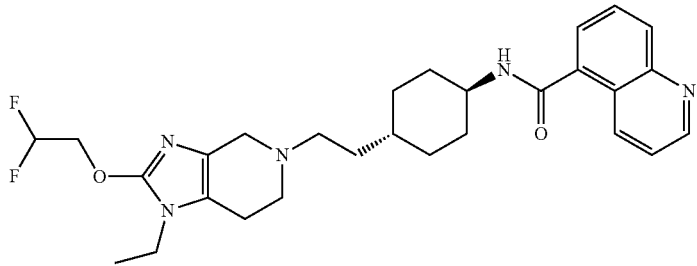 | 1 | 1.78 | 512 |
| I-127 | 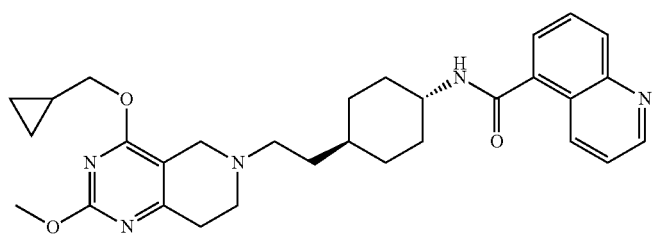 | 3 | 1.02 | 516.3 |
| I-128 | 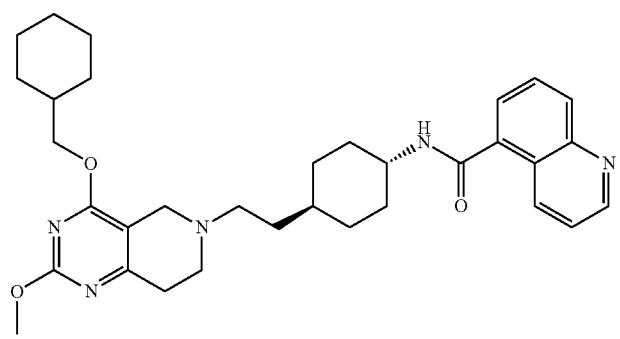 | 3 | 1.41 | 558.4 |
| I-129 | 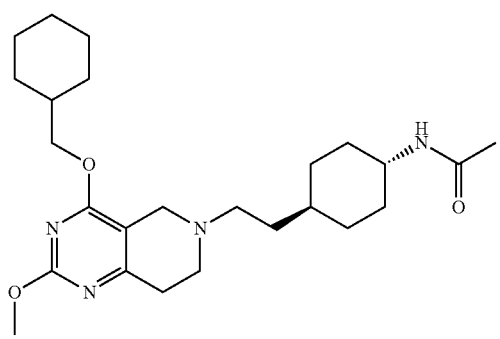 | 3 | 1.4 | 445.4 |
| I-130 | 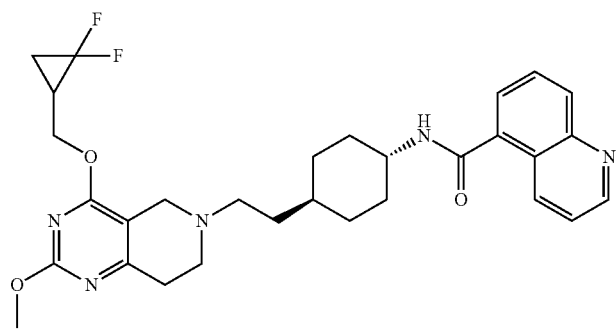 | 3 | 1.15 | 552.3 |

| | | | | |
|---|---|---|---|---|
| | -continued | | | |
| I-131 | | 3 | 1.14 | 558.3 |
| I-132 | | 3 | 0.89 | 458 |
| I-133 | | 3 | 0.88 | 470 |
| I-134 | | 3 | 0.77 | 458 |
| I-135 | | 3 | 0.79 | 470 |
| I-136 | | 3 | 0.87 | 496 |

| | | | | |
|---|---|---|---|---|
| I-137 | 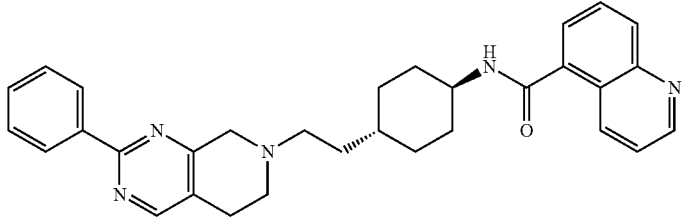 | 3 | 1.21 | 492 |
| I-138 | 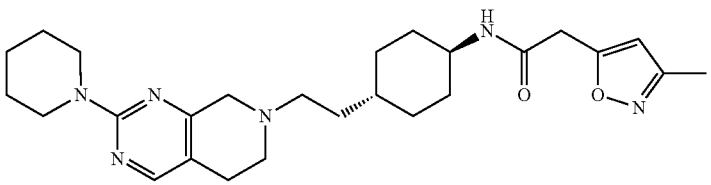 | 3 | 1.28 | 467 |
| I-139 | 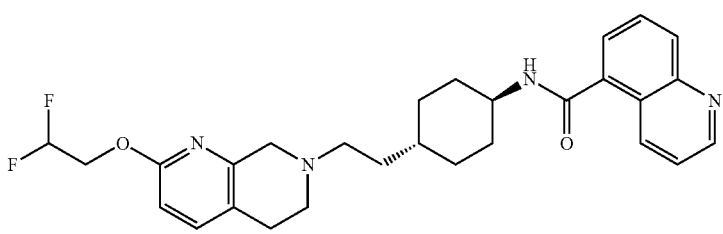 | 3 | 1.07 | 495 |
| I-140 | 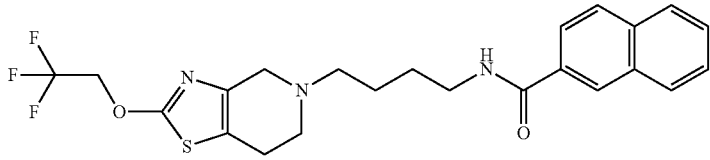 | 4 | 1.65 | 464.15 |
| I-141 | 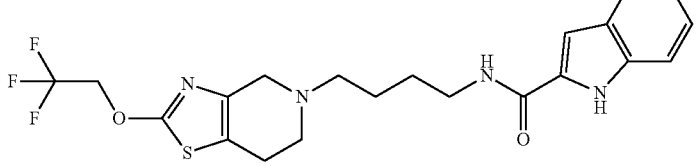 | 4 | 1.58 | 453.15 |
| I-142 | 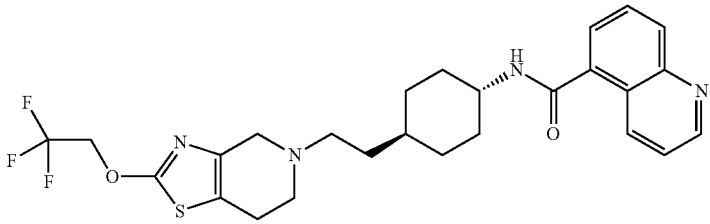 | 3 | 1.07 | 521.25 |
| Compound No. | Structure | NMR or LC/MS |
|---|---|---|
| I-143 | 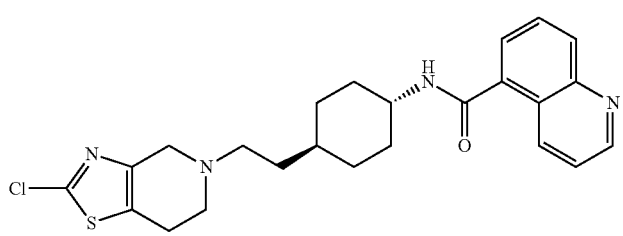 | 1H-NMR (CDCl₃) δ: 1.15-1.40 (m, 5H), 1.50-1.56 (m, 2H), 1.87-1.90 (m, 2H), 2.18-2.22 (m, 2H), 2.58-2.62 (m, 2H), 2.78-2.84 (m, 4H), 3.60 (s, 2H), 3.99-4.08 (m, 1H), 5.84 (d, J = 8.3 Hz, 1H), 7.47 (dd, J = 8.6, 4.2 Hz, 1H), 7.64-7.71 (m, 2H), 8.18 (d, J = 8.0 Hz, 1H), 8.74 (d, J = 8.3 Hz, 1H), 8.95 (dd, J = 4.1, 1.5 Hz, 1H). |

-continued
I-144 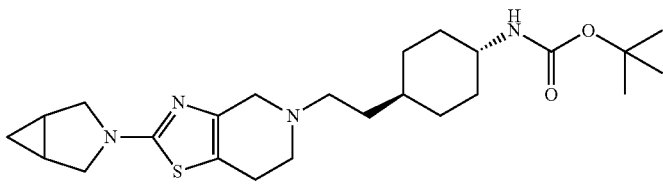
1H-NMR (CDCl₃) δ: 0.27-0.31 (m, 1H), 0.72-0.78 (m, 1H), 0.97-1.11 (m, 4H), 1.22-1.30 (m, 1H), 1.44-1.48 (m, 11H), 1.60-1.63 (m, 2H), 1.75-1.78 (m, 2H), 1.96-2.00 (m, 2H), 2.50-2.54 (m, 2H), 2.66-2.74 (m, 4H), 3.36 (br, 1H), 3.45-3.47 (m, 4H), 3.54-3.57 (m, 2H), 4.35 (br, 1H).
I-145 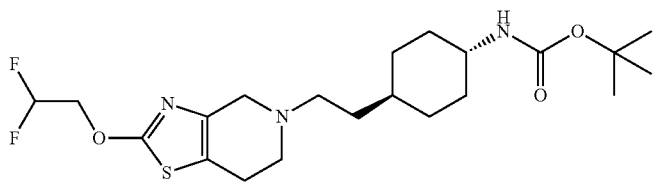
1H-NMR (CDCl₃) δ: 0.99-1.12 (m, 4H), 1.26 (br, 1H), 1.42-1.49 (m, 11H), 1.75-1.80 (m, 2H), 1.97-2.02 (m, 2H), 2.52-2.56 (m, 2H), 2.71-2.75 (m, 2H), 3.37 (br, 1H), 3.44 (s,2H), 4.35 (br, 1H), 4.53 (t, J = 13.0 Hz, 2H), 6.11 (t, J = 55.3 Hz, 1H).
I-146 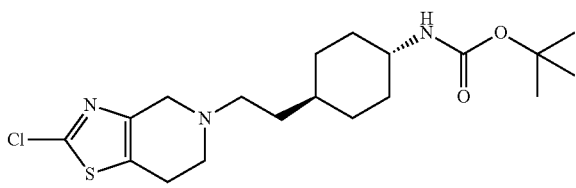
1H-NMR (CDCl₃) δ: 0.99-1.12 (m, 4H), 1.28 (br, 1H), 1.44-1.49 (m, 11H), 1.76-1.79 (m, 2H), 1.97-2.01 (m, 2H), 2.54-2.58 (m, 2H), 2.76-2.82 (m, 4H), 3.37 (br, 1H), 3.58 (s, 2H), 4.36 (br, 1H).
I-147 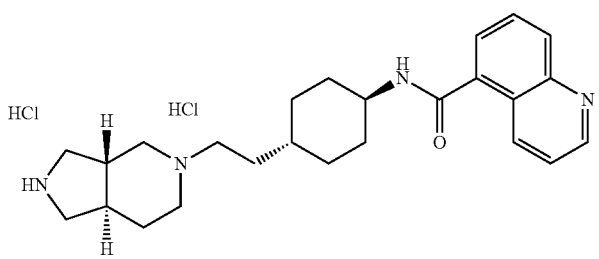
LC/MS:
[M + H] 407.3, method 1, retention time 1.01 min
I-148 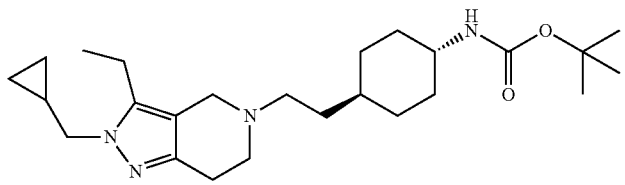
1H NMR (CD₃OD): δ 0.32-0.34 (m, 2H), 0.50-0.54 (m, 2H), 0.84-0.89 (m,1H), 1.08-1.32 (m, 8H), 1.42 (s, 9H), 1.51-1.60 (m, 2H), 1.79-1.82 (d, J = 12.4 Hz, 2H), 1.87-1.91 (m, 2H), 2.51-2.57 (m, 2H), 2.81-2.87 (m, 4H), 3.05-3.08 (m, 2H), 3.21-3.27 (m, 1H), 3.71 (s, 2H),3.93-3.94 (d, J = 6.8 Hz, 2H), .
I-149 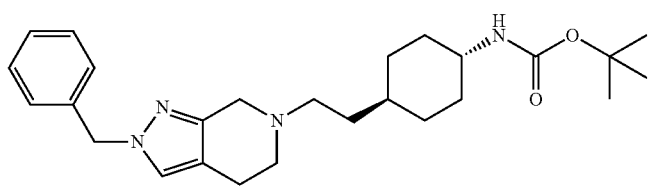
1H NMR (CD₃OD): δ, 1.02-1.24 (m, 5H), 1.42 (s, 9H), 1.54-1.64 (m, 2H), 1.77-1.85 (m, 2H), 1.85-1.94 (m, 2H), 2.77-2.83 (m, 2H), 2.85-2.92 (m, 2H), 3.03-3.10 (m, 2H), 3.20-3.30 (m, 1H), 3.88 (s, 2H), 5.27 (s, 2H), 7.21 (d, J = 6.8 Hz, 2H), 7.24-7.34 (m, 3H), 7.51 (s, 1H).

| Compound No. | Structure | LC/MS method | RT (min) | MS (m/z) |
|---|---|---|---|---|
| II-001 | 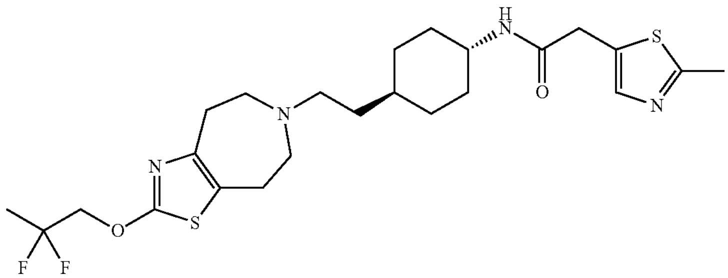 | 4 | 1.35 | 257 |
| II-002 | 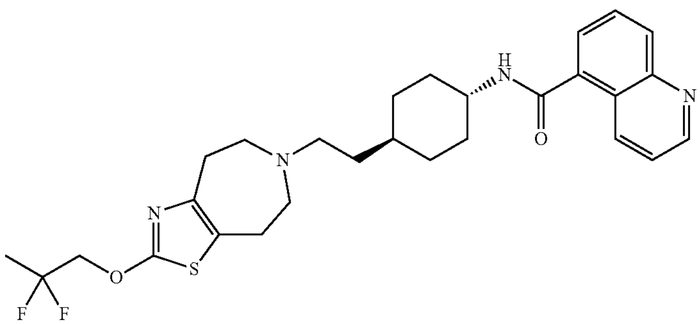 | 4 | 1.35 | 265 |
| II-003 | 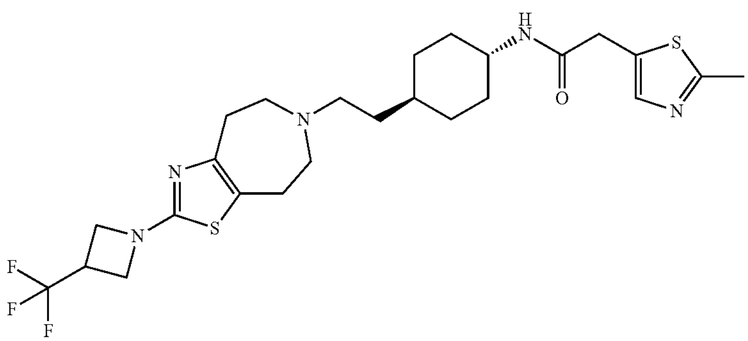 | 3 | 1.11 | 542 |
| II-004 | 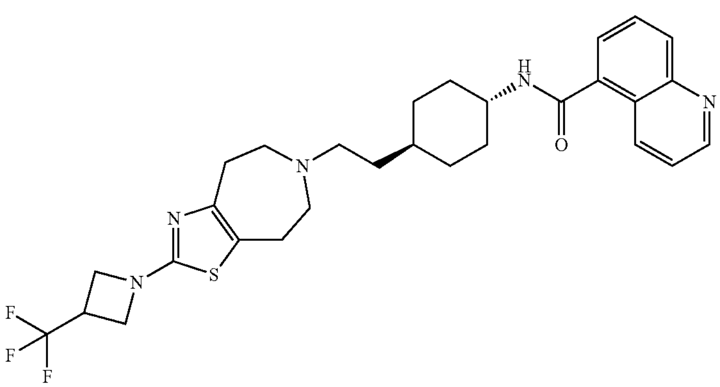 | 3 | 1.06 | 558 |
| II-005 | 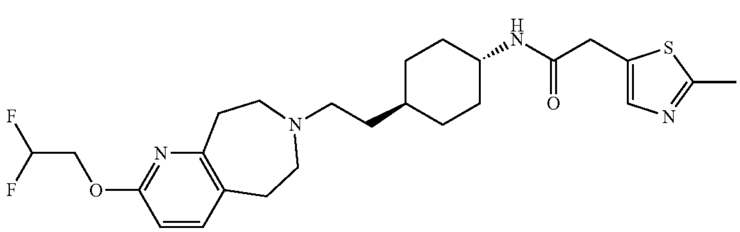 | 3 | 1.17 | 493 |

-continued
| | | | | |
|---|---|---|---|---|
| II-006 | 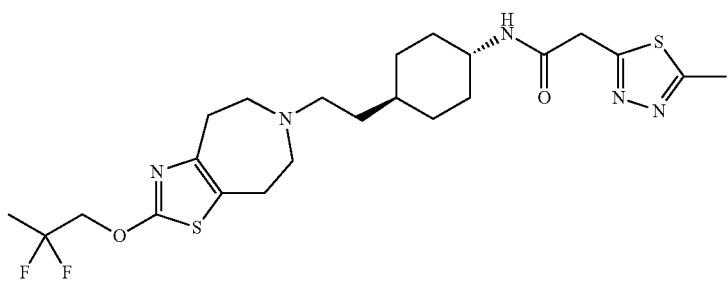 | 2 | 1.37 | 514 |
| II-007 | 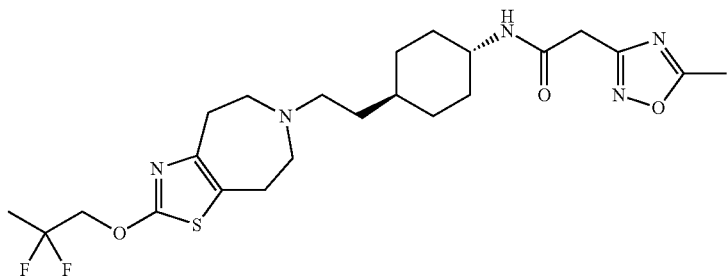 | 2 | 1.38 | 498 |
| II-008 | 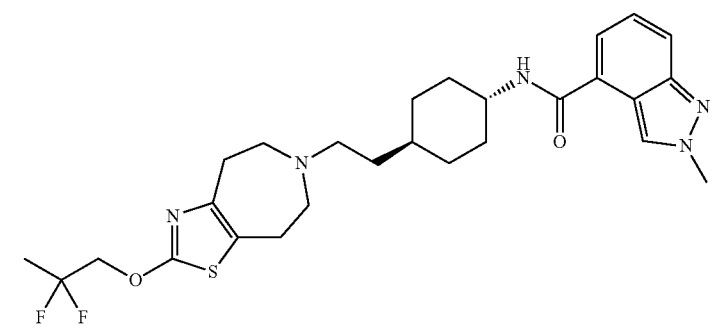 | 2 | 1.5 | 532 |
| II-009 | 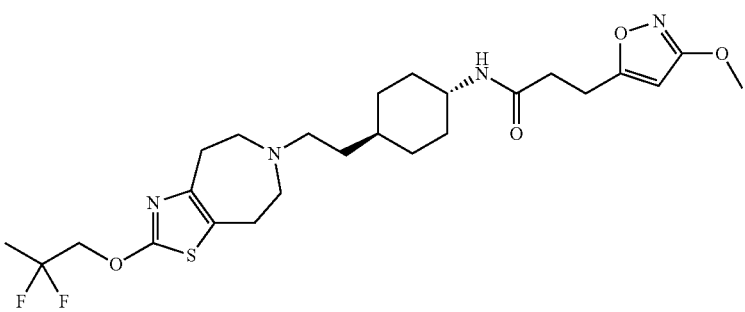 | 2 | 1.49 | 527 |
| II-010 | 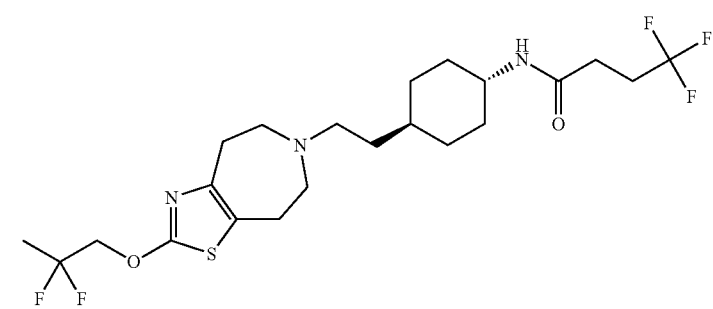 | 2 | 1.58 | 498 |

-continued
| | | | | |
|---|---|---|---|---|
| II-011 | 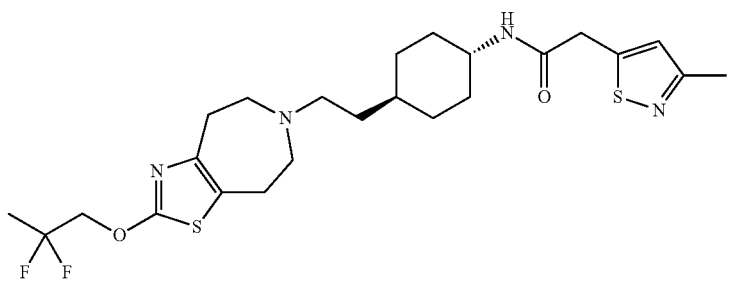 | 2 | 1.47 | 513 |
| II-012 | 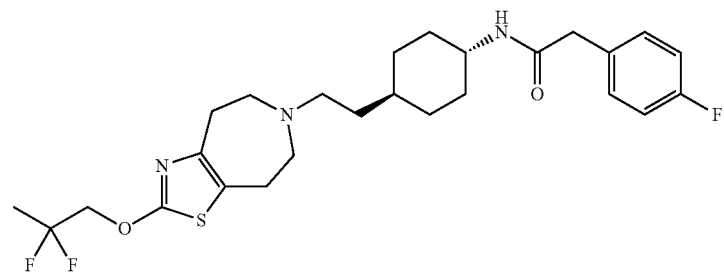 | 2 | 1.66 | 510 |
| II-013 | 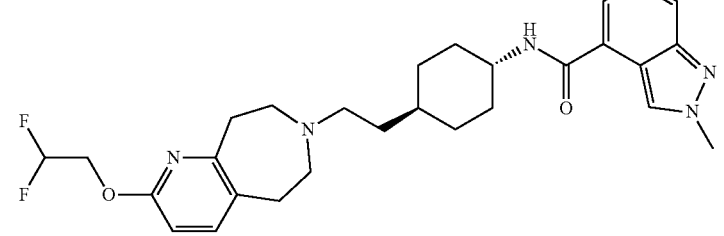 | 3 | 1.21 | 512 |
| II-014 | 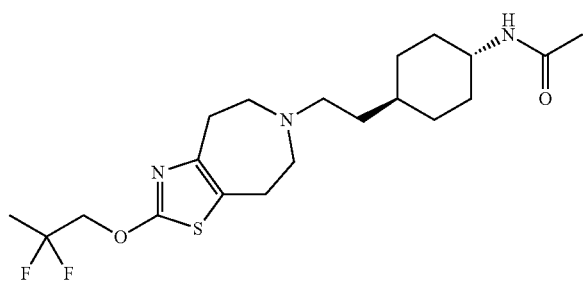 | 3 | 1.11 | 416.3 |
| II-015 | 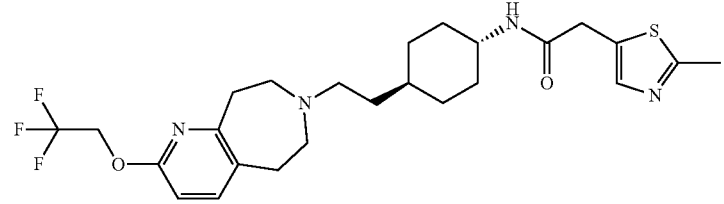 | 3 | 1.34 | 511 |
| II-016 | 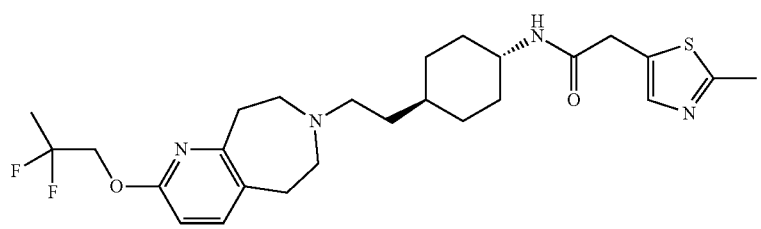 | 2 | 1.42 | 507 |

| | | | | |
|---|---|---|---|---|
| II-017 | 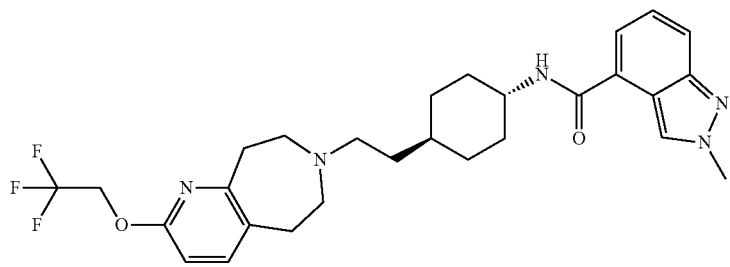 | 3 | 1.31 | 530 |
| II-018 | 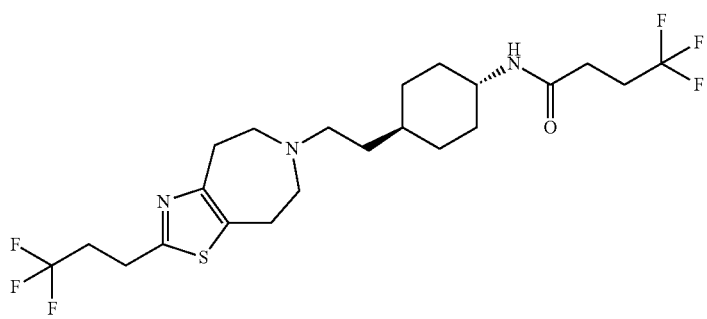 | 3 | 1.43 | 500.3 |
| II-019 | 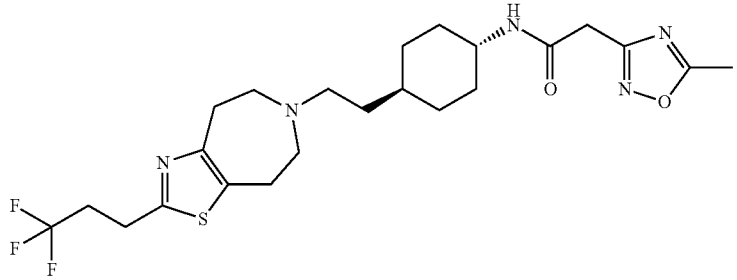 | 3 | 1.18 | 500.3 |
| II-020 | 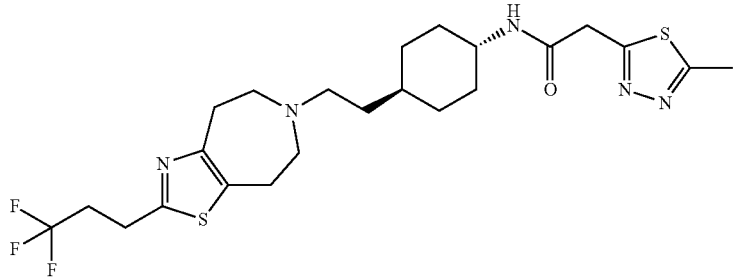 | 3 | 1.17 | 516.25 |
| II-021 | 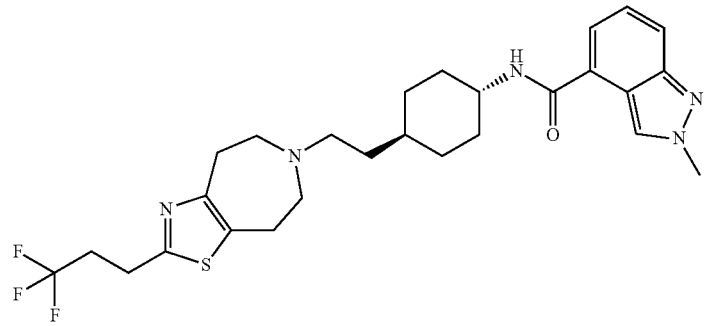 | 3 | 1.32 | 534.3 |

| | | | | |
|---|---|---|---|---|
| II-022 | 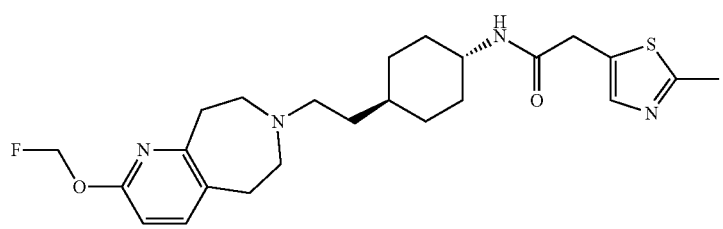 | 3 | 0.91 | 461 |
| II-023 | 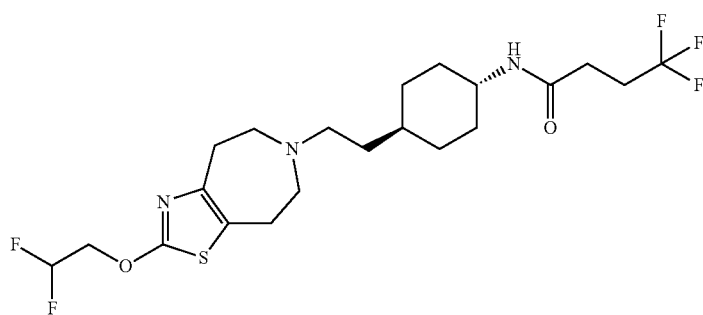 | 3 | 1.37 | 484.3 |
| II-024 | 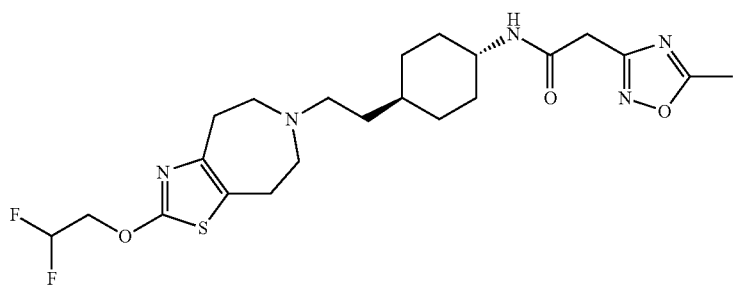 | 3 | 1.1 | 484.3 |
| II-025 | 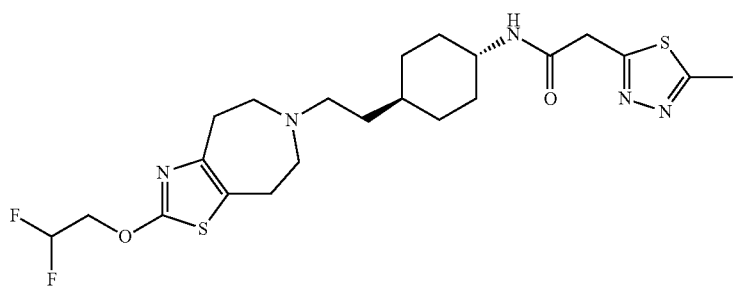 | 3 | 1.1 | 500.25 |
| II-026 | 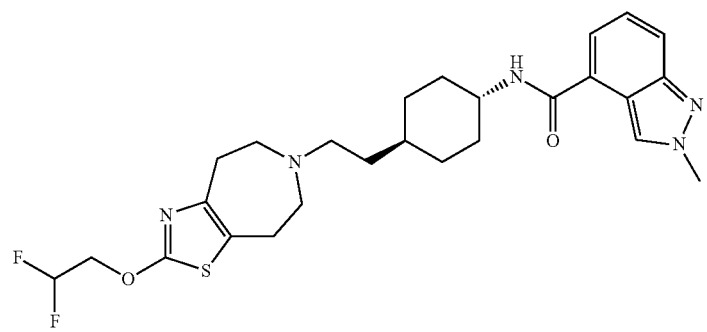 | 3 | 1.27 | 518.35 |

-continued
| | | | | |
|---|---|---|---|---|
| II-027 | 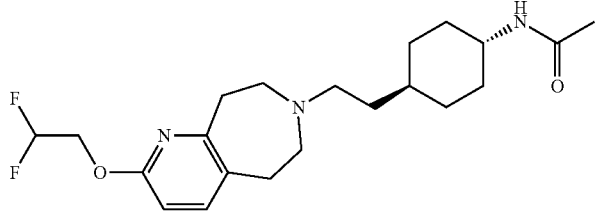 | 3 | 0.99 | 396 |
| II-028 | 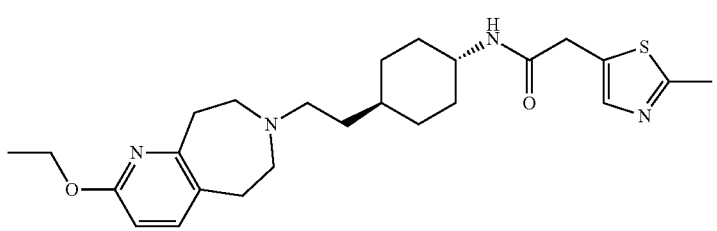 | 3 | 1.13 | 457 |
| II-029 | 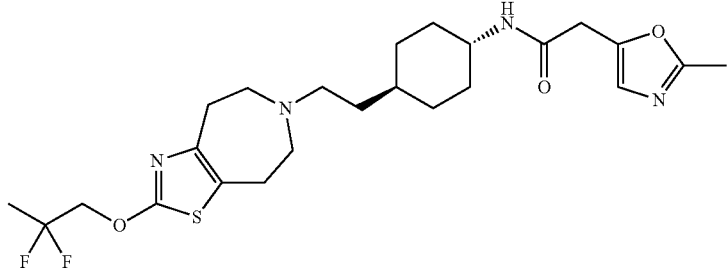 | 3 | 1.19 | 497.3 |
| II-030 | 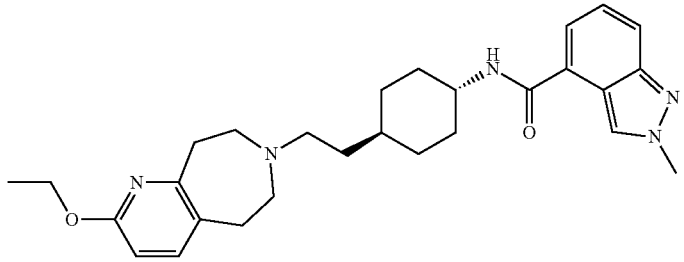 | 3 | 1.14 | 476 |
| II-031 | 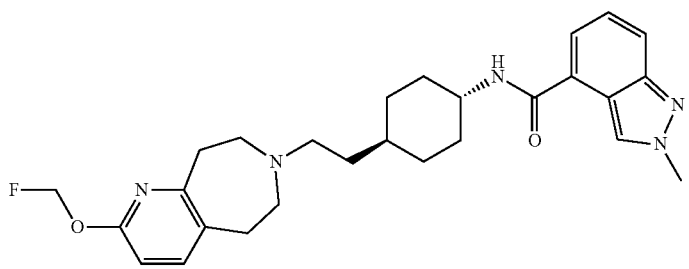 | 3 | 1.08 | 480 |
| II-032 | 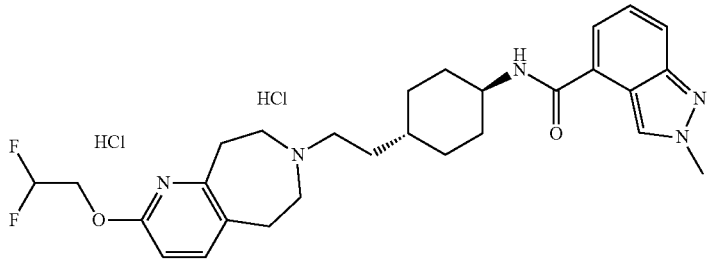 | 3 | 1.21 | 512.25 |

-continued
| | | | | |
|---|---|---|---|---|
| II-033 | 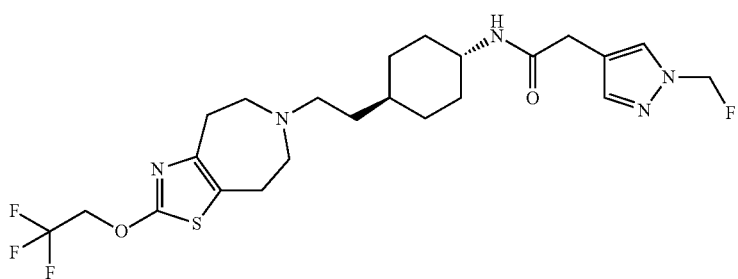 | 3 | 1.29 | 518.3 |
| II-034 | 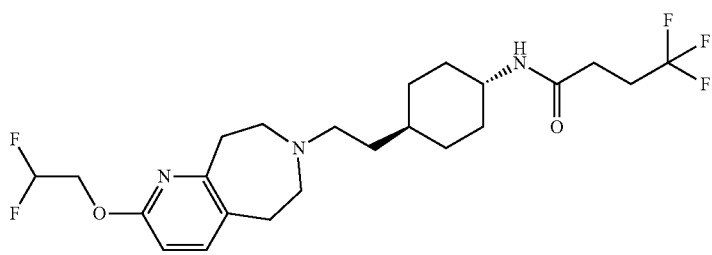 | 2 | 1.57 | 478 |
| II-035 | 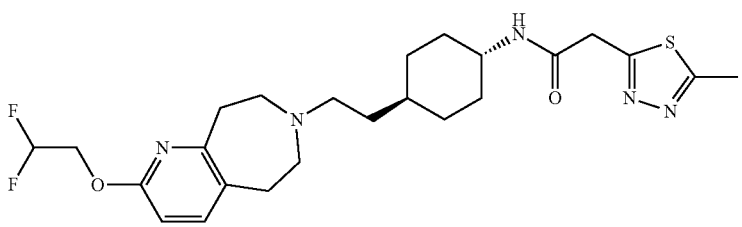 | 2 | 1.36 | 494 |
| II-036 | 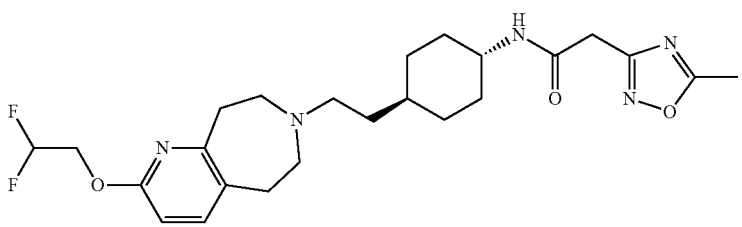 | 2 | 1.37 | 478 |
| II-037 | 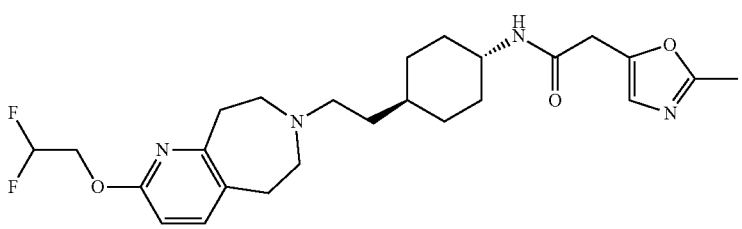 | 2 | 1.36 | 477 |
| II-038 | 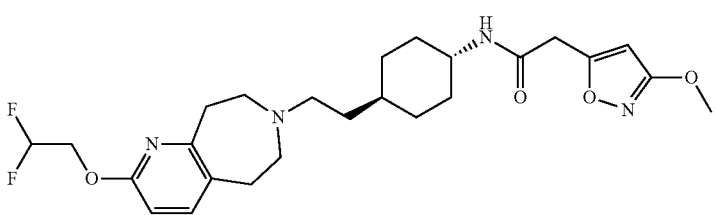 | 2 | 1.47 | 493 |

| | | | | |
|---|---|---|---|---|
| II-039 | 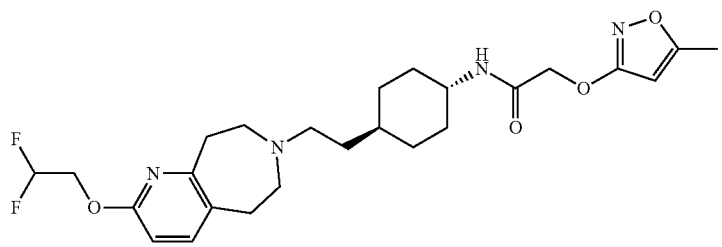 | 2 | 1.52 | 493 |
| II-040 | 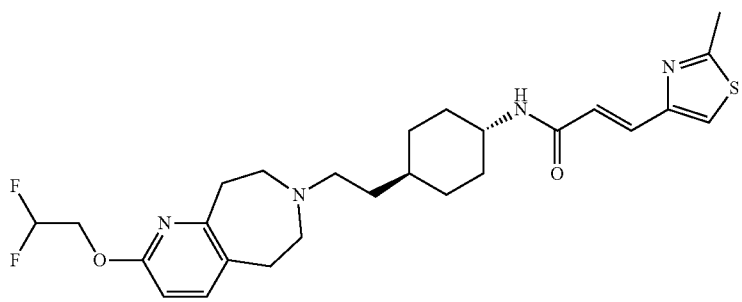 | 2 | 1.53 | 505 |
| II-041 | 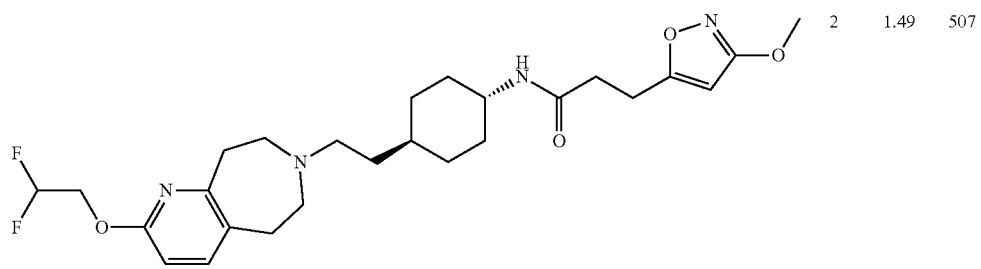 | 2 | 1.49 | 507 |
| II-042 | 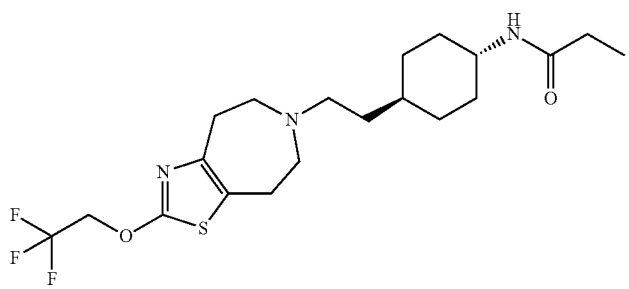 | 2 | 1.43 | 434 |
| II-043 | 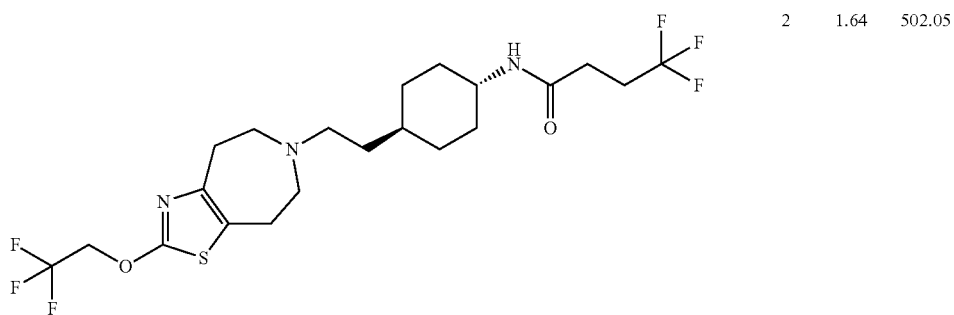 | 2 | 1.64 | 502.05 |

| | | | | |
|---|---|---|---|---|
| II-044 | 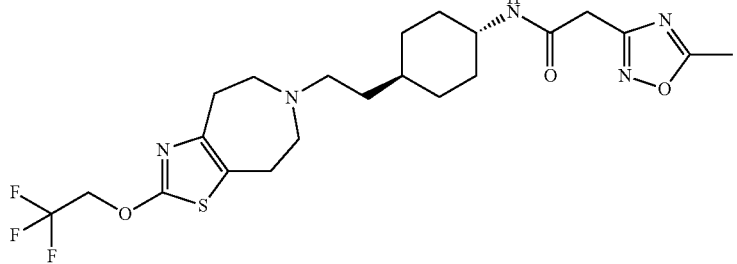 | 2 | 1.43 | 502.1 |
| II-045 | 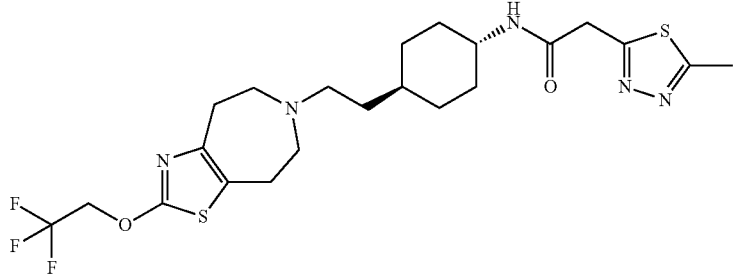 | 2 | 1.42 | 518.1 |
| II-046 | 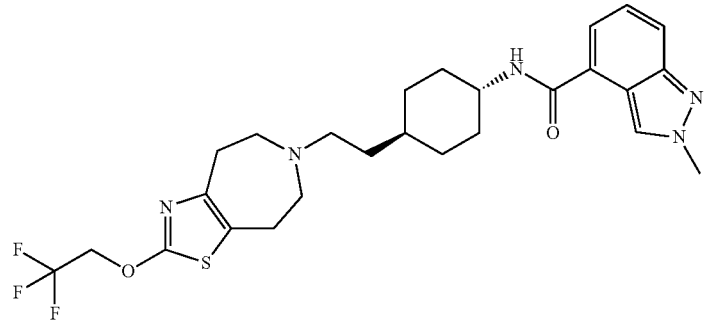 | 2 | 1.55 | 536.1 |
| II-047 | 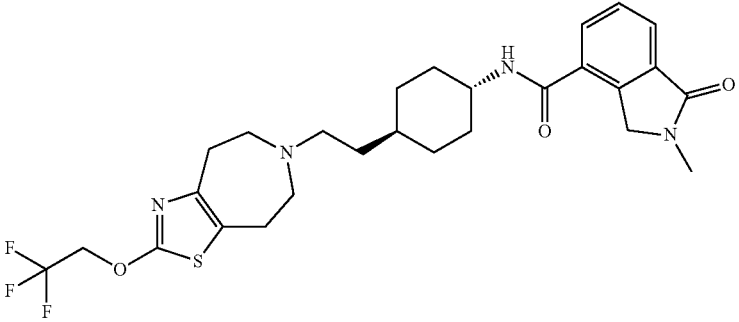 | 2 | 1.5 | 551.15 |
| II-048 | 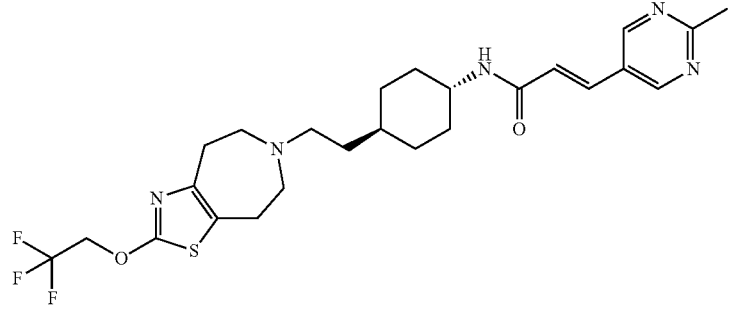 | 2 | 1.44 | 524.1 |

| | | | | |
|---|---|---|---|---|
| II-049 | 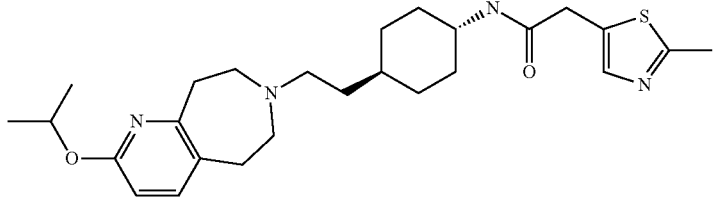 | 3 | 1.26 | 471 |
| II-050 | 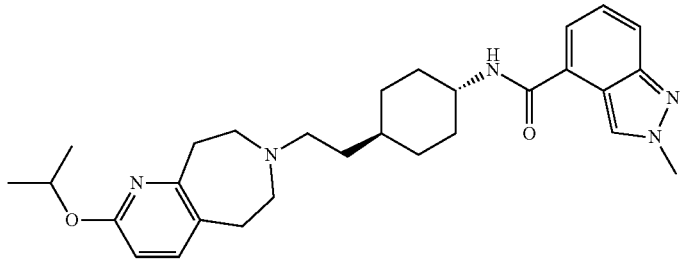 | 3 | 1.38 | 490 |
| II-051 | 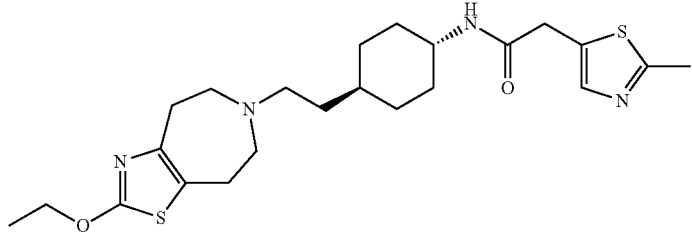 | 3 | 1.17 | 463.3 |
| II-052 | 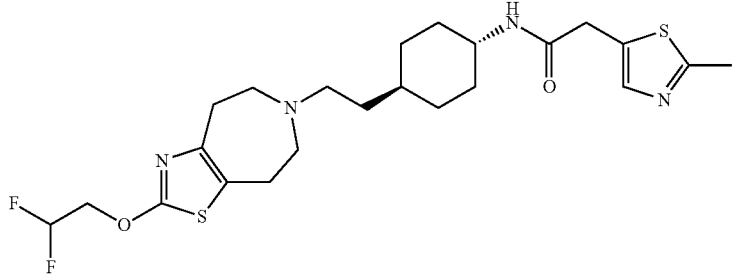 | 3 | 1.2 | 499.3 |
| II-053 | 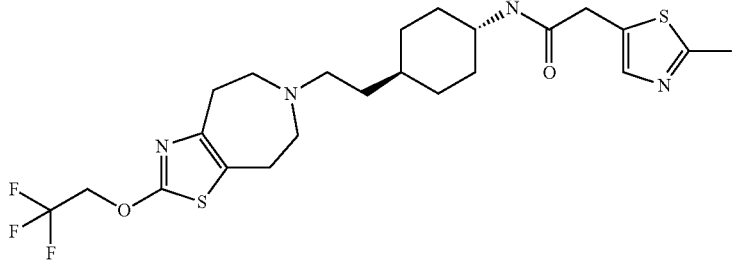 | 3 | 1.35 | 517.3 |
| II-054 | 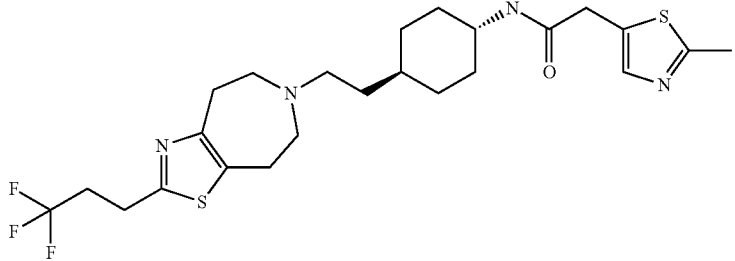 | 3 | 1.29 | 515.3 |

-continued
| | | | | |
|---|---|---|---|---|
| II-055 | 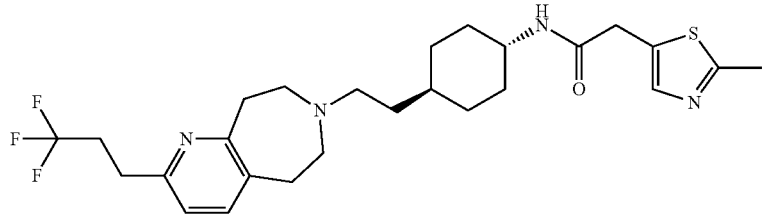 | 2 | 1.19 | 255 |
| II-056 | 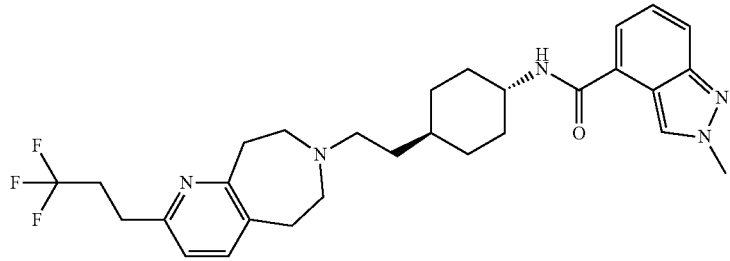 | 2 | 1.39 | 265 |
| II-057 | 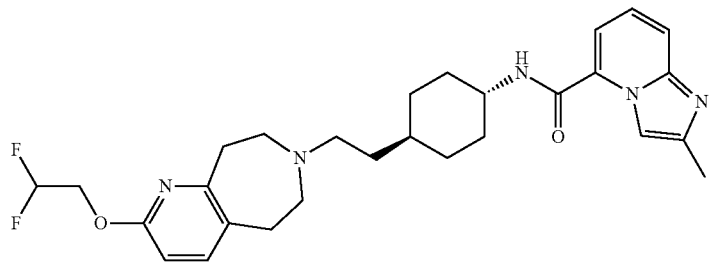 | 3 | 1.15 | 512 |
| II-058 | 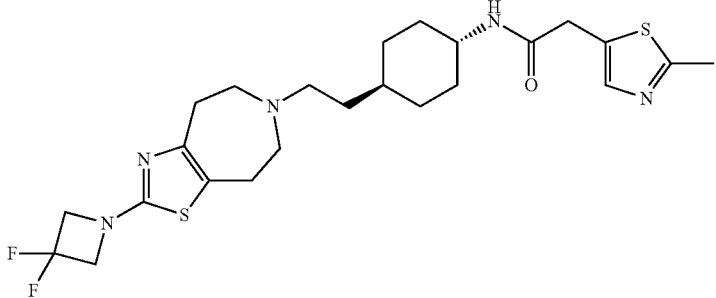 | 2 | 1.19 | 510.2 |
| II-059 | 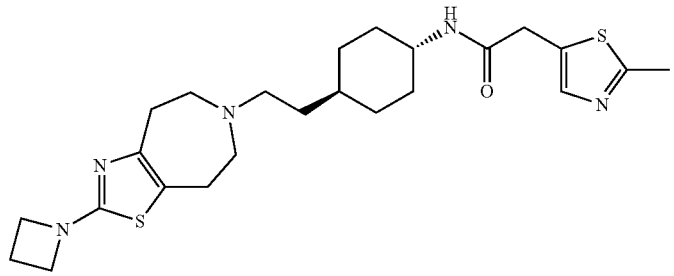 | 2 | 0.89 | 474.2 |
| II-060 | 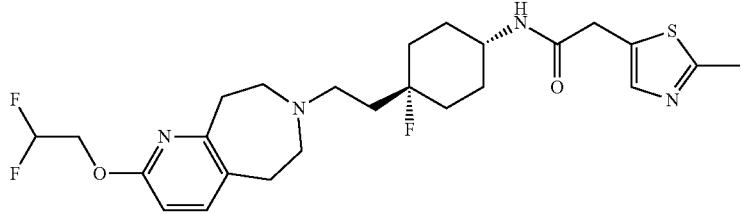 | 3 | 1.18 | 511 |

-continued
| | | | | |
|---|---|---|---|---|
| II-061 | 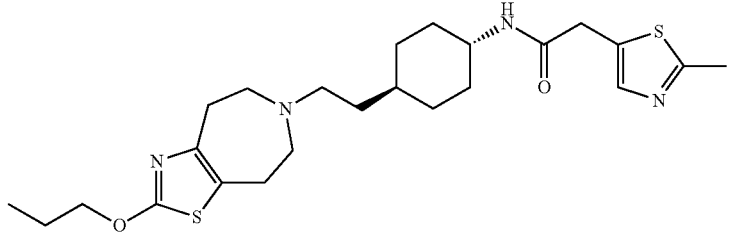 | 3 | 1.23 | 477.3 |
| II-062 | 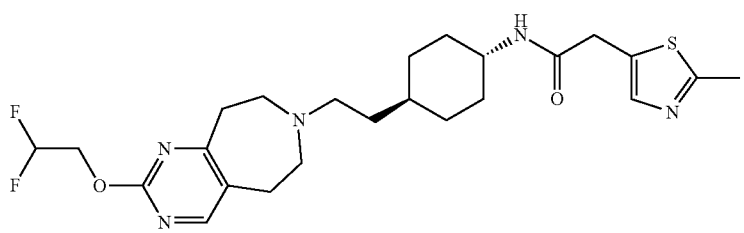 | 3 | 0.98 | 494 |
| II-063 | 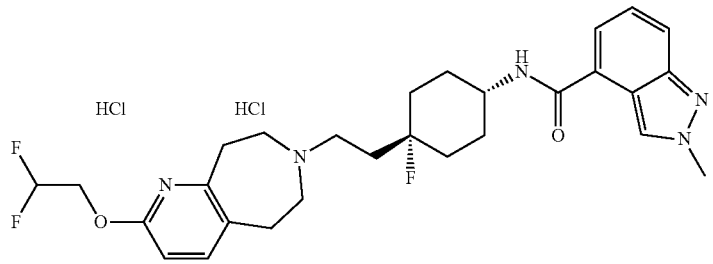 | 3 | 1.33 | 530 |
| II-064 | 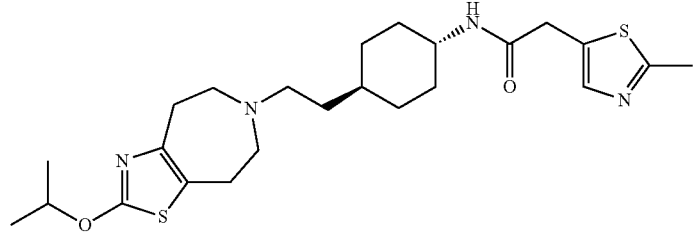 | 3 | 1.24 | 477.3 |
| II-065 | 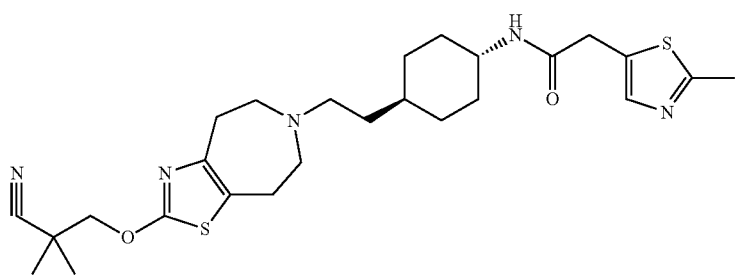 | 3 | 1.16 | 516.35 |
| II-066 | 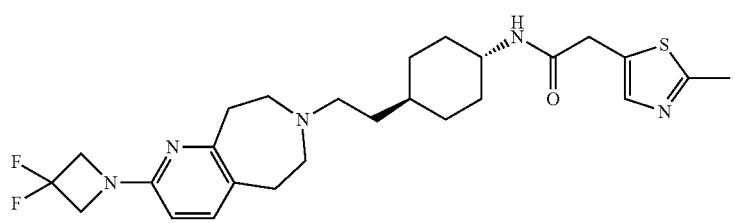 | 3 | 1.04 | 504 |

| | | | | |
|---|---|---|---|---|
| II-067 | 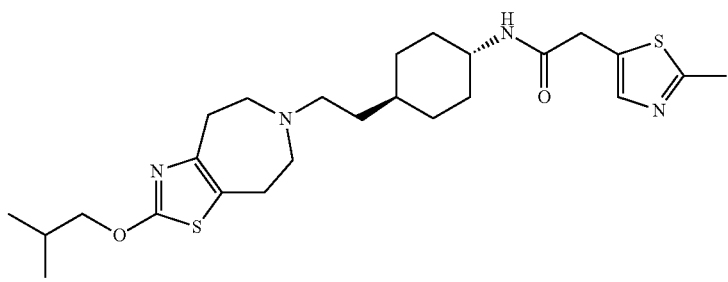 | 3 | 1.36 | 491.35 |
| II-068 | 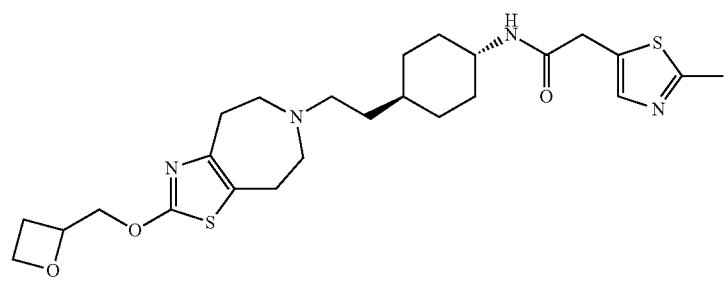 | 3 | 0.95 | 505.3 |
| II-069 | 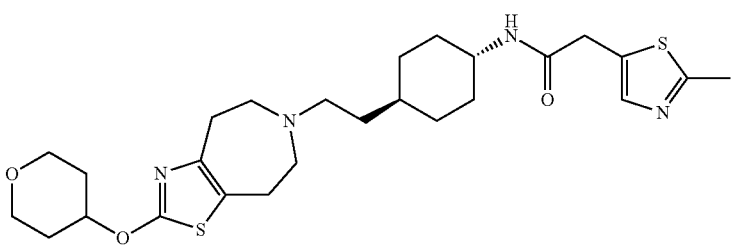 | 3 | 1.05 | 519.35 |
| II-070 | 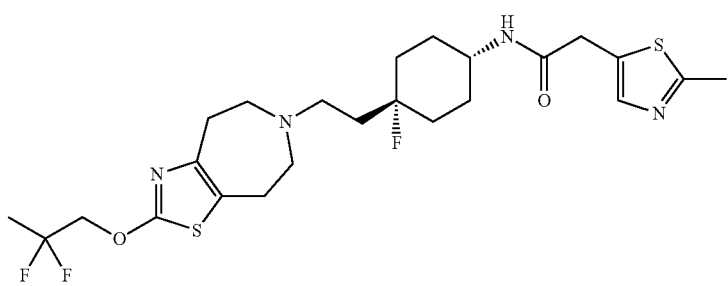 | 3 | 1.23 | 531.3 |
| II-071 | 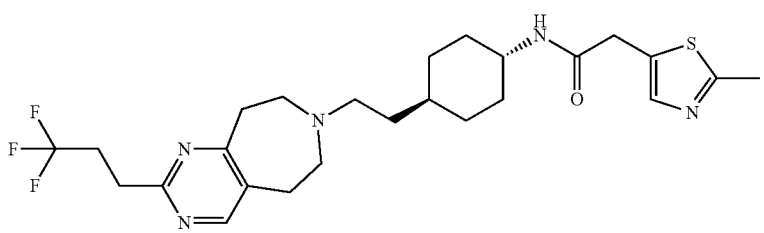 | 3 | 0.98 | 510 |
| II-072 | 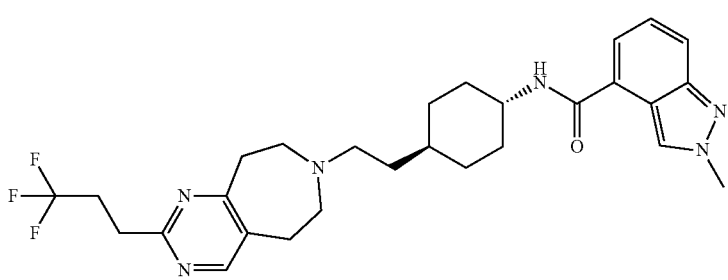 | 3 | 1.21 | 529 |

| | | | | |
|---|---|---|---|---|
| II-073 | 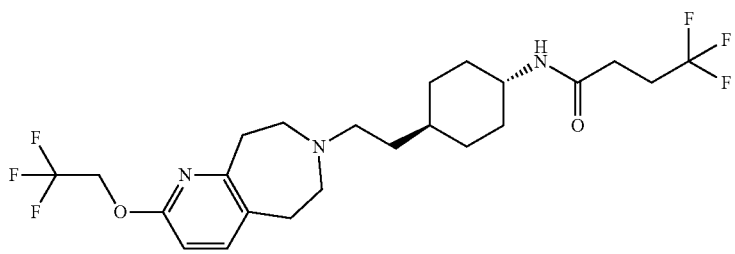 | 2 | 1.686 | 496 |
| II-074 | 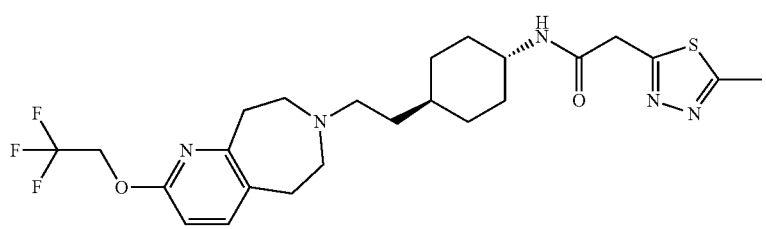 | 2 | 1.46 | 512 |
| II-075 | 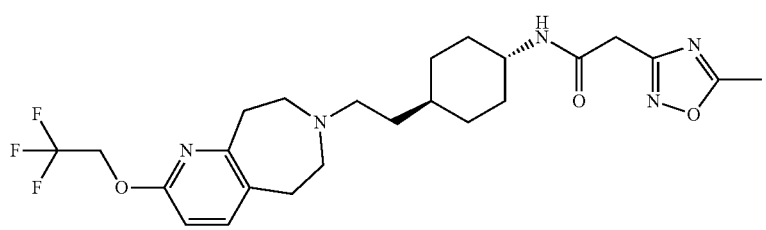 | 2 | 1.506 | 496 |
| II-076 | 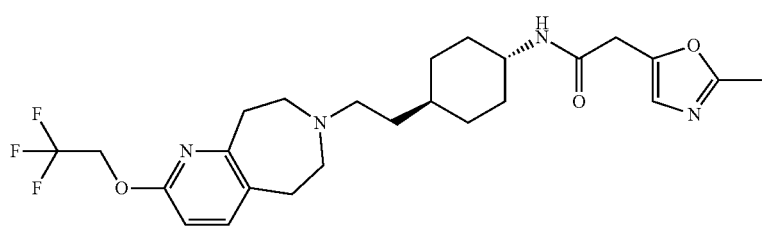 | 2 | 1.475 | 495 |
| II-077 | 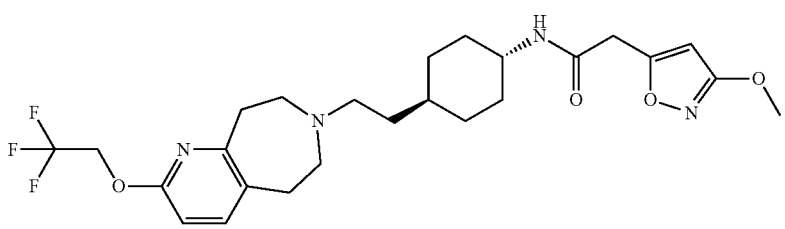 | 2 | 1.582 | 511 |
| II-078 | 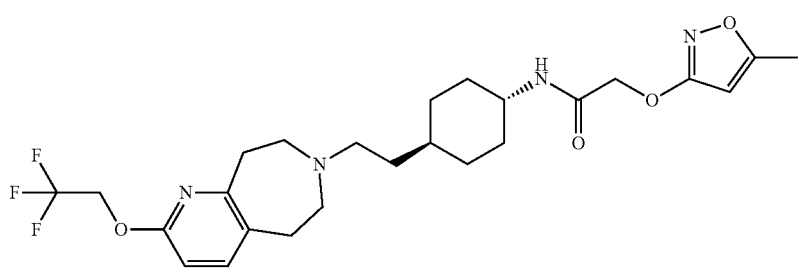 | 2 | 1.594 | 511 |

| | | | | |
|---|---|---|---|---|
| II-079 | 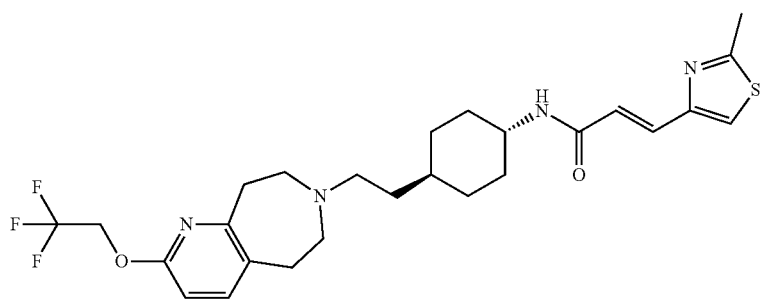 | 2 | 1.628 | 523 |
| II-080 | 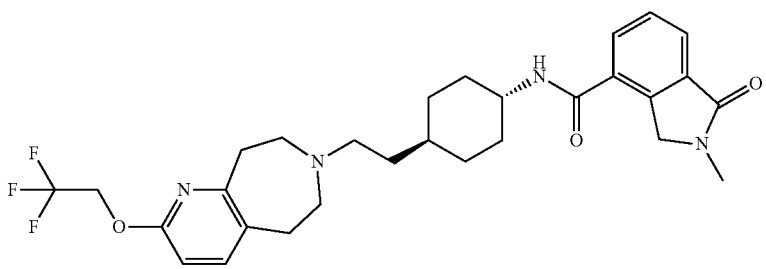 | 2 | 1.555 | 545 |
| II-081 | 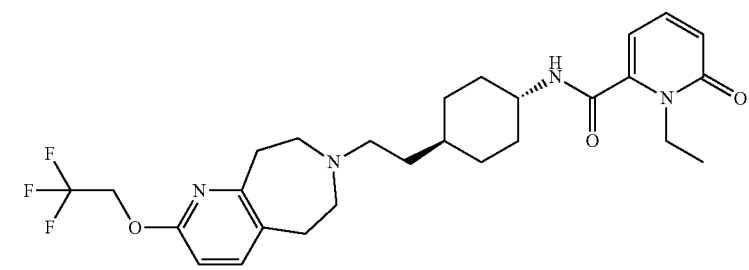 | 2 | 1.502 | 521 |
| II-082 | 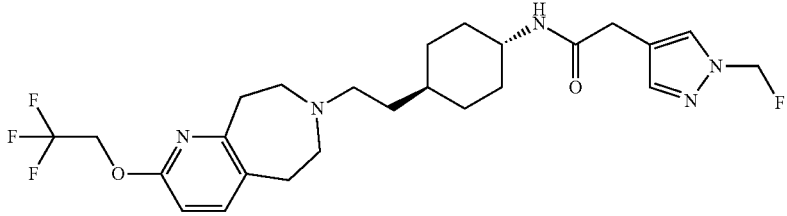 | 2 | 1.486 | 512 |
| II-083 | 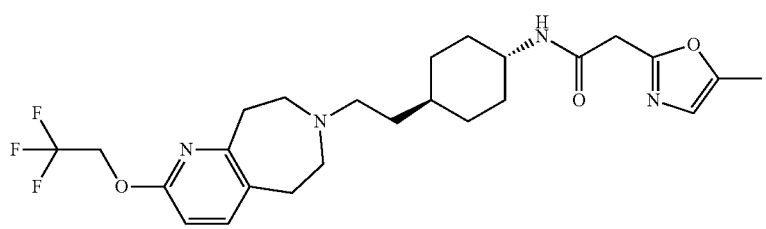 | 2 | 1.535 | 495 |
| II-084 | 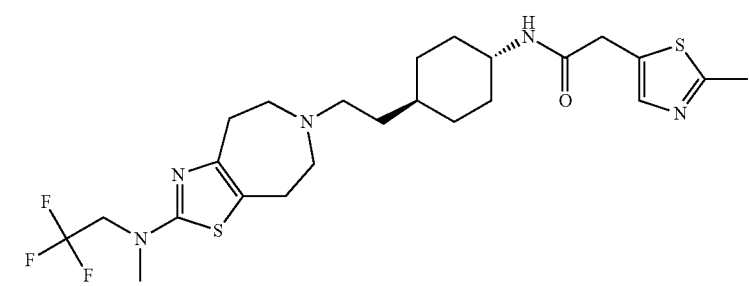 | 3 | 1.24 | 530.3 |

-continued
| | | | | |
|---|---|---|---|---|
| II-085 | 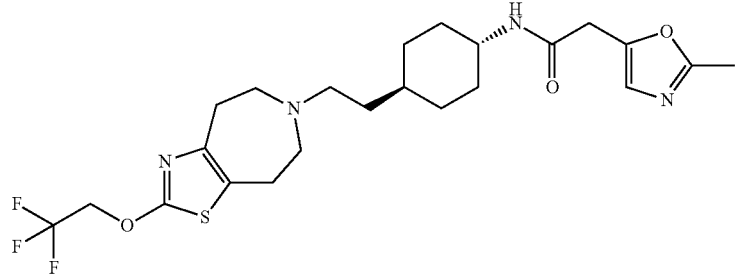 | 3 | 1.21 | 501.3 |
| II-086 | 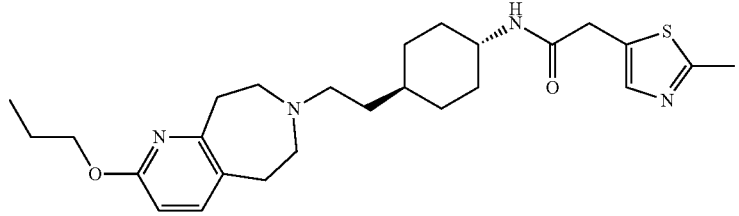 | 3 | 1.28 | 471 |
| II-087 | 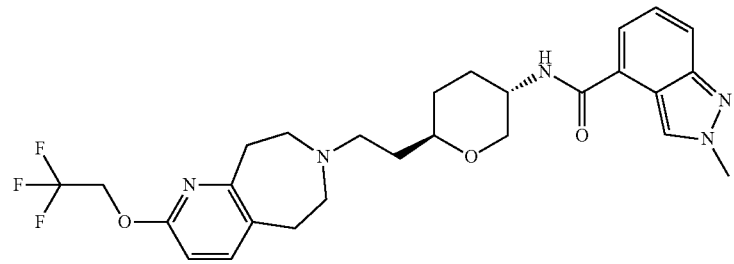 | 3 | 1.32 | 532 |
| II-088 | 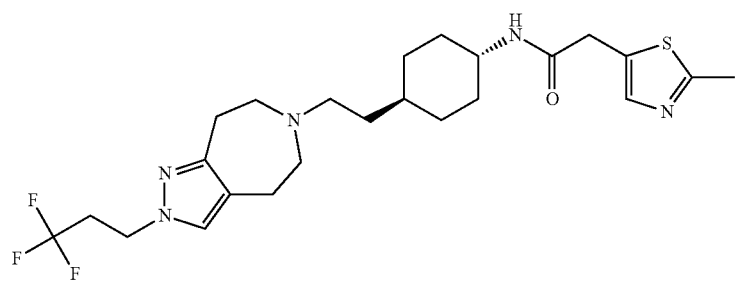 | 3 | 1.02 | 498 |
| II-089 | 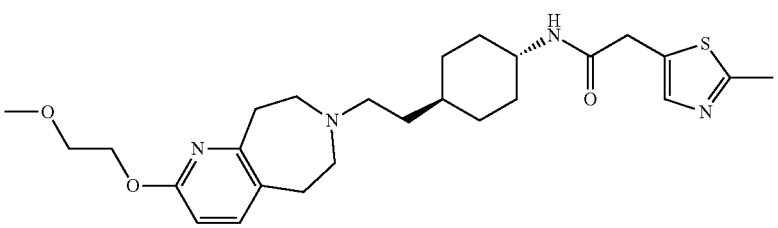 | 3 | 0.99 | 487 |
| II-090 | 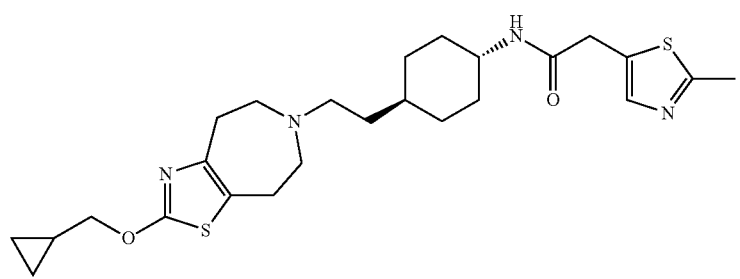 | 2 | 1.38 | 489.1 |

-continued
| | | | | |
|---|---|---|---|---|
| II-091 | 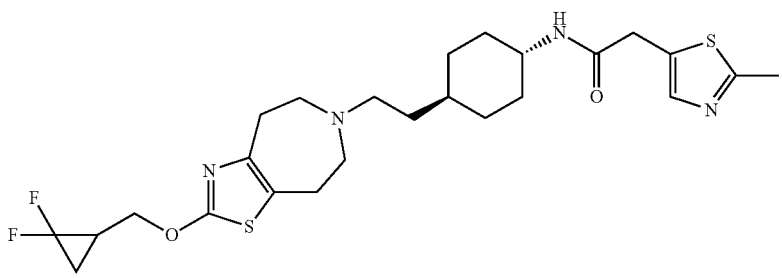 | 2 | 1.4 | 525.1 |
| II-092 | 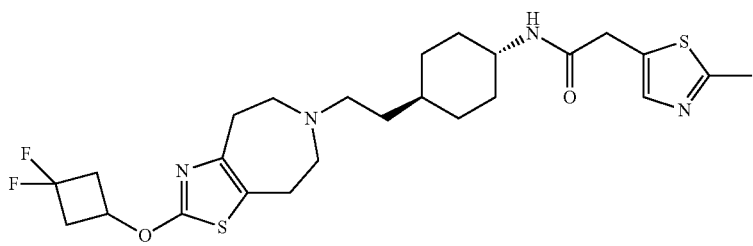 | 2 | 1.41 | 525.1 |
| II-093 | 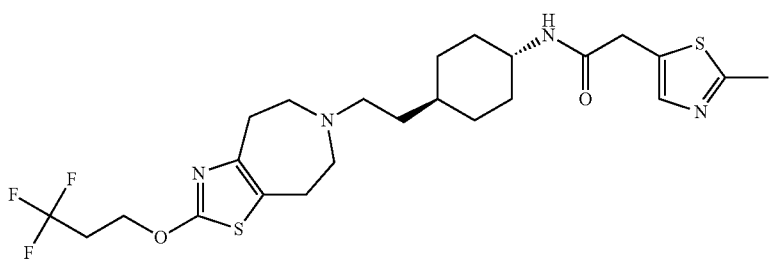 | 2 | 1.42 | 531.1 |
| II-094 | 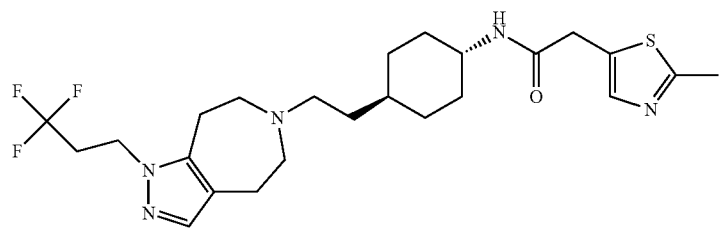 | 3 | 0.95 | 498 |
| II-095 | 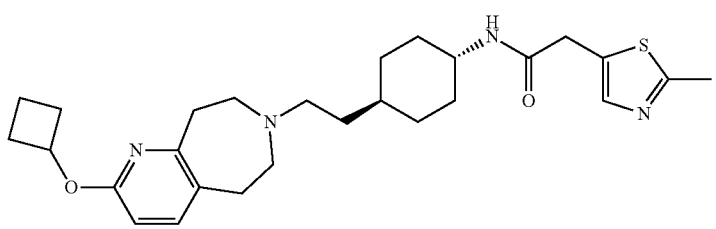 | 3 | 1.27 | 483 |
| II-096 | 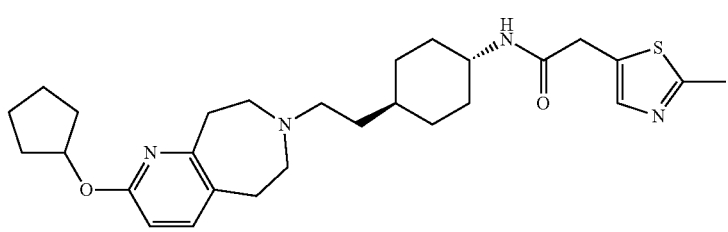 | 3 | 1.4 | 497 |

| | | | | |
|---|---|---|---|---|
| II-097 | 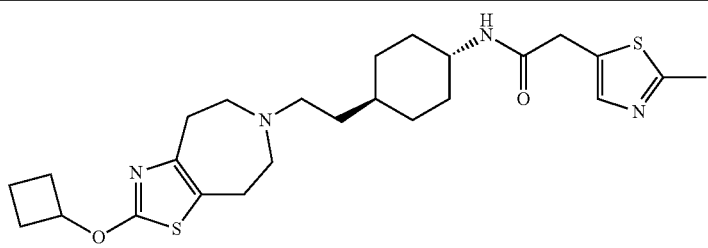 | 2 | 1.39 | 489.1 |
| II-098 | 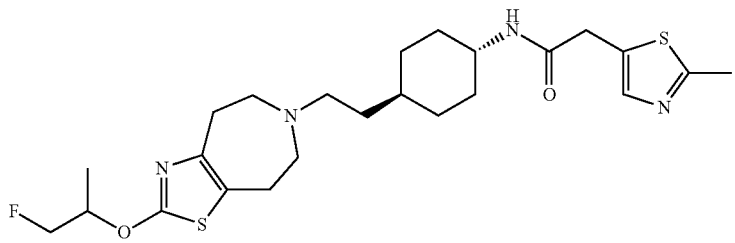 | 2 | 1.3 | 495.1 |
| II-099 | 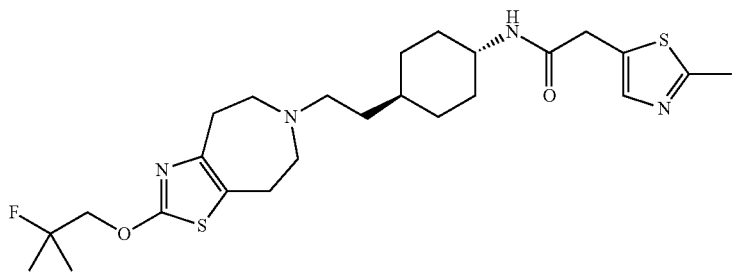 | 2 | 1.37 | 509.1 |
| II-100 | 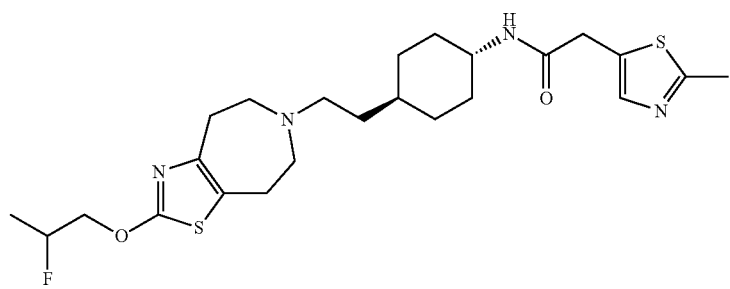 | 2 | 1.29 | 495.1 |
| II-101 | 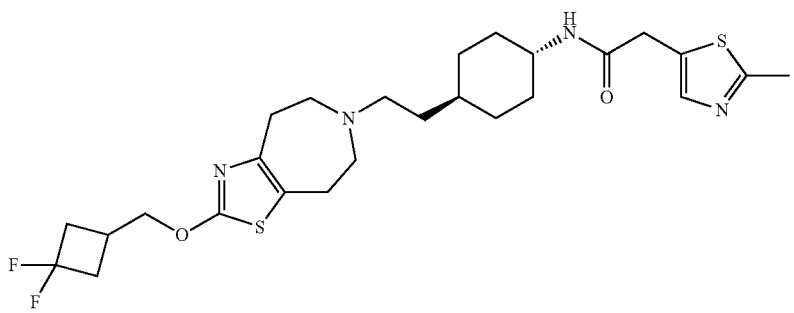 | 2 | 1.46 | 539.1 |
| II-102 | 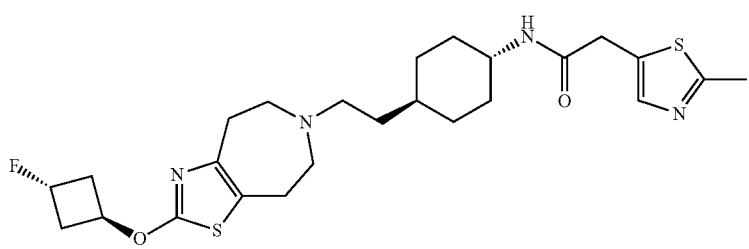 | 2 | 1.32 | 507.1 |

-continued
| | | | | |
|---|---|---|---|---|
| II-103 | 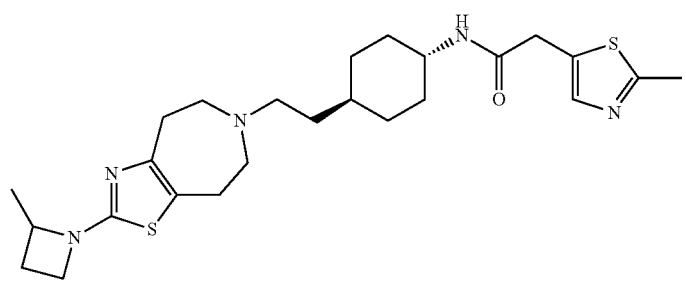 | 3 | 0.9 | 488.35 |
| II-104 | 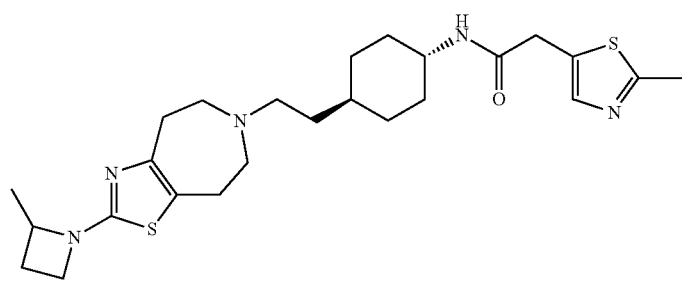 | 3 | 0.91 | 488.35 |
| II-105 | 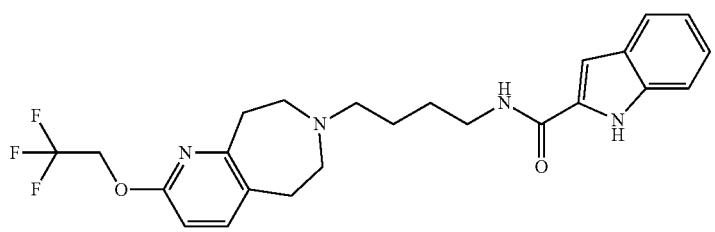 | 2 | 1.68 | 461.15 |
| II-106 | 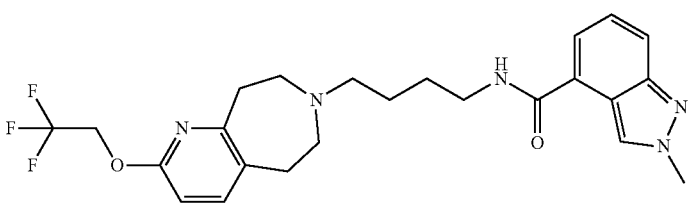 | 2 | 1.4 | 476.2 |
| II-107 | 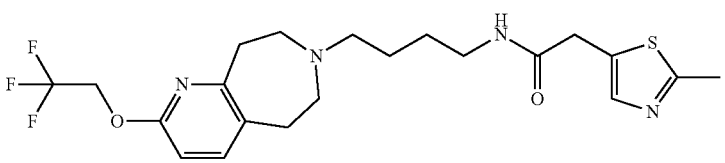 | 2 | 1.3 | 457.1 |
| II-108 | 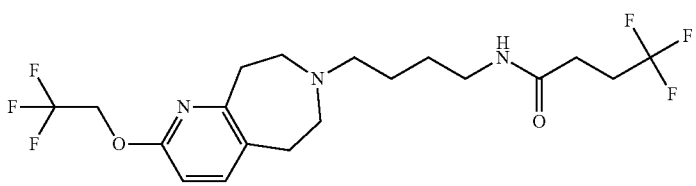 | 2 | 1.49 | 442.05 |

-continued

| Compound No | Structure | NMR |
|---|---|---|
| II-109 | 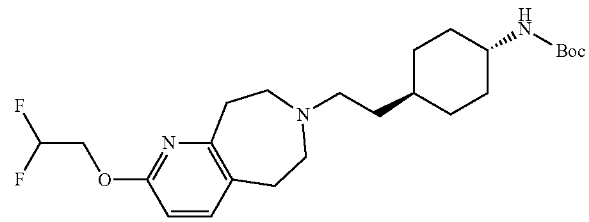 | 1H-NMR (CDCl3) δ: 1.05 (m, 4H), 1.21 (m, 1H), 1.41 (m, 2H), 1.44 (s, 9H), 1.77 (m, 2H), 1.99 (m, 2H), 2.48 (m, 2H), 2.58-2.64 (m, 4H), 2.81 (m, 2H), 3.02 (m, 2H), 3.37 (m, 1H), 4.36 (m, 1H), 4.51 (td, J = 13.7, 4.3 Hz, 2H), 6.13 (tt, J = 56.0, 4.3 Hz, 1H), 6.54 (d, J = 8.0 Hz, 1H), 7.30 (d, J = 8.0 Hz, 1H). |
| II-110 | 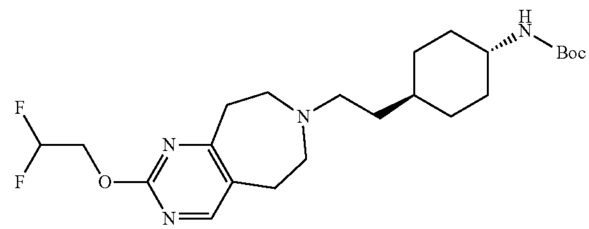 | 1H-NMR (CDCl3) δ: 1.05 (m, 4H), 1.22 (m, 1H), 1.41 (m, 2H), 1.45 (s, 9H), 1.76 (m, 2H), 1.99 (m, 2H), 2.52 (m, 2H), 2.60-2.70 (m, 4H), 2.81 (m, 2H), 3.04 (m, 2H), 3.37 (m, 1H), 4.36 (m, 1H), 4.55 (td, J = 13.2, 4.4 Hz, 2H), 6.14 (tt, J = 55.5, 4.3 Hz, 1H), 8.15 (s, 1H). |
| II-111 | 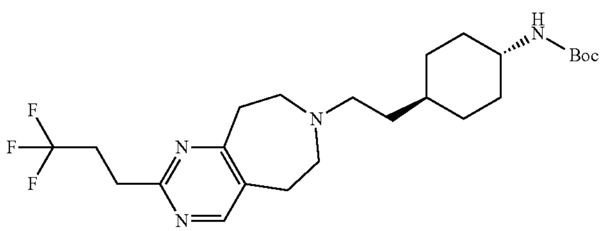 | 1H-NMR (CDCl3) δ: 1.05 (m, 4H), 1.23 (m, 1H), 1.41 (m, 2H), 1.44 (s, 9H), 1.77 (m, 2H), 1.99 (m, 2H), 2.52 (m, 2H), 2.61-2.73 (m, 6H), 2.84 (m, 2H), 3.07 (m, 2H), 3.15 (m, 2H), 3.37 (m, 1H), 4.36 (m, 1H), 8.31 (s, 1H). |
| II-112 | 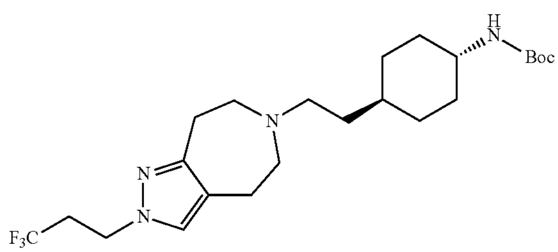 | 1H-NMR (CDCl3) δ: 1.05 (m, 4H), 1.24 (m, 1H), 1.39-1.44 (m, 11H), 1.77 (m, 2H), 1.99 (m, 2H), 2.59-2.85 (m, 12H), 3.37 (m, 1H), 4.21 (t, J = 7.4 Hz, 2H), 4.36 (m, 1H), 7.06 (s, 1H). |
| II-113 | 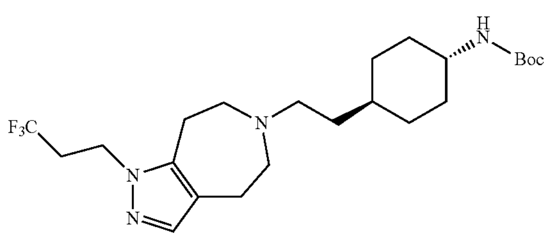 | 1H-NMR (CDCl3) δ: 1.06 (m, 4H), 1.25 (m, 1H), 1.38-1.45 (m, 11H), 1.77 (m, 2H), 1.99 (m, 2H), 2.59-2.70 (m, 6H), 2.77 (m, 2H), 2.82 (m, 2H), 2.88 (m, 2H), 3.37 (m, 1H), 4.24 (t, J = 7.4 Hz, 2H), 4.35 (m, 1H), 7.22 (s, 1H). |
| II-114 | 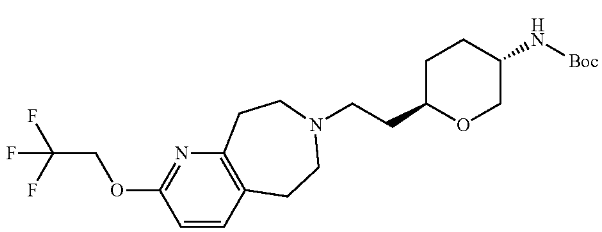 | 1H-NMR (CDCl3) δ: 1.22-1.76 (m, 14H), 2.08 (d, J = 12.5 Hz, 1H), 2.49-2.67 (m, 6H), 2.80-2.83 (m, 2H), 2.95-3.03 (m, 3H), 3.22-3.28 (m, 1H), 3.58 (brs, 1H), 4.03-4.07 (m, 1H), 4.23 (brs, 1H), 4.74 (q, J = 8.7 Hz, 2H), 6.59 (d, J = 8.3 Hz, 1H), 7.32 (d, J = 8.3 Hz, 1H). |

-continued
| | | | | |
|---|---|---|---|---|
| II-115 | 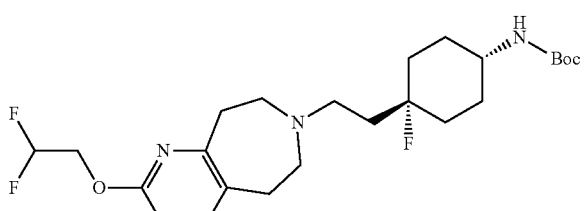 | | | 1H-NMR (CDCl3) δ: 1.41-1.52 (m, 13H), 1.76-1.98 (m, 6H), 2.58-2.66 (m, 6H), 2.81 (m, 2H), 3.02 (m, 2H), 3.44 (m, 1H), 4.42 (m, 1H), 4.51 (td, J = 13.6, 4.3 Hz, 2H), 6.13 (tt, J = 55.8, 4.3 Hz, 1H), 6.55 (d, J = 8.0 Hz, 1H), 7.31 (d, J = 8.3 Hz, 1H). |
| Compound No. | Structure | LC/MS method | RT (min) | MS (m/z) |
|---|---|---|---|---|
| III-001 | 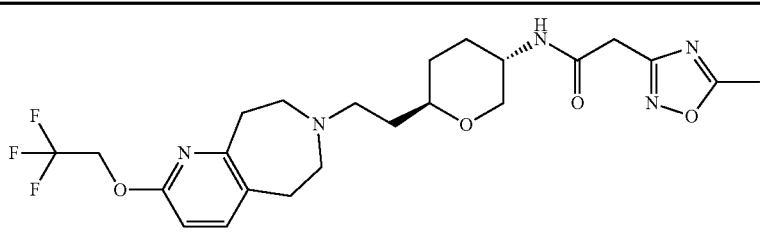 | 2 | 1.42 | 498.1 |
| III-002 | 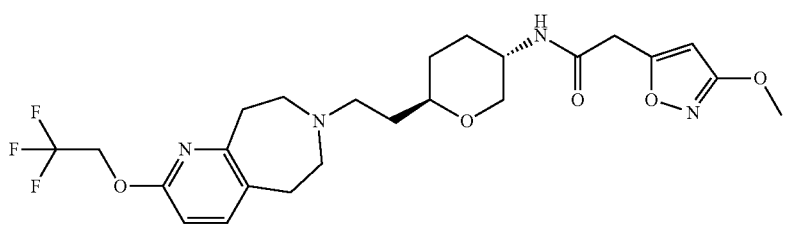 | 2 | 1.52 | 513.1 |
| III-003 | 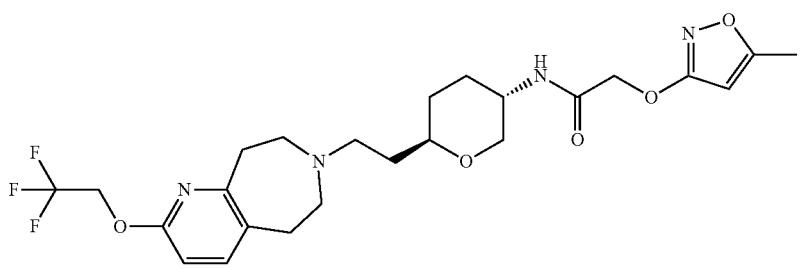 | 2 | 1.55 | 513.1 |
| III-004 | 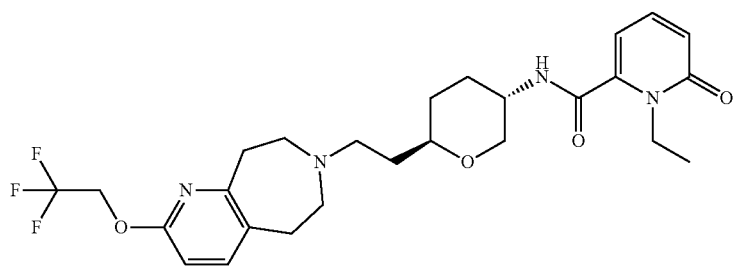 | 2 | 1.45 | 523.1 |
| III-005 | 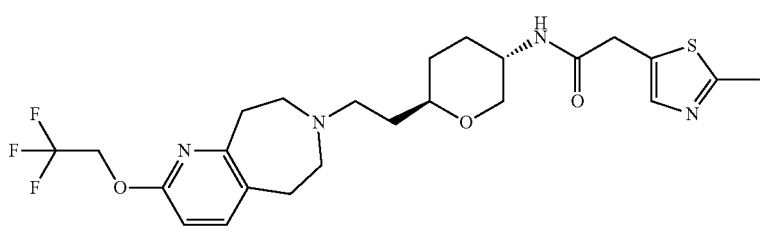 | 2 | 1.41 | 513.1 |

-continued

| Compound No. | Structure | LC/MS method | RT (min) | MS (m/z) |
|---|---|---|---|---|
| III-006 | 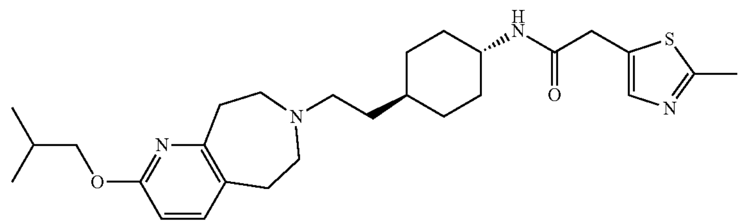 | 3 | 1.46 | 485 |
| III-007 | 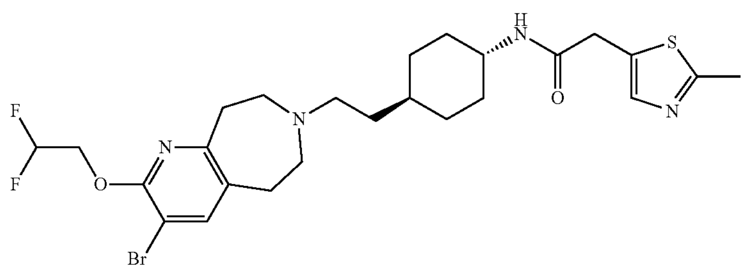 | 3 | 1.35 | 571 |
| III-008 | 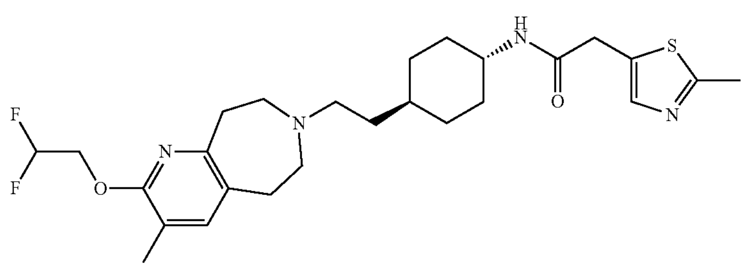 | 3 | 1.35 | 507 |
| III-009 | 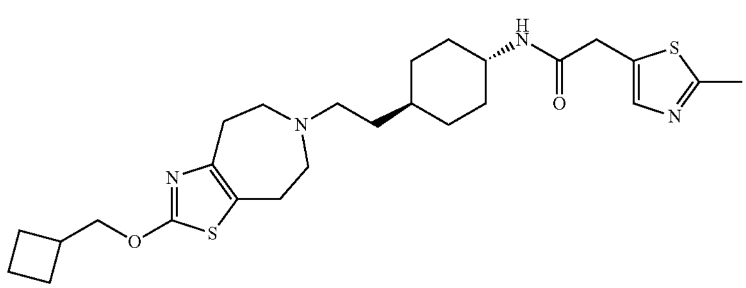 | 2 | 1.51 | 503.1 |
| III-010 | 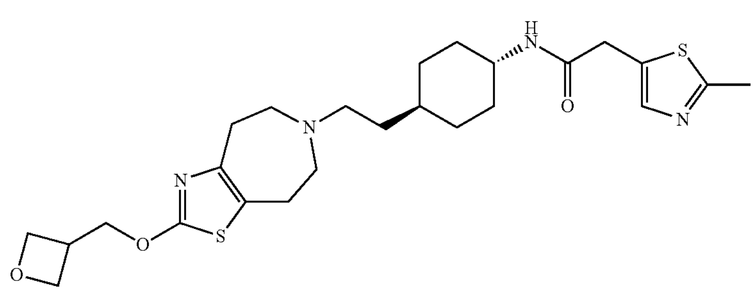 | 2 | 1.06 | 505.1 |

-continued

| Compound No. | Structure | LC/MS method | RT (min) | MS (m/z) |
|---|---|---|---|---|
| III-011 | 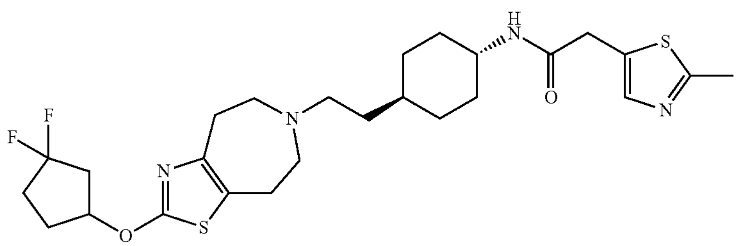 | 2 | 1.46 | 539.1 |
| III-012 | 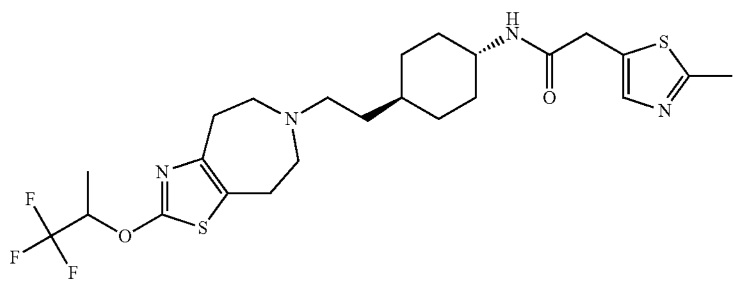 | 2 | 1.49 | 531.2 |
| III-013 | 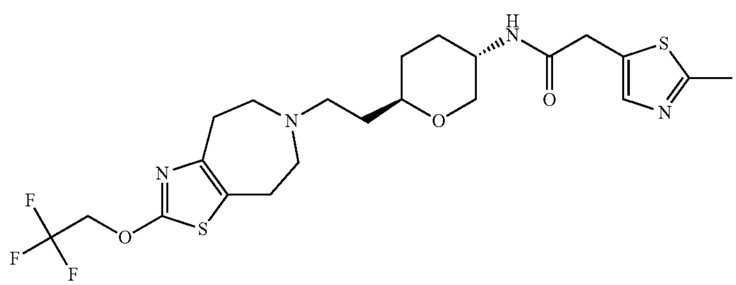 | 2 | 1.31 | 519.1 |
| III-014 | 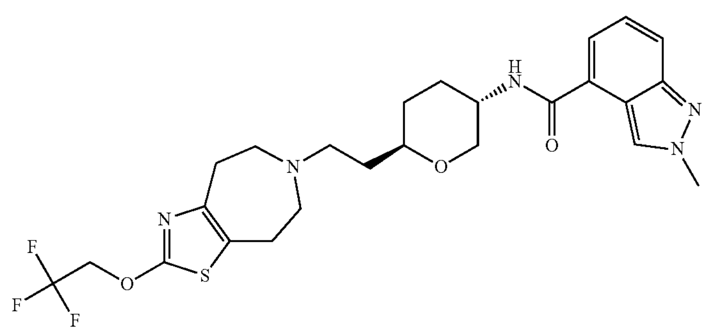 | 2 | 1.42 | 538.2 |
| III-015 | 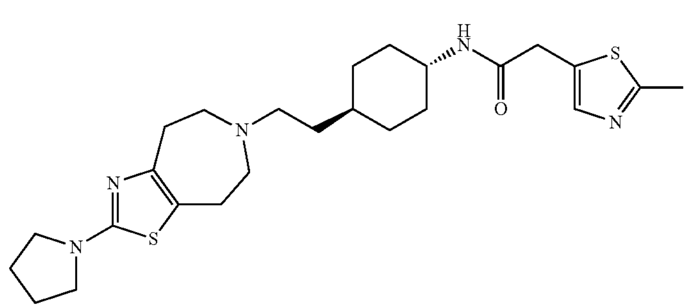 | 1 | 1.40 | 488.29 |

| Compound No. | Structure | LC/MS method | RT (min) | MS (m/z) |
|---|---|---|---|---|
| III-016 | 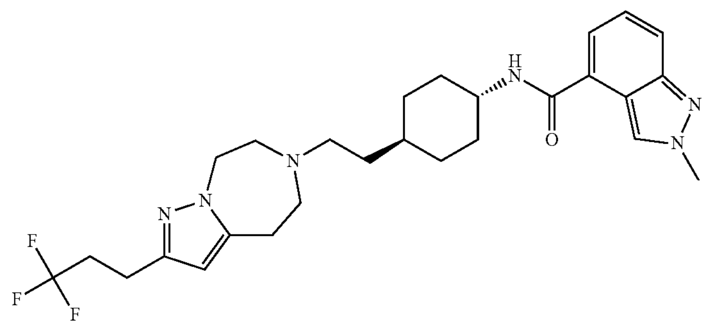 | 2 | 1.40 | 517 |
| III-017 | 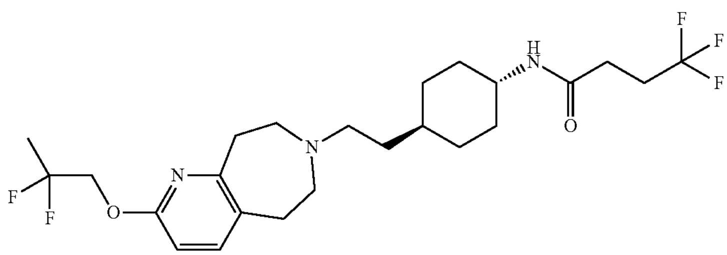 | 2 | 1.63 | 492.1 |
| III-018 | 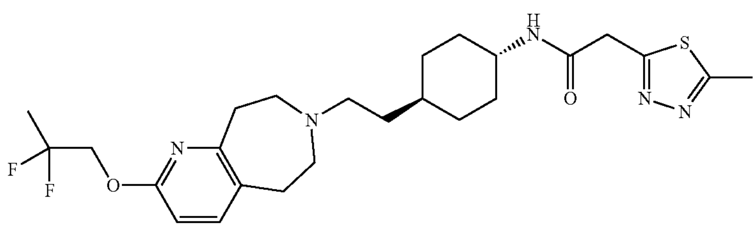 | 2 | 1.44 | 508.1 |
| III-019 | 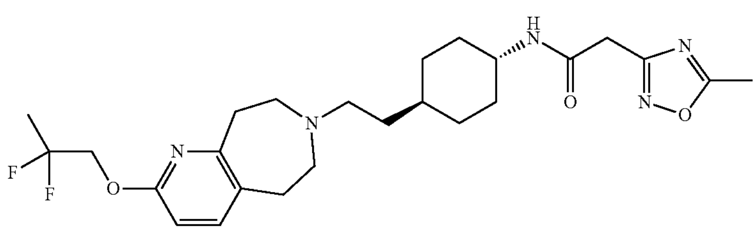 | 2 | 1.46 | 492.1 |
| III-020 | 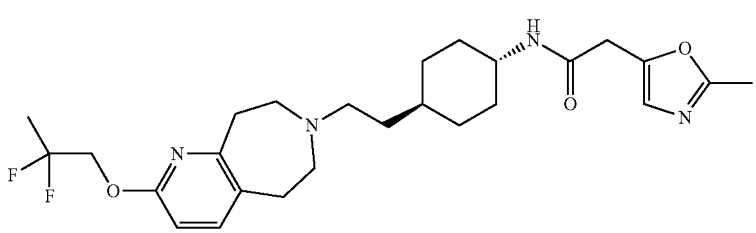 | 2 | 1.44 | 491.1 |
| III-021 | 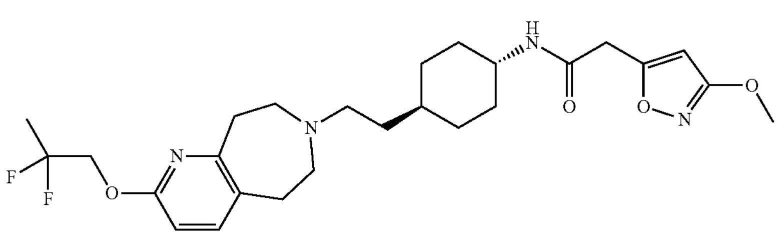 | 2 | 1.53 | 507.2 |

-continued

| Compound No. | Structure | LC/MS method | RT (min) | MS (m/z) |
|---|---|---|---|---|
| III-022 | 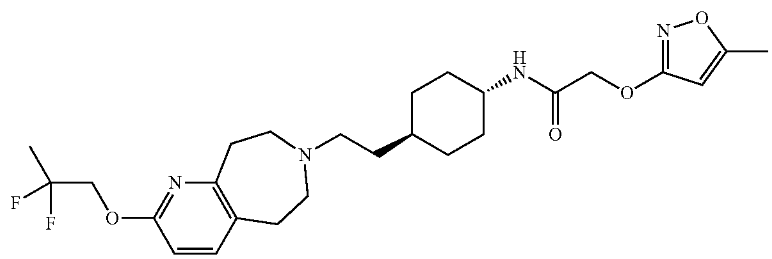 | 2 | 1.57 | 507.2 |
| III-023 | 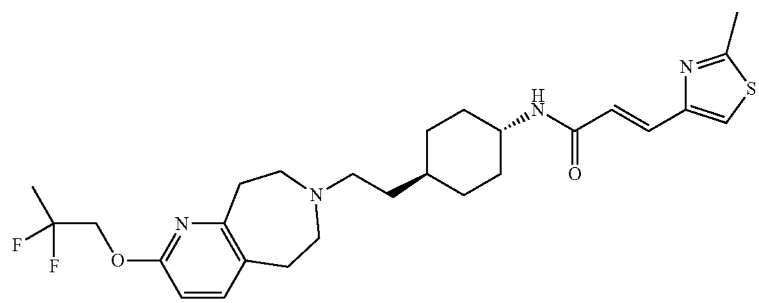 | 2 | 1.59 | 519.1 |
| III-024 | 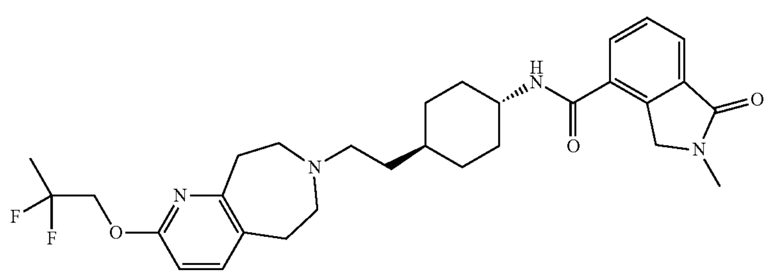 | 2 | 1.52 | 541.1 |
| III-025 | 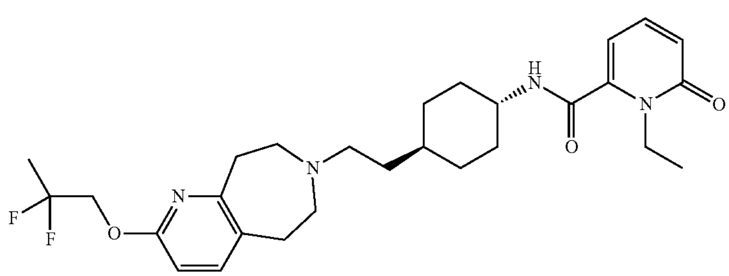 | 2 | 1.45 | 517.2 |
| III-026 | 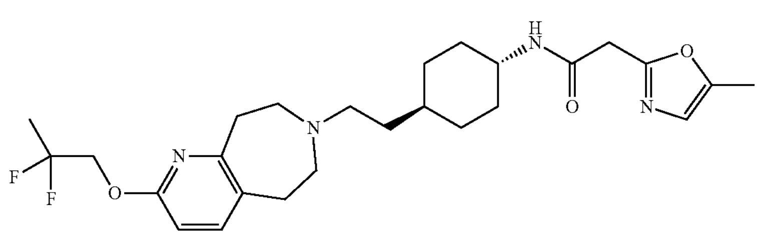 | 2 | 1.48 | 491.1 |

-continued
| Compound No. | Structure | LC/MS method | RT (min) | MS (m/z) |
|---|---|---|---|---|
| III-027 | 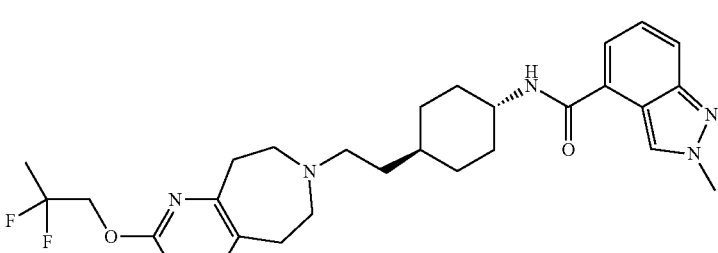 | 2 | 1.56 | 526.2 |
| III-028 | 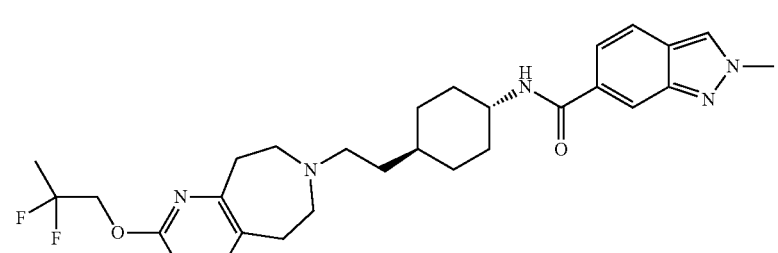 | 2 | 1.54 | 526.2 |
| III-029 | 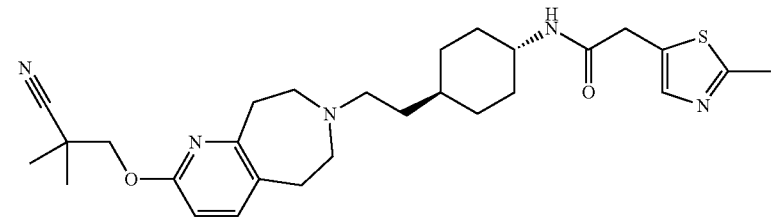 | 3 | 1.23 | 510 |
| III-030 | 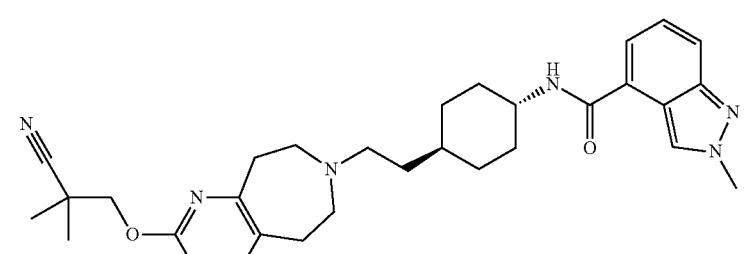 | 3 | 1.32 | 529 |
| III-031 | 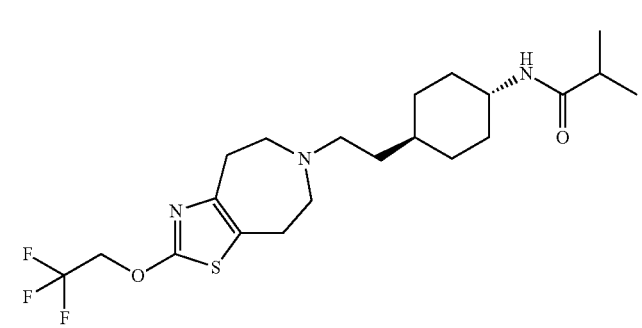 | 2 | 1.49 | 448.1 |

-continued
| Compound No. | Structure | LC/MS method | RT (min) | MS (m/z) |
|---|---|---|---|---|
| III-032 | 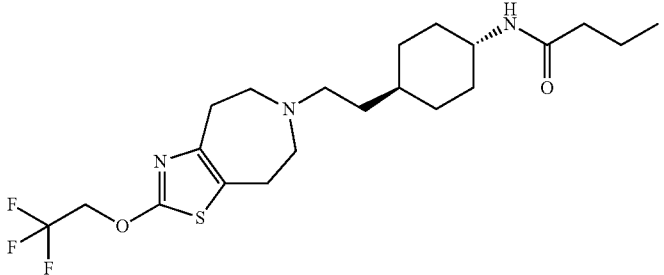 | 2 | 1.49 | 448.1 |
| III-03 | 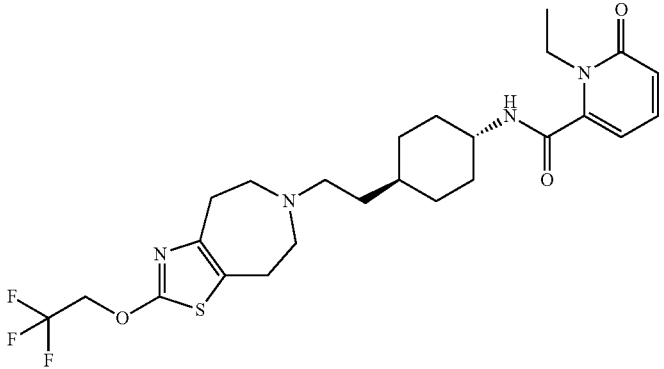 | 2 | 1.43 | 527.1 |
| III-034 | 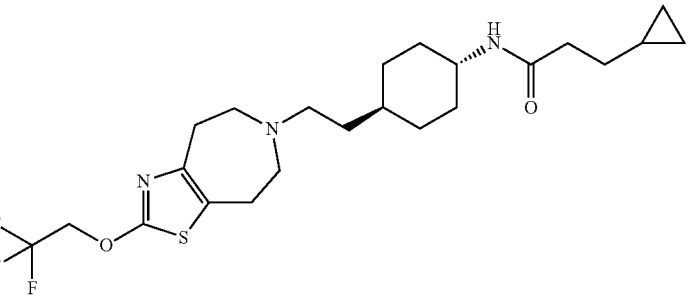 | 2 | 1.60 | 474.15 |
| III-035 | 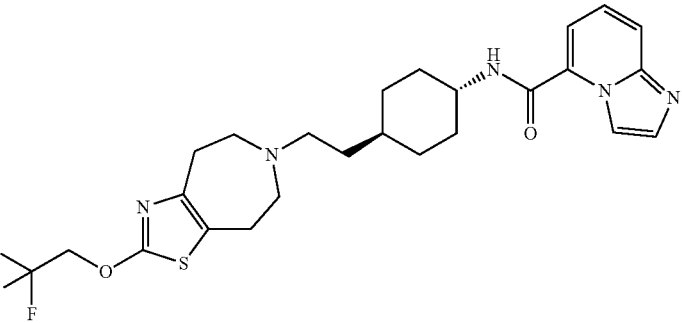 | 3 | 1.10 | 522.3 |

-continued

| Compound No. | Structure | LC/MS method | RT (min) | MS (m/z) |
|---|---|---|---|---|
| III-036 | 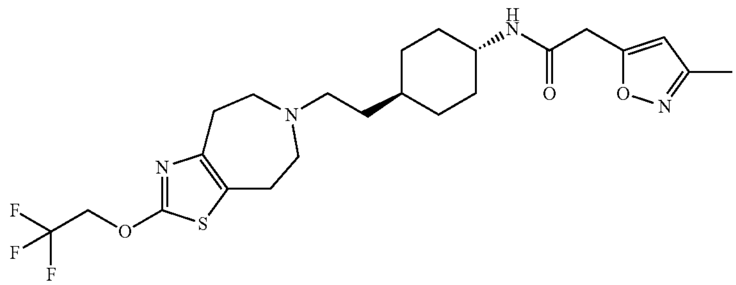 | 2 | 1.49 | 501.05 |
| III-037 | 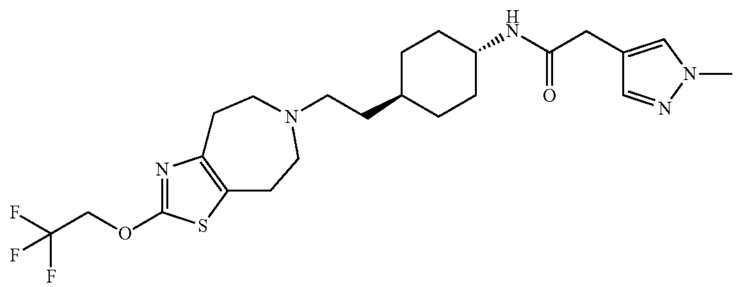 | 2 | 1.39 | 500.1 |
| III-038 | 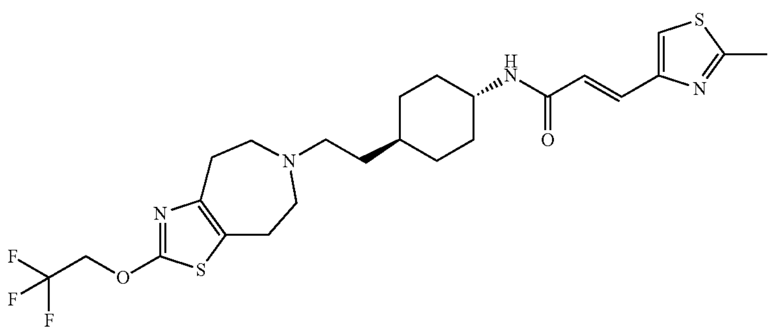 | 2 | 1.57 | 529.05 |
| III-039 | 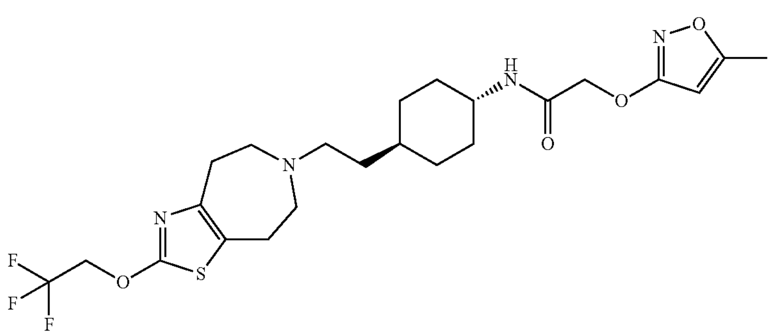 | 2 | 1.55 | 517.15 |
| III-040 | 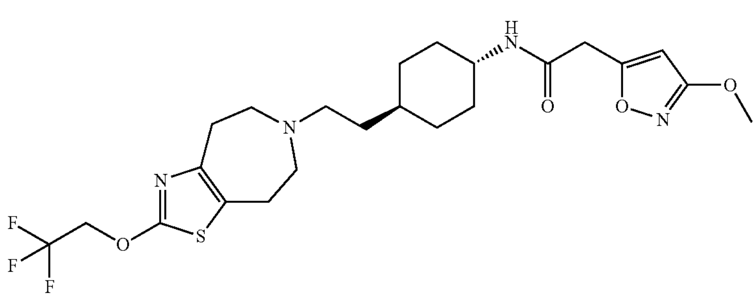 | 2 | 1.51 | 517.1 |

-continued

| Compound No. | Structure | LC/MS method | RT (min) | MS (m/z) |
|---|---|---|---|---|
| III-041 | 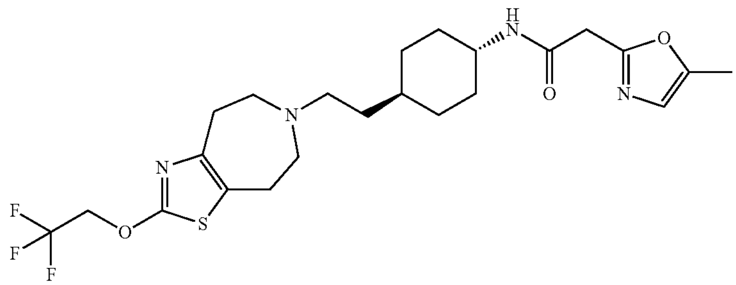 | 2 | 1.47 | 501.1 |
| III-042 | 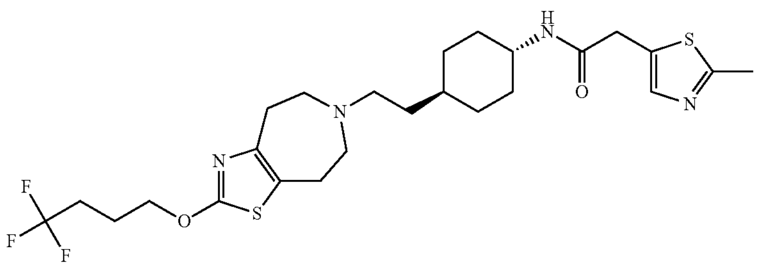 | 2 | 1.52 | 545.1 |
| III-043 | 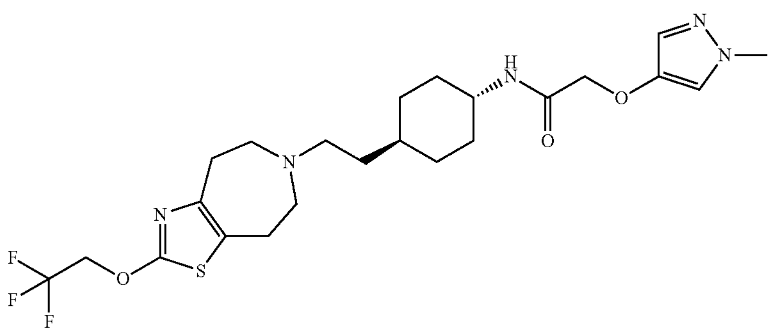 | 2 | 1.44 | 516.1 |
| III-044 | 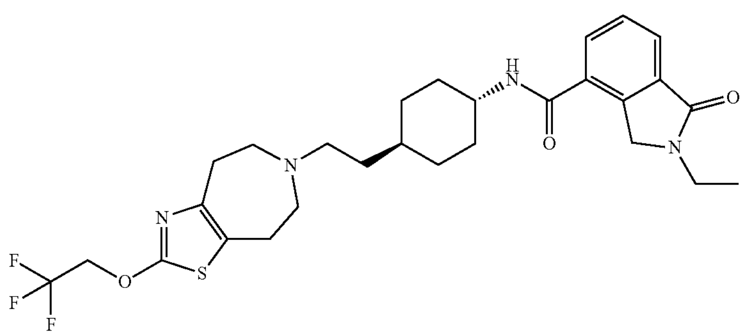 | 2 | 1.55 | 565.2 |
| III-045 | 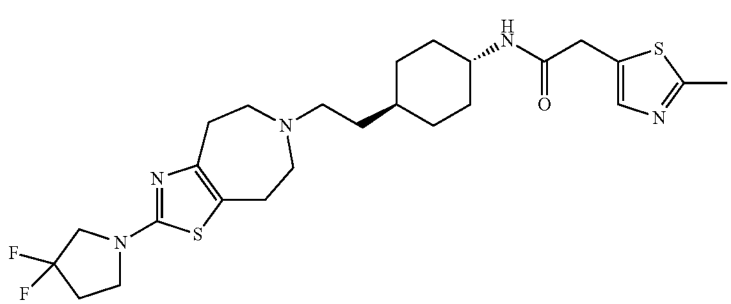 | 3 | 1.07 | 524.3 |

-continued

| Compound No. | Structure | LC/MS method | RT (min) | MS (m/z) |
|---|---|---|---|---|
| III-046 | 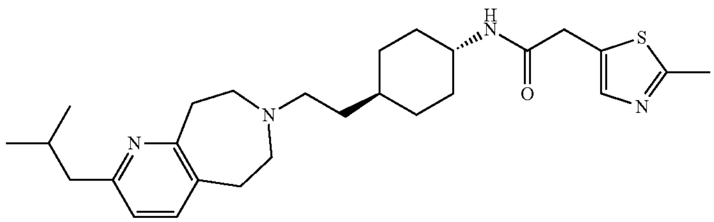 | 3 | 0.88 | 469 |
| III-047 | 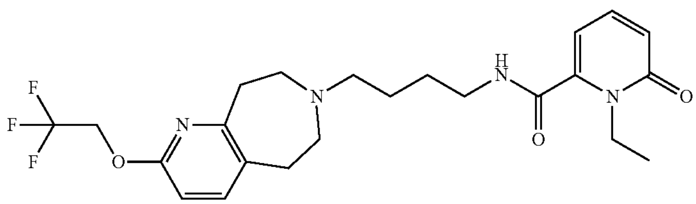 | 2 | 1.34 | 467.15 |
| III-048 | 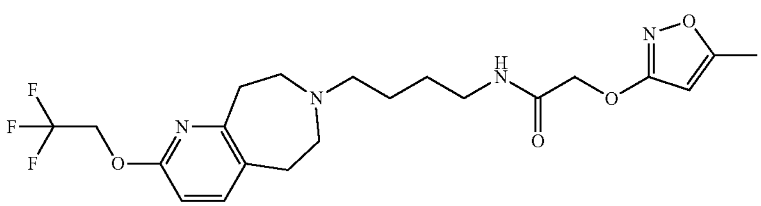 | 2 | 1.48 | 457.1 |
| III-049 | 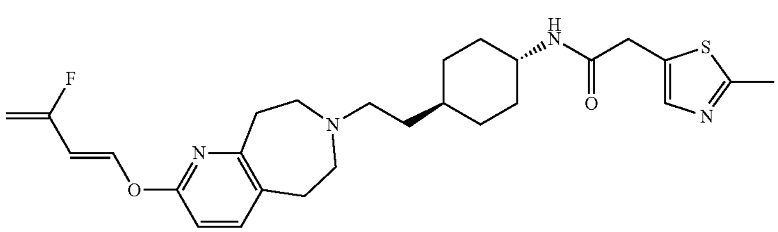 | 3 | 1.46 | 499 |
| III-050 | 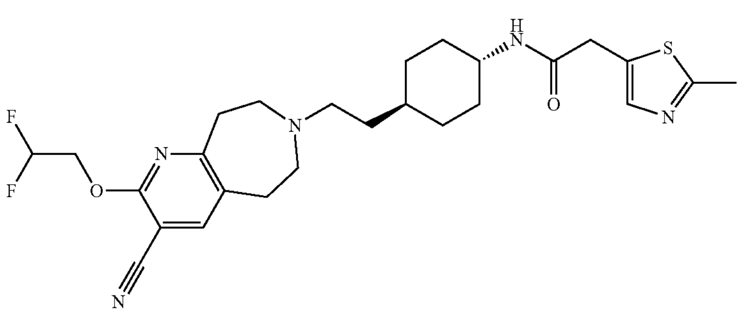 | 3 | 1.20 | 518 |
| III-051 | 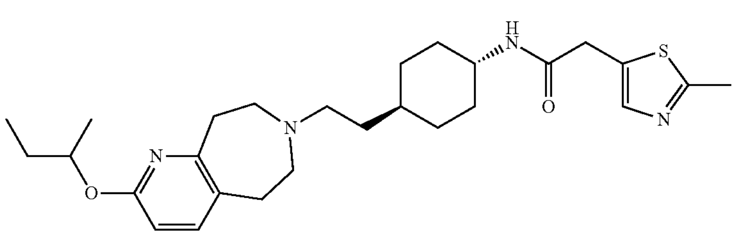 | 2 | 1.45 | 485 |

-continued

| Compound No. | Structure | LC/MS method | RT (min) | MS (m/z) |
|---|---|---|---|---|
| III-052 | 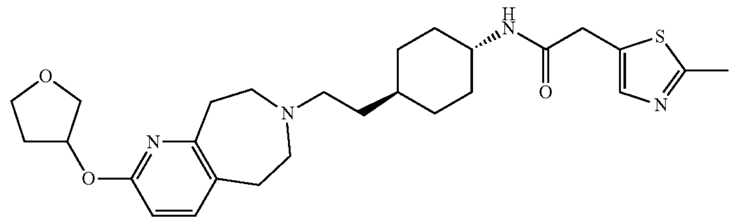 | 2 | 1.14 | 499 |
| III-053 | 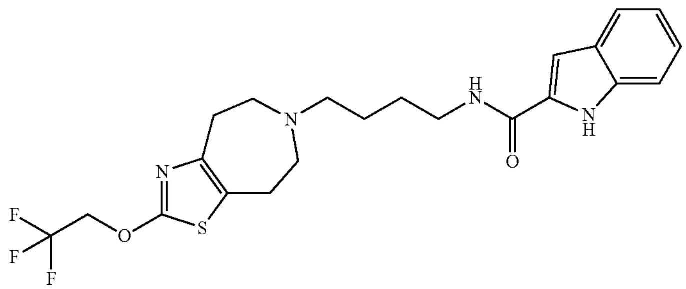 | 2 | 1.61 | 467.1 |
| III-054 | 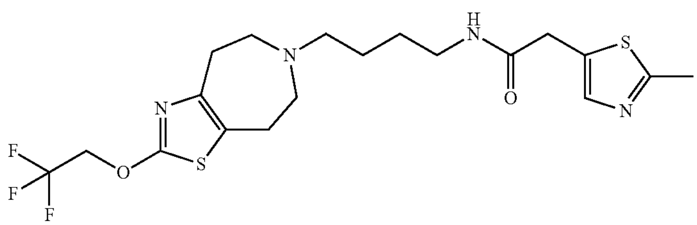 | 2 | 1.23 | 463.1 |
| III-055 | 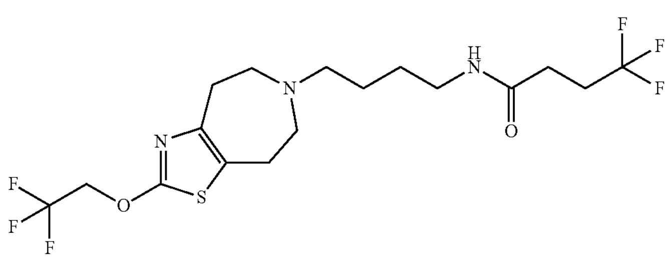 | 2 | 1.43 | 448.1 |
| III-056 | 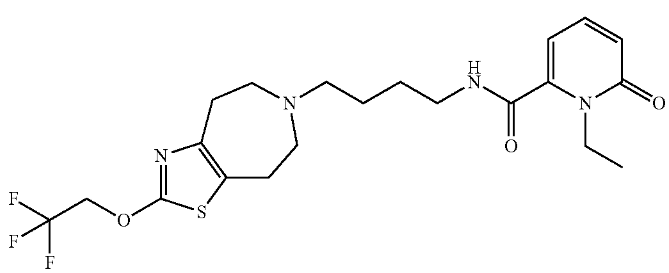 | 2 | 1.25 | 473.15 |
| III-057 | 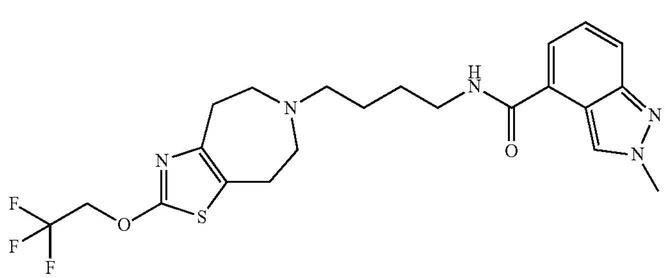 | 2 | 1.35 | 482.1 |

| Compound No. | Structure | LC/MS method | RT (min) | MS (m/z) |
|---|---|---|---|---|
| III-058 | 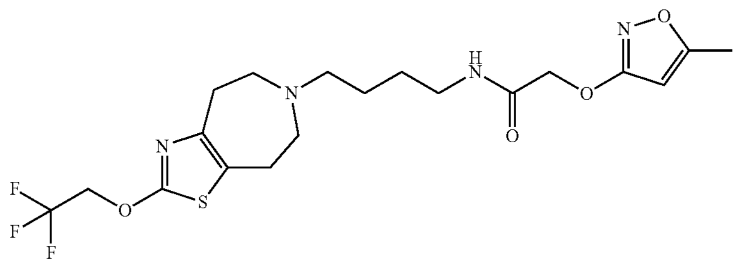 | 2 | 1.38 | 463.1 |
| III-059 | 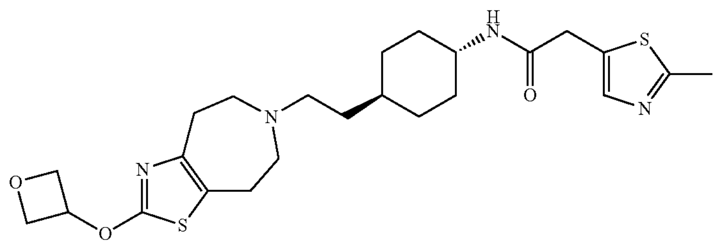 | 2 | 1.08 | 491.2 |
| III-060 | 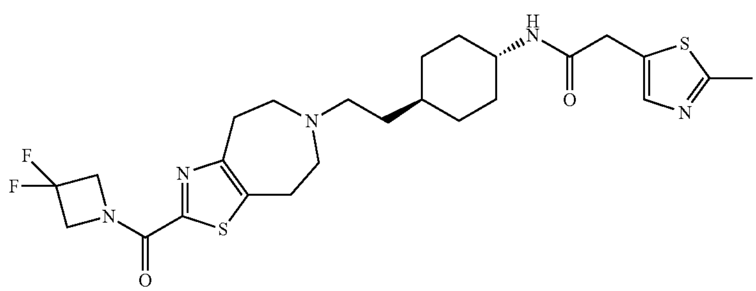 | 3 | 1.05 | 538.35 |
| III-061 | 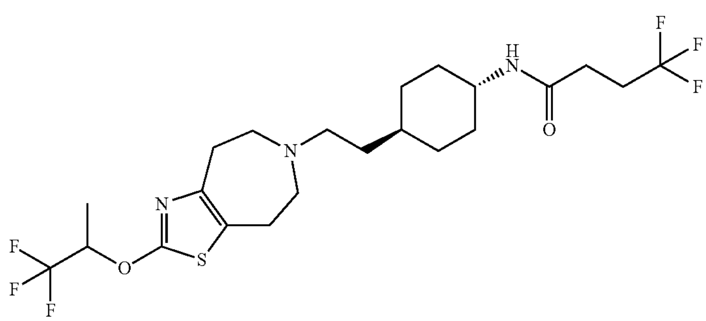 | 2 | 1.70 | 516.15 |
| III-062 | 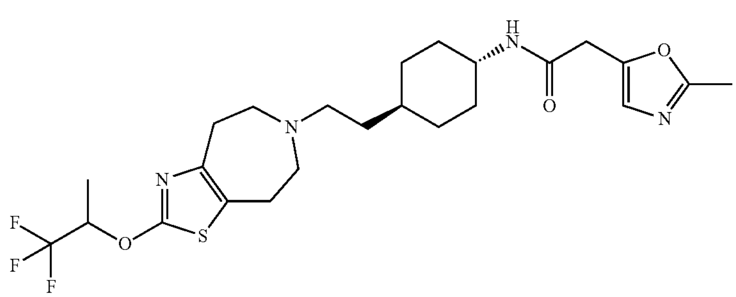 | 2 | 1.49 | 515.2 |

| Compound No. | Structure | LC/MS method | RT (min) | MS (m/z) |
| --- | --- | --- | --- | --- |
| III-063 | 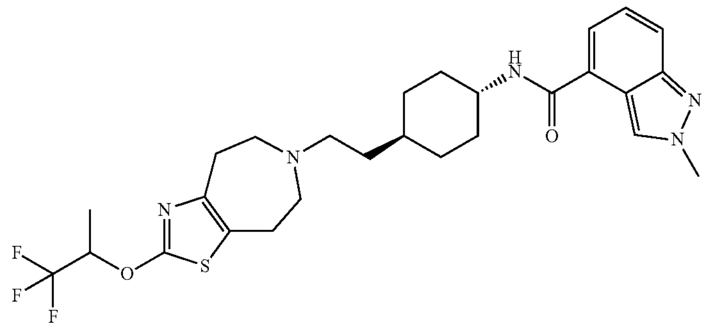 | 2 | 1.61 | 550.2 |
| III-064 | 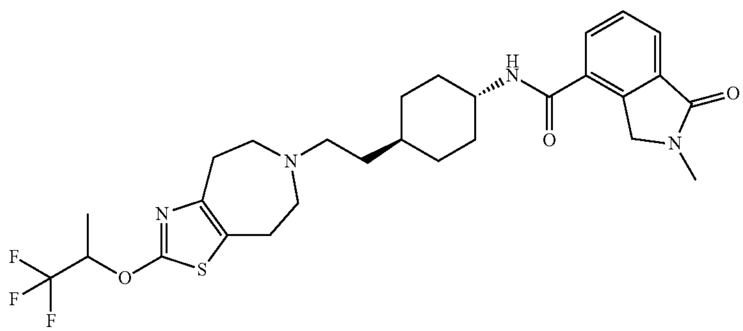 | 2 | 1.56 | 565.2 |
| III-065 | 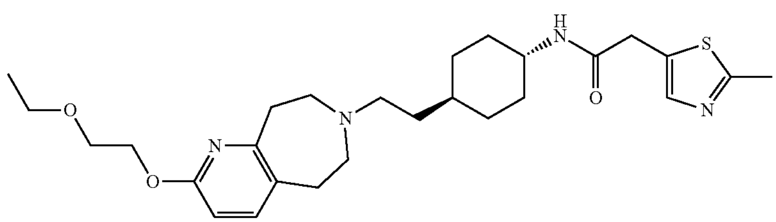 | 2 | 1.23 | 501 |
| III-066 | 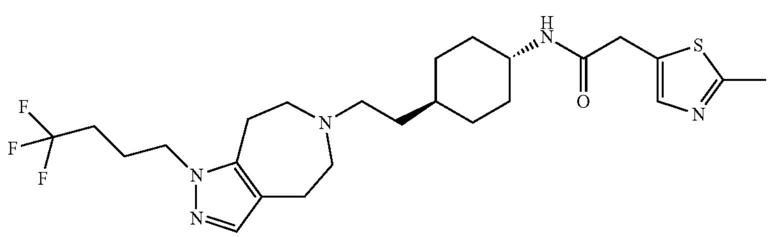 | 3 | 1.04 | 256 |
| III-067 | 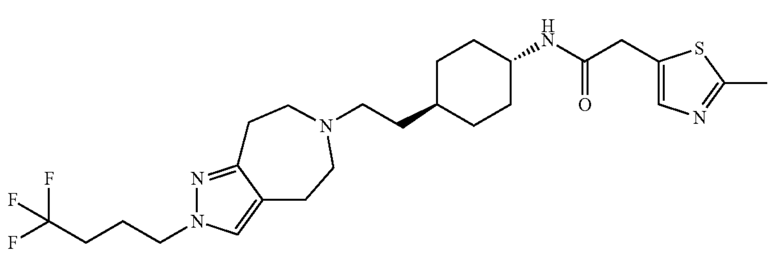 | 3 | 1.08 | 512 |

| Compound No. | Structure | LC/MS method | RT (min) | MS (m/z) |
|---|---|---|---|---|
| III-068 | 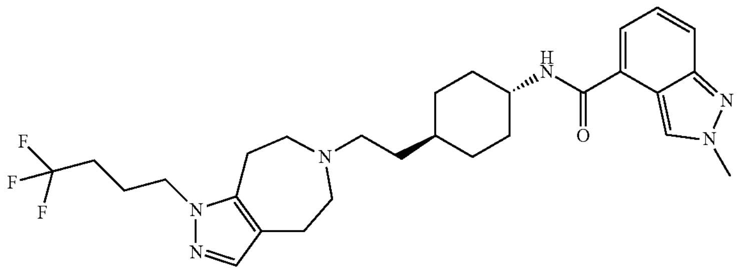 | 3 | 1.18 | 531 |
| III-069 | 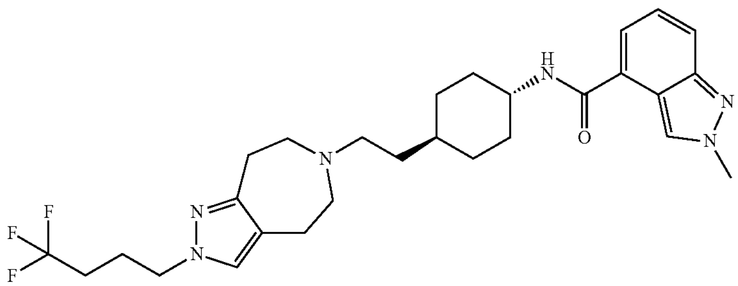 | 3 | 1.21 | 531 |
| III-070 | 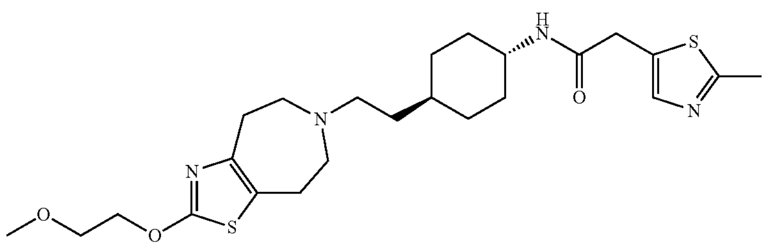 | 2 | 1.12 | 493.15 |
| III-071 | 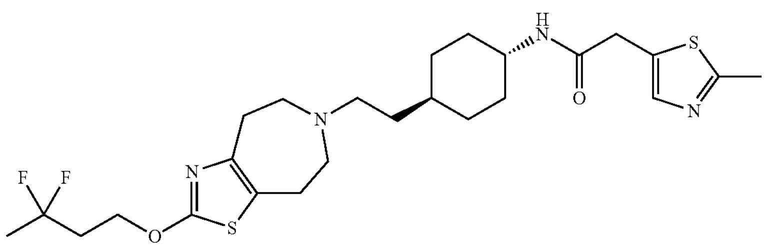 | 2 | 1.37 | 527.2 |
| III-072 | 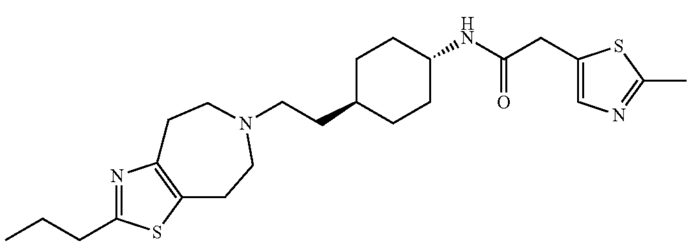 | 2 | 1.25 | 461.28 |
| III-073 | 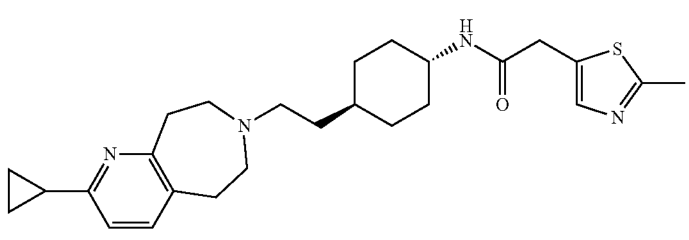 | 2 | 0.79 | 227 |

-continued

| Compound No. | Structure | LC/MS method | RT (min) | MS (m/z) |
|---|---|---|---|---|
| III-074 | 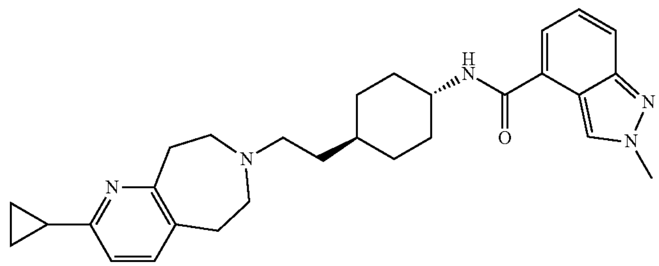 | 2 | 0.98 | 236.7 |
| III-075 | 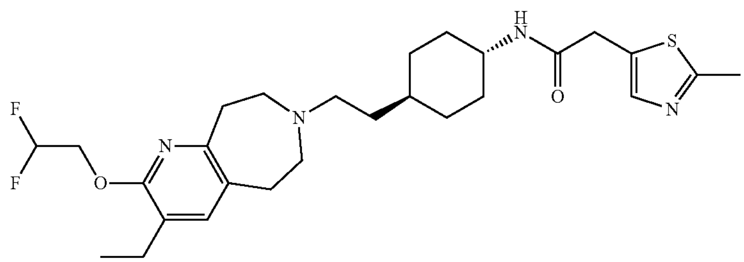 | 2 | 1.57 | 261 |
| III-076 | 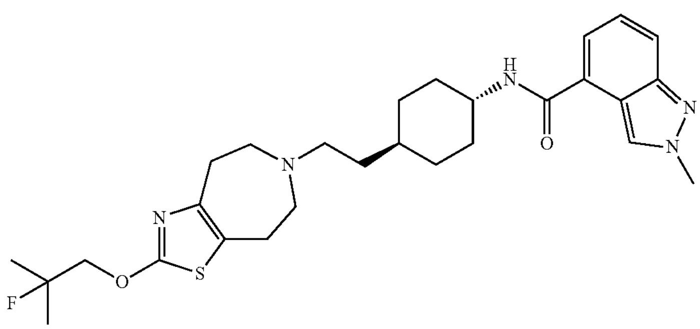 | 2 | 1.50 | 528.1 |
| III-077 | 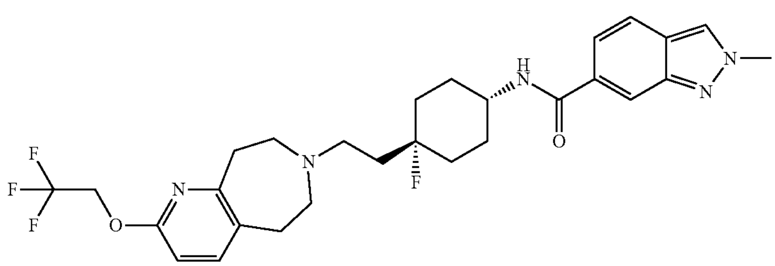 | 2 | 1.61 | 548 |
| III-078 | 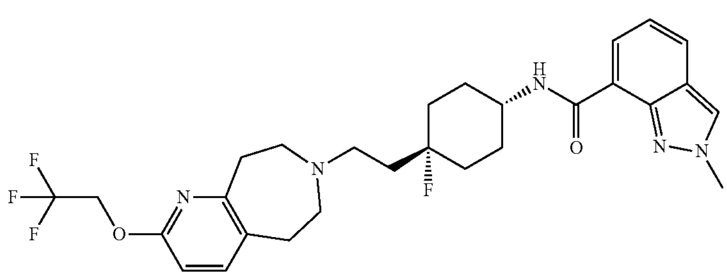 | 2 | 1.67 | 548 |

-continued

| Compound No. | Structure | LC/MS method | RT (min) | MS (m/z) |
|---|---|---|---|---|
| III-079 | 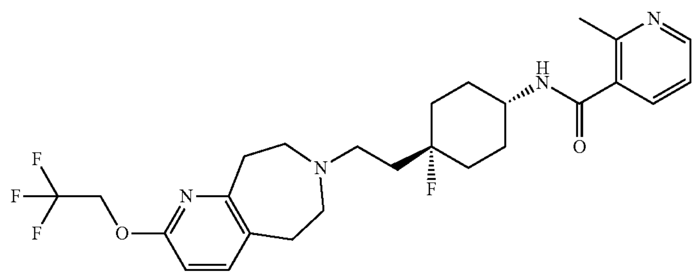 | 2 | 1.29 | 509 |
| III-080 | 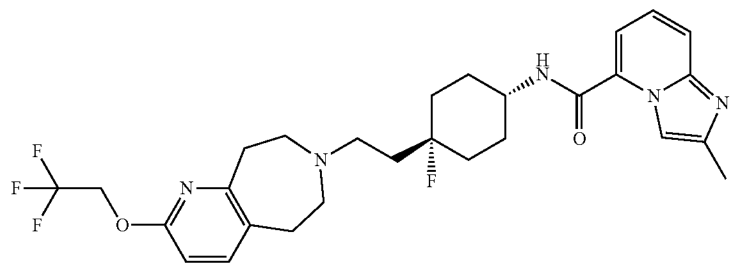 | 2 | 1.31 | 548 |
| III-081 | 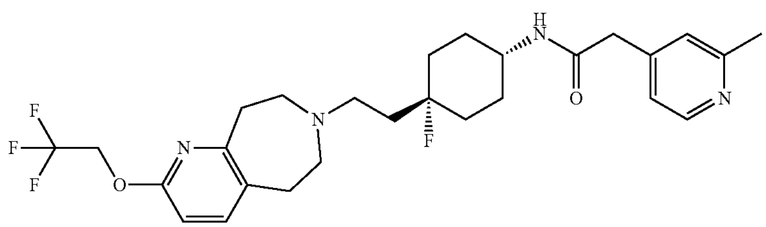 | 2 | 1.22 | 523 |
| III-082 | 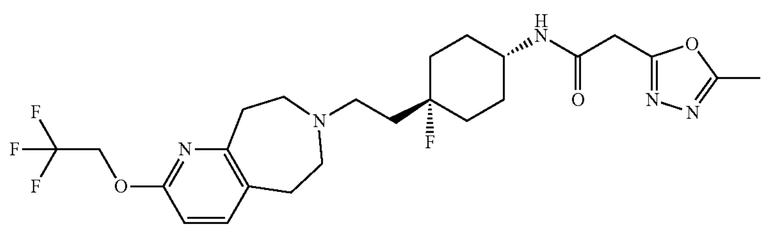 | 2 | 1.44 | 514 |
| III-083 | 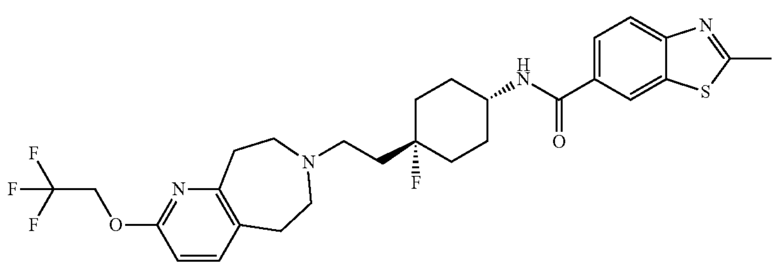 | 2 | 1.72 | 565 |
| III-084 | 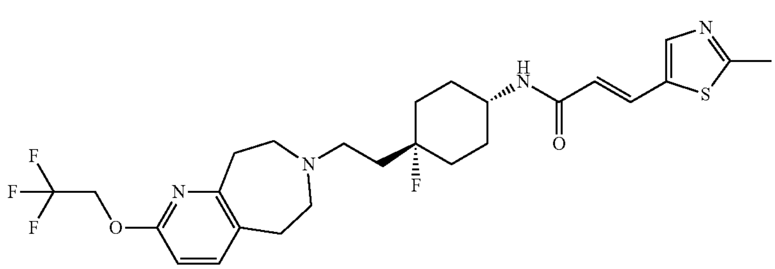 | 2 | 1.64 | 541 |

-continued
| Compound No. | Structure | LC/MS method | RT (min) | MS (m/z) |
|---|---|---|---|---|
| III-085 | 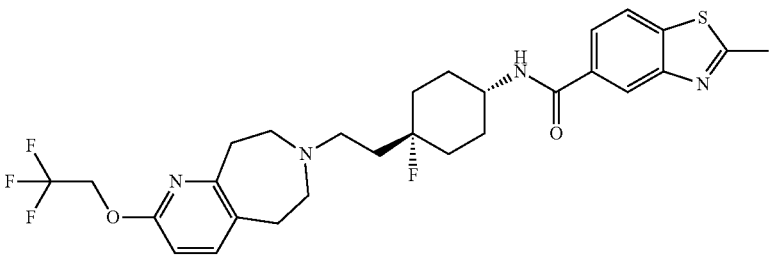 | 2 | 1.75 | 565 |
| III-086 | 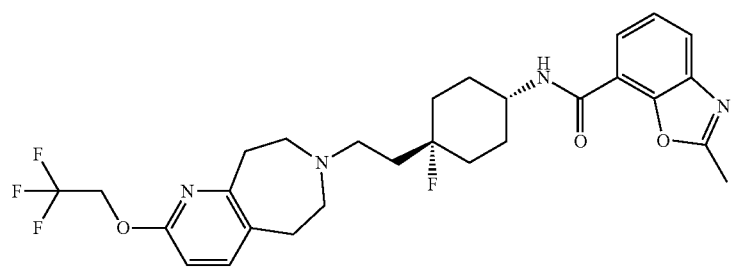 | 2 | 1.66 | 549 |
| III-087 | 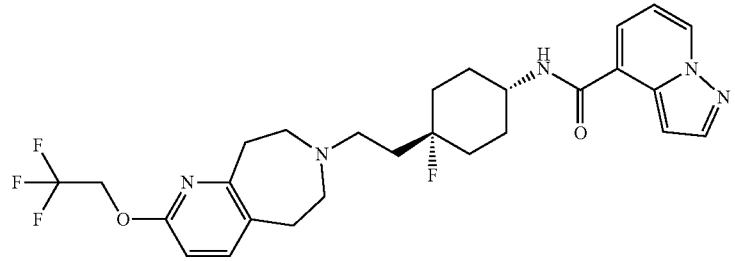 | 2 | 1.58 | 534 |
| III-088 | 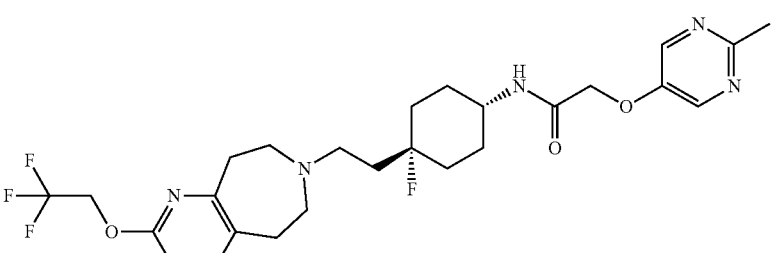 | 2 | 1.48 | 540 |
| III-089 | 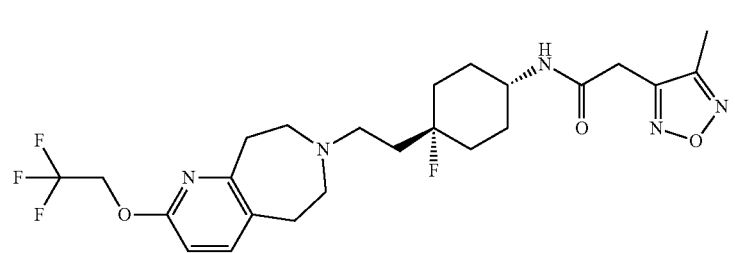 | 2 | 1.63 | 514 |

| Compound No. | Structure | LC/MS method | RT (min) | MS (m/z) |
| --- | --- | --- | --- | --- |
| III-090 | 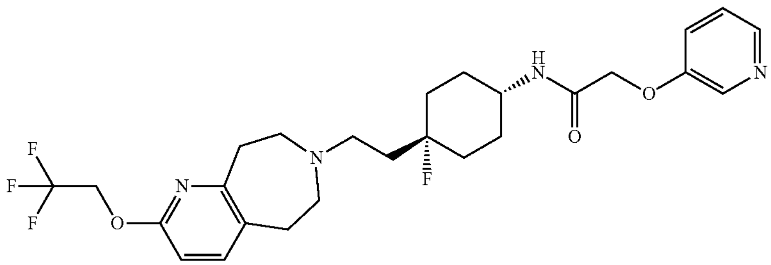 | 2 | 1.33 | 525 |
| III-091 | 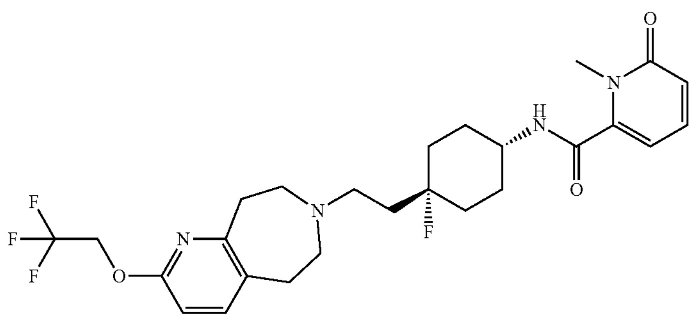 | 2 | 1.45 | 525 |
| III-092 | 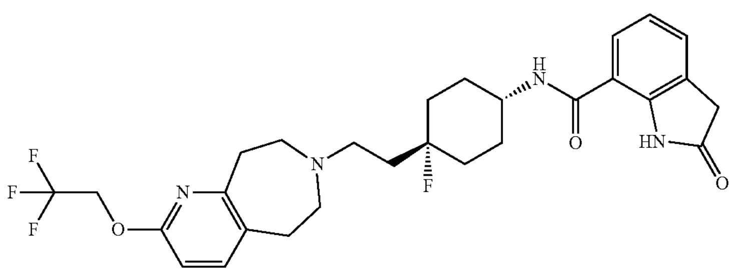 | 2 | 1.64 | 549 |
| III-093 | 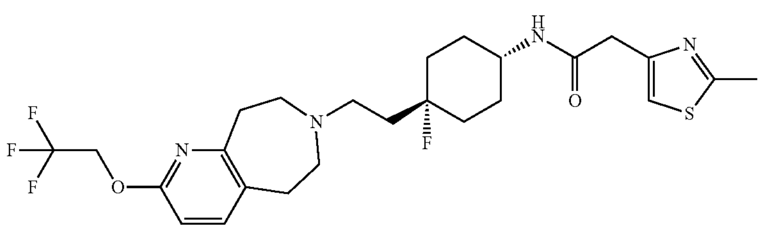 | 2 | 1.55 | 529 |
| III-094 | 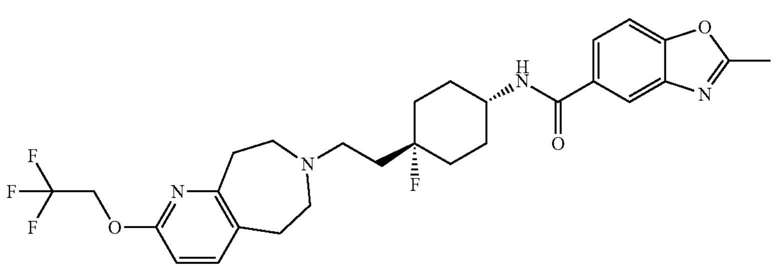 | 2 | 1.68 | 549 |

-continued

| Compound No. | Structure | LC/MS method | RT (min) | MS (m/z) |
|---|---|---|---|---|
| III-095 | 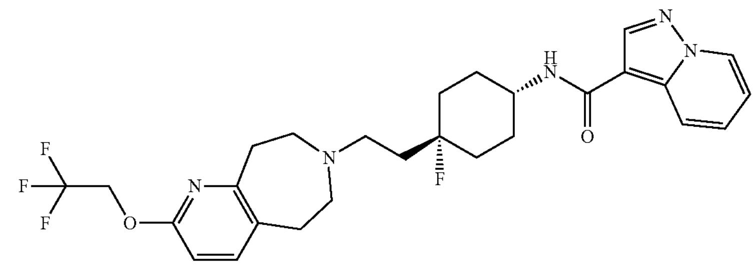 | 2 | 1.62 | 534 |
| III-096 | 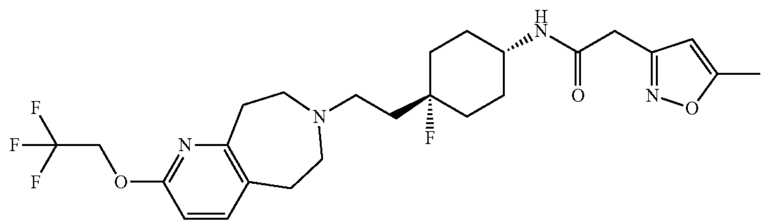 | 2 | 1.57 | 513 |
| III-097 | 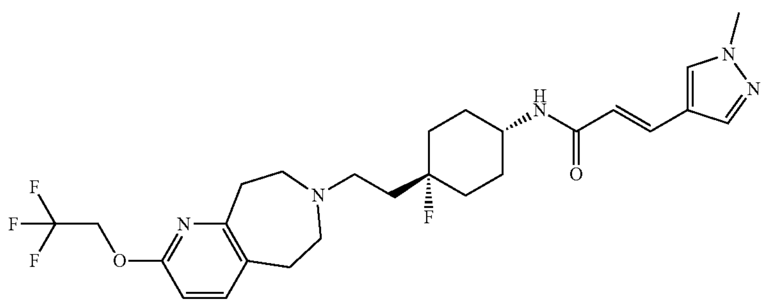 | 2 | 1.53 | 524 |
| III-098 | 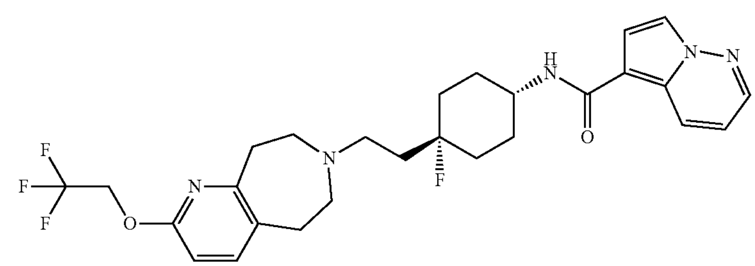 | 2 | 1.69 | 534 |
| III-099 | 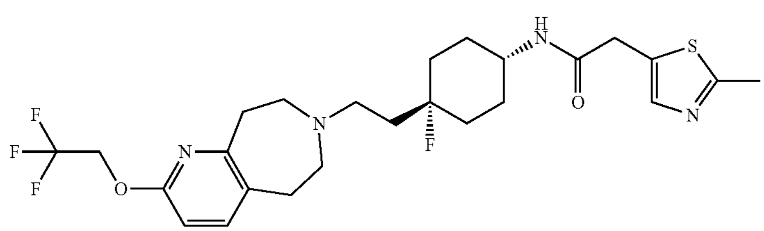 | 2 | 1.47 | 529.1 |
| III-100 | 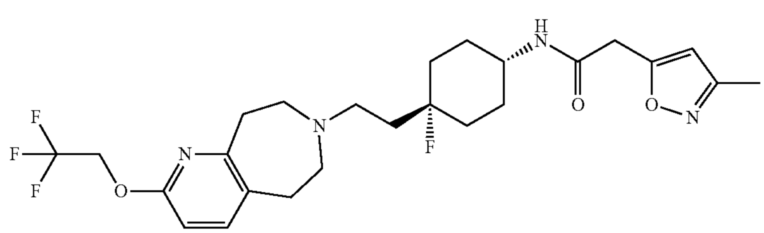 | 2 | 1.55 | 513.1 |

-continued

| Compound No. | Structure | LC/MS method | RT (min) | MS (m/z) |
|---|---|---|---|---|
| III-101 | 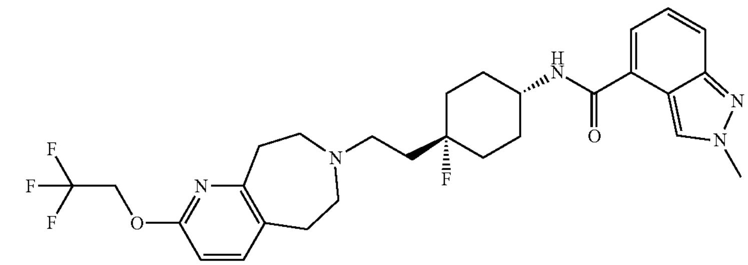 | 2 | 1.62 | 548.1 |
| III-102 | 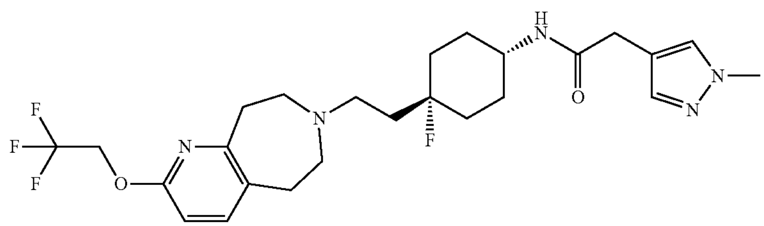 | 2 | 1.46 | 512.1 |
| III-103 | 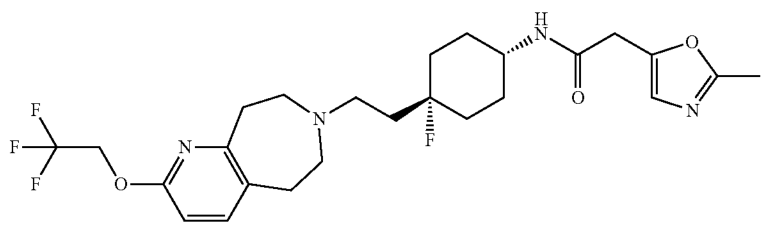 | 2 | 1.47 | 513.1 |
| III-104 | 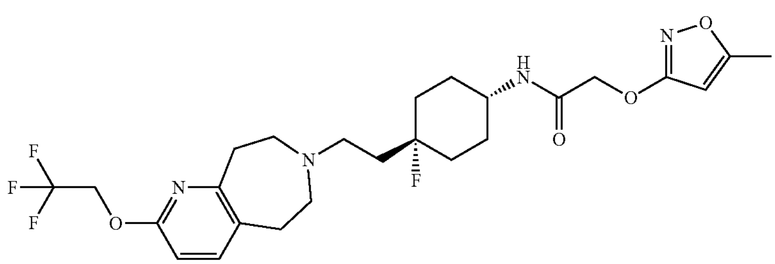 | 2 | 1.63 | 529.1 |
| III-105 | 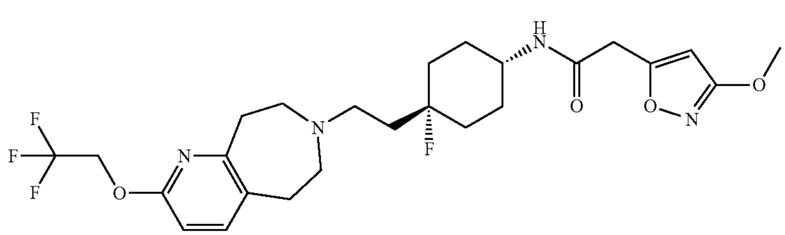 | 2 | 1.58 | 529.1 |
| III-106 | 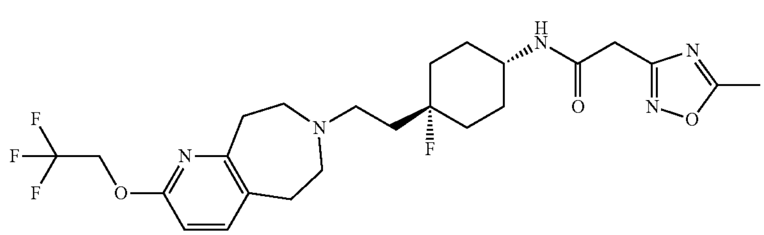 | 2 | 1.51 | 514.1 |

| Compound No. | Structure | LC/MS method | RT (min) | MS (m/z) |
|---|---|---|---|---|
| III-107 | 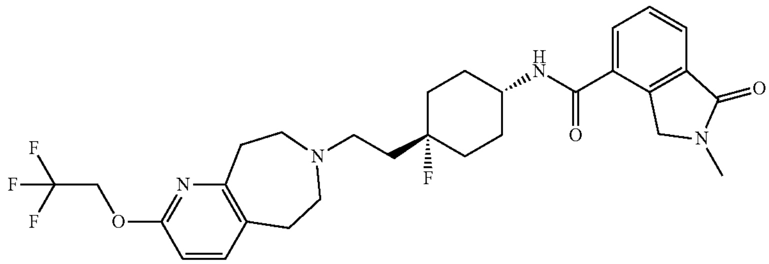 | 2 | 1.54 | 563.1 |
| III-108 | 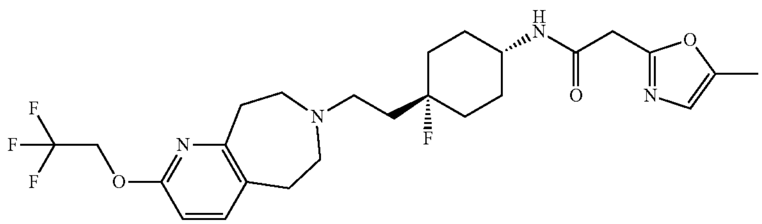 | 2 | 1.57 | 513.1 |
| III-109 | 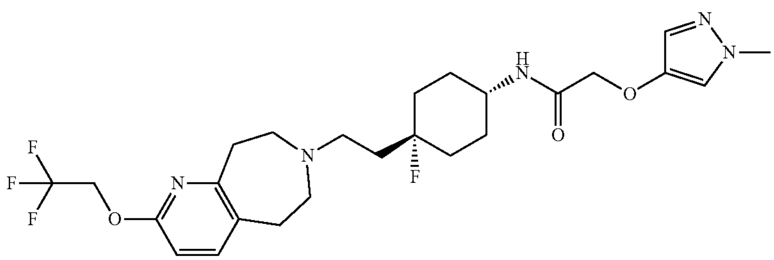 | 2 | 1.50 | 528 |
| III-110 | 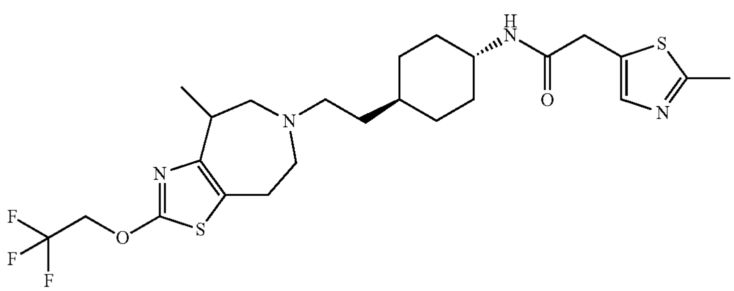 | 2 | 1.49 | 531.15 |
| III-111 | 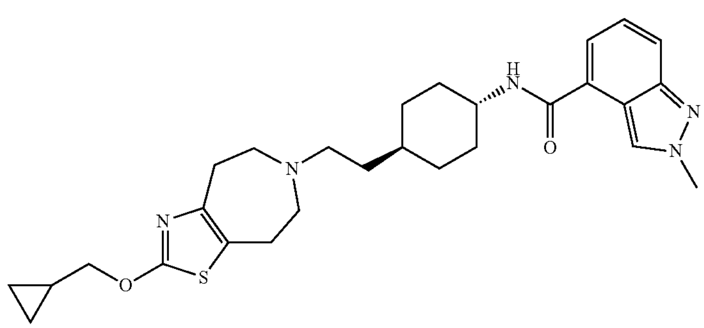 | 2 | 1.47 | 508.25 |

-continued

| Compound No. | Structure | LC/MS method | RT (min) | MS (m/z) |
| --- | --- | --- | --- | --- |
| III-112 | 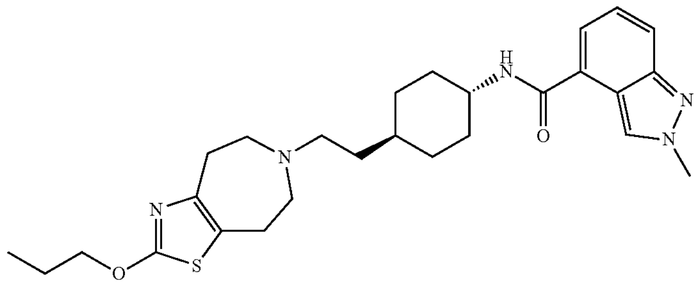 | 2 | 1.45 | 496.2 |
| III-113 | 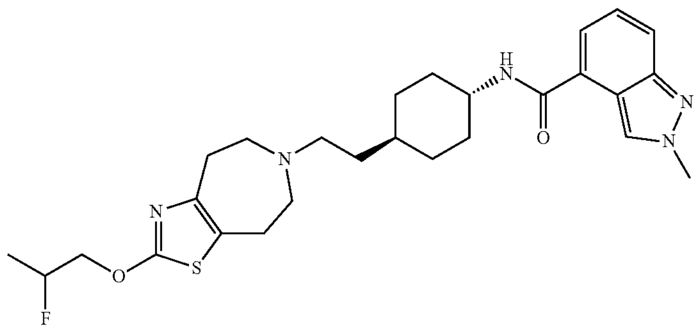 | 2 | 1.37 | 514.2 |
| III-114 | 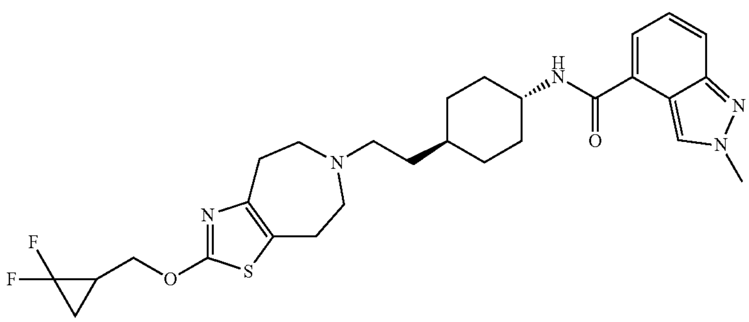 | 2 | 1.49 | 544.25 |
| III-115 | 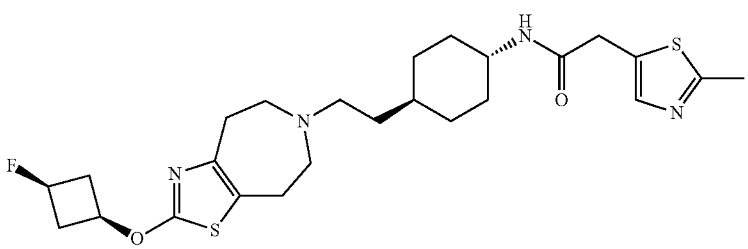 | 2 | 1.35 | 507.26 |
| III-116 | 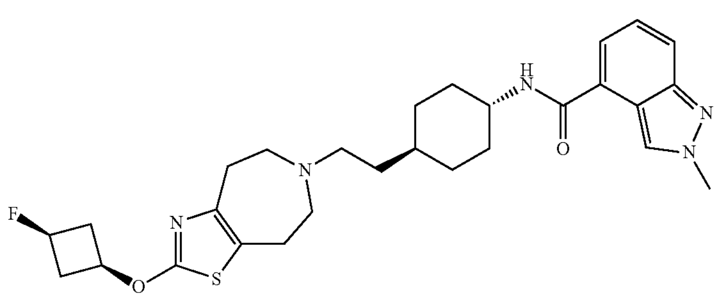 | 2 | 1.53 | 526.31 |

-continued

| Compound No. | Structure | LC/MS method | RT (min) | MS (m/z) |
|---|---|---|---|---|
| III-117 | 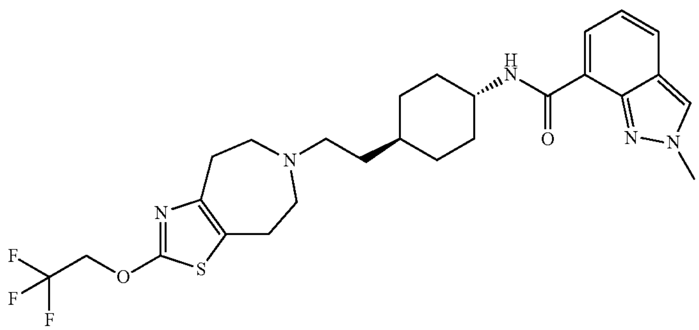 | 2 | 1.55 | 536.2 |
| III-118 | 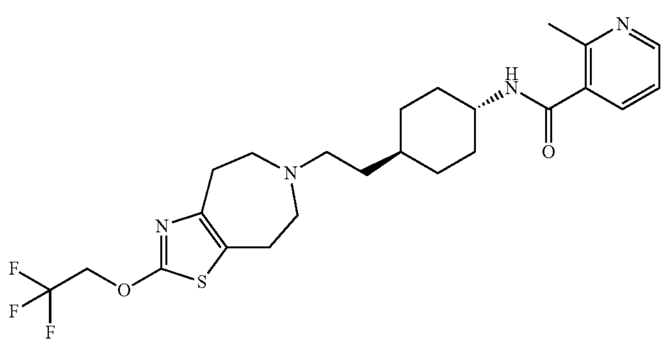 | 2 | 1.16 | 497.2 |
| III-119 | 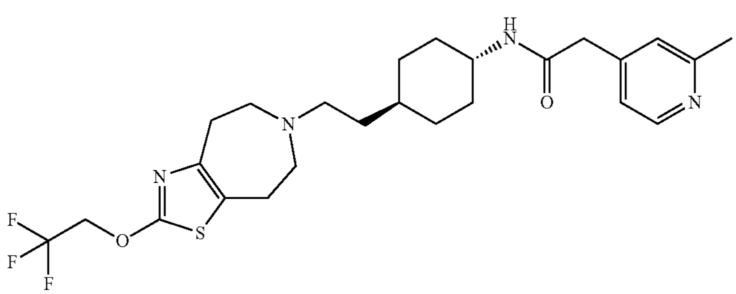 | 2 | 1.10 | 511.2 |
| III-120 | 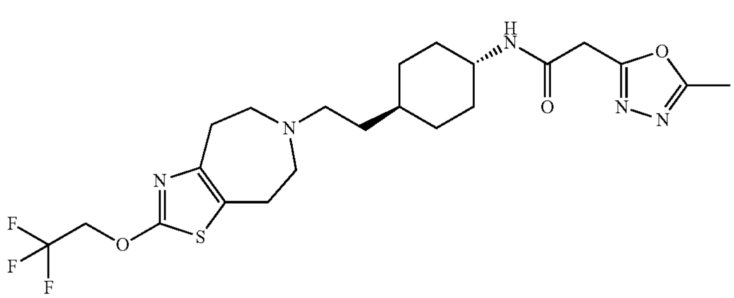 | 2 | 1.32 | 502.1 |

-continued
| Compound No. | Structure | LC/MS method | RT (min) | MS (m/z) |
|---|---|---|---|---|
| III-121 | 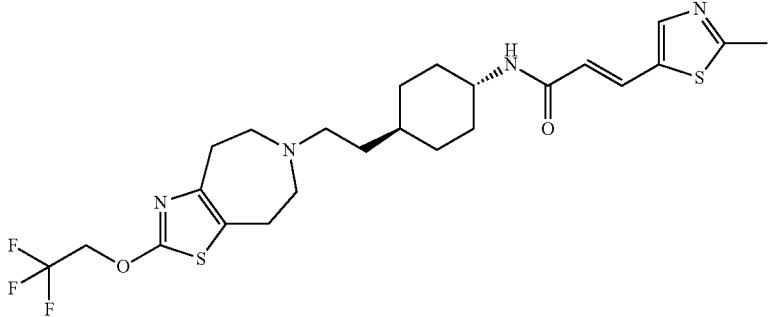 | 2 | 1.51 | 529.2 |
| III-122 | 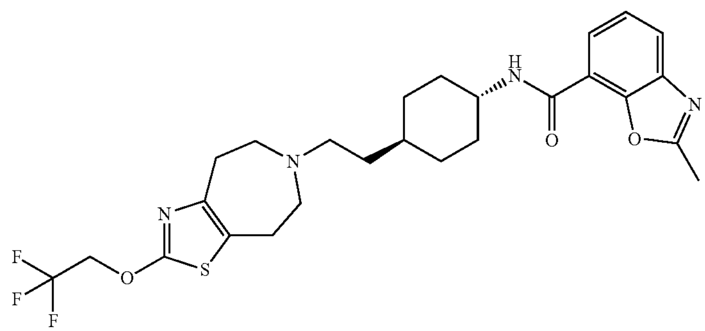 | 2 | 1.56 | 537.2 |
| III-123 | 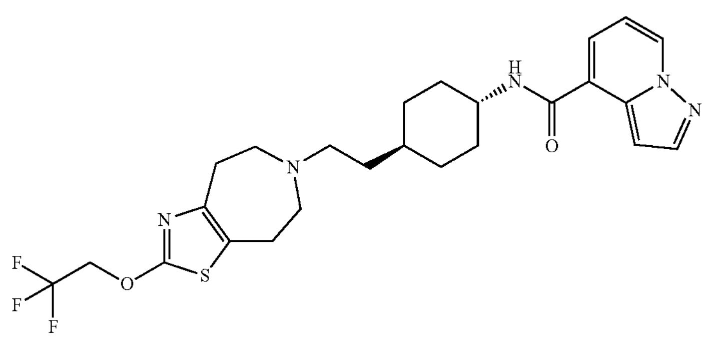 | 2 | 1.48 | 522.15 |
| III-124 | 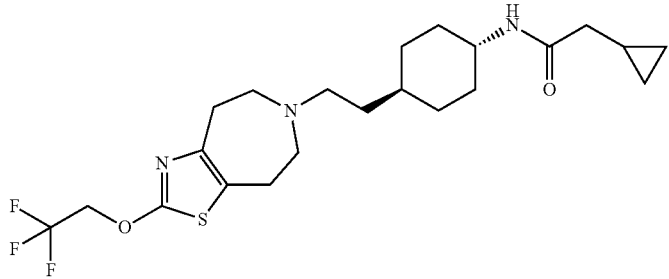 | 2 | 1.49 | 460.2 |

-continued
| Compound No. | Structure | LC/MS method | RT (min) | MS (m/z) |
|---|---|---|---|---|
| III-125 | 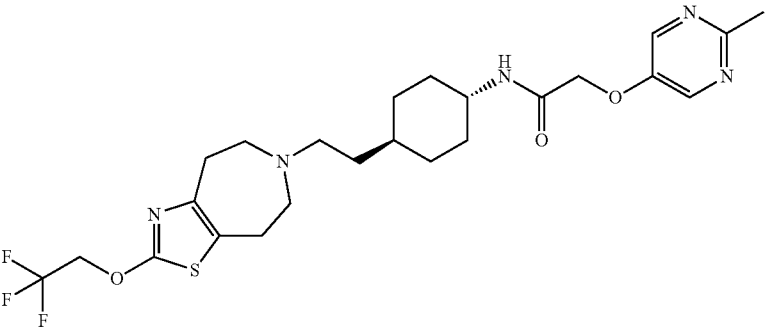 | 2 | 1.37 | 528.2 |
| III-126 | 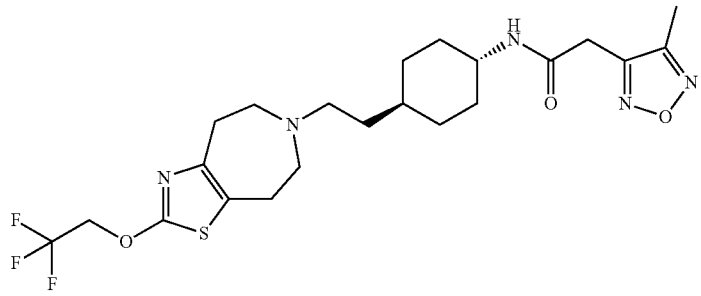 | 2 | 1.52 | 502.2 |
| III-127 | 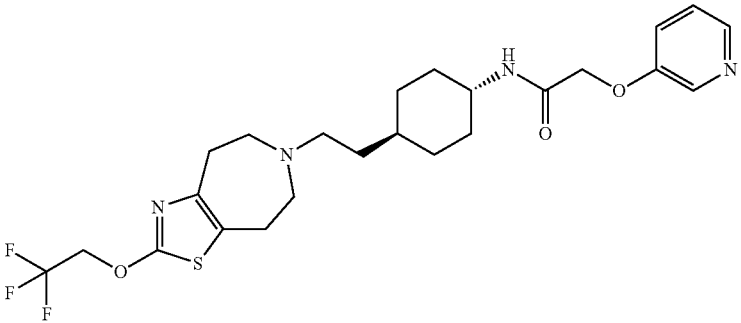 | 2 | 1.21 | 513.2 |
| III-128 | 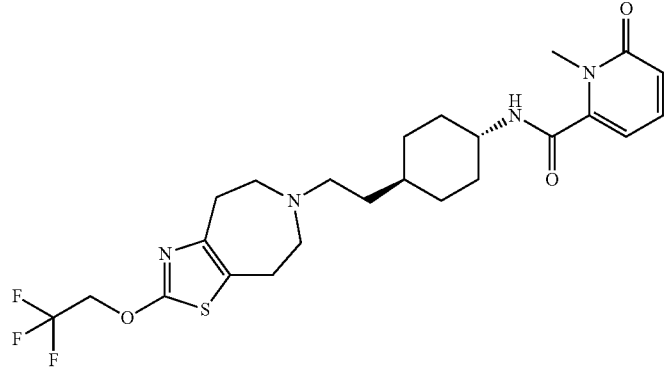 | 2 | 1.34 | 513.2 |

-continued

| Compound No. | Structure | LC/MS method | RT (min) | MS (m/z) |
| --- | --- | --- | --- | --- |
| III-129 | 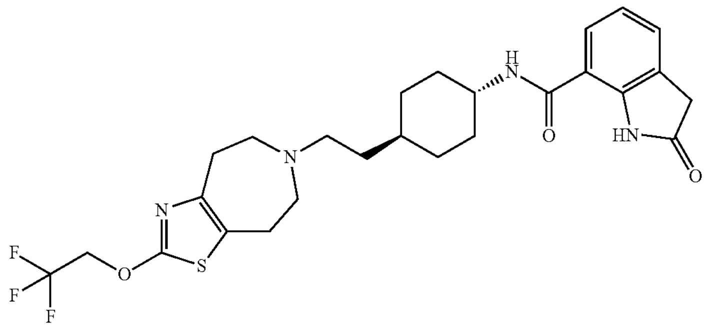 | 2 | 1.53 | 537.2 |
| III-130 | 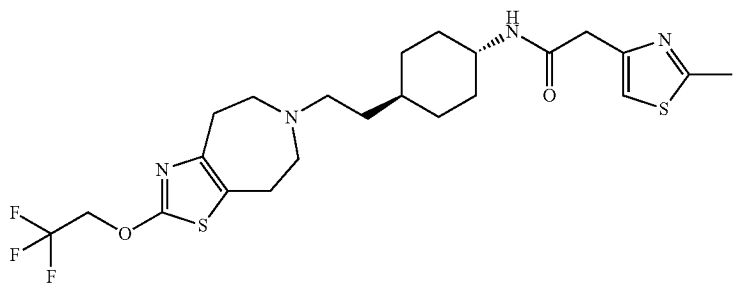 | 2 | 1.43 | 517.2 |
| III-131 | 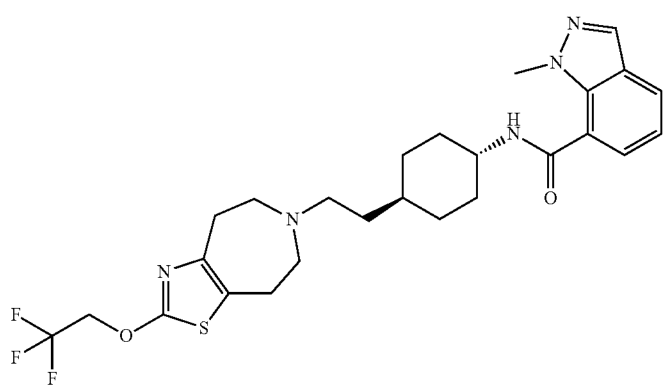 | 2 | 1.56 | 536.2 |
| III-132 | 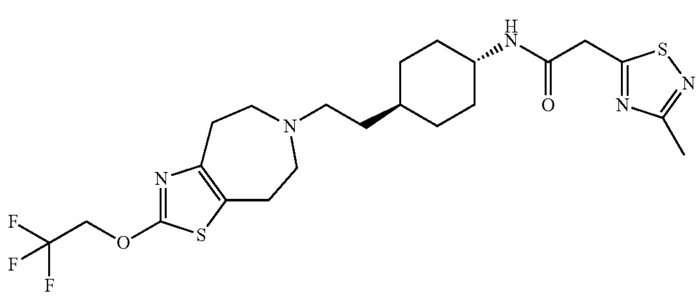 | 2 | 1.45 | 518.1 |

-continued

| Compound No. | Structure | LC/MS method | RT (min) | MS (m/z) |
|---|---|---|---|---|
| III-133 | 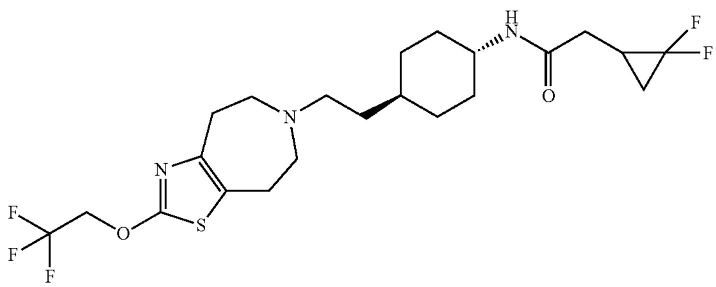 | 2 | 1.55 | 496.1 |
| III-134 | 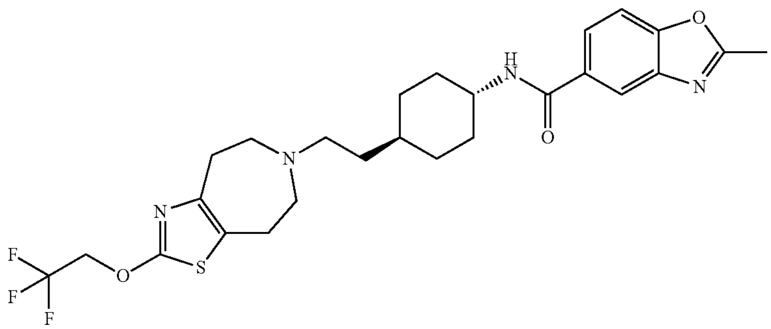 | 2 | 1.56 | 537.2 |
| III-135 | 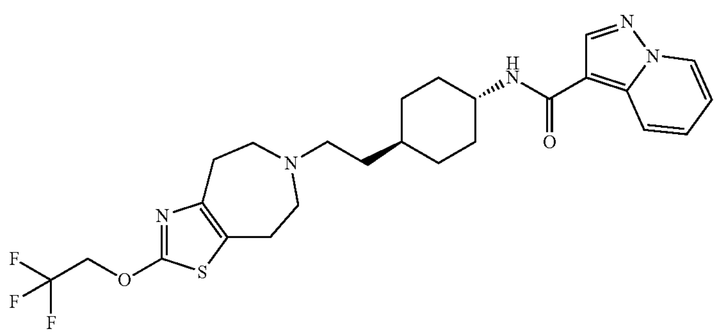 | 2 | 1.51 | 522.2 |
| III-136 | 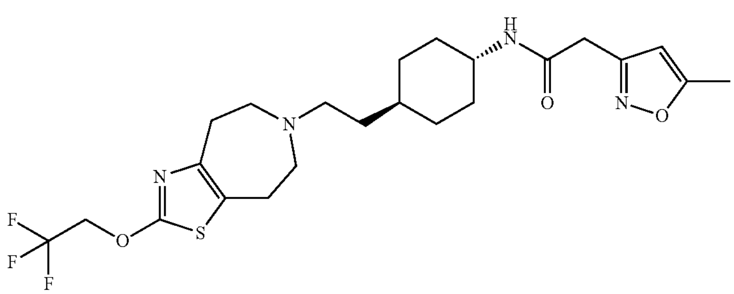 | 2 | 1.47 | 501.2 |
| III-137 | 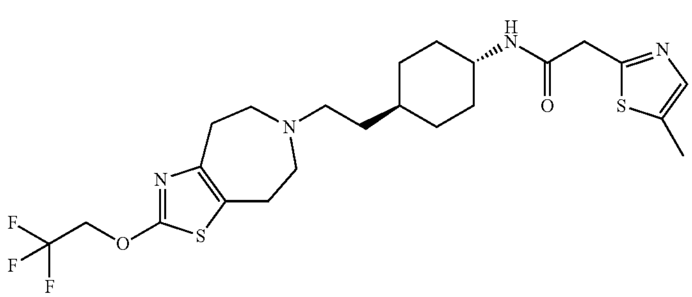 | 2 | 1.49 | 517.1 |

-continued
| Compound No. | Structure | LC/MS method | RT (min) | MS (m/z) |
|---|---|---|---|---|
| III-138 | 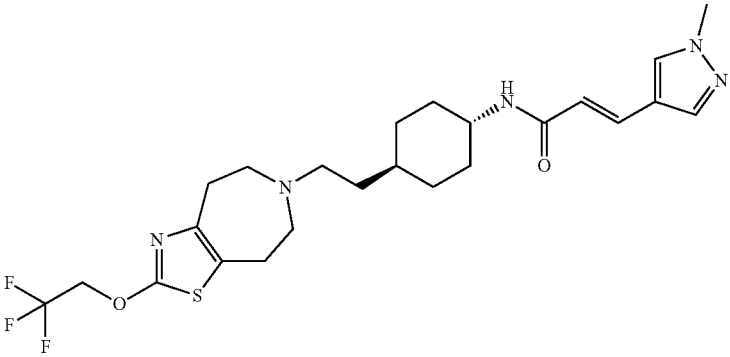 | 2 | 1.42 | 512.2 |
| III-139 | 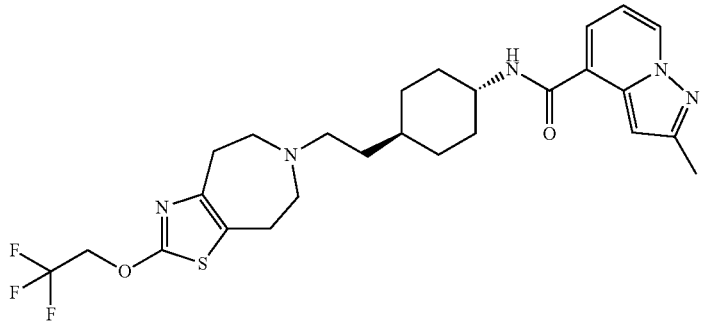 | 2 | 1.53 | 536.2 |
| III-140 | 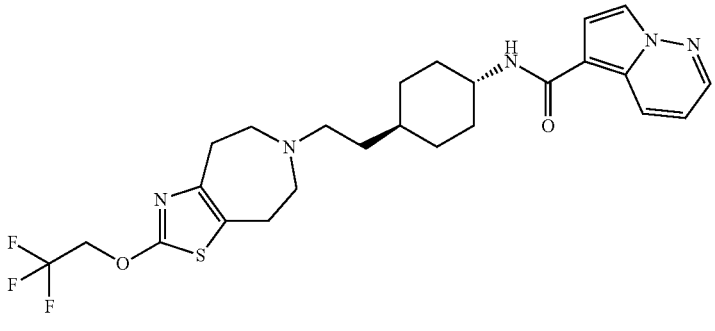 | 2 | 1.58 | 522.2 |
| III-141 | 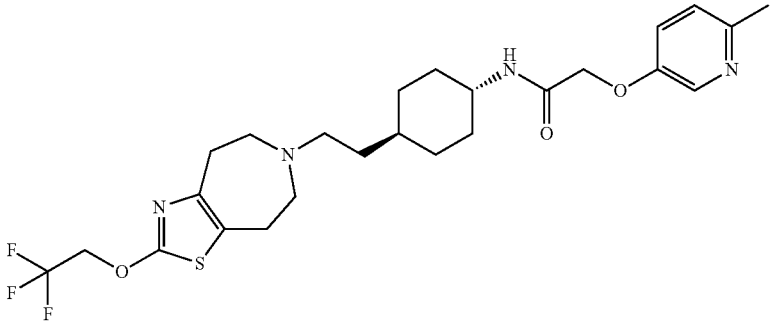 | 2 | 1.16 | 527.2 |

| Compound No. | Structure | LC/MS method | RT (min) | MS (m/z) |
|---|---|---|---|---|
| III-142 | 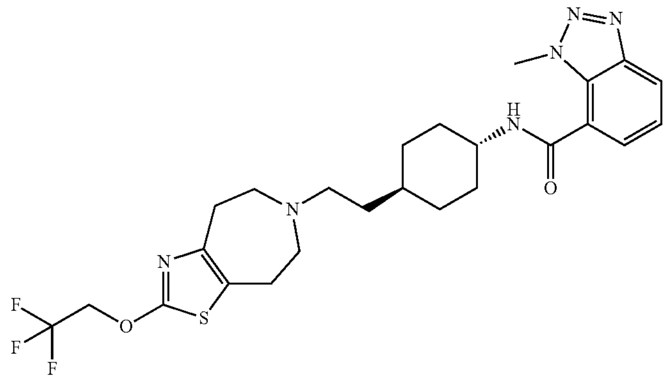 | 2 | 1.49 | 537.2 |
| III-143 | 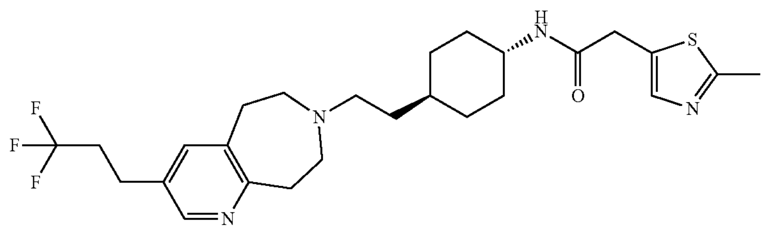 | 2 | 1.07 | 255.3 |
| III-144 | 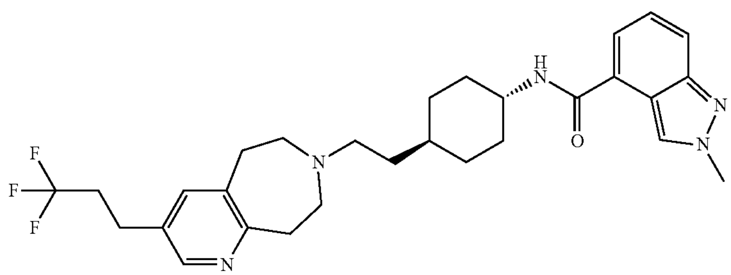 | 2 | 1.22 | 264.8 |
| III-145 | 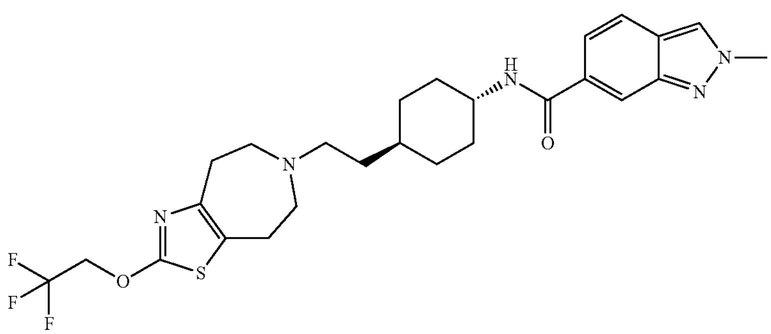 | 2 | 1.48 | 536 |
| III-146 | 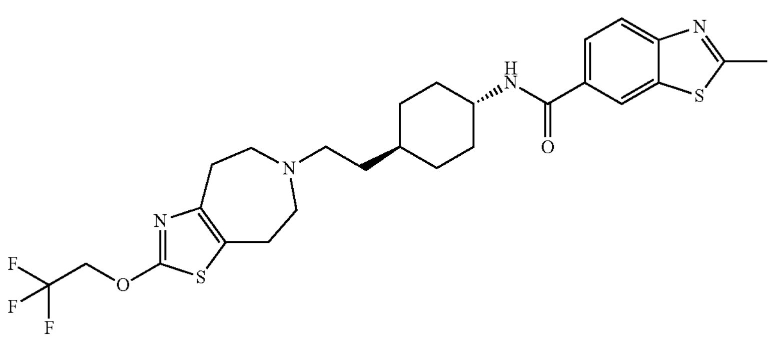 | 2 | 1.61 | 553.15 |

-continued

| Compound No. | Structure | LC/MS method | RT (min) | MS (m/z) |
|---|---|---|---|---|
| III-147 | 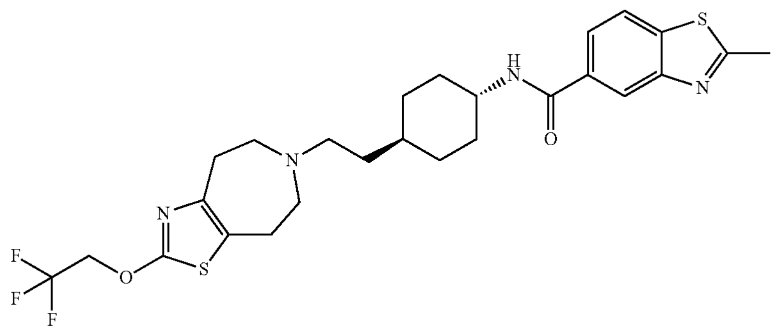 | 2 | 1.62 | 553 |
| III-148 | 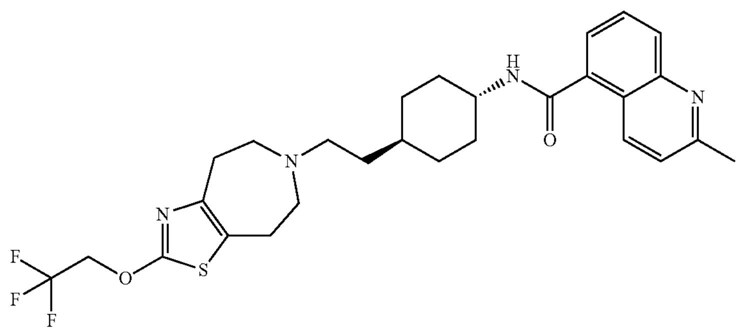 | 2 | 1.22 | 547 |
| III-149 | 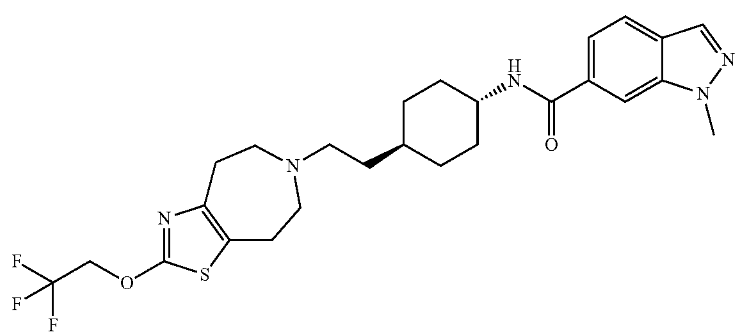 | 2 | 1.56 | 536 |
| III-150 | 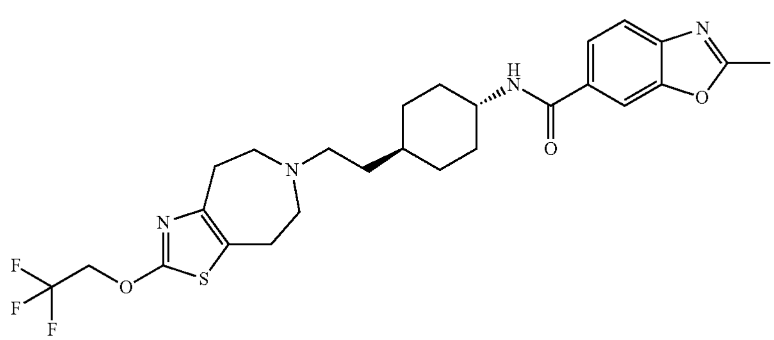 | 2 | 1.55 | 537 |

-continued
| Compound No. | Structure | LC/MS method | RT (min) | MS (m/z) |
|---|---|---|---|---|
| III-151 | 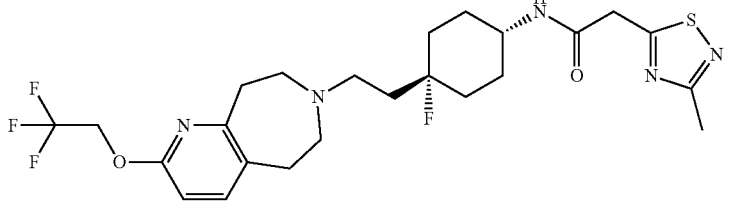 | 2 | 1.55 | 530 |
| III-152 | 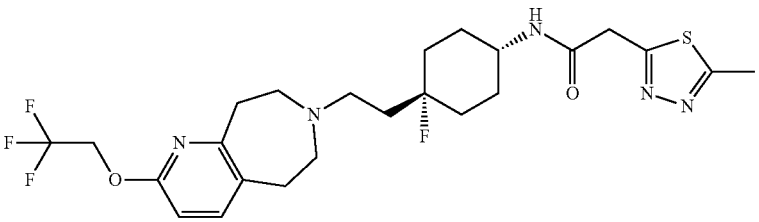 | 2 | 1.47 | 530 |
| III-153 | 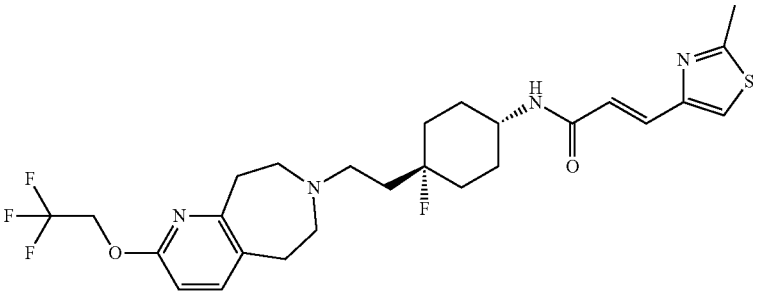 | 2 | 1.64 | 541 |
| III-154 | 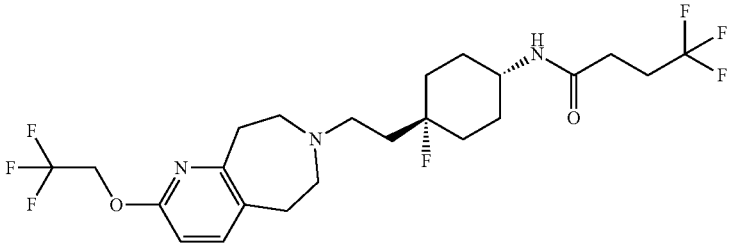 | 2 | 1.70 | 514 |
| III-155 | 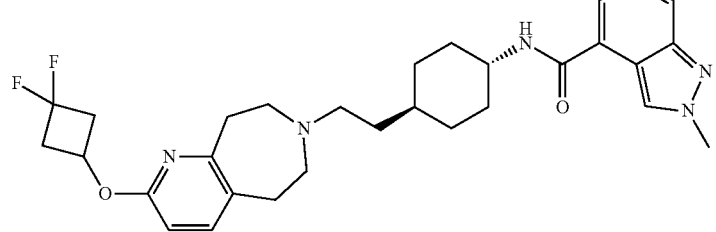 | 2 | 1.53 | 269.8 |

-continued

| Compound No. | Structure | LC/MS method | RT (min) | MS (m/z) |
|---|---|---|---|---|
| III-156 | 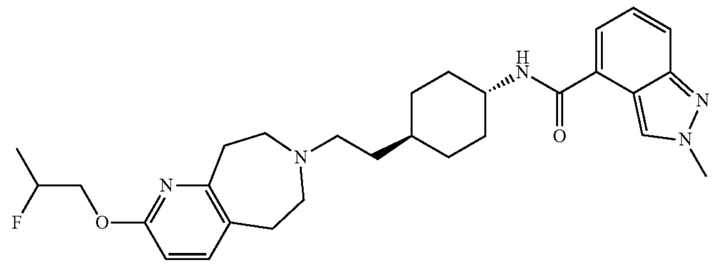 | 2 | 1.40 | 254.8 |
| III-157 | 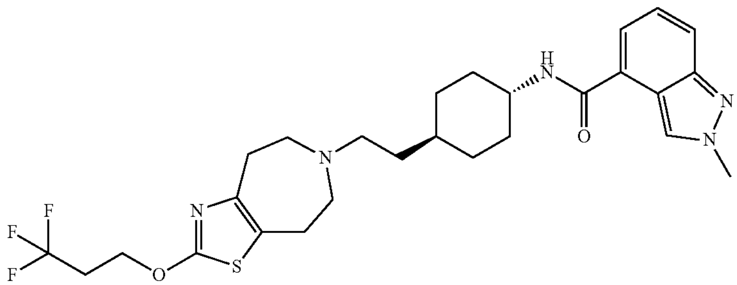 | 2 | 1.55 | 550.1 |
| III-158 | 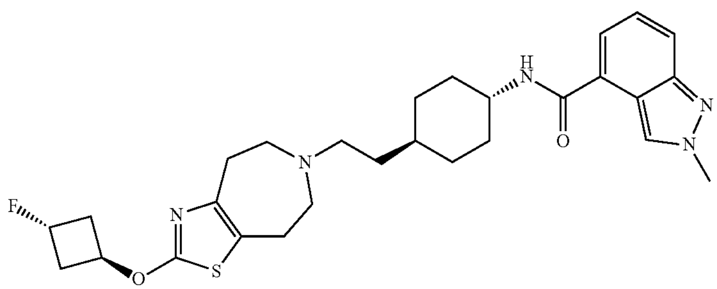 | 2 | 1.42 | 526.25 |
| III-159 | 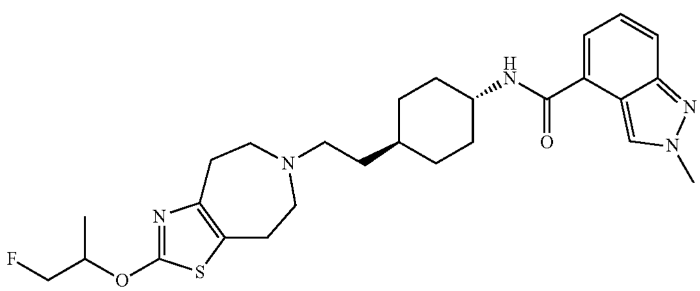 | 2 | 1.42 | 514.36 |
| III-160 | 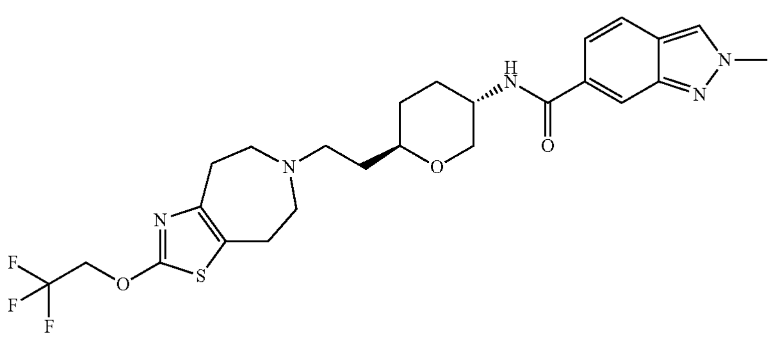 | 2 | 1.42 | 538 |

-continued

| Compound No. | Structure | LC/MS method | RT (min) | MS (m/z) |
| --- | --- | --- | --- | --- |
| III-161 | 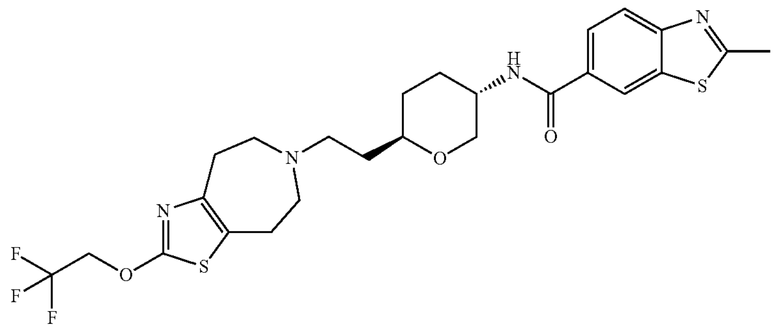 | 2 | 1.51 | 555 |
| III-162 | 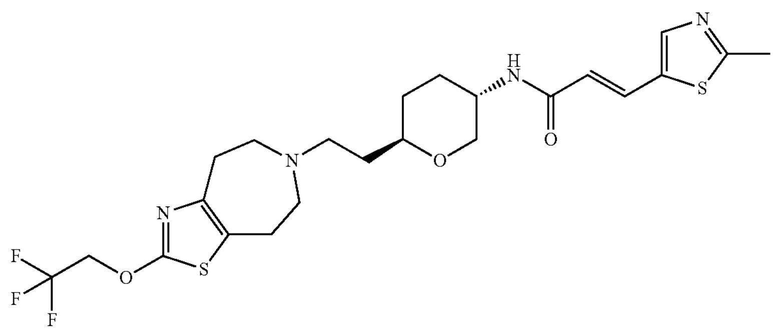 | 2 | 1.43 | 531 |
| III-163 | 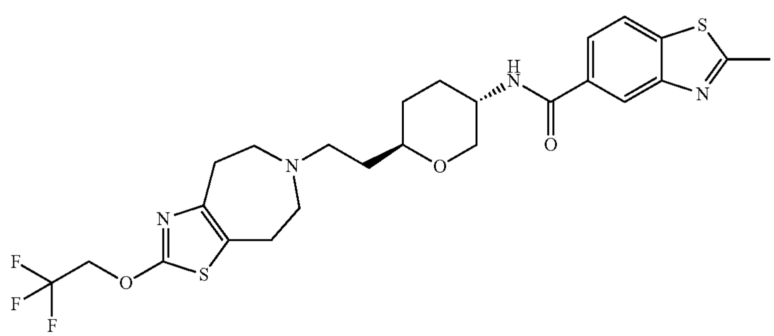 | 2 | 1.54 | 555 |
| III-164 | 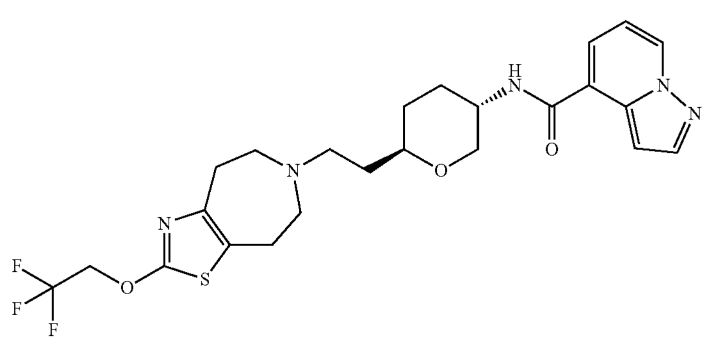 | 2 | 1.40 | 524 |

-continued

| Compound No. | Structure | LC/MS method | RT (min) | MS (m/z) |
|---|---|---|---|---|
| III-165 | 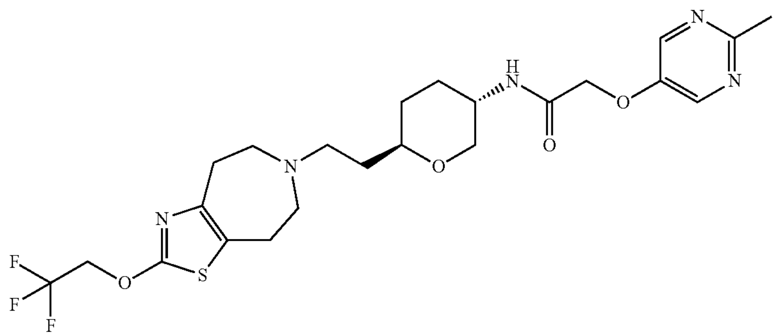 | 2 | 1.29 | 530 |
| III-166 | 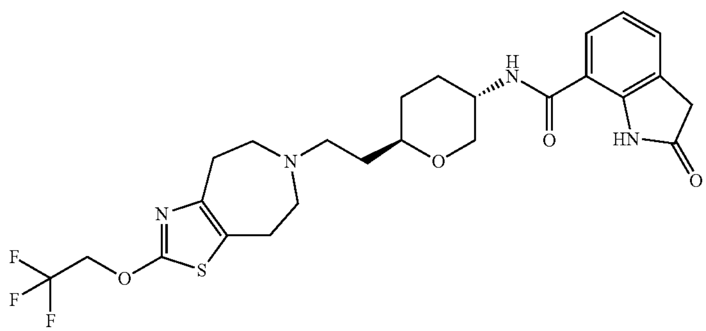 | 2 | 1.43 | 539 |
| III-167 | 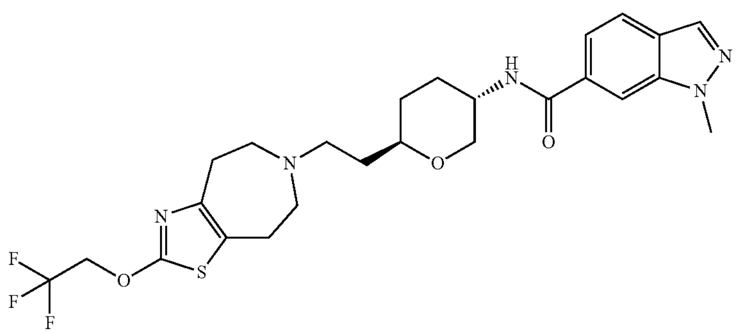 | 2 | 1.48 | 538 |
| III-168 | 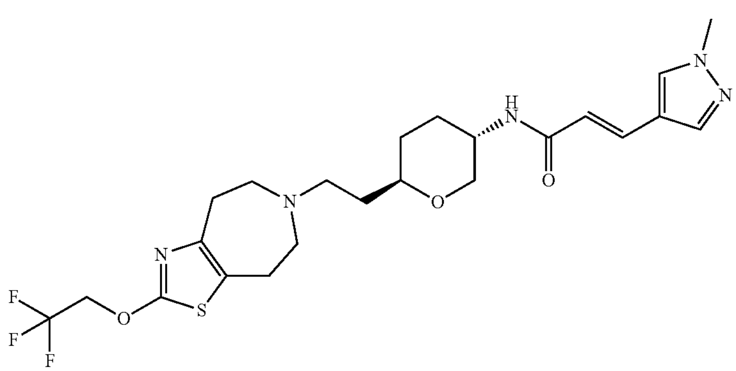 | 2 | 1.38 | 514 |

-continued

| Compound No. | Structure | LC/MS method | RT (min) | MS (m/z) |
|---|---|---|---|---|
| III-169 | 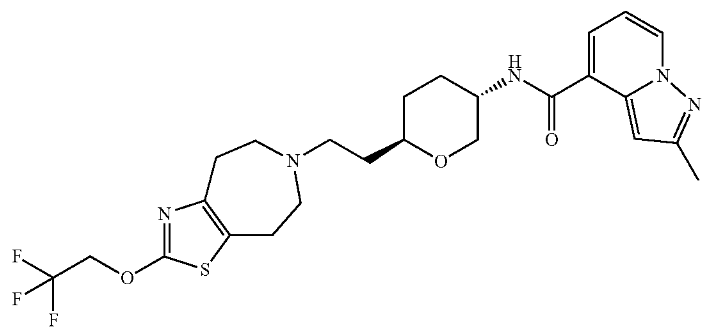 | 2 | 1.48 | 538 |
| III-170 | 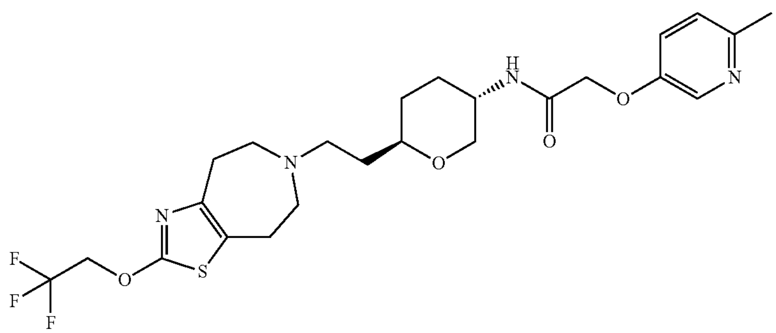 | 2 | 1.08 | 529 |
| III-171 | 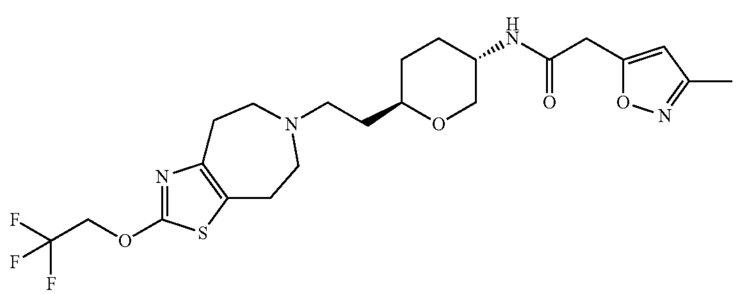 | 2 | 1.40 | 503 |
| III-172 | 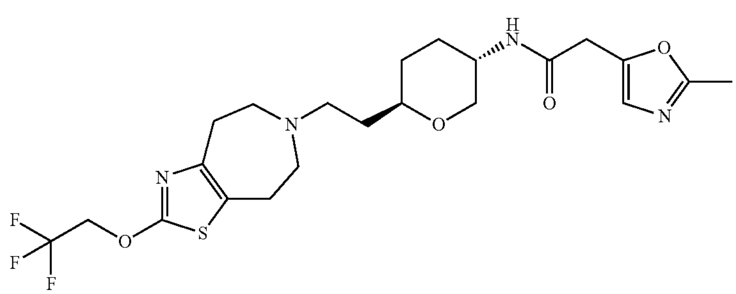 | 2 | 1.32 | 503 |

-continued
| Compound No. | Structure | LC/MS method | RT (min) | MS (m/z) |
|---|---|---|---|---|
| III-173 | 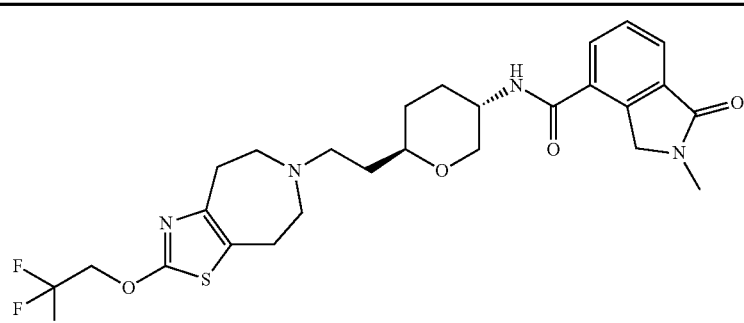 | 2 | 1.42 | 553 |
| III-174 | 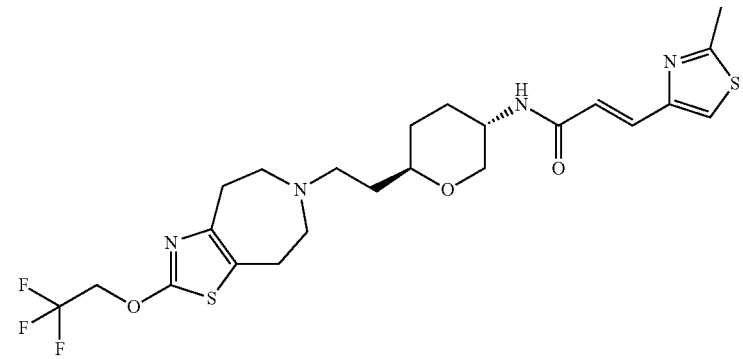 | 2 | 1.51 | 531 |
| III-175 | 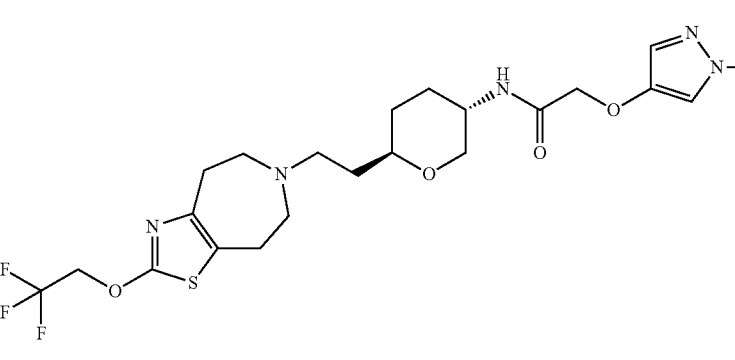 | 2 | 1.35 | 518 |
| III-176 | 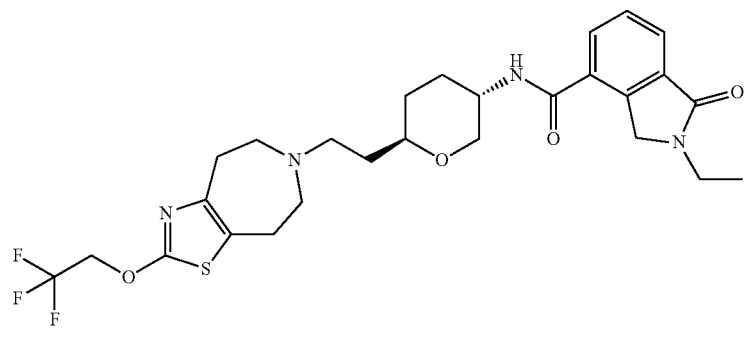 | 2 | 1.47 | 567 |

-continued

| Compound No. | Structure | LC/MS method | RT (min) | MS (m/z) |
| --- | --- | --- | --- | --- |
| III-177 | 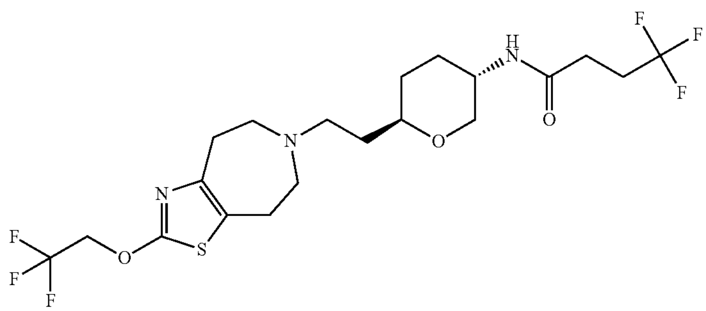 | 2 | 1.53 | 504 |
| III-178 | 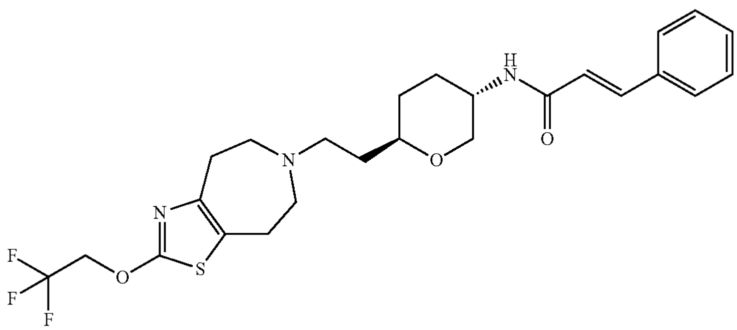 | 2 | 1.68 | 510 |
| III-179 | 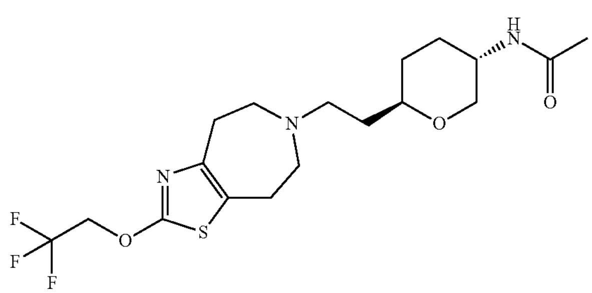 | 2 | 1.25 | 422 |
| III-180 | 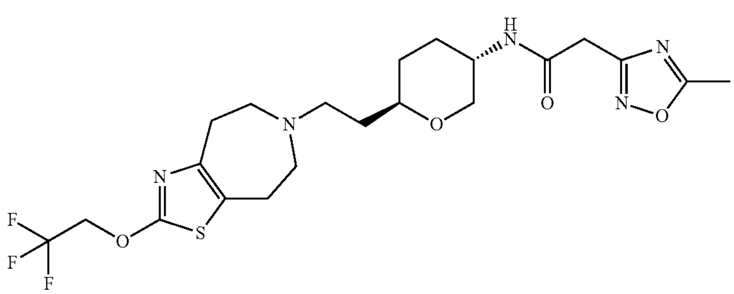 | 2 | 1.33 | 504 |
| III-181 | 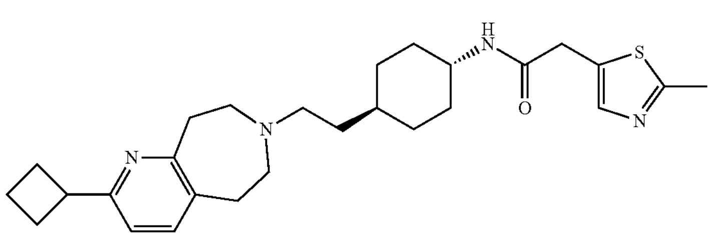 | 2 | 0.89 | 234.3 |

-continued

| Compound No. | Structure | LC/MS method | RT (min) | MS (m/z) |
|---|---|---|---|---|
| III-182 | 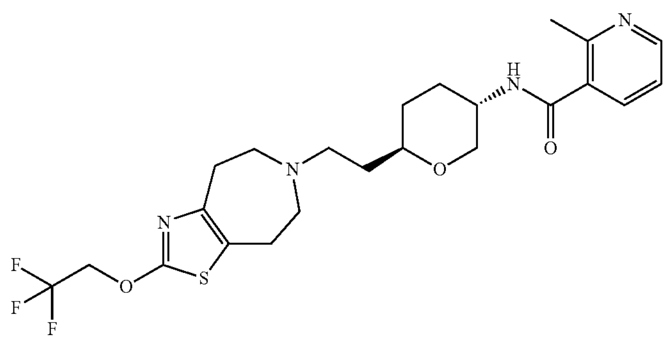 | 2 | 1.10 | 499 |
| III-183 | 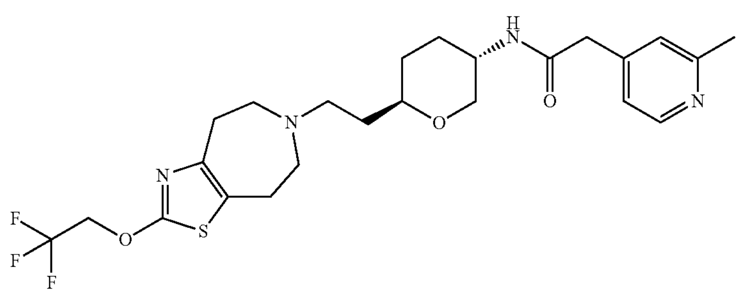 | 2 | 1.03 | 513 |
| III-184 | 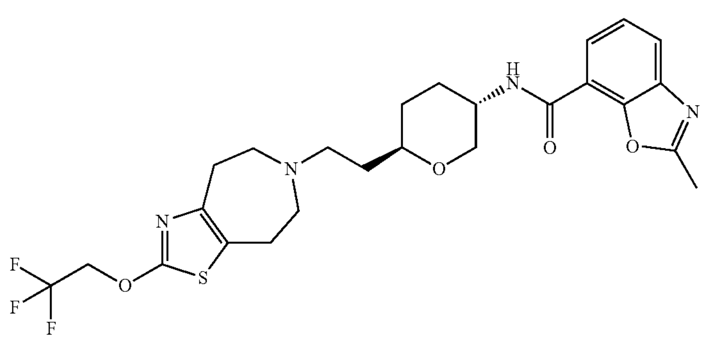 | 2 | 1.47 | 539 |
| III-185 | 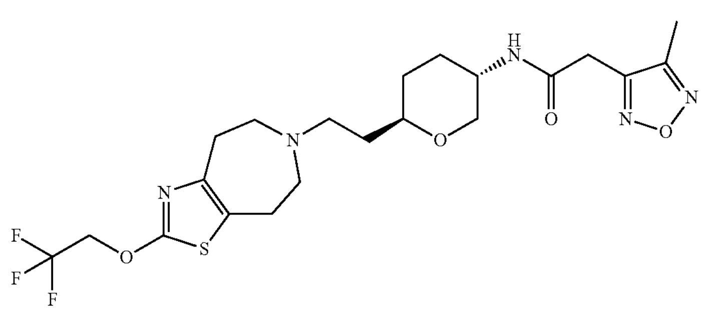 | 2 | 1.44 | 504 |

-continued

| Compound No. | Structure | LC/MS method | RT (min) | MS (m/z) |
|---|---|---|---|---|
| III-186 | 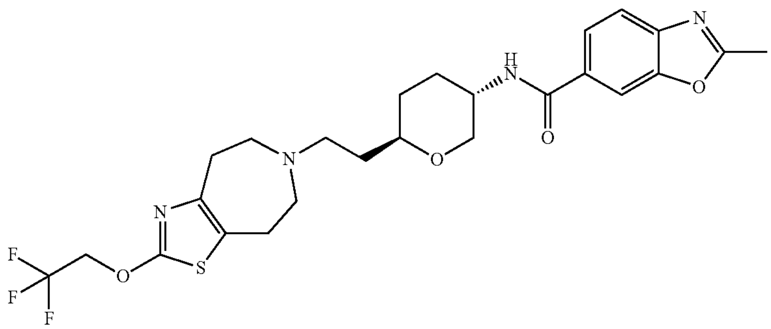 | 2 | 1.47 | 539 |
| III-187 | 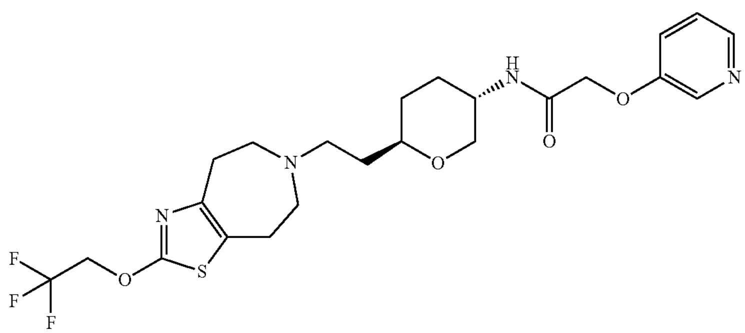 | 2 | 1.12 | 515 |
| III-188 | 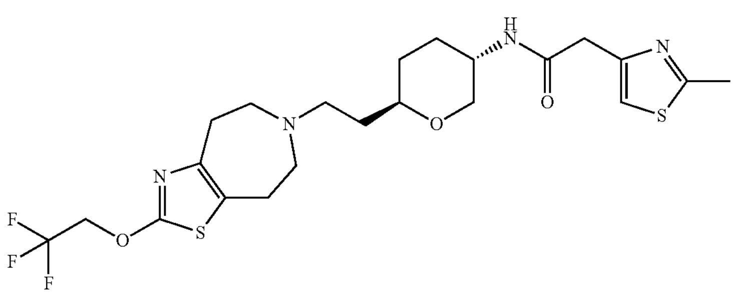 | 2 | 1.35 | 519 |
| III-189 | 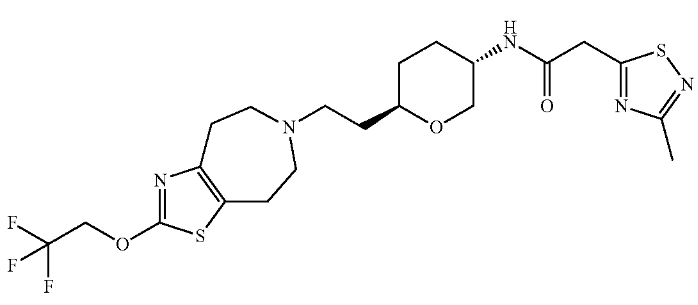 | 2 | 1.38 | 520 |

| Compound No. | Structure | LC/MS method | RT (min) | MS (m/z) |
|---|---|---|---|---|
| III-190 | 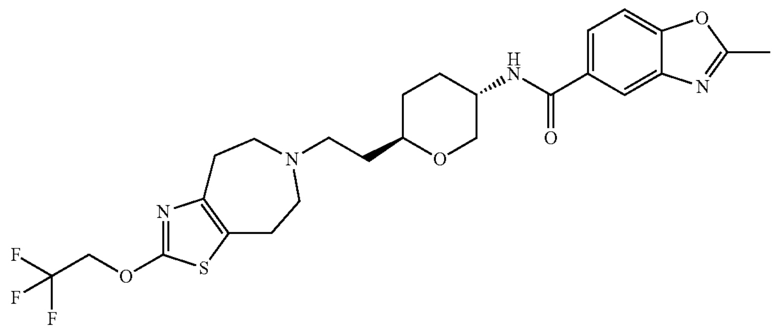 | 2 | 1.48 | 539 |
| III-191 | 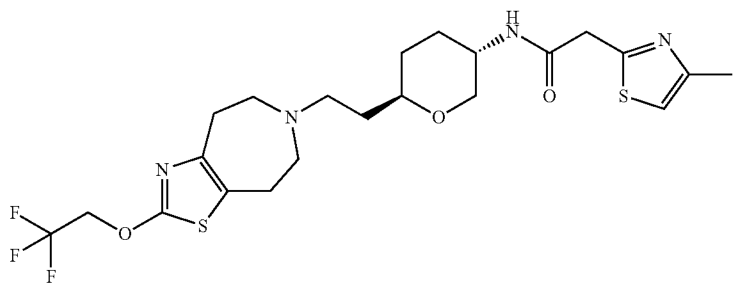 | 2 | 1.39 | 519 |
| III-192 | 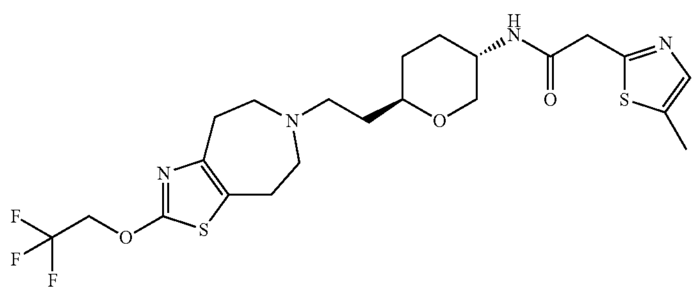 | 2 | 1.41 | 519 |
| III-193 | 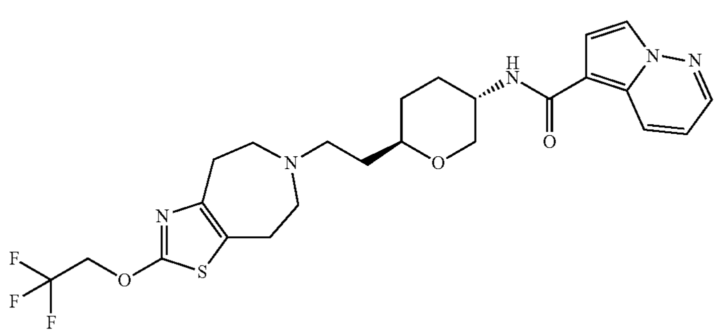 | 2 | 1.53 | 524 |
| III-194 | 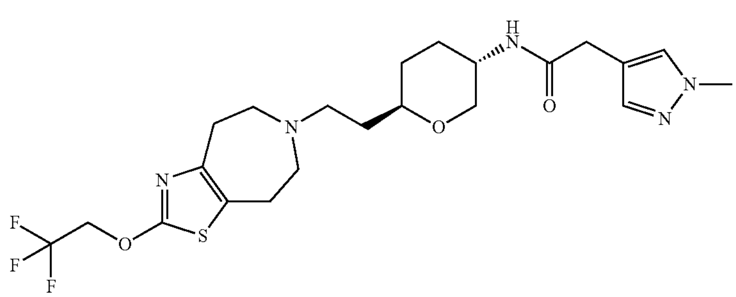 | 2 | 1.31 | 502 |

| Compound No. | Structure | LC/MS method | RT (min) | MS (m/z) |
|---|---|---|---|---|
| III-195 | 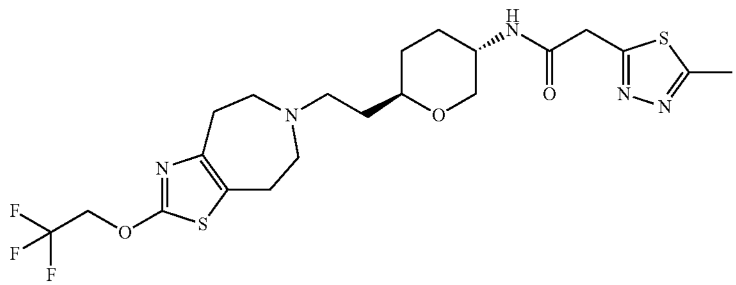 | 2 | 1.34 | 520 |
| III-196 | 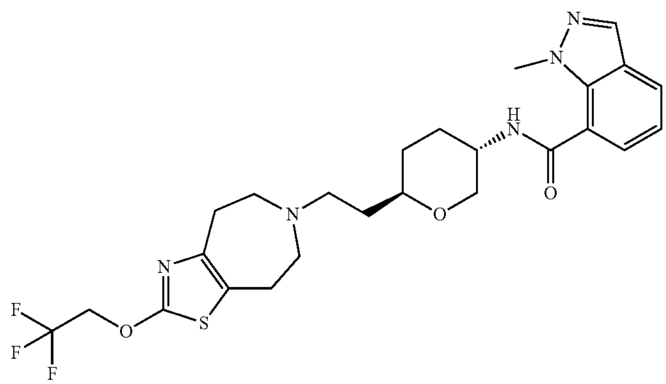 | 2 | 1.50 | 538 |
| III-197 | 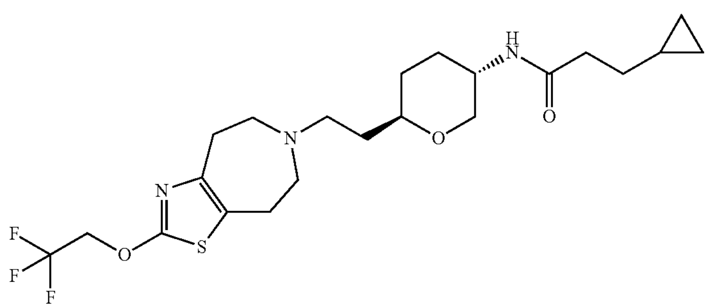 | 2 | 1.52 | 476 |
| III-198 | 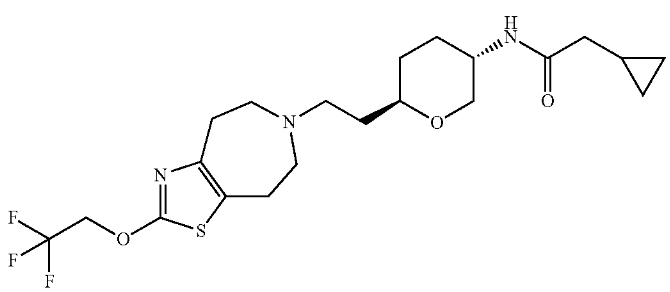 | 2 | 1.42 | 462 |
| III-199 | 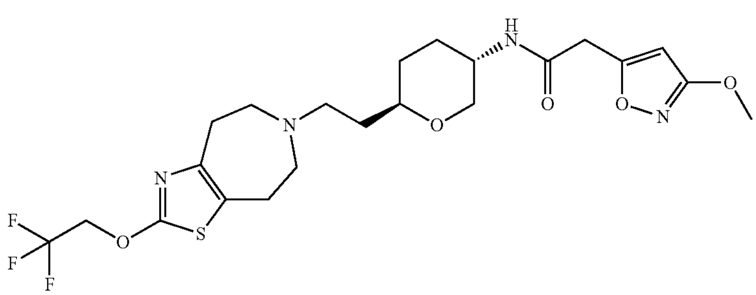 | 2 | 1.44 | 519 |

| Compound No. | Structure | LC/MS method | RT (min) | MS (m/z) |
|---|---|---|---|---|
| III-200 | 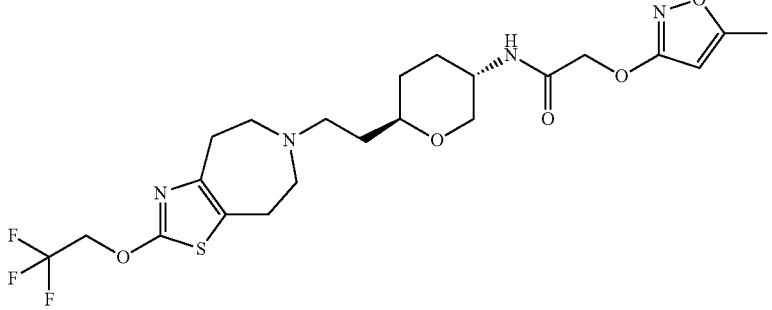 | 2 | 1.47 | 519 |
| III-201 | 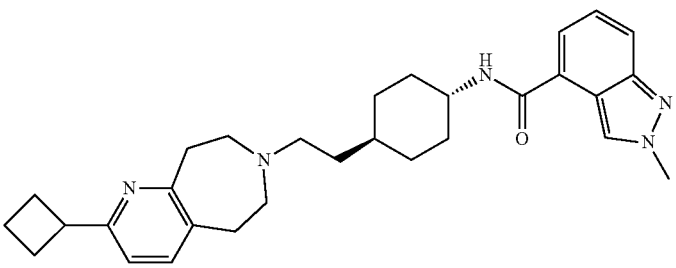 | 1 | 1.38 | 486 |
| III-202 | 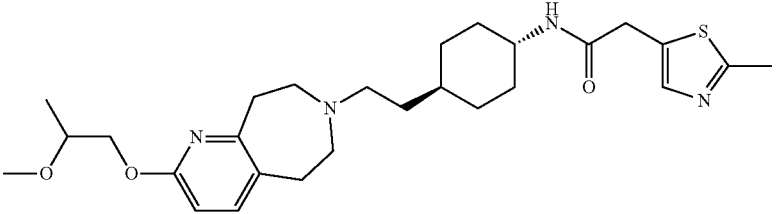 | 2 | 1.25 | 501 |
| III-203 | 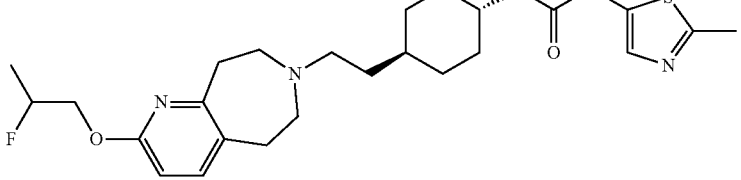 | 2 | 1.33 | 489 |
| III-204 | 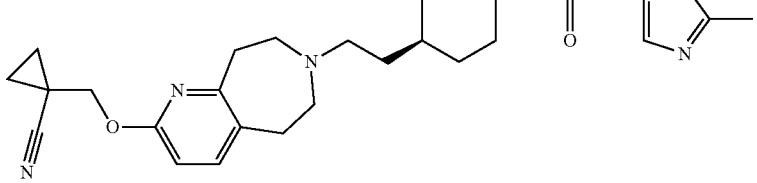 | 2 | 1.35 | 508 |
| III-205 | 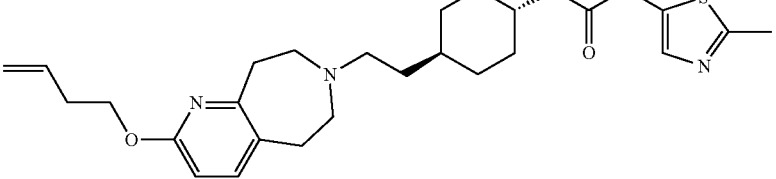 | 2 | 1.45 | 483 |

-continued
| Compound No. | Structure | LC/MS method | RT (min) | MS (m/z) |
|---|---|---|---|---|
| III-206 | 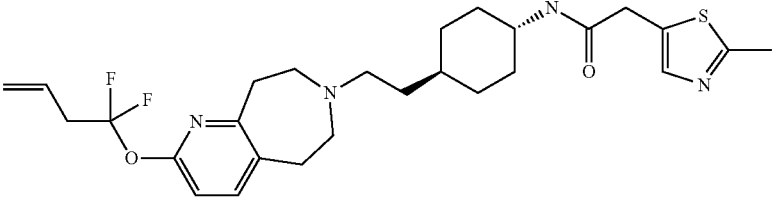 | 2 | 1.47 | 519 |
| III-207 | 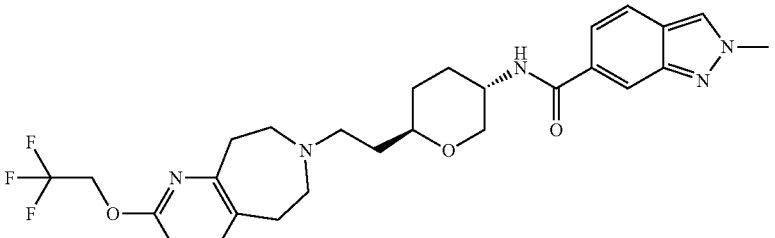 | 2 | 1.52 | 532.1 |
| III-208 | 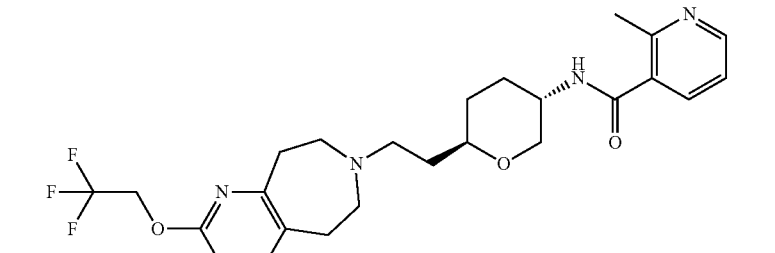 | 2 | 1.20 | 493.1 |
| III-209 | 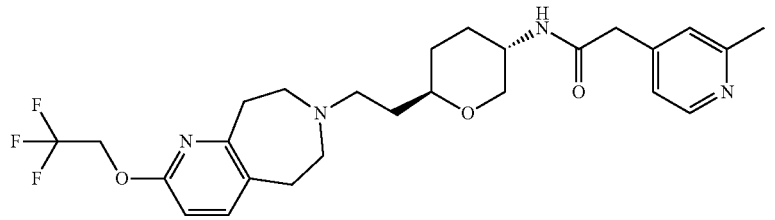 | 2 | 1.11 | 507.1 |
| III-210 | 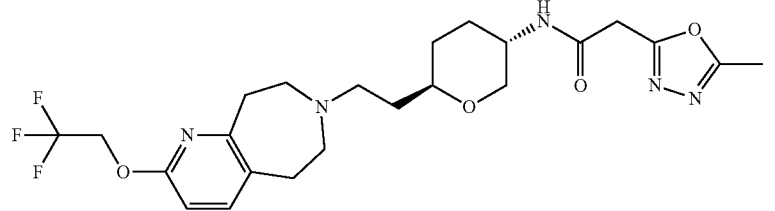 | 2 | 1.36 | 498.1 |
| III-211 | 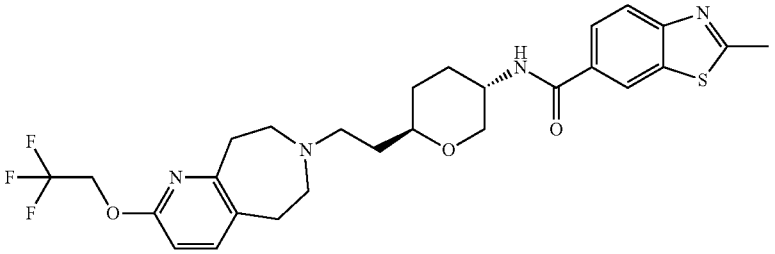 | 2 | 1.61 | 549.1 |

-continued
| Compound No. | Structure | LC/MS method | RT (min) | MS (m/z) |
|---|---|---|---|---|
| III-212 | 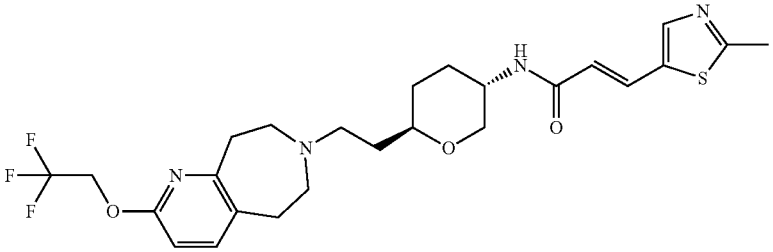 | 2 | 1.53 | 525 |
| III-213 | 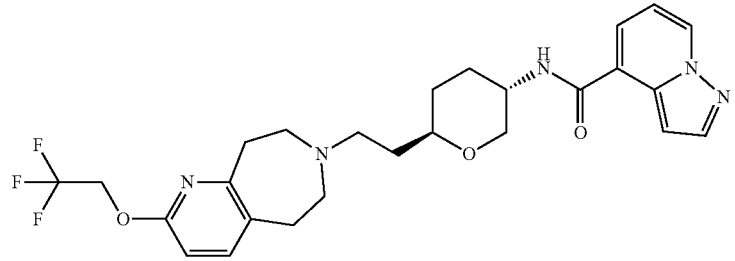 | 2 | 1.51 | 518.1 |
| III-214 | 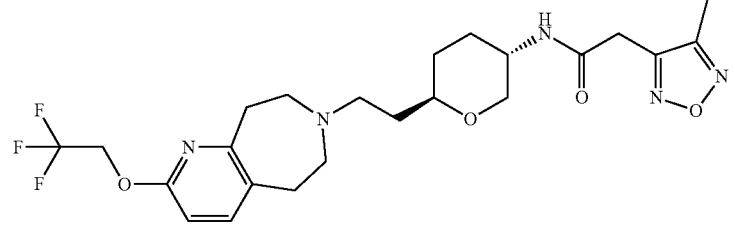 | 2 | 1.54 | 498.1 |
| III-215 | 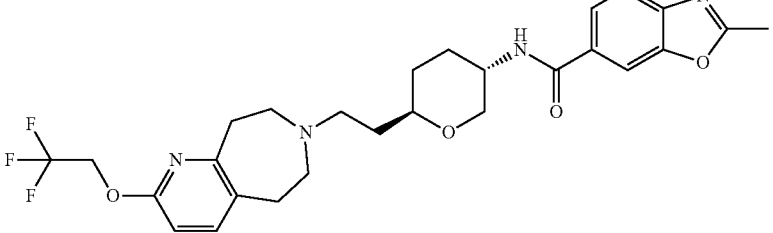 | 2 | 1.56 | 533.1 |
| III-216 | 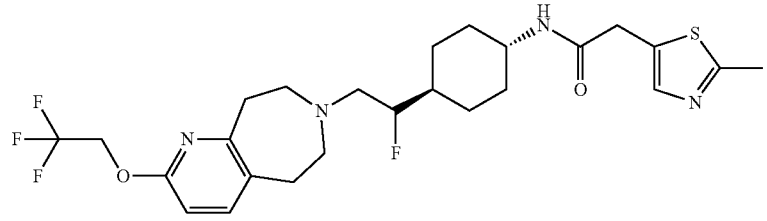 | 2 | 1.42 | 265 |
| III-217 | 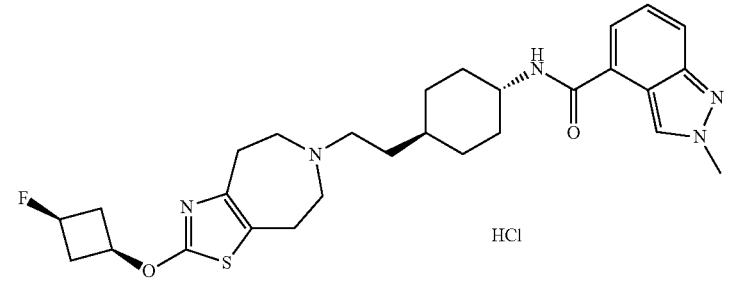 | 2 | 1.53 | 526.31 |

-continued

| Compound No. | Structure | LC/MS method | RT (min) | MS (m/z) |
|---|---|---|---|---|
| III-218 | 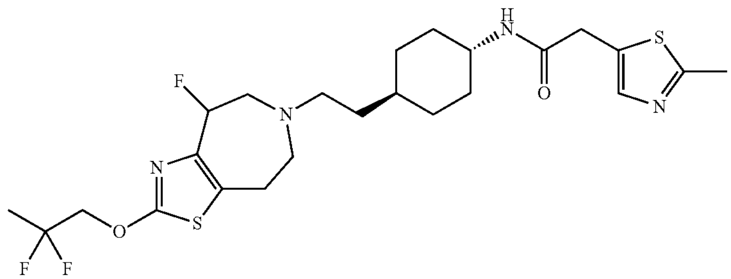 | 2 | 1.39 | 531.3 |
| III-219 | 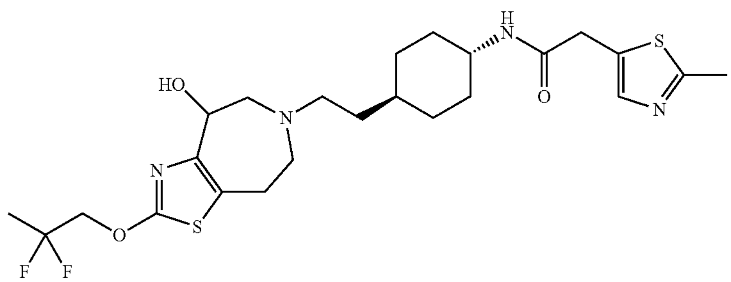 | 2 | 1.25 | 529.3 |
| III-220 | 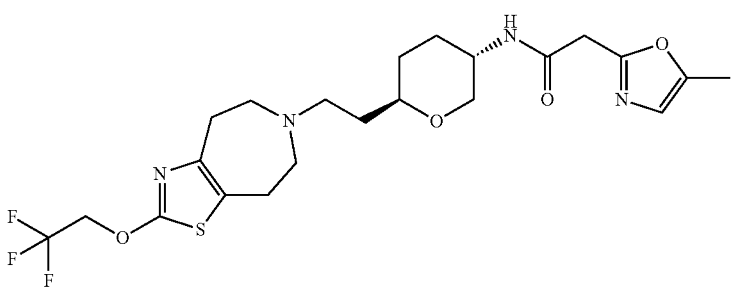 | 2 | 1.40 | 503.15 |
| III-221 | 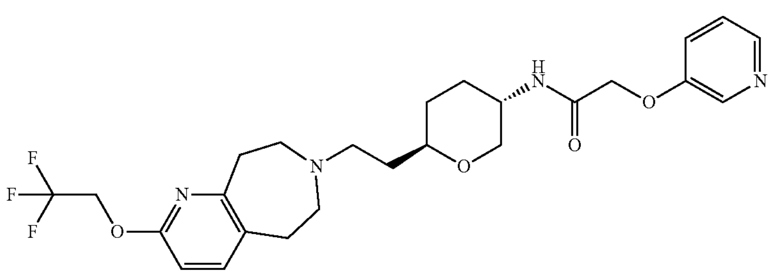 | 2 | 1.23 | 509 |
| III-222 | 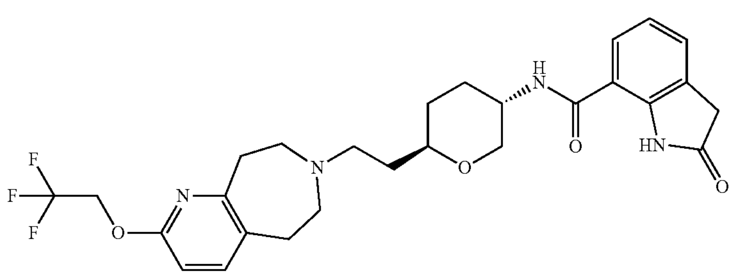 | 2 | 1.54 | 533 |

-continued

| Compound No. | Structure | LC/MS method | RT (min) | MS (m/z) |
|---|---|---|---|---|
| III-223 | 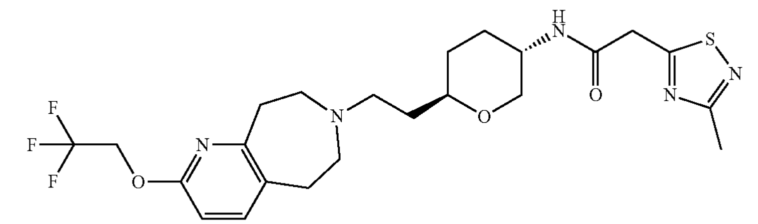 | 2 | 1.49 | 514 |
| III-224 | 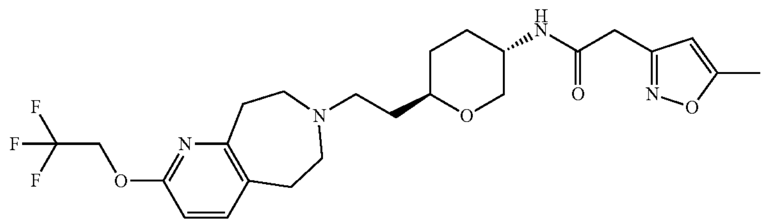 | 2 | 1.49 | 497 |
| III-225 | 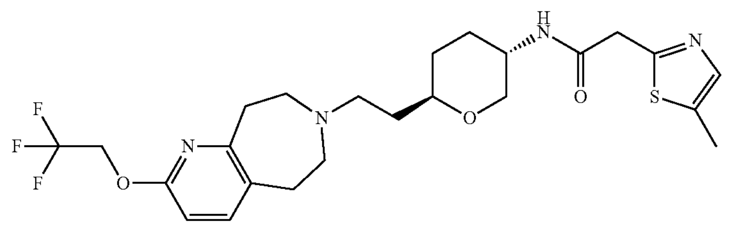 | 2 | 1.52 | 513 |
| III-226 | 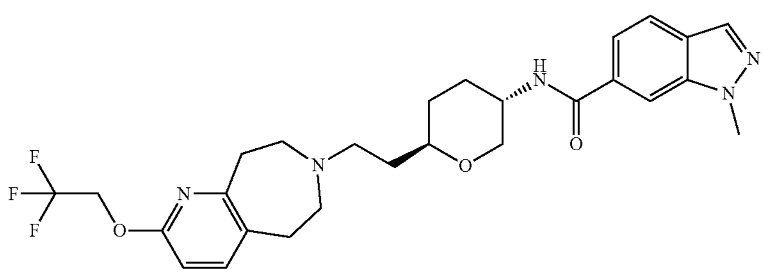 | 2 | 1.59 | 532 |
| III-227 | 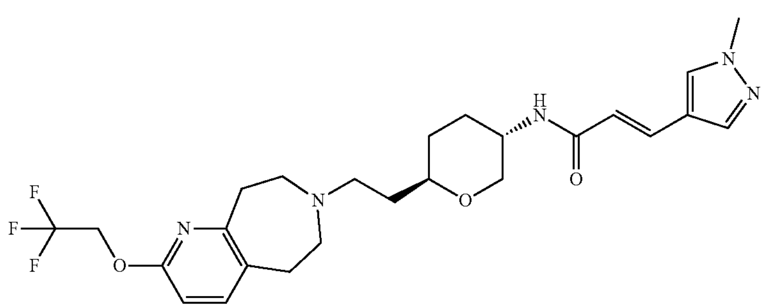 | 2 | 1.45 | 508 |
| III-228 | 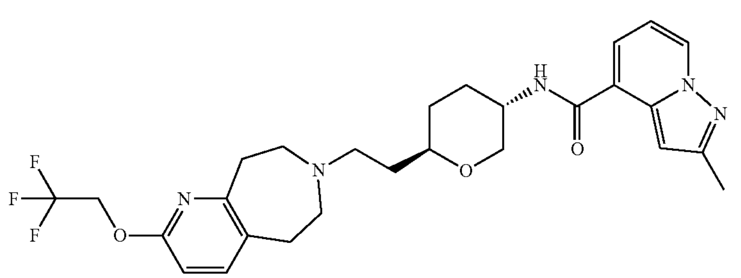 | 2 | 1.56 | 532 |

-continued

| Compound No. | Structure | LC/MS method | RT (min) | MS (m/z) |
|---|---|---|---|---|
| III-229 | 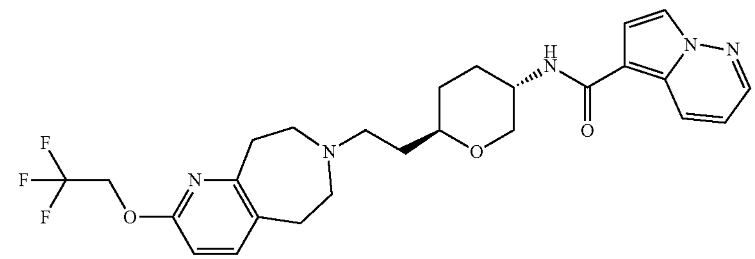 | 2 | 1.60 | 518 |
| III-230 | 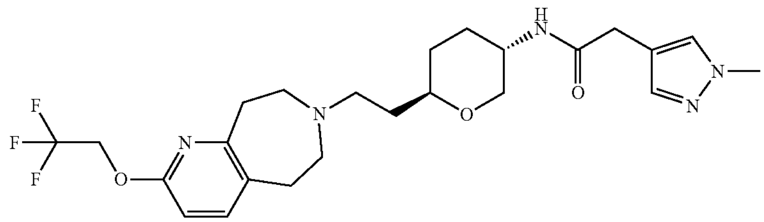 | 2 | 1.38 | 496 |
| III-231 | 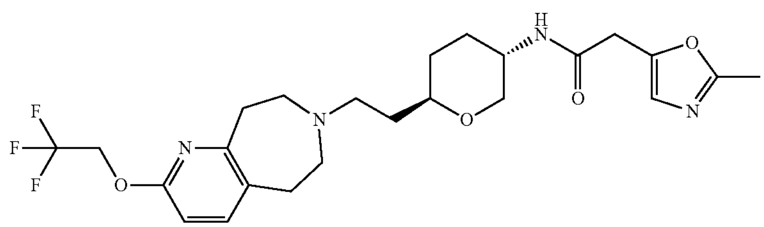 | 2 | 1.39 | 497 |
| III-232 | 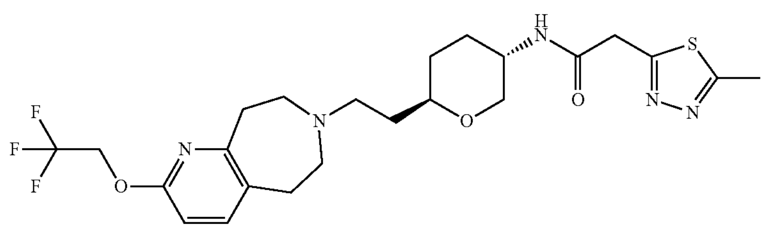 | 2 | 1.41 | 514 |
| III-233 | 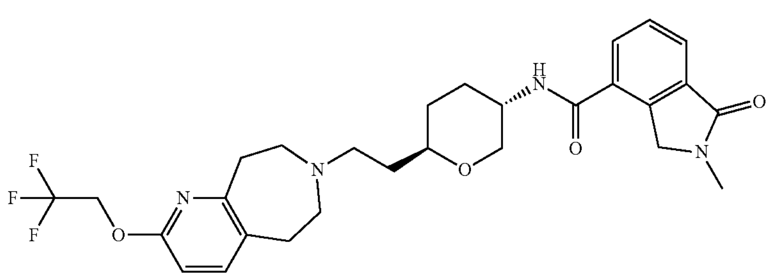 | 2 | 1.47 | 547 |
| III-234 | 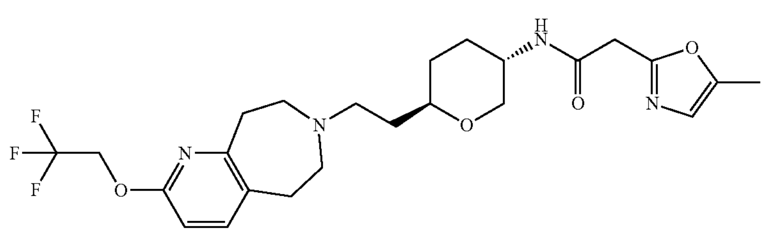 | 2 | 1.46 | 497 |

| Compound No. | Structure | LC/MS method | RT (min) | MS (m/z) |
|---|---|---|---|---|
| III-235 | 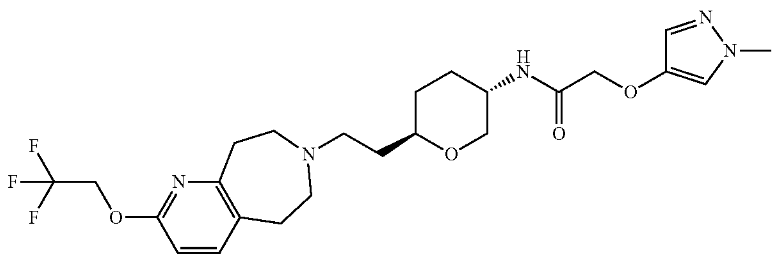 | 2 | 1.42 | 512 |
| III-236 | 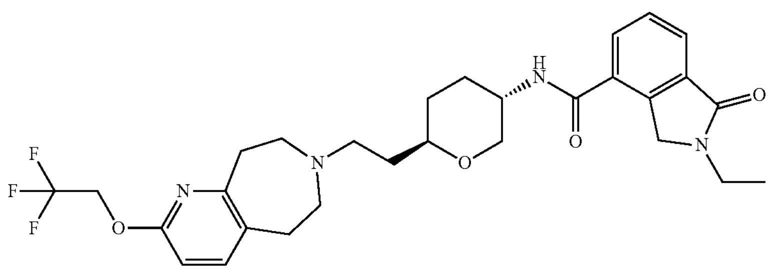 | 2 | 1.53 | 561 |
| III-237 | 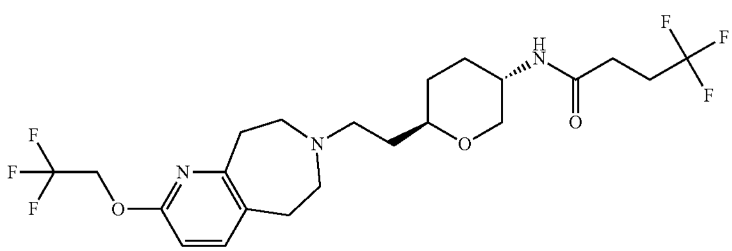 | 2 | 1.60 | 498 |
| III-238 | 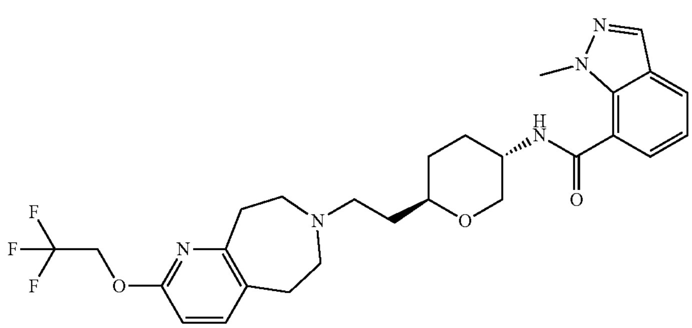 | 2 | 1.58 | 532 |
| III-239 | 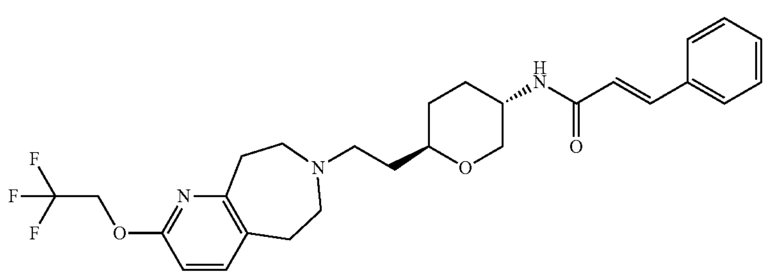 | 2 | 1.75 | 504 |

-continued
| Compound No. | Structure | LC/MS method | RT (min) | MS (m/z) |
|---|---|---|---|---|
| III-240 | 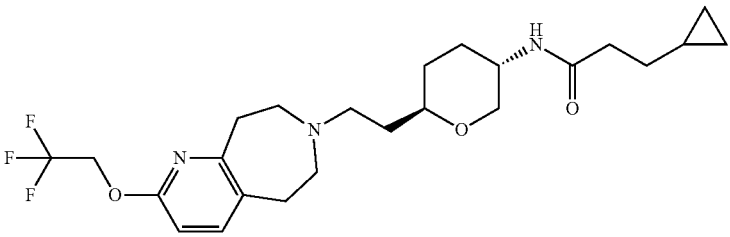 | 2 | 1.60 | 470 |
| III-241 | 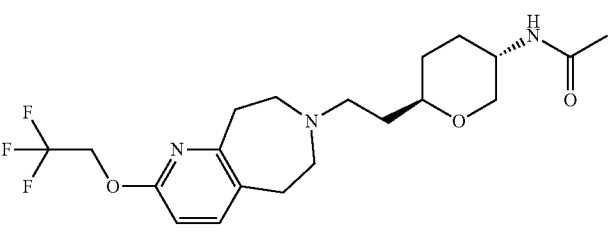 | 2 | 1.34 | 416 |
| III-242 | 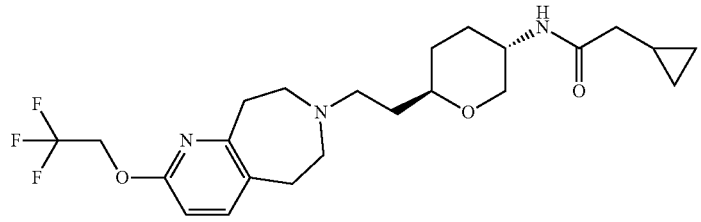 | 2 | 1.51 | 456 |
| III-243 | 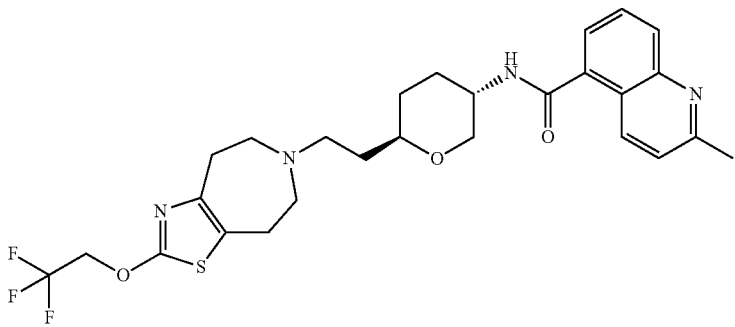 | 2 | 1.18 | 549 |
| III-244 | 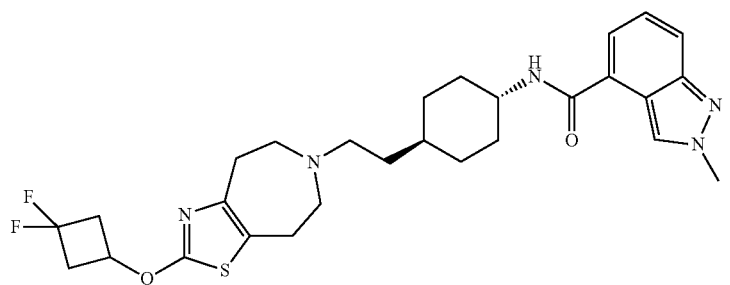 | 2 | 1.59 | 544.32 |

-continued

| Compound No. | Structure | LC/MS method | RT (min) | MS (m/z) |
|---|---|---|---|---|
| III-245 | 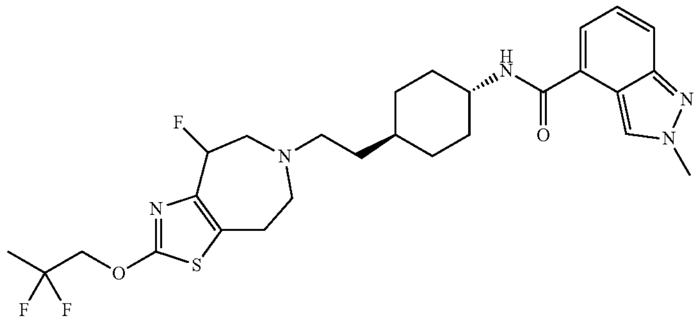 | 2 | 1.53 | 550.3 |
| III-246 | 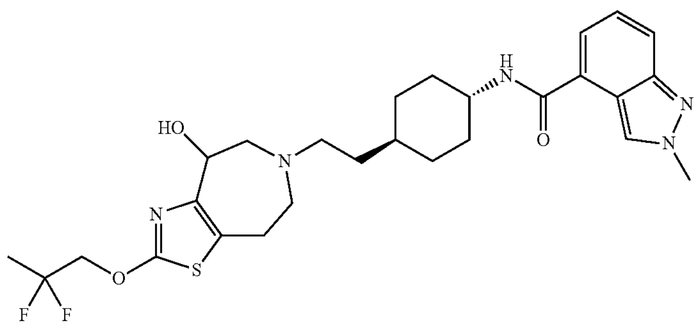 | 2 | 1.41 | 548.3 |
| III-247 | 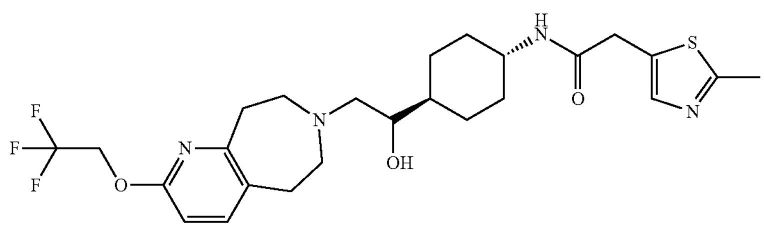 | 2 | 1.35 | 527.2 |
| III-248 | 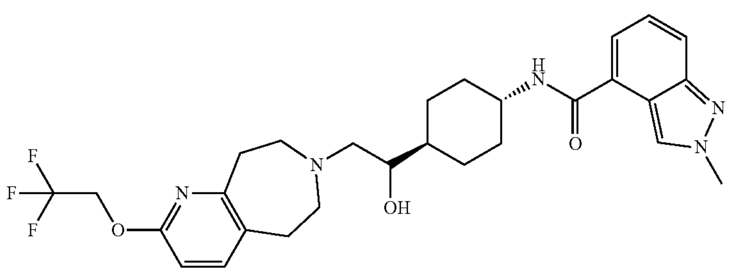 | 2 | 1.48 | 546.3 |
| III-249 | 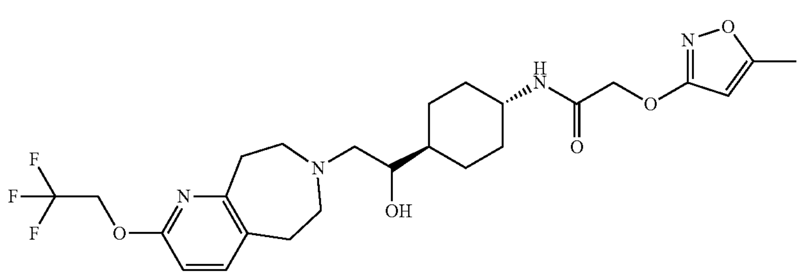 | 2 | 1.50 | 527.2 |

| Compound No. | Structure | LC/MS method | RT (min) | MS (m/z) |
|---|---|---|---|---|
| III-250 | 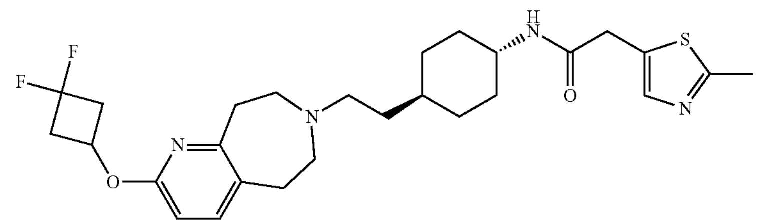 | 2 | 1.40 | 260.3 |
| III-251 | 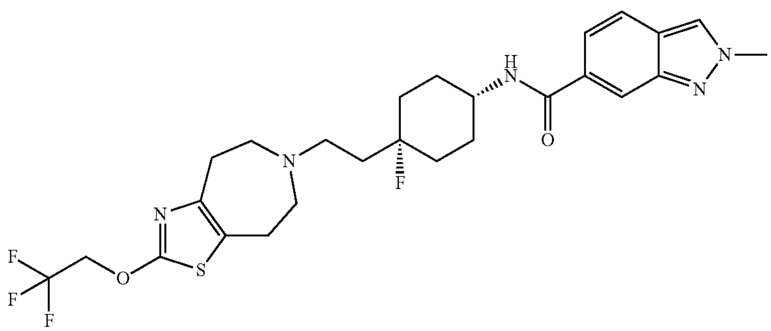 | 2 | 1.50 | 554.2 |
| III-252 | 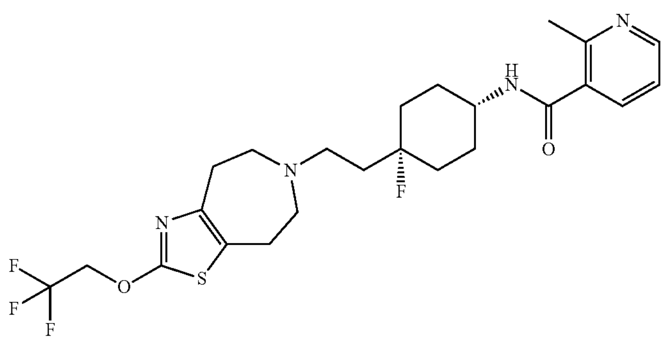 | 2 | 1.16 | 515.2 |
| III-253 | 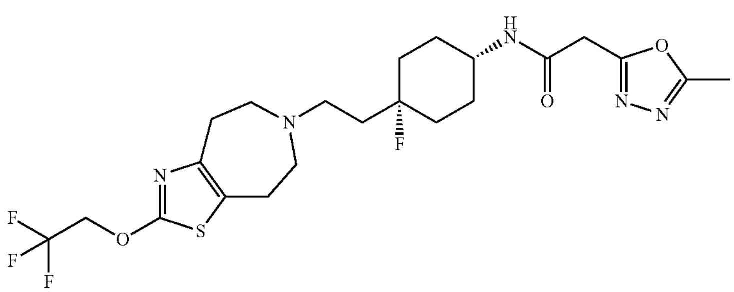 | 2 | 1.33 | 520.2 |
| III-254 | 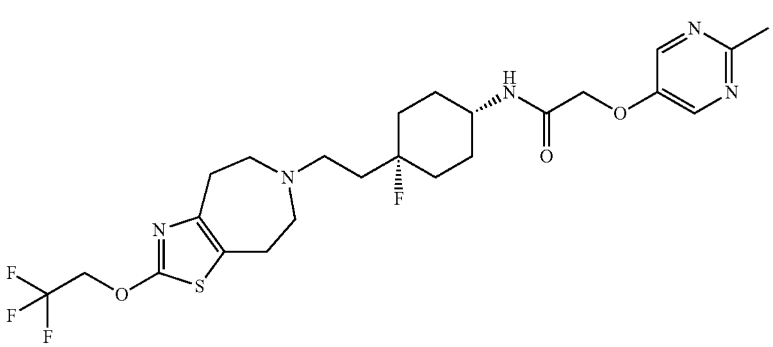 | 2 | 1.38 | 546.2 |

-continued
| Compound No. | Structure | LC/MS method | RT (min) | MS (m/z) |
|---|---|---|---|---|
| III-255 | 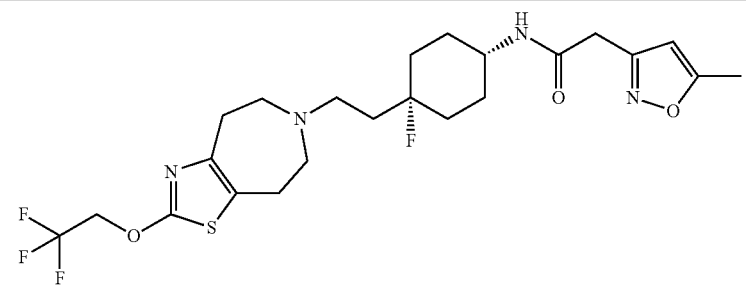 | 2 | 1.47 | 519.1 |
| III-256 | 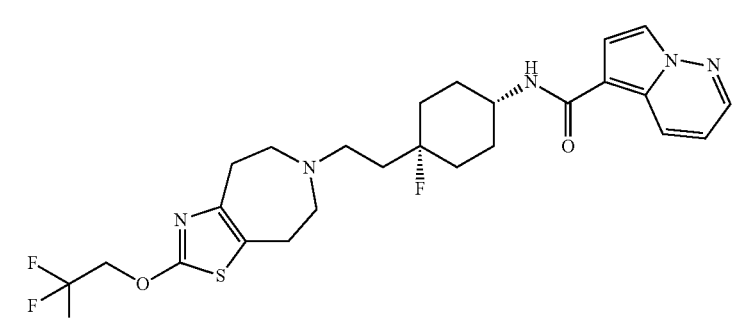 | 2 | 1.59 | 540.2 |
| III-257 | 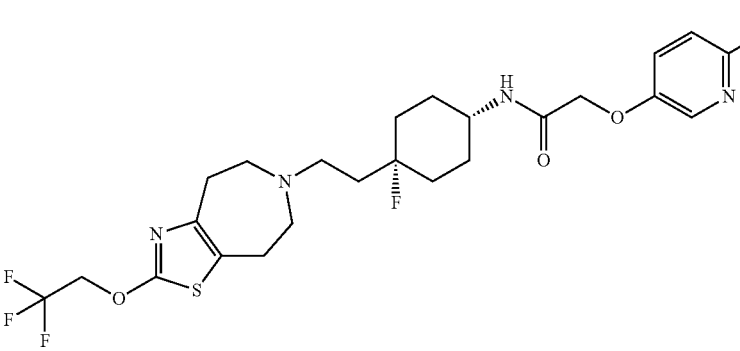 | 2 | 1.17 | 545.2 |
| III-258 | 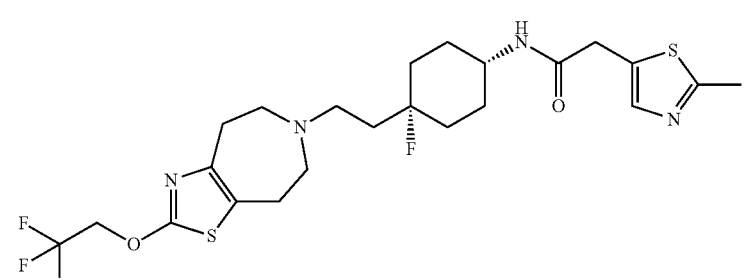 | 2 | 1.37 | 535.2 |
| III-259 | 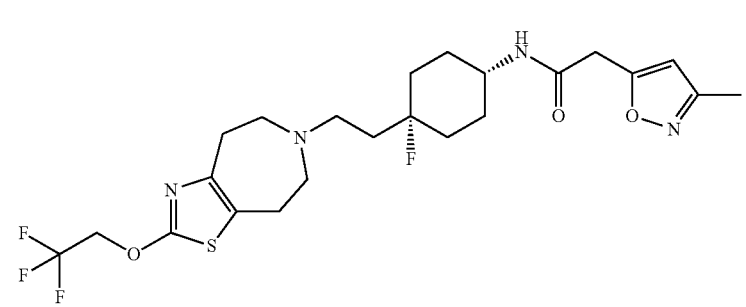 | 2 | 1.45 | 519.1 |

-continued

| Compound No. | Structure | LC/MS method | RT (min) | MS (m/z) |
|---|---|---|---|---|
| III-260 | 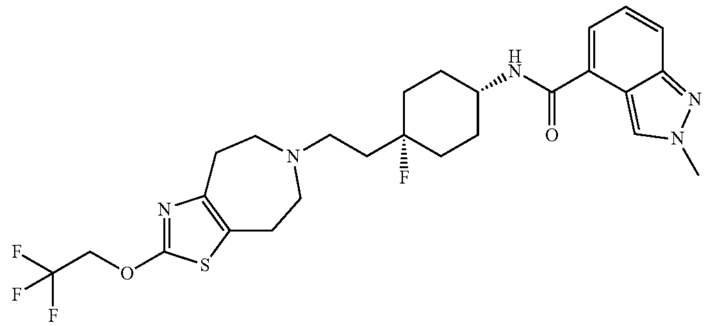 | 2 | 1.50 | 554.2 |
| III-261 | 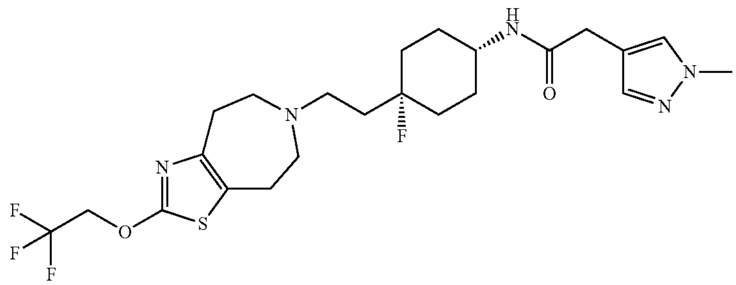 | 2 | 1.36 | 518.2 |
| III-262 | 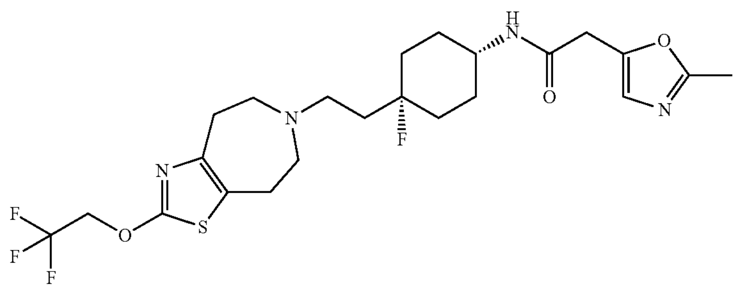 | 2 | 1.38 | 519.2 |
| III-263 | 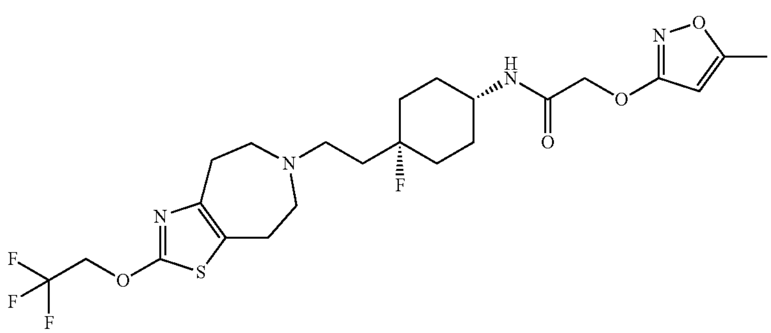 | 2 | 1.53 | 535.2 |
| III-264 | 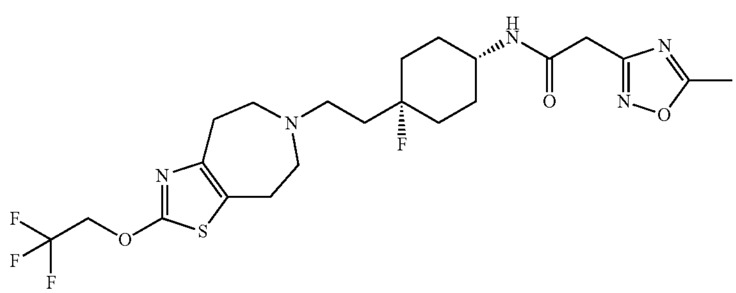 | 2 | 1.39 | 520.1 |

-continued
| Compound No. | Structure | LC/MS method | RT (min) | MS (m/z) |
|---|---|---|---|---|
| III-265 | 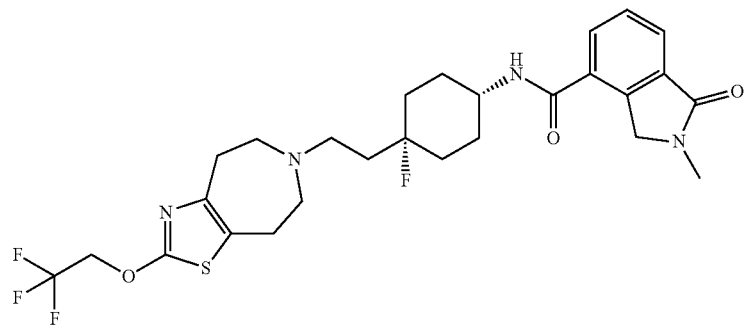 | 2 | 1.44 | 569.2 |
| III-266 | 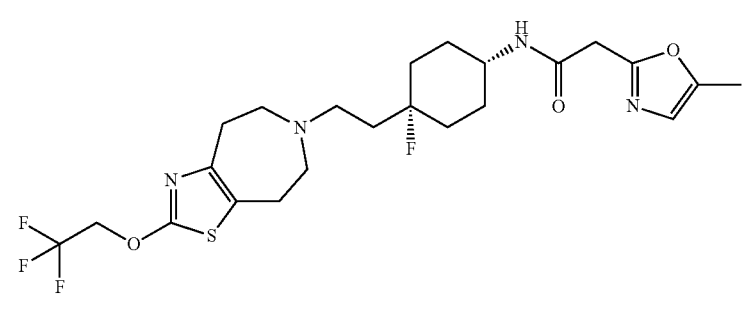 | 2 | 1.44 | 519.2 |
| III-267 | 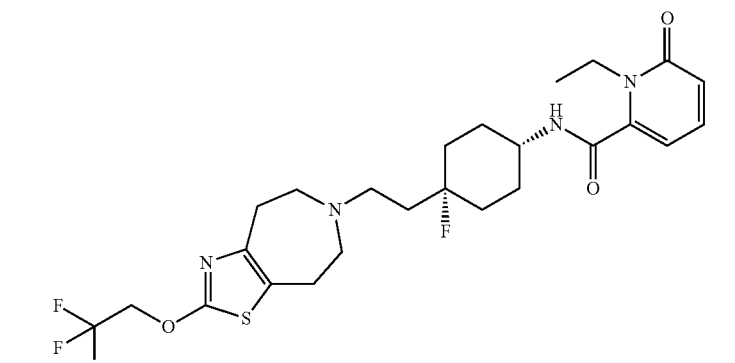 | 2 | 1.38 | 545.2 |
| III-268 | 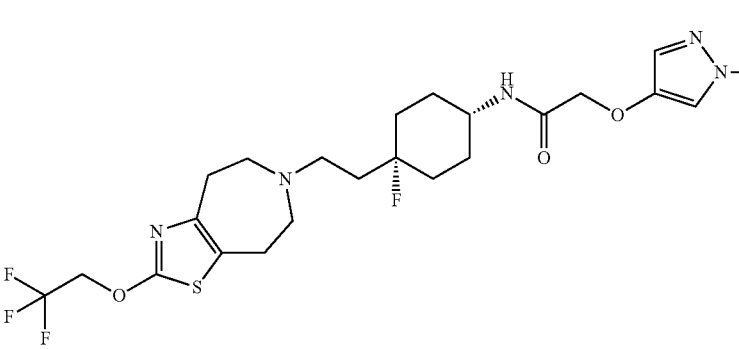 | 2 | 1.40 | 534.2 |

-continued

| Compound No. | Structure | LC/MS method | RT (min) | MS (m/z) |
|---|---|---|---|---|
| III-269 | 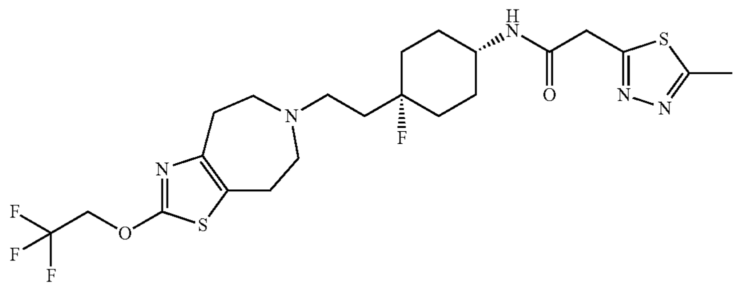 | 2 | 1.36 | 536.1 |
| III-270 | 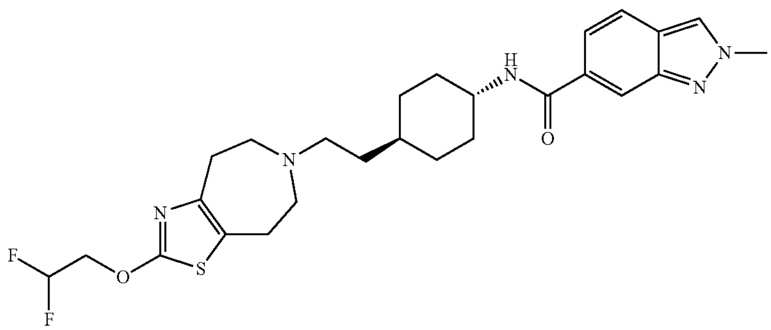 | 2 | 1.40 | 518.2 |
| III-271 | 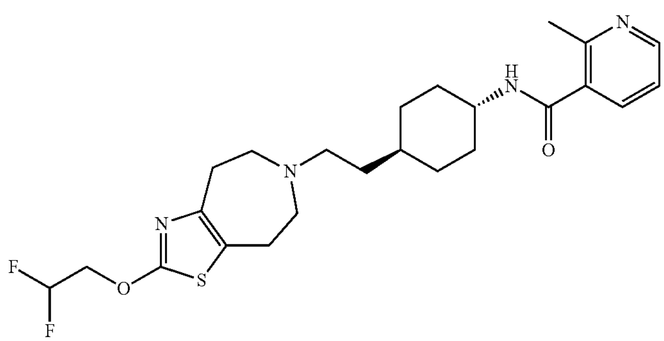 | 2 | 1.04 | 479.2 |
| III-272 | 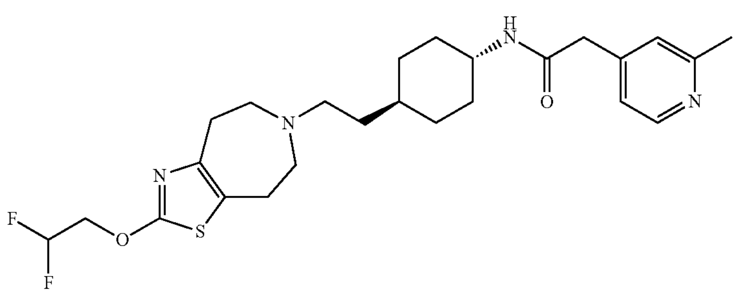 | 2 | 0.98 | 493.2 |
| III-273 | 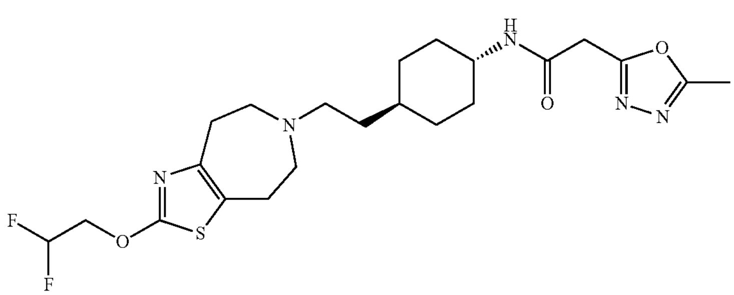 | 2 | 1.21 | 484.1 |

-continued

| Compound No. | Structure | LC/MS method | RT (min) | MS (m/z) |
|---|---|---|---|---|
| III-274 | 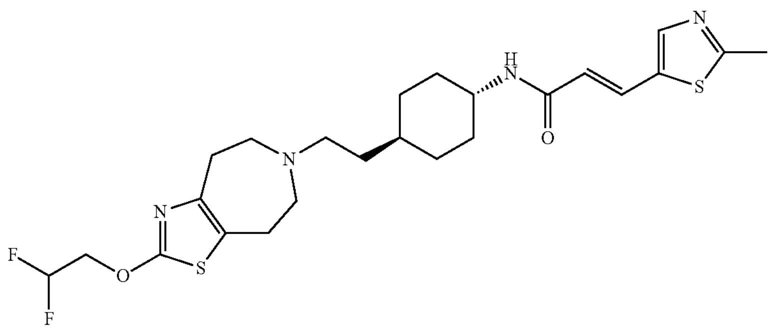 | 2 | 1.42 | 511.2 |
| III-275 | 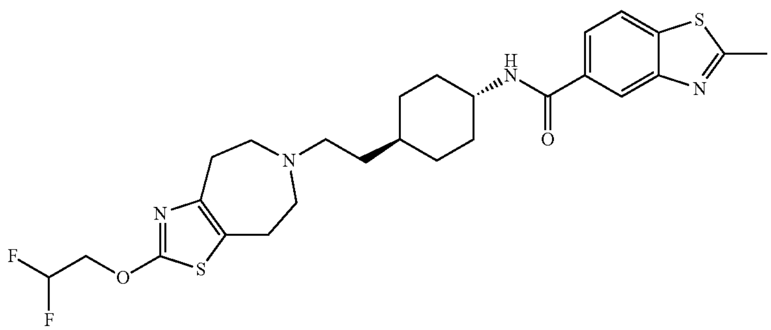 | 2 | 1.53 | 535.1 |
| III-276 | 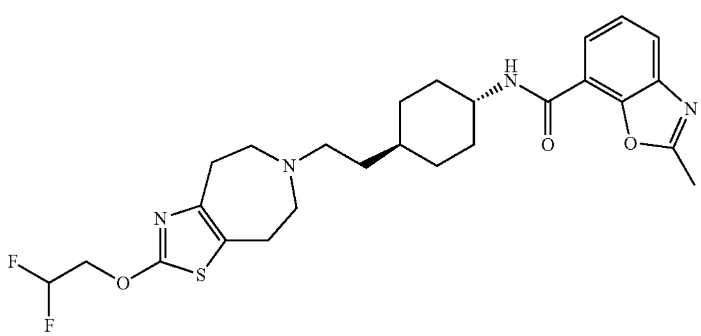 | 2 | 1.45 | 519.1 |
| III-277 | 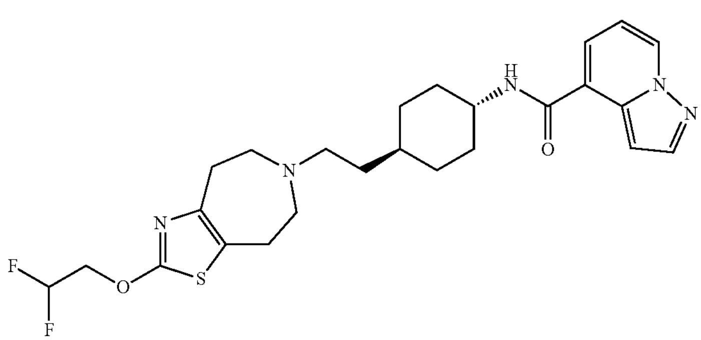 | 2 | 1.36 | 504.2 |

-continued
| Compound No. | Structure | LC/MS method | RT (min) | MS (m/z) |
|---|---|---|---|---|
| III-278 | 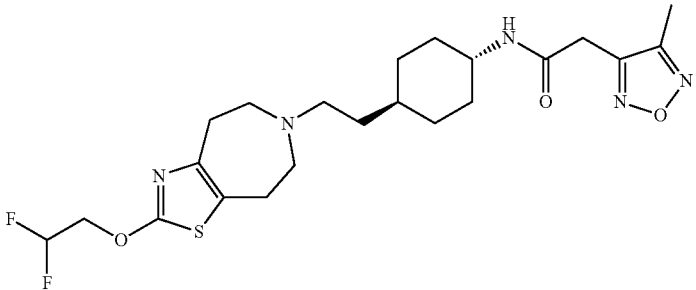 | 2 | 1.39 | 484.1 |
| III-279 | 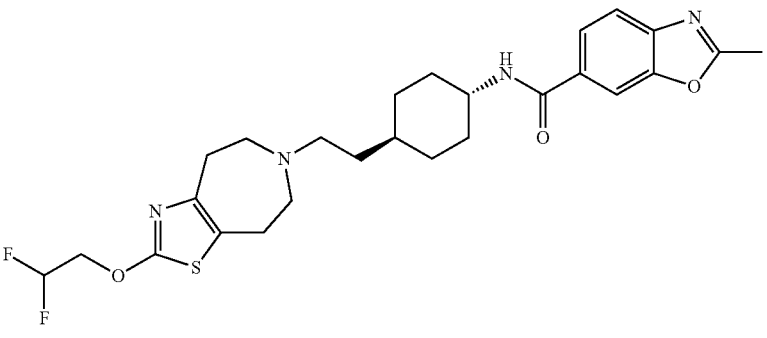 | 2 | 1.45 | 519.2 |
| III-280 | 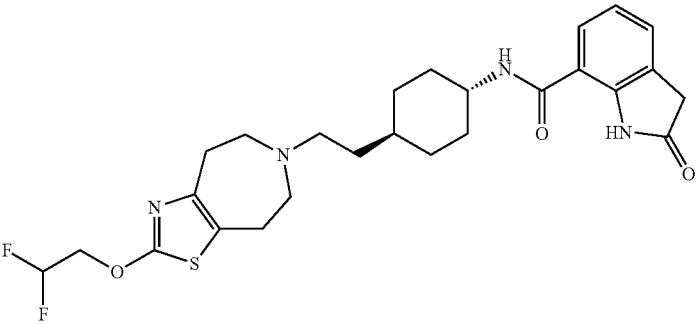 | 2 | 1.43 | 519.1 |
| III-281 | 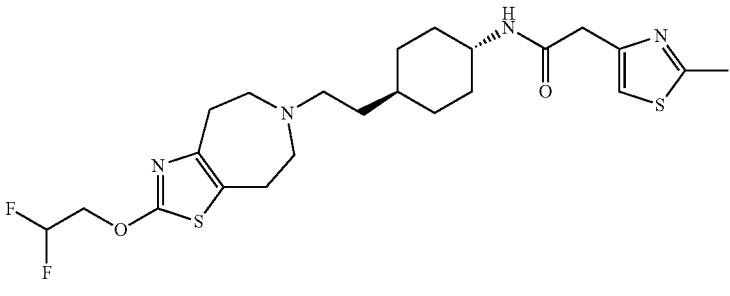 | 2 | 1.32 | 499.2 |
| III-282 | 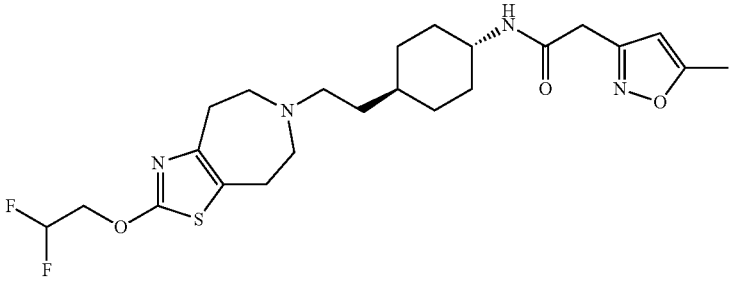 | 2 | 1.34 | 483.1 |

| Compound No. | Structure | LC/MS method | RT (min) | MS (m/z) |
|---|---|---|---|---|
| III-283 | 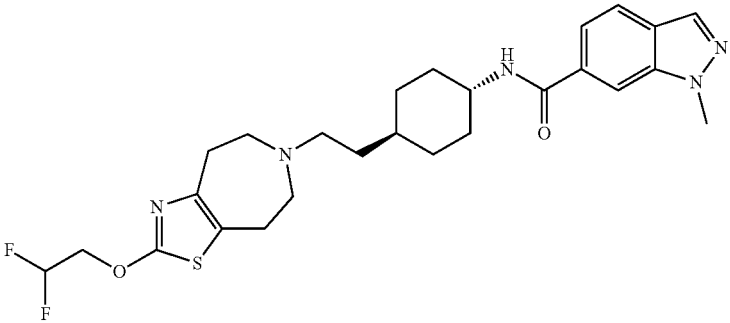 | 2 | 1.45 | 518.1 |
| III-284 | 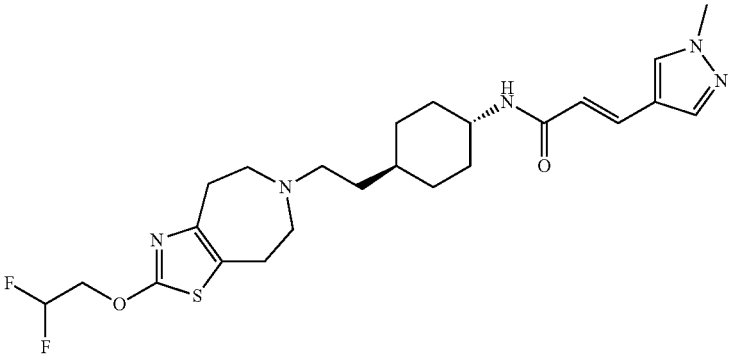 | 2 | 1.30 | 494.2 |
| III-285 | 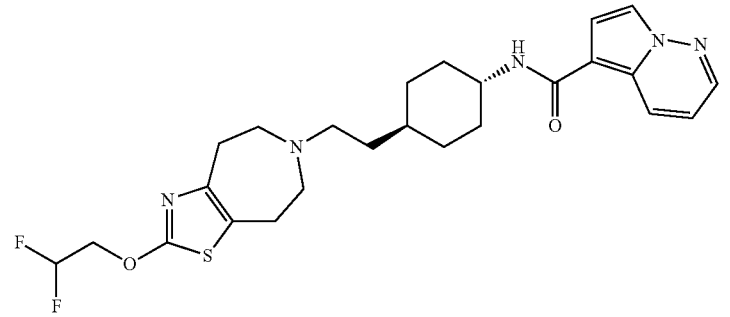 | 2 | 1.48 | 504.2 |
| III-286 | 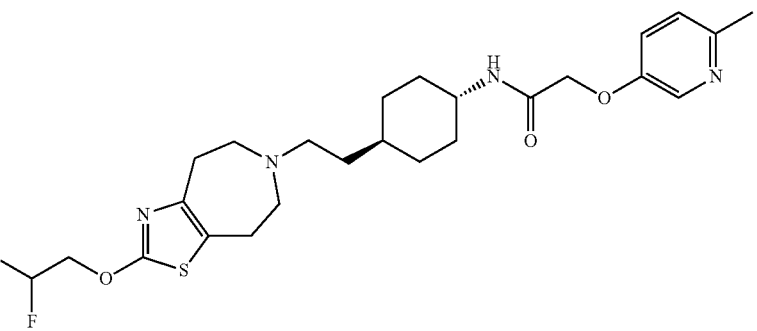 | 2 | 1.06 | 509.2 |

-continued

| Compound No. | Structure | LC/MS method | RT (min) | MS (m/z) |
|---|---|---|---|---|
| III-287 | 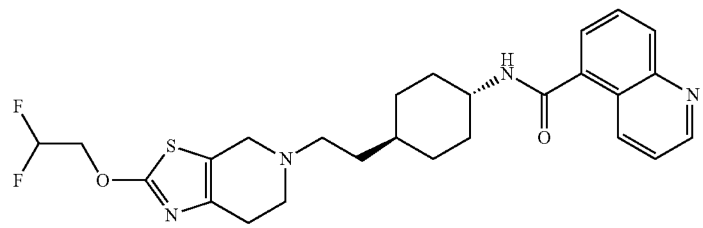 | 2 | 1.07 | 501.2 |
| III-288 | 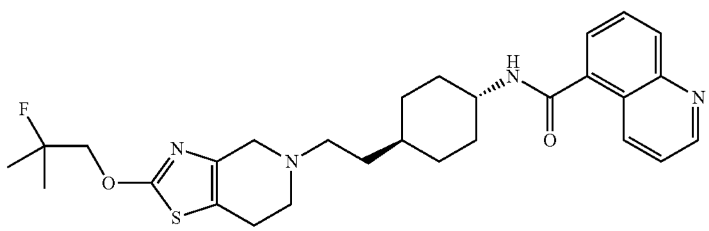 | 2 | 1.32 | 511.3 |
| III-289 | 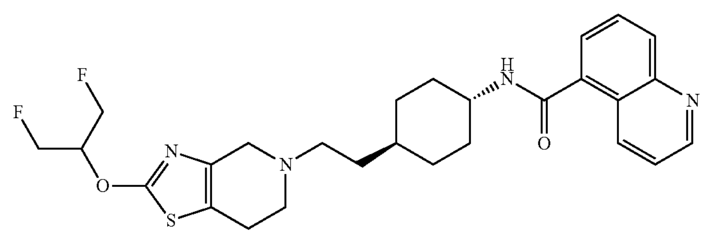 | 2 | 1.15 | 515.2 |
| III-290 | 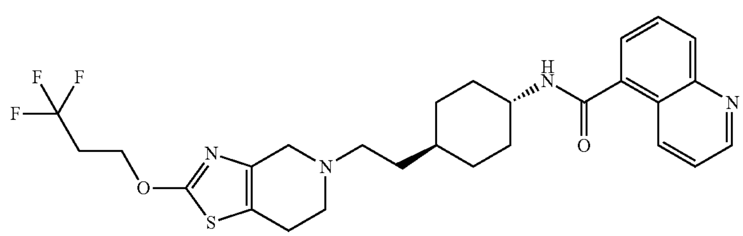 | 2 | 1.39 | 533.3 |
| III-291 | 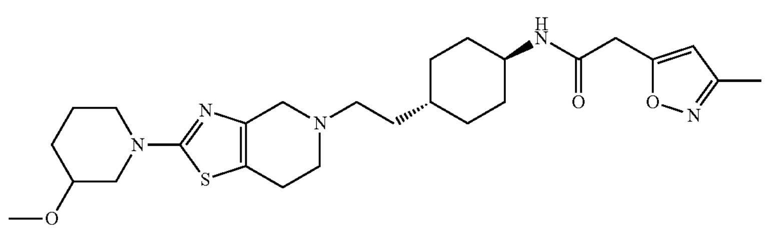 | 3 | 1.07 | 502 |
| III-292 | 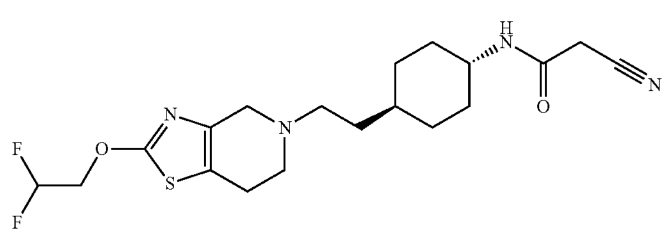 | 1 | 1.96 | 413.1 |

-continued
| Compound No. | Structure | LC/MS method | RT (min) | MS (m/z) |
|---|---|---|---|---|
| III-293 | 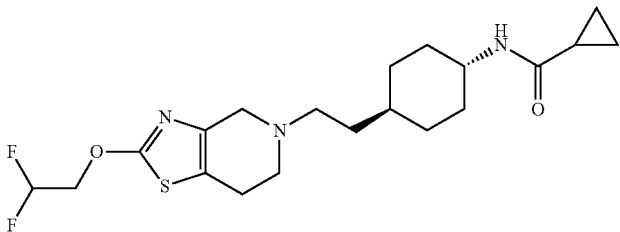 | 1 | 2.07 | 414.1 |
| III-294 | 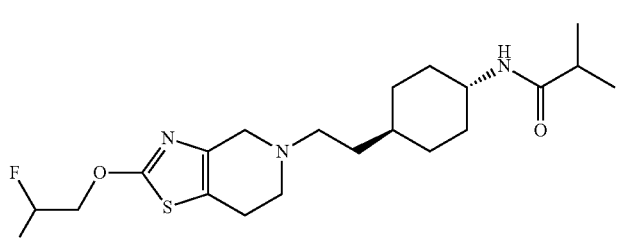 | 1 | 2.12 | 416.1 |
| III-295 | 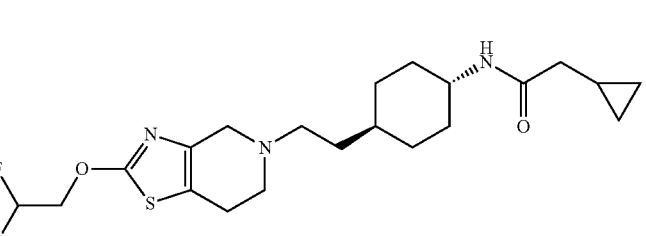 | 1 | 2.15 | 428.1 |
| III-296 | 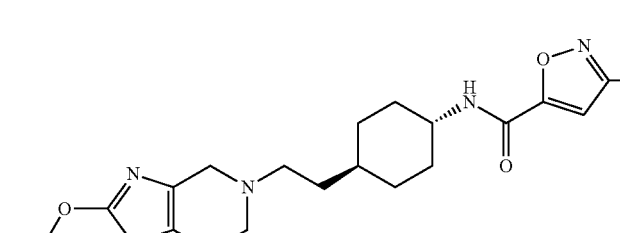 | 1 | 2.19 | 455.1 |
| III-297 | 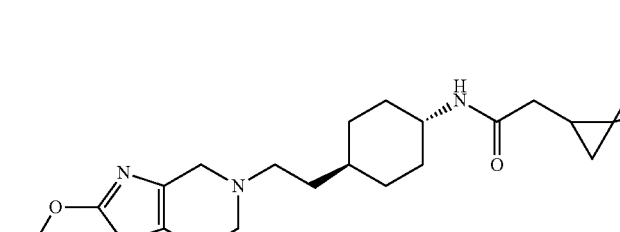 | 1 | 2.22 | 464.1 |
| III-298 | 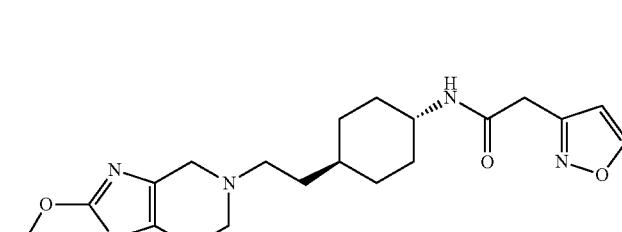 | 1 | 2.08 | 469.1 |

-continued

| Compound No. | Structure | LC/MS method | RT (min) | MS (m/z) |
|---|---|---|---|---|
| III-299 | 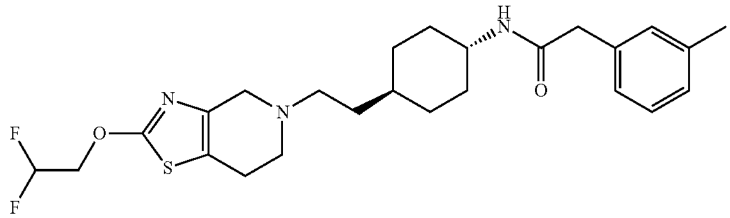 | 1 | 2.46 | 478.1 |
| III-300 | 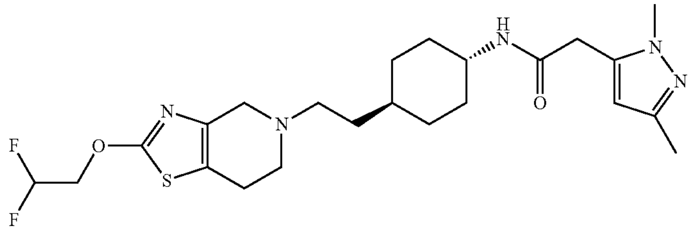 | 1 | 1.96 | 482.2 |
| III-301 | 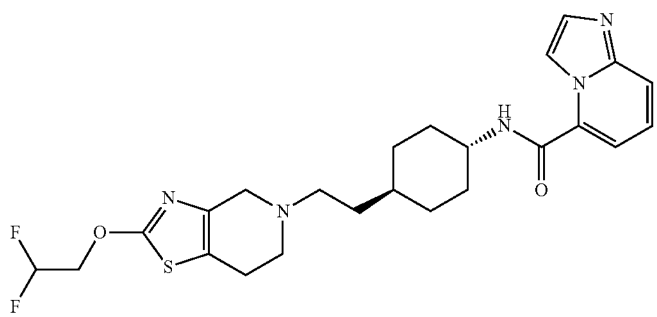 | 1 | 2.10 | 490.1 |
| III-302 | 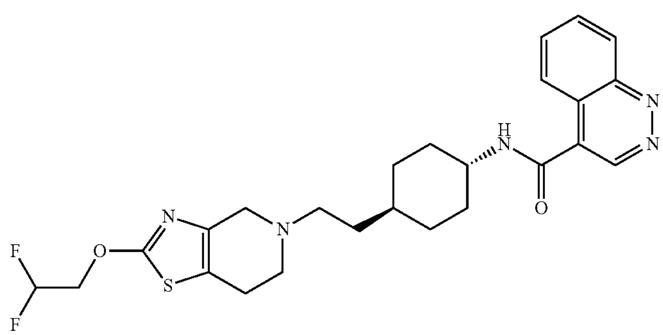 | 1 | 2.13 | 502.1 |
| III-303 | 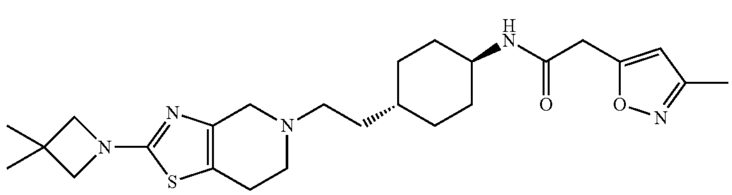 | 3 | 1.20 | 472 |
| III-304 | 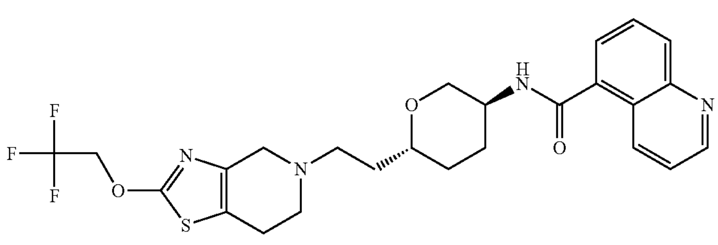 | 3 | 1.07 | 521.25 |

-continued

| Compound No. | Structure | LC/MS method | RT (min) | MS (m/z) |
|---|---|---|---|---|
| III-305 | 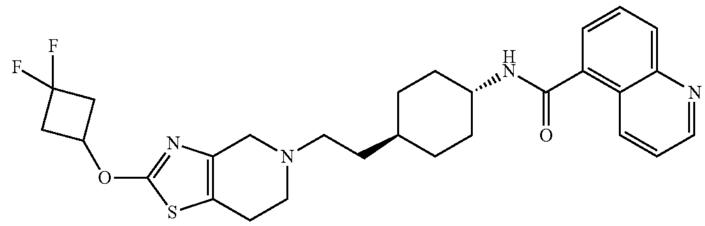 | 2 | 1.51 | 527.2 |
| III-306 | 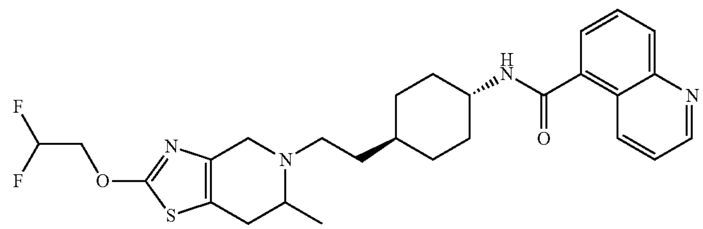 | 2 | 1.30 | 515.2 |
| III-307 | 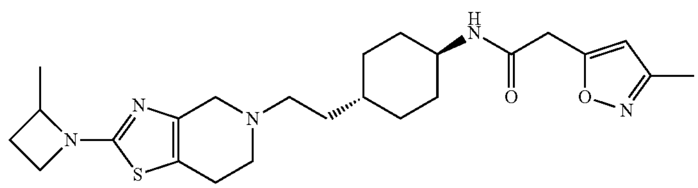 | 3 | 1.04 | 458 |
| III-308 | 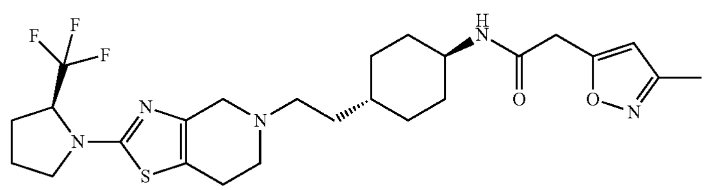 | 3 | 1.23 | 526 |
| III-309 | 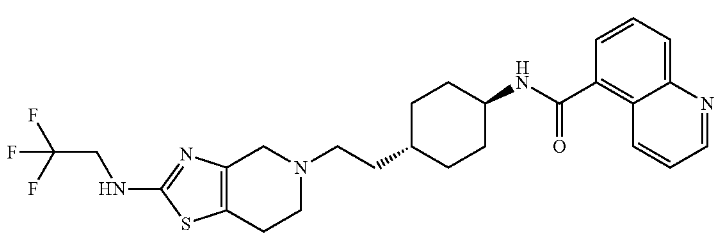 | 3 | 0.90 | 518 |
| III-310 | 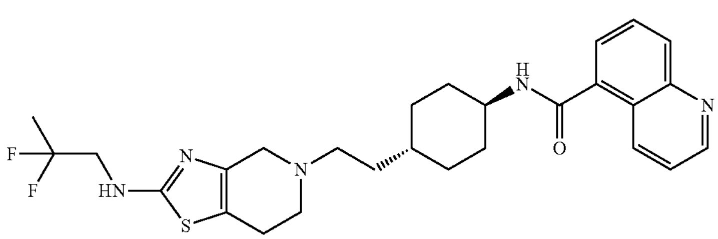 | 3 | 0.93 | 514 |

-continued

| Compound No. | Structure | LC/MS method | RT (min) | MS (m/z) |
| --- | --- | --- | --- | --- |
| III-311 | 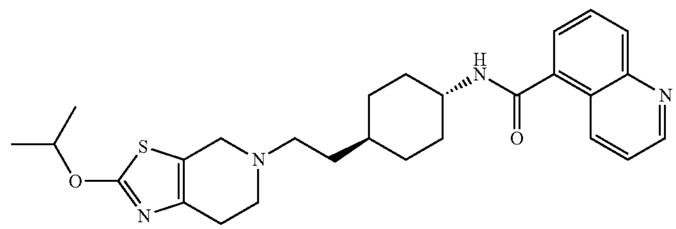 | 2 | 1.15 | 479.2 |
| III-312 | 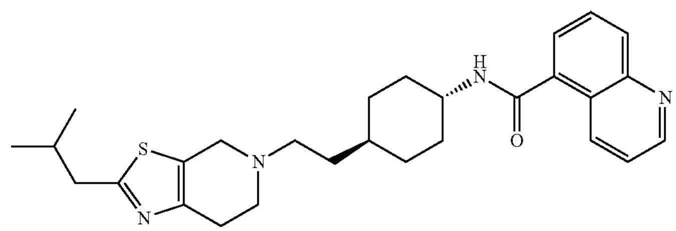 | 2 | 1.27 | 477.3 |
| III-313 | 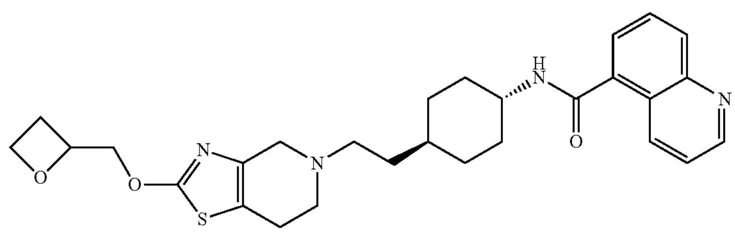 | 2 | 0.89 | 507.3 |
| III-314 | 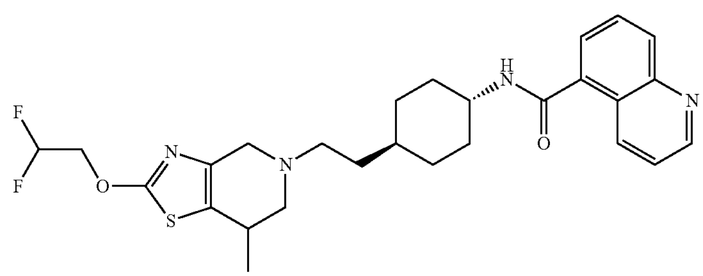 | 2 | 1.23 | 515.3 |
| III-315 | 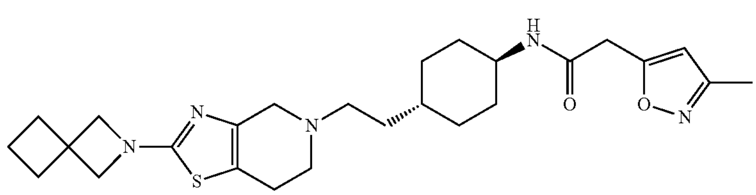 | 3 | 1.14 | 484 |
| III-316 | 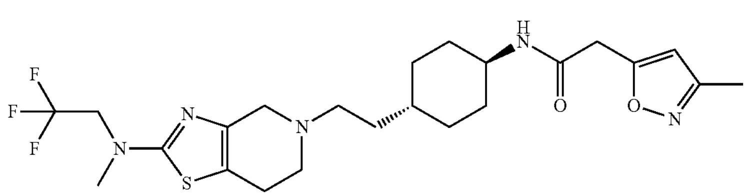 | 3 | 1.15 | 500 |

-continued

| Compound No. | Structure | LC/MS method | RT (min) | MS (m/z) |
|---|---|---|---|---|
| III-317 | 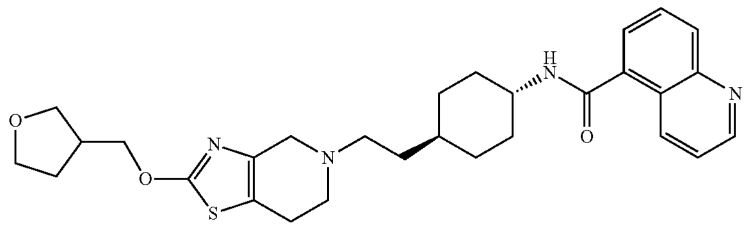 | 2 | 1.12 | 521.3 |
| III-318 | 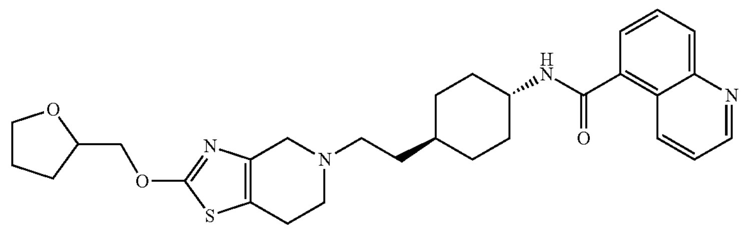 | 2 | 1.11 | 521.3 |
| III-319 | 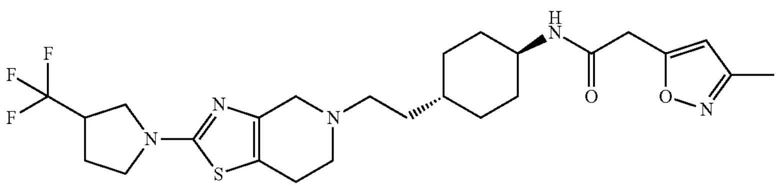 | 3 | 1.23 | 526 |
| III-320 | 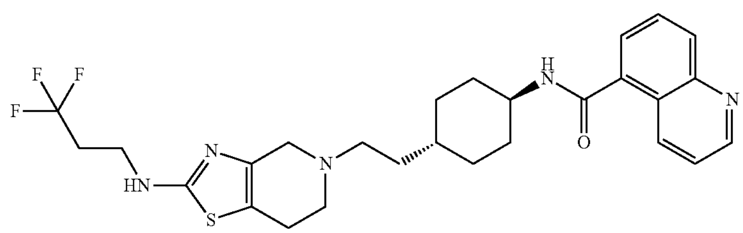 | 3 | 1.02 | 532 |
| III-321 | 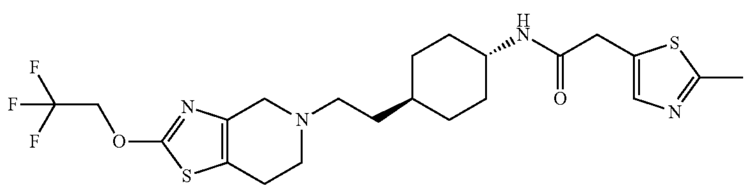 | 2 | 1.41 | 503.1 |
| III-322 | 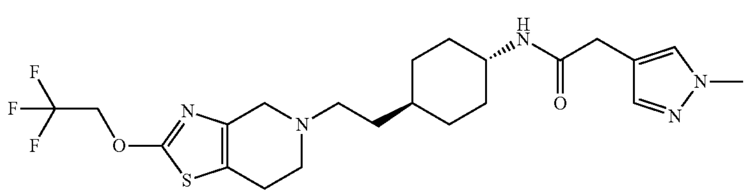 | 2 | 1.32 | 486.2 |
| III-323 | 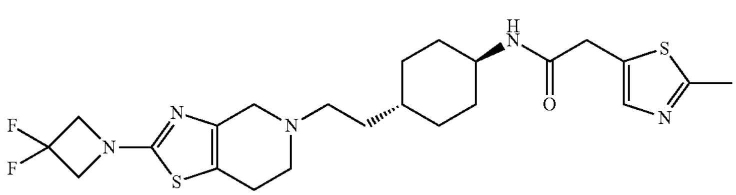 | 3 | 0.96 | 496 |

-continued

| Compound No. | Structure | LC/MS method | RT (min) | MS (m/z) |
|---|---|---|---|---|
| III-324 | 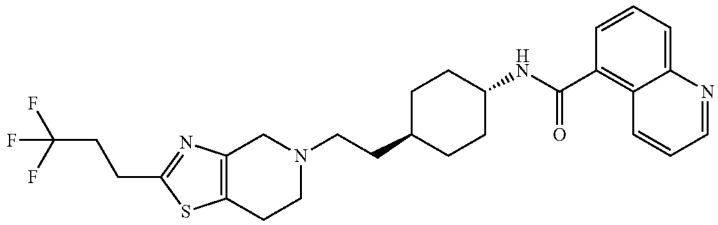 | 2 | 1.29 | 517.2 |
| III-325 | 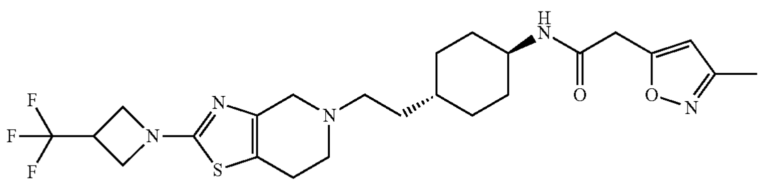 | 3 | 1.15 | 512 |
| III-326 | 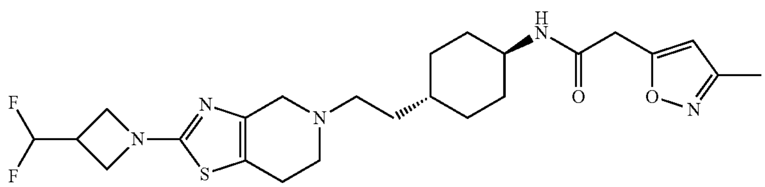 | 3 | 1.03 | 494 |
| III-327 | 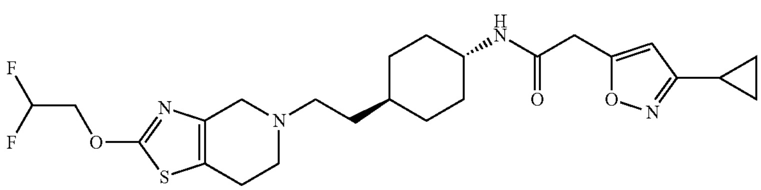 | 2 | 1.47 | 495.3 |
| III-328 | 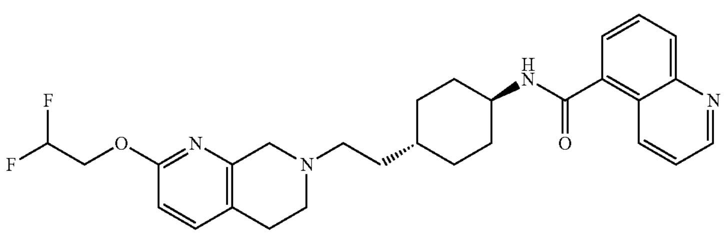 | 3 | 1.07 | 495 |
| III-329 | 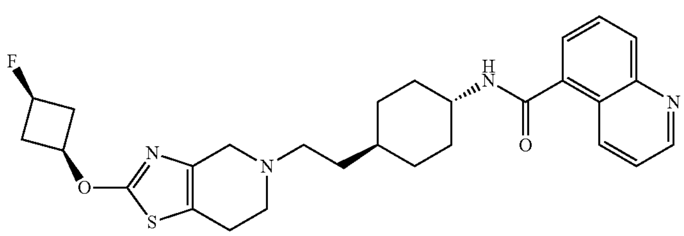 | 2 | 1.31 | 509.3 |
| III-330 | 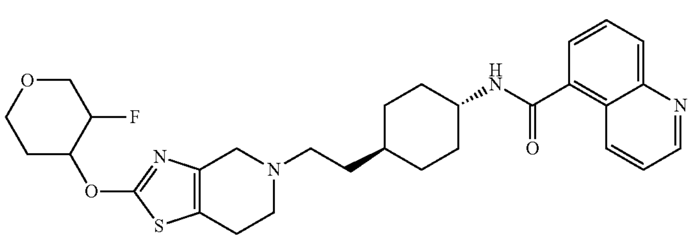 | 2 | 1.17 | 539.3 |

-continued

| Compound No. | Structure | LC/MS method | RT (min) | MS (m/z) |
|---|---|---|---|---|
| III-331 | 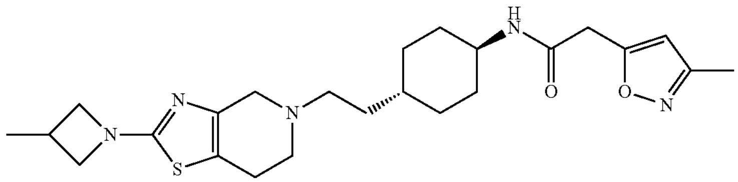 | 3 | 0.98 | 458 |
| III-332 | 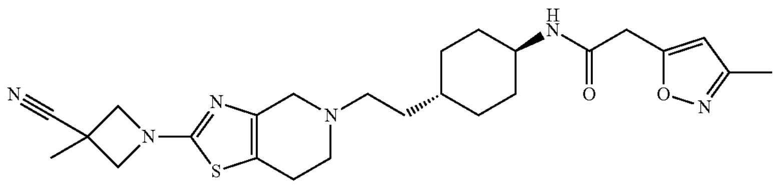 | 3 | 0.91 | 483 |
| III-333 | 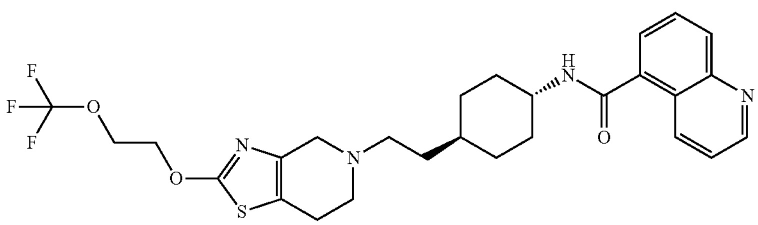 | 2 | 1.51 | 549.2 |
| III-334 | 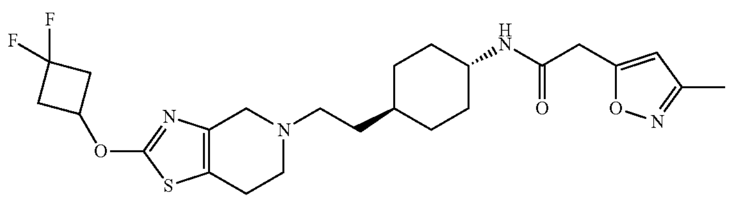 | 2 | 1.42 | 495.3 |
| III-335 | 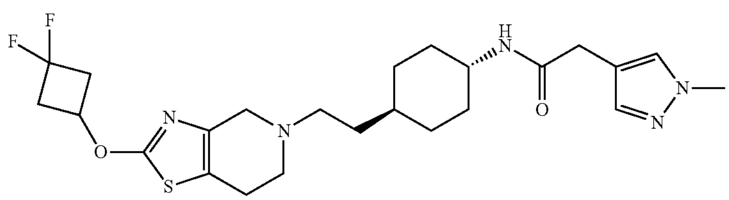 | 2 | 1.30 | 494.3 |
| III-336 | 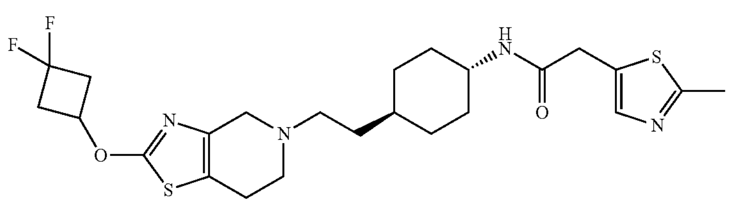 | 2 | 1.36 | 511.2 |
| III-337 | 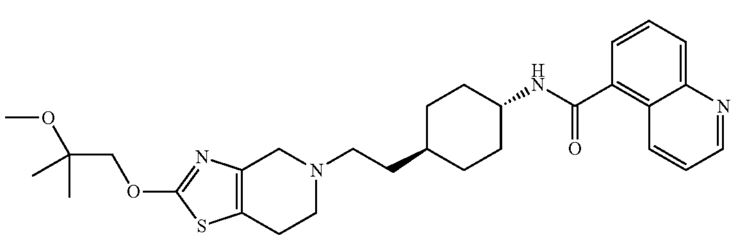 | 2 | 1.21 | 523.3 |

-continued

| Compound No. | Structure | LC/MS method | RT (min) | MS (m/z) |
|---|---|---|---|---|
| III-338 | 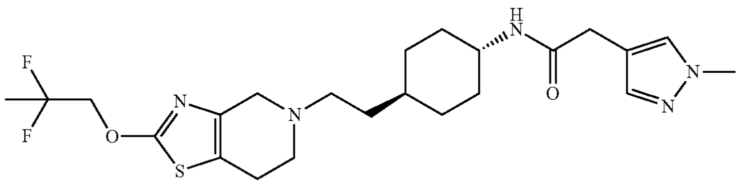 | 2 | 1.26 | 482.3 |
| III-339 | 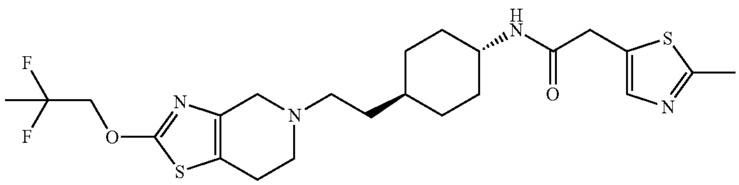 | 2 | 1.32 | 499.3 |
| III-340 | 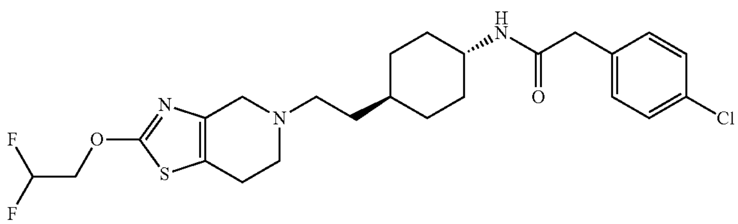 | 2 | 1.66 | 498.1 |
| III-341 | 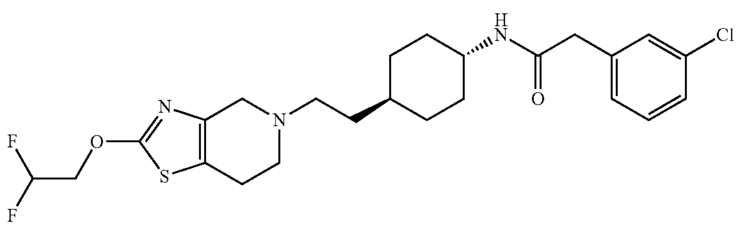 | 2 | 1.64 | 498.1 |
| III-342 | 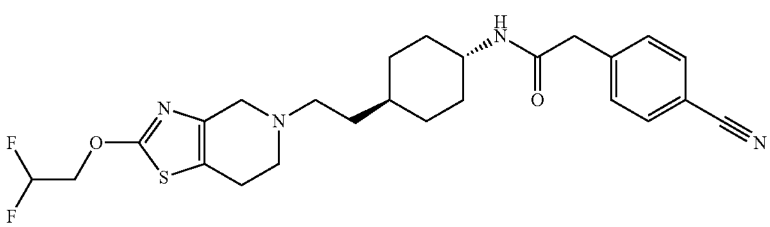 | 2 | 1.45 | 489.1 |
| III-343 | 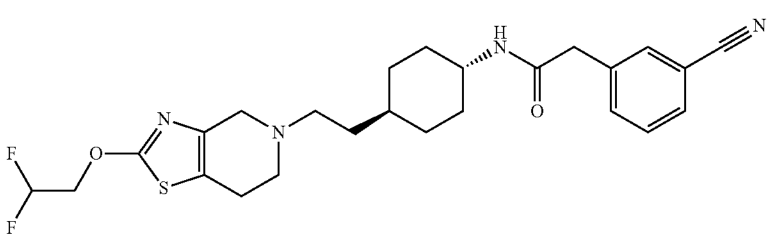 | 2 | 1.47 | 489.1 |
| III-344 | 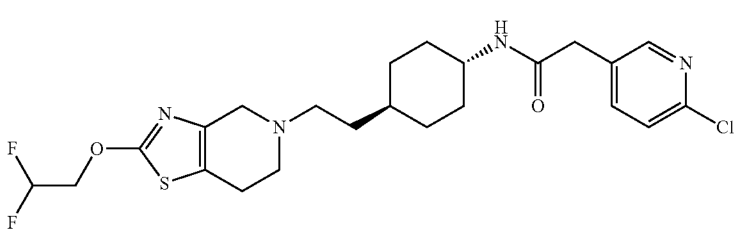 | 2 | 1.41 | 499.1 |

-continued

| Compound No. | Structure | LC/MS method | RT (min) | MS (m/z) |
|---|---|---|---|---|
| III-345 | 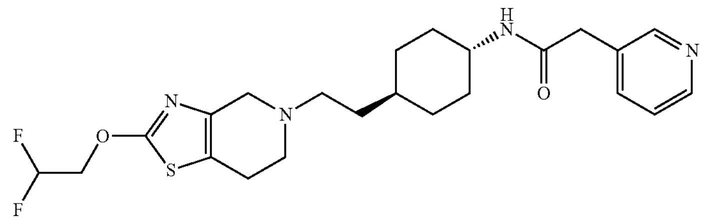 | 2 | 0.98 | 465.2 |
| III-346 | 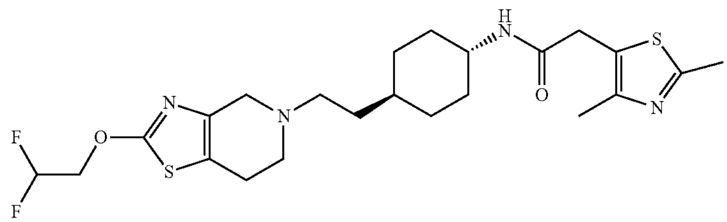 | 2 | 1.16 | 499.2 |
| III-347 | 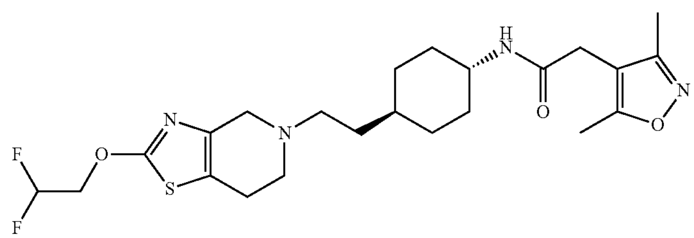 | 2 | 1.33 | 483.1 |
| III-348 | 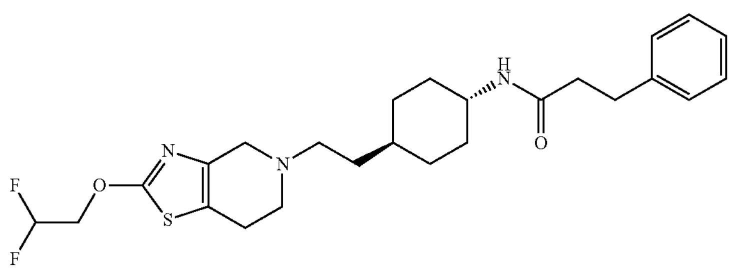 | 2 | 1.58 | 478.1 |
| III-349 | 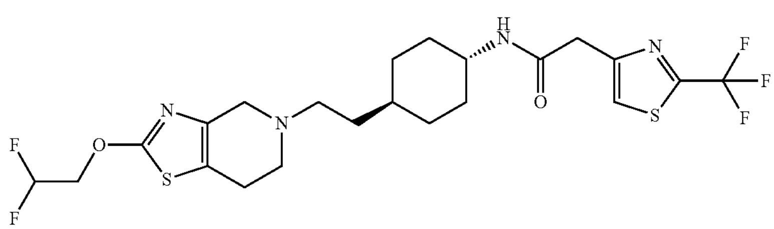 | 2 | 1.58 | 539 |
| III-350 | 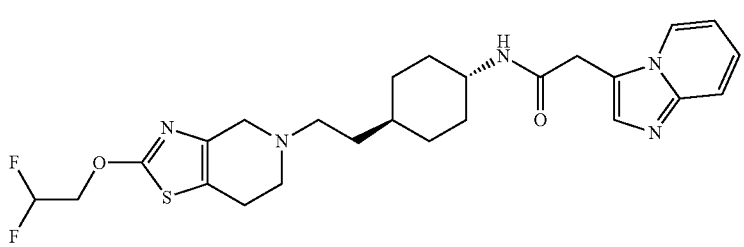 | 2 | 0.99 | 504.2 |

-continued

| Compound No. | Structure | LC/MS method | RT (min) | MS (m/z) |
|---|---|---|---|---|
| III-351 | 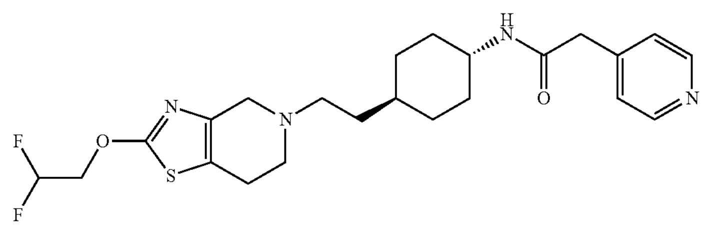 | 2 | 0.96 | 465.2 |
| III-352 | 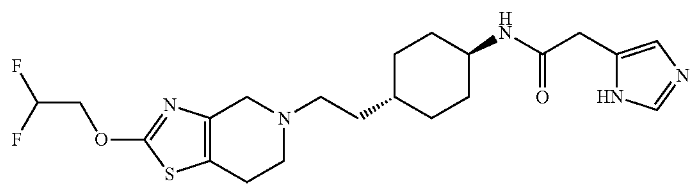 | 1 | 1.45 | 454 |
| III-353 | 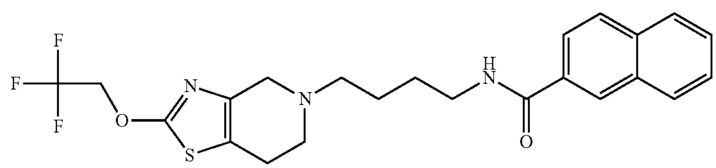 | 4 | 1.65 | 464.15 |
| III-354 | 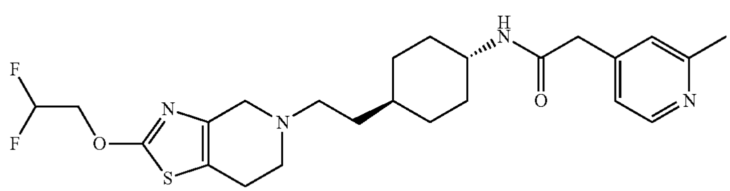 | 2 | 0.94 | 479.3 |
| III-355 | 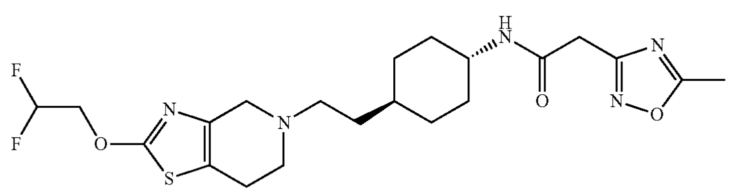 | 2 | 1.16 | 470.2 |
| III-356 | 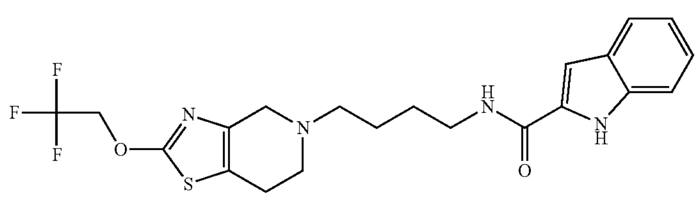 | 4 | 1.58 | 453.15 |
| III-357 | 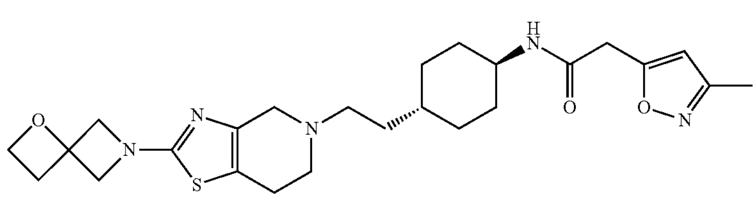 | 3 | 0.88 | 486 |

-continued
| Compound No. | Structure | LC/MS method | RT (min) | MS (m/z) |
| --- | --- | --- | --- | --- |
| III-359 | 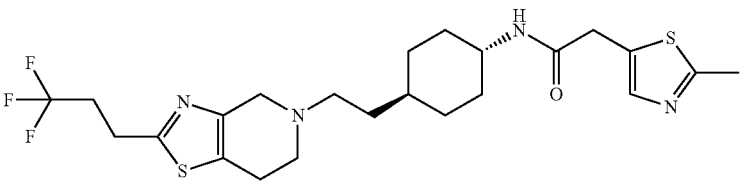 | 2 | 1.34 | 501.3 |
| III-360 | 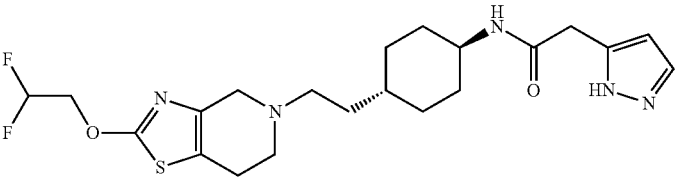 | 3 | 0.85 | 454 |
| III-361 | 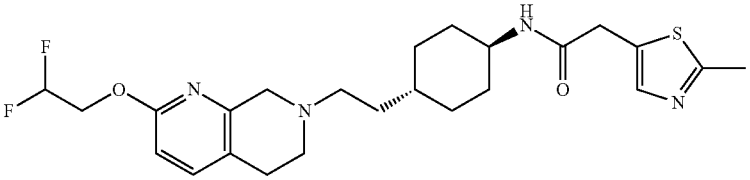 | 3 | 1.11 | 479 |
| III-362 | 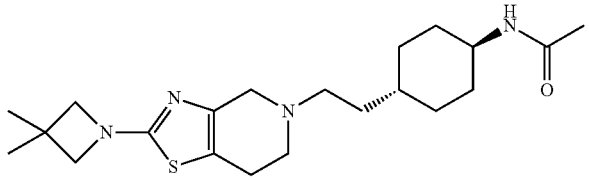 | 3 | 1.01 | 391 |
| III-363 | 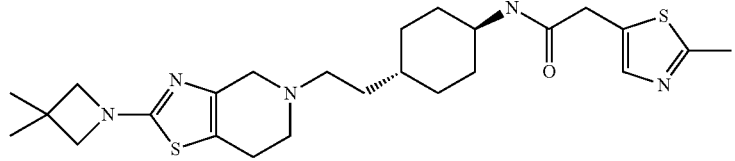 | 3 | 1.03 | 488 |
| III-364 | 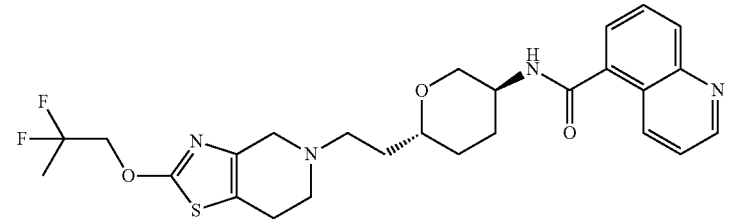 | 3 | 1.05 | 517.3 |
| III-365 | 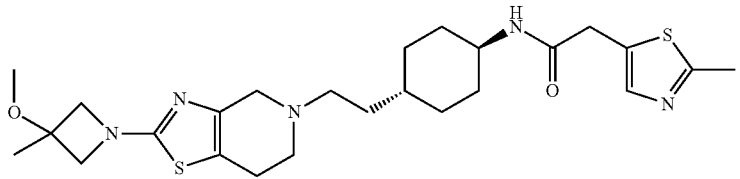 | 3 | 0.99 | 504 |

-continued

| Compound No. | Structure | LC/MS method | RT (min) | MS (m/z) |
|---|---|---|---|---|
| III-366 | 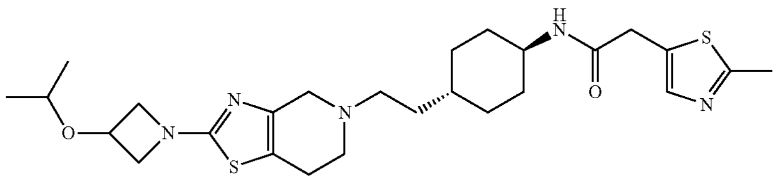 | 3 | 1.13 | 518 |
| III-367 | 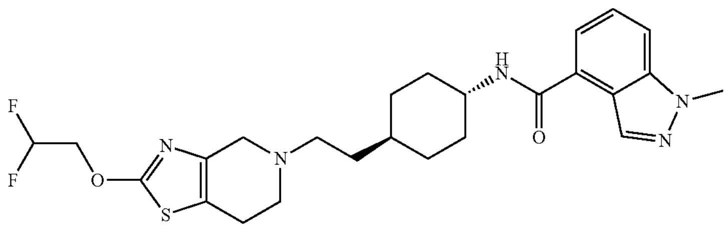 | 4 | 1.41 | 504.2 |
| III-368 | 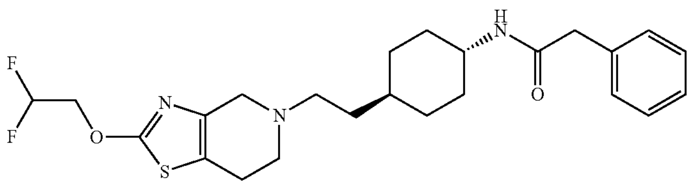 | 2 | 1.55 | 464.3 |
| III-369 | 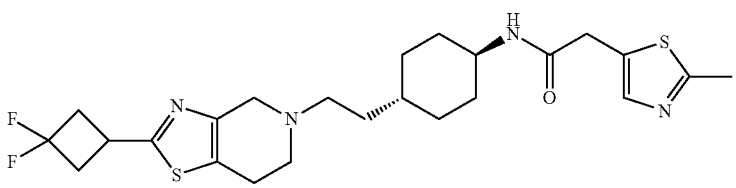 | 2 | 1.23 | 495.3 |
| III-370 | 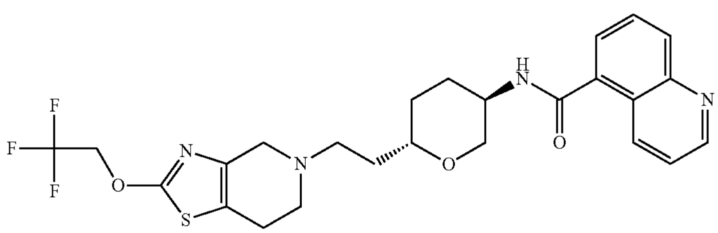 | 3 | 1.09 | 521.3 |
| III-371 | 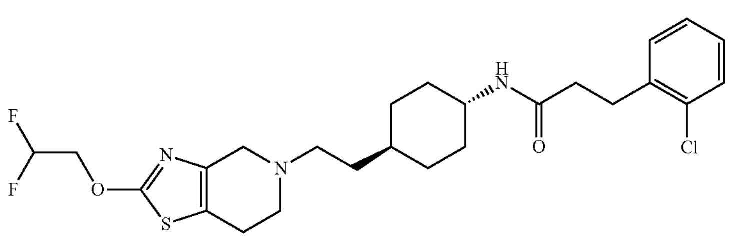 | 2 | 1.76 | 512.1 |
| III-372 | 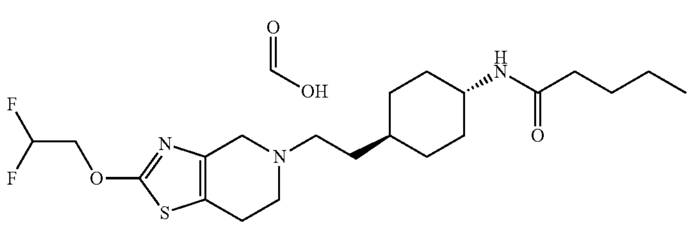 | 2 | 1.45 | 430.1 |

-continued

| Compound No. | Structure | LC/MS method | RT (min) | MS (m/z) |
|---|---|---|---|---|
| III-373 | 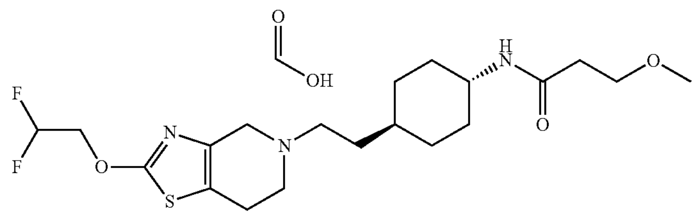 | 2 | 1.16 | 432.1 |
| III-374 | 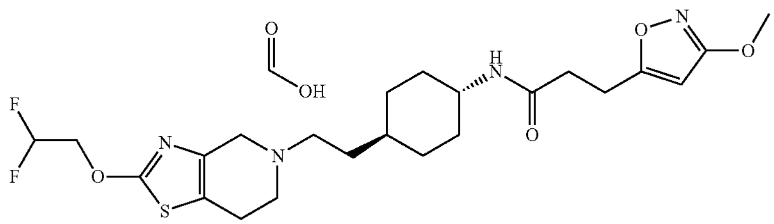 | 2 | 1.38 | 499.1 |
| III-375 | 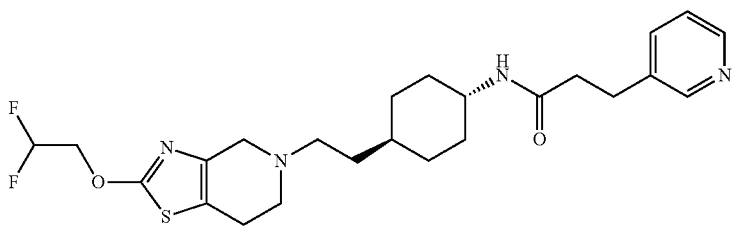 | 2 | 0.87 | 479.1 |
| III-376 | 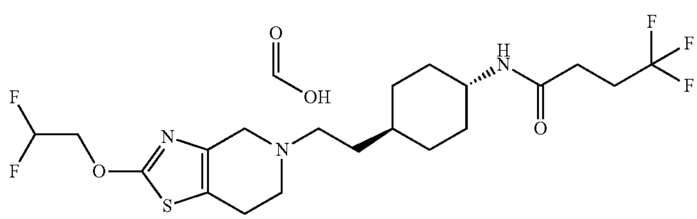 | 2 | 1.47 | 470.1 |
| III-377 | 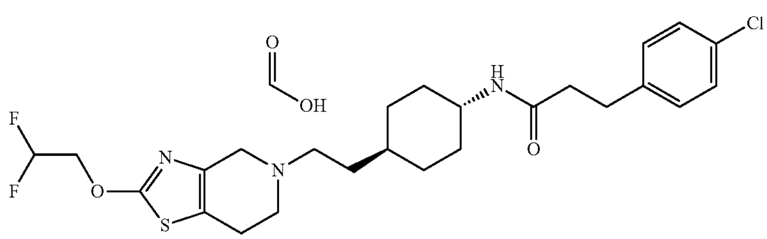 | 2 | 1.75 | 512.1 |
| III-378 | 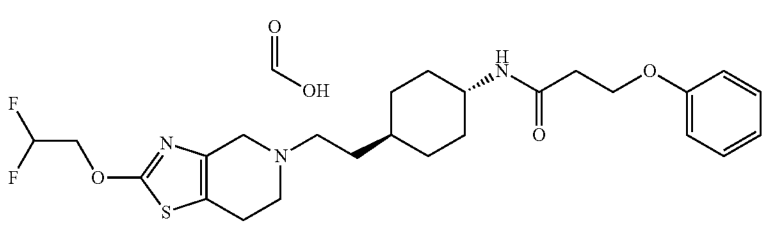 | 2 | 1.62 | 494.1 |

| Compound No. | Structure | LC/MS method | RT (min) | MS (m/z) |
| --- | --- | --- | --- | --- |
| III-379 | 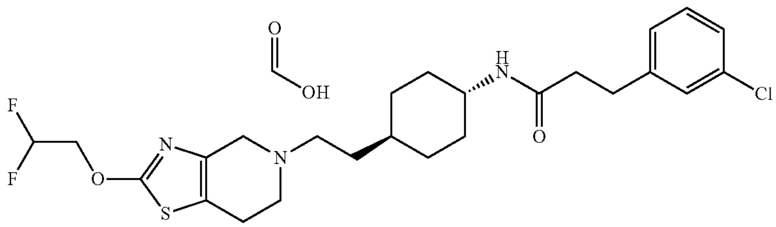 | 2 | 1.73 | 512.1 |
| III-380 | 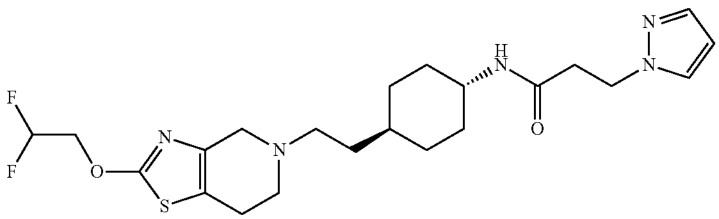 | 2 | 1.25 | 468.1 |
| III-381 | 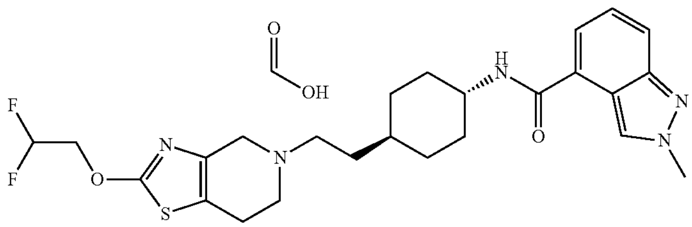 | 2 | 1.41 | 504.1 |
| III-382 | 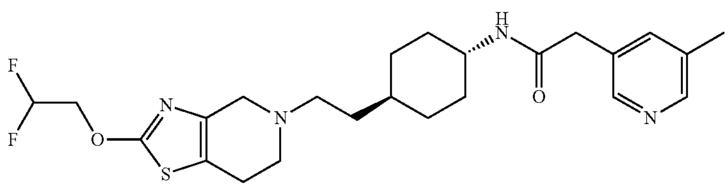 | 2 | 0.91 | 479.1 |
| III-383 | 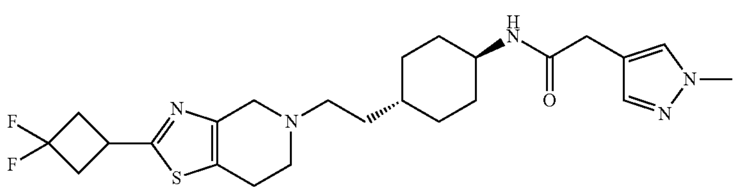 | 2 | 1.15 | 478.3 |
| III-384 | 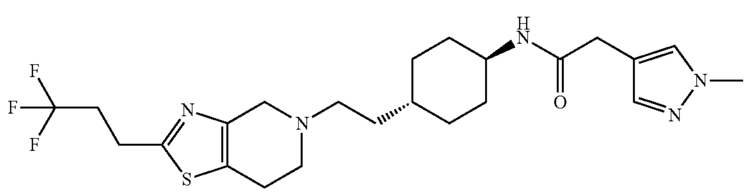 | 2 | 1.16 | 484.3 |
| III-385 | 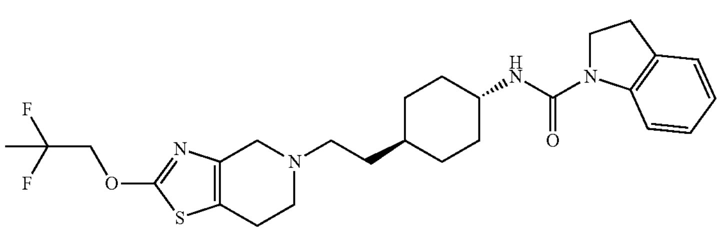 | 2 | 1.91 | 505.3 |

-continued

| Compound No. | Structure | LC/MS method | RT (min) | MS (m/z) |
|---|---|---|---|---|
| III-386 | 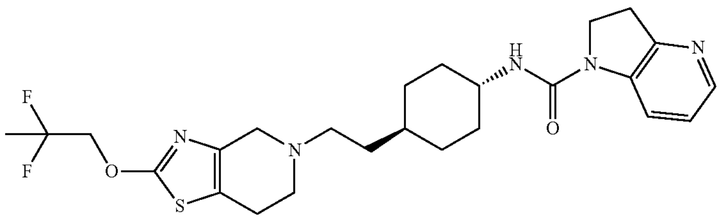 | 2 | 1.22 | 506.3 |
| III-387 | 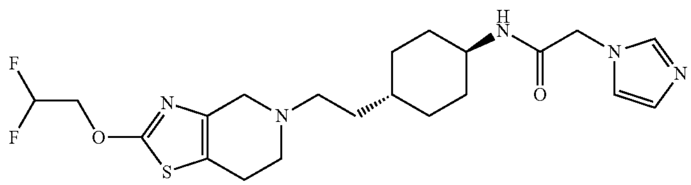 | 3 | 0.72 | 454 |
| III-388 | 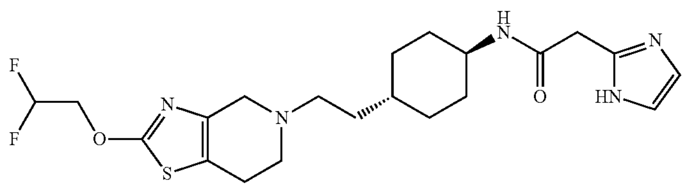 | 3 | 0.75 | 454 |
| III-389 | 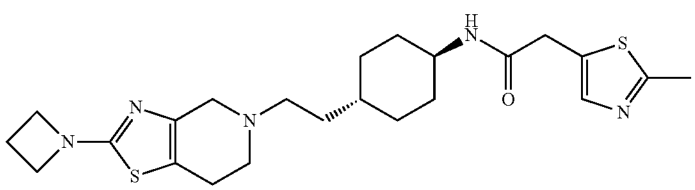 | 2 | 1.08 | 460.2 |
| III-390 | 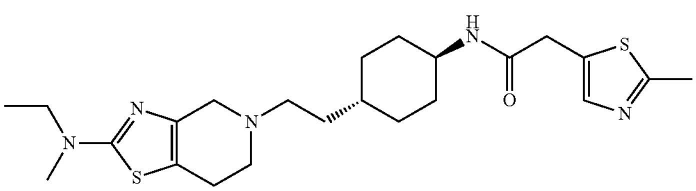 | 2 | 1.12 | 462.1 |
| III-391 | 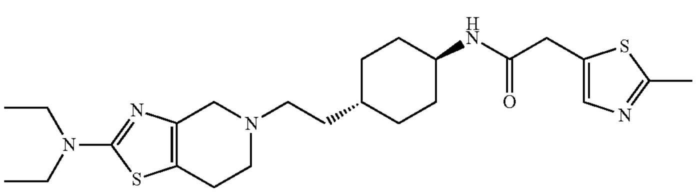 | 2 | 1.22 | 476.2 |
| III-392 | 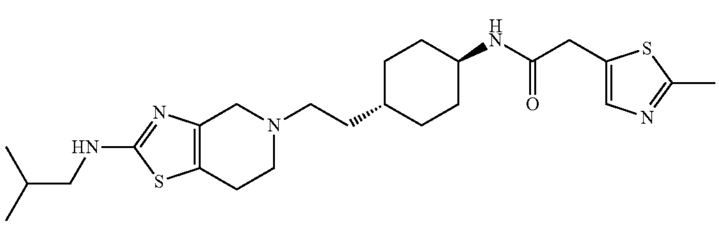 | 2 | 1.24 | 476.2 |

-continued
| Compound No. | Structure | LC/MS method | RT (min) | MS (m/z) |
|---|---|---|---|---|
| III-393 | 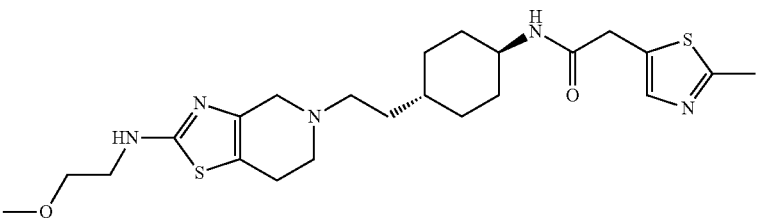 | 2 | 1.00 | 478.2 |
| III-394 | 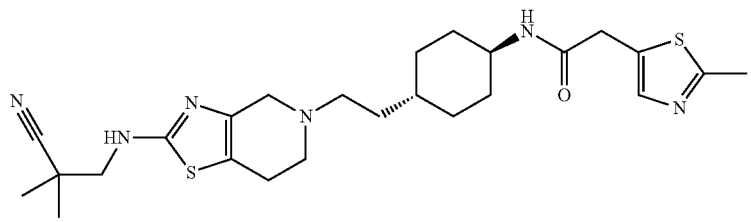 | 2 | 1.15 | 501.2 |
| III-395 | 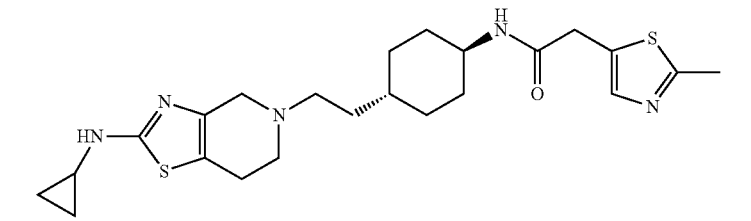 | 2 | 1.09 | 460.2 |
| III-396 | 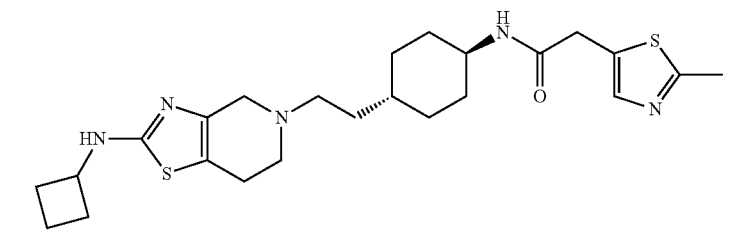 | 2 | 1.19 | 474.2 |
| III-397 | 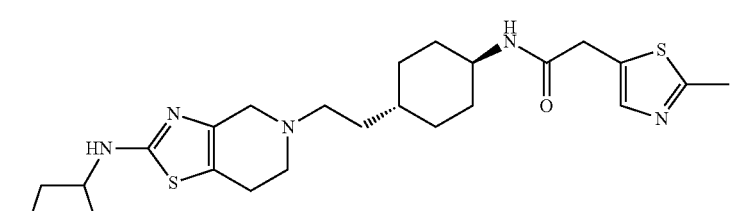 | 2 | 1.25 | 488.2 |
| III-398 | 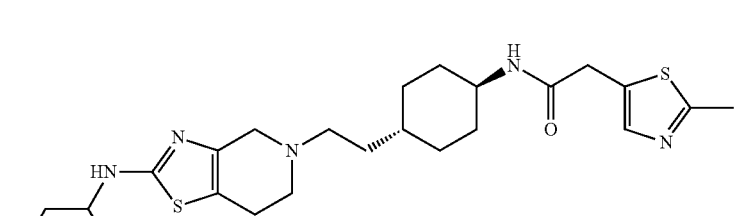 | 2 | 1.35 | 502.3 |

-continued

| Compound No. | Structure | LC/MS method | RT (min) | MS (m/z) |
|---|---|---|---|---|
| III-399 | 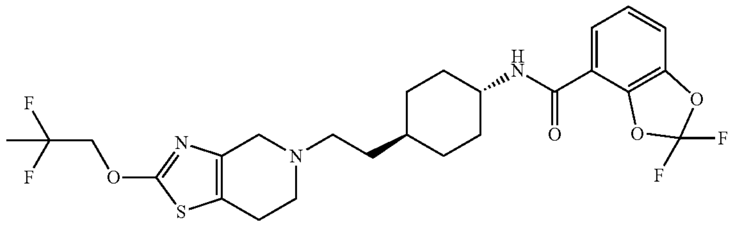 | 2 | 1.83 | 544.1 |
| III-400 | 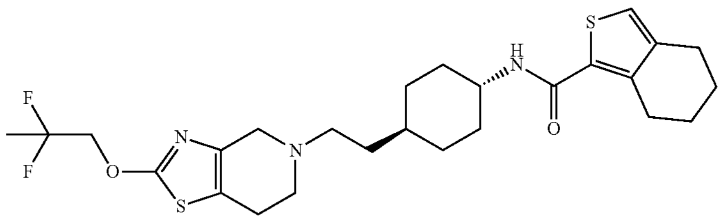 | 2 | 1.92 | 524.2 |
| III-401 | 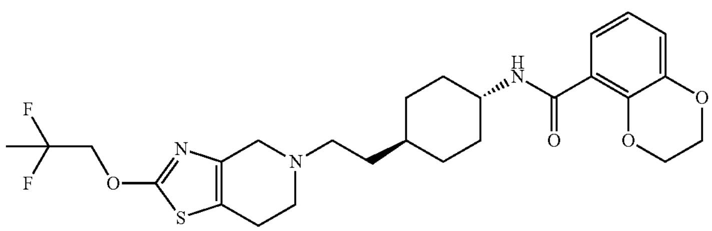 | 2 | 1.63 | 522.1 |
| III-402 | 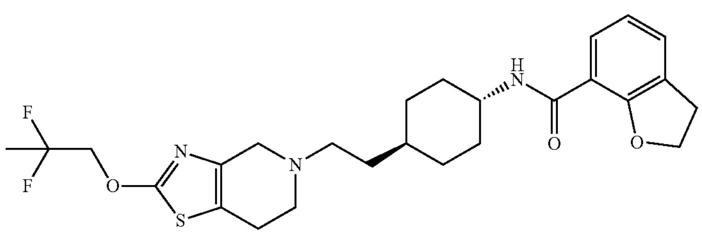 | 2 | 1.70 | 506.2 |
| III-403 | 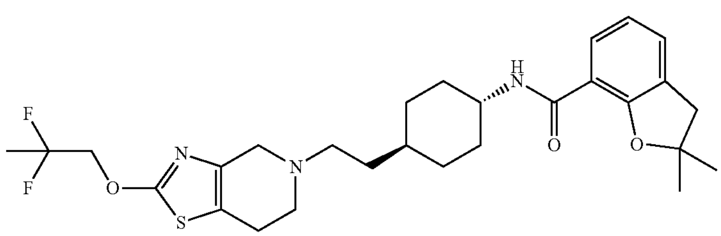 | 2 | 1.88 | 534.2 |
| III-404 | 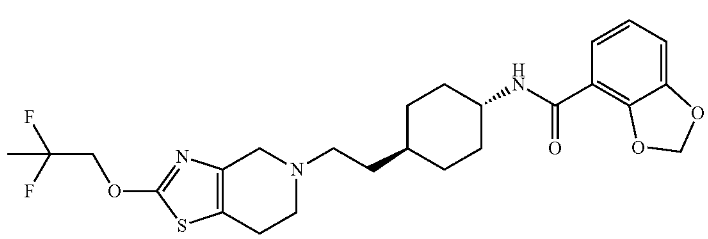 | 2 | 1.66 | 508.1 |

| Compound No. | Structure | LC/MS method | RT (min) | MS (m/z) |
|---|---|---|---|---|
| III-405 | 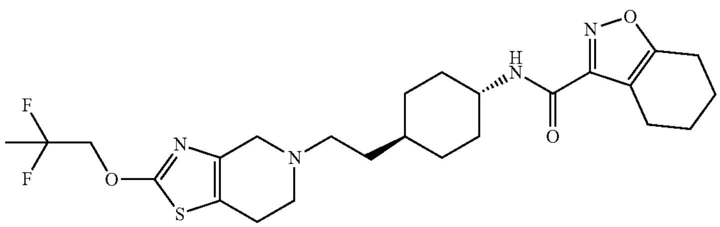 | 2 | 1.77 | 509.2 |
| III-406 | 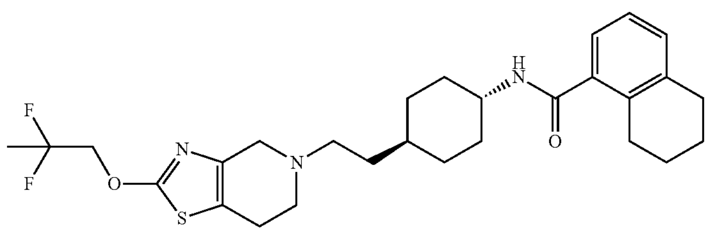 | 2 | 1.84 | 518.1 |
| III-407 | 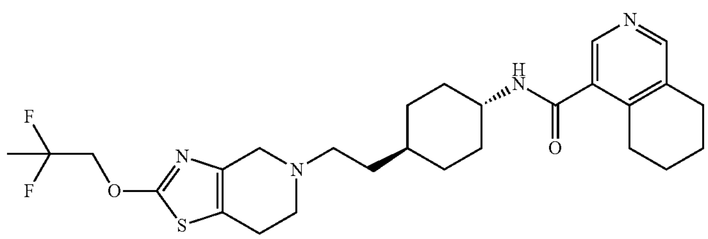 | 2 | 1.26 | 519.3 |
| III-408 | 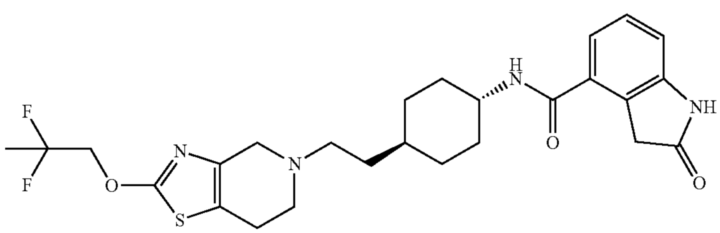 | 2 | 1.38 | 519.2 |
| III-409 | 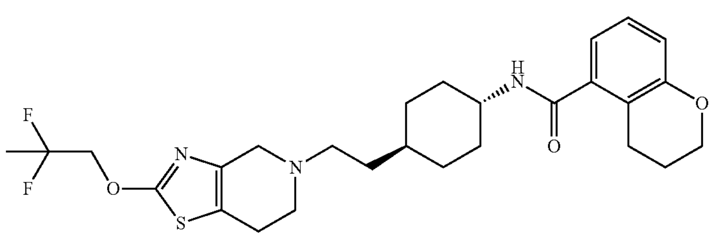 | 2 | 1.63 | 520.2 |
| III-410 | 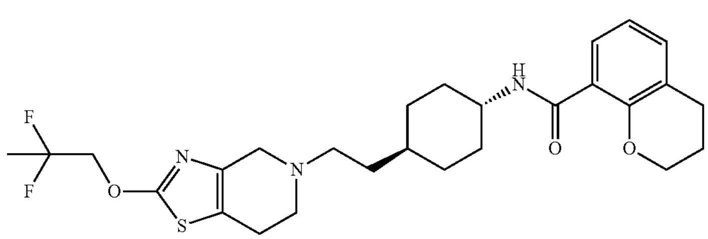 | 2 | 1.76 | 520.2 |

| Compound No. | Structure | LC/MS method | RT (min) | MS (m/z) |
|---|---|---|---|---|
| III-411 | 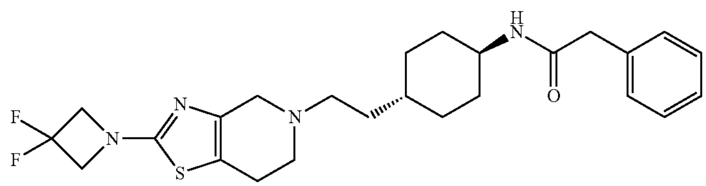 | 3 | 1.27 | 475 |
| III-412 | 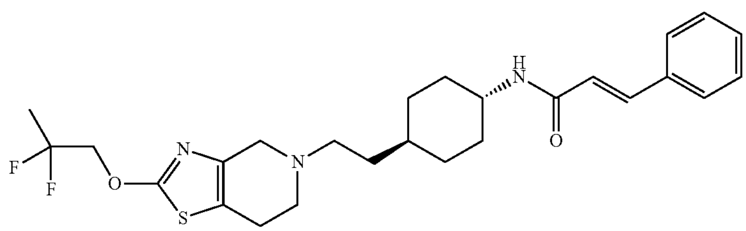 | 2 | 1.72 | 490.1 |
| III-413 | 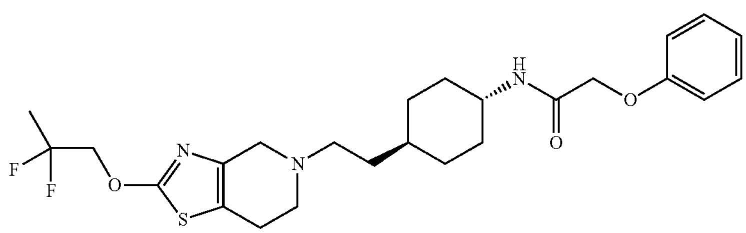 | 2 | 1.66 | 494.1 |
| III-414 | 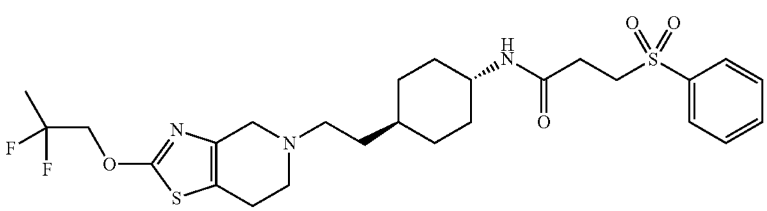 | 2 | 1.51 | 556.1 |
| III-415 | 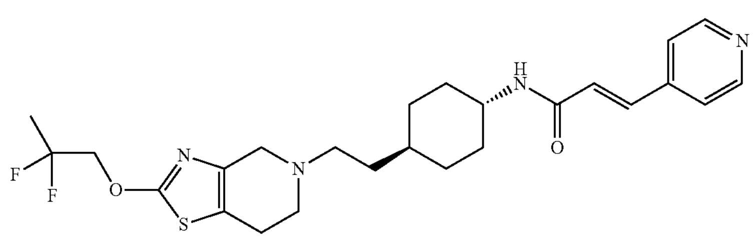 | 2 | 1.12 | 491.1 |
| III-416 | 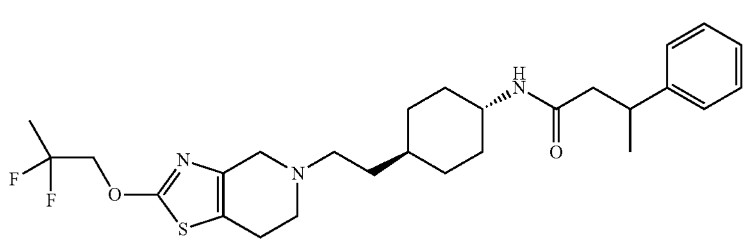 | 2 | 1.71 | 506.2 |

-continued

| Compound No. | Structure | LC/MS method | RT (min) | MS (m/z) |
|---|---|---|---|---|
| III-417 | 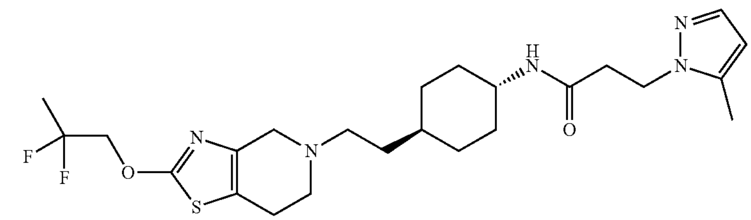 | 2 | 1.38 | 496.2 |
| III-418 | 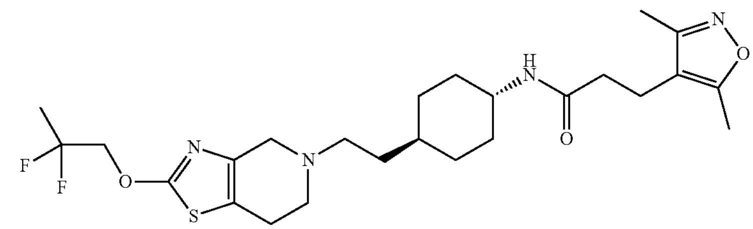 | 2 | 1.44 | 511.2 |
| III-419 | 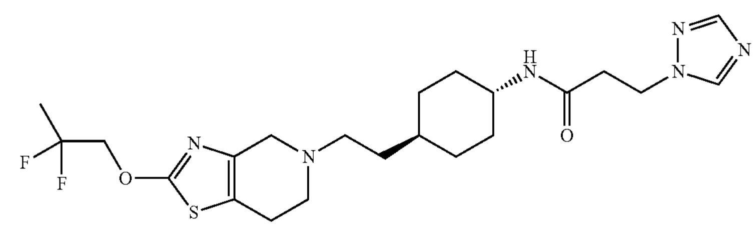 | 2 | 1.22 | 483.1 |
| III-420 | 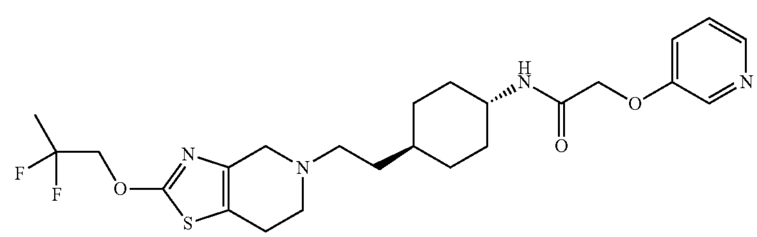 | 2 | 1.14 | 495.1 |
| III-421 | 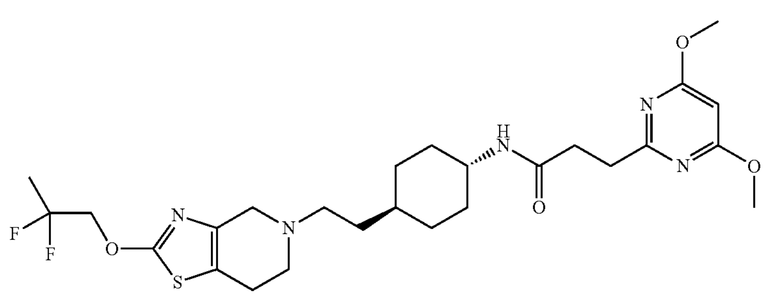 | 2 | 1.53 | 554.2 |
| III-422 | 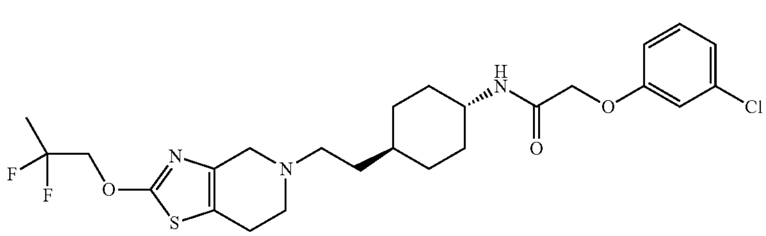 | 2 | 1.82 | 528.1 |

-continued

| Compound No. | Structure | LC/MS method | RT (min) | MS (m/z) |
|---|---|---|---|---|
| III-423 | 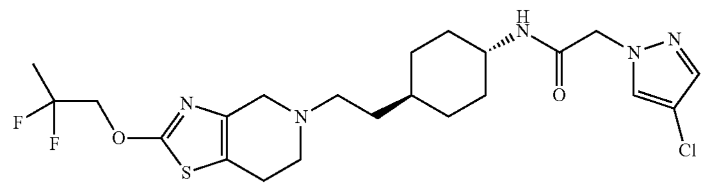 | 2 | 1.51 | 502.1 |
| III-424 | 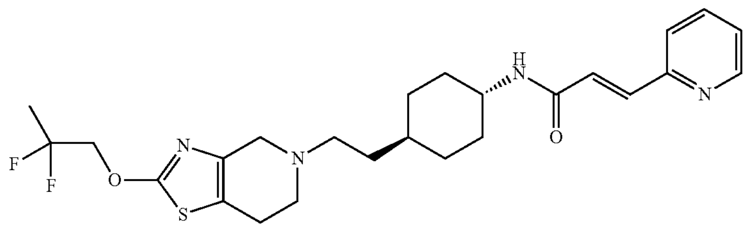 | 2 | 1.32 | 491.2 |
| III-425 | 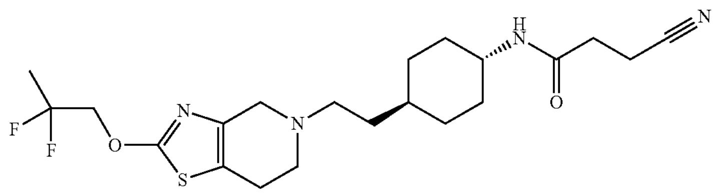 | 2 | 1.32 | 441.1 |
| III-426 | 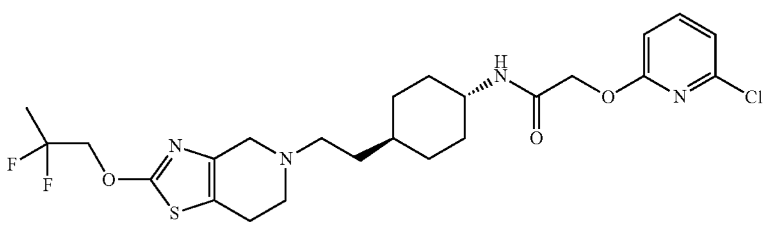 | 2 | 1.67 | 529.1 |
| III-427 | 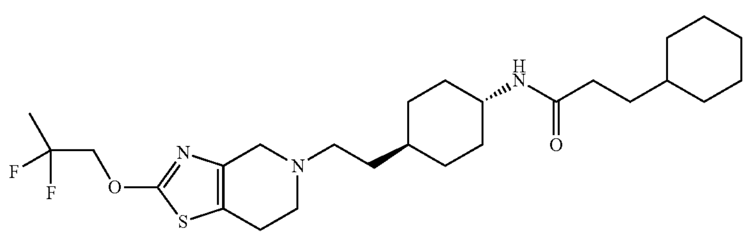 | 2 | 1.92 | 498.3 |
| III-428 | 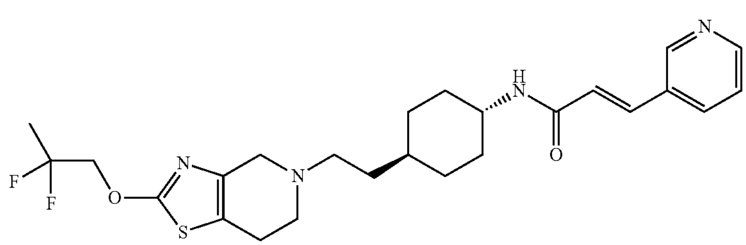 | 2 | 1.19 | 491.2 |

| Compound No. | Structure | LC/MS method | RT (min) | MS (m/z) |
|---|---|---|---|---|
| III-429 | 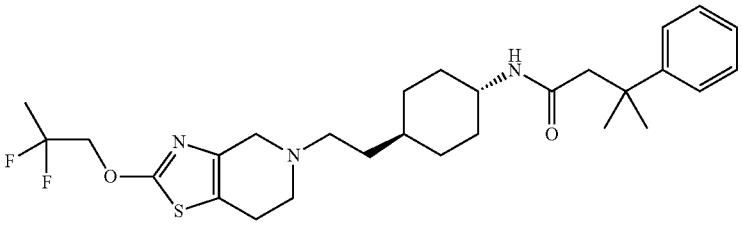 | 2 | 1.81 | 520.3 |
| III-430 | 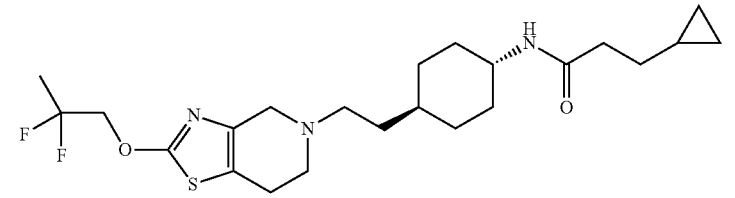 | 2 | 1.54 | 456.1 |
| III-431 | 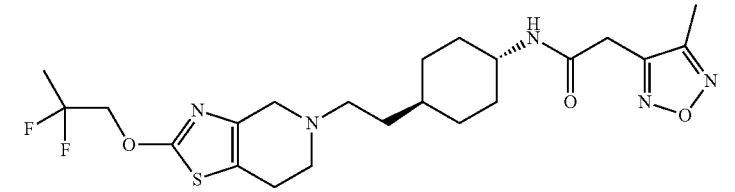 | 2 | 1.47 | 484.1 |
| III-432 | 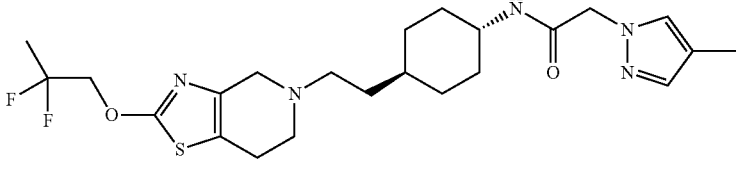 | 2 | 1.42 | 482.1 |
| III-433 | 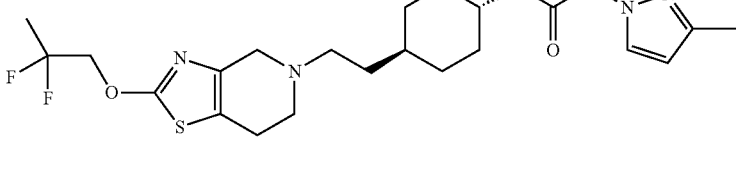 | 2 | 1.40 | 482.2 |
| III-434 | 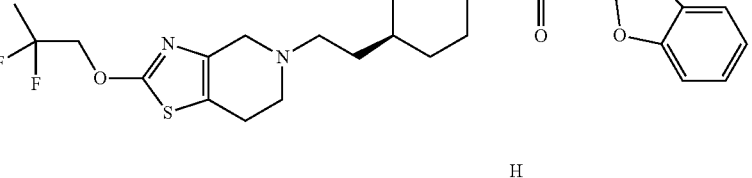 | 2 | 1.58 | 519.1 |
| III-435 | 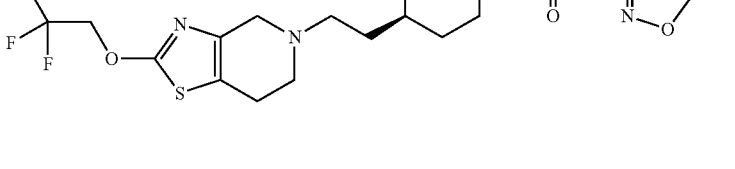 | 2 | 1.34 | 484.1 |

| Compound No. | Structure | LC/MS method | RT (min) | MS (m/z) |
|---|---|---|---|---|
| III-436 | 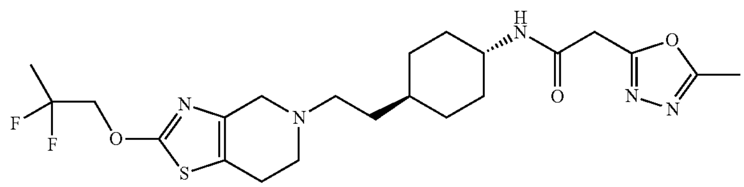 | 2 | 1.28 | 484.1 |
| III-437 | 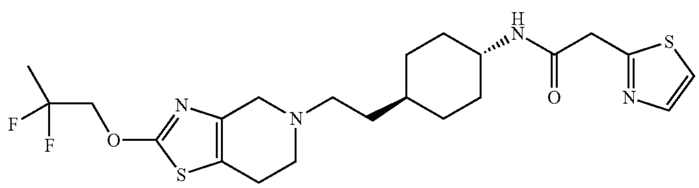 | 2 | 1.36 | 485.1 |
| III-438 | 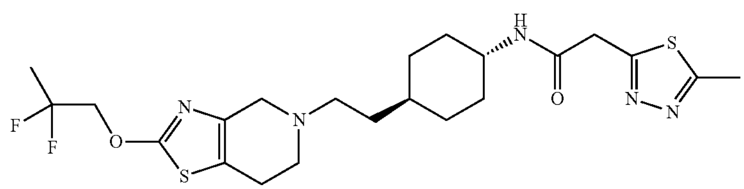 | 2 | 1.32 | 500.1 |
| III-439 | 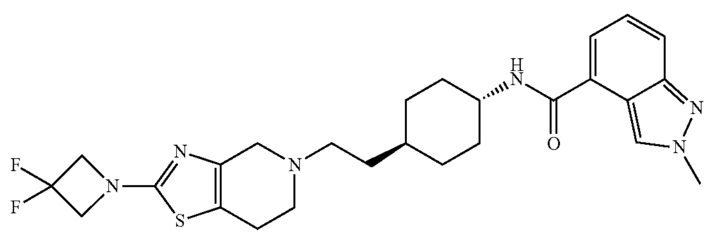 | 3 | 1.11 | 515 |
| III-440 | 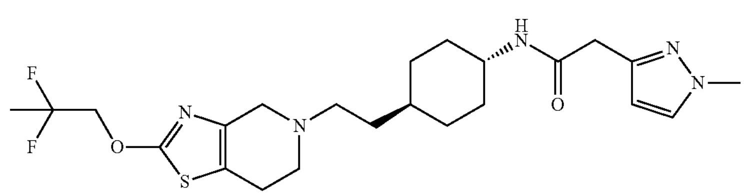 | 2 | 1.21 | 482.3 |
| III-441 | 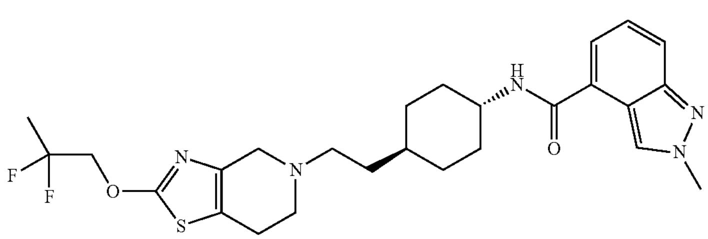 | 4 | 1.37 | 518.15 |
| III-442 | 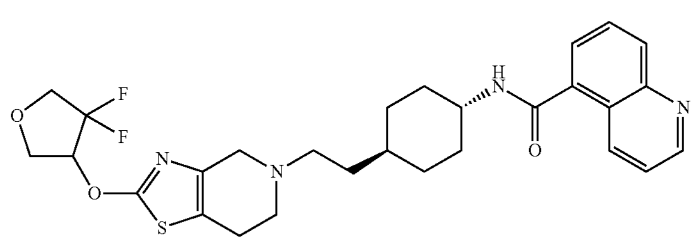 | 2 | 1.05 | 543.3 |

| Compound No. | Structure | LC/MS method | RT (min) | MS (m/z) |
|---|---|---|---|---|
| III-443 | 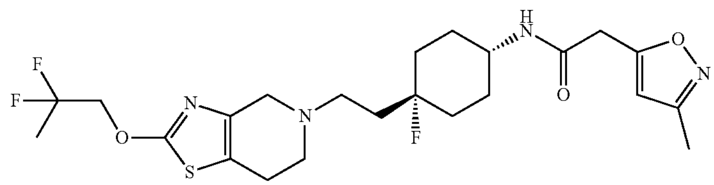 | 3 | 1.46 | 501.3 |
| III-444 | 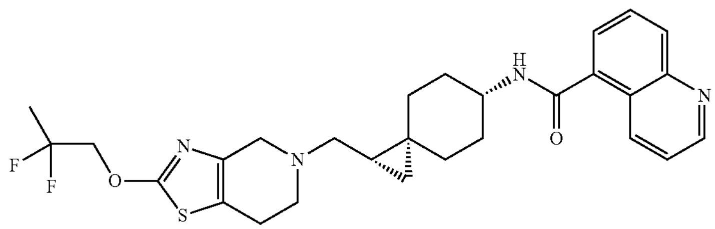 | 2 | 1.25 | 527.4 |
| III-445 | 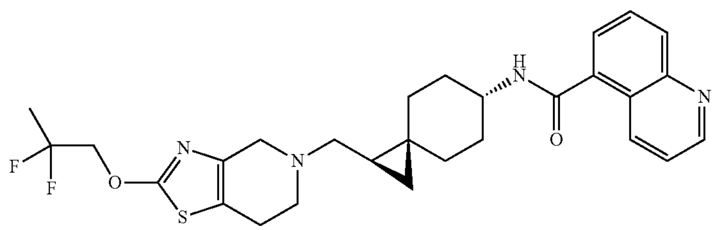 | 2 | 1.28 | 527.4 |
| III-446 | 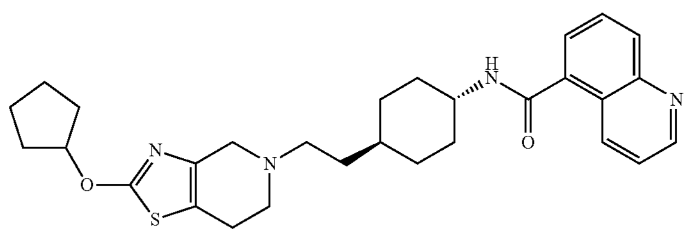 | 2 | 1.45 | 505.4 |
| III-447 | 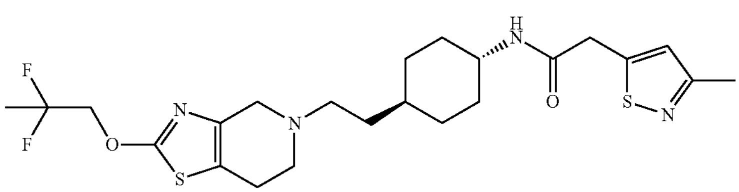 | 2 | 1.38 | 499.3 |
| III-448 | 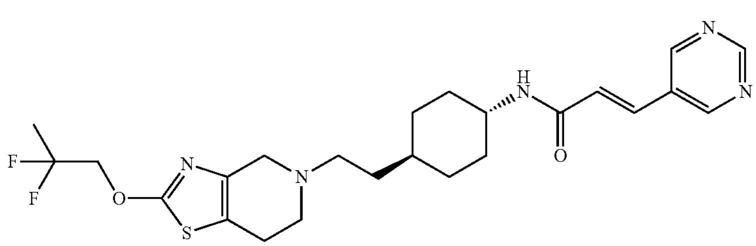 | 3 | 1.10 | 492 |

-continued

| Compound No. | Structure | LC/MS method | RT (min) | MS (m/z) |
|---|---|---|---|---|
| III-449 | 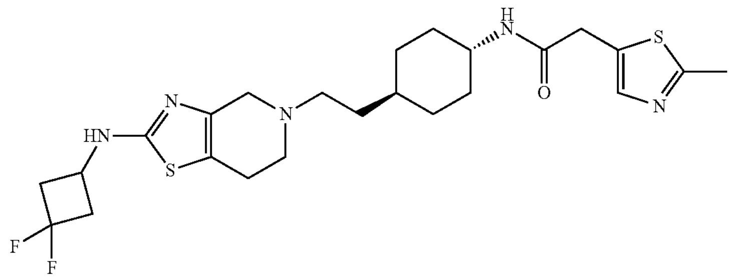 | 3 | 1.04 | 510 |
| III-450 | 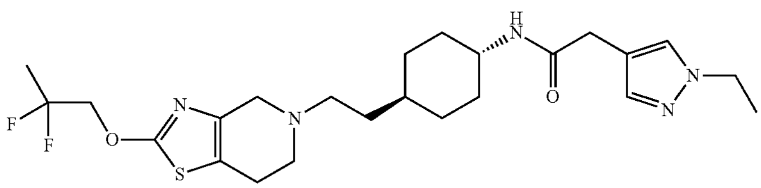 | 4 | 1.36 | 496.25 |
| III-451 | 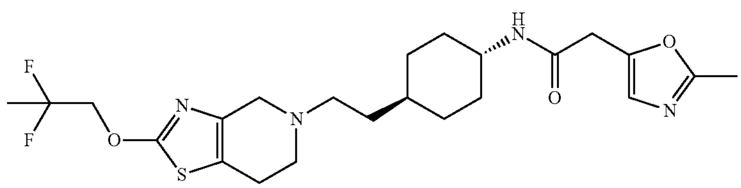 | 2 | 1.32 | 483.3 |
| III-452 | 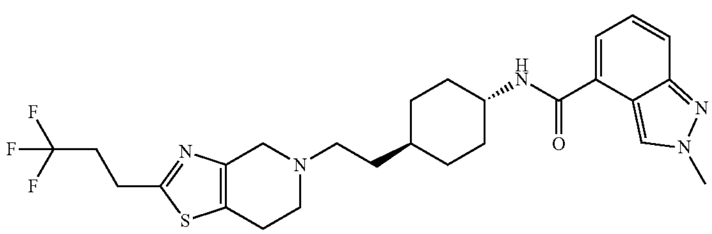 | 2 | 1.36 | 520.4 |
| III-453 | 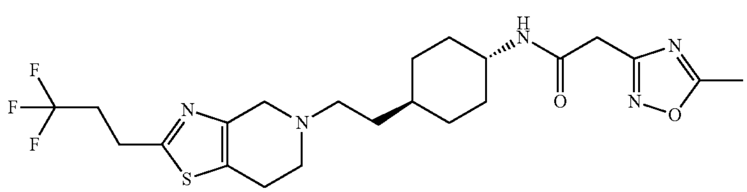 | 2 | 1.20 | 486.3 |
| III-454 | 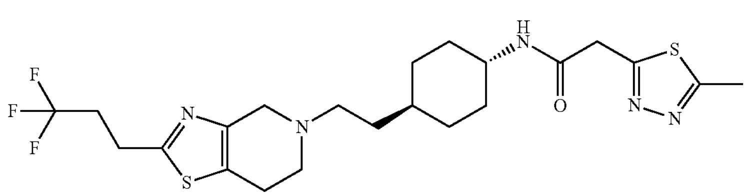 | 2 | 1.19 | 502.3 |
| III-455 | 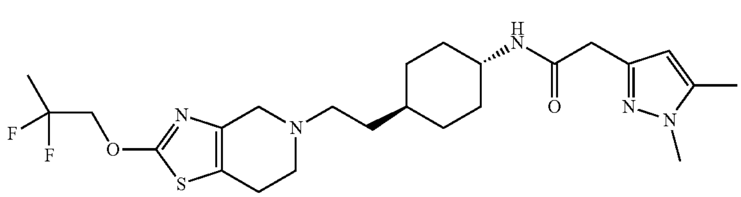 | 2 | 1.37 | 496 |

-continued
| Compound No. | Structure | LC/MS method | RT (min) | MS (m/z) |
|---|---|---|---|---|
| III-456 | 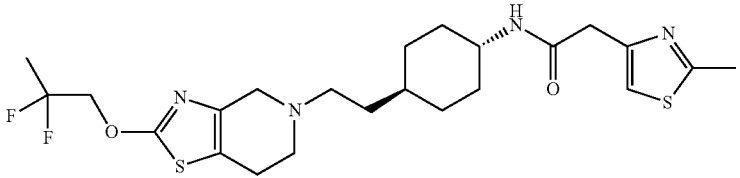 | 2 | 1.38 | 499 |
| III-457 | 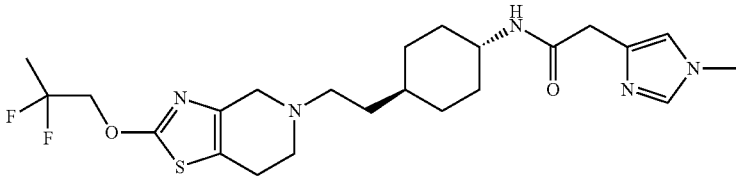 | 2 | 1.01 | 482 |
| III-458 | 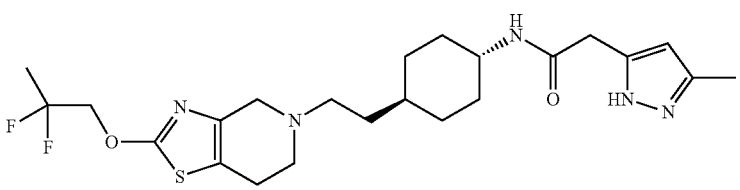 | 2 | 1.29 | 482 |
| III-459 | 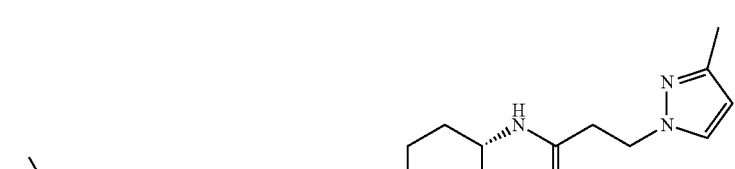 | 2 | 1.39 | 496 |
| III-460 | 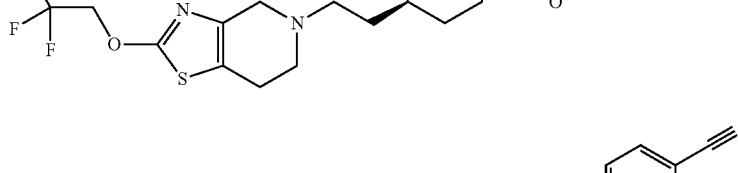 | 2 | 1.60 | 517 |
| III-461 | 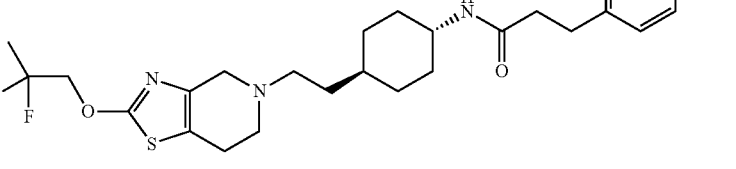 | 2 | 1.34 | 504 |
| III-462 | 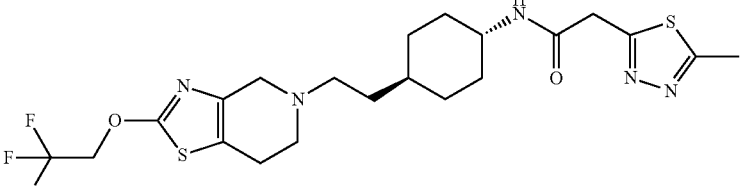 | 2 | 1.35 | 488 |

-continued

| Compound No. | Structure | LC/MS method | RT (min) | MS (m/z) |
|---|---|---|---|---|
| III-463 | 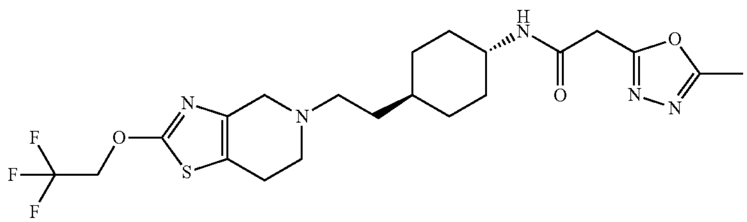 | 2 | 1.28 | 488 |
| III-464 | 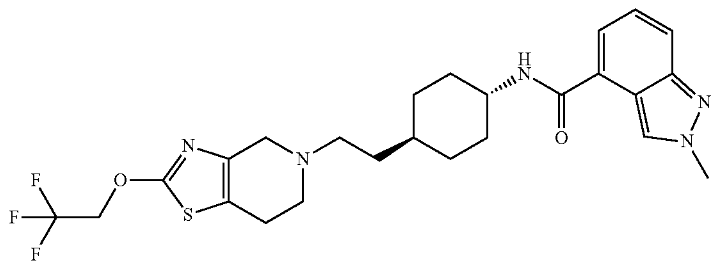 | 2 | 1.43 | 522 |
| III-465 | 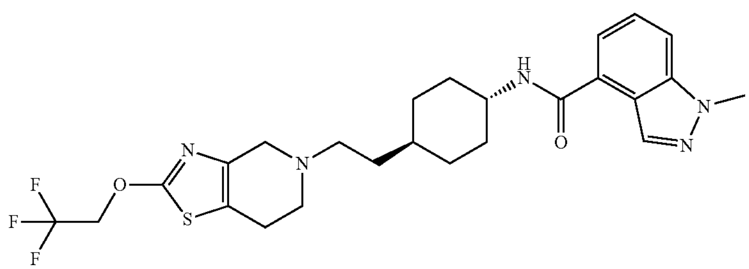 | 2 | 1.52 | 522 |
| III-466 | 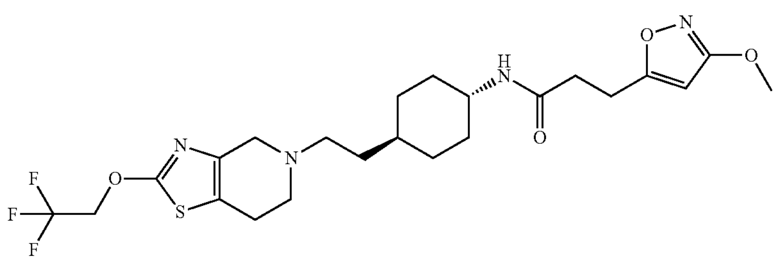 | 2 | 1.47 | 517 |
| III-467 | 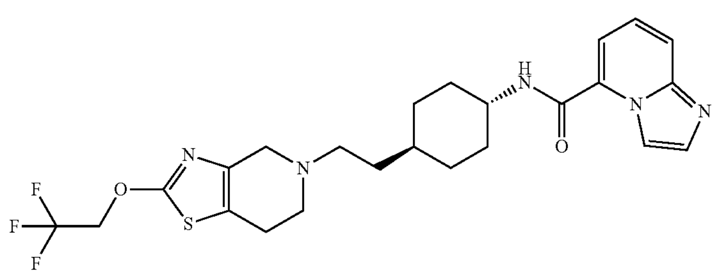 | 2 | 1.10 | 508 |
| III-468 | 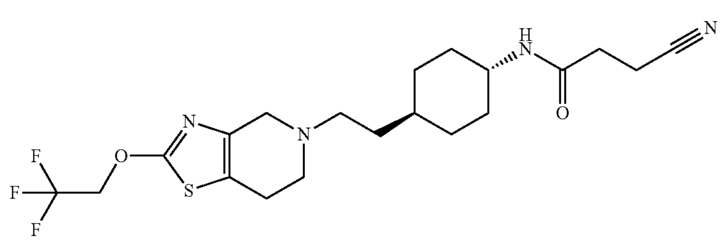 | 2 | 1.34 | 445 |

| Compound No. | Structure | LC/MS method | RT (min) | MS (m/z) |
|---|---|---|---|---|
| III-469 | 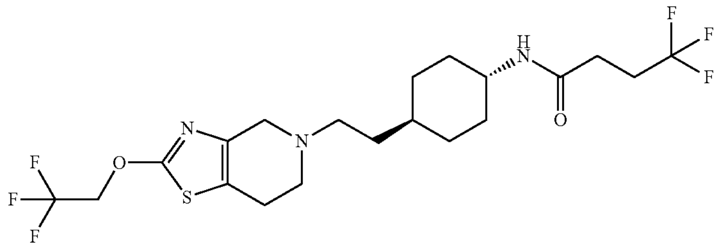 | 2 | 1.57 | 488 |
| III-470 | 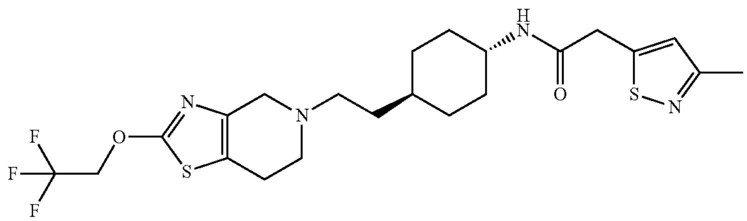 | 2 | 1.47 | 503 |
| III-471 | 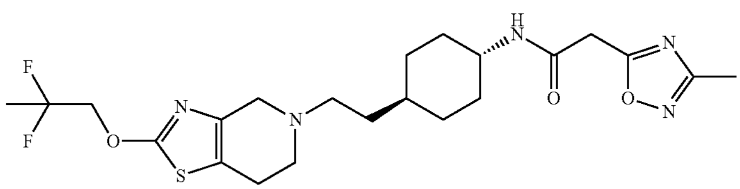 | 2 | 1.32 | 484.3 |
| III-472 | 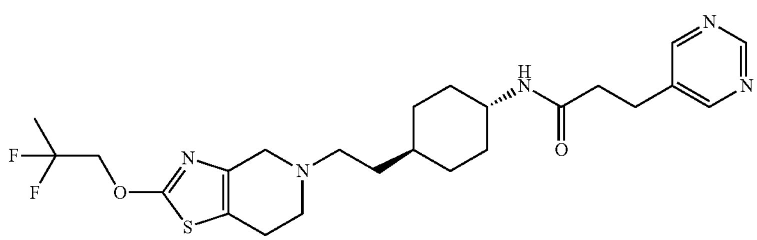 | 3 | 1.04 | 494 |
| III-473 | 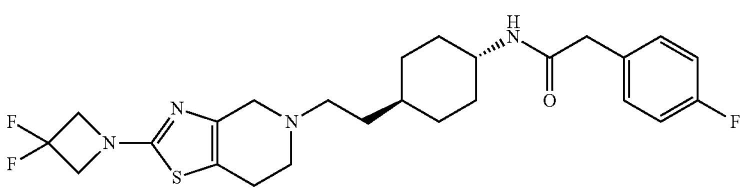 | 3 | 1.30 | 493 |
| III-474 | 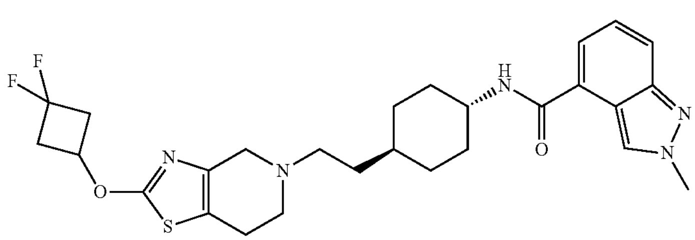 | 3 | 1.29 | 530.3 |
| III-475 | 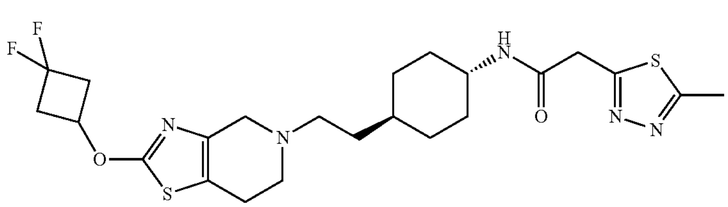 | 3 | 1.12 | 512.25 |

| Compound No. | Structure | LC/MS method | RT (min) | MS (m/z) |
|---|---|---|---|---|
| III-476 | 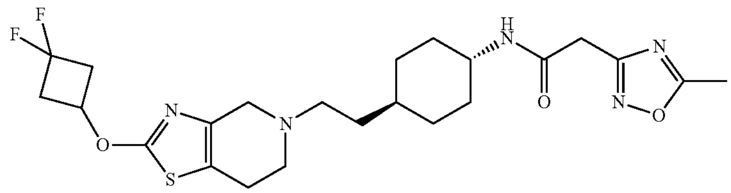 | 3 | 1.14 | 496.25 |
| III-477 | 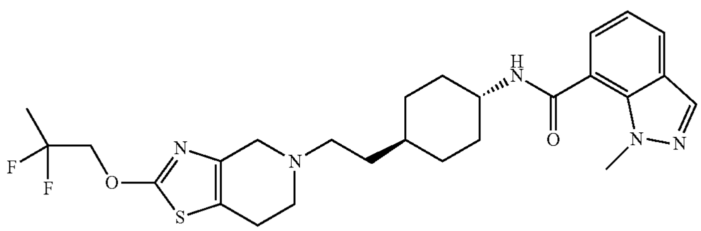 | 3 | 1.22 | 518.25 |
| III-478 | 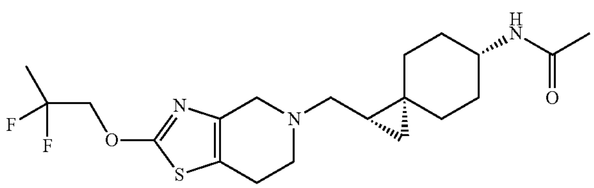 | 2 | 1.16 | 414.3 |
| III-479 | 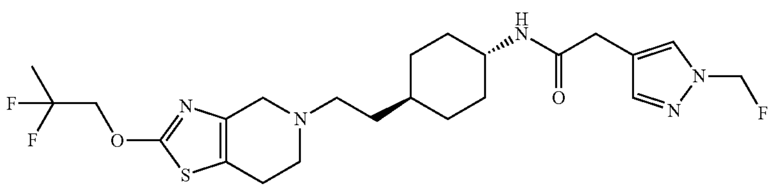 | 3 | 1.17 | 500 |
| III-480 | 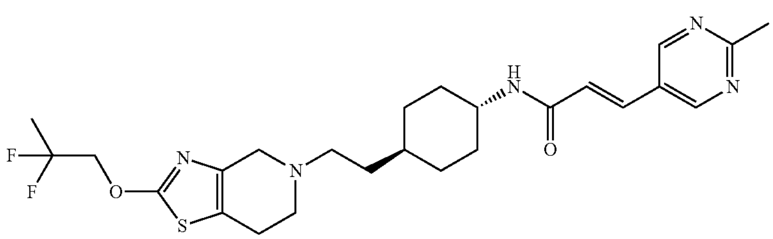 | 3 | 1.18 | 506 |
| III-481 | 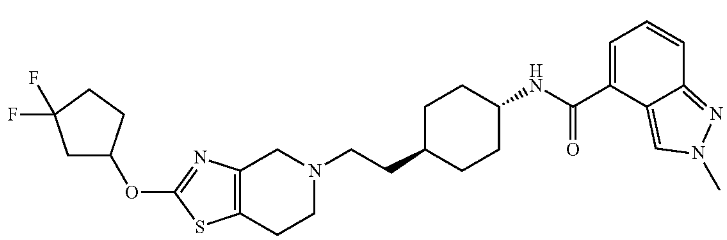 | 2 | 1.54 | 544 |
| III-482 | 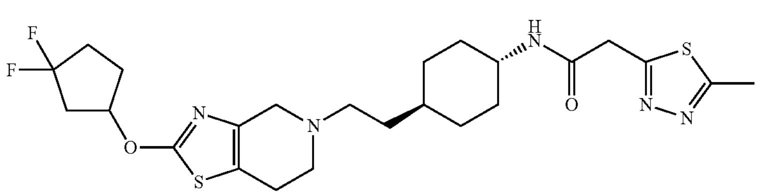 | 2 | 1.40 | 526 |

| Compound No. | Structure | LC/MS method | RT (min) | MS (m/z) |
|---|---|---|---|---|
| III-483 | 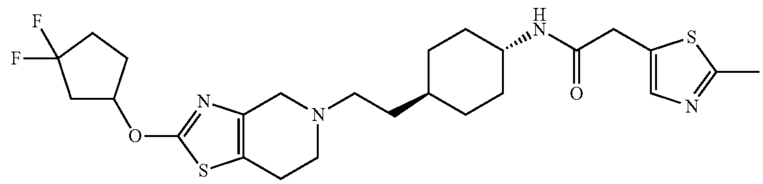 | 2 | 1.39 | 525 |
| III-484 | 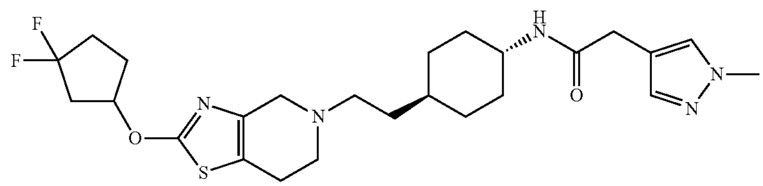 | 2 | 1.38 | 508 |
| III-485 | 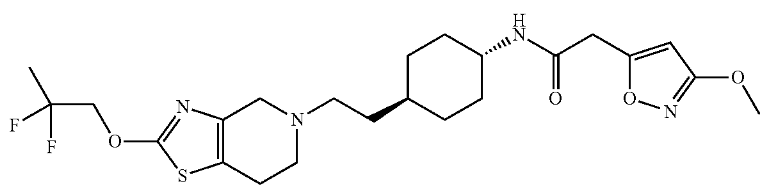 | 2 | 1.43 | 499 |
| III-486 | 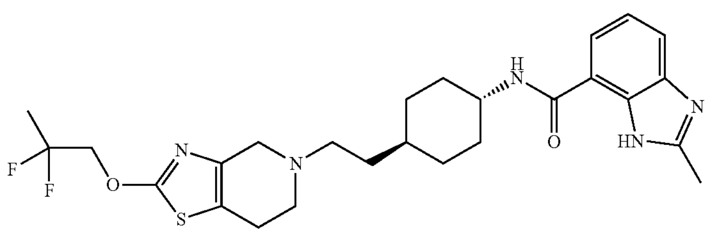 | 3 | 0.90 | 518 |
| III-487 | 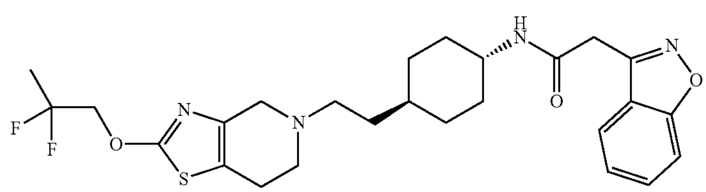 | 2 | 1.60 | 519 |
| III-488 | 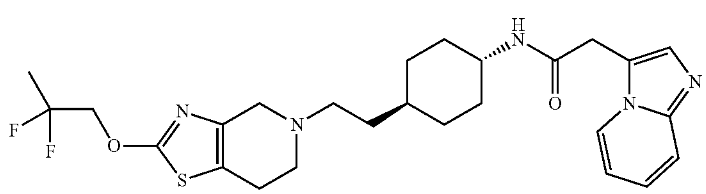 | 2 | 1.01 | 518 |
| III-489 | 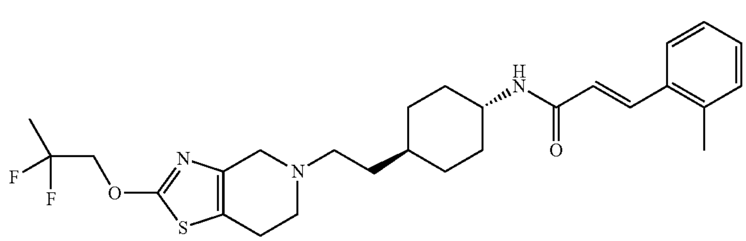 | 3 | 1.64 | 504 |

-continued

| Compound No. | Structure | LC/MS method | RT (min) | MS (m/z) |
|---|---|---|---|---|
| III-490 | 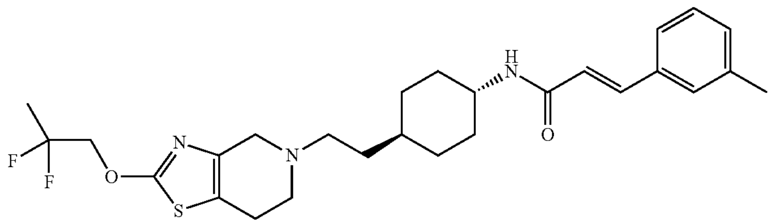 | 3 | 1.67 | 504 |
| III-491 | 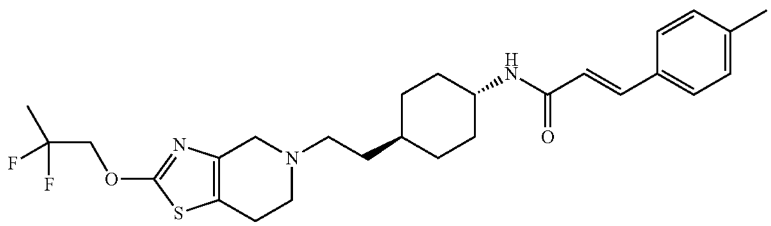 | 3 | 1.50 | 504 |
| III-492 | 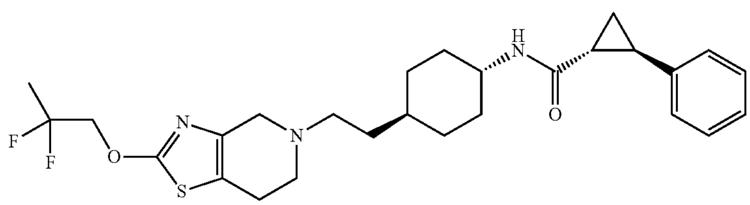 | 2 | 1.77 | 504 |
| III-493 | 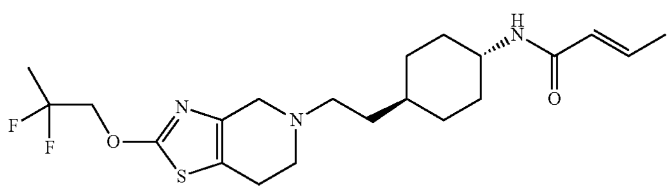 | 2 | 1.40 | 428 |
| III-494 | 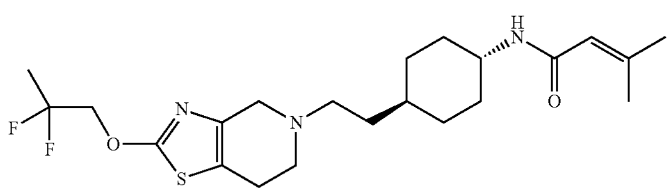 | 2 | 1.51 | 442 |
| III-495 | 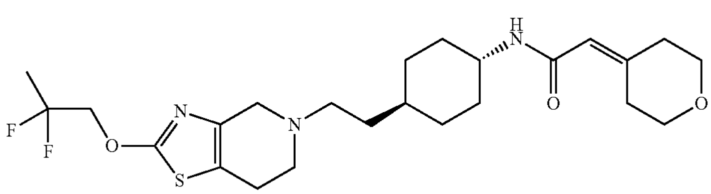 | 2 | 1.40 | 484 |
| III-496 | 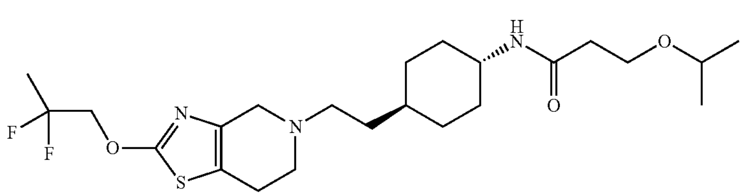 | 2 | 1.45 | 474 |

-continued

| Compound No. | Structure | LC/MS method | RT (min) | MS (m/z) |
|---|---|---|---|---|
| III-497 | 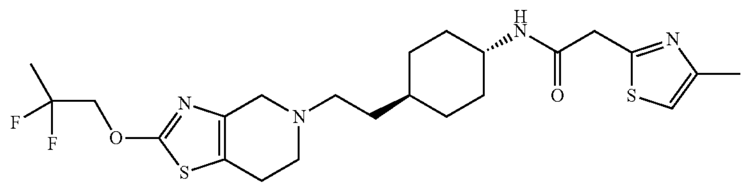 | 2 | 1.42 | 499 |
| III-498 | 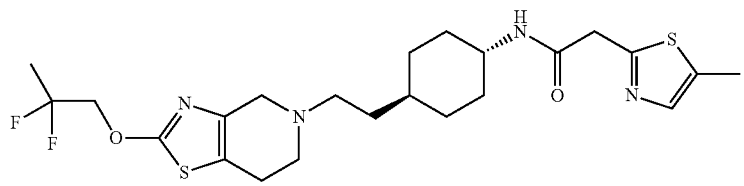 | 2 | 1.44 | 499 |
| III-499 | 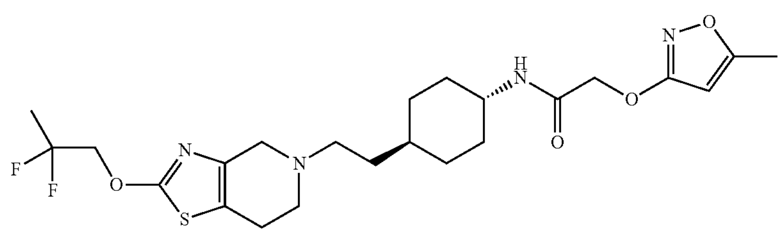 | 2 | 1.49 | 499 |
| III-500 | 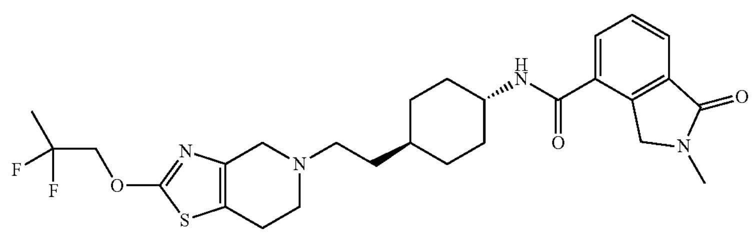 | 2 | 1.41 | 533 |
| III-501 | 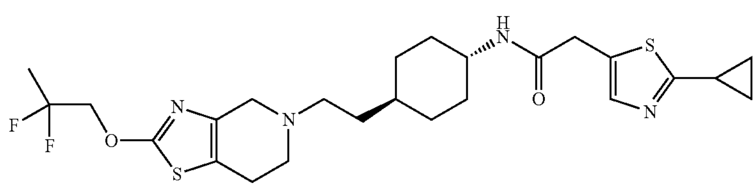 | 3 | 1.30 | 525 |
| III-502 | 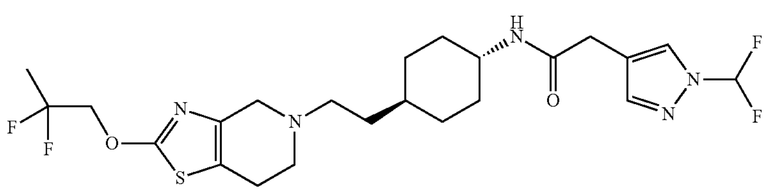 | 3 | 1.25 | 518 |
| III-503 | 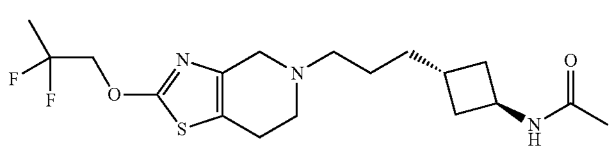 | 3 | 1.00 | 388.25 |

-continued
| Compound No. | Structure | LC/MS method | RT (min) | MS (m/z) |
|---|---|---|---|---|
| III-504 | 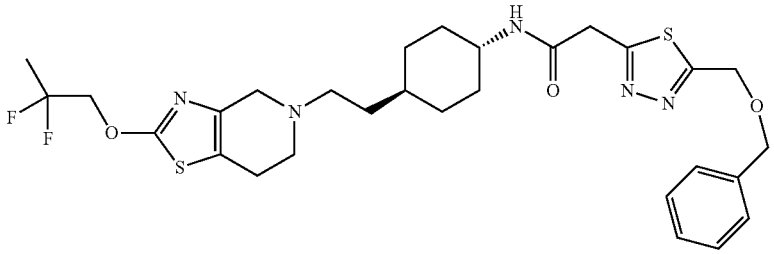 | 2 | 1.90 | 606.4 |
| III-505 | 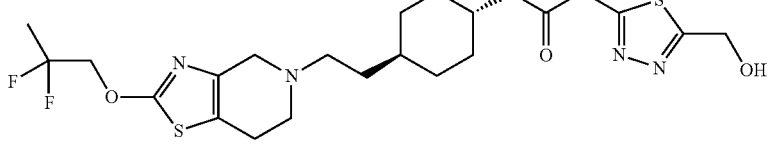 | 2 | 1.21 | 516.2 |
| III-506 | 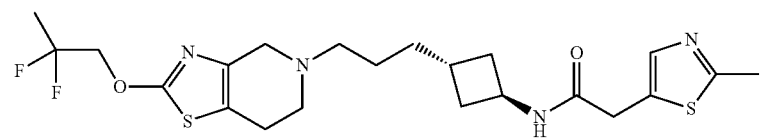 | 2 | 1.29 | 485.15 |
| III-507 | 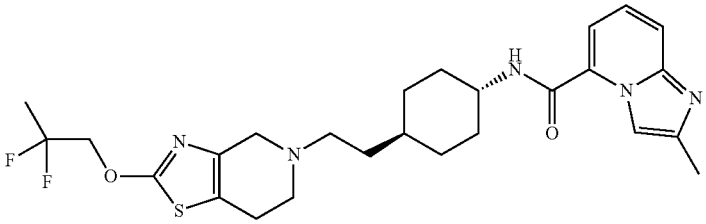 | 3 | 0.89 | 518 |
| III-508 | 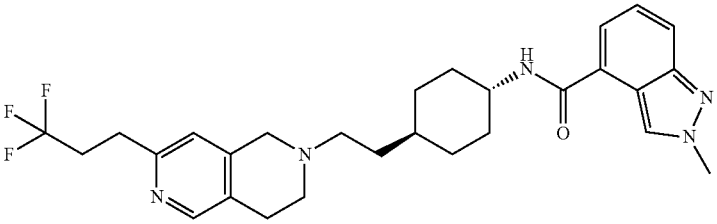 | 3 | 1.11 | 514 |
| III-509 | 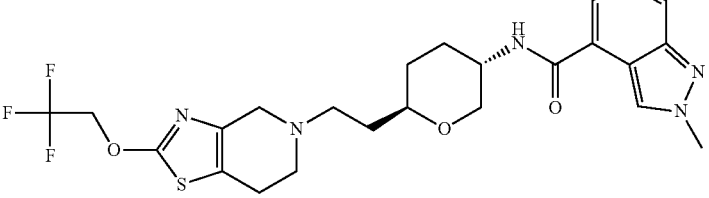 | 3 | 1.24 | 524.25 |
| III-510 | 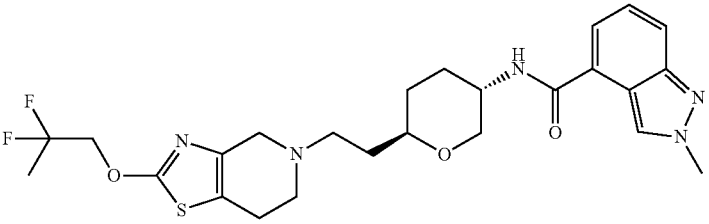 | 3 | 1.21 | 520.3 |

-continued

| Compound No. | Structure | LC/MS method | RT (min) | MS (m/z) |
|---|---|---|---|---|
| III-511 | 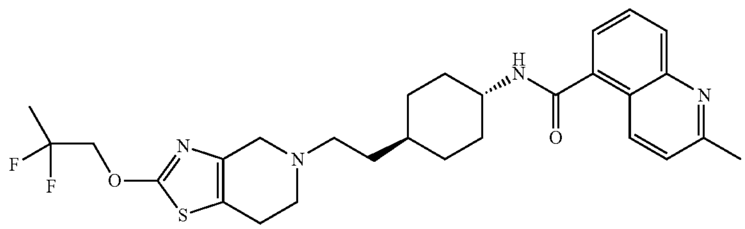 | 2 | 1.29 | 265 |
| III-512 | 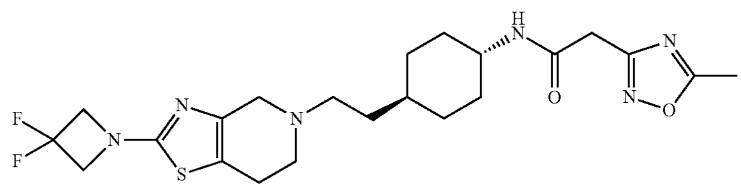 | 3 | 0.93 | 481 |
| III-513 | 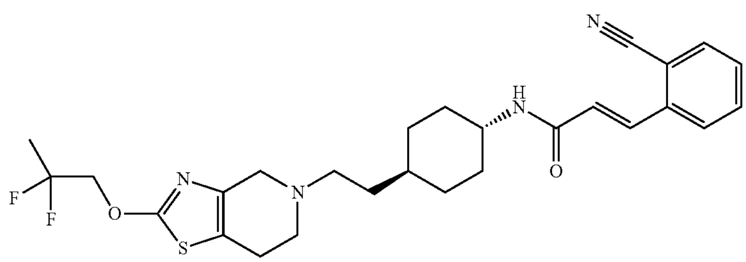 | 2 | 1.64 | 515 |
| III-514 | 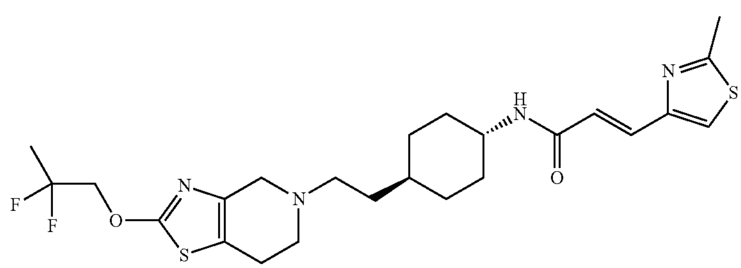 | 2 | 1.49 | 511 |
| III-515 | 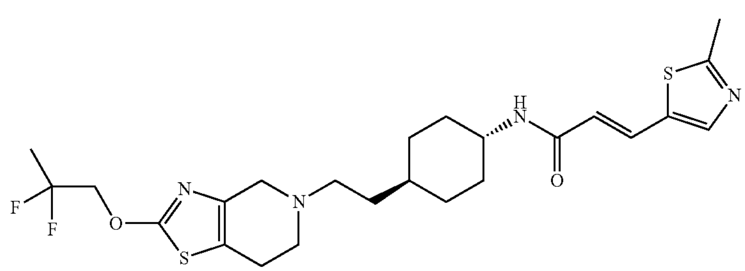 | 2 | 1.47 | 511 |
| III-516 | 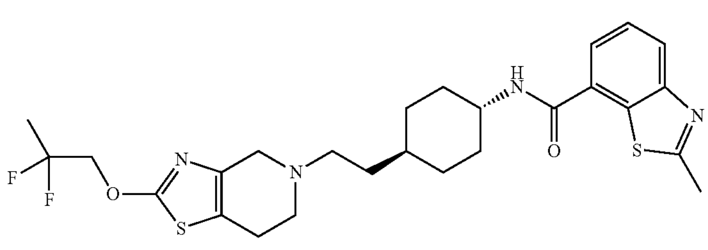 | 2 | 1.58 | 535 |

-continued

| Compound No. | Structure | LC/MS method | RT (min) | MS (m/z) |
|---|---|---|---|---|
| III-517 | 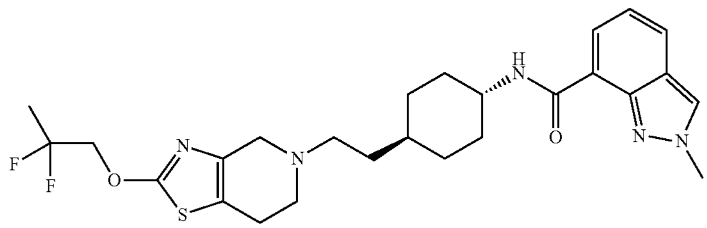 | 2 | 1.50 | 518 |
| III-518 | 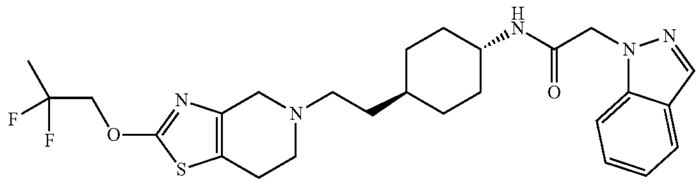 | 2 | 1.55 | 518 |
| III-519 | 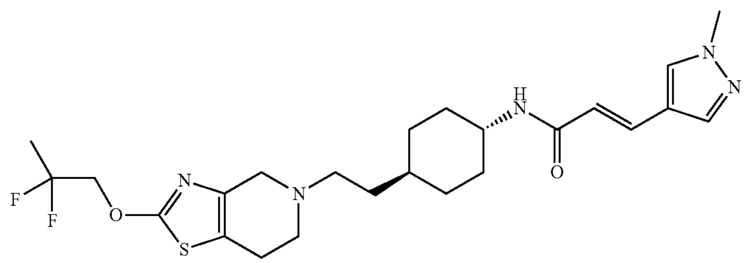 | 2 | 1.39 | 494 |
| III-520 | 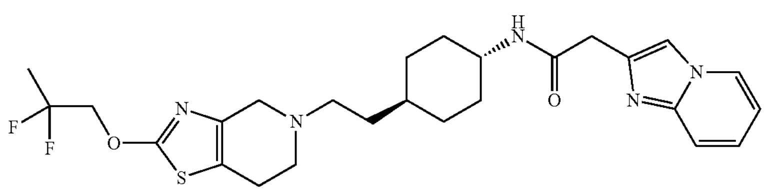 | 2 | 1.03 | 518 |
| III-521 | 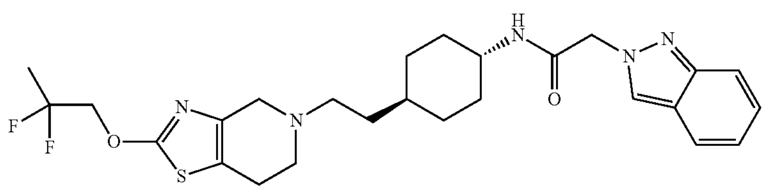 | 2 | 1.57 | 518 |
| III-522 | 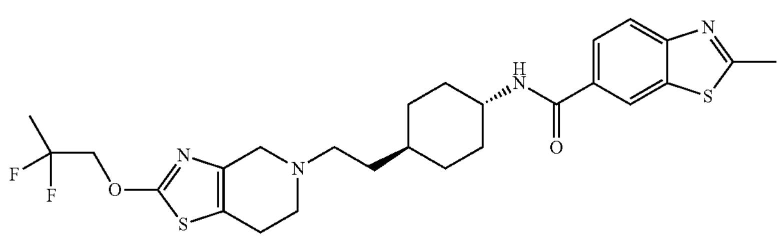 | 2 | 1.58 | 535 |
| III-523 | 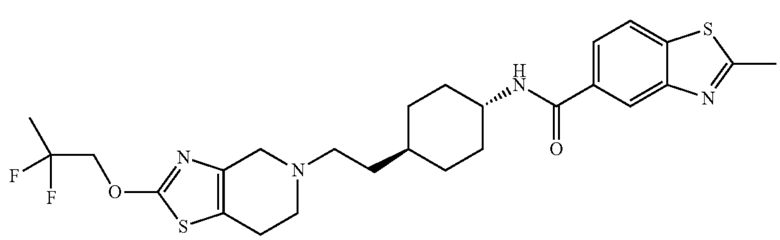 | 2 | 1.60 | 535 |

-continued

| Compound No. | Structure | LC/MS method | RT (min) | MS (m/z) |
|---|---|---|---|---|
| III-524 | 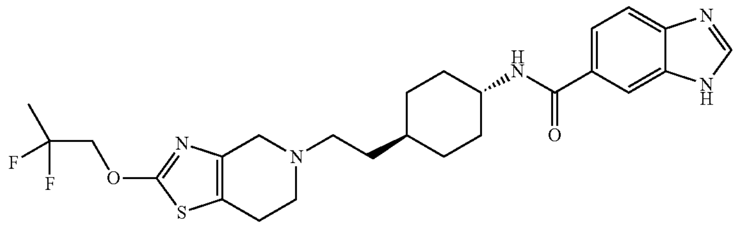 | 2 | 1.11 | 504 |
| III-525 | 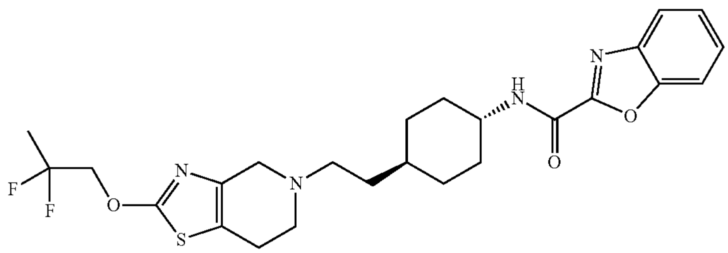 | 2 | 1.65 | 505 |
| III-526 | 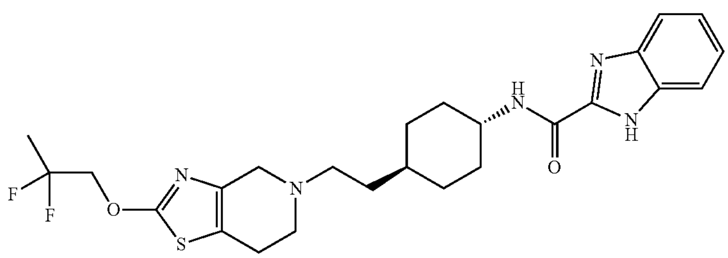 | 2 | 1.59 | 504 |
| III-527 | 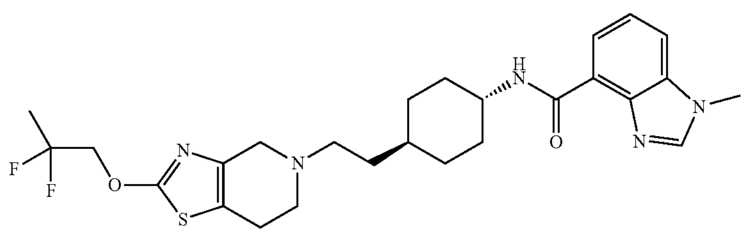 | 2 | 1.37 | 518 |
| III-528 | 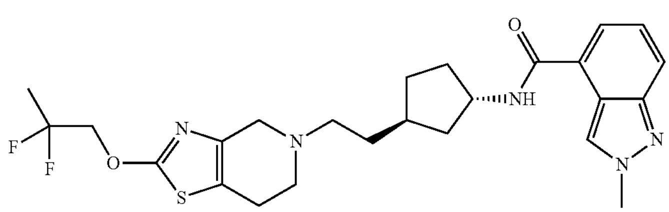 | 2 | 1.47 | 504.3 |
| III-529 | 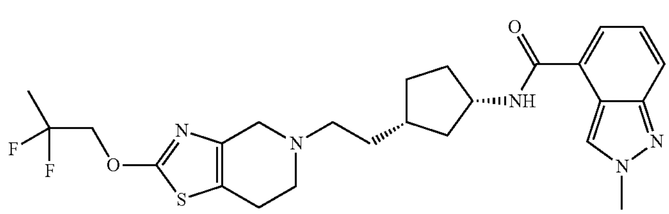 | 2 | 1.47 | 504.3 |

| Compound No. | Structure | LC/MS method | RT (min) | MS (m/z) |
|---|---|---|---|---|
| III-530 | 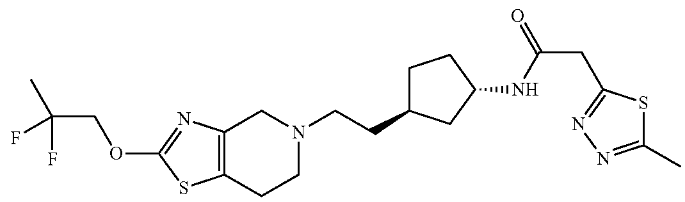 | 2 | 1.25 | 486.2 |
| III-531 | 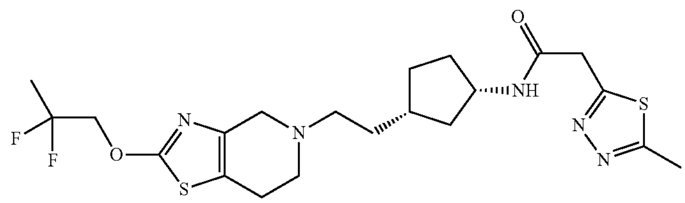 | 2 | 1.25 | 486.2 |
| III-532 | 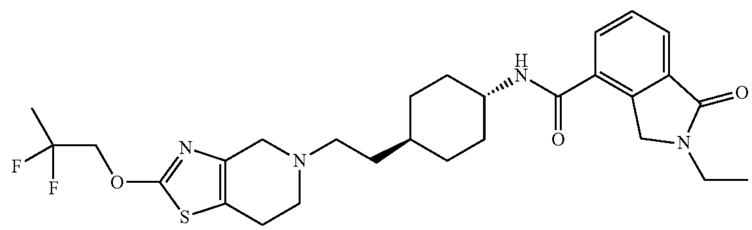 | 2 | 1.52 | 547.4 |
| III-533 | 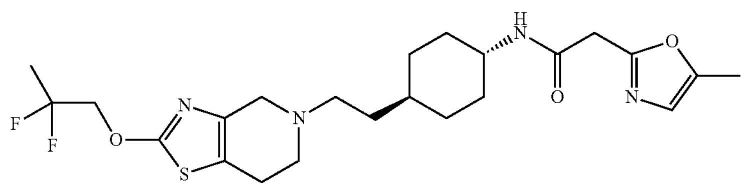 | 2 | 1.39 | 483 |
| III-534 | 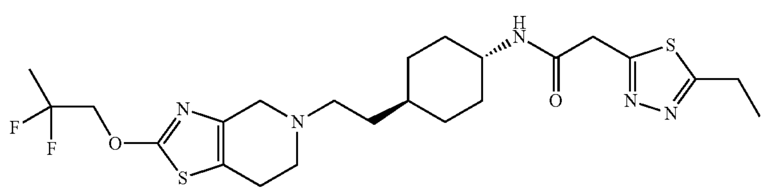 | 2 | 1.41 | 514 |
| III-535 | 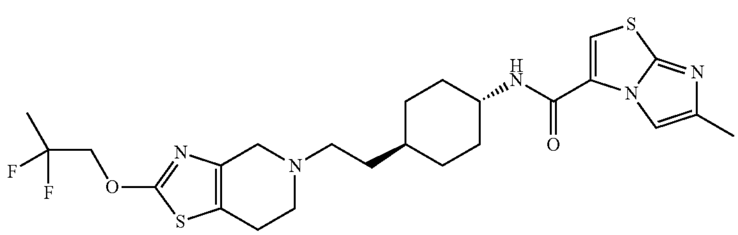 | 2 | 1.23 | 524 |
| III-536 | 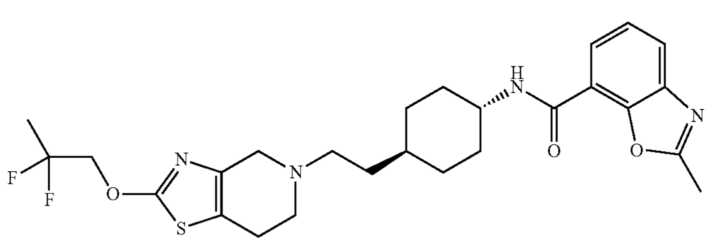 | 2 | 1.52 | 519 |

-continued

| Compound No. | Structure | LC/MS method | RT (min) | MS (m/z) |
|---|---|---|---|---|
| III-537 | 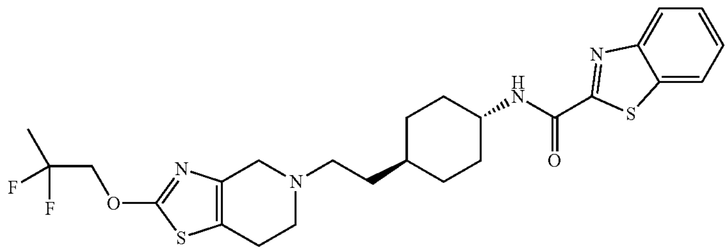 | 2 | 1.62 | 521 |
| III-538 | 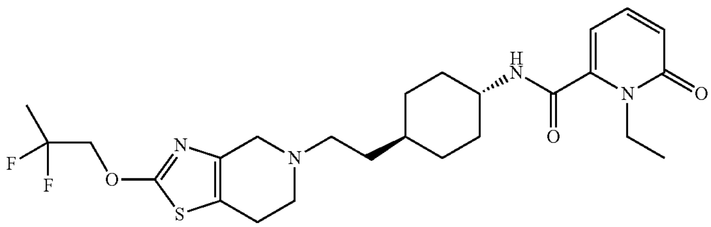 | 2 | 1.34 | 509 |
| III-539 | 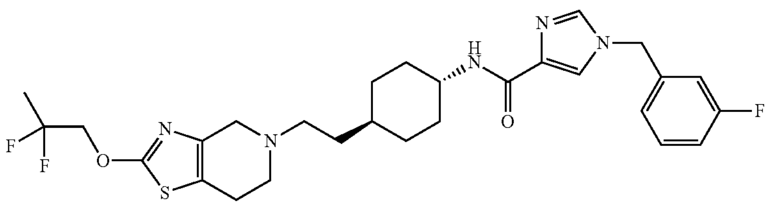 | 2 | 1.42 | 563 |
| III-540 | 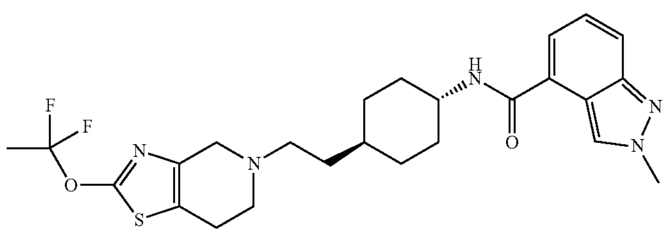 | 2 | 1.34 | 504.3 |
| III-541 | 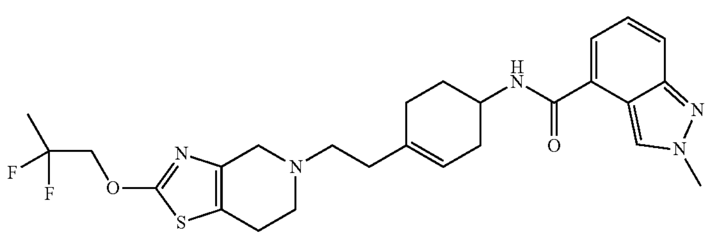 | 2 | 1.19 | 516.2 |
| III-542 | 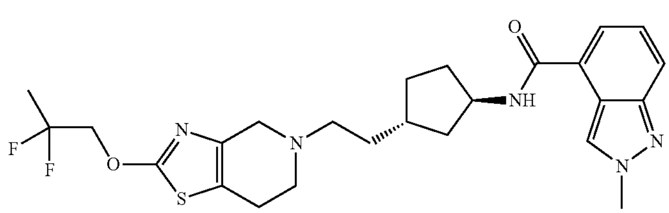 | 2 | 1.46 | 504.3 |

-continued

| Compound No. | Structure | LC/MS method | RT (min) | MS (m/z) |
|---|---|---|---|---|
| III-543 | 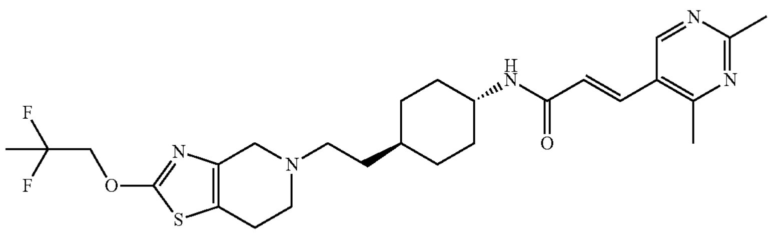 | 2 | 1.37 | 520 |
| III-544 | 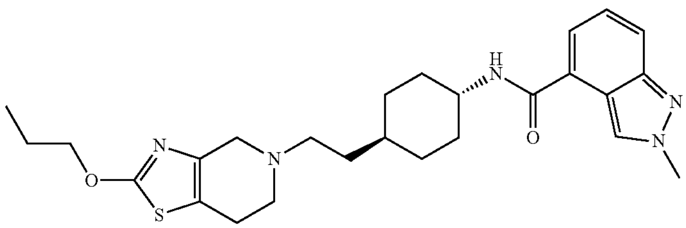 | 2 | 1.52 | 482.3 |
| III-545 | 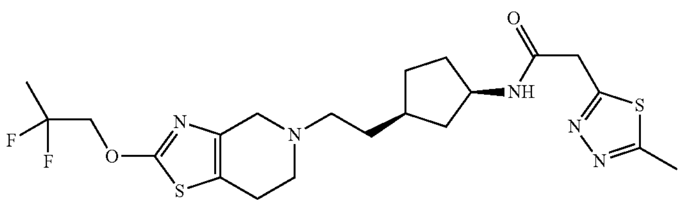 | 2 | 1.25 | 486.3 |
| III-546 | 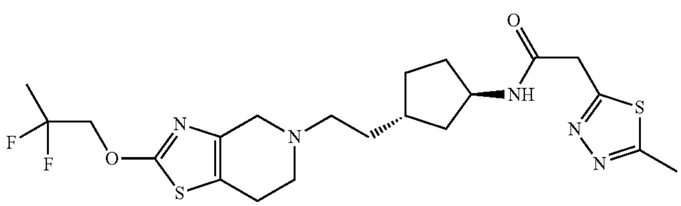 | 2 | 1.25 | 486.3 |
| III-547 | 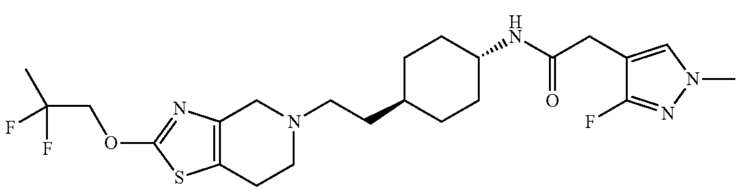 | 2 | 1.35 | 500.3 |
| III-548 | 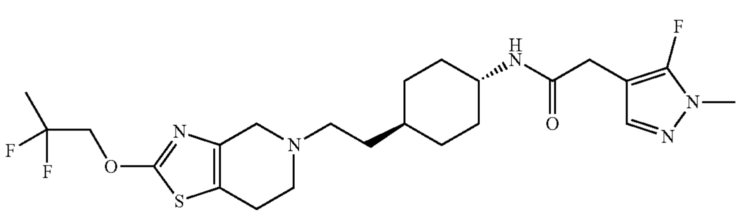 | 2 | 1.37 | 500.3 |
| III-549 | 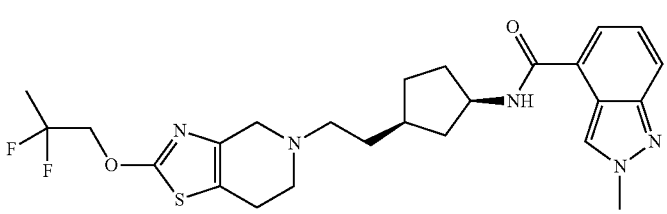 | 2 | 1.47 | 504.3 |

-continued

| Compound No. | Structure | LC/MS method | RT (min) | MS (m/z) |
|---|---|---|---|---|
| III-550 | 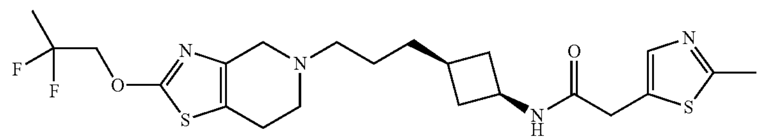 | 3 | 1.17 | 485.25 |
| III-551 | 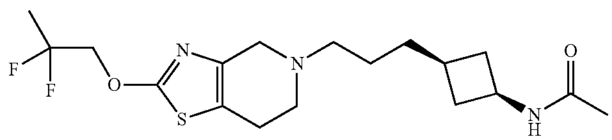 | 3 | 1.03 | 388.25 |
| III-552 | 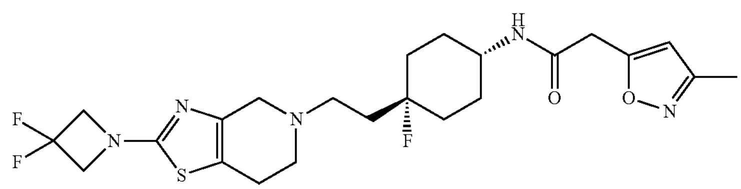 | 3 | 1.07 | 498 |
| III-553 | 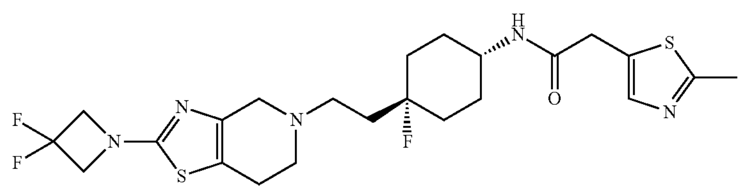 | 3 | 1.03 | 514 |
| III-554 | 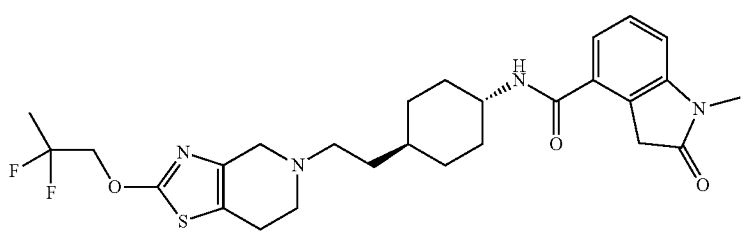 | 2 | 1.52 | 533.3 |
| III-555 | 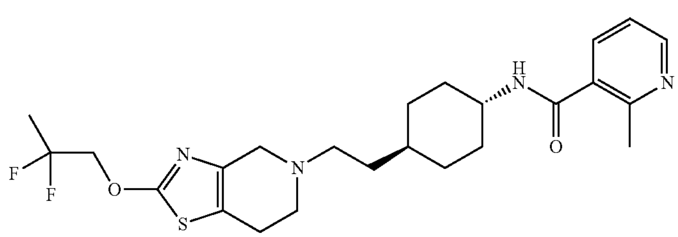 | 2 | 1.08 | 479 |
| III-556 | 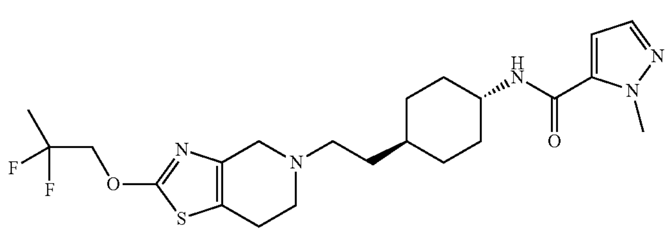 | 2 | 1.38 | 468 |

| Compound No. | Structure | LC/MS method | RT (min) | MS (m/z) |
|---|---|---|---|---|
| III-557 | 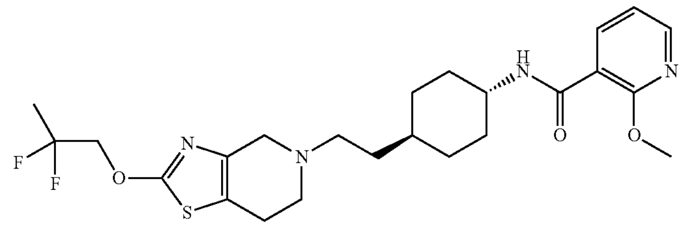 | 2 | 1.54 | 495 |
| III-558 | 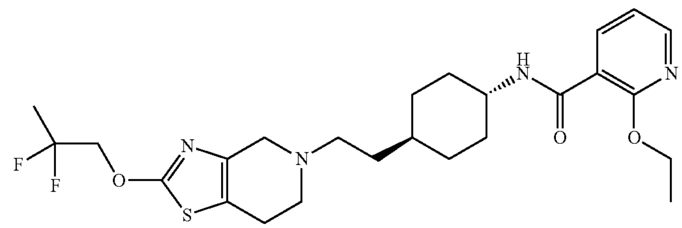 | 2 | 1.65 | 509 |
| III-559 | 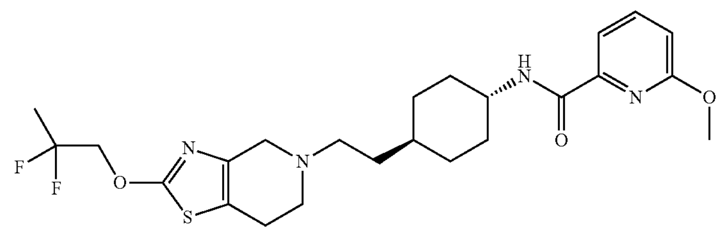 | 2 | 1.66 | 495 |
| III-560 | 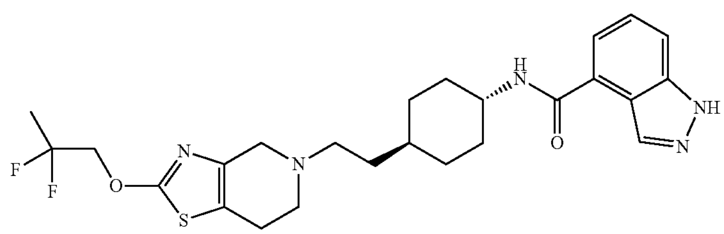 | 2 | 1.41 | 504 |
| III-561 | 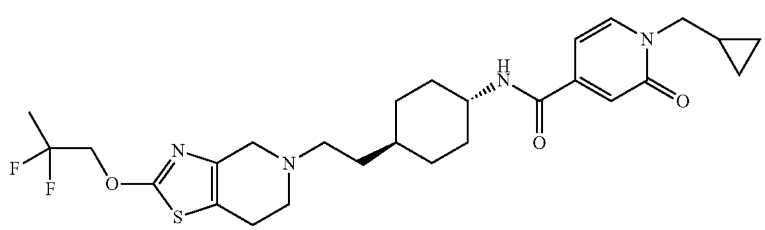 | 2 | 1.43 | 535 |
| III-562 | 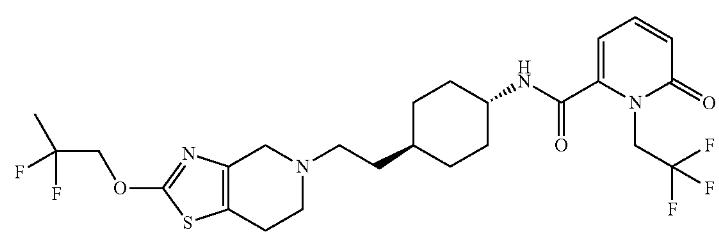 | 2 | 1.48 | 563 |

-continued

| Compound No. | Structure | LC/MS method | RT (min) | MS (m/z) |
| --- | --- | --- | --- | --- |
| III-563 | 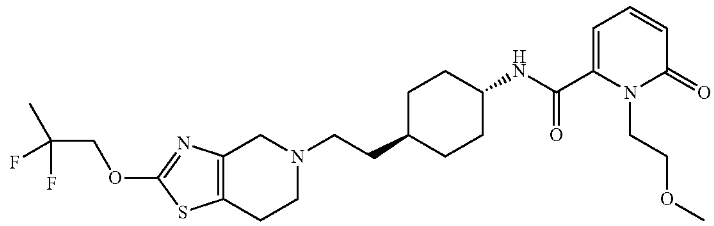 | 2 | 1.63 | 539 |
| III-564 | 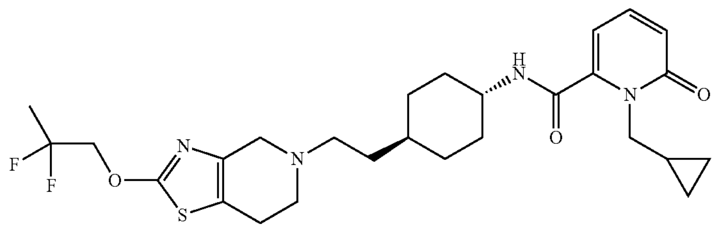 | 2 | 1.42 | 535 |
| III-565 | 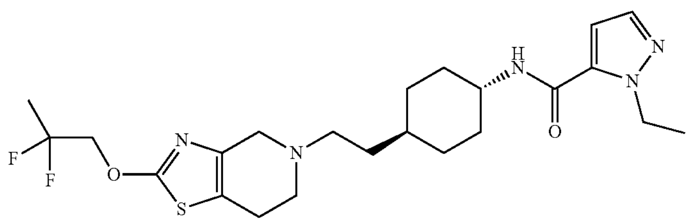 | 2 | 1.45 | 482 |
| III-566 | 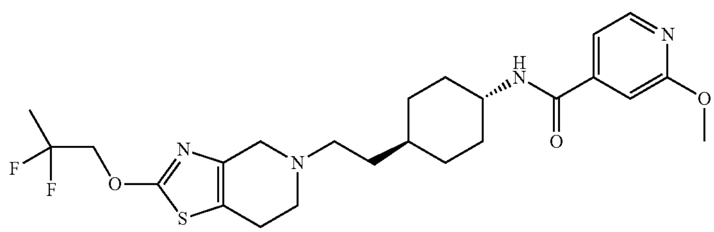 | 2 | 1.47 | 495 |
| III-567 | 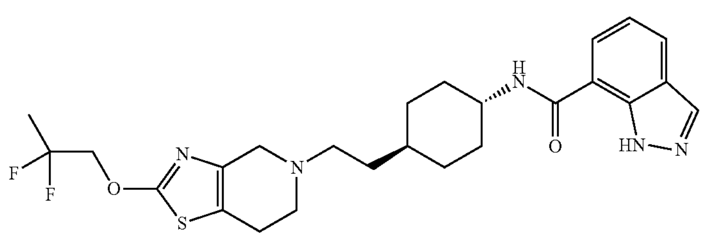 | 2 | 1.52 | 504 |
| III-568 | 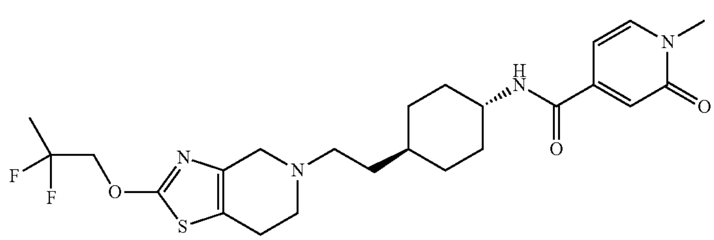 | 2 | 1.26 | 495 |

-continued

| Compound No. | Structure | LC/MS method | RT (min) | MS (m/z) |
|---|---|---|---|---|
| III-569 | 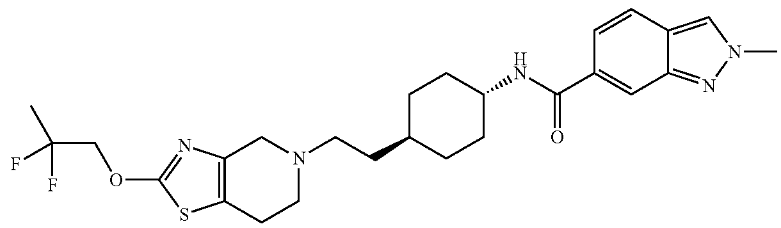 | 2 | 1.43 | 518 |
| III-570 | 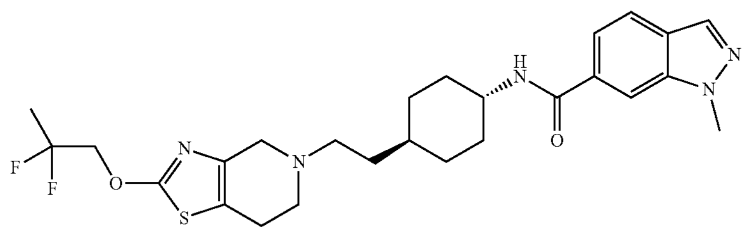 | 2 | 1.50 | 518 |
| III-571 | 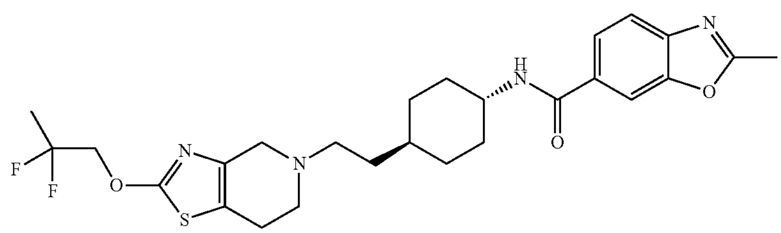 | 2 | 1.49 | 519 |
| III-572 | 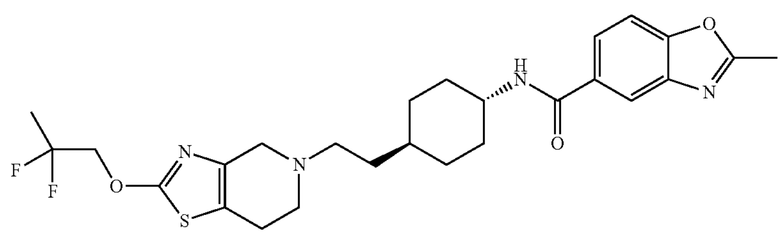 | 2 | 1.51 | 519 |
| III-573 | 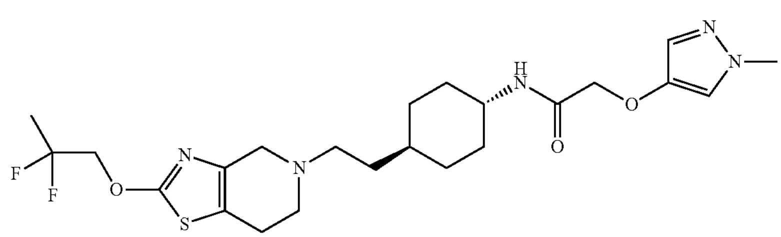 | 2 | 1.33 | 498 |
| III-574 | 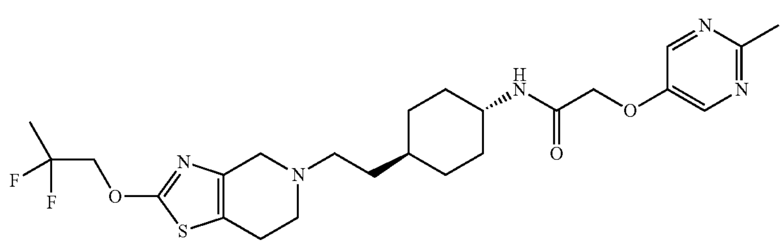 | 2 | 1.30 | 510 |

-continued

| Compound No. | Structure | LC/MS method | RT (min) | MS (m/z) |
|---|---|---|---|---|
| III-575 | 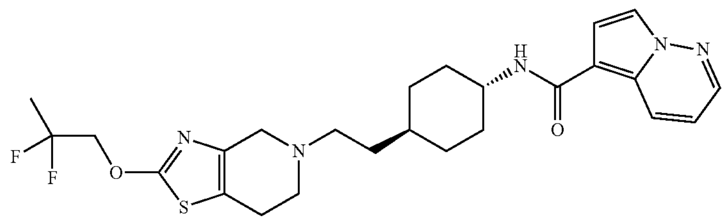 | 2 | 1.54 | 504.3 |
| III-576 | 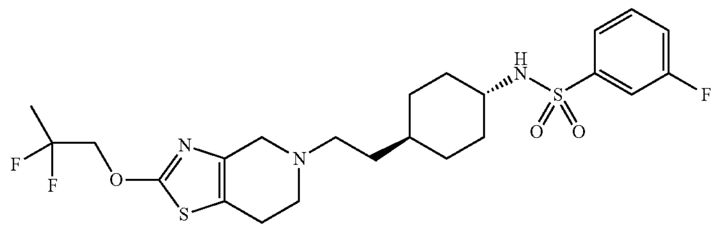 | 2 | 1.69 | 518.15 |
| III-577 | 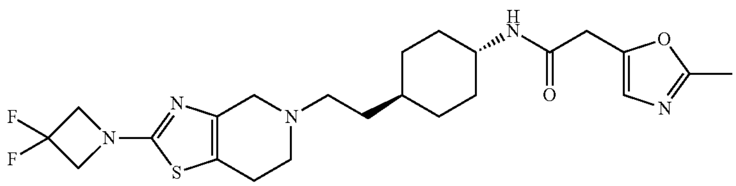 | 2 | 1.18 | 480 |
| III-578 | 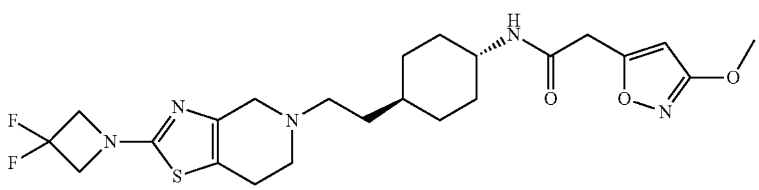 | 2 | 1.31 | 496 |
| III-579 | 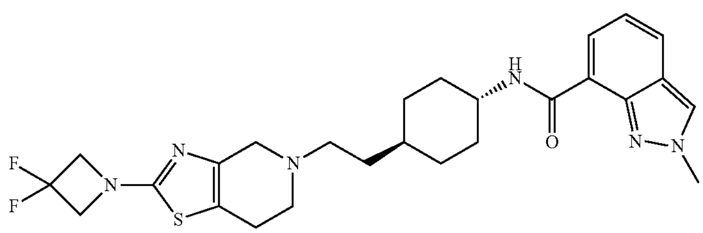 | 2 | 1.40 | 515 |
| III-580 | 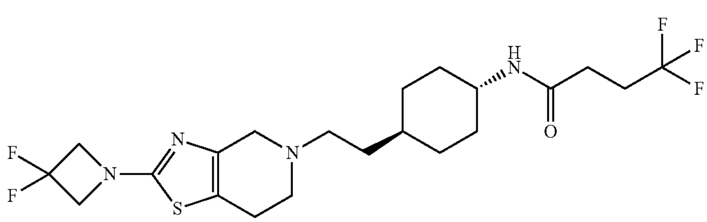 | 2 | 1.42 | 481 |
| III-581 | 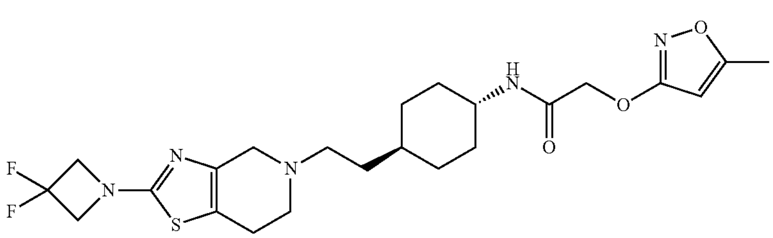 | 2 | 1.36 | 496 |

-continued

| Compound No. | Structure | LC/MS method | RT (min) | MS (m/z) |
|---|---|---|---|---|
| III-582 | 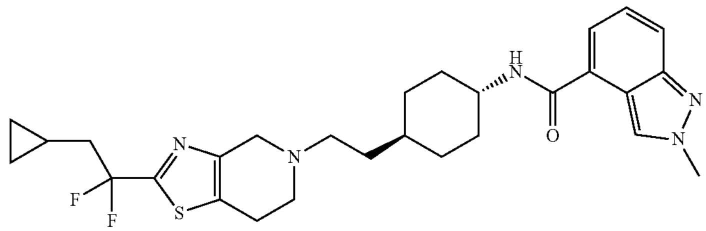 | 2 | 1.71 | 528.3 |
| III-583 | 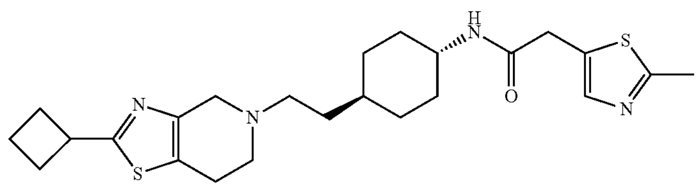 | 2 | 1.24 | 459.4 |
| III-584 | 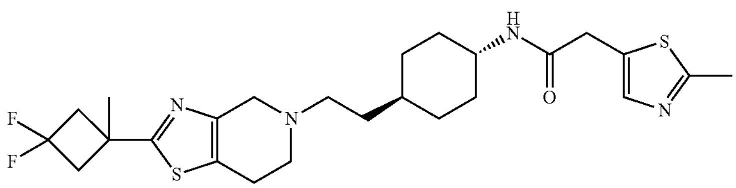 | 2 | 1.39 | 509.4 |
| III-585 | 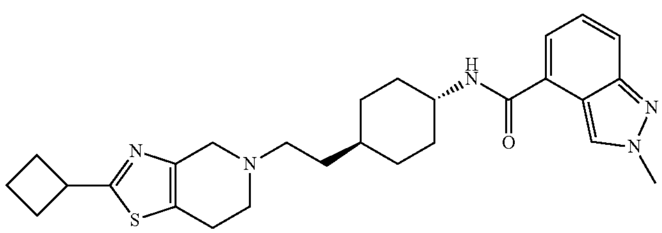 | 2 | 1.42 | 478.4 |
| III-586 | 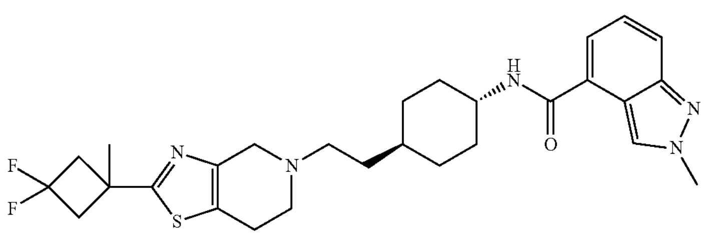 | 2 | 1.55 | 528.4 |
| III-587 | 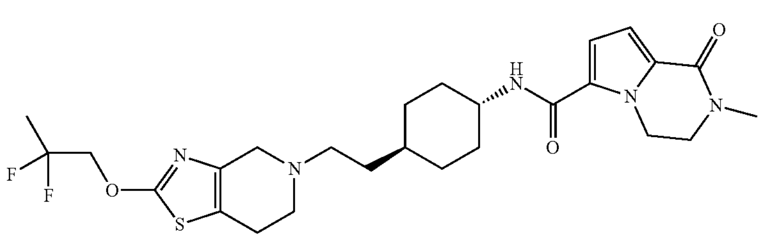 | 2 | 1.31 | 536.4 |
| III-588 | 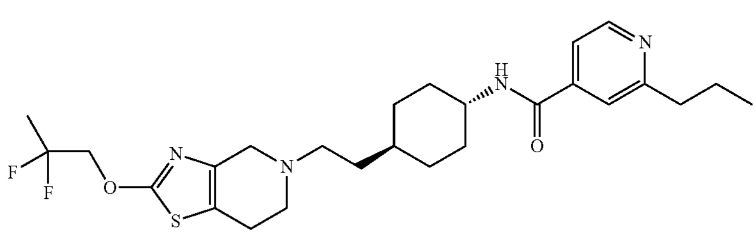 | 2 | 1.28 | 507 |

| Compound No. | Structure | LC/MS method | RT (min) | MS (m/z) |
|---|---|---|---|---|
| III-589 | 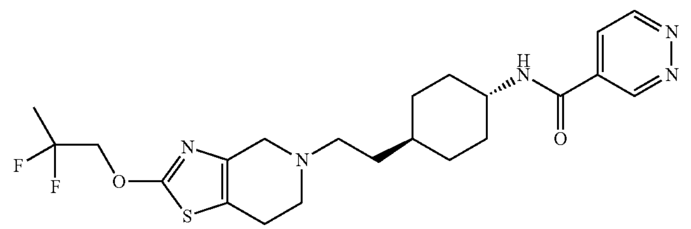 | 2 | 1.24 | 466 |
| III-590 | 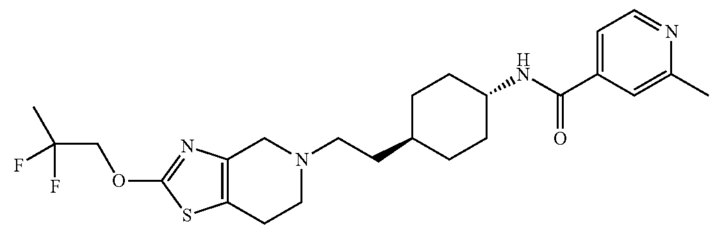 | 2 | 1.11 | 479 |
| III-591 | 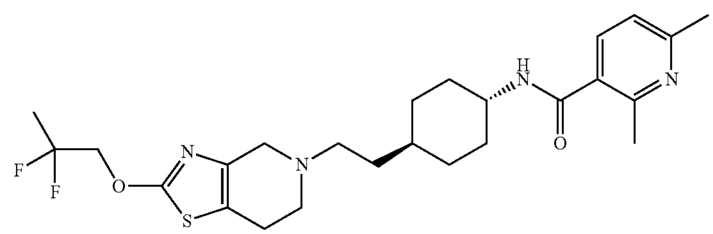 | 2 | 1.04 | 493 |
| III-592 | 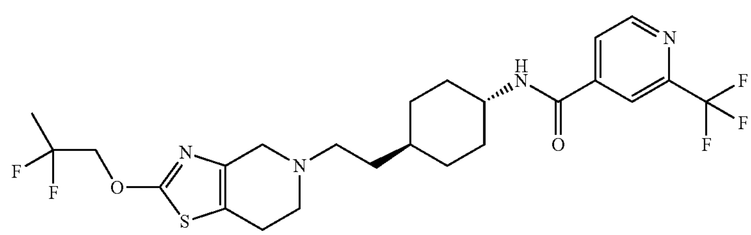 | 2 | 1.62 | 533 |
| III-593 | 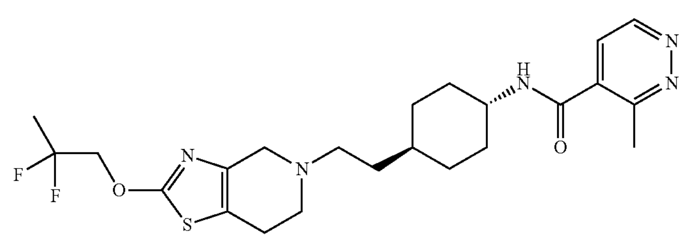 | 2 | 1.24 | 480 |
| III-594 | 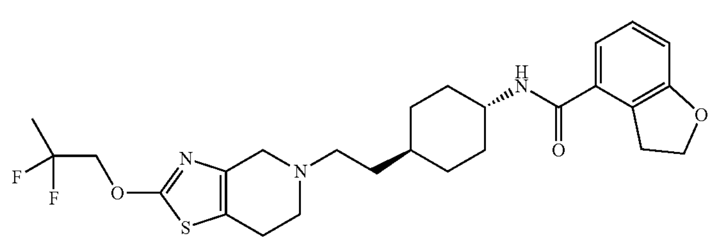 | 2 | 1.57 | 506 |

-continued

| Compound No. | Structure | LC/MS method | RT (min) | MS (m/z) |
|---|---|---|---|---|
| III-595 | 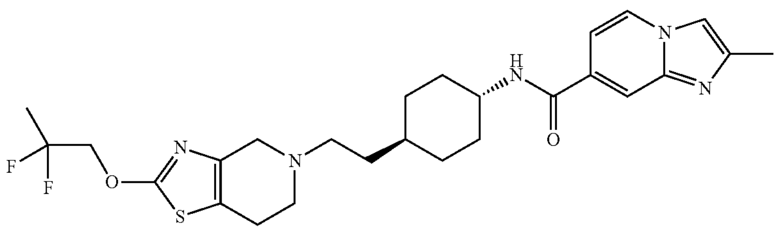 | 2 | 1.10 | 518 |
| III-596 | 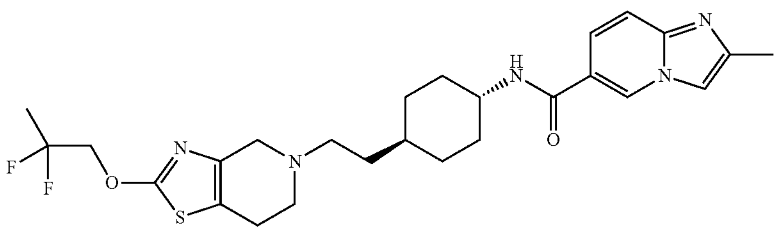 | 2 | 1.09 | 518 |
| III-597 | 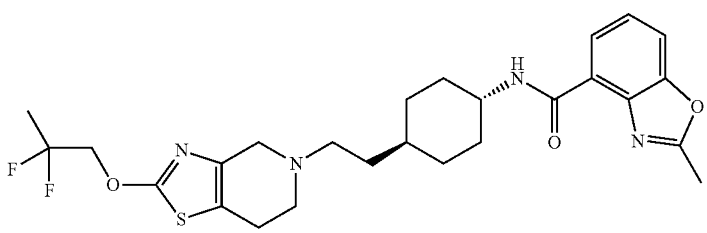 | 2 | 1.71 | 519 |
| III-598 | 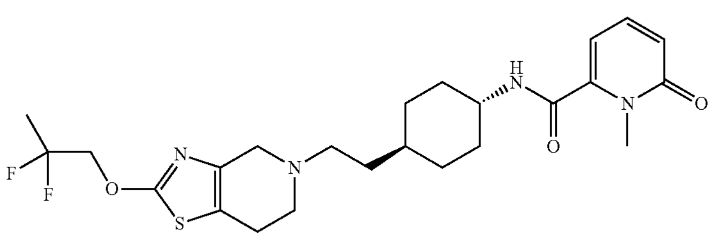 | 2 | 1.26 | 495 |
| III-599 | 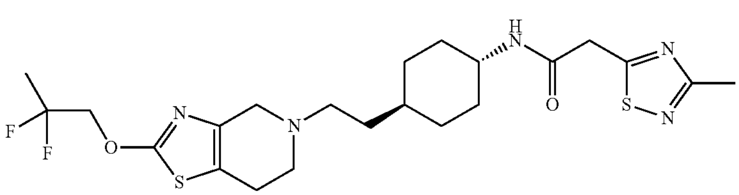 | 2 | 1.37 | 500 |
| III-600 | 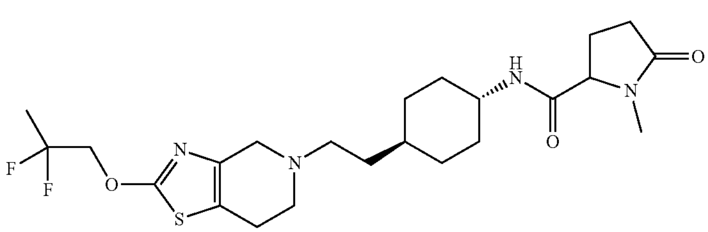 | 2 | 1.22 | 485 |

-continued

| Compound No. | Structure | LC/MS method | RT (min) | MS (m/z) |
|---|---|---|---|---|
| III-601 | 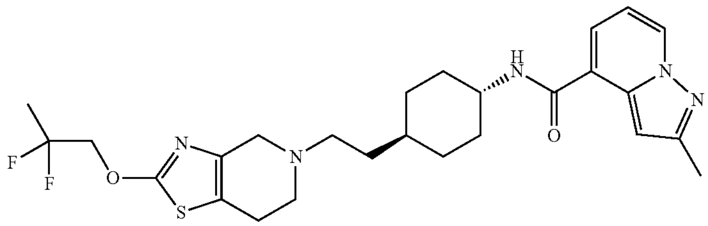 | 2 | 1.46 | 518 |
| III-602 | 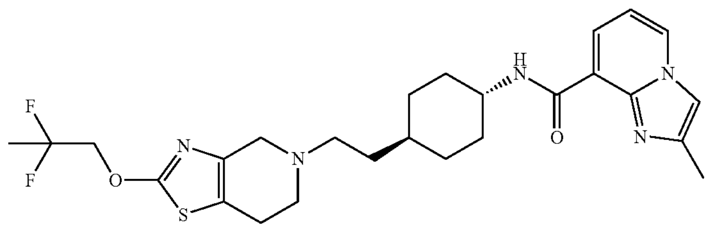 | 3 | 0.92 | 518 |
| III-603 | 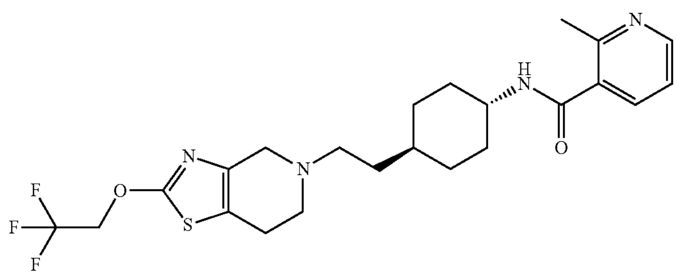 | 2 | 1.10 | 483 |
| III-604 | 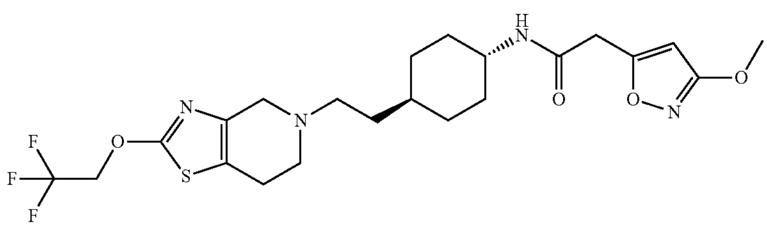 | 2 | 1.43 | 503 |
| III-605 | 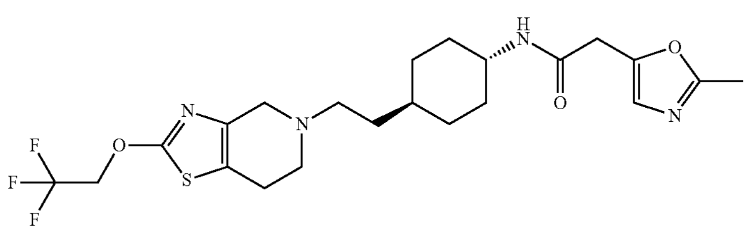 | 2 | 1.31 | 487 |
| III-606 | 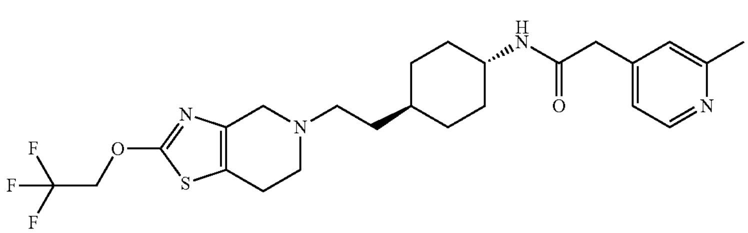 | 2 | 1.05 | 497 |

-continued

| Compound No. | Structure | LC/MS method | RT (min) | MS (m/z) |
|---|---|---|---|---|
| III-607 | 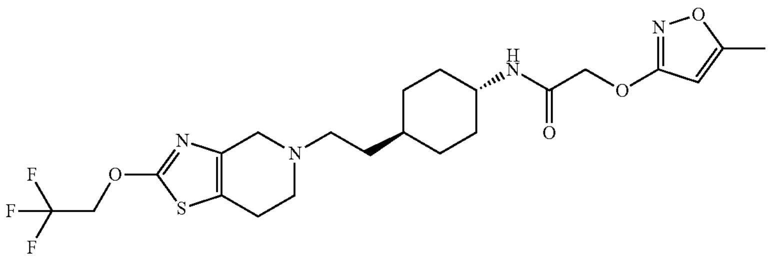 | 2 | 1.48 | 503 |
| III-608 | 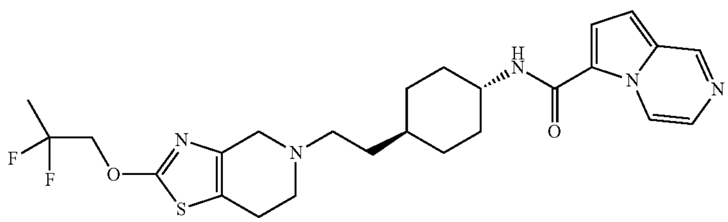 | 2 | 1.24 | 504.3 |
| III-609 | 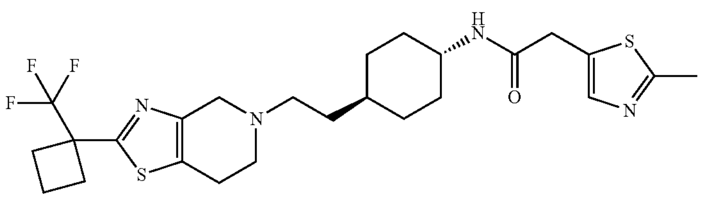 | 2 | 1.60 | 527.4 |
| III-610 | 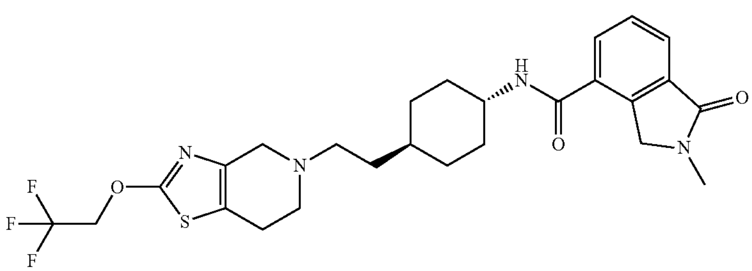 | 2 | 1.38 | 537.2 |
| III-611 | 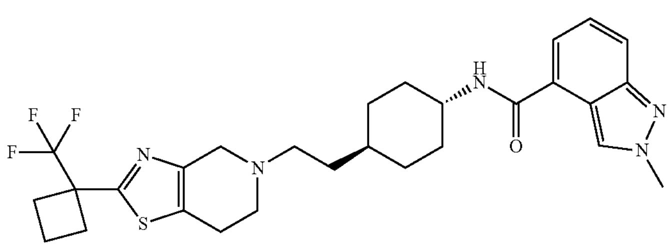 | 2 | 1.73 | 546.3 |
| III-612 | 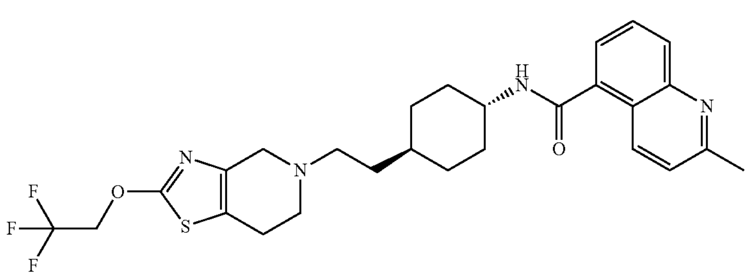 | 2 | 1.15 | 533.2 |

-continued

| Compound No. | Structure | LC/MS method | RT (min) | MS (m/z) |
|---|---|---|---|---|
| III-613 | 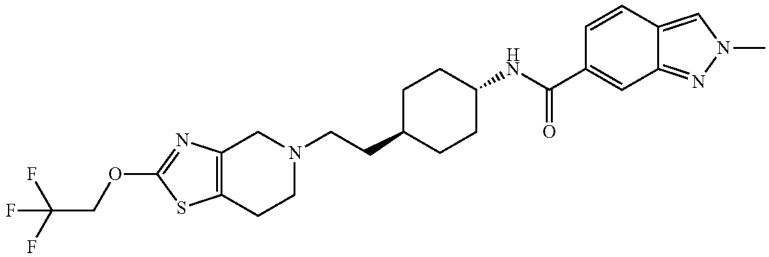 | 2 | 1.43 | 522.15 |
| III-614 | 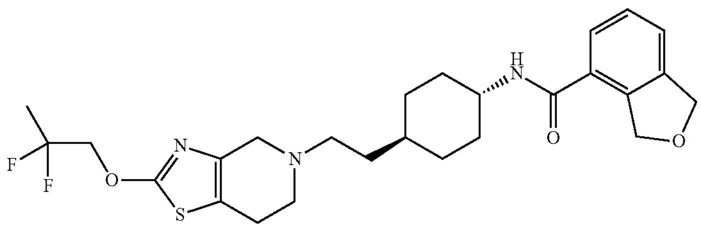 | 2 | 1.62 | 506 |
| III-615 | 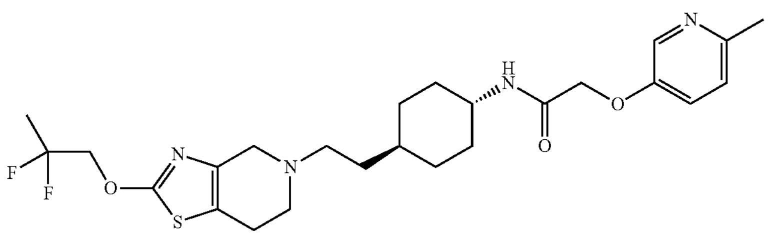 | 2 | 1.05 | 509 |
| III-616 | 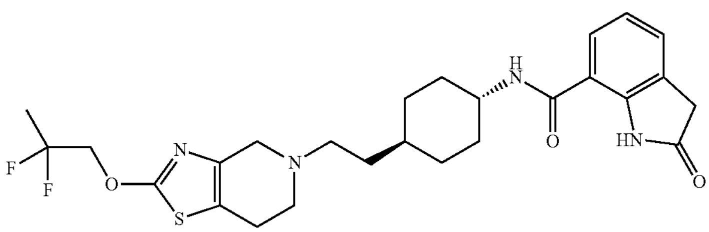 | 2 | 1.49 | 519 |
| III-617 | 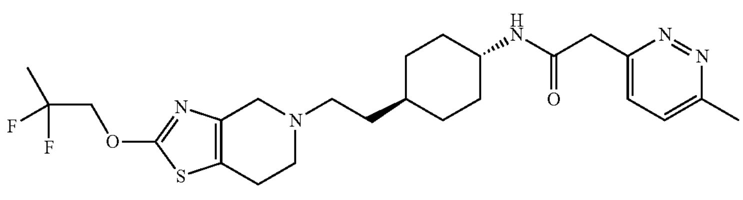 | 2 | 1.23 | 494 |
| III-618 | 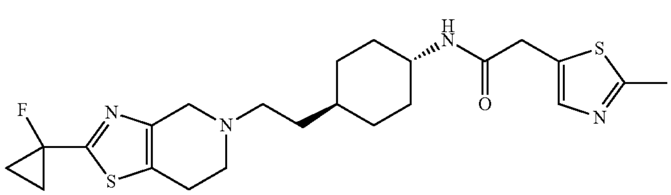 | 2 | 1.13 | 463.2 |

-continued

| Compound No. | Structure | LC/MS method | RT (min) | MS (m/z) |
|---|---|---|---|---|
| III-619 | 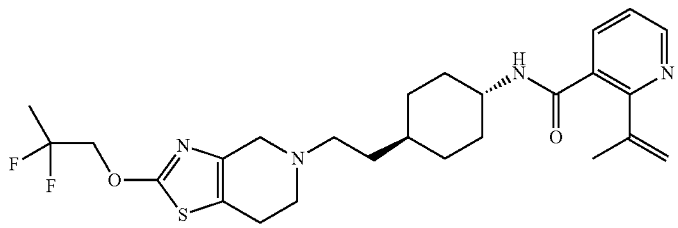 | 2 | 1.31 | 505.3 |
| III-620 | 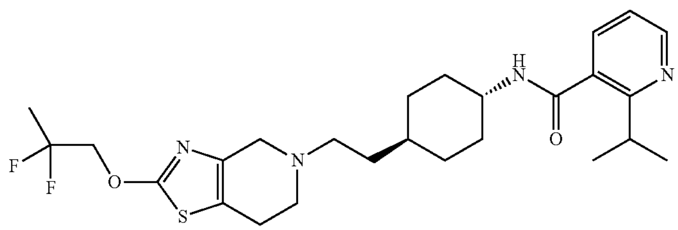 | 2 | 1.26 | 507.3 |
| III-621 | 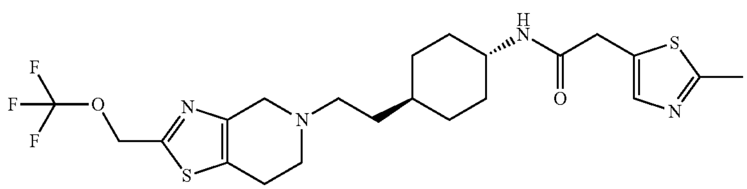 | 2 | 1.25 | 503 |
| III-622 | 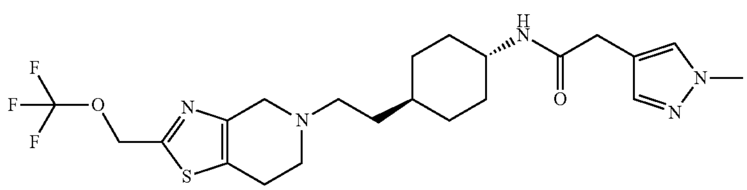 | 2 | 1.24 | 486 |
| III-623 | 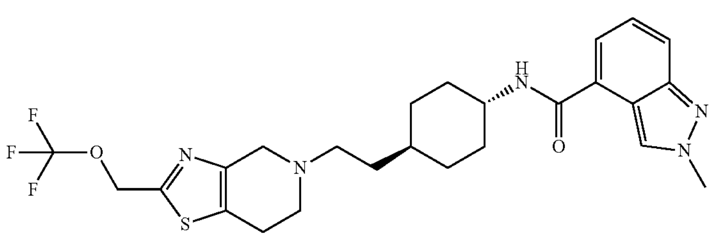 | 2 | 1.40 | 522 |
| III-624 | 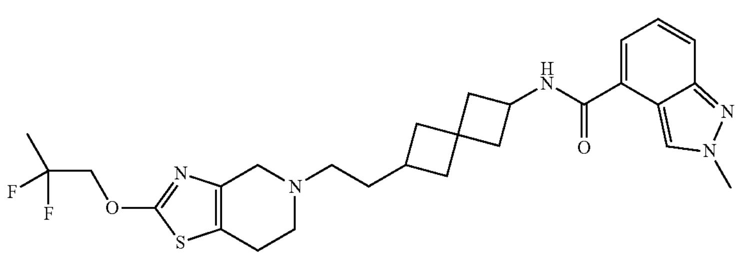 | 2 | 1.57 | 530.3 |

| Compound No. | Structure | LC/MS method | RT (min) | MS (m/z) |
|---|---|---|---|---|
| III-625 | 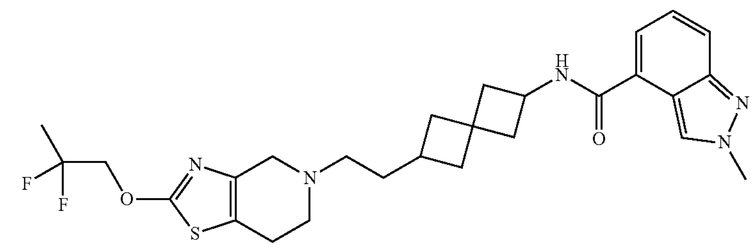 | 2 | 1.59 | 530.3 |
| III-626 | 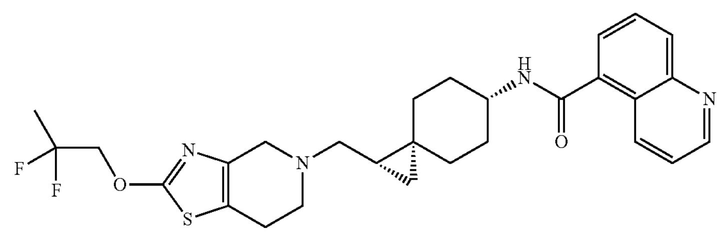 | 2 | 1.50 | 527.2 |
| III-627 | 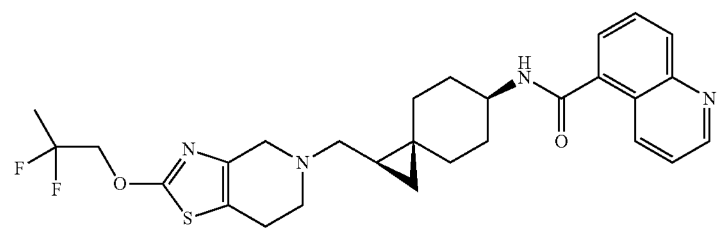 | 2 | 1.50 | 527.2 |
| III-628 | 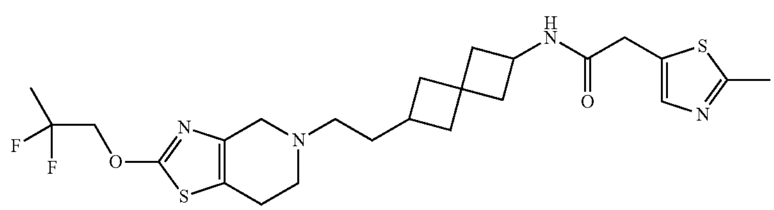 | 2 | 1.51 | 511.2 |
| III-629 | 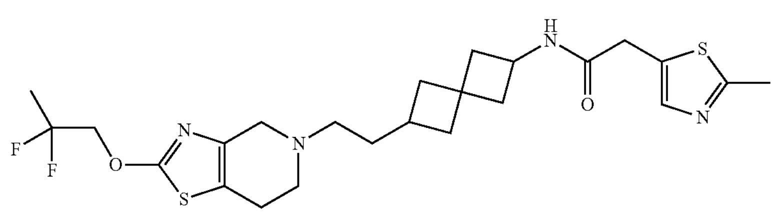 | 2 | 1.51 | 511.2 |
| III-630 | 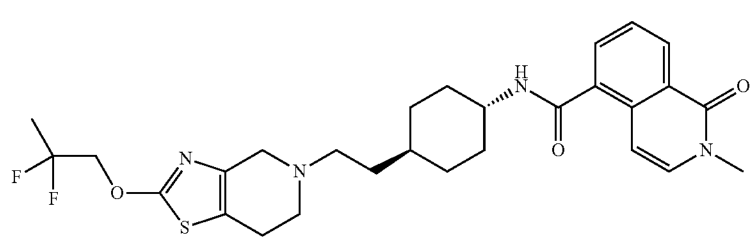 | 2 | 1.38 | 545 |

-continued

| Compound No. | Structure | LC/MS method | RT (min) | MS (m/z) |
| --- | --- | --- | --- | --- |
| III-631 | 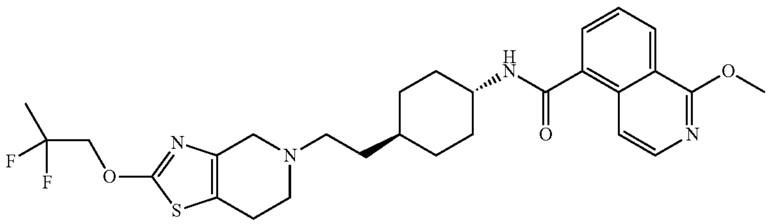 | 2 | 1.62 | 545 |
| III-632 | 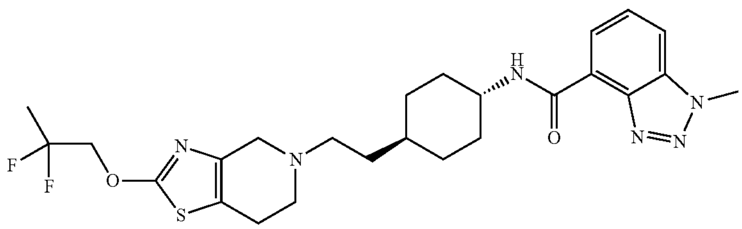 | 2 | 1.57 | 519 |
| III-633 | 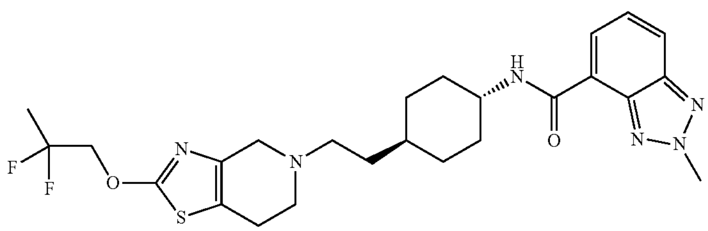 | 2 | 1.58 | 519 |
| III-634 | 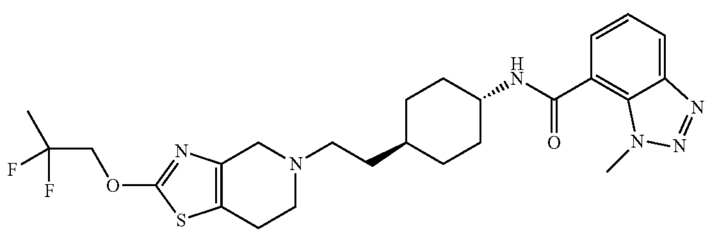 | 2 | 1.41 | 519 |
| III-635 | 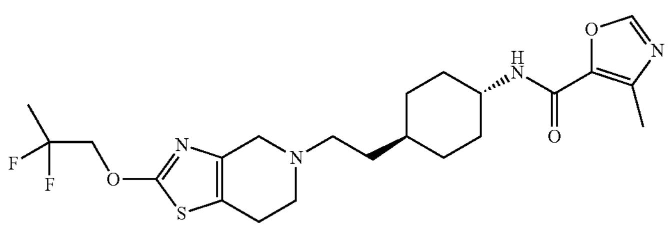 | 2 | 1.34 | 469 |
| III-636 | 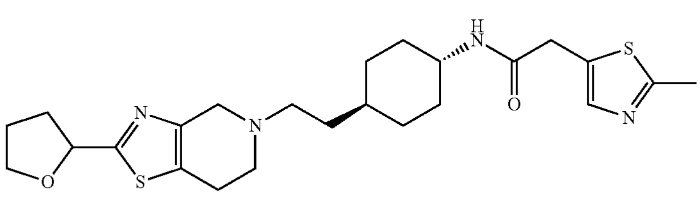 | 2 | 1.08 | 475 |

-continued

| Compound No. | Structure | LC/MS method | RT (min) | MS (m/z) |
|---|---|---|---|---|
| III-637 | 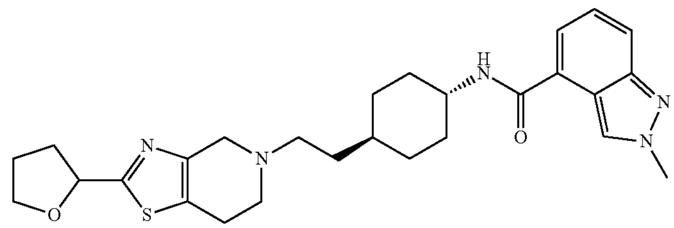 | 2 | 1.24 | 494 |
| III-638 | 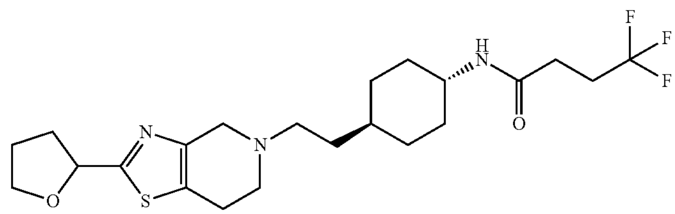 | 2 | 1.31 | 460 |
| III-639 | 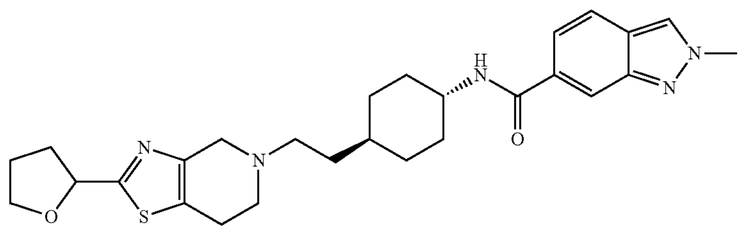 | 2 | 1.24 | 494 |
| III-640 | 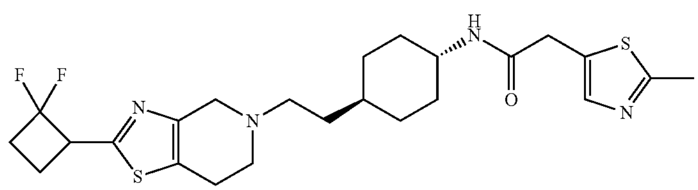 | 2 | 1.21 | 495.3 |
| III-641 | 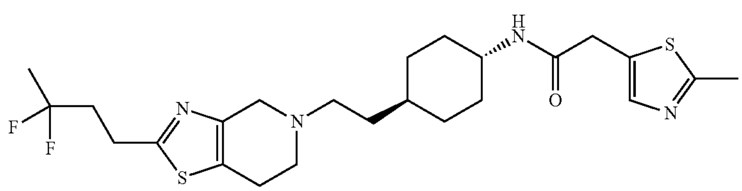 | 2 | 1.29 | 497.1 |
| III-642 | 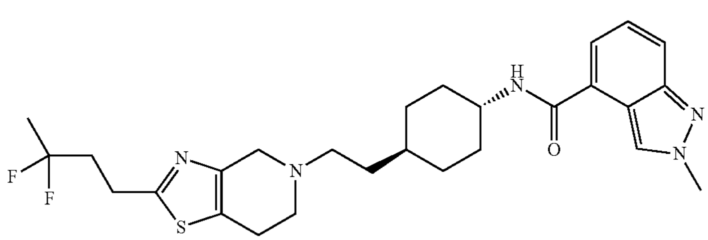 | 2 | 1.41 | 516.1 |
| III-643 | 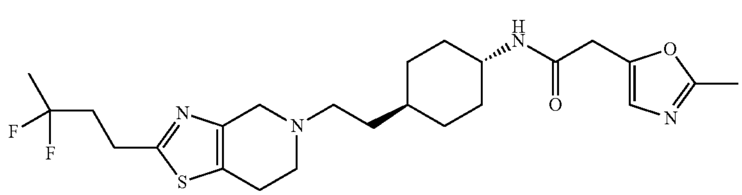 | 2 | 1.28 | 481.1 |

| Compound No. | Structure | LC/MS method | RT (min) | MS (m/z) |
|---|---|---|---|---|
| III-644 | 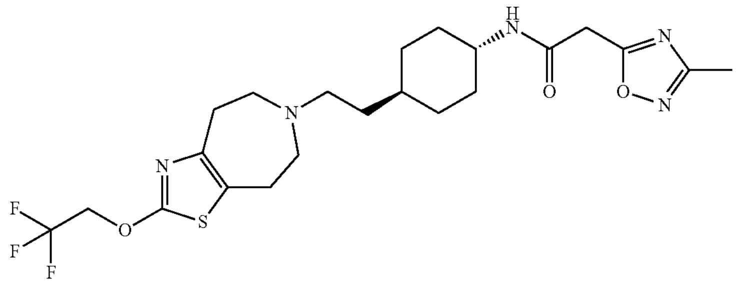 | 2 | 1.43 | 502.3 |
| III-645 | 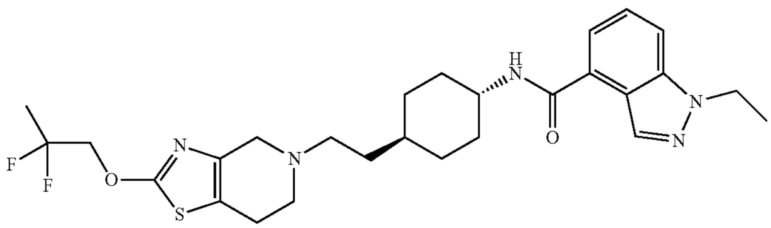 | 2 | 1.56 | 532.3 |
| III-646 | 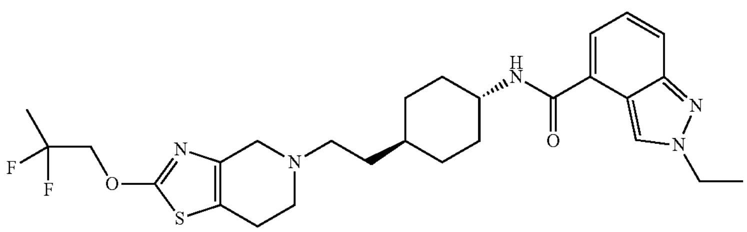 | 2 | 1.48 | 532.3 |
| III-647 | 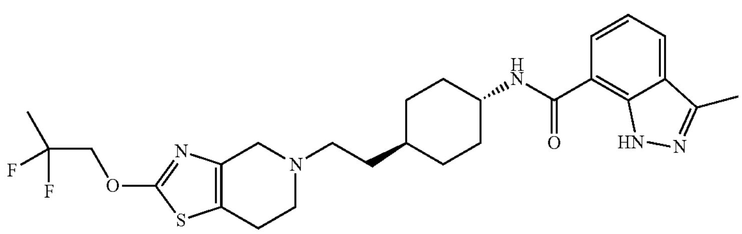 | 2 | 1.56 | 518.1 |
| III-648 | 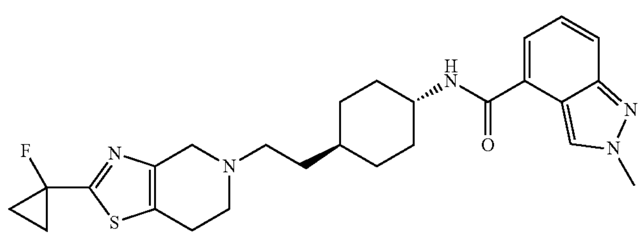 | 2 | 1.31 | 482.3 |
| III-649 | 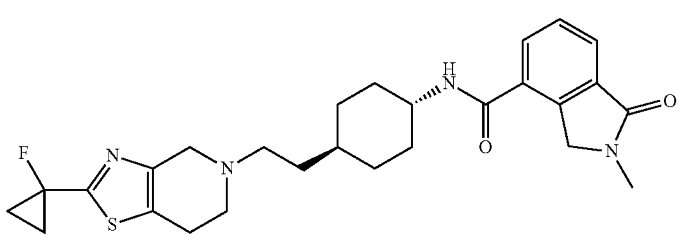 | 2 | 1.26 | 497.4 |

-continued

| Compound No. | Structure | LC/MS method | RT (min) | MS (m/z) |
| --- | --- | --- | --- | --- |
| III-650 | 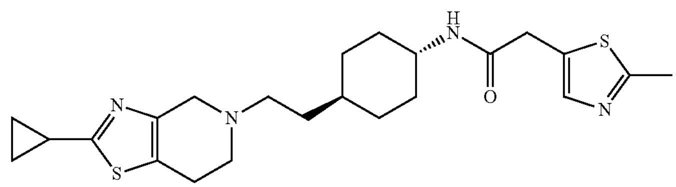 | 2 | 1.10 | 445.1 |
| III-651 | 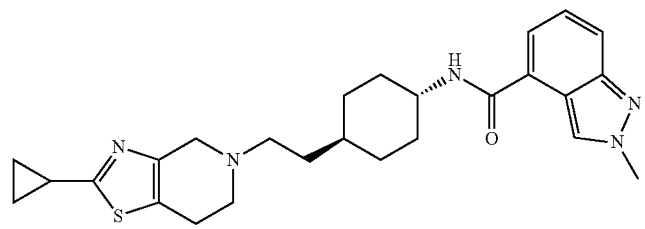 | 2 | 1.24 | 464.2 |
| III-652 | 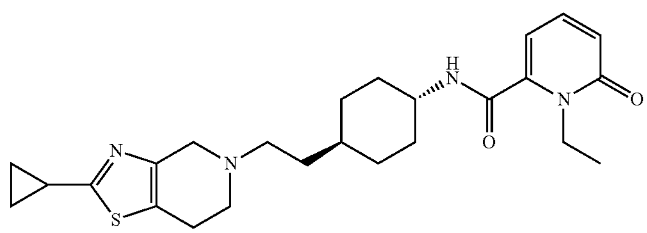 | 2 | 1.13 | 455.2 |
| III-653 | 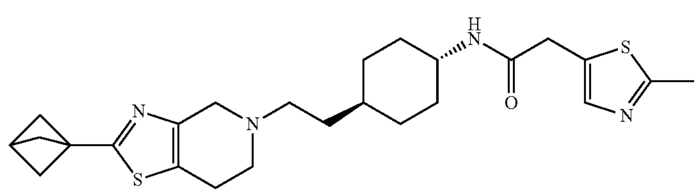 | 2 | 1.27 | 471.2 |
| III-654 | 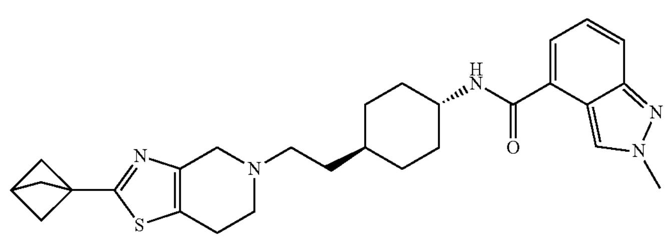 | 2 | 1.40 | 490.2 |
| III-655 | 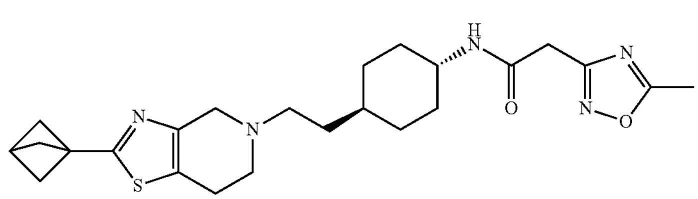 | 2 | 1.28 | 456.1 |
| III-656 | 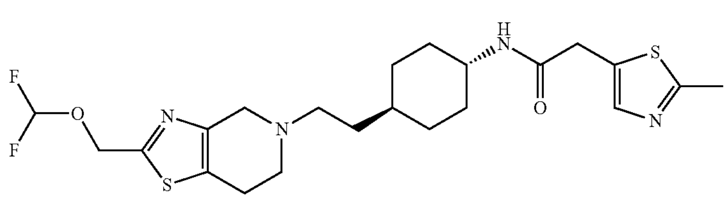 | 2 | 1.11 | 485.2 |

-continued

| Compound No. | Structure | LC/MS method | RT (min) | MS (m/z) |
|---|---|---|---|---|
| III-657 | 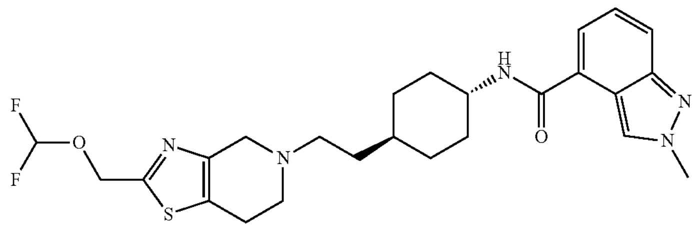 | 2 | 1.28 | 504.2 |
| III-658 | 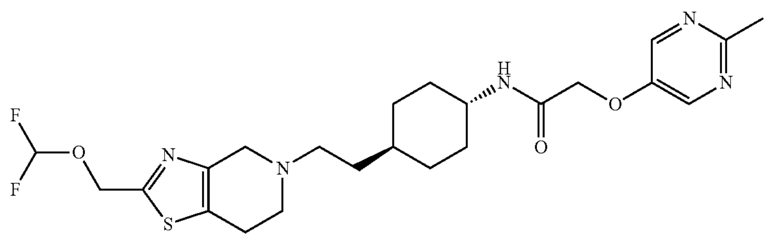 | 2 | 1.14 | 496.2 |
| III-659 | 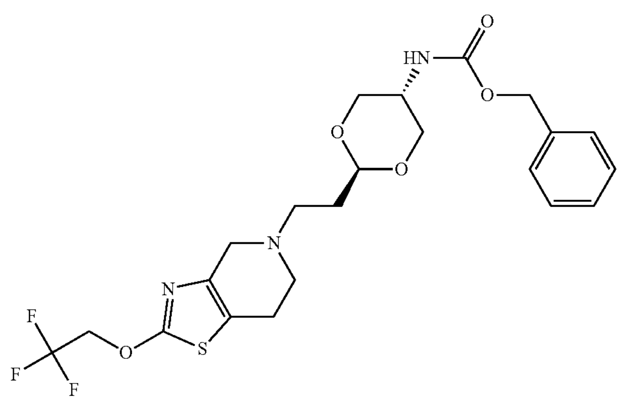 | 2 | 1.81 | 502 |
| III-660 | 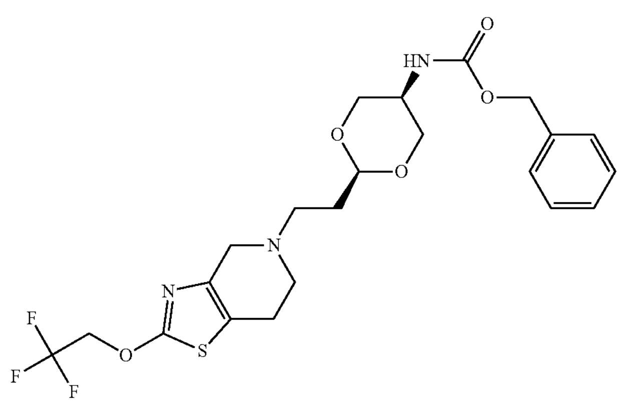 | 2 | 1.78 | 502 |

-continued

| Compound No. | Structure | LC/MS method | RT (min) | MS (m/z) |
|---|---|---|---|---|
| III-661 | 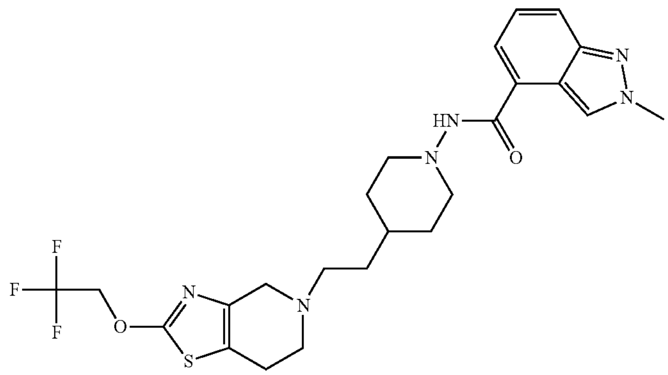 | 2 | 1.16 | 523 |
| III-662 | 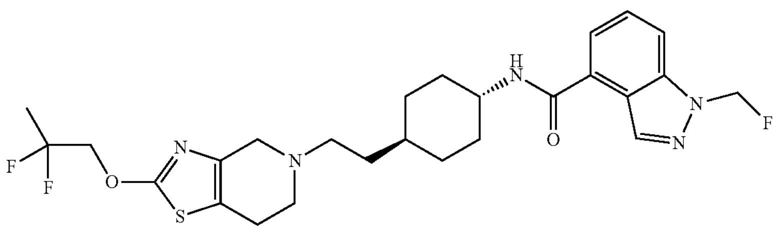 | 2 | 1.51 | 536 |
| III-663 | 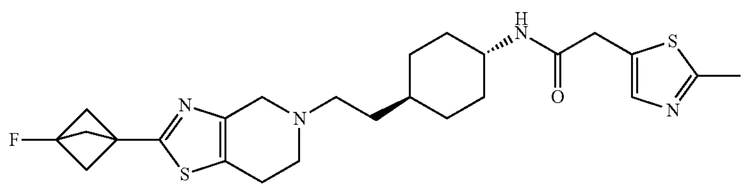 | 2 | 1.27 | 489.1 |
| III-664 | 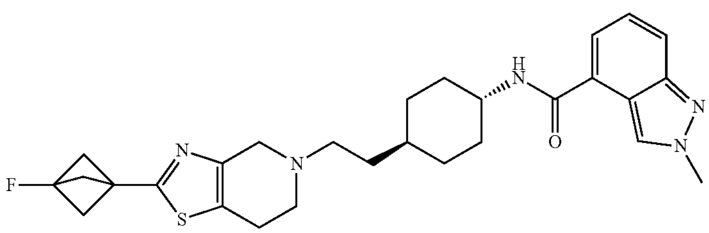 | 2 | 1.41 | 508.1 |
| III-665 | 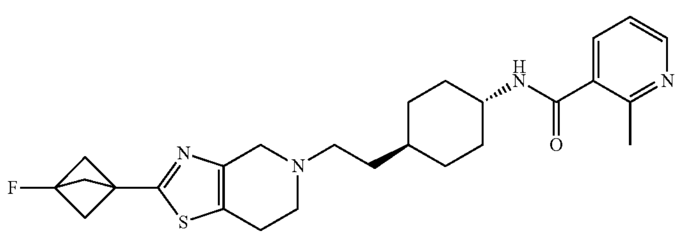 | 2 | 0.99 | 469.1 |
| III-666 | 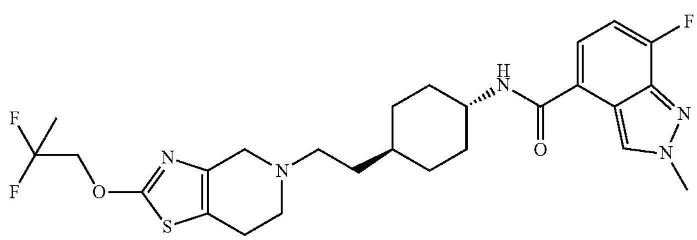 | 2 | 1.60 | 536 |

-continued
| Compound No. | Structure | LC/MS method | RT (min) | MS (m/z) |
|---|---|---|---|---|
| III-667 | 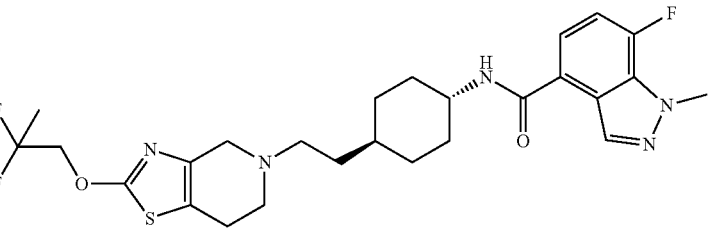 | 2 | 1.76 | 536 |
| III-668 | 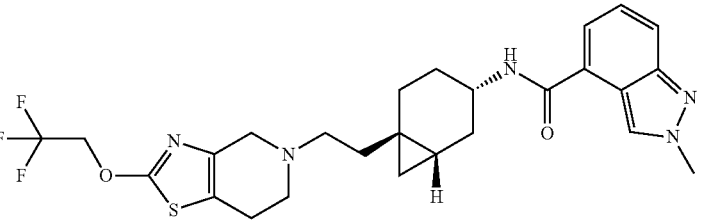 | 2 | 1.65 | 534.3 |
| III-669 | 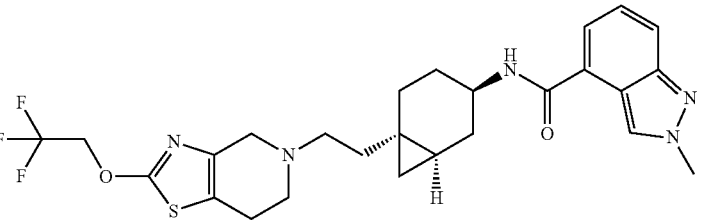 | 2 | 1.65 | 534.3 |
| III-670 | 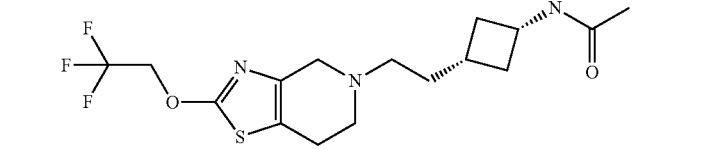 | 2 | 1.07 | 378.15 |
| III-671 | 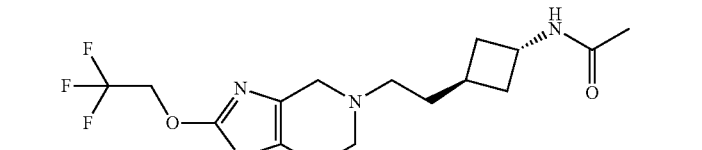 | 2 | 1.11 | 378.15 |
| III-672 | 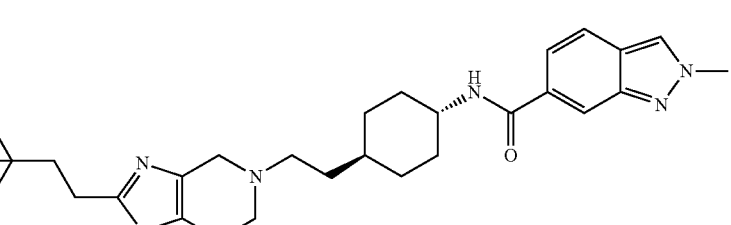 | 2 | 1.38 | 520.2 |
| III-673 | 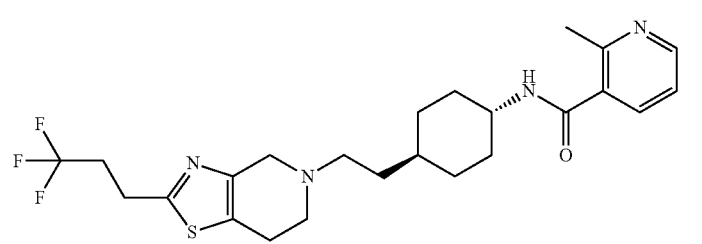 | 2 | 1.02 | 481.2 |

-continued
| Compound No. | Structure | LC/MS method | RT (min) | MS (m/z) |
|---|---|---|---|---|
| III-674 | 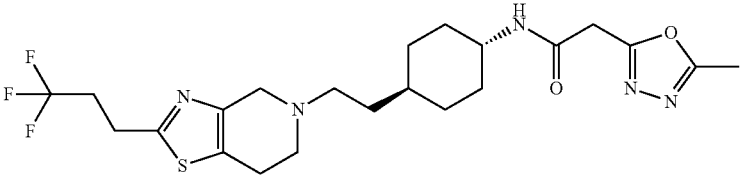 | 2 | 1.19 | 486.1 |
| III-675 | 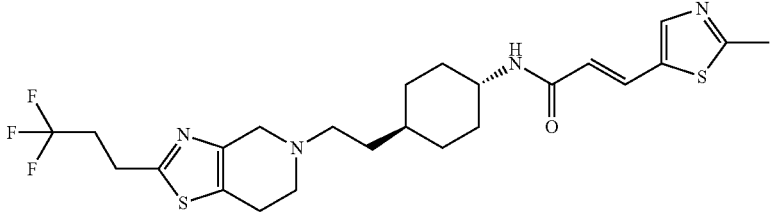 | 2 | 1.40 | 513.2 |
| III-676 | 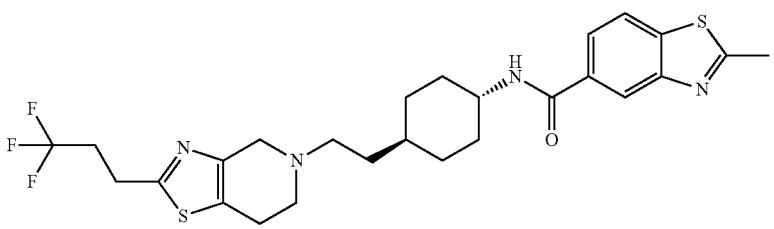 | 2 | 1.52 | 537.2 |
| III-677 | 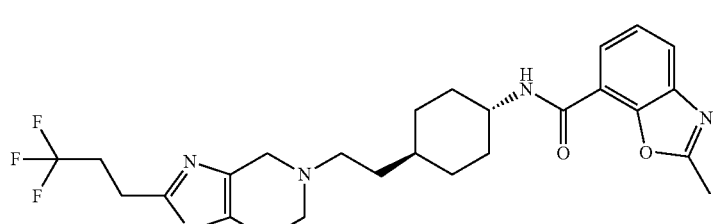 | 2 | 1.44 | 521.1 |
| III-678 | 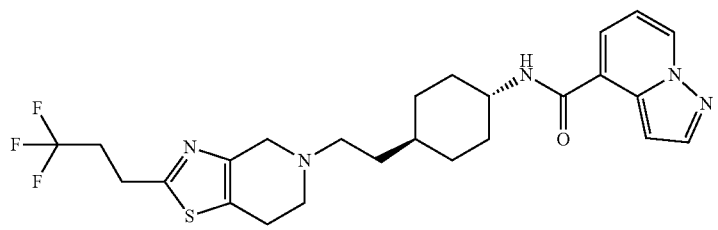 | 2 | 1.35 | 506.2 |
| III-679 | 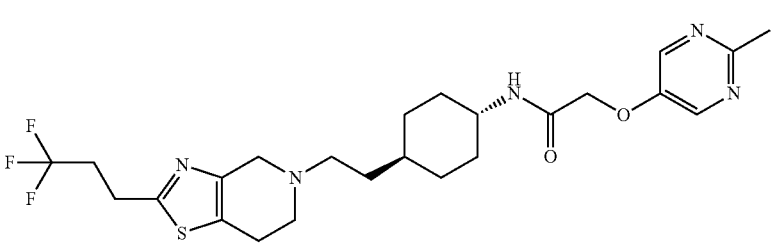 | 2 | 1.25 | 512.2 |

-continued

| Compound No. | Structure | LC/MS method | RT (min) | MS (m/z) |
| --- | --- | --- | --- | --- |
| III-680 | 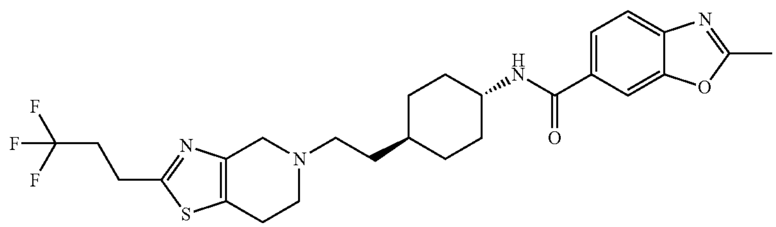 | 2 | 1.43 | 521.2 |
| III-681 | 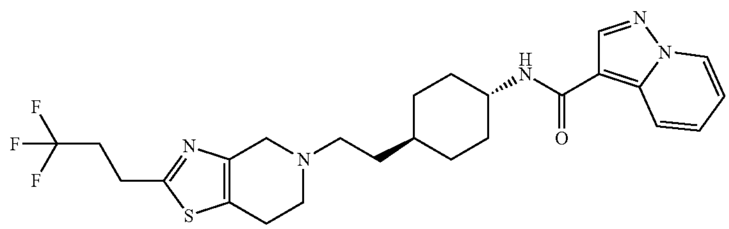 | 2 | 1.40 | 506.2 |
| III-682 | 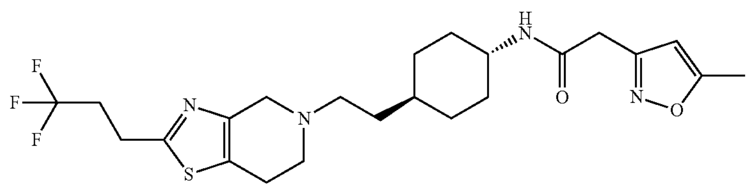 | 2 | 1.33 | 485.2 |
| III-683 | 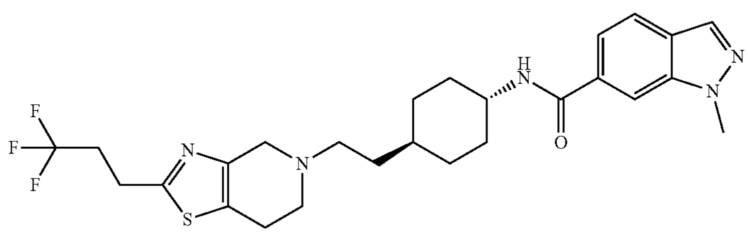 | 2 | 1.45 | 520.2 |
| III-684 | 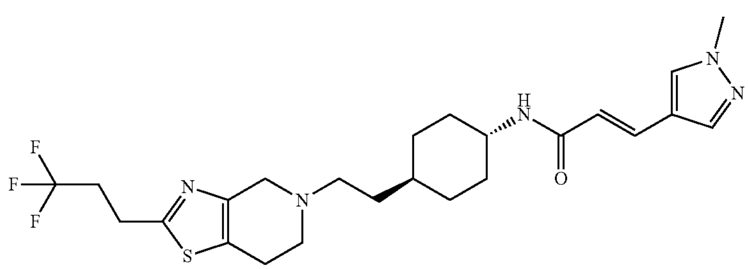 | 2 | 1.30 | 496.2 |
| III-685 | 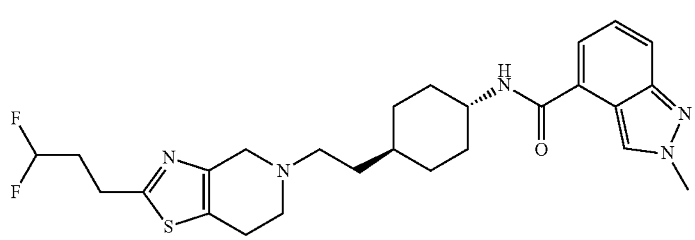 | 2 | 1.31 | 502.3 |

-continued
| Compound No. | Structure | LC/MS method | RT (min) | MS (m/z) |
|---|---|---|---|---|
| III-686 | 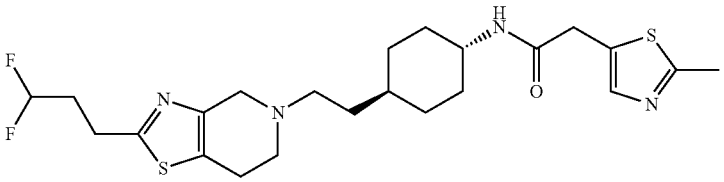 | 2 | 1.12 | 483.3 |
| III-687 | 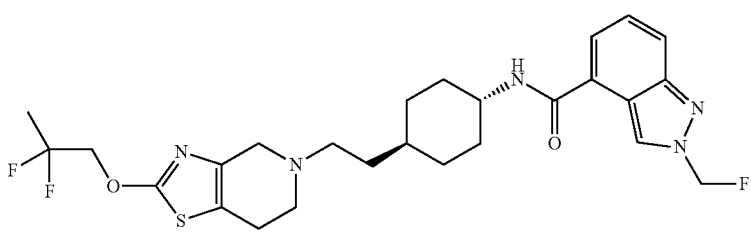 | 2 | 1.46 | 536 |
| III-688 | 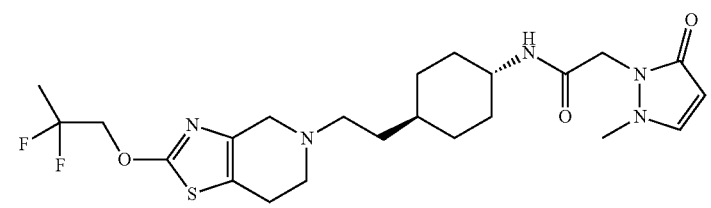 | 2 | 1.13 | 498 |
| III-689 | 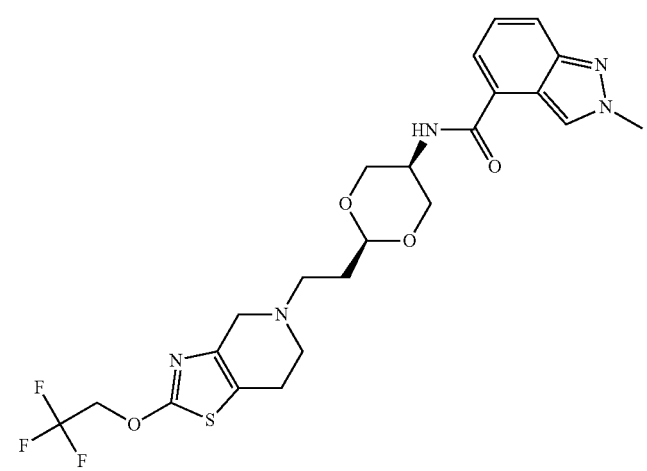 | 2 | 1.34 | 526 |

-continued
| Compound No. | Structure | LC/MS method | RT (min) | MS (m/z) |
|---|---|---|---|---|
| III-690 | 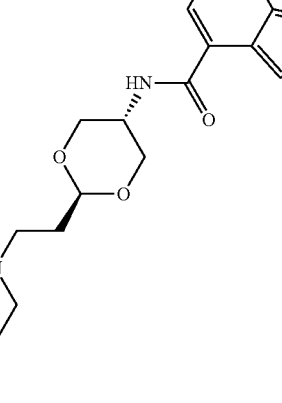 | 2 | 1.40 | 526 |
| III-691 | 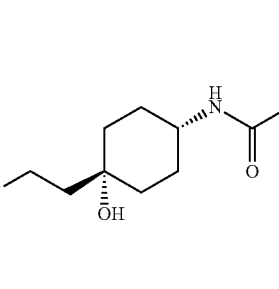 | 2 | 1.33 | 538 |
| III-692 | 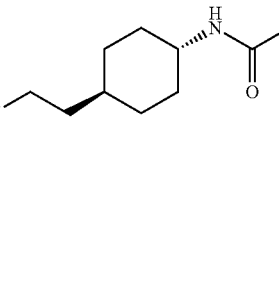 | 2 | 1.40 | 520.2 |
| III-693 | 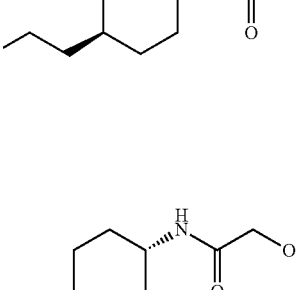 | 2 | 1.46 | 506.2 |
| III-694 | 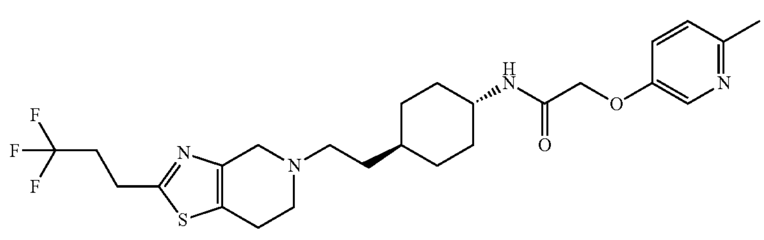 | 2 | 1.03 | 511.2 |

| Compound No. | Structure | LC/MS method | RT (min) | MS (m/z) |
|---|---|---|---|---|
| III-695 | 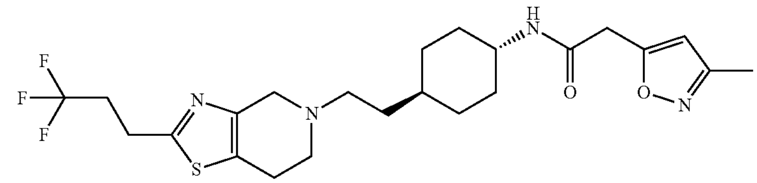 | 2 | 1.31 | 485.1 |
| III-696 | 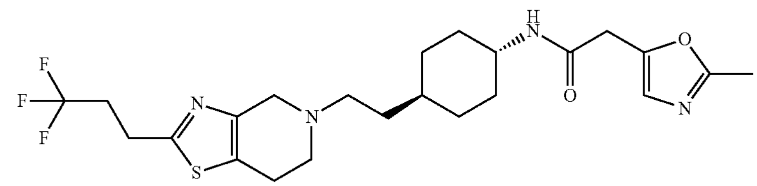 | 2 | 1.24 | 485.2 |
| III-697 | 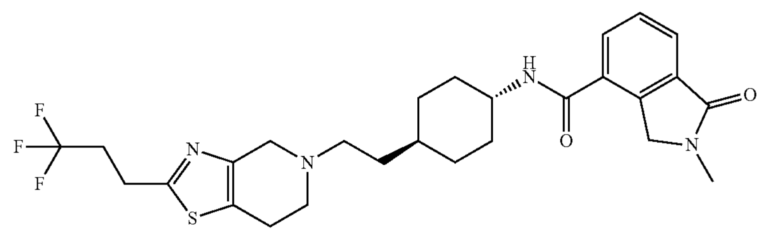 | 2 | 1.32 | 535.2 |
| III-698 | 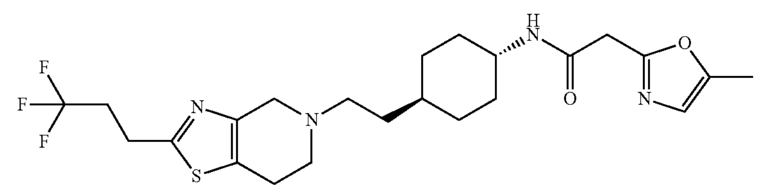 | 2 | 1.31 | 485.1 |
| III-699 | 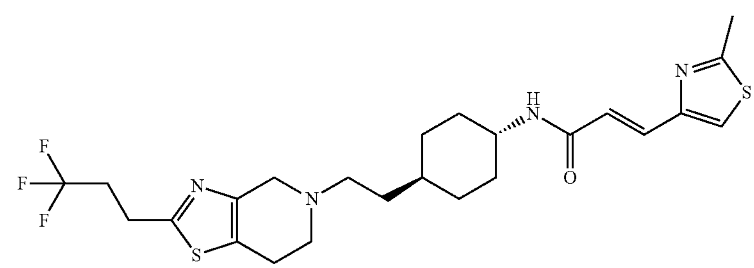 | 2 | 1.43 | 513.2 |
| III-700 | 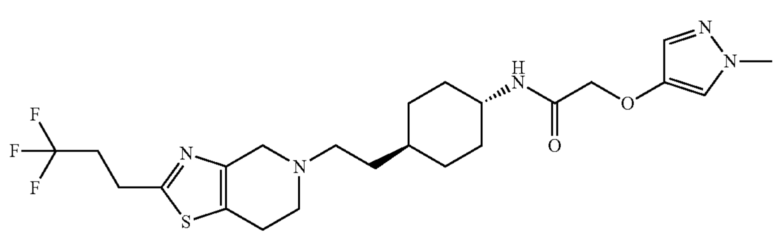 | 2 | 1.27 | 500.2 |
| III-701 | 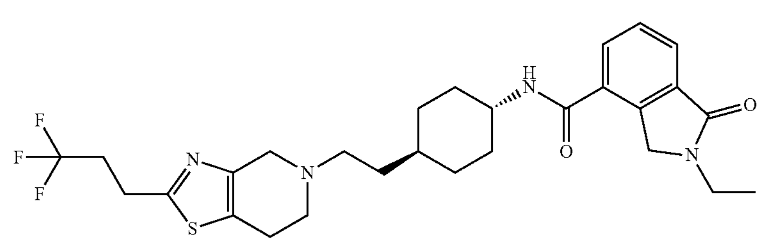 | 2 | 1.39 | 549.2 |

-continued

| Compound No. | Structure | LC/MS method | RT (min) | MS (m/z) |
|---|---|---|---|---|
| III-702 | 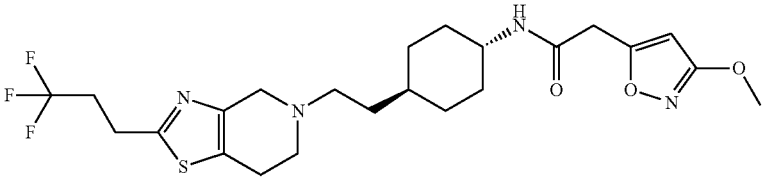 | 2 | 1.35 | 501.1 |
| III-703 | 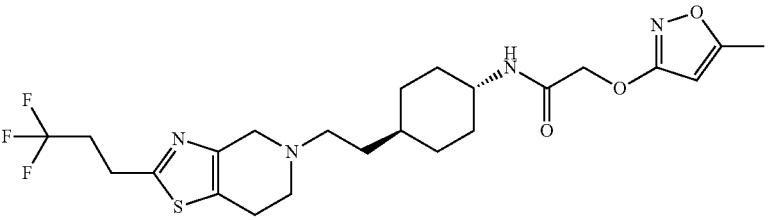 | 2 | 1.40 | 501.1 |
| III-704 | 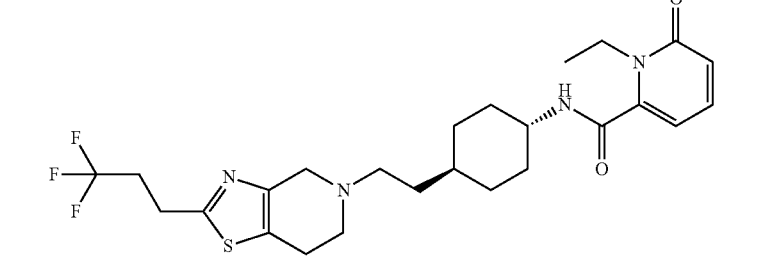 | 2 | 1.27 | 511.2 |
| III-705 | 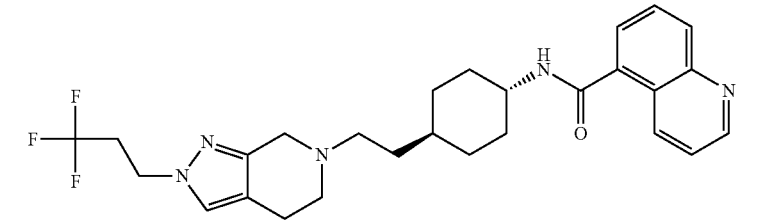 | 3 | 0.86 | 500.3 |
| III-706 | 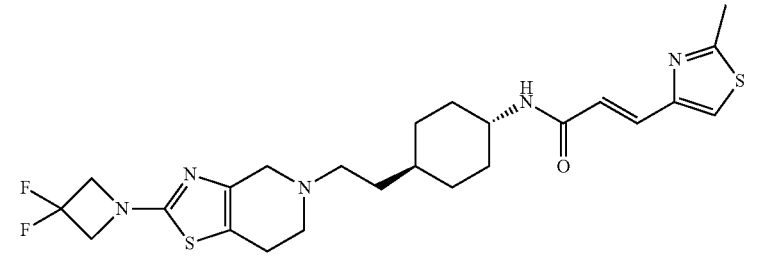 | 2 | 1.39 | 508 |

Test examples for the compounds of the present invention are described below.

Test Example 1: Test of Binding Inhibition for the Human Dopamine D2 Receptor

Experimental Conditions

Cell membranes: Jump-In HEK cell membranes expressing human recombinant dopamine D2 receptor (2 μg/well)
Buffer solution: 50 mM Tris-HCl (35409-45, Nacalai Tesque) (pH 7.4) containing 120 mM NaCl (31320-05, Nacalai Tesque), 1 mM $MgCl_2.6H_2O$ (20909-55, Nacalai Tesque), 5 mM KCl (28514-75, Nacalai Tesque) and 2 mM $CaCl_2$ (067-31, Nacalai Chemical, Ltd)
Radioligand: (final concentration) 1.2 nM [$^3$H]-Metylspiperone ([$^3$H—N-methyl-]-Metylspiperone, NET-856, 83.8 Ci/mmol, PerkinElmer)
Non-specific ligand: (final concentration) 10 μM Butaclamol [(+)-Butaclamol Hydrochloride, D033, Sigma]
SPA beads: SPA beads [WGA PVT SPA Scintillation Beads, RPNQ0001 (500 mg), RPNQ0060 (2 g), PerkinElmer] (0.2 mg/well)
Incubation time and temperature: 120 min at 25° C.
Kd: 0.272 nM (Preparation of the Non-Specific Ligand and the Compounds of the Present Invention)

Butaclamol or the compounds of the present invention were weighed and DMSO was added to make a 10 mM solution. This solution was diluted to each concentration.

(Preparation of the Radioligand)

[$^3$H]-Metylspiperone was weighed and the buffer solution was added to make a 3.6 nM solution.

(Preparation of the SPA Beads)

SPA beads were weighed and stirred in water to moke a 50 mg/mL solution. Using this solution, a mixed solution with the cell membranes was prepared.

(Binding Assay)

225 nL of the solutions of the non-specific ligand or the compounds of the present invention at each concentration (in case of vehicle, final concentration 0.3% DMSO) were added in each well of a 384-well white/clear bottom microplate (3706, Corning). Jump-In HEK Cell membranes (final reaction amount: 2 μg protein/well), SPA beads (final reaction amount: 0.2 mg/well) and the buffer were mixed and the mixed solution was left still for more than or equal to 1 h at 4° C. Then, 50 μL of the mixture was added to each well of the plate. In addition, 25 μL of 3.6 nM [$^3$H]-Metylspiperone (final concentration: 1.2 nM) was added to each well. The plate was sealed by putting TopSeal-A 96/384 well (6050185, PerkinElmer) on the top of the plate, mixed using stirring deaerator (Welltornado, FK-62, Sakaki) and incubated for 120 min at 25° C. After incubation, the radioactivity of [$^3$H]-Metylspiperone which was binded to D2 receptor was determined by liquid scintillation counter (1450 Microbeta, PerkinElmer) in each well. Non-specific binding was calculated based on the radioactivity of [$^3$H]-Metylspiperone in the presence of 10 μM non-labeled Butaclamol. The total binding was calculated using the radioactivity of [$^3$H]-Metylspiperone in the absence of the compounds of the present invention (Vehicle). The Ki values were calculated from dose-response curves.

Binding activities of the compounds of the present invention were calculated from the following Binding Inhibition Rate (%):

Inhibition Rate (%)=[1−(c−a)(b−a)]×100(%)

a: Average cpm of non-specific binding
b: Average cpm of total binding
c: Cpm in the presence of each test compound The test results of the compounds of the present invention are shown in the following table.

TABLE 119

| Compound No. | hD2_Ki (nM) |
|---|---|
| III-001 | 1100 |
| III-008 | 480 |
| III-019 | 550 |
| III-024 | 140 |
| III-027 | 330 |
| III-031 | 240 |
| III-037 | 530 |
| III-052 | >1800 |
| III-063 | >1900 |
| III-064 | 640 |
| III-074 | >1800 |
| III-076 | >1700 |
| III-082 | 410 |
| III-088 | 310 |
| III-102 | 400 |
| III-104 | >1700 |
| III-110 | 610 |
| III-128 | 370 |
| III-138 | 44 |
| III-155 | >1700 |
| III-158 | >1700 |
| III-159 | >1700 |
| III-165 | 670 |
| III-168 | 140 |
| III-169 | 380 |
| III-171 | >1700 |
| III-175 | 650 |
| III-180 | 460 |
| III-182 | 520 |
| III-199 | 520 |
| III-203 | 1400 |
| III-216 | >1700 |
| III-220 | 1100 |
| III-228 | 330 |
| III-230 | 640 |
| III-231 | 490 |
| III-234 | 460 |
| III-236 | 120 |
| III-244 | >1900 |
| III-248 | >1900 |
| III-252 | 590 |
| III-253 | 610 |
| III-254 | 570 |
| III-255 | >1800 |
| III-261 | 480 |
| III-262 | 560 |
| III-264 | >1800 |
| III-266 | >1800 |
| III-268 | 340 |
| III-269 | 290 |
| III-270 | 1100 |
| III-271 | 1100 |
| III-273 | 570 |
| III-274 | 140 |
| III-280 | 500 |
| III-282 | 1400 |
| III-439 | 500 |
| III-441 | 170 |
| III-451 | 650 |
| III-452 | 1000 |
| III-464 | 580 |
| III-484 | 850 |
| III-512 | 1100 |
| III-544 | >1700 |
| III-547 | 800 |
| III-548 | 830 |
| III-555 | 310 |
| III-573 | 350 |
| III-576 | 79 |
| III-578 | >1700 |
| III-580 | 540 |
| III-581 | 810 |
| III-603 | 610 |
| III-610 | 330 |
| III-622 | >1800 |
| III-623 | >1800 |
| III-624 | 400 |
| III-630 | >1900 |
| III-642 | 920 |
| III-659 | 1500 |
| III-661 | 1300 |
| III-666 | 210 |
| III-674 | 1100 |
| III-685 | 280 |
| III-696 | 800 |
| III-697 | 220 |
| III-698 | 770 |
| III-701 | 190 |
| III-704 | 380 |
| III-706 | 290 |
| II-005 | 430 |
| II-026 | >1700 |
| II-029 | 1300 |
| II-046 | 1200 |

TABLE 119-continued

| Compound No. | hD2_Ki (nM) |
|---|---|
| II-050 | >1800 |
| II-053 | 730 |
| II-062 | >1700 |
| II-077 | >1800 |
| II-085 | 740 |
| II-090 | >1900 |
| II-099 | >1900 |

TABLE 120

| Compound No. | hD2_Ki (nM) |
|---|---|
| I-001 | >1700 |
| I-003 | >1900 |
| I-014 | >1700 |
| I-018 | >1700 |
| I-033 | 170 |
| I-052 | 1100 |
| I-070 | 500 |
| I-071 | 150 |
| I-073 | >1700 |
| I-098 | 1600 |
| I-101 | >1700 |
| I-107 | 370 |
| I-108 | 1400 |
| I-113 | >1700 |
| I-124 | 860 |
| I-133 | >1700 |
| I-136 | >1800 |
| I-139 | >1700 |
| I-140 | 1200 |
| I-142 | 650 |
| II-014 | 230 |
| II-018 | >1800 |
| II-019 | >1800 |
| II-041 | 290 |
| II-047 | 280 |
| II-048 | >1700 |
| II-050 | >1800 |
| II-055 | 690 |
| II-057 | >1700 |
| II-066 | >1900 |
| II-070 | 820 |
| II-072 | >1800 |
| II-078 | >1800 |
| II-081 | 230 |
| II-084 | 510 |
| II-087 | 260 |
| II-088 | >1900 |
| II-105 | 1100 |

Test Example 2: Test of Binding Inhibition for the Human Dopamine D3 Receptor

Experimental Conditions

Cell membranes: Jump-In HEK cell membranes expressing human recombinant dopamine D3 receptor (4 μg/well)

Buffer solution: 50 mM Tris-HCl (35409-45, Nacalai Tesque) (pH 7.4) containing 120 mM NaCl (31320-05, Nacalai Tesque), 1 mM $MgCl_2 \cdot 6H_2O$ (20909-55, Nacalai Tesque), 5 mM KCl (28514-75, Nacalai Tesque) and 2 mM $CaCl_2$ (067-31, Nacalai Chemical, Ltd)

Radioligand: (final concentration) 2 nM [$^3$H]-Metylspiperone ([3H—N-methyl-]-Metylspiperone, NET-856, 83.8 Ci/mmol, PerkinElmer)

Non-specific ligand: (final concentration) 10 μM Butaclamol [(+)-Butaclamol Hydrochloride, D033, Sigma]

SPA beads: SPA beads [WGA PVT SPA Scintillation Beads, RPNQ0001 (500 mg), RPNQ0060 (2 g), PerkinElmer] (0.2 mg/well)

Incubation time and temperature: 120 min at 25° C.

Kd: 0.321 nM (Preparation of the Non-Specific Ligand and the Compounds of the Present Invention)

Butaclamol or the compounds of the present invention were weighed and DMSO was added to make a 10 mM solution. This solution was diluted to each concentration.

(Preparation of the Radioligand)

[$^3$H]-Metylspiperone was weighed and the buffer solution was added to make a 6 nM solution.

(Preparation of the SPA Beads)

SPA beads were weighed and stirred in water to make a 50 mg/mL solution. Using this solution, a mixed solution with the cell membranes was prepared.

(Binding Assay)

225 nL of the solutions of the non-specific ligand or the compounds of the present invention at each concentration (in case of vehicle, final concentration 0.3% DMSO) were added in each well of a 384-well white/clear bottom microplate (3706, Corning). Jump-In HEK Cell membranes (final reaction amount: 4 μg/well), SPA beads (final reaction amount: 0.2 mg/well) and Tris-HCl buffer were mixed and the mixed solution was left still for more than 60 min at 4° C. Then, 50 μL of the mixture was added to each well of the plate. In addition, 25 μL of 6 nM [$^3$H]-Metylspiperone (final concentration: 2 nM) was added to each well. The plate was sealed by putting TopSeal-A 96/384 well (6050185, PerkinElmer) on the top of the plate, mixed using stirring deaerator (Welltornado, FK-62, Sakaki) and incubated for 120 min at 25° C. After incubation, the radioactivity of [$^3$H]-Metylspiperone which was binded to D3 receptor was determined by liquid scintillation counter (1450 Microbeta, PerkinElmer) in each well. Non-specific binding was calculated based on the radioactivity of [$^3$II]-Metylspiperone in the presence of 10 μM non-labeled Butaclamol. The total binding was calculated based on the radioactivity of [$^3$H]-Metylspiperone in the absence of the compounds of the present invention (Vehicle). The Ki values were calculated from dose-response curves.

Binding activities of the compounds of the present invention were calculated from the following Binding Inhibition Rate (%):

$$\text{Inhibition Rate (\%)} = [1-(c-a)(b-a)]*100(\%)$$

a: Average cpm of non-specific binding
b: Average cpm of total binding
c: Cpm in the presence of each test compound The test results of the compounds of the present invention are shown in the following table.

TABLE 121

| Compound No. | hD3_Ki (nM) |
|---|---|
| III-001 | 0.5 |
| III-008 | 0.25 |
| III-019 | 0.14 |
| III-024 | 0.012 |
| III-027 | 0.064 |
| III-031 | 0.31 |
| III-037 | 0.2 |
| III-052 | 1.1 |
| III-063 | 0.13 |
| III-064 | 0.026 |
| III-074 | 0.66 |

TABLE 121-continued

| Compound No. | hD3_Ki (nM) |
| --- | --- |
| III-076 | 0.73 |
| III-082 | 0.45 |
| III-088 | 0.31 |
| III-102 | 0.11 |
| III-104 | 0.53 |
| III-110 | 0.49 |
| III-128 | 0.12 |
| III-138 | 0.057 |
| III-155 | 0.25 |
| III-158 | 0.34 |
| III-159 | 0.91 |
| III-165 | 0.81 |
| III-168 | 0.13 |
| III-169 | 0.4 |
| III-171 | 0.47 |
| III-175 | 0.68 |
| III-180 | 0.72 |
| III-182 | 0.56 |
| III-199 | 0.2 |
| III-203 | 0.79 |
| III-216 | 1.3 |
| III-220 | 0.78 |
| III-228 | 0.16 |
| III-230 | 0.99 |
| III-231 | 0.7 |
| III-234 | 0.77 |
| III-236 | 0.086 |
| III-244 | 0.24 |
| III-248 | 1.6 |
| III-252 | 0.43 |
| III-253 | 0.58 |
| III-254 | 0.43 |
| III-255 | 0.67 |
| III-261 | 0.57 |
| III-262 | 0.22 |
| III-264 | 0.25 |
| III-266 | 0.15 |
| III-268 | 0.39 |
| III-269 | 0.36 |
| III-270 | 0.6 |
| III-271 | 1.2 |
| III-273 | 0.78 |
| III-274 | 0.12 |
| III-280 | 0.11 |
| III-282 | 0.82 |
| III-439 | 0.29 |
| III-441 | 0.24 |
| III-451 | 0.48 |
| III-452 | 0.29 |
| III-464 | 0.37 |
| III-484 | 0.44 |
| III-512 | 0.9 |
| III-544 | 0.55 |
| III-547 | 0.64 |
| III-548 | 0.46 |
| III-555 | 0.4 |
| III-573 | 0.32 |
| III-576 | 0.44 |
| III-578 | 0.05 |
| III-580 | 0.25 |
| III-581 | 0.035 |
| III-603 | 0.44 |
| III-610 | 0.077 |
| III-622 | 1.2 |
| III-623 | 0.83 |
| III-624 | 0.092 |
| III-630 | 0.16 |
| III-642 | 0.37 |
| III-659 | 9.6 |
| III-661 | 0.5 |
| III-666 | 0.2 |
| III-674 | 1.1 |
| III-685 | 0.1 |
| III-696 | 0.2 |
| III-697 | 0.23 |
| III-698 | 0.52 |
| III-701 | 0.15 |
| III-704 | 0.51 |
| III-706 | 0.051 |
| II-005 | 0.085 |
| II-026 | 0.2 |
| II-029 | 0.12 |
| II-046 | 0.2 |
| II-050 | 0.51 |
| II-053 | 0.067 |
| II-062 | 1.1 |
| II-077 | 0.095 |
| II-085 | 0.096 |
| II-090 | 0.64 |
| II-099 | 0.52 |

TABLE 122

| Compound No. | hD3_Ki (nM) |
| --- | --- |
| I-001 | 11 |
| I-003 | 2.6 |
| I-014 | 1.3 |
| I-018 | 12 |
| I-033 | 3.6 |
| I-052 | 1 |
| I-070 | 1.4 |
| I-071 | 0.13 |
| I-073 | 0.08 |
| I-098 | 0.12 |
| I-101 | 8.1 |
| I-107 | 0.82 |
| I-108 | 1.5 |
| I-113 | 4.7 |
| I-124 | 0.91 |
| I-133 | 7.9 |
| I-136 | 25 |
| I-139 | 0.69 |
| I-140 | 1.9 |
| I-142 | 0.72 |
| II-014 | 0.45 |
| II-018 | 2.7 |
| II-019 | 2.3 |
| II-041 | 0.058 |
| II-047 | 0.022 |
| II-048 | 0.82 |
| II-050 | 0.51 |
| II-055 | 0.24 |
| II-057 | 0.014 |
| II-066 | 0.84 |
| II-070 | 0.44 |
| II-072 | 0.48 |
| II-078 | 0.075 |
| II-081 | 0.048 |
| II-084 | 0.052 |
| II-087 | 0.059 |
| II-088 | 7.4 |
| II-105 | 0.11 |

Test Example 3-1: Effect of Suppressing Impulsivity in Rat

Male Crl: WI rats were obtained at post-natal day 14 and weaning was occurred at post-natal day 21. Starting from then, the rats were housed 2-3 per cage and food-restricted (Day 1). The feeding amount was 5 g/day at post-natal day 21-28 (Day 1-8), 8.5 g/day at post-natal day 29-32 (Day 9-12), and 10 g/day at post-natal day 33-36 (Day 13-16), preventing their body weight from being 60% or less of the weight of the free feeding rats.

4 days after the beginning of the food restriction (Day 5), pellets were put on goal boxes located in the left-side and the right-side of T-maze. Then, the rats were allowed to freely explore the T-maze-box for 5 min to get habituated to the T-maze box and learn that the pellets were put on the goal boxes located in the left-side and the right-side. For 4 consecutive days from the next day (Day 6-9), one pellet (20 mg×1) was put in one side of the goal box as a small reward, and 5 pellets (20 mg×5) were put in the other side of the goal box as a large reward, and the rats were trained to learn their positions. Each rat underwent 10-trial per day trainings. The rats that did not select the large reward more than or equal to 9 times of the 10 trials in the 4 days trainings were given additional training until they selected the large reward more than or equal to 9 times of the 10 trials. The evaluations of the drug efficacy were started on Day 12. The compounds of the present invention were dissolved in distilled water containing 3% of 1 mol/L hydrochloric acid and administered i.p. to the trained rats to attain the dose of 1, 3 or 10 mg/kg. Vehicle control group was administered only distilled water containing 3% of 1 mol/L hydrochloric acid. The administering tests were conducted with 6*8 rats in each group. The administrations were conducted daily over 5 days from Day 12-16. After 40 min from the administration, it was tested whether which of large reward and small reward was selected. When the rat selected the arm leading to the large reward, the rats were shut for 15 seconds in the arm to introduce delay before the rats were allowed to access to the reward. In the arm leading to the small reward, the door was opened immediately and no delay was introduced. These tests are conducted over 5 days from Day 12-16, 10 trials per day. The numbers of choices of the large reward during total 50 trials of 5 days were compared between the vehicle control group and the group which was treated with the compounds of the present invention.

Compound 1-085 (3 mg/kg, i.p.), significantly increased the number of choices for the large reward, which indicated that the compound has effect of improving impulsivity. The results are shown in the FIGURE.

Test Example 3-2: Effect of Suppressing Impulsivity in Rat

Male Crl: WI rats are obtained at post-natal day 14 and weaning is occurred at post-natal day 21. Starting from then, the rats are housed 2-3 per cage and food-restricted (Day 1). The feeding amount is 5 g/day at post-natal day 21-28 (Day 1-8), 8.5 g/day at post-natal day 29-32 (Day 9-12), and 10 g/day at post-natal day 33-36 (Day 13-16), preventing their body weight from being 60% or less of the weight of the free feeding rats.

4 days after the beginning of the food restriction (Day 5), pellets are put on goal boxes located in the left-side and the right-side of T-maze. Then, the rats are allowed to freely explore the T-maze-box for 5 min to get habituated to the T-maze box and learn that the pellets are put on the goal boxes located in the left-side and the right-side. For 4 consecutive days from the next day (Day 6-9), one pellet (20 mg×1) is put in one side of the goal box as a small reward, and 5 pellets (20 mg×5) are put in the other side of the goal box as a large reward, and the rats are trained to learn their positions. Each rat underwent 10-trial per day trainings. The rats that did not select the large reward more than or equal to 9 times of the 10 trials in the 4 days trainings are given additional training until they select the large reward more than or equal to 9 times of the 10 trials. The evaluations of the drug efficacy were started on Day 12. The compounds of the present invention are dissolved in 0.5% methylcellulose (WAKO) and administered p.o. to the trained rats to attain the dose of 1, 3 or 10 mg/kg. Vehicle control group is administered 0.5% methylcellulose. The administering tests are conducted with 6-8 rats in each group. The administrations are conducted daily over 5 days from Day 12-16. After 40 min from the administration, it is tested whether which of large reward and small reward is selected. When the rat selects the arm leading to the large reward, the rats are shut for 15 seconds in the arm to introduce delay before the rats are allowed to access to the reward. In the arm leading to the small reward, the door is opened immediately and no delay is introduced. These tests are conducted over 6 days from Day 12-16, 10 trials per day. The numbers of choices of the large reward during total 50 trials of 6 days are compared between the vehicle control group and the group which is treated with the compounds of the present invention.

Test Example 4: CYP Inhibition Test

Using commercially available pooled human liver microsomes, an inhibitory degree of each metabolite production amount by the compound of the present invention is assessed as marker reactions of human main five CYP isoforms (CYP1A2, 2C9, 2C19, 2D6, and 3A4), 7-ethoxy-resorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation (CYP3A4).

The reaction conditions are as follows: substrate, 0.5 μmol/L ethoxyresorufin (CYP1A2), 100 μmol/L tolbutamide (CYP2C9), 50 μmol/L S-mephenitoin (CYP2C19), 5 μmol/L dextromethorphan (CYP2D6), 1 μmol/L terfenedine (CYP3A4); reaction time, 15 minutest reaction temperature, 37° C.; enzyme, pooled human liver microsomes 0.2 mg protein/mL; concentration of the compound of the present invention, 1, 5, 10, 20 μmol/L (four points).

Each five kinds of substrates, human liver microsomes, and the compound of the present invention in 50 mmol/L Hepes buffer are added as reaction solutions to a 96-well plate at the composition as described above, and NADPH, as a cofactor, is added to initiate the marker metabolism reactions. After the incubation at 37° C. for 15 minutes, a methanol/acetonitrile=1/1 (V/V) solution is added to stop the reaction. After the centrifugation at 3000 rpm for 16 minutes, resorufin (CYP1A2 metabolite) in the supernatant is quantified by a fluorescent multilabel counter or LC/MS/MS and hydroxytolbutamide (CYP2C9 metabolite), 4' hydroxymephenytoin (CYP2C19 metabolite), dextromethorphan (CYP2D6 metabolite), and terfenadine alcohol metabolite (CYP3A4 metabolite) are quantified by LC/MS/MS.

The sample adding only DMSO which is a solvent of the compound of the present invention to a reaction system is adopted as a control (100%). Remaining activity (%) is calculated at each concentration of the compound of the present invention compared to the control, and $IC_{50}$ is calculated by reverse presumption by a logistic model using a concentration and an inhibition rate.

Test Example 6: BA Test

Materials and Methods for experiments to evaluate oral absorption
(1) Animals: The SD rats are used
(2) Breeding conditions: The SD rats are allowed to freely take solid food and sterilized tap water.

(3) Dose and grouping: orally or intravenously administered at a predetermined dose; grouping is as follows (Dose can be changed depends on the compound)

Oral administration: 1 mg/kg or 2 µmol/kg (n=2)
Intravenous administration: 0.5 mg/kg or 1 µmol/kg (n=2)

(4) Preparation of dosing solution: for oral administration, in a solution or a suspension state using 0.5% methylcellulose solution or dimethyl sulfoxide/0.5% methylcellulose solution=1/4 solution; for intravenous administration, in a solubilized state using dimethylacetamide/propylene glycol=1/1 or dimethyl sulfoxide/propylene glycol=1/1 solvent.

(5) Administration method: in oral administration, forcedly administer into ventriculus with oral probe; in intravenous administration, administer from caudal vein with a needle-equipped syringe (6) Evaluation items: blood is collected over time, and the plasma concentration of drug is measured by LC/MS/MS (7) Statistical analysis: regarding the transition of the plasma concentration of the compound of the present invention, the area under the plasma concentration-time curve (AUC) is calculated by non-linear least squares program WinNonlin (Registered trade name), and the bioavailability (BA) is calculated from the AUCs of the oral administration group and intravenous administration group.

Test Example 6: Metabolism Stability Test

Using commercially available pooled human liver microsomes, the compound of the present invention is reacted for a constant time, a remaining rate is calculated by comparing a reacted sample and an unreacted sample, thereby, a degree of metabolism in liver of the compound of the present invention is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution is added to 100 µL of a methanol/acetonitrile=1/1 (v/v), mixed and centrifuged at 3000 rpm for 15 minutes. The compound of the present invention in the supernatant is quantified by LC/MS/MS or Solid-Phase Extraction (SPE)/MS, and a remaining amount of the compound of the present invention after the reaction is calculated, letting a compound amount at 0 minute reaction time to be 100%.

Test Example 7: CYP3A4(MDZ)MBI Test

CYP3A4(MDZ) MBI test is a Lest of investigating Mechanism based inhibition (MBI) potential on CYP3A4 by the enhancement of inhibitory degree of a metabolic reaction caused by the compound of the present invention. CYP3A4 inhibition is evaluated using pooled human liver microsomes by 1-hydroxylation reaction of midazolam (MDZ) as a marker reaction.

The reaction conditions are as follows: substrate, 10 µmol/L MDZ; pre-reaction time, 0 or 30 minutes: substrate reaction Lime, 2 minutes; reaction temperature, 37° C.; protein content of pooled human liver microsomes, at pre-reaction time 0.5 mg/mL, at reaction time 0.05 pmg/mL (at 10-fold dilution); concentrations of the compound of the present invention, 1, 5, 10, 20 µmol/L (four points).

Pooled human liver microsomes and a solution of the compound of the present invention in 100 mmol/L K-Pi buffer (pH 7.4) as a pre-reaction solution are added to a 96-well plate at the composition of the pre-reaction. A part of pre-reaction solution is transferred to another 96-well plate, and 1/10 diluted by 100 mmol/L K-Pi buffer containing a substrate. NADPH as a co-factor is added to initiate a reaction as a marker reaction (without preincubation). After a predetermined time of a reaction, methanol/acetonitrile=1/1 (V/V) solution is added to stop the reaction. In addition, NADPH is added to a remaining pre-reaction solution to initiate a pre-reaction (with preincubation). After a predetermined time of a pre-reaction, a part is transferred to another 96-well plate, and 1/10 diluted by K-Pi buffer containing a substrate to initiate a reaction as a marker reaction. After a predetermined time of a reaction, methanol/acetonitrile=1/1 (V/V) solution is added to stop the reaction. After centrifuged at 3000 rpm for 15 minutes, 1-hydroxymidazolam in the supernatant is quantified by LC/MS/MS.

The sample adding only DMSO which is a solvent of the compound of the present invention to a reaction system is adopted as a control (100%). Remaining activity (%) is calculated at each concentration of the compound of the present invention compared to control, and IC value is calculated by reverse-presumption by a logistic model using a concentration and an inhibition rate. Shifted IC value is calculated as "IC of preincubation at 0 min/IC of preincubation at 30 min". When a shifted IC is 1.5 or more, this is defined as positive. When a shifted IC is 1.0 or less, this is defined as negative.

Test Example 8-1: Fluctuation Ames Test

Mutagenicity of the compound of the present invention is evaluated.

A 20 µL of freezing-stored *Salmonella typhimurium* (TA98 strain, TA100 strain) is inoculated on 10 mL of a liquid nutrient medium (2.5% Oxoid nutrient broth No. 2), and this is incubated at 37° C. for 10 hours under shaking. The 9 mL of TA98 culture medium is centrifuged (2000×g, 10 minutes) and TA98 is suspended in 9 mL Micro F buffer ($K_2HPO_4$: 3.5 g/L, $KH_2PO_4$: 1 g/L, $(NH_4)_2SQ_4$: 1 g/L, trisodium citrate dehydrate: 0.25 g/L, $MgSO_4.7H_2O$: 0.1 g/L) after removing the culture medium. The TA98 suspension is mixed with 110 mL Exposure medium (Micro F buffer containing Biotin: 8 µg/mL, histidine: 0.2 µg/mL, glucose: 8 mg/mL). The 3.16 mL of TA100 culture medium strain is mixed with 120 mL Exposure medium. Each 12 µL of DMSO solution of the compound of the present invention (several stage dilution from maximum dose 60 mg/mL at 2 to 3 fold ratio), DMSO as a negative control, and 50 µg/mL of 4-nitroquinoline 1-oxide DMSO solution for the TA98 strain and 0.25 µg/mL of 2-(2-furyl)-3-(5-nitro-2-furyl)acrylamide DMSO solution for the TA100 strain in the assay without metabolic activation, 40 µg/mL of 2-aminoanthracene DMSO solution for the TA98 strain and 20 µg/mL of 2-aminoanthracene DMSO solution for the TA100 strain in the assay with metabolic activation as a positive control, and 588 µL of the test bacterial suspension (498 µL of the test bacterial suspension and 90 µL of S9 mixture in the case of metabolic activation assay) are mixed, and this is incubated at 37° C. for 90 minutes under shaking. A 460 µL of the mixture is mixed with 2300 µL of Indicator medium (Micro F buffer containing 8 µg/mL biotin, 0.2 µg/mL histidine, 8 mg/mL glucose, 37.5 µg/mL bromocresol purple), each 50 µL is dispensed to microplate 48 wells/dose, and this is incubated at 37° C. for 3 days. Since the wells containing the bacteria which gained growth ability by point mutation in amino acid (histidine) synthesizing enzyme gene turns from purple to yellow due to a pH change, the number of yellow wells in 48 wells is counted per dose, and is compared with the negative control group. (−) and (+) means negative and positive in mutagenicity respectively.

Test Example 8-2: Fluctuation Ames Test

Mutagenicity of the compound of the present invention is evaluated.

A 20 µL of freezing-stored *Salmonella typhimurium* (TA98 strain, TA100 strain) is inoculated on 10 mL of a liquid nutrient medium (2.5% Oxoid nutrient broth No. 2), and this is incubated at 37° C. for 10 hours under shaking. The 8 mL of TA98 culture medium is centrifuged (2000×g, 10 minutes) and TAOS is suspended in 8 mL Micro F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4.7H_2O$: 0.1 g/L) after removing the culture medium. The TAOS suspension is mixed with 120 mL Exposure medium (Micro F buffer containing Biotin: 8 µg/mL, histidine: 0.2 µg/mL, glucose: 8 mg/mL). The 3.1 mL of TA100 culture medium strain is mixed with 120 mL Exposure medium. Each 12 µL of DMSO solution of the compound of the present invention (several stage dilution from maximum dose 60 mg/mL at 2 to 3 fold ratio), DMSO as a negative control, and 50 µg/mL of 4-nitroquinoline 1-oxide DMSO solution for the TA98 strain and 0.25 µg/mL of 2-(2-furyl)-3-(5-nitro-2-furyl)acrylamide DMSO solution for the TA100 strain in the assay without metabolic activation, 12 µL of 40 µg/mL of 2-aminoanthracene DMSO solution for the TA98 strain and 6 µL of 20 µg/mL of 2-aminoanthracene DMSO solution for the TA100 strain in the assay with metabolic activation as a positive control, and 588 µL of the test bacterial suspension (498 µL of the test bacterial suspension and 90 µL of S9 mixture in the case of metabolic activation assay) are mixed, and this is incubated at 37° C. for 90 minutes under shaking. A 460 µL of the mixture is mixed with 2300 µL of Indicator medium (Micro F buffer containing 8 µg/mL biotin, 0.2 µg/mL histidine, 8 mg/mL glucose, 37.5 µg/mL bromocresol purple), each 50 µL is dispensed to microplate 48 wells/dose, and this is incubated at 37° C. for 3 days. Since the wells containing the bacteria which gained growth ability by point mutation in amino acid (histidine) synthesizing enzyme gene turns from purple to yellow due to a pH change, the number of yellow wells in 48 wells is counted per dose, and is compared with the negative control group. (−) and (+) means negative and positive in mutagenicity respectively.

Test Example 9-1: hERG Test

For the purpose of assessing risk of an electrocardiogram QT interval prolongation of the compound of the present invention, effects of the compound of the present invention on delayed rectifier K+ current ($I_{Kr}$), which plays an important role in the ventricular repolarization process, is studied using CHO cells expressing human ether-a-go-go related gene (hERG) channel.

After a cell is retained at a membrane potential of −80 mV by whole cell patch clamp method using an automated patch clamp system (QPatch; Biolin Scientific) and gave a leak potential of −50 mV, $I_{Kr}$ induced by depolarization pulse stimulation at +20 mV for 2 seconds and, further, repolarization pulse stimulation at −50 mV for 2 seconds, is recorded. After the generated current is stabilized, extracellular solution (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration in the extracellular solution, is applied to the cell at room temperature for 10 minutes. From the recording $I_{Kr}$, an absolute value of the tail peak current is measured based on the current value at the resting membrane potential using analysis software (Falster Patch; Sophion Bioscience A/S). Further, the % inhibition of tail peak current for the compound of the present invention relative to the tail peak current after application of the vehicle (0.1% dimethyl sulfoxide solution) is calculated to assess influence of the compound of the present invention on $I_{Kr}$.

Test Example 9-2: hERG Test

For the purpose of assessing risk of an electrocardiogram QT interval prolongation of the compound of the present invention, effects of the compound of the present invention on delayed rectifier K+ current ($I_{Kr}$), which plays an important role in the ventricular repolarization process, is studied using CHO cells expressing human ether-a-go-go related gene (hERG) channel.

After a cell is retained at a membrane potential of −80 mV by whole cell patch clamp method using an automated patch clamp system (QPatch; Sophion Bioscience A/S) and gave a leak potential of −50 mV, $I_{Kr}$ induced by depolarization pulse stimulation at +20 mV for 2 seconds and, further, repolarization pulse stimulation at −50 mV for 2 seconds, is recorded. After the generated current is stabilized, extracellular solution (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration in the extracellular solution, is applied to the cell at room temperature for 7 minutes or more. From the recording $I_{Kr}$, an absolute value of the tail peak current is measured based on the current value at the resting membrane potential using analysis software (QPatch assay software; Sophion Bioscience A/S). Further, the % inhibition of tail peak current for the compound of the present invention relative to the tail peak current before application of the solution (0.1% dimethyl sulfoxide solution) is calculated to assess influence of the compound of the present invention on $I_{Kr}$.

Test Example 10-1: Solubility Test

The solubility of the compound of the present invention is determined under 1% DMSO addition conditions. 10 mmol/L solution of the compound is prepared with DMSO. 2 µL of the solution of the compound of the present invention is respectively added to 198 µL of JP-1 fluid (water is added to 2.0 g of sodium chloride and 7.0 mL of hydrochloric acid to reach 1000 mL) or JP-2 fluid (1 volume of water is added to 1 volume of the solution in which 3.40 g of potassium dihydrogen phosphate and 3.55 g of anhydrous disodium hydrogen phosphate are dissolved in water to reach 1000 mL). The mixture is shaking at room temperature for 1 hour, and the mixture is filtered. The filtrate is 10-fold diluted with methanol/water=1/1 (v/v), and the compound concentration in the filtrate is measured with LC/MS or SPE/MS by the absolute calibration method.

Test Example 10-2: Solubility Test

The solubility of the compound of the present invention is determined under 1% DMSO addition conditions. 10 mmol/L solution of the compound is prepared with DMSO. 2 µL of the solution of the compound of the present invention is respectively added to 198 µL of JP-1 fluid or JP-2 fluid, or 6 μL of the solution of the compound of the present invention is respectively added to 594 μL of JP-1 fluid or JP-2 fluid. The mixture is left standing for 16 hours at 25° C. (condition 1) or shaking at room temperature for 3 hours (condition 2), and the mixture is vacuum-filtered. The filtrate is 10- or 100-fold diluted with methanol/water=1/1 (v/v) or acetonitrile/methanol/water=1/1/2 (v/v/v), and the compound concentration in the filtrate is measured with LC/MS or Solid-Phase Extraction (SPE)/MS by the absolute calibration method.

The composition of the JP-1 fluid is as below.
Water is added to 2.0 g of sodium chloride and 7.0 mL of hydrochloric acid to reach 1000 mL.

The composition of the JP-2 fluid is as below.
Composition 1. 3.40 g of potassium dihydrogen phosphate and 3.55 g of anhydrous disodium hydrogen phosphate are dissolved in water to reach 1000 mL. Composition 2. 1 volume of water is added to 1 volume of the solution in which 3.40 g of potassium dihydrogen phosphate and 3.55 g of anhydrous disodium hydrogen phosphate are dissolved in water to reach 1000 mL.

Test Example 11: Powder Solubility Test

Appropriate quantity of the compound of the present invention is put in suitable containers. 200 μL of JP-1 fluid (water is added to 2.0 g of sodium chloride and 7.0 mL of hydrochloric acid to reach 1000 mL), 200 μL of JP-2 fluid (500 mL of water is added to 500 mL of pH 6.8 phosphate buffer solution)) or 20 mmol/L sodium taurocholate (TCA)/JP-2 fluid (JP-2 fluid is added to 1.08 g of TCA to reach 100 mL) is independently added to each container. When total amount is dissolved after adding the test reagent, the compound of the present invention is added appropriately. After sealing and shaking at 37° C. for 1 hour, solution is filtrated and 100 μL of methanol is added to 100 μL of each filtrate to dilute two-fold. The dilution rate is changed as necessary. After checking that there is no bubble and precipitate, the container is sealed and shaken. The compound of the present invention is measured using HPLC by absolute calibration curve method.

FORMULATION EXAMPLE

The following Formulation Examples are only exemplified and not intended to limit the scope of the invention.

Formulation Example 1: Tablets

The compounds of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compounds of the present invention, lactose and calcium stearate are mixed uniformly to obtain powder medicines in the form of powders or fine granules. The powder medicines are filled into capsule containers to give capsules.

Formulation Example 3: Granules

The compounds of the present invention, lactose and calcium stearate are mixed uniformly and the mixture is compressed and molded. Then, it is crushed, granulated and sieved to give suitable sizes of granules.

Formulation Example 4: Orally Dispersing Tablets

The compounds of the present invention and crystalline cellulose are mixed, granulated and tablets are made to give orally dispersing tablets.

Formulation Example 5: Dry Syrups

The compounds of the present invention and lactose are mixed, crushed, granulated and sieved to give suitable sizes of dry syrups.

Formulation Example 6: Injections

The compounds of the present invention and phosphate buffer are mixed to give injections.

Formulation Example 7: Infusions

The compounds of the present invention and phosphate buffer are mixed to give infusions.

Formulation Example 8: Inhalations

The compound of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster or the like are mixed to give patches.

INDUSTRIAL APPLICABILITY

The compound of the present invention can be a medicament useful as an agent for treating or preventing diseases associated with D3 receptor.

The invention claimed is:
1. A compound represented by Formula (I):

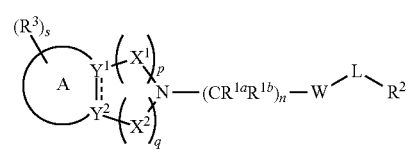

wherein

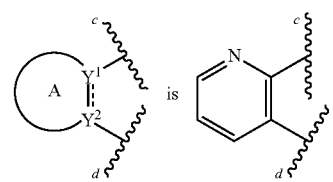

$X^1$ is each independently $CR^{4a}R^{4b}$,
$X^2$ is each independently $CR^{4c}R^{4d}$,
p is 2;
q is 2;

$R^{4a}$ is each independently a hydrogen atom, halogen, hydroxy, substituted or unsubstituted alkyl, or substituted or unsubstituted alkyloxy;

$R^{4b}$ is each independently a hydrogen atom, halogen, hydroxy, substituted or unsubstituted alkyl, or substituted or unsubstituted alkyloxy;

$R^{4a}$ and $R^{4b}$ attached to a same carbon atom may be taken together with the carbon atom to which they are attached to form a substituted or unsubstituted 3- to 5-membered non-aromatic carbocycle or a substituted or unsubstituted 3- to 5-membered non-aromatic heterocycle;

two $R^{4a}$s attached to adjacent carbon atoms may be taken together with the carbon atoms to which they are attached to form a substituted or unsubstituted 3- to 5-membered non-aromatic carbocycle or a substituted or unsubstituted 3- to 5-membered non-aromatic heterocycle;

$R^{4c}$ is each independently a hydrogen atom, halogen, hydroxy, substituted or unsubstituted alkyl, or substituted or unsubstituted alkyloxy;

$R^{4d}$ is each independently a hydrogen atom, halogen, hydroxy, substituted or unsubstituted alkyl, or substituted or unsubstituted alkyloxy;

$R^{4c}$ and $R^{4d}$ attached to a same carbon atom may be taken together with the carbon atom to which they are attached to form a substituted or unsubstituted 3- to 5-membered non-aromatic carbocycle or a substituted or unsubstituted 3- to 5-membered non-aromatic heterocycle;

two $R^{4c}$s attached to adjacent carbon atoms may be taken together with the carbon atoms to which they are attached to form a substituted or unsubstituted 3- to 5-membered non-aromatic carbocycle or a substituted or unsubstituted 3- to 5-membered non-aromatic heterocycle;

any one of $R^{4a}$s and any one of $R^{4c}$s may be taken together to form a substituted or unsubstituted (C1-C3) bridge, wherein one of carbon atoms constituting the (C1-C3) bridge may be replaced with an oxygen atom or a nitrogen atom;

$R^{1a}$ is each independently a hydrogen atom, halogen, hydroxy, substituted or unsubstituted alkyl, or substituted or unsubstituted alkyloxy;

$R^{1b}$ is each independently a hydrogen atom, halogen, hydroxy, substituted or unsubstituted alkyl, or substituted or unsubstituted alkyloxy;

n is an integer of 1 to 4;

—W— is a group represented by:

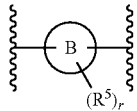

wherein

Ring B is a non-aromatic carbocycle, a non-aromatic heterocycle, an aromatic carbocycle, or an aromatic heterocycle;

$R^5$ is each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkyl sulfonyl, substituted or unsubstituted alkenyl sulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkyl sulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkyl sulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, or substituted or unsubstituted alkynyloxycarbonylamino;

two $R^5$s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom; and r is an integer of 0 to 4, or —$(CR^{1c}R^{1d})_m$—;

$R^{1c}$ is each independently a hydrogen atom, halogen, hydroxy, substituted or unsubstituted alkyl (provided that the substituents are not aromatic heterocyclylcarbamoyloxy), or substituted or unsubstituted alkyloxy;

$R^{1d}$ is each independently a hydrogen atom, halogen, hydroxy, substituted or unsubstituted alkyl (provided that the substituents are not aromatic heterocyclylcarbamoyloxy), or substituted or unsubstituted alkyloxy;

m is an integer of 1 to 3;

-L- is —N($R^6$)—C(=O)—, —C(=O)—N($R^6$)—, —N($R^6$)—$SO_2$—, or —$SO_2$—N($R^6$)—;

$R^6$ is a hydrogen atom, or substituted or unsubstituted alkyl;

$R^2$ is substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or substituted or unsubstituted non-aromatic heterocyclylamino;

$R^3$ is each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkyl sulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkyl sulfonyl, substituted or unsubstituted alkenyl sulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkyl sulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkyl sulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkyl sulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

s is an integer of 0 to 3, or a pharmaceutically acceptable salt thereof.

2. The compound according to claim 1, wherein

-L- is —N($R^6$)—C(=O)— or —N($R^6$)—SO$_2$—;

Ring B is a non-aromatic carbocycle, a non-aromatic heterocycle, or an aromatic heterocycle;

n is an integer of 2 to 4; and m is 2, or a pharmaceutically acceptable salt thereof.

3. The compound according to claim 1, wherein
-L- is —N(R⁶)—C(=O)—;
Ring B is a non-aromatic carbocycle or a non-aromatic heterocycle;
n is 2; and
m is 2;
or a pharmaceutically acceptable salt thereof.

4. The compound according to claim 1, wherein

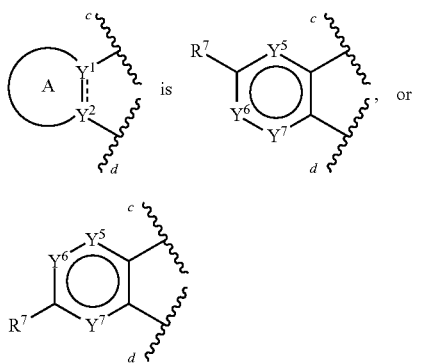

wherein
a bonding hand "c" is bonded to $CR^{4a}R^{4b}$; a bonding hand "d" is bonded to $CR^{4c}R^{4d}$;
$Y^5$ is N; $Y^6$ is $CR^{9c}$; $Y^7$ is $CR^{9d}$; the ring constituted of $Y^5$ to $Y^7$ and carbon atoms is pyridine;
$R^7$ is each independently a hydrogen atom, halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonylamino, substituted or unsubstituted alkynylcarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, or substituted or unsubstituted aromatic heterocyclylcarbonylamino;

$R^{9c}$ and $R^{9d}$ are each independently a hydrogen atom, halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonylamino, substituted or unsubstituted alkynylcarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, or substituted or unsubstituted aromatic heterocyclylcarbonylamino; the other symbols are the same as defined in claim 1;

or a pharmaceutically acceptable salt thereof.

5. The compound according to claim 1, wherein the compound is represented by the formula (II-1):

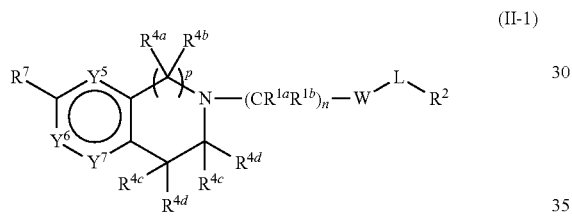

(II-1)

wherein

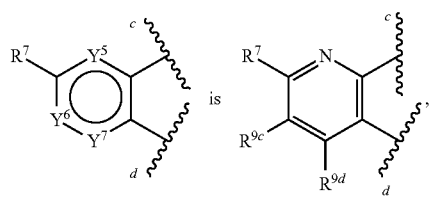

is $R^7$ is each independently a hydrogen atom, halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonylamino, substituted or unsubstituted alkynylcarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, or substituted or unsubstituted aromatic heterocyclylcarbonylamino;

$R^{9c}$ and $R^{9d}$ are each independently a hydrogen atom, halogen, hydroxy, cyano, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonylamino, substituted or unsubstituted alkynylcarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, or substituted or unsubstituted aromatic heterocyclylcarbonylamino; the other symbols are the same as defined in claim 1;

or a pharmaceutically acceptable salt thereof.

6. The compound according to claim 5, wherein

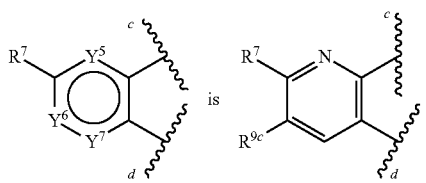

or a pharmaceutically acceptable salt thereof.

7. The compound according to claim 5, wherein
$R^7$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or unsubstituted non-aromatic heterocyclylamino; and
$R^{9c}$ and $R^{9d}$ are each independently a hydrogen atom, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy, or a pharmaceutically acceptable salt thereof.

8. The compound according claim 1, wherein
$R^2$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

9. The compound according to claim 1, wherein
—W— is a group represented by:

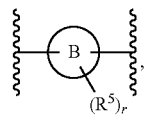

or a pharmaceutically acceptable salt thereof.

10. The compound according to claim 1, wherein
—W— is —$(CR^{1c}R^{1d})_m$—, or a pharmaceutically acceptable salt thereof.

11. The compound according to claim 1, wherein
$R^{4a}$ is each independently a hydrogen atom, halogen, hydroxy, substituted or unsubstituted alkyl, or substituted or unsubstituted alkyloxy;
$R^{4b}$ is each independently a hydrogen atom, halogen, hydroxy, substituted or unsubstituted alkyl, or substituted or unsubstituted alkyloxy;
$R^{4c}$ is each independently a hydrogen atom, halogen, hydroxy, substituted or unsubstituted alkyl, or substituted or unsubstituted alkyloxy; and
$R^{4d}$ is each independently a hydrogen atom, halogen, hydroxy, substituted or unsubstituted alkyl, or substituted or unsubstituted alkyloxy;

or a pharmaceutically acceptable salt thereof.

12. The compound according to claim 1, wherein
$R^{1a}$ and $R^{1b}$ are hydrogen atoms, and
$R^{4a}$, $R^{4b}$, $R^{4c}$ and $R^{4d}$ are hydrogen atoms,
or a pharmaceutically acceptable salt thereof.

13. The compound according to claim 2, wherein $R^6$ is a hydrogen atom,
or a pharmaceutically acceptable salt thereof.

14. The compound according to claim 1, wherein the compound is represented by Formula (Ih):

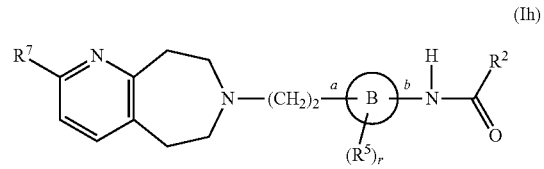

wherein
Ring B is a non-aromatic carbocycle or a non-aromatic heterocycle;
$R^5$ is each independently halogen;
r is an integer of 0 to 2,
$R^7$ is substituted or unsubstituted alkyl, substituted or unsubstituted alkyloxy, substituted or unsubstituted alkylamino, substituted or unsubstituted aromatic carbocyclyl, substituted or unsubstituted non-aromatic carbocyclyl, substituted or unsubstituted non-aromatic heterocyclyl, or substituted or unsubstituted non-aromatic carbocyclyloxy; and R² is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

15. The compound according to claim 14, wherein
R² is non-aromatic heterocyclyl optionally substituted with one or more group(s) selected from alkyl and oxy, aromatic heterocyclyl optionally substituted with alkyl, aromatic heterocyclylalkyl (aromatic heterocycle of the aromatic heterocyclylalkyl can be further substituted with one or more group(s) selected from alkyl and alkyloxy), alkyl substituted with aromatic heterocyclyloxy optionally substituted with alkyl, or, alkenyl substituted with aromatic heterocyclyloxy optionally substituted with alkyl;

R⁷ is alkyl substituted with halogen, or alkyloxy substituted with halogen;

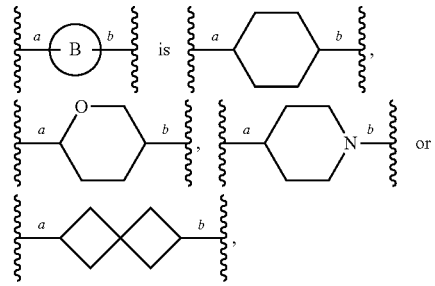

or a pharmaceutically acceptable salt thereof.

16. The compound according to claim 1, wherein the compound is selected from the group consisting of

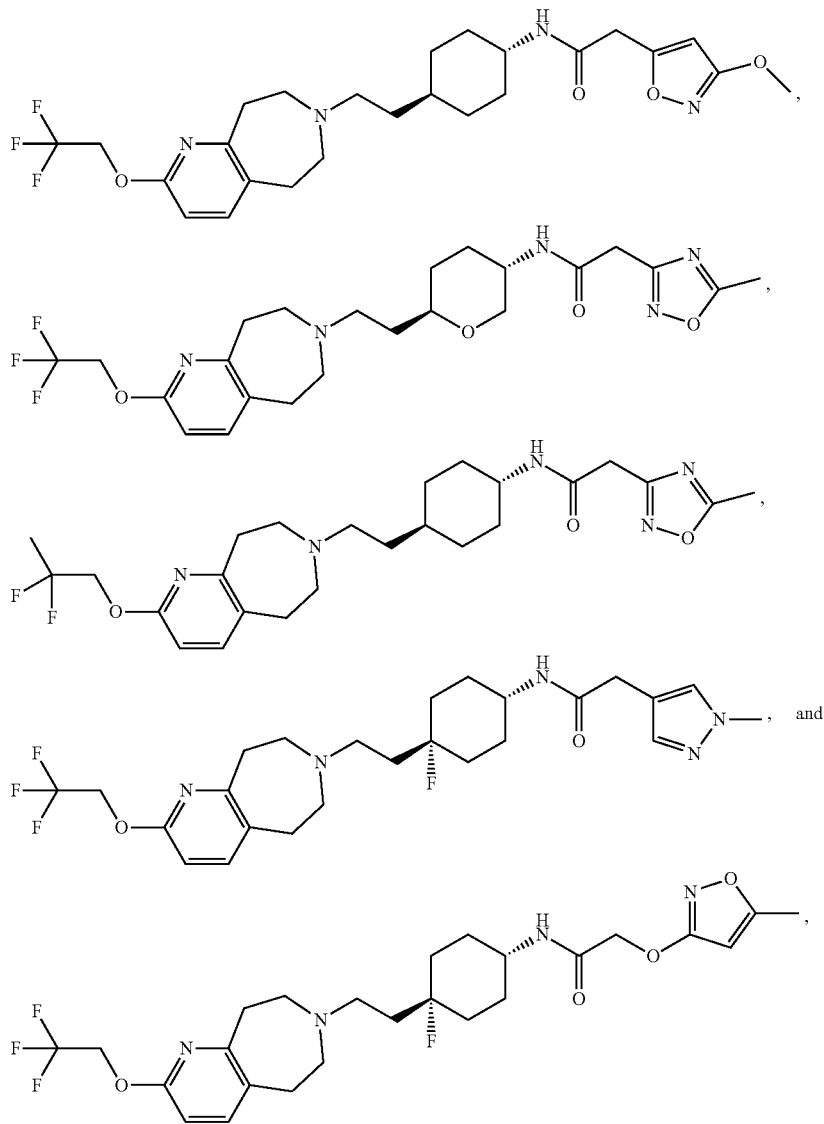

or a pharmaceutically acceptable salt thereof.

17. A pharmaceutical composition comprising the compound according to claim 1 or a pharmaceutically acceptable salt thereof, and a pharmaceutical additive.

18. A method for treating a disease associated with dopamine D3 receptor comprising administering an effective amount of the compound according to claim 1 or a pharmaceutically acceptable salt thereof to a patient in need thereof, wherein the disease associated with the dopamine D3 receptor is selected from the group consisting of depression, anxiety, gambling addiction, dementias, memory impairment, schizophrenia, bipolar disorder, mania, acute mania, psychoses, attention-deficit/hyperactivity disorder (AD/HD), attention deficit disorder (ADD), obsessive-compulsive disorder (OCD), dyskinesia disorder, Parkinson's disease, neuroleptic-induced Parkinson's syndrome and tardive dyskinesia, sexual dysfunction, a learning disability, emesis, amnesia, aggression, autism, vertigo, a circadian rhythm disorder, and a gastric motility disorder.

* * * * *